(12) United States Patent
Takasu et al.

(10) Patent No.: US 8,722,663 B2
(45) Date of Patent: May 13, 2014

(54) DI-SUBSTITUTED PYRIDINE DERIVATIVES AS ANTICANCERS

(75) Inventors: Hideki Takasu, Osaka (JP); Shigekazu Fujita, Osaka (JP); Shinya Ohtsuka, Osaka (JP); Toshiyuki Hirose, Osaka (JP); Yosuke Sato, Osaka (JP); Satoshi Yamada, Osaka (JP); Keisuke Miyajima, Osaka (JP); Koji Sakai, Osaka (JP); Yutaka Kojima, Osaka (JP); Kazuo Sekiguchi, Osaka (JP); Yasuo Yanagihara, Osaka (JP); Takashi Suzuki, Osaka (JP); Hideo Tanaka, Osaka (JP); Kazuhisa Sugiyama, Osaka (JP); Mitsuhiro Okuno, Osaka (JP); Takumi Sumida, Osaka (JP)

(73) Assignee: Otsuka Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 13/318,053

(22) PCT Filed: Jan. 28, 2011

(86) PCT No.: PCT/JP2011/052302
§ 371 (c)(1),
(2), (4) Date: Jan. 6, 2012

(87) PCT Pub. No.: WO2011/093524
PCT Pub. Date: Aug. 4, 2011

(65) Prior Publication Data
US 2012/0283242 A1     Nov. 8, 2012

Related U.S. Application Data

(60) Provisional application No. 61/359,729, filed on Jun. 29, 2010, provisional application No. 61/299,631, filed on Jan. 29, 2010.

(51) Int. Cl.
| | | |
|---|---|---|
| A61K 31/44 | (2006.01) | |
| A61K 31/4439 | (2006.01) | |
| A61K 31/4545 | (2006.01) | |
| A61K 31/4725 | (2006.01) | |
| A61K 31/443 | (2006.01) | |
| A61K 31/496 | (2006.01) | |
| A61K 31/551 | (2006.01) | |
| A61K 31/553 | (2006.01) | |
| C07D 213/69 | (2006.01) | |
| C07D 401/12 | (2006.01) | |
| C07D 405/12 | (2006.01) | |
| C07D 413/12 | (2006.01) | |

(52) U.S. Cl.
USPC .......... 514/211.08; 514/218; 514/253.12; 514/253.1; 514/318; 514/343; 540/545; 540/575; 544/360; 544/364; 546/194; 546/279.1

(58) Field of Classification Search
None
See application file for complete search history.

(56) References Cited

U.S. PATENT DOCUMENTS

2010/0261720 A1    10/2010   Sumida et al.

FOREIGN PATENT DOCUMENTS

| DE | 20 2009 007 345 U1 | 10/2009 |
|---|---|---|
| WO | WO 2006/014012 A2 | 2/2006 |
| WO | WO 2007/066784 A2 | 6/2007 |
| WO | WO 2008/044667 A1 | 4/2008 |
| WO | WO 2009/057811 A2 | 5/2009 |

OTHER PUBLICATIONS

Cancer Drug Design and Discovery, Neidle, Stephen, ed. (Elsevier/Academic Press), pp. 427-431 (2008).*
International Search Report from the European Patent Office in International Application No. PCT/JP2011/052302 mailed May 2, 2011.

* cited by examiner

*Primary Examiner* — Emily Bernhardt
(74) *Attorney, Agent, or Firm* — Finnegan, Henderson, Farabow, Garrett & Dunner, L.L.P.

(57) ABSTRACT

The present invention provides a novel compound having an excellent antitumor effect. The compound of the present invention is represented by the following general formula (1) wherein $R^1$ and $R^2$ are aryl or the like; A is lower alkylene; Ring X is optionally substituted arylene; E is bond or lower alkenylene; Ring Y is optionally substituted heterocycloalkylene containing one or more nitrogen atoms, one of which is attached to the adjacent carbonyl group; G is —NH-$G_2$-, —N(lower alkyl)-$G_2$-, —NH—$CH_2$-$G_2$-, —N(lower alkyl)-$CH_2$-$G_2$- or —$CH_2$-$G_2$-, [wherein $G_2$ binds to $R^2$, $G_2$-$R^2$ is bond-$R^2$, phenylene-$G_3$-$R^2$, phenylene-$G_4$-O—$R^2$, phenylene-$G_5$-NH—$R^2$, phenylene-$G_6$-N(lower alkyl)-$R^2$ or quinolinediyl-O—$R^2$, the phenylene of said phenylene-containing groups being optionally substituted with one or more substituents; $G_3$-$R^2$ is —O-lower alkylene-$R^2$ or the like; $G_4$-O— is lower alkylene-O— or the like; $G_5$ is lower alkylene; $G_6$ is lower alkylene].

(1)

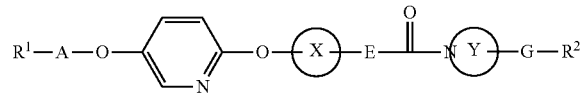

10 Claims, No Drawings

DI-SUBSTITUTED PYRIDINE DERIVATIVES AS ANTICANCERS

CROSS REFERENCE TO RELATED APPLICATIONS

This application is a national phase application based on PCT/JP2011/052302, filed Jan. 28, 2011, which claims the benefit of U.S. Provisional Application No. 61/299,631, filed Jan. 29, 2010 and U.S. Provisional Application No. 61/359,729, filed Jun. 29, 2010; the content of all of which is incorporated herein by reference.

TECHNICAL FIELD

The present invention relates to a heterocyclic compound.

BACKGROUND ART

Since the clinical use of nitrogen mustard as an anticancer agent in the 1940s for the first time in the world, numerous anticancer drugs have ever been developed. Actually, for example, antimetabolites such as 5-fluorouracil, antitumor antibiotics such as adriamycin, platinum complex such as cisplatin, and plant-derived carcinostatics such as vindesine have been subjected to clinical use.

However, most of these carcinostatics have significant side effects such as digestive disorders, myelosuppression and alopecia since they are cytotoxic also to normal cells. Due to the side effects, their range of application is limited. In addition, the therapeutic effects themselves are partial and short, in most cases.

Developments of new carcinostatics in place of these has been made; however, satisfactory results have not yet been obtained. Patent Documents 1, 2, 3 and 4 disclose that certain kinds of compounds have fibrosing inhibitory actions, antitumor actions and STAT3/5 activation inhibitory actions, respectively. However, it is not known whether the specific compounds of the present invention have an antitumor effect.

CITATION LIST

Patent Literature

[Patent Document 1] WO/2006/014012
[Patent Document 2] WO/2007/066784
[Patent Document 3] WO/2008/044667
[Patent Document 4] WO/2009/057811

SUMMARY OF INVENTION

Technical Problem

An object of the present invention is therefore to provide a compound which has an antitumor effect with less side effects, and excellent safety.

Solution to Problem

The present inventors intensively conducted studies with the view to attaining the aforementioned object. As a result, they found that a compound represented by the general formula (1) below and a salt thereof have an excellent antiproliferative activity with less side effects, and excellent safety, and therefore they are useful as a medical drug for treating or preventing various cancer types. Examples of the cancer include sex-steroid hormone related cancer (for example, prostate cancer, breast cancer, ovarian cancer, uterine cancer, testicular cancer) and solid cancer (for example, lung cancer, colon cancer, bladder cancer, thyroid cancer, esophageal cancer, liver cancer). The present invention has been achieved based on the finding.

More specifically, the present invention provides a heterocyclic compound shown in the following items:

Item 1. A compound represented by the following general formula (1) or a salt thereof;

[Formula 1]

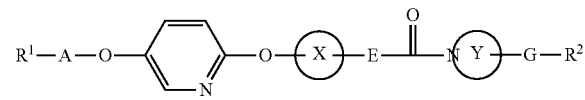

(1)

wherein
$R^1$ and $R^2$ are each independently aryl or unsaturated heterocyclic ring, each of which is optionally substituted with one or more substituents,
A is lower alkylene,
Ring X is optionally substituted arylene,
E is bond or lower alkenylene,
the partial structural formula:

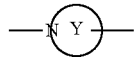

is optionally substituted heterocycloalkylene containing one or more nitrogen atoms, one of which is attached to the adjacent carbonyl group,
G is —NH-$G_2$-, —N(lower alkyl)-$G_2$-, —NH—$CH_2$-$G_2$-, —N(lower alkyl)-$CH_2$-$G_2$- or —$CH_2$-$G_2$-,
wherein $G_2$ of said G binds to $R^2$,
$G_2$-$R^2$ is bond-$R^2$, phenylene-$G_3$-$R^2$, phenylene-$G_4$-O—$R^2$, phenylene-$G_5$-NH—$R^2$, phenylene-$G_6$-N(lower alkyl)-$R^2$ or quinolinediyl-O—$R^2$, wherein the phenylene of said phenylene-$G_3$-$R^2$, phenylene-$G_4$-O—$R^2$, phenylene-$G_5$-NH—$R^2$ and phenylene-$G_6$-N(lower alkyl)-$R^2$ is optionally substituted with one or more substituents selected from the group consisting of halogen and lower alkyl,
$G_3$-$R^2$ is bond-$R^2$, —O-lower alkylene-$R^2$, lower alkylene-O-lower alkylene-$R^2$ or —O-lower alkylene-CO—$R^2$,
$G_4$-O— is bond-O—, lower alkylene-O—, lower alkenylene-O—, —O-lower alkylene-O— or —CO-lower alkylene-O—,
$G_5$ and $G_6$ are each lower alkylene.

Item 2. The compound according to Item 1 or a salt thereof; wherein
$R^1$ is phenyl, pyridyl, benzothiazolyl or thiazolyl, each of which is optionally substituted with one or more substituents,
the partial structural formula:

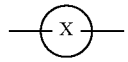

is the following formula:

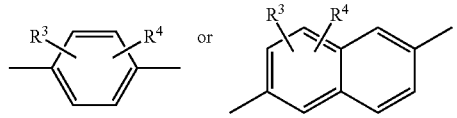

wherein $R^3$ and $R^4$ are the same or different, and are each independently hydrogen, halogen, lower alkyl or lower alkoxy, the partial structural formula:

is piperazinediyl, piperidinediyl, pyrrolidinediyl, diazepanediyl or oxadiazepanediyl, each of which is optionally substituted with one or more substituents, and $R^2$ is:

(i) aryl which may be substituted with one or more substituents selected from the group consisting of halogen, cyano, nitro, methylenedioxy, trimethylene, tetramethylene, pyrrolyl, lower alkyl carbonyl, lower alkyl sulfonyl, lower alkyl which may be substituted with one or more halogen, lower alkoxy which may be substituted with one or more halogen, cyclo lower alkyl, lower alkoxy lower alkyl, lower alkenyl, hydroxy lower alkenyl, lower alkoxy lower alkenyl, hydroxy lower alkyl, amino which may be substituted with one or more lower alkyl, and hydroxy lower alkoxy, (ii) unsaturated heterocyclic ring which may be substituted with one or more substituents selected from the group consisting of halogen, lower alkyl which may be substituted with one or more halogen, and lower alkoxy.

Item 3. The compound according to Item 2 or a salt thereof; wherein $R^1$ is the following formula:

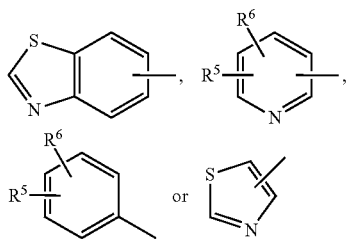

wherein $R^5$ and $R^6$ are the same or different, and are each independently hydrogen, halogen, cyano, nitro, lower alkoxy which may be substituted with one or more halogen, or lower alkyl which may be substituted with one or more halogen, the partial structural formula:

is the following formula:

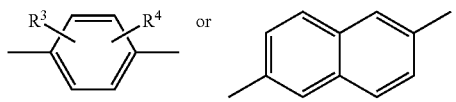

and, the partial structural formula:

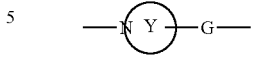

is the following formula:

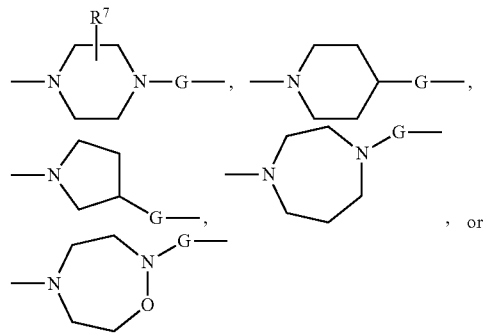

wherein $R^7$ is hydrogen or lower alkyl.

Item 4. The compound according to Item 3 or a salt thereof; wherein $R^2$ is:

(i) phenyl which may be substituted with one or more substituents selected from the group consisting of halogen, cyano, nitro, methylenedioxy, trimethylene, tetramethylene, pyrrolyl, lower alkyl carbonyl, lower alkyl sulfonyl, lower alkyl which may be substituted with one or more halogen, lower alkoxy which may be substituted with one or more halogen, cyclo lower alkyl, lower alkoxy lower alkyl, lower alkenyl, hydroxy lower alkenyl, lower alkoxy lower alkenyl, hydroxy lower alkyl, amino which may be substituted with one or more lower alkyl, and hydroxy lower alkoxy, (ii) naphtyl, (iii) pyridyl which may be substituted with one or more substituents selected from the group consisting of halogen, lower alkyl which may be substituted with one or more halogen, and lower alkoxy, (iv) benzoxazolyl which may be substituted with one or more halogen, (v) benzothiazolyl which may be substituted with one or more lower alkyl, or (vi) quinolyl.

Item 5. The compound according to Item 4 or a salt thereof; wherein

G is —NH-$G_2$-, —N(lower alkyl)-$CH_2$-$G_2$- or —$CH_2$-$G_2$-, wherein $G_2$ of said G binds to $R^2$, $G_2$-$R^2$ is phenylene-$G_3$-$R^2$, phenylene-$G_4$-O—$R^2$, phenylene-$G_5$-NH—$R^2$, phenylene-$G_6$-N(lower alkyl)-$R^2$ or quinolinediyl-O—$R^2$, wherein the phenylene of said phenylene-$G_3$-$R^2$, phenylene-$G_4$-O—$R^2$, phenylene-$G_5$-NH—$R^2$ and phnylene-$G_6$-N(lower alkyl)-$R^2$ is optionally substituted with one or more substituents selected from the group consisting of halogen and lower alkyl.

Item 6. The compound according to Item 4 or a salt thereof, wherein G is methylene.

Item 7. The compound according to Item 1 or a salt thereof, which is selected from the group consisting of:

(2E)-3-[4-({5[(4-methoxybenzyl)oxy]pyridin-2-yl}oxy)-3,5-dimethylphenyl]-1-(4-{-4[(1E)-3-(4-methylphenoxy)prop-1-en-1-yl]benzyl}piperazin-1-yl)prop-2-en-1-one, (E)-3-[3-chloro-5-methyl-4-({5[(4-methylbenzyl)oxy]pyridin-2-yl}oxy)phenyl]-1-[4-(4-{2-[4-(propan-2-yl)phenoxy]ethyl}benzyl)-1,4-diazepan-1-yl]prop-2-en-1-one, 4-{2-[4-({-4-[(E)-3-{3-chloro-5-methyl-4-[(5-{[4-(trifluoromethyl)benzyl]oxy}pyridin-2-yl)oxy]phenyl}prop-2-enoyl]piperazin-1-yl}methyl)phenyl]ethoxy}benzonitrile, (E)-3-[3-chloro-5-methyl-4-({5[(4-methylbenzyl)oxy]pyridin-2-yl}oxy)phenyl]-1-(4-{4-[2-(4-ethoxyphenoxy)ethoxy]benzyl}piperazin-1-yl)prop-2-en-1-one, (E)-3-[3-chloro-5-methyl-4-({5-[(4-methylbenzyl)oxy]pyridin-2-yl}oxy)phenyl]-1-[4-(4-{2-[4-(dimethylamino)phenoxy]ethyl}benzyl)piperazin-1-yl]prop-2-en-1-one, (E)-3-{3-chloro-5-methyl-4-[(5-{[4-(propan-2-yl)benzyl]oxy}pyridin-2-yl)oxy]phenyl}-1-[4-(4-methylbenzyl)piperazin-1-yl]prop-2-en-1-one, (E)-3-[3-chloro-5-methyl-4-({5[(4-methylbenzyl)oxy]pyridin-2-yl}oxy)phenyl]-1-[4-(4-methylbenzyl)piperazin-1-yl]prop-2-en-1-one, (E)-1-[4-(4-{2-[(4-chlorobenzyl)oxy]ethyl}benzyl)piperazin-1-yl]-3-(3,5-dimethyl-4-{[5-(pyridin-4-ylmethoxy)pyridin-2-yl]oxy}phenyl)prop-2-en-1-one, (E)-3-[3-chloro-4-({5-[(2-chlorobenzyl)oxy]pyridin-2-yl}oxy)-5-methylphenyl]-1-[4-(4-ethenylbenzyl)piperazin-1-yl]prop-2-en-1-one, (E)-3-[3-chloro-5-methyl-4-({5-[(4-methylbenzyl)oxy]pyridin-2-yl}oxy)phenyl]-1-[(3S)-4-{4-[2-(4-fluorophenoxy)ethyl]benzyl}-3-methylpiperazin-1-yl]prop-2-en-1-one, 4-{[(6-{4-[(E)-3-(2-{4-[2-(4-methoxyphenoxy)ethyl]benzyl}-1,2,5-oxadiazepan-5-yl)-3-oxoprop-1-en-1-yl]-2,6-dimethylphenoxy}pyridin-3-yl)oxy]methyl}benzonitrile, (2E)-3-[4-({5-[(4-fluorobenzyl)oxy]pyridin-2-yl}oxy)-3,5-dimethylphenyl]-1-(4-{3-methyl-4-[(1E)-3-(4-methylphenoxy)prop-1-en-1-yl]benzyl}piperazin-1-yl)prop-2-en-1-one, (E)-3-[3-chloro-5-methyl-4-({5-[(4-methylbenzyl)oxy]pyridin-2-yl}oxy)phenyl]-1-(4-{4-[2-(4-chlorophenoxy)ethyl]benzyl}piperazin-1-yl)prop-2-en-1-one, (E)-3-[3-chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)prop-2-en-1-one, (E)-3-[3-chloro-4-({5-[(3-fluoro-4-methylbenzyl)oxy]pyridin-2-yl}oxy)-5-methylphenyl]-1-(4-{4-[2-(4-chlorophenoxy)ethyl]benzyl}piperazin-1-yl)prop-2-en-1-one, (E)-3-[3-chloro-4-({5-[(3-fluoro-4-methylbenzyl)oxy]pyridin-2-yl}oxy)-5-methylphenyl]-1-(4-{4-[2-(4-methoxyphenoxy)ethyl]benzyl}piperazin-1-yl)prop-2-en-1-one, (E)-3-[3-chloro-4-({5-[(4-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)prop-2-en-1-one, (E)-3-[3-chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one, (E)-3-[3-chloro-4-({5-[(4-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one, (E)-3-[3-chloro-4-({5-[(4-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one, (E)-3-[3-chloro-5-methyl-4-({5-[(4-methylbenzyl)oxy]pyridin-2-yl}oxy)phenyl]-1-(4-{4-[2-(4-methoxyphenoxy)ethyl]benzyl}piperazin-1-yl)prop-2-en-1-one, (E)-3-[3-chloro-4-({5-[(6-chloropyridin-3-yl)methoxy]pyridin-2-yl}oxy)-5-methylphenyl]-1-[4-(4-{2-[4-(propan-2-yl)phenoxy]ethyl}benzyl)piperazin-1-yl]prop-2-en-1-one, (E)-3-(3-chloro-5-methyl-4-{[5-(pyridin-3-ylmethoxy)pyridin-2-yl]oxy}phenyl)-1-[4-(4-{2-[4-(propan-2-yl)phenoxy]ethyl}benzyl)piperazin-1-yl]prop-2-en-1-one, (E)-3-[3-chloro-4-({5-[(2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one, (E)-3-[3-chloro-5-methyl-4-({5-[(2-methylbenzyl)oxy]pyridin-2-yl}oxy)phenyl]-1-(4-{4-[2-(4-fluorophenoxy)ethyl]benzyl}piperazin-1-yl)prop-2-en-1-one, (E)-3-[3-chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one, (E)-3-[3-chloro-4-({5-[(2-fluorobenzyl)oxy]pyridin-2-yl}oxy)-5-methylphenyl]-1-(4-{4-[2-(4-methylphenoxy)ethyl]benzyl}piperazin-1-yl)prop-2-en-1-one, (E)-3-[3-chloro-4-({5-[(2-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one, (E)-3-[3-chloro-4-({5-[(2-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one, (E)-3-[3-chloro-4-({5-[(2-chlorobenzyl)oxy]pyridin-2-yl}oxy)-5-methylphenyl]-1-(4-{4-[2-(4-chlorophenoxy)ethyl]benzyl}piperazin-1-yl)prop-2-en-1-one, (E)-3-[4-({5-[(2-chlorobenzyl)oxy]pyridin-2-yl}oxy)-3-methoxyphenyl]-1-(4-{4-[2-(4-methylphenoxy)ethyl]benzyl}piperazin-1-yl)prop-2-en-1-one, (E)-3-[3-chloro-4-({5-[(3-chloro-2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one, (E)-3-[3-chloro-4-({5-[(2,3-difluorobenzyl)oxy]pyridin-2-yl}oxy)-5-methylphenyl]-1-(4-{4-[2-(4-methylphenoxy)ethyl]benzyl}piperazin-1-yl)prop-2-en-1-one, (E)-3-[4-({5-[(2-chlorobenzyl)oxy]pyridin-2-yl}oxy)-3-methylphenyl]-1-[4-(4-{2-[4-(propan-2-yl)phenoxy]ethyl}benzyl)piperazin-1-yl]prop-2-en-1-one, (E)-3-[3-chloro-5-methyl-4-({5-[(4-methylbenzyl)oxy]pyridin-2-yl}oxy)phenyl]-1-(4-{4-[2-(4-methylphenoxy)propyl]benzyl}piperazin-1-yl)prop-2-en-1-one,

[6-({5-[(2,3-difluorobenzyl)oxy]pyridin-2-yl}oxy)naphthalen-2-yl][4-(4-{2-[4-(propan-2-yl)phenoxy]ethyl}benzyl)piperazin-1-yl]methanone, 4-{[(6-{4-[(E)-3-(4-{4-[2-(4-chlorophenoxy)ethyl]benzyl}piperazin-1-yl)-3-oxoprop-1-en-1-yl]-2,6-dimethylphenoxy}pyridin-3-yl)oxy]methyl}benzonitrile, 4-({[6-(2-fluoro-4-{(E)-3-oxo-3-[4-(4-{2-[4-(propan-2-yl)phenoxy]ethyl}benzyl)piperazin-1-yl]prop-1-en-1-yl}phenoxy)pyridin-3-yl]oxy}methyl)benzonitrile, (E)-3-(3,5-dimethyl-4-{[5-(1,3-thiazol-5-ylmethoxy)pyridin-2-yl]oxy}phenyl)-1-(4-{4-[2-(3-ethoxyphenoxy)ethyl]benzyl}piperazin-1-yl)prop-2-en-1-one, (E)-3-(3,5-dimethyl-4-{[5-(1,3-thiazol-5-ylmethoxy)pyridin-2-yl]oxy}phenyl)-1-[4-(4-{2-[4-(propan-2-yl)phenoxy]ethyl}benzyl)piperazin-1-yl]prop-2-en-1-one, (E)-3-(3,5-dimethyl-4-{[5-(1,3-thiazol-5-ylmethoxy)pyridin-2-yl]oxy}phenyl)-1-(4-{4-[2-(4-methylphenoxy)ethyl]benzyl}piperazin-1-yl)prop-2-en-1-one, (E)-3-(3,5-dimethyl-4-{[5-(1,3-thiazol-4-ylmethoxy)pyridin-2-yl]oxy}phenyl)-1-[4-(4-{2-[4-(propan-2-yl)phenoxy]ethyl}benzyl)piperazin-1-yl]prop-2-en-1-one, (E)-3-(3,5-dimethyl-4-{[5-(1,3-thiazol-4-ylmethoxy)pyridin-2-yl]oxy}phenyl)-1-(4-{4-[2-(4-methylphenoxy)ethyl]benzyl}piperazin-1-yl)prop-2-en-1-one, (E)-3-[3-chloro-4-({5-[(2-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one, (E)-3-[4-({5-[(4-methoxybenzyl)oxy]pyridin-2-yl}oxy)-3,5-dimethylphenyl]-1-(4-{2-methyl-4-[2-(4-methylphenoxy)ethyl]benzyl}piperazin-1-yl)prop-2-en-1-one, 4-{[(6-{2-chloro-6-methyl-4-[(E)-3-oxo-3-{4-[4-(2-{[5-(trifluoromethyl)pyridin-2-yl]oxy}ethyl)benzyl]piperazin-1-yl}prop-1-en-1-yl]phenoxy}pyridin-3-yl)oxy]methyl}benzonitrile, 4-{[(6-{4-[(E)-3-(4-{4-[2-(4-chlorophenoxy)ethyl]-3-fluorobenzyl}piperazin-1-yl)-3-oxoprop-1-en-1-yl]-2,6-dimethylphenoxy}pyridin-3-yl)oxy]methyl}benzonitrile, 4-({[6-(4-{(E)-3-[4-(2-fluoro-4-{2-[4-(trifluoromethyl)phenoxy]ethyl}benzyl)piperazin-1-yl]-3-oxoprop-1-en-1-yl}-2,6-dimethylphenoxy)pyridin-3-yl]oxy}methyl)benzonitrile, 4-{[(6-{2-chloro-4-[(E)-3-(4-{4-[3-(4-fluorophenoxy)propyl]benzyl}piperazin-1-yl)-3-oxoprop-1-en-1-yl]-6-methylphenoxy}pyridin-3-yl)oxy]methyl}benzonitrile, 4-{[(6-{2-chloro-6-methyl-4-[(E)-3-(4-{4-[3-(4-methylphenoxy)propyl]benzyl}piperazin-1-yl)-3-oxoprop-1-en-1-yl]phenoxy}pyridin-3-yl)oxy]methyl}benzonitrile, 4-({[6-(2-chloro-4-{(E)-3-[4-(3-fluoro-4-{[4-(propan-2-yloxy)phenoxy]methyl}benzyl)piperazin-1-yl]-3-oxoprop-1-en-1-yl}-6-methylphenoxy)pyridin-3-yl]oxy}methyl)benzonitrile, 4-{[(6-{2-chloro-4-[(E)-3-(4-{3-fluoro-4-[(4-fluorophenoxy)methyl]benzyl}piperazin-1-yl)-3-oxoprop-1-en-1-yl]-6-methylphenoxy}pyridin-3-yl)oxy]methyl}benzonitrile 4-({[6-(2,6-dimethyl-4-{(E)-3-oxo-3-[4-(4-{[4-(propan-2-yloxy)phenoxy]methyl}benzyl)piperazin-1-yl]prop-1-en-1-yl}phenoxy)pyridin-3-yl]oxy}methyl)benzonitrile, (E)-3-(3,5-dimethyl-4-{[5-(1,3-thiazol-4-ylmethoxy)pyridin-2-yl]oxy}phenyl)-1-[4-(4-{[4-(propan-2-yl)phenoxy]methyl}benzyl)piperazin-1-yl]prop-2-en-1-one, 4-({[6-(4-{(1E)-3-[4-(4-{(1E)-3-[(5-bromopyridin-2-yl)oxy]prop-1-en-1-yl}benzyl)piperazin-1-yl]-3-oxoprop-1-en-1-yl}-2-chloro-6-methylphenoxy)pyridin-3-yl]oxy}methyl)benzonitrile, 4-({[6-(2-chloro-4-{(E)-3-[4-(4-{2-[(4-methoxyphenyl)amino]ethyl}benzyl)piperazin-1-yl]-3-oxoprop-1-en-1-yl}phenoxy)pyridin-3-yl]oxy}methyl)benzonitrile, (E)-3-[3-chloro-4-({5-[(2-chlorobenzyl)oxy]pyridin-2-yl}oxy)-5-methylphenyl]-1-(4-{[2-(4-methoxyphenoxy)quinolin-6-yl]methyl}piperazin-1-yl)prop-2-en-1-one, (E)-3-{3-chloro-5-methyl-4-[(5-{[4-(trifluoromethyl)benzyl]oxy}pyridin-2-yl)oxy]phenyl}-1-(4-{4-[2-(4-methoxyphenyl)ethoxy]benzyl}piperazin-1-yl)prop-2-en-1-one, 4-{[(6-{4-[(E)-3-{4-[4-(4-chlorophenoxy)benzyl]piperazin-1-yl}-3-oxoprop-1-en-1-yl]-2,6-dimethylphenoxy}pyridin-3-yl)oxy]methyl}benzonitrile, (E)-3-[3-chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)but-2-en-1-one, (E)-3-[3-chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)but-2-en-1-one, (E)-1-(4-{4-[2-(4-fluorophenoxy)propyl]benzyl}piperazin-1-yl)-3-[4-({5-[(4-methoxybenzyl)oxy]pyridin-2-yl}oxy)-3,5-dimethylphenyl]prop-2-en-1-one, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)but-2-en-1-one, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)-2-methylbut-2-en-1-one, (E)-3-[3-chloro-4-({5-[(4-fluorobenzyl)oxy]pyridin-2-yl}oxy)phenyl]-1-(4-{4-[2-(3-methoxyphenoxy)ethyl]benzyl}piperazin-1-yl)prop-2-en-1-one, (E)-1-[4-(4-chlorobenzyl)piperazin-1-yl]-3-[3-chloro-4-({5-[2-(4-chlorophenyl)ethoxy]pyridin-2-yl}oxy)-5-methylphenyl]prop-2-en-1-one, (E)-3-[3-chloro-4-({5-[(4-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one, (E)-3-[3-chloro-4-({5-[(4-fluorobenzyl)oxy]pyridin-2-yl}oxy)-5-methylphenyl]-1-[4-(4-methylbenzyl)piperazin-1-yl]prop-2-en-1-one, and (E)-3-[3-chloro-4-({5-[(4-chlorobenzyl)oxy]pyridin-2-yl}oxy)-5-methylphenyl]-1-[4-(4-methylbenzyl)piperazin-1-yl]prop-2-en-1-one.

Item 8. The compound according to Item 1, which is selected from the group consisting of:

(2E)-3-[4-({5-[(4-methoxybenzyl)oxy]pyridin-2-yl}oxy)-3,5-dimethylphenyl]-1-(4-{4-[(1E)-3-(4-methylphenoxy)prop-1-en-1-yl]benzyl}piperazin-1-yl)prop-2-en-1-one, (E)-3-[3-chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)-1,4-diazepan-1-yl]prop-2-en-1-one, 4-{2-[4-({4-[(E)-3-{3-chloro-5-methyl-4-[(5-{[4-(trifluoromethyl)benzyl]oxy}pyridin-2-yl)oxy]phenyl}prop-2-enoyl]piperazin-1-yl}methyl)phenyl]ethoxy}benzonitrile, (E)-3-[3-chloro-5-methyl-4-({5-[(4-methylbenzyl)oxy]pyridin-2-yl}oxy)phenyl]-1-(4-{4-[2-(4-ethoxyphenoxy)ethoxy]benzyl}piperazin-1-yl)prop-2-en-1-one, (E)-3-[3-chloro-5-methyl-4-({5-[(4-methylbenzyl)oxy]pyridin-2-yl}oxy)phenyl]-1-(4-{4-{2-[4-(dimethylamino)phenoxy]ethyl}benzyl)piperazin-1-yl)prop-2-en-1-one, (E)-3-{3-chloro-5-methyl-4-[(5-{[4-(propan-2-yl)benzyl]oxy}pyridin-2-yl)oxy]phenyl}-1-[4-(4-methylbenzyl)piperazin-1-yl]prop-2-en-1-one, (E)-3-[3-chloro-5-methyl-4-({5-[(4-methylbenzyl)oxy]pyridin-2-yl}oxy)phenyl]-1-[4-(4-methylbenzyl)piperazin-1-yl]prop-2-en-1-one, (E)-1-[4-(4-{2-[(4-chlorobenzyl)oxy]ethyl}benzyl)piperazin-1-yl]-3-(3,5-dimethyl-4-{[5-(pyridin-4-ylmethoxy)pyridin-2-yl]oxy}phenyl)prop-2-en-1-one, (E)-3-[3-chloro-4-({5-[(2-chlorobenzyl)oxy]pyridin-2-yl}oxy)-5-methylphenyl]-1-[4-(4-ethenylbenzyl)piperazin-1-yl]prop-2-en-1-one, (E)-3-[3-chloro-5-methyl-4-({5-[(4-methylbenzyl)oxy]pyridin-2-yl}oxy)phenyl]-1-[(3S)-4-{4-[2-(4-fluorophenoxy)ethyl]benzyl}-3-methylpiperazin-1-yl]prop-2-en-1-one, 4-{[(6-{4-[(E)-3-(2-{4-[2-(4-methoxyphenoxy)ethyl]benzyl}-1,2,5-oxadiazepan-5-yl)-3-oxoprop-1-en-1-yl]-2,6-dimethylphenoxy}pyridin-3-yl)oxy]methyl}benzonitrile, (2E)-3-[4-({5-[(4-fluorobenzyl)oxy]pyridin-2-yl}oxy)-3,5-dimethylphenyl]-1-(4-{3-methyl-4-[(1E)-3-(4-methylphenoxy)prop-1-en-1-yl]benzyl}piperazin-1-yl)prop-2-en-1-one, (E)-3-[3-chloro-5-methyl-4-({5-[(4-methylbenzyl)oxy]pyridin-2-yl}oxy)phenyl]-1-(4-{4-[2-(4-chlorophenoxy)ethyl]benzyl}piperazin-1-yl)prop-2-en-1-one hydrochloride, (E)-3-[3-chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)prop-2-en-1-one hydrochloride, (E)-3-[3-chloro-4-({5-[(3-fluoro-4-methylbenzyl)oxy]pyridin-2-yl}oxy)-5-methylphenyl]-1-(4-{4-[2-(4-chlorophenoxy)ethyl]benzyl}piperazin-1-yl)prop-2-en-1-one hydrochloride, (E)-3-[3-chloro-4-({5-[3-fluoro-4-methylbenzyl)oxy]pyridin-2-yl}oxy)-5-methylphenyl]-1-(4-{4-[2-(4-methoxyphenoxy)ethyl]benzyl}piperazin-1-yl)prop-2-en-1-one hydrochloride, (E)-3-[3-chloro-4-({5-[(4-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)prop-2-en-1-one hydrochloride, (E)-3-[3-chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one hydrochloride, (E)-3-[3-chloro-4-({5-[(4-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-4-({5-[(4-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride, (E)-3-[3-chloro-5-methyl-4-({5-[(4-methylbenzyl)oxy]pyridin-2-yl}oxy)phenyl]-1-(4-{4-[2-(4-methoxyphenoxy)ethyl]benzyl}piperazin-1-yl)prop-2-en-1-one hydrochloride, (E)-3-[3-chloro-4-({5-[(6-chloropyridin-3-yl)methoxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride, (E)-3-(3-chloro-5-methyl-4-{[5-(pyridin-3-ylmethoxy)pyridin-2-yl]oxy}phenyl)-1-[4-(4-{2-[4-(propan-2-yl)phenoxy]ethyl}benzyl)piperazin-1-yl]prop-2-en-1-one hydrochloride, (E)-3-[3-chloro-4-({5-[(2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-5-methyl-4-({5-[(2-methylbenzyl)oxy]pyridin-2-yl}oxy)phenyl]-1-(4-{4-[2-(4-fluorophenoxy)ethyl]benzyl}piperazin-1-yl)prop-2-en-1-one hydrochloride, (E)-3-[3-chloro-4-({5-[2-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-4-({5-[(2-fluorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride, (E)-3-[3-chloro-4-({5-[(2-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride, (E)-3-[3-chloro-4-({5-[(2-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride, (E)-3-[3-chloro-4-({5-[2-chlorobenzyl)oxy]pyridin-2-yl}oxy)-5-methylphenyl]-1-(4-{4-[2-(4-chlorophenoxy)ethyl]benzyl}piperazin-1-yl)prop-2-en-1-one hydrochloride, (E)-3-[4-({5-[(2-chlorobenzyl)oxy]pyridin-2-yl}oxy)-3-methoxyphenyl]-1-(4-{4-[2-(4-methylphenoxy)ethyl]benzyl}piperazin-1-yl)prop-2-en-1-one hydrochloride, (E)-3-[3-chloro-4-({5-[(3-chloro-2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-4-({5-[(2,3-difluorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride, (E)-3-[4-({5-[(2-chlorobenzyl)oxy]pyridin-2-yl}oxy)-3-methylphenyl]-1-[4-(4-{2-[4-(propan-2-yl)phenoxy]ethyl}benzyl)piperazin-1-yl]prop-2-en-1-one hydrochloride, (E)-3-[3-chloro-5-methyl-4-({5-[4-methylbenzyl)oxy]pyridin-2-yl}oxy)phenyl]-1-(4-{4-[2-(4-methylphenoxy)propyl]benzyl}piperazin-1-yl)prop-2-en-1-one hydrochloride,

[6-({5-[(2,3-difluorobenzyl)oxy]pyridin-2-yl}oxy)naphthalen-2-yl][4-(4-{2-[4-(propan-2-yl)phenoxy]ethyl}benzyl)piperazin-1-yl]methanone hydrochloride, 4-[(6-{4-[(E)-3-(4-{4-[2-(4-chlorophenoxy)ethyl]benzyl}piperazin-1-yl)-3-oxoprop-1-en-1-yl]-2,6-dimethylphenoxy)pyridin-3-yl)oxy]methyl}benzonitrile hydrochloride, 4-({[6-(2-fluoro-4-{(E)-3-oxo-3-[4-(4-{2-[4-(propan-2-yl)phenoxy]ethyl}benzyl)piperazin-1-yl]prop-1-en-1-yl}phenoxy)pyridin-3-yl]oxy}methyl)benzonitrile hydrochloride, (E)-3-(3,5-dimethyl-4-{[5-(1,3-thiazol-5-ylmethoxy)pyridin-2-yl]oxy}phenyl)-1-(4-{4-[2-(3-ethoxyphenoxy)ethyl]benzyl}piperazin-1-yl)prop-2-en-1-one hydrochloride, (E)-3-(3,5-dimethyl-4-{[5-(1,3-thiazol-5-ylmethoxy)pyridin-2-yl]oxy}phenyl)-1-[4-(4-{2-[4-(propan-2-yl)phenoxy]ethyl}benzyl)piperazin-1-yl]prop-2-en-1-one hydrochloride, (E)-3-(3,5-dimethyl-4-{[5-(1,3-thiazol-5-ylmethoxy)pyridin-2-yl]oxy}phenyl)-1-[4-(4-{2-[4-(methylphenoxy)ethyl]benzyl}piperazin-1-yl)prop-2-en-1-one hydrochloride, (E)-3-(3,5-dimethyl-4-{[5-(1,3-thiazol-4-ylmethoxy)pyridin-2-yl]oxy}phenyl)-1-[4-(4-{2-[4-(propan-2-yl)phenoxy]ethyl}benzyl)piperazin-1-yl]prop-2-en-1-one hydrochloride, (E)-3-(3,5-dimethyl-4-{[5-(1,3-thiazol-4-ylmethoxy)pyridin-2-yl]oxy}phenyl)-1-[4-(4-{4-[2-(4-methylphenoxy)ethyl]benzyl}piperazin-1-yl)prop-2-en-1-one hydrochloride, (E)-3-[3-chloro-4-({5-[(2-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride, (E)-3-[4-({5-[(4-methoxybenzyl)oxy]pyridin-2-yl}oxy)-3,5-dimethylphenyl]-1-(4-{2-methyl-4-[2-(4-methylphenoxy)ethyl]benzyl}piperazin-1-yl)prop-2-en-1-one hydrochloride, 4-{[(6-{2-chloro-6-methyl-4-[(E)-3-oxo-3-{4-[4-(2-{[5-(trifluoromethyl)pyridin-2-yl]oxy}ethyl)benzyl]piperazin-1-yl}prop-1-en-1-yl]phenoxy}pyridin-3-yl)oxy]methyl}benzonitrile hydrochloride, 4-{[(6-{4-[(E)-3-(4-{4-[2-(4-chlorophenoxy)ethyl]-3-fluorobenzyl}piperazin-1-yl)-3-oxoprop-1-en-1-yl]-2,6-dimethylphenoxy}pyridin-3-yl)oxy]methyl}benzonitrile hydrochloride, 4-({[6-(4-{(E)-3-[4-(2-fluoro-4-{2-[4-(trifluoromethyl)phenoxy]ethyl}benzyl)piperazin-1-yl]-3-oxoprop-1-en-1-yl}-2,6-dimethylphenoxy)pyridin-3-yl]oxy}methyl)benzonitrile hydrochloride, 4-{[(6-{2-chloro-4-[(E)-3-(4-{4-[3-(4-fluorophenoxy)propyl]benzyl}piperazin-1-yl)-3-oxoprop-1-en-1-yl]-6-methylphenoxy}pyridin-3-yl)oxy]methyl}benzonitrile hydrochloride, 4-{[(6-{2-chloro-6-methyl-4-[(E)-3-(4-{4-[3-(4-methylphenoxy)propyl]benzyl}piperazin-1-yl)-3-oxoprop-1-en-1-yl]phenoxy}pyridin-3-yl)oxy]methyl}benzonitrile hydrochloride, 4-({[6-(2-chloro-4-{(E)-3-[4-(3-fluoro-4-{[4-(propan-2-yloxy)phenoxy]methyl}benzyl)piperazin-1-yl]-3-oxoprop-1-en-1-yl}-6-methylphenoxy)pyridin-3-yl]oxy}methyl)benzonitrile hydrochloride, 4-{[(6-{2-chloro-4-[(E)-3-(4-{3-fluoro-4-[(4-fluorophenoxy)methyl]benzyl}piperazin-1-yl)-3-oxoprop-1-en-1-yl]-6-methylphenoxy}pyridin-3-yl)oxy]methyl}benzonitrile hydrochloride, 4-({[6-(2,6-dimethyl-4-{(E)-3-oxo-3-[4-(4-{[4-(propan-2-yloxy)phenoxy]methyl}benzyl)piperazin-1-yl]prop-1-en-1-yl}phenoxy)pyridin-3-yl]oxy}methyl)benzonitrile hydrochloride, (E)-3-(3,5-dimethyl-4-{[5-(1,3-thiazol-4-ylmethoxy)pyridin-2-yl]oxy}phenyl)-1-[4-(4-{[4-(propan-2-yl)phenoxy]methyl}benzyl)piperazin-1-yl]prop-2-en-1-one hydrochloride, 4-({[6-(4-{(1E)-3-[4-(4-{(1E)-3-[(5-bromopyridin-2-yl)oxy]prop-1-en-1-yl}benzyl)piperazin-1-yl]-3-oxoprop-1-en-1-yl}-2-chloro-6-methylphenoxy)pyridin-3-yl]oxy}methyl)benzonitrile hydrochloride, 4-({[6-(2-chloro-4-{(E)-3-[4-(4-{2-[4-(4-methoxyphenyl)amino]ethyl}benzyl)piperazin-1-yl]-3-oxoprop-1-en-1-yl}phenoxy)pyridin-3-yl]oxy}methyl)benzonitrile dihydrochloride, (E)-3-[3-chloro-4-({5-[(2-chlorobenzyl)oxy]pyridin-2-yl}oxy)-5-methylphenyl]-1-(4-{[2-(4-methoxyphenoxy)quinolin-6-yl]methyl}piperazin-1-yl)prop-2-en-1-one hydrochloride, (E)-3-{3-chloro-5-methyl-4-[(5-{[4-(trifluoromethyl)benzyl]oxy}pyridin-2-yl)oxy]phenyl}-1-(4-{4-[2-(4-methoxyphenyl)ethoxy]benzyl}piperazin-1-yl)prop-2-en-1-one hydrochloride, 4-{[(6-{4-[(E)-3-{4-[4-(4-chlorophenoxy)benzyl]piperazin-1-yl}-3-oxoprop-1-en-1-yl]-2,6-dimethylphenoxy}pyridin-3-yl)oxy]methyl}benzonitrile hydrochloride, (E)-3-[3-chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)but-2-en-1-one hydrobromide, (E)-3-[3-chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)but-2-en-1-one hydrobromide, (E)-1-(4-{4-[2-(4-fluorophenoxy)propyl]benzyl}piperazin-1-yl)-3-[4-({5-[(4-methoxybenzyl)oxy]pyridin-2-yl}oxy)-3,5-dimethylphenyl]prop-2-en-1-one hydrobromide, (E)-3-[3-chloro-5-methyl-4-({5-[4-methylbenzyl)oxy]pyridin-2-yl}oxy)phenyl]-1-(4-{4-[2-(4-fluorophenoxy)ethyl]benzyl}piperazin-1-yl)but-2-en-1-one ethanedioate, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)-2-methylbut-2-en-1-one ethanedioate, (E)-3-[3-chloro-4-({5-[(4-fluorobenzyl)oxy]pyridin-2-yl}oxy)phenyl]-1-(4-{4-[2-(3-methoxyphenoxy)ethyl]benzyl}piperazin-1-yl)prop-2-en-1-one hydrochloride, (E)-1-[4-(4-chlorobenzyl)piperazin-1-yl]-3-[3-chloro-4-({5-[2-(4-chlorophenyl)ethoxy]pyridin-2-yl}oxy)-5-methylphenyl]prop-2-en-1-one hydrochloride, (E)-3-[3-chloro-4-({5-[(4-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride, (E)-3-[3-chloro-4-({5-[4-fluorobenzyl)oxy]pyridin-2-yl}oxy)-5-methylphenyl]-1-[4-(4-methylbenzyl)piperazin-1-yl]prop-2-en-1-one hydrochloride, and (E)-3-[3-chloro-4-({5-[(4-chlorobenzyl)oxy]pyridin-2-yl}oxy)-5-methylphenyl]-1-[4-(4-methylbenzyl)piperazin-1-yl]prop-2-en-1-one hydrochloride.

Item 9. A pharmaceutical composition comprising a compound represented by the general formula (1) or a salt thereof according to Item 1, and a pharmacologically acceptable carrier.

Item 10. A pharmaceutical composition according to Item 9 for preventing and/or treating cancer.

Item 11. A compound represented by the general formula (1) or a salt thereof according to Item 1 for use in the pharmaceutical composition.

Item 12. Use of a compound represented by the general formula (1) or a salt thereof according to Item 1 as a pharmaceutical composition.

Item 13. Use of a compound represented by the general formula (1) or a salt thereof according to Item 1 for the production of a pharmaceutical composition.

Item 14. A method of preventing and/or treating cancer, comprising administering to a patient a compound represented by the general formula (1) or a salt thereof according to Item 1.

Specific examples of individual groups shown in the general formula (1) are as follows.

Examples of the "lower alkoxy" include linear or branched alkoxy groups having 1 to 6 carbon atoms and cycloalkylalkoxy groups having 4 to 7 carbon atoms such as methoxy, ethoxy, propoxy, isopropoxy, cyclopropylmethoxy, butoxy, tert-butoxy, pentyloxy, and hexyloxy groups.

Examples of the "lower alkyl" include linear or branched alkyl groups having 1 to 6 carbon atoms such as methyl, ethyl, propyl, isopropyl, 2,2-dimethylpropyl, 1-ethylpropyl, butyl, isobutyl, tert-butyl, isopentyl, pentyl, cyclopropylmethyl, and hexyl groups.

Examples of the "cyclo lower alkyl" include cyclo alkyl groups having 3 to 6 carbon atoms such as cyclopropyl, cyclobutyl, cyclopentyl, and cyclohexyl.

Examples of the "halogen" are fluorine, chlorine, bromine, and iodine.

Examples of the "lower alkylene" include linear or branched alkylene groups having 1 to 6 carbon atoms, such as methylene, ethylene, 1-methylethylene, 2-methylethylene, trimethylene, 2-methyltrimethylene, 2,2 dimethyltrimethylene, 1-methyltrimethylene, methylmethylene, ethylmethylene, dimethylmethylene, tetramethylene, pentamethylene, and hexamethylene.

Examples of the "lower alkenylene" include linear or branched alkenylene group having 1 to 3 double bonds and 2 to 6 carbon atoms such as vinylene, 1-methylvinylene, 2-methylvinylene, 1,2-dimethylvinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, and 1,4-hexadienylene.

Examples of the "unsaturated heterocyclic ring" include unsaturated monocyclic or bicyclic heterocyclic ring containing at least one hetero atom selected from among oxygen, sulfur and nitrogen. Examples of preferable unsaturated heterocyclic ring include the following (a) to (i):

(a) unsaturated 3 to 8-membered, preferably 5 or 6-membered heteromonocyclic ring containing 1 to 4 nitrogen atoms, for example, pyrrolyl, pyrrolinyl, imidazolyl, pyrazolyl, pyridyl, and its N-oxide, tetrahydropyridyl (e.g., 1,2,3,6-tetrahydropyridyl), pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

(b) unsaturated condensed 7 to 12-membered heterocyclic rings containing 1 to 3 oxygen atoms, for example, benzofuranyl, dihydrobenzofuranyl(e.g. 2,3-dihydrobenzo[b]furanyl, etc.), chromanyl, benzodioxanyl (e.g., 1,4-benzodioxanyl, etc.), benzodioxolyl (benzo[1,3]dioxolyl, etc.), etc.;

(c) unsaturated condensed 7 to 12-membered heterocyclic rings containing 1 to 5 nitrogen atoms, for example, decahydroquinolyl, indolyl, dihydroindolyl (e.g., 2,3-dihydroindolyl, etc.), isoindolyl, indolizinyl, benzimidazolyl, dihydrobenzimidazolyl (e.g., 2,3-dihydro-1H-benzo[d]imidazolyl, etc.), quinolyl, dihydroquinolyl (e.g. 1,4-dihydroquinolyl, 1,2-dihydroquinolyl, etc.), tetrahydroquinolyl (1,2,3,4-tetrahydroquinolyl, etc.), isoquinolyl, dihydroisoquinolyl (e.g., 3,4-dihydro-1H-isoquinolyl, 1,2-dihydroisoquinolyl, etc.), tetrahydroisoquinolyl (e.g., 1,2,3,4-tetrahydro-1H-isoquinolyl, 5,6,7,8-tetrahydroisoquinolyl, etc.), carbostyril, dihydrocarbostyril (e.g., 3,4-dihydrocarbostyril, etc.), indazolyl, benzotriazolyl (e.g. benzo[d][1,2,3]triazolyl, etc.), tetrazolopyridyl, tetrazolopyridazinyl (e.g., tetrazolo[1,5-b]pyridazinyl, etc.), dihydrotriazolopyridazinyl, imidazopyridyl (e.g., imidazo[1,2-a]pyridyl, imidazo[4,5-c]pyridyl, imidazo[1,5-a]pyridyl, etc.), naphthyridinyl, cinnolinyl, quinoxalinyl, quinazolinyl, pyrazolopyridyl (e.g., pyrazolo[2,3-a]pyridyl, etc.), tetrahydropyridoindolyl (e.g., 2,3,4,9-tetrahydro-1H-pyrido[3,4-b]indolyl, etc.), etc.;

(d) unsaturated 3 to 8-membered, preferably 5 or 6-membered heteromonocyclic rings containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.), etc.;

(e) unsaturated condensed 7 to 12-membered heterocyclic rings containing 1 to 2 oxygen atoms and 1 to 3 nitrogen atoms, for example, benzoxazolyl, benzoxadiazolyl, benzisoxazolyl, dihydrobenzoxazinyl (e.g., 2,3-dihydrobenz-1,4-oxazinyl, etc.), furopyridyl (e.g., furo[2,3-c]pyridyl, 6,7-dihydrofuro[2,3-c]pyridyl, furo[3,2-c]pyridyl, 4,5-dihydrofuro[3,2-c]pyridyl, furo[2,3-b]pyridyl, 6,7-dihydrofuro[2,3-b]pyridyl, etc.), furopyrrolyl (e.g., furo[3,2-b]pyrrolyl etc.), etc.;

(f) unsaturated 3 to 8-membered, preferably 5 or 6-membered heteromonocyclic rings containing 1 to 2 sulfur atoms and 1 to 3 nitrogen atoms, for example, thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl, etc.), isothiazolyl , etc.;

(g) unsaturated 3 to 8-membered, preferably 5 or 6-membered heteromonocyclic rings containing a sulfur atom, for example, thienyl, etc.;

(h) unsaturated condensed 7 to 12-membered heterocyclic rings containing 1 to 3 sulfur atoms, for example, benzothienyl (e.g. benzo[b]thienyl, etc.);

(i) unsaturated condensed 7 to 12-membered heterocyclic groups containing 1 to 2 sulfur atoms and 1 to 3 nitrogen atoms, for example, benzothiazolyl, benzothiadiazolyl, thienopyridyl (e.g., thieno[2,3-c]pyridyl, 6,7-dihydrothieno[2,3-c]pyridyl, thieno[3,2-c]pyridyl, 4,5-dihydrothieno[3,2-c]pyridyl, thieno[2,3-b]pyridyl, 6,7-dihydrothieno[2,3-b]pyridyl, 4,5,6,7-tetrahydrothieno[2,3-c]pyridyl, etc.), imidazothiazolyl (e.g., imidazo[2,1-b]thiazolyl, etc.), dihydroimidazothiazolyl (e.g., 2,3-dihydroimidazo[2,1-b]thiazolyl, etc.), thienopyrazinyl (e.g., thieno[2,3-b]pyrazinyl, etc.), etc.; and the like.

The term "heterocycloalkylene" refers to the bivalent group derived from heterocyclyl (including substituted heterocyclyl).

Examples of heterocycloalkylene which contains one or more nitrogen atoms and optionally contains another hetero atom include the following (j) to (m):

(j) 3 to 8-membered, preferably 5 to 7-membered, heterocycloalkylene containing 1 to 4 nitrogen atoms, for example, azetidinediyl, pyrrolidinediyl, imidazolidinediyl, piperidinediyl, pyrazolidinediyl, piperazinediyl, azepanediyl, 1,4-diazepandiyl, etc.;

(k) 3 to 8-membered, preferably 5 or 6-membered heterocycloalkylene containing 1 to 2 oxygen atoms and 1 to 3 nitrogen atoms, for example, morpholinediyl, oxadiazepanediyl, etc (l) 3 to 8-membered, preferably 5 or 6-heterocycloalkylene containing 1 to 2 sulfur atoms and 1 to 3 nitrogen atoms, for example, thiazolidinediyl, etc.; and the like.

Examples of "aryl" include monocyclic or polycyclic aryl, such as phenyl and naphthyl.

Examples of the "arylene" include monocyclic or polycyclic arylene such as phenylene, naphthalenediyl, anthracenediyl, indenediyl, phenanthrenediyl, azulenediyl, heptalenediyl etc., in which preferred are $(C_{6-14})$arylene such as phenylene, naphthalenediyl, etc.

Table 1 lists abbreviations used throughout the specification.

TABLE 1

List of Abbreviation

| Abbreviation | Description |
|---|---|
| AcOEt | ethyl acetate |
| BINAP | 2,2'-bis(diphenylphosphino)-1,1'-binaphthyl |
| DABCO | 1,4-diazabicyclo[2.2.2]octane |
| DBN | 1,5-diazabicyclo [4.3.0]nonene-5 |
| DBU | 1,8-diazabicyclo[5.4.0]undecene-7 |
| DCC | dicyclohexylcarbodiimide |
| DEAD | diethyl azodicarboxylate |
| DEPC | diethyl pyrocarbonate |
| DIBAH | diisobutylaluminium hydride |
| DIPEA | N,N-diisopropylethylamine |
| DMAP | 4-(N,N-dimethylamino)pyridine |
| DMF | N,N-dimethylformamide |
| DMSO | dimethyl sulfoxide |
| ELISA | enzyme-linked immunosorbent assay |
| Et$_2$O | diethyl ether |
| Et$_3$N | triethylamine |
| EtOH | ethyl alcohol |
| HOBT | 1-hydroxybenzotriazole |
| MeOH | methyl alcohol |
| MS-3A | molecular sieve 3A |
| MS-4A | molecular sieve 4A |
| NaBH(OAc)$_3$ | sodium triacetoxyborohydride |
| n-BuLi | n-butyllithium |
| NMP | N-methylpyrrolidone |
| Pd(OAc)$_2$ | palladium(II) acetate |
| Pd(PPh$_3$)$_4$ | tetrakis(triphenylphosphine)palladium(0) |
| Pd/C | palladium on carbon |

TABLE 1-continued

List of Abbreviation

| Abbreviation | Description |
|---|---|
| Pd$_2$(dba)$_3$ | Tris(dibenzylideneacetone)dipalladium(0) |
| PPTS | pyridinium p-toluenesulfonate |
| PSA | prostatic specific antigen |
| Pt/C | platinum on carbon |
| TBAF | tetra-n-butylammonium fluoride |
| TBDMSCl | tert-butyldimethylsilyl chloride |
| TFA | trifluoroacetic acid |
| THF | tetrahydrofuran |
| WSC | 1-(3-dimethylaminopropyl)-3-ethylcarbodiimide |

Methods for producing compounds according to the present invention will be described below.

The compound of the present invention represented by the general formula (1) or its salt can be readily produced by persons skilled in the art using technical knowledge, based on the EXAMPLES of the present specification. For example, the compound (1) or its salt can be produced according to the processes shown in the following reaction formulae.

[Reaction formula 1]

[Formula 2]

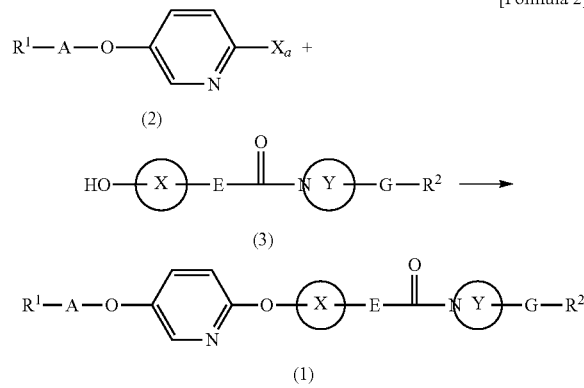

wherein R$^1$, R$^2$, Ring X, Ring Y, A, E and G are the same as described above, and Xa is a leaving group.

Examples of the leaving group for Xa include halogen (e.g., fluorine, chlorine, bromine, iodine), optionally halogenated C1-6 alkylsulfonyloxy (e.g., methanesulfonyloxy, ethanesulfonyloxy, trichloromethanesulfonyloxy, trifluoromethanesulfonyloxy, etc.), arylsulfonyloxy (e.g., C6-10 arylsulfonyloxy (e.g., phenylsulfonyloxy, naphthylsulfonyloxy) optionally substituted by 1 to 3 substituents selected from the group of C1-6 alkyl group (e.g., methyl, ethyl, etc.), C1-6 alkoxy (e.g., methoxy, ethoxy, etc.) and a nitro group), and the like. Specific examples include phenylsulfonyloxy, m-nitrophenylsulfonyloxy, p-toluenesulfonyloxy and the like, acyloxy (e.g., trichloroacetoxy, trifluoroacetoxy and the like) and the like.

The reaction of the compound (2) with the compound (3) is carried out by the known palladium- and copper-catalyzed cross-coupling, etc. For example, the reaction can be carried out in a solvent (e.g., toluene, THF, DMF, NMP and DMSO), in the presence of transition metal compound (e.g., Pd(OAc)$_2$, Pd$_2$(dba)$_3$ and copper iodide), a basic compound (e.g., sodium tert-butoxide, K$_3$PO$_4$ and Cs$_2$CO$_3$), and if necessary a phosphine (e.g., xantphos, BINAP, tetrafluoroborate, N,N'-dimethylethylenediamine, and L-proline).

The reaction is carried out typically at −30 to 200° C., and preferably at about 0 to 180° C., and is generally completed in about 5 minutes to 80 hours.

The compound (2) and the compound (3) can be easily obtained as a commercial product, and also can be produced according to a method known per se or similar manner to EXAMPLES as mentioned below.

[Reaction Formula 2]

[Formula 3]

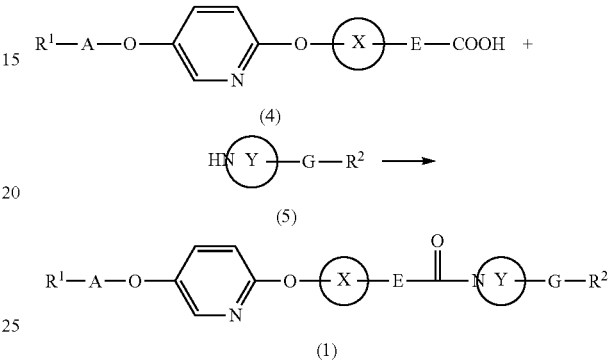

wherein R$^1$, R$^2$, Ring X, Ring Y, A, E and G are the same as described above.

Known reactions for producing an amide bond may be applied to the reaction of the compound (4) with the compound (5). Specific methods thereof include: (i) a mixed acid anhydride method, in which Carboxylic Acid (4) is reacted with an alkyl halocarboxylate to form a mixed acid anhydride, which is then reacted with Amine (5); (ii) an active ester method, in which Carboxylic Acid (4) is converted to an activated ester such as a phenyl ester, p-nitrophenyl ester, N-hydroxysuccinimide ester, or 1-hydroxybenzotriazole ester, or to an activated amide with benzoxazoline-2-thione, and the activated ester or amide is reacted with Amine (5); (iii) a carbodiimide method, in which Carboxylic Acid (4) is subjected to a condensation reaction with Amine (5) in the presence of an activating agent such as DCC, WSC, or carbonyldiimidazole; and (iv) other methods, for example, a method in which Carboxylic Acid (4) is converted to a carboxylic anhydride using a dehydrating agent such as acetic anhydride, and the carboxylic anhydride is reacted with Amine (5), a method in which an ester of Carboxylic Acid (4) with a lower (C1-6) alcohol is reacted with Amine (5) at a high pressure and a high temperature, and a method in which an acid halide of Carboxylic Acid (4), i.e., a carboxylic acid halide, is reacted with Amine (5).

Generally, the mixed acid anhydride method (i) is performed in a solvent, in the presence or absence of a basic compound. Any solvents used for conventional mixed acid anhydride methods are usable. Specific examples of usable solvents include halogenated hydrocarbons such as chloroform, dichloromethane, dichloroethane, and carbon tetrachloride; aromatic hydrocarbons such as benzene, toluene, and xylene; ethers such as Et$_2$O, diisopropyl ether, THF, and dimethoxyethane; esters such as methyl acetate, AcOEt, and isopropyl acetate; aprotic polar solvents such as DMF, DMSO, and hexamethylphosphoric triamide; and mixtures thereof.

Examples of usable basic compounds include organic bases such as Et$_3$N, trimethylamine, pyridine, dimethylaniline, DIPEA, dimethylaminopyridine, N-methylmorpholine, DBN, DBU and DABCO; inorganic bases, for example, carbonates such as sodium carbonate, potassium carbonate, sodium hydrogencarbonate, and potassium hydrogencarbonate; metal hydroxides such as sodium hydroxide, potassium hydroxide, and calcium hydroxide; potassium hydride; sodium hydride; potassium; sodium; sodium amide; and metal alcoholates such as sodium methoxide and sodium ethoxide.

Examples of alkyl halocarboxylates usable in the mixed acid anhydride method include methyl chloroformate, methyl bromoformate, ethyl chloroformate, ethyl bromoformate, and isobutyl chloroformate. In this method, Carboxylic Acid (4), an alkyl halocarboxylate, and Amine (5) are preferably used in equimolar amounts, but each of the alkyl halocarboxylate and Carboxylic Acid (4) can also be used in an amount of about 1 to about 1.5 moles per mole of Amine (5).

The reaction is typically performed at about −20 to about 150° C., and preferably at about 10 to about 50° C., typically for about 5 minutes to about 30 hours.

Method (iii), in which a condensation reaction is performed in the presence of an activating agent, can be performed in a suitable solvent in the presence or absence of a basic compound. Solvents and basic compounds usable in this method include those mentioned hereinafter as solvents and basic compounds usable in the method in which a carboxylic acid halide is reacted with Amine (5) mentioned above as one of the other methods (iv). A suitable amount of activating agent is typically at least 1 mole, and preferably 1 to 5 moles per mole of Compound (5). When WSC is used as an activating agent, the addition of 1-hydroxybenzotriazol to the reaction system allows the reaction to proceed advantageously. The reaction is typically performed at about −20 to about 180° C., and preferably at about 0 to about 150° C., and is typically completed in about 5 minutes to about 90 hours.

When the method in which a carboxylic acid halide is reacted with Amine (5), mentioned above as one of the other methods (iv), is employed, the reaction is performed in the presence of a basic compound in a suitable solvent.

Examples of usable basic compounds include a wide variety of known basic compounds, such as those for use in the method (i).

In addition to those usable in the mixed acid anhydride method, usable solvents include alcohols such as MeOH, EtOH, 2-propanol, propanol, butanol, 3-methoxy-1-butanol, ethyl cellosolve, and methyl cellosolve; acetonitrile; pyridine; acetone; and water.

The ratio of the carboxylic acid halide to Amine (5) is not limited, and can be suitably selected from a wide range. It is typically suitable to use, for example, at least about 1 mole, and preferably about 1 to about 5 moles of the carboxylic acid halide per mole of Amine (5).

The reaction is typically performed at about −20 to about 180° C., and preferably at about 0 to about 150° C., and is typically completed in about 5 minutes to about 30 hours.

The amide bond formation reaction shown in Reaction Formula 2 can also be performed by reacting Carboxylic Acid (4) with Amine (5) in the presence of a phosphorus compound serving as a condensing agent, such as triphenylphosphine, diphenylphosphinyl chloride, phenyl-N-phenylphosphoramide chloridate, diethyl chlorophosphate, diethyl cyanophosphate, diphenylphosphoric azide, bis(2-oxo-3-oxazolidinyl) phosphinic chloride, or the like.

The reaction is performed in the presence of a solvent and a basic compound usable for the method in which a carboxylic acid halide is reacted with Amine (5), typically at about −20 to about 150° C., and preferably at about 0 to about 100° C., and is typically completed in about 5 minutes to about 30 hours. It is suitable to use each of the condensing agent and Carboxylic Acid (4) in amounts of at least about 1 mole, and preferably about 1 to about 2 moles, per mole of Amine (5).

The compound (4) and the compound (5) can be easily obtained as a commercial product, and also can be produced according to a method known per se or similar manner to EXAMPLES as mentioned below.

[Reaction formula 3]

[Formula 4]

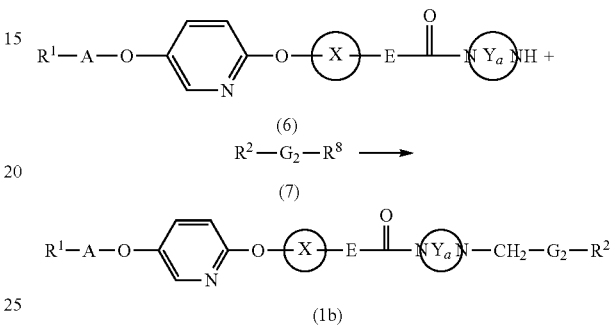

wherein $R^1$, $R^2$, Ring X, A, E and $G^2$ are the same as described above, $R^8$ is —$CH_2$-Xb or formyl, Xb is a leaving group, Ring Ya is optionally substituted heterocycloalkylene containing at least two nitrogen atoms.

Examples of the leaving group for Xb include those recited for a leaving group Xa.

Examples of the "optionally substituted heterocycloalkylene containing at least two nitrogen atoms" include imidazolidinediyl, pyrazolidinediyl, piperazinediyl, 1,4-diazepandiyl, oxadiazepanediyl, each of which is optionally substituted with one or more lower alkyl, and the like.

(i) When $R^8$ is formyl, the reaction between the compound (6) and the compound (7) is performed, for example, in a suitable solvent or without using any solvent, in the presence of a reducing agent.

Examples of usable solvents include water; lower (C1-6) alcohols such as MeOH, EtOH, isopropanol, butanol, tert-butanol, and ethylene glycol; aliphatic acids such as formic acid, and acetic acid; ethers such as $Et_2O$, THF, dioxane, monoglyme, and diglyme; aromatic hydrocarbons such as benzene, toluene, and xylene; halogenated hydrocarbons such as dichloromethane, dichloroethane, chloroform, and carbon tetrachloride; acetonitrile; and mixtures thereof.

Examples of reducing agents include aliphatic acids such as formic acid; aliphatic acid alkali metal salts such as sodium formate; hydride reducing agents such as sodium borohydride, sodium cyanoborohydride, $NaBH(OAc)_3$, sodium trimethoxyborohydride, lithium aluminium hydride, and mixtures thereof, or mixtures of aliphatic acids or aliphatic acid alkali metal salts with hydride reducing agents; and catalytic hydrogenation reducing agents such as palladium black, palladium on carbon, platinum oxide, platinum black, and Raney nickel.

When an aliphatic acid such as formic acid, or an aliphatic acid alkali metal salt such as sodium formate is used as a reducing agent, a suitable reaction temperature is typically about room temperature to about 200° C., and preferably about 50 to about 150° C. The reaction is typically completed in about 10 minutes to about 10 hours. Preferably, the aliphatic acid or aliphatic acid alkali metal salt is used in large excess relative to the compound (6).

When a hydride reducing agent is used, a suitable reaction temperature is typically about −80 to about 100° C., and preferably about −80 to about 70° C. The reaction is typically completed in about 30 minutes to about 100 hours. The hydride reducing agent is typically used in an amount of about 1 to about 20 moles, and preferably about 1 to about 10 moles, per mole of the compound of (6). Particularly when lithium aluminium hydride is used as a hydride reducing agent, it is preferable to use as a solvent an ether such as Et$_2$O, THF, dioxane, monoglyme, or diglyme; or an aromatic hydrocarbon such as benzene, toluene, or xylene. To the reaction system may be added an amine such as trimethylamine, Et$_3$N, or DIPEA; or a molecular sieve such as MS-3A or MS-4A.

When a catalytic hydrogenation reducing agent is used, the reaction is typically performed at about −30 to about 100° C., and preferably at about 0 to about 60° C., in a hydrogen atmosphere at typically about atmospheric pressure to about 20 atm, and preferably at about atmospheric pressure to about 10 atm, or in the presence of a hydrogen donor such as formic acid, ammonium formate, cyclohexene, or hydrazine hydrate. The reaction is typically completed in about 1 to about 12 hours. The catalytic hydrogenation reducing agent is typically used in an amount of about 0.1 to about 40 wt %, and preferably about 1 to about 20 wt %, based on the compound (6).

In the reaction of the compound of (6) and the compound (7), the compound (7) is typically used in an amount of at least 1 mole, and preferably 1 to 5 moles, per mole of the compound (7).

The compound (6) may also be a hydrated compound wherein a water molecule is attached to a carbonyl group.

(ii) When R$^8$ is —CH$_2$-Xb, the reaction of the compound (6) with the compound (7) can be performed in a general inert solvent or without using any solvent, in the presence or absence of a basic compound and/or catalyst.

Examples of inert solvents include water; ethers such as dioxane, THF, Et$_2$O, diethylene glycol dimethyl ether, and ethylene glycol dimethyl ether; aromatic hydrocarbons such as benzene, toluene, and xylene; halogenated hydrocarbons such as dichloromethane, dichloroethane, chloroform, and carbon tetrachloride; lower (C1-6) alcohols such as MeOH, EtOH, and isopropanol; ketones such as acetone and methyl ethyl ketone; polar solvents such as DMF, DMSO, hexamethylphosphoric triamide, and acetonitrile; and mixtures thereof.

A wide variety of known basic compounds can be used as the basic compound. Examples of such basic compounds include inorganic bases, for example, alkali metal hydroxides such as sodium hydroxide, potassium hydroxide, cesium hydroxide, and lithium hydroxide; alkali metal carbonates such as sodium carbonate, potassium carbonate, cesium carbonate, lithium carbonate, lithium hydrogencarbonate, sodium hydrogencarbonate, and potassium hydrogencarbonate; alkali metals such as sodium and potassium; sodium amide; sodium hydride; and potassium hydride; and organic bases, for example, alkali metal alcoholates such as sodium methoxide, sodium ethoxide, potassium methoxide, and potassium ethoxide; Et$_3$N; DIPEA; tripropylamine; pyridine; quinoline; DBN; DBU; and DABCO. These basic compounds can be used singly or in a combination of two or more.

Examples of the catalyst include palladium compounds such as palladium acetate, bis(tributyltin)/bis(dibenzylideneacetone)palladium, copper iodide/2,2'-bipyridyl, bis (dibenzylideneacetone)palladium, copper iodide/bis(triphenylphosphine)palladium dichloride, tris(dibenzylideneacetone)dipalladium, R-tris(dibenzylideneacetone)-dipalladium, S-tris(dibenzylideneacetone)dipalladium, palladium(II) acetate, [1,1'-bis(diphenylphosphino)-ferrocene]dichloropalladium (II), and Pd(PPh$_3$)$_4$.

Additives (ligands etc.) can be used together with the catalyst. Examples of the additive include compounds such as BINAP, and 2,2-bis(diphenylimidazolidinyliden), xanthene compounds such as 4,5-bis(diphenylphosphino)-9,9-dimethylxanthene, and borates such as tri-tert-butylphosphine tetrafluoroborate, and a mixture thereof.

The above reaction may be performed by adding to the reaction system, as required, an alkali metal iodide serving as a reaction accelerator, such as potassium iodide or sodium iodide.

The compound (6) is typically used in an amount of at least 0.5 moles, and preferably about 0.5 to about 10 moles, per mole of the compound (6).

The amount of basic compound is typically 0.5 to 10 moles, and preferably 0.5 to 6 moles, per mole of the compound (6).

The catalyst is appropriately used in a typical catalytic amount, preferably 0.0001 to 1 moles, and more preferably 0.001 to 0.5 moles, per mole of the compound (6).

The reaction is typically performed at a temperature of 0 to 250° C., and preferably 0 to 200° C., and is typically completed in about 1 to about 80 hours.

The compound (6) and the compound (7) can be easily obtained as a commercial product, and also can be produced according to a method known per se or similar manner to EXAMPLES as mentioned below.

[Reaction formula 4]

[Formula 5]

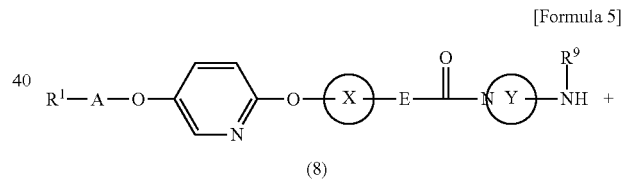

(8)

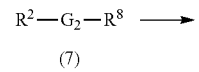

(7)

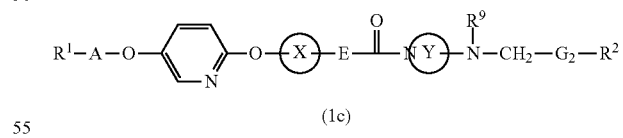

(1c)

wherein R$^1$, R$^2$, R$^8$, Ring X, Ring Y, A, E and G$_2$ are the same as described above, R$^9$ is hydrogen or lower alkyl.

The reaction of the compound (8) with the compound (7) can be performed under the same reaction conditions as those for the reaction of the compound (6) with the compound (7) shown in Reaction Formula 3 above.

The compound (8) can be easily obtained as a commercial product, and also can be produced according to a method known per se or similar manner to EXAMPLES as mentioned below.

[Reaction Formula 5]

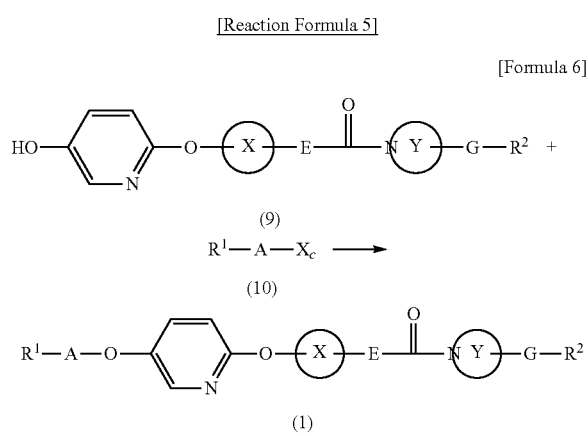

wherein $R^1$, $R^2$, Ring X, Ring Y, A, E and G are the same as described above, Xc is hydroxy or a leaving group.

Examples of the leaving group for Xc include those recited for leaving group Xa. (i) When Xc is leaving group, the reaction of the compound (9) with the compound (10) is carried out in an appropriate solvent or with no solvent in the presence or absence of a basic compound.

Examples of the inert solvent used include aromatic hydrocarbons such as benzene, toluene, and xylene, ethers such as $Et_2O$, THF, dioxane, monoglyme, and diglyme, halogenated hydrocarbons such as dichloromethane, dichloroethane, chloroform, and carbon tetrachloride, lower alcohols such as MeOH, EtOH, 2-propanol, butanol, tert-butanol, and ethylene glycol, fatty acids such as acetic acid, esters such as AcOEt and methyl acetate, ketones such as acetone and methyl ethyl ketone, acetonitrile, pyridine, DMSO, DMF, NMP, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, sodium hydride, potassium hydride, potassium, sodium, sodium amide, metal alcoholates such as sodium methoxide, sodium ethoxide, and sodium n-butoxide, and organic bases such as pyridine, imidazole, DIPEA, dimethylaminopyridine, $Et_3N$, trimethylamine, dimethylaniline, N-methylmorpholine, DBN, DBU, and DABCO, and a mixture thereof.

When the reaction is carried out in the presence of a basic compound, the basic compound is used in an amount typically equimolar to the compound (9), and preferably 1 to 10 times of the compound (9) on a molar basis The compound (10) is used in an amount typically at least equimolar to the compound (9), and preferably 1 to 10 times of the compound (9) on a molar basis.

The reaction is carried out typically at −30 to 200° C., and preferably at about 0 to 180° C., and is generally completed in about 5 minutes to 80 hours.

To this reaction system, an alkali metal halide such as sodium iodide or potassium iodide may be added, and a phase-transfer catalyst may be added.

Examples of the phase-transfer catalyst include quaternary ammonium salts substituted with a group selected from the group consisting of a linear or branched alkyl group having 1 to 18 carbon atoms, a phenyl alkyl group of which alkyl moiety is a linear or branched alkyl group having 1 to 6 carbon atoms and a phenyl group, such as tetrabutylammonium chloride, tetrabutylammonium bromide, tetrabutylammonium fluoride, tetrabutylammonium iodide, tetrabutylammonium hydroxide, tetrabutylammonium hydrogensulfite, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride, tetramethylammonium chloride; phosphonium salts substituted with a linear or branched alkyl group having 1 to 18 carbon atoms such as tetrabutylphosphonium chloride; and pyridinium salts substituted with a linear or branched alkyl group having 1 to 18 carbon atoms such as 1-dodecanylpyridinium chloride. These phase-transfer catalysts are used singly or in a combination of two or more.

Typically the phase-transfer catalyst is used in an amount of 0.1 to 1 times of the compound (9), and preferably 0.1 to 0.5 times of the compound (9). (ii) When Xc is hydroxy, the reaction of the compound (9) with the compound (10) is carried out in an appropriate solvent in the presence of a condensation agent.

Specific examples of the solvent include halogenated hydrocarbons such as chloroform, dichloromethane, dichloroethane, and carbon tetrachloride, aromatic hydrocarbons such as benzene, toluene and xylene, ethers such as $Et_2O$, diisopropyl ether, THF, and dimethoxyethane, esters such as methyl acetate, AcOEt, and isopropyl acetate, and aprotic polar solvents such as DMF, DMSO, and hexamethylphosphoric acid triamide, and a mixture thereof.

Examples of the condensation agent used include a mixture of an azocarboxylate (such as diethyl azocarboxylate) with a phosphorus compound (such as triphenylphosphine).

The condensation agent is appropriately used in an amount typically at least equimolar to the compound (9), and preferably 1 to 2 times of the compound (9) on a molar basis.

The compound (9) is appropriately used in an amount typically at least equimolar to the compound (9), and preferably 1 to 2 times of the compound (9) on a molar basis.

The above described reaction favorably proceeds typically at 0 to 200° C., preferably at around 0 to 150° C. and is, in general, completed in around 1 to 10 hours.

The compound (9) and the compound (10) can be easily obtained as a commercial product, and also can be produced according to a method known per se or similar manner to EXAMPLES as mentioned below.

The compounds obtained by the above Processes 1 to 5 can be successively prepared by a conventional method within the scope of the compound (1).

In addition, compounds in the form in which a solvate (for example, a hydrate, ethanolate, etc.) was added to the starting material compounds and object compounds shown in each of the reaction formulae are included in each of the formulae.

The compound (1) according to the present invention includes stereoisomers and optical isomers.

The starting material compounds and object compounds represented by each of the reaction formulae can be used in an appropriate salt form.

Each of the object compounds obtained according to the above reaction formulae can be isolated and purified from the reaction mixture by, for example, after cooling the reaction mixture, performing an isolation procedure such as filtration, concentration, extraction, etc., to separate a crude reaction product, and then subjecting the crude reaction product to a general purification procedure such as column chromatography, recrystallization, etc.

Among the compounds of the present invention, those having a basic group or groups can easily form salts with common pharmaceutically acceptable acids. Examples of such acids include hydrochloric acid, hydrobromic acid, nitric acid, sulfuric acid, phosphoric acid and other inorganic acids, methansulfonic acid, p-toluenesulfonic acid, acetic acid, citric acid, tartaric acid, maleic acid, fumaric acid, malic acid, lactic acid and other organic acids, etc.

Among the compounds of the present invention, those having an acidic group or groups can easily form salts by reacting with pharmaceutically acceptable basic compounds. Examples of such basic compounds include sodium hydroxide, potassium hydroxide, calcium hydroxide, sodium carbonate, potassium carbonate, sodium hydrogencarbonate, potassium hydrogencarbonate, etc.

In the compound of the present invention, one or more atoms can be substituted with one or more isotopic atoms. Examples of the isotopic atoms include deuterium ($^2$H), tritium ($^3$H), $^{13}$C, $^{14}$N, $^{18}$O, etc.

The following is an explanation of pharmaceutical preparations comprising the compound of the present invention as an active ingredient. Such pharmaceutical preparations are obtained by formulating the compound of the present invention into general pharmaceutical preparations, using typically employed diluents or excipients such as fillers, extenders, binders, wetting agents, disintegrants, surfactants, lubricants, etc.

The form of such pharmaceutical preparations can be selected from various forms according to the purpose of therapy. Typical examples include tablets, pills, powders, solutions, suspensions, emulsions, granules, capsules, suppositories, injections (solutions, suspensions, etc.) and the like.

To form tablets, any of various known carriers can be used, including, for example, lactose, white sugar, sodium chloride, glucose, urea, starch, calcium carbonate, kaolin, crystalline cellulose and other excipients; water, EtOH, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminaran powder, sodium hydrogencarbonate, calcium carbonate, aliphatic acid esters of polyoxyethylenesorbitan, sodium laurylsulfate, stearic acid monoglyceride, starch, lactose and other disintegrants; white sugar, stearin, cacao butter, hydrogenated oils and other disintegration inhibitors; quaternary ammonium base, sodium lauryl sulfate and other absorption promoters; glycerin, starch and other wetting agents; starch, lactose, kaolin, bentonite, colloidal silicic acid and other adsorbents; purified talc, stearates, boric acid powder, polyethylene glycol and other lubricants; etc.

Such tablets may be coated with general coating materials as required, to prepare, for example, sugar-coated tablets, gelatin-coated tablets, enteric-coated tablets, film-coated tablets, double- or multi-layered tablets, etc. To form pills, any of various known carriers can be used, including, for example, glucose, lactose, starch, cacao butter, hydrogenated vegetable oils, kaolin, talc and other excipients; gum arabic powder, tragacanth powder, gelatin, EtOH and other binders; laminaran, agar and other disintegrants; etc.

To form suppositories, any of various known carriers can be used, including, for example, polyethylene glycol, cacao butter, higher alcohols, esters of higher alcohols, gelatin, semisynthetic glycerides, etc.

To form an injection, a solution, emulsion or suspension is sterilized and preferably made isotonic with blood. Any of various known widely used diluents can be employed to prepare the solution, emulsion or suspension. Examples of such diluents include water, EtOH, propylene glycol, ethoxylated isostearyl alcohol, polyoxylated isostearyl alcohol, aliphatic acid esters of polyoxyethylene sorbitan, etc. In this case, the pharmaceutical preparation may contain sodium chloride, glucose or glycerin in an amount sufficient to prepare an isotonic solution, and may contain general solubilizers, buffers, analgesic agents, etc., and further, if necessary, coloring agents, preservatives, flavors, sweetening agents, etc., and/or other medicines.

The proportion of the compound of the present invention in the pharmaceutical preparation is not limited and can be suitably selected from a wide range. It is typically preferable that the pharmaceutical preparation contain the compound of the present invention in a proportion of 1 to 70 wt. %.

The route of administration of the pharmaceutical preparation according to the present invention is not limited, and the preparation can be administered by a route suitable for the form of the preparation, the patient's age and sex, the conditions of the disease, and other conditions.

For example, tablets, pills, solutions, suspensions, emulsions, granules and capsules are administered orally.

Injections are intravenously administered singly or as mixed with general injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation is suitably selected according to the method of use, the patient's age and sex, the severity of the disease, and other conditions, and is typically about 0.001 to about 100 mg/kg body weight/day, and preferably 0.001 to 50 mg/kg body weight/day, in single or divided doses.

EXAMPLES

Manufacturing examples of compounds used in the invention are shown below, being followed by the Pharmacological Test results of these compounds.

Reference Example 1

To a 1,2-dichloroethane (15 mL) solution of 4-(2-{[tert-butyl(dimethyl)silyl]-oxy}ethyl)benzaldehyde (0.70 g) and tert-butyl piperazine-1-carboxylate (0.52 g) was added NaBH(OAc)$_3$ (0.83 g) at 0° C. The resultant mixture was stirred at room temperature for 66 hours. To the reaction mixture was added saturated aqueous NaHCO$_3$, and extracted with CH$_2$Cl$_2$. The organic layer was washed with saturated aqueous NaCl, dried over anhydrous MgSO$_4$, and concentrated under reduced pressure. The residue was purified by silica gel column chromatography (n-hexane/AcOEt=9/1 to 2/1) to afford tert-butyl 4-[4-(2-{[tert-butyl(dimethyl)silyl]oxy}ethyl)benzyl]piperazine-1-carboxylate (0.96 g) as a colorless oil.

$^1$H-NMR (CDCl$_3$) δ: −0.02 (6H, s), 0.86 (9H, s), 1.45 (9H, s), 2.36 (4H, t, J=4.9 Hz), 2.80 (2H, t, J=6.9 Hz), 3.41 (4H, t, J=4.9 Hz), 3.47 (2H, s), 3.79 (2H, t, J=6.9 Hz), 7.15 (2H, d, J=7.9 Hz), 7.22 (2H, d, J=7.9 Hz).

The following compounds were produced in the same manner as in Reference Example 1 using appropriate starting materials.

Reference Example 2 tert-Butyl 4-(4-bromo-2-fluorobenzyl)piperazine-1-carboxylate

¹H-NMR (CDCl₃) δ: 1.45 (9H, s), 2.39-2.41 (4H, m), 3.41-3.43 (4H, m), 3.53 (2H, s), 7.20-7.28 (3H, m).

Reference Example 3 tert-Butyl 4-{[4-(2-hydroxyethyl)phenyl]amino}piperidine-1-carboxylate

¹H-NMR (CDCl₃) δ: 1.30-1.45 (2H, m), 1.46 (9H, s), 1.80-1.90 (1H, m), 1.98-2.05 (2H, m), 2.92 (2H, t, J=11.9 Hz), 2.95-3.08 (1H, m), 3.35-3.51 (2H, m), 3.75-3.91 (3H, m), 3.95-4.11 (2H, m), 6.52-6.60 (2H, m), 7.00-7.08 (2H, m).

Reference Example 4 tert-Butyl 4-[4-(3-hydroxypropyl)benzyl]piperazine-1-carboxylate

¹H-NMR (CDCl₃) δ: 1.45 (9H, s), 1.65 (1H, brs), 1.86-1.93 (2H, m), 2.37 (4H, t, J=5.0 Hz), 2.70 (2H, t, J=7.7 Hz), 3.42 (4H, t, J=5.0 Hz), 3.47 (2H, s), 3.68 (2H, t, J=6.2 Hz), 7.15 (2H, d, J=8.1 Hz), 7.23 (2H, d, J=8.1 Hz).

Reference Example 5 tert-Butyl 4-(3-fluoro-4-hydroxybenzyl)piperazine-1-carboxylate

¹H-NMR (CDCl₃) δ: 1.45 (9H, s), 2.38-2.40 (4H, m), 3.43-3.45 (6H, m), 6.85-6.92 (2H, m), 7.02 (1H, d, J=11.7 Hz).

Reference Example 6 tert-Butyl 4-{4-[(E)-3-methoxyprop-1-en-1-yl]benzyl}piperazine-1-carboxylate

¹H-NMR (CDCl₃) δ: 1.45 (9H, s), 2.38 (4H, t, J=5.0 Hz), 3.39 (3H, s), 3.42 (4H, t, J=5.0 Hz), 3.49 (2H, s), 4.09 (2H, dd, J=6.1, 1.5 Hz), 6.27 (1H, dt, J=16.1, 6.1 Hz), 6.60 (1H, d, J=16.1 Hz), 7.26 (2H, d, J=8.3 Hz), 7.34 (2H, d, J=8.3 Hz).

Reference Example 7 tert-Butyl 4-{4-[2-(4-methylphenyl)-2-oxoethoxy]benzyl}piperazine-1-carboxylate

¹H-NMR (CDCl₃) δ: 1.45 (9H, s), 2.35 (4H, t, J=4.9 Hz), 2.43 (3H, s), 3.41 (4H, t, J=4.9 Hz), 3.43 (2H, s), 5.24 (2H, s), 6.87-6.90 (2H, m), 7.19-7.23 (2H, m), 7.28-7.31 (2H, m), 7.89-7.92 (2H, m).

Reference Example 8 tert-Butyl 4-(biphenyl-4-ylmethyl)piperazine-1-carboxylate

¹H-NMR (CDCl₃) or 1.46 (9H, s), 2.41-2.43 (4H, m), 3.44-3.45 (4H, m), 3.55 (2H, s), 7.31-7.47 (5H, m), 7.52-7.61 (4H, m).

Reference Example 9 tert-Butyl 4-[4-(4-chlorophenoxy)benzyl]piperazine-1-carboxylate

¹H-NMR (CDCl₃) δ: 1.46 (9H, s), 2.38-2.39 (4H, m), 3.42-3.43 (4H, m), 3.48 (2H, s), 6.92-6.95 (4H, m), 7.26-7.29 (4H, m).

Reference Example 10 tert-Butyl 4-{4-[4-(propan-2-yl)phenoxy]benzyl}piperazine-1-carboxylate

¹H-NMR (CDCl₃) δ: 1.25 (6H, d, J=6.8 Hz), 1.46 (9H, s), 2.36-2.40 (4H, m), 2.87-2.93 (1H, m), 3.42-3.43 (4H, m), 3.47 (2H, s), 6.94 (4H, dd, J=8.5, 2.2 Hz), 7.18 (2H, d, J=8.5 Hz), 7.25 (2H, d, J=9.3 Hz).

Reference Example 11

To a solution of (4-bromobenzyloxy)(tert-butyl)dimethylsilane (3.080 g) in THF (20 mL) were added Mg (0.288 g) and I₂ (cat) at room temperature under an Ar atmosphere. The mixture was heated at 50° C. for 1 hour, and then cooled to room temperature. To the mixture was added 1,2-epoxypropane (0.77 mL) at room temperature under an Ar atmosphere, and the mixture was stirred at room temperature for 14.5 hours, and then heated at 50° C. for 1 hour, and then cooled to room temperature. To the mixture was added saturated aqueous NH₄Cl, and the mixture was extracted with AcOEt. The organic layer was washed with saturated aqueous NaCl, dried over anhydrous Na₂SO₄, and concentrated under reduced pressure. The residue was purified by silica gel column chromatography (n-hexane/AcOEt=2/1) to afford 1-[4-({[tert-butyl(dimethyl)silyl]oxy}methyl)phenyl]propan-2-ol (1.485 g) as a colorless oil.

¹H-NMR (CDCl₃) δ: 0.10 (6H, s), 0.94 (9H, s), 1.25 (3H, d, J=6.1 Hz), 1.48 (1H, d, J=3.7 Hz), 2.67 (1H, dd, J=13.6, 8.1 Hz), 2.79 (1H, dd, J=13.6, 4.8 Hz), 3.99-4.03 (1H, m), 4.72 (2H, s), 7.18 (2H, d, J=8.3 Hz), 7.28 (2H, d, J=8.3 Hz).

The following compounds were produced in the same manner as in Reference Example 11 using appropriate starting materials.

Reference Example 12

2-[4-({[tert-Butyl(dimethyl)silyl]oxy}methyl)-2-methylphenyl]ethanol

¹H-NMR (CDCl₃) δ: 0.10 (6H, s), 0.94 (9H, s), 1.35 (1H, t, J=6.0 Hz), 2.33 (3H, s), 2.88 (2H, t, J=6.8 Hz), 3.80-3.85 (2H, m), 4.68 (2H, s), 7.09-7.14 (3H, m).

Reference Example 13

1-[4-(Diethoxymethyl)phenyl]propan-2-ol

¹H-NMR (CDCl₃) δ: 1.24 (6H, t, J=7.0 Hz), 1.25 (3H, d, J=6.1 Hz), 1.49 (1H, brs), 2.69 (1H, dd, J=13.6, 7.9 Hz), 2.79 (1H, dd, J=13.6, 4.6 Hz), 3.50-3.67 (4H, m), 4.02 (1H, brs), 5.48 (1H, s), 7.21 (2H, d, J=8.3 Hz), 7.42 (2H, d, J=8.3 Hz).

Reference Example 14

2-[4-({[tert-Butyl(dimethyl)silyl]oxy}methyl)-3-methylphenyl]ethanol

¹H-NMR (CDCl₃) δ: 0.10 (6H, s), 0.94 (9H, s), 1.35 (1H, t, J=6.1 Hz), 2.26 (3H, s), 2.83 (2H, t, J=6.5 Hz), 3.82-3.87 (2H, m), 4.68 (2H, s), 7.00 (1H, d, J=1.5 Hz), 7.05 (1H, dd, J=7.6, 1.5 Hz), 7.35 (1H, d, J=7.6 Hz).

Reference Example 15

To a THF (8 mL) solution of tert-butyl 4-[4-(2-{[tert-butyl (dimethyl)silyl]oxy}-ethyl)benzyl]piperazine-1-carboxylate (0.96 g) was added 1.0 M solution of TBAF in THF (2.32 mL) at 0° C. The resultant mixture was stirred at room temperature for 2.5 hours. After cooling to 0° C., the reaction mixture was diluted with AcOEt and water. The organic layer was washed with saturated aqueous NaCl, dried over anhydrous MgSO$_4$, and concentrated under reduced pressure. The residue was purified by silica gel column chromatography (CH$_2$Cl$_2$/MeOH=40/1) to afford tert-butyl 4-[4-(2-hydroxyethyl)benzyl]piperazine-1-carboxylate (0.55 g) as a colorless oil.

$^1$H-NMR (DMSO-d$_6$) δ: 1.38 (9H, s), 2.28 (4H, t, J=4.9 Hz), 2.69 (2H, t, J=6.9 Hz), 3.29 (4H, t, J=4.9 Hz), 3.42 (2H, s), 3.54-3.62 (2H, m), 4.60 (1H, t, J=5.3 Hz), 7.13-7.20 (4H, m).

The following compounds were produced in the same manner as in Reference Example 15 using appropriate starting materials.

Reference Example 16

{4-[2-(4-Methylphenoxy)propyl]phenyl}methanol $^1$H-NMR (CDCl$_3$) δ: 1.28 (3H, d, J=6.1 Hz), 1.56 (1H, t, J=6.0 Hz), 2.27 (3H, s), 2.81 (1H, dd, J=13.7, 6.6 Hz), 3.07 (1H, dd, J=13.7, 6.0 Hz), 4.47-4.55 (1H, m), 4.66 (2H, d, J=6.0 Hz), 6.79 (2H, dt, J=9.0, 2.4 Hz), 7.06 (2H, d, J=8.1 Hz), 7.23 (2H, d, J=8.1 Hz), 7.29 (2H, d, J=8.1 Hz).

Reference Example 17

{3-Methyl-4-[2-(4-methylphenoxy)ethyl] phenyl}methanol $^1$H-NMR (CDCl$_3$) δ: 1.55 (1H, t, J=5.9 Hz), 2.28 (3H, s), 2.38 (3H, s), 3.09 (2H, t, J=7.3 Hz), 4.11 (2H, t, J=7.3 Hz), 4.64 (2H, d, J=5.9 Hz), 6.79 (2H, dt, J=9.2, 2.6 Hz), 7.07 (2H, dt, J=9.2, 2.6 Hz), 7.15-7.23 (3H, m).

Reference Example 18

{3-Methyl-4-[(E)-3-(4-methylphenoxy)prop-1-en-1-yl]phenyl}methanol $^1$H-NMR (CDCl$_3$) δ: 1.61 (1H, brs), 2.29 (3H, s), 2.35 (3H, s), 4.65 (2H, d, J=5.6 Hz), 4.69 (2H, dd, J=5.8, 1.6 Hz), 6.30 (1H, dt, J=15.9, 5.8 Hz), 6.87 (2H, dt, J=9.2, 2.6 Hz), 6.92 (1H, d, J=15.9 Hz), 7.09 (2H, d, J=8.1 Hz), 7.16-7.17 (2H, m), 7.47 (1H, d, J=8.5 Hz).

Reference Example 19

{2-Methyl-4-[(E)-3-(4-methylphenoxy)prop-1-en-1-yl]phenyl}methanol $^1$H-NMR (CDCl$_3$) δ: 1.48 (1H, t, J=5.7 Hz), 2.29 (3H, s), 2.35 (3H, s), 4.67 (2H, dd, J=5.8, 1.5 Hz), 4.69 (2H, d, J=5.7 Hz), 6.41 (1H, dt, J=16.1, 5.8 Hz), 6.69 (1H, dt, J=16.1, 1.5 Hz), 6.86 (2H, dt, J=9.3, 2.6 Hz), 7.09 (2H, dd, J=8.7, 0.6 Hz), 7.23-7.25 (2H, m), 7.31 (1H, d, J=7.6 Hz).

Reference Example 20

To a THF (40 mL) solution of tert-butyl 4-[4-(2-hydroxyethyl)benzyl]piperazine-1-carboxylate (4.74 g) and p-cresol (1.76 g) were added triphenylphosphine (4.27 g) and 2.2 M solution of DEAD in toluene (7.40 mL) at 0° C. After stirring at room temperature for 85 hours, the solvent was removed under reduced pressure. The residue was purified by silica gel column chromatography (n-hexane/AcOEt=3/1 to 1/2), then the concentrated eluate was diluted with CH$_2$Cl$_2$, and washed with 5 M NaOH and saturated aqueous NaCl, dried over anhydrous MgSO$_4$, and concentrated under reduced pressure to give tert-butyl 4-{4-[2-(4-methylphenoxy)ethyl] benzyl}piperazine-1-carboxylate as a yellow solid (3.87 g).

$^1$H-NMR (CDCl$_3$) δ: 1.45 (9H, s), 2.26 (3H, s), 2.37 (4H, t, J=4.9 Hz), 3.07 (2H, t, J=6.9 Hz), 3.42 (4H, t, J=4.9 Hz), 3.48 (2H, s), 4.14 (2H, t, J=6.9 Hz), 6.79 (2H, d, J=8.2 Hz), 7.06 (2H, d, J=8.2 Hz), 7.20-7.27 (4H, m).

The following compounds were produced in the same manner as in Reference Example 20 using appropriate starting materials.

Reference Example 21 tert-Butyl 4-{4-[2-(4-methoxyphenoxy)ethyl] benzyl}piperazine-1-carboxylate $^1$H-NMR (CDCl$_3$) δ: 1.45 (9H, s), 2.37 (4H, t, J=4.9 Hz), 3.05 (2H, t, J=6.9 Hz), 3.42 (4H, t, J=4.9 Hz), 3.48 (2H, s), 3.76 (3H, s), 4.11 (2H, t, J=6.9 Hz), 6.79-6.86 (4H, m), 7.20-7.27 (4H, m).

Reference Example 22 tert-Butyl 4-(4-{2-[4-(propan-2-yl)phenoxy] ethyl}benzyl)piperazine-1-carboxylate $^1$H-NMR (CDCl$_3$) δ: 1.21 (6H, d, J=6.9 Hz), 1.45 (9H, s), 2.37 (4H, t, J=4.9 Hz), 2.85 (1H, septet, J=6.9 Hz), 3.06 (2H, t, J=6.9 Hz), 3.42 (4H, t, J=6.9 Hz), 3.48 (2H, s), 4.14 (2H, t, J=6.9 Hz), 6.81-6.85 (2H, m), 7.11-7.14 (2H, m), 7.20-7.26 (4H, m).

Reference Example 23 tert-Butyl 4-(4-{2-[4-(propan-2-yloxy)phenoxy] ethyl}benzyl)piperazine-1-carboxylate $^1$H-NMR (CDCl$_3$) δ: 1.29 (6H, d, J=5.9 Hz), 1.45 (9H, s), 2.38 (4H, t, J=4.9 Hz), 3.06 (2H, t, J=6.9 Hz), 3.42 (4H, t, J=4.9 Hz), 3.48 (2H, s), 4.14 (2H, t, J=6.9 Hz), 4.41 (1H, septet, J=5.9 Hz), 6.81 (4H, s), 7.19-7.30 (4H, m).

Reference Example 24 tert-Butyl 4-{4-[2-(4-chlorophenoxy)ethyl] benzyl}piperazine-1-carboxylate $^1$H-NMR (CDCl$_3$) δ: 1.45 (9H, s), 2.36-2.39 (4H, m), 3.04-3.09 (2H, m), 3.40-3.44 (4H, m), 3.48 (2H, s), 4.10-4.16 (2H, m), 6.81 (2H, d, J=9.2 Hz), 7.18-7.28 (6H, m).

Reference Example 25 tert-Butyl 4-{4-[2-(4-bromophenoxy)ethyl] benzyl}piperazine-1-carboxylate $^1$H-NMR (CDCl$_3$) δ: 1.45 (9H, s), 2.37 (4H, t, J=5.0 Hz), 3.07 (2H, t, J=6.9 Hz), 3.40-3.44 (4H, m), 3.48 (2H, s), 4.13

(2H, t, J=6.9 Hz), 6.77 (2H, d, J=8.9 Hz), 7.22 (2H, d, J=8.2 Hz), 7.26 (2H, d, J=8.2 Hz), 7.35 (2H, d, J=8.9 Hz).

Reference Example 26 tert-Butyl 4-{4-[2-(4-ethoxyphenoxy)ethyl]benzyl}piperazine-1-carboxylate $^1$H-NMR (CDCl$_3$) δ: 1.38 (3H, t, J=6.9 Hz), 1.45 (9H, s), 2.38 (4H, t, J=4.9 Hz), 3.05 (2H, t, J=6.9 Hz), 3.42 (4H, t, J=4.9 Hz), 3.48 (2H, s), 3.96 (2H, q, J=6.9 Hz), 4.14 (2H, t, J=6.9 Hz), 6.81 (4H, s), 7.20-7.30 (4H, m).

Reference Example 27 tert-Butyl 4-{4-[2-(3-chlorophenoxy)ethyl]benzyl}piperazine-1-carboxylate $^1$H-NMR (CDCl$_3$) δ: 1.45 (9H, s), 2.38 (4H, t, J=4.9 Hz), 3.07 (2H, t, J=6.9 Hz), 3.42 (4H, t, J=4.9 Hz), 3.49 (2H, s), 4.14 (2H, t, J=6.9 Hz), 6.73-6.83 (1H, m), 6.85-6.95 (2H, m), 7.12-7.32 (5H, m).

Reference Example 28 tert-Butyl 4-{4-[2-(4-cyanophenoxy)ethyl]benzyl}piperazine-1-carboxylate $^1$H-NMR (CDCl$_3$) δ: 1.45 (9H, s), 2.38 (4H, t, J=4.9 Hz), 3.10 (2H, t, J=6.9 Hz), 3.42 (4H, t, J=4.9 Hz), 3.50 (2H, s), 4.21 (2H, t, J=6.9 Hz), 6.94 (2H, d, J=8.9 Hz), 7.20-7.29 (4H, m), 7.57 (2H, d, J=8.9 Hz).

Reference Example 29 tert-Butyl 4-{4-[2-(3-ethoxyphenoxy)ethyl]benzyl}piperazine-1-carboxylate $^1$H-NMR (CDCl$_3$) δ: 1.40 (3H, t, J=6.9 Hz), 1.45 (9H, s), 2.38 (4H, t, J=4.6 Hz), 3.07 (2H, t, J=6.9 Hz), 3.42 (4H, t, J=4.6 Hz), 3.48 (2H, s), 4.00 (2H, q, J=6.9 Hz), 4.14 (2H, t, J=6.9 Hz), 6.43-6.54 (3H, m), 7.15 (1H, t, J=8.2 Hz), 7.20-7.30 (4H, m).

Reference Example 30 tert-Butyl 4-{4-[2-(3-methylphenoxy)ethyl]benzyl}piperazine-1-carboxylate $^1$H-NMR (CDCl$_3$) δ: 1.45 (9H, s), 2.31 (3H, s), 2.38 (4H, t, J=4.9 Hz), 3.07 (2H, t, J=7.1 Hz), 3.44 (4H, t, J=4.9 Hz), 3.48 (2H, s), 4.15 (2H, t, J=6.9 Hz), 6.69-6.76 (3H, m), 7.15 (1H, t, J=7.6 Hz), 7.22-7.27 (4H, m).

Reference Example 31 tert-Butyl 4-(4-{2-[3-(propan-2-yl)phenoxy]ethyl}benzyl)piperazine-1-carboxylate $^1$H-NMR (CDCl$_3$) δ: 1.23 (6H, d, J=6.9 Hz), 1.45 (9H, s), 2.38 (4H, t, J=4.9 Hz), 2.86 (1H, septet, J=6.9 Hz), 3.08 (2H, t, J=7.3 Hz), 3.42 (4H, t, J=4.9 Hz), 3.49 (2H, s), 4.16 (2H, t, J=7.3 Hz), 6.67-6.85 (3H, m), 7.19 (1H, d, J=7.6 Hz), 7.23-7.30 (4H, m).

Reference Example 32 tert-Butyl 4-{4-[2-(3,4-dimethylphenoxy)ethyl]benzyl}piperazine-1-carboxylate $^1$H-NMR (CDCl$_3$) δ: 1.45 (9H, s), 2.18 (3H, s), 2.22 (3H, s), 2.38 (4H, t, J=4.9 Hz), 3.06 (2H, t, J=7.3 Hz), 3.42 (4H, t, J=4.9 Hz), 3.48 (2H, s), 4.13 (2H, t, J=7.3 Hz), 6.63 (1H, dd, J=8.2, 2.6 Hz), 6.71 (1H, d, J=2.6 Hz), 7.01 (1H, d, J=8.2 Hz), 7.20-7.30 (4H, m).

Reference Example 33 tert-Butyl 4-{4-[2-(3-methoxyphenoxy)ethyl]benzyl}piperazine-1-carboxylate $^1$H-NMR (CDCl$_3$) δ: 1.45 (9H, s), 2.38 (4H, t, J=4.9 Hz), 3.08 (2H, t, J=7.3 Hz), 3.42 (4H, t, J=4.9 Hz), 3.48 (2H, s), 3.78 (3H, s), 4.15 (2H, t, J=7.3 Hz), 6.43-6.55 (3H, m), 7.16 (1H, t, J=8.2 Hz), 7.20-7.30 (4H, m).

Reference Example 34 tert-Butyl 4-{4-[2-(4-tert-butylphenoxy)ethyl]benzyl}piperazine-1-carboxylate $^1$H-NMR (CDCl$_3$) δ: 1.29 (9H, s), 1.45 (9H, s), 2.37 (4H, t, J=4.9 Hz), 3.07 (2H, t, J=6.9 Hz), 3.42 (4H, t, J=4.9 Hz), 3.48 (2H, s), 4.15 (2H, t, J=6.9 Hz), 6.86-6.80 (2H, m), 7.31-7.24 (6H, m).

Reference Example 35 tert-Butyl 4-{4-[2-(4-iodophenoxy)ethyl]benzyl}piperazine-1-carboxylate $^1$H-NMR (CDCl$_3$) δ: 1.45 (9H, s), 2.37 (4H, t, J=4.9 Hz), 3.06 (2H, t, J=7.1 Hz), 3.42 (4H, t, J=4.9 Hz), 3.48 (2H, s), 4.12 (2H, t, J=7.1 Hz), 6.66 (2H, d, J=6.9 Hz), 7.20-7.27 (4H, m), 7.53 (2H, d, J=6.9 Hz).

Reference Example 36 tert-Butyl 4-{4-[2-(4-butylphenoxy)ethyl]benzyl}piperazine-1-carboxylate $^1$H-NMR (CDCl$_3$) δ: 0.91 (3H, t, J=7.3 Hz), 1.26-1.40 (2H, m), 1.45 (9H, s), 1.50-1.61 (2H, m), 2.38 (4H, t, J=5.1 Hz), 2.54 (2H, t, J=7.6 Hz), 3.07 (2H, t, J=7.1 Hz), 3.42 (4H, t, J=5.1 Hz), 3.48 (2H, s), 4.14 (2H, t, J=7.1 Hz), 6.78-6.84 (2H, m), 7.04-7.10 (2H, m), 7.21-7.27 (4H, m).

Reference Example 37 tert-Butyl 4-(4-{2-[4-(methylsulfonyl)phenoxy]ethyl}benzyl)piperazine-1-carboxylate $^1$H-NMR (CDCl$_3$) δ: 1.45 (9H, s), 2.38 (4H, t, J=4.9 Hz), 3.01 (3H, s), 3.11 (2H, t, J=7.1 Hz), 3.42 (4H, t, J=4.9 Hz), 3.49 (2H, s), 4.23 (2H, t, J=7.1 Hz), 7.01 (2H, d, J=8.9 Hz), 7.21-7.29 (4H, m), 7.84 (2H, d, J=8.9 Hz).

Reference Example 38 tert-Butyl 4-{4-[2-(2-methylphenoxy)ethyl]
benzyl}piperazine-1-carboxylate

¹H-NMR (CDCl₃) δ: 1.45 (9H, s), 2.19 (3H, s), 2.37 (4H, t, J=4.9 Hz), 3.10 (2H, t, J=6.8 Hz), 3.42 (4H, t, J=5.1 Hz), 3.48 (2H, s), 4.16 (2H, t, J=6.8 Hz), 6.77-6.86 (2H, m), 7.08-7.15 (2H, m), 7.25 (4H, s).

Reference Example 39 tert-Butyl 4-{4-[2-(1,3-benzodioxol-5-yloxy)ethyl]
benzyl}piperazine-1-carboxylate ¹H-NMR (CDCl₃) δ: 1.45 (9H, s), 2.37 (4H, t, J=4.9 Hz), 3.04 (2H, t, J=6.9 Hz), 3.42 (4H, t, J=4.9 Hz), 3.48 (2H, s), 4.08 (2H, t, J=6.9 Hz), 5.90 (2H, s), 6.31 (1H, dd, J=8.6, 2.3 Hz), 6.47 (1H, d, J=2.3 Hz), 6.68 (1H, d, J=8.6 Hz), 7.20-7.27 (4H, m).

Reference Example 40 tert-Butyl 4-{4-[2-(2-chlorophenoxy)ethyl]
benzyl}piperazine-1-carboxylate

¹H-NMR (CDCl₃) δ: 1.45 (9H, s), 2.37-2.38 (4H, m), 3.14 (2H, t, J=6.9 Hz), 3.41-3.43 (4H, m), 3.49 (2H, s), 4.21 (2H, t, J=6.9 Hz), 6.85-6.91 (2H, m), 7.15-7.36 (6H, m).

Reference Example 41 tert-Butyl 4-{4-[2-(2,3-dimethylphenoxy)ethyl]
benzyl}piperazine-1-carboxylate

¹H-NMR (CDCl₃) δ: 1.45 (9H, s), 2.11 (3H, s), 2.25 (3H, s), 2.37-2.38 (4H, m), 3.09 (2H, t, J=6.8 Hz), 3.41-3.42 (4H, m), 3.48 (2H, s), 4.14 (2H, t, J=6.8 Hz), 6.68 (1H, d, J=8.3 Hz), 6.76 (1H, d, J=7.8 Hz), 7.02 (1H, t, J=7.8 Hz), 7.21-7.27 (4H, m).

Reference Example 42 tert-Butyl 4-{4-[2-(3,5-dimethylphenoxy)ethyl]
benzyl}piperazine-1-carboxylate

¹H-NMR (CDCl₃) δ: 1.45 (9H, s), 2.27 (6H, s), 2.36-2.40 (4H, m), 3.06 (2H, t, J=7.1 Hz), 3.40-3.45 (4H, m), 3.48 (2H, s), 4.13 (2H, t, J=7.1 Hz), 6.53 (2H, s), 6.59 (1H, s), 7.23-7.28 (4H, m).

Reference Example 43 tert-Butyl 4-{4-[2-(quinolin-6-yloxy)ethyl]
benzyl}piperazine-1-carboxylate

¹H-NMR (CDCl₃) δ: 1.45 (9H, s), 2.37-2.38 (4H, m), 3.14 (2H, t, J=6.8 Hz), 3.41-3.44 (4H, m), 3.48 (2H, s), 4.26 (2H, t, J=6.8 Hz), 7.03 (1H, d, J=2.4 Hz), 7.25-7.32 (5H, m), 7.36 (1H, dd, J=9.3, 2.4 Hz), 7.94-8.01 (2H, m), 8.73 (1H, d, J=3.4 Hz).

Reference Example 44 tert-Butyl 4-{4-[2-(3,4-dichlorophenoxy)ethyl]
benzyl}piperazine-1-carboxylate

¹H-NMR (CDCl₃) δ: 1.45 (9H, s), 2.37-2.39 (4H, m), 3.07 (2H, t, J=7.0 Hz), 3.42-3.43 (4H, m), 3.49 (2H, s), 4.12 (2H, t, J=7.0 Hz), 6.74 (1H, dd, J=8.9, 2.8 Hz), 6.98 (1H, d, J=2.9 Hz), 7.21-7.31 (5H, m).

Reference Example 45 tert-Butyl 4-{4-[2-(4-fluoro-3-methylphenoxy)ethyl]
benzyl}piperazine-1-carboxylate ¹H-NMR (CDCl₃) δ: 1.45 (9H, s), 2.21 (3H, d, J=1.7 Hz), 2.37 (4H, t, J=4.9 Hz), 3.04 (2H, t, J=7.1 Hz), 3.42 (4H, t, J=4.9 Hz), 3.47 (2H, s), 4.08 (2H, t, J=7.1 Hz), 6.61-6.69 (2H, m), 6.86 (1H, t, J=9.0 Hz), 7.20-7.26 (4H, m).

Reference Example 46 tert-Butyl 4-{4-[2-(2,3-dihydro-1H-inden-5-yloxy)
ethyl]benzyl}piperazine-1-carboxylate ¹H-NMR (CDCl₃) δ: 1.45 (9H, s), 2.01-2.08 (2H, m), 2.36 (4H, t, J=4.9 Hz), 2.80-2.86 (4H, m), 3.05 (2H, t, J=7.1 Hz), 3.42 (4H, t, J=4.9 Hz), 3.46 (2H, s), 4.12 (2H, t, J=7.1 Hz), 6.67 (1H, dd, J=8.1, 2.4 Hz), 6.77 (1H, s), 7.08 (1H, d, J=8.1 Hz), 7.22-7.25 (4H, m).

Reference Example 47 tert-Butyl 4-{4-[2-(5,6,7,8-tetrahydronaphthalen-2-
yloxy)ethyl]benzyl}piperazine-1-carboxylate ¹H-NMR (CDCl₃) δ: 1.45 (9H, s), 1.74-1.77 (4H, m), 2.37 (4H, t, J=4.9 Hz), 2.68-2.71 (4H, m), 3.05 (2H, t, J=7.1 Hz), 3.42 (4H, t, J=4.9 Hz), 3.47 (2H, s), 4.12 (2H, t, J=7.1 Hz), 6.59-6.61 (1H, m), 6.66 (1H, dd, J=8.3, 2.7 Hz), 6.95 (1H, d, J=8.3 Hz), 7.22-7.25 (4H, m).

Reference Example 48 tert-Butyl 4-{4-[2-(naphthalen-2-yloxy)ethyl]
benzyl}piperazine-1-carboxylate

¹H-NMR (CDCl₃) δ: 1.45 (9H, s), 2.36 (4H, brs), 3.12 (2H, t, J=7.1 Hz), 3.42 (4H, brs), 3.46 (2H, s), 4.24 (2H, t, J=7.1 Hz), 7.10-7.15 (2H, m), 7.25-7.32 (5H, m), 7.40 (1H, t, J=7.0 Hz), 7.66-7.74 (3H, m).

Reference Example 49 tert-Butyl 4-{4-[2-(4-acetylphenoxy)ethyl]
benzyl}piperazine-1-carboxylate

¹H-NMR (CDCl₃) δ: 1.45 (9H, s), 2.38 (4H, t, J=4.9 Hz), 2.55 (3H, s), 3.11 (2H, t, J=7.1 Hz), 3.42 (4H, t, J=4.9 Hz), 3.49 (2H, s), 4.22 (2H, t, J=7.1 Hz), 6.92 (2H, d, J=8.3 Hz), 7.22-7.28 (4H, m), 7.92 (2H, d, J=8.3 Hz).

Reference Example 50 tert-Butyl 4-(4-{2-[(6-bromopyridin-3-yl)oxy]
ethyl}benzyl)piperazine-1-carboxylate ¹H-NMR (CDCl₃) δ: 1.45 (9H, s), 2.38 (4H, t, J=4.9 Hz), 3.09 (2H, t, J=6.8 Hz), 3.42 (4H, t, J=4.9 Hz), 3.49 (2H, s), 4.19 (2H, t, J=6.8 Hz), 7.08 (1H, dd, J=8.5, 3.2 Hz), 7.22 (2H, d, J=7.8 Hz), 7.27 (2H, d, J=7.8 Hz), 7.34 (1H, d, J=8.5 Hz), 8.04 (1H, d, J=3.2 Hz).

Reference Example 51 tert-Butyl 4-{4-[2-(pyridin-2-yloxy)ethyl]benzyl}piperazine-1-carboxylate $^1$H-NMR (CDCl$_3$) δ: 1.45 (9H, s), 2.36 (4H, t, J=5.0 Hz), 3.07 (2H, t, J=7.1 Hz), 3.42 (4H, t, J=5.0 Hz), 3.47 (2H, s), 4.51 (2H, t, J=7.1 Hz), 6.71 (1H, d, J=8.5 Hz), 6.81-6.85 (1H, m), 7.24 (4H, s), 7.51-7.55 (1H, m), 8.13 (1H, dd, J=5.1, 1.2 Hz).

Reference Example 52 tert-Butyl 4-(4-{2-[(5-chloropyridin-2-yl)oxy]ethyl}benzyl)piperazine-1-carboxylate $^1$H-NMR (CDCl$_3$) δ: 1.45 (9H, s), 2.37 (4H, t, J=4.9 Hz), 3.05 (2H, t, J=7.1 Hz), 3.42 (4H, t, J=4.9 Hz), 3.47 (2H, s), 4.47 (2H, t, J=7.1 Hz), 6.66 (1H, d, J=8.8 Hz), 7.20-7.27 (4H, m), 7.48 (1H, dd, J=8.8, 2.7 Hz), 8.07 (1H, d, J=2.7 Hz).

Reference Example 53 tert-Butyl 4-(4-{2-[(6-chloropyridin-3-yl)oxy]ethyl}benzyl)piperazine-1-carboxylate $^1$H-NMR (CDCl$_3$) δ: 1.45 (9H, s), 2.38 (4H, t, J=5.0 Hz), 3.09 (2H, t, J=7.1 Hz), 3.42 (4H, t, J=5.0 Hz), 3.49 (2H, s), 4.20 (2H, t, J=7.1 Hz), 7.14-7.28 (6H, m), 8.03 (1H, d, J=2.4 Hz).

Reference Example 54 tert-Butyl 4-(4-{2-[(5-bromopyridin-2-yl)oxy]ethyl}benzyl)piperazine-1-carboxylate $^1$H-NMR (CDCl$_3$) δ: 1.45 (9H, s), 2.37 (4H, t, J=5.0 Hz), 3.05 (2H, t, J=7.1 Hz), 3.42 (4H, t, J=5.0 Hz), 3.47 (2H, s), 4.47 (2H, t, J=7.1 Hz), 6.63 (1H, dd, J=8.8, 0.7 Hz), 7.20-7.26 (4H, m), 7.61 (1H, dd, J=8.8, 2.7 Hz), 8.16 (1H, t, J=1.2 Hz).

Reference Example 55 tert-Butyl 4-(4-{2-[(6-methoxypyridin-3-yl)oxy]ethyl}benzyl)piperazine-1-carboxylate $^1$H-NMR (CDCl$_3$) δ: 1.45 (9H, s), 2.38 (4H, brs), 3.06 (2H, t, J=7.1 Hz), 3.42 (4H, t, J=5.0 Hz), 3.48 (2H, s), 3.87 (3H, s), 4.19 (2H, t, J=7.1 Hz), 6.66 (1H, d, J=9.0 Hz), 7.17-7.27 (5H, m), 7.79 (1H, d, J=2.7 Hz).

Reference Example 56 tert-Butyl 4-(4-{2-[(6-chloro-1,3-benzoxazol-2-yl)oxy]ethyl}benzyl)piperazine-1-carboxylate $^1$H-NMR (CDCl$_3$) δ: 1.46 (9H, s), 2.32 (4H, brs), 3.04 (2H, t, J=7.1 Hz), 3.41-3.44 (6H, m), 4.02 (2H, t, J=7.1 Hz), 6.56 (1H, d, J=8.3 Hz), 7.00 (1H, dd, J=8.3, 2.0 Hz), 7.08-7.12 (2H, m), 7.16-7.21 (3H, m).

Reference Example 57 tert-Butyl 4-{4-[2-(1,3-benzothiazol-2-yloxy)ethyl]benzyl}piperazine-1-carboxylate $^1$H-NMR (CDCl$_3$) δ: 1.46 (9H, s), 2.32 (4H, t, J=5.0 Hz), 2.99 (2H, t, J=7.6 Hz), 3.41 (4H, t, J=5.0 Hz), 3.44 (2H, s), 4.12 (2H, t, J=7.6 Hz), 6.89 (1H, d, J=7.8 Hz), 7.08-7.15 (3H, m), 7.19-7.23 (3H, m), 7.36-7.38 (1H, m).

Reference Example 58 tert-Butyl 4-(4-{2-[(2-methyl-1,3-benzothiazol-5-yl)oxy]ethyl}benzyl)piperazine-1-carboxylate $^1$H-NMR (CDCl$_3$) δ: 1.45 (9H, s), 2.38 (4H, t, J=4.9 Hz), 2.79 (3H, s), 3.11 (2H, t, J=7.0 Hz), 3.42 (4H, t, J=4.9 Hz), 3.48 (2H, s), 4.23 (2H, t, J=7.0 Hz), 6.97 (1H, dd, J=8.8, 2.4 Hz), 7.23-7.28 (4H, m), 7.45 (1H, d, J=2.4 Hz), 7.63 (1H d, J=8.8 Hz).

Reference Example 59 tert-Butyl 4-(4-{2-[4-(2-{[tert-butyl(dimethyl)silyl]oxy}ethyl)phenoxy]ethyl}benzyl)piperazine-1-carboxylate $^1$H-NMR (CDCl$_3$) δ: −0.01 (6H, s), 0.87 (9H, s), 1.45 (9H, s), 2.38-2.39 (4H, m), 2.75 (2H, t, J=7.2 Hz), 3.07 (2H, t, J=7.1 Hz), 3.41-3.43 (4H, m), 3.48 (2H, s), 3.75 (2H, t, J=7.2 Hz), 4.14 (2H, t, J=7.1 Hz), 6.81 (2H, d, J=8.5 Hz), 7.10 (2H, d, J=8.5 Hz), 7.23-7.25 (4H, m).

Reference Example 60 tert-Butyl 4-{2-fluoro-4-[(4-fluorophenoxy)methyl]benzyl}piperazine-1-carboxylate $^1$H-NMR (CDCl$_3$) δ: 1.45 (9H, s), 2.41-2.44 (4H, m), 3.42-3.43 (4H, m), 3.59 (2H, s), 5.00 (2H, s), 6.87-7.00 (4H, m), 7.12 (1H, d, J=10.5 Hz), 7.15 (1H, d, J=8.1 Hz), 7.36-7.40 (1H, m).

Reference Example 61 tert-Butyl 4-(3-fluoro-4-{[4-(propan-2-yloxy)phenoxy]methyl}benzyl)piperazine-1-carboxylate $^1$H-NMR (CDCl$_3$) δ: 1.30 (6H, d, J=5.9 Hz), 1.46 (9H, s), 2.36-2.40 (4H, m), 3.42-3.43 (4H, m), 3.49 (2H, s), 4.40-4.45 (1H, m), 5.05 (2H, s), 6.83 (2H, d, J=9.3 Hz), 6.90 (2H, d, J=9.0 Hz), 7.08 (1H, d, J=1.7 Hz), 7.11 (1H, s), 7.43 (1H, t, J=7.7 Hz).

Reference Example 62 tert-Butyl 4-{3-fluoro-4-[(4-fluorophenoxy)methyl]benzyl}piperazine-1-carboxylate $^1$H-NMR (CDCl$_3$) δ: 1.46 (9H, s), 2.38-2.39 (4H, m), 3.42-3.44 (4H, m), 3.50 (2H, s), 5.06 (2H, s), 6.90-7.00 (4H, m), 7.11 (2H, d, J=9.0 Hz), 7.42 (1H, t, J=7.6 Hz).

Reference Example 63 tert-Butyl 4-{3-fluoro-4-[(4-propylphenoxy)methyl]benzyl}piperazine-1-carboxylate $^1$H-NMR (CDCl$_3$) δ: 0.93 (3H, t, J=7.3 Hz), 1.46 (9H, s), 1.57-1.64 (2H, m), 2.36-2.40 (4H, m), 2.52-2.54 (2H, m), 3.42-3.43 (4H, m), 3.49 (2H, s), 5.08 (2H, s), 6.90 (2H, d, J=8.3 Hz), 7.10 (4H, d, J=8.5 Hz), 7.44 (1H, t, J=7.6 Hz).

Reference Example 64 tert-Butyl 4-[4-(2-{[(2-nitrophenyl)sulfonyl][4-(propan-2-yl)phenyl]amino}ethyl)benzyl]-piperazine-1-carboxylate $^1$H-NMR (CDCl$_3$) δ: 1.24 (6H, d, J=6.8 Hz), 2.36 (4H, t, J=4.9 Hz), 2.77-2.86 (2H, m), 2.91 (1H, septet, J=6.8 Hz), 3.41 (4H, t, J=4.9 Hz), 3.46 (2H, s), 3.93-4.03 (2H, m), 7.07-7.12 (4H, m), 7.12-7.24 (4H, m), 7.40-7.52 (2H, m), 7.55-7.65 (2H, m).

Reference Example 65 tert-Butyl 4-[4-(2-{(4-fluorophenyl)[(2-nitrophenyl)sulfonyl]amino}ethyl)benzyl]piperazine-1-carboxylate $^1$H-NMR (CDCl$_3$) δ: 1.45 (9H, s), 2.36 (4H, t, J=4.9 Hz), 2.77-2.86 (2H, m), 3.42 (4H, t, J=4.9 Hz), 3.46 (2H, s), 3.96-4.04 (2H, m), 6.06-7.05 (2H, m), 7.08 (2H, d, J=8.1 Hz), 7.01-7.18 (2H, m), 7.20 (2H, d, J=7.8 Hz), 7.43-7.54 (2H, m), 7.58-7.72 (2H, m).

Reference Example 66 tert-Butyl 4-[4-(2-{(4-methoxyphenyl)[(2-nitrophenyl)sulfonyl]amino}ethyl)benzyl]piperazine-1-carboxylate $^1$H-NMR (CDCl$_3$) δ: 1.45 (9H, s), 2.36 (4H, t, J=4.9 Hz), 2.77-2.86 (2H, m), 3.42 (4H, t, J=4.9 Hz), 3.46 (2H, s), 3.81 (3H, s), 3.93-4.00 (2H, m), 6.79-6.86 (2H, m), 7.06-7.12 (4H, m), 7.20 (2H, d, J=8.1 Hz), 7.43-7.52 (2H, m), 7.56-7.66 (2H, m).

Reference Example 67 tert-Butyl 4-{[4-(2-{[(2-nitrophenyl)sulfonyl][4-(propan-2-yl)phenyl]amino}ethyl)phenyl]-amino}piperidine-1-carboxylate $^1$H-NMR (CDCl$_3$) δ: 1.24 (6H, d, J=6.8 Hz), 1.27-1.38 (2H, m), 1.46 (9H, s), 1.96-2.07 (2H, m), 2.67-2.75 (2H, m), 2.83-2.98 (3H, m), 333-3.47 (2H, m), 3.87-3.95 (2H, m), 3.96-4.12 (2H, m), 6.48-6.55 (2H, m), 6.92-6.98 (2H, m), 7.07-7.12 (2H, m), 7.14-7.19 (2H, m), 7.41-7.53 (2H, m), 7.54-7.66 (2H, m).

Reference Example 68 tert-Butyl 4-({4-[2-(4-methylphenoxy)ethyl]phenyl}amino)piperidine-1-carboxylate $^1$H-NMR (CDCl$_3$) δ: 1.26-1.38 (2H, m), 1.46 (9H, s), 1.98-2.07 (2H, m), 2.27 (3H, s), 2.86-3.00 (4H, m), 3.35-3.45 (2H, m), 3.95-4.12 (4H, m), 6.53-6.59 (2H, m), 6.75-6.83 (2H, m), 7.00-7.11 (4H, m).

Reference Example 69 tert-Butyl 4-({4-[2-(4-fluorophenoxy)ethyl]phenyl}amino)piperidine-1-carboxylate $^1$H-NMR (CDCl$_3$) δ: 1.25-1.39 (2H, m), 1.46 (9H, s), 1.98-2.08 (2H, m), 2.86-3.00 (4H, m), 3.35-3.53 (2H, m), 3.95-4.15 (4H, m), 6.54-6.60 (2H, m), 6.79-6.85 (2H, m), 6.90-7.00 (2H, m), 7.04-7.11 (2H, m).

Reference Example 70

4-[2-(4-Methoxyphenyl)ethoxy]benzaldehyde $^1$H-NMR (CDCl$_3$) δ: 3.04-3.09 (2H, m), 3.80 (3H, s), 4.19-4.24 (2H, m), 6.87 (2H, d, J=8.6 Hz), 6.99 (2H, d, J=8.6 Hz), 7.20 (2H, d, J=8.6 Hz), 7.82 (2H, d, J=8.6 Hz), 9.87 (1H, brs).

Reference Example 71

4-[2-(4-Methylphenyl)ethoxy]benzaldehyde $^1$H-NMR (CDCl$_3$) δ: 2.33 (3H, s), 3.09 (2H, t, J=7.3 Hz), 4.23 (2H, t, J=7.3 Hz), 6.95-7.04 (2H, m), 7.10-7.22 (4H, m), 7.77-7.88 (2H, m), 9.87 (1H, s).

Reference Example 72

4-{2-[4-(Propan-2-yl)phenyl]ethoxy}benzaldehyde $^1$H-NMR (CDCl$_3$) δ: 1.25 (6H, d, J=6.9 Hz), 2.89 (1H, septet, J=6.9 Hz), 3.09 (2H, t, J=7.3 Hz), 4.23 (2H, t, J=7.3 Hz), 6.95-7.04 (2H, m), 7.13-7.27 (4H, m), 7.77-7.86 (2H, m), 9.87 (1H, s).

Reference Example 73

4-[3-(4-Fluorophenoxy)propyl]benzaldehyde $^1$H-NMR (CDCl$_3$) δ: 2.04-2.17 (2H, m), 2.90 (2H, t, J=7.7 Hz), 3.92 (2H, t, J=6.1 Hz), 6.79-6.86 (2H, m), 6.92-7.01 (2H, m), 7.38 (2H, d, J=8.1 Hz), 7.81 (2H, d, J=8.2 Hz), 9.98 (1H, s).

Reference Example 74

4-{3-[4-(Propan-2-yl)phenoxy]propyl}benzaldehyde $^1$H-NMR (CDCl$_3$) δ: 1.22 (6H, d, J=6.9 Hz), 2.06-2.17 (2H, m), 2.81-2.93 (3H, m), 3.95 (2H, t, J=6.1 Hz), 6.82 (2H, d, J=8.7 Hz), 7.14 (2H, d, J=8.4 Hz), 7.38 (2H, d, J=8.1 Hz), 7.81 (2H, d, J=8.2 Hz), 9.98 (1H, s).

Reference Example 75

4-{[(E)-3-(4-Formylphenyl)prop-2-en-1-yl]oxy}benzonitrile $^1$H-NMR (CDCl$_3$) δ: 4.79 (2H, dd, J=5.5, 1.6 Hz), 6.55 (1H, dt, J=15.8, 5.5 Hz), 6.80 (1H, d, J=15.8), 7.00-7.03 (2H, m), 7.55-7.63 (4H, m), 7.85-7.87 (2H, m), 10.00 (1H, s).

Reference Example 76

1-Bromo-4-[2-(4-fluorophenoxy)ethyl]benzene $^1$H-NMR (CDCl$_3$) δ: 3.02 (2H, t, J=6.6 Hz), 4.10 (2H, t, J=6.6 Hz), 6.76-6.84 (2H, m), 6.90-7.00 (2H, m), 7.13-7.16 (2H, m), 7.40-7.44 (2H, m).

Reference Example 77

1-Bromo-4-{2-[4-(propan-2-yl)phenoxy]ethyl}benzene

¹H-NMR (CDCl₃) δ: 1.21 (6H, d, J=6.9 Hz), 2.85 (1H, septet, J=6.9 Hz), 3.03 (2H, t, J=6.9 Hz), 4.13 (2H, t, J=6.9 Hz), 6.77-6.85 (2H, m), 7.09-7.20 (4H, m), 7.38-7.47 (2H, m).

Reference Example 78

1-Bromo-4-[2-(4-methoxyphenoxy)ethyl]benzene

¹H-NMR (CDCl₃) δ: 3.02 (2H, t, J=6.9 Hz), 3.76 (3H, s), 4.10 (2H, t, J=6.8 Hz), 6.82 (4H, s), 7.14-7.17 (2H, m), 7.41-7.44 (2H, m).

Reference Example 79

1-Bromo-4-[2-(4-methylphenoxy)ethyl]benzene

¹H-NMR (CDCl₃) δ: 2.28 (3H, s), 3.03 (2H, t, J=6.9 Hz), 4.12 (2H, t, J=6.9 Hz), 6.73-6.83 (2H, m), 7.07 (2H, d, J=8.2 Hz), 7.15 (2H, d, J=8.6 Hz), 7.43 (2H, d, J=8.9 Hz).

Reference Example 80

1-Bromo-4-[2-(4-ethoxyphenoxy)ethyl]benzene

¹H-NMR (CDCl₃) δ: 1.38 (3H, t, J=6.9 Hz), 3.01 (2H, t, J=6.9 Hz), 3.97 (2H, q, J=6.9 Hz), 4.09 (2H, t, J=6.9 Hz), 6.81 (4H, s), 7.15 (2H, d, J=8.2 Hz), 7.42 (2H, d, J=8.2 Hz).

Reference Example 81

1-Bromo-4-[1-(4-methylphenoxy)propan-2-yl]benzene

¹H-NMR (CDCl₃) δ: 1.37 (3H, d, J=7.1 Hz), 2.27 (3H, s), 3.14-3.23 (1H, m), 3.92 (1H, dd, J=9.2, 7.2 Hz), 4.00 (1H, dd, J=9.2, 6.3 Hz), 6.76 (2H, d, J=8.5 Hz), 7.05 (2H, d, J=8.5 Hz), 7.16 (2H, d, J=8.5 Hz), 7.44 (2H, d, J=8.5 Hz).

Reference Example 82

(E)-3-(4-Bromophenyl)but-2-en-1-yl 4-methylphenyl ether

¹H-NMR (CDCl₃) δ: 2.10 (3H, d, J=1.2 Hz), 2.29 (3H, s), 4.68-4.70 (2H, m), 6.02-6.06 (1H, m), 6.84 (2H, dt, J=9.3, 2.5 Hz), 7.09 (2H, d, J=8.7 Hz), 7.29 (2H, dt, J=9.0, 2.3 Hz), 7.44 (2H, dt, J=9.0, 2.3 Hz).

Reference Example 83

2-(4-Bromo-2-fluorophenyl)ethyl 4-chlorophenyl ether

¹H-NMR (CDCl₃) δ: 3.07 (2H, t, J=6.7 Hz), 4.12 (2H, t, J=6.7 Hz), 6.79 (2H, d, J=9.0 Hz), 7.17-7.21 (5H, m).

Reference Example 84 tert-Butyl(dimethyl)({4-[2-(4-methylphenoxy)propyl]benzyl}oxy)silane

¹H-NMR (CDCl₃) δ: 0.09 (6H, s), 0.93 (9H, s), 1.26 (3H, d, J=6.1 Hz), 2.27 (3H, s), 2.77 (1H, dd, J=13.6, 6.8 Hz), 3.08 (1H, dd, J=13.6, 5.7 Hz), 4.46-4.54 (1H, m), 4.71 (2H, s), 6.79 (2H, d, J=8.3 Hz), 7.06 (2H, d, J=8.3 Hz), 7.19 (2H, d, J=8.1 Hz), 7.24 (2H, d, J=8.1 Hz).

Reference Example 85 tert-Butyl(dimethyl)({3-methyl-4-[2-(4-methylphenoxy)ethyl]benzyl}oxy)silane

¹H-NMR (CDCl₃) δ: 0.10 (6H, s), 0.94 (9H, s), 2.28 (3H, s), 2.36 (3H, s), 3.08 (2H, t, J=7.6 Hz), 4.09 (2H, t, J=7.6 Hz), 4.69 (2H, s), 6.79 (2H, dt, J=9.3, 2.6 Hz), 7.05-7.12 (4H, m), 7.18 (1H, d, J=8.5 Hz).

Reference Example 86 tert-Butyl(dimethyl)({3-methyl-4-[(E)-3-(4-methylphenoxy)prop-1-en-1-yl]benzyl}oxy)silane ¹H-NMR (CDCl₃) δ: 0.09 (6H, s), 0.94 (9H, s), 2.29 (3H, s), 2.34 (3H, s), 4.67-4.69 (4H, m), 6.28 (1H, dt, J=15.9, 5.7 Hz), 6.87 (2H, dt, J=9.1, 2.5 Hz), 6.92 (1H, d, J=15.9 Hz), 7.08-7.13 (4H, m), 7.44 (1H, d, J=7.8 Hz).

Reference Example 87 tert-Butyl(dimethyl)({2-methyl-4-[(E)-3-(4-methylphenoxy)prop-1-en-1-yl]benzyl}oxy)silane ¹H-NMR (CDCl₃) δ: 0.09 (6H, s), 0.93 (9H, s), 2.25 (3H, s), 2.28 (3H, s), 4.65 (2H, dd, J=6.1, 1.2 Hz), 4.68 (2H, s), 6.38 (1H, dt, J=16.1, 6.1 Hz), 6.67 (1H, d, J=16.1 Hz), 6.85 (2H, d, J=8.8 Hz), 7.08 (2H, d, J=8.8 Hz), 7.17 (1H, brs), 7.22 (1H, dd, J=7.9, 1.3 Hz), 7.35 (1H, d, J=7.9 Hz).

Reference Example 88

1-(Diethoxymethyl)-4-[(E)-3-(4-methylphenoxy)prop-1-en-1-yl]benzene

¹H-NMR (CDCl₃) δ: 1.23 (6H, t, J=7.1 Hz), 2.29 (3H, s), 3.49-3.65 (4H, m), 4.67 (2H, dd, J=5.9, 1.5 Hz), 5.49 (1H, s), 6.42 (1H, dt, J=16.0, 5.9 Hz), 6.72 (1H, dt, J=16.0, 1.5 Hz), 6.86 (2H, dt, J=9.3, 2.5 Hz), 7.09 (2H, d, J=8.3 Hz), 7.39 (2H, d, J=8.5 Hz), 7.43 (2H, d, J=8.5 Hz).

Reference Example 89

1-(Diethoxymethyl)-4-[(E)-3-(4-fluorophenoxy)prop-1-en-1-yl]benzene

¹H-NMR (CDCl₃) δ: 1.24 (6H, t, J=7.1 Hz), 3.49-3.65 (4H, m), 4.66 (2H, dd, J=5.9, 1.5 Hz), 5.49 (1H, s), 6.40 (1H, dt, J=16.1, 5.9 Hz), 6.72 (1H, d, J=16.1 Hz), 6.87-6.92 (2H, m), 6.95-7.00 (2H, m), 7.40 (2H, d, J=8.3 Hz), 7.44 (2H, d, J=8.3 Hz).

Reference Example 90

1-(Diethoxymethyl)-4-[(E)-3-phenoxyprop-1-en-1-yl]benzene

¹H-NMR (CDCl₃) δ: 1.23 (6H, t, J=7.1 Hz), 3.49-3.65 (4H, m), 4.70 (2H, dd, J=5.8, 1.5 Hz), 5.49 (1H, s), 6.43 (1H, dt, J=16.0, 5.8 Hz), 6.73 (1H, d, J=16.0 Hz), 6.94-6.98 (3H, m), 7.27 (2H, m), 7.39-7.45 (4H, m).

Reference Example 91

1-(Diethoxymethyl)-4-[(E)-3-(4-methoxyphenoxy)prop-1-en-1-yl]benzene $^1$H-NMR (CDCl$_3$) δ: 1.23 (6H, t, J=7.1 Hz), 3.49-3.65 (4H, m), 3.77 (3H, s), 4.65 (2H, dd, J=5.9, 1.3 Hz), 5.49 (1H, s), 6.41 (1H, dt, J=15.9, 5.9 Hz), 6.72 (1H, d, J=15.9 Hz), 6.82-6.92 (4H, m), 7.38-7.44 (4H, m).

Reference Example 92

5-({(E)-3-[4-(Diethoxymethyl)phenyl]prop-2-en-1-yl}oxy)-2-methylpyridine $^1$H-NMR (CDCl$_3$) δ: 1.23 (6H, t, J=7.1 Hz), 2.25 (3H, s), 3.49-3.64 (4H, m), 4.97 (2H, dd, J=6.1, 1.5 Hz), 5.49 (1H, s), 6.47 (1H, dt, J=16.0, 6.0 Hz), 6.69-6.75 (2H, m), 7.38-7.44 (5H, m), 7.96-7.97 (1H, m).

Reference Example 93

2-Chloro-5-({(E)-3-[4-(diethoxymethyl)phenyl]prop-2-en-1-yl}oxy)pyridine $^1$H-NMR (CDCl$_3$) δ: 1.24 (6H, t, J=7.1 Hz), 3.50-3.65 (4H, m), 4.73 (2H, dd, J=5.9, 1.5 Hz), 5.50 (1H, s), 6.37 (1H, dt, J=16.0, 5.9 Hz), 6.74 (1H, d, J=16.0 Hz), 7.24 (2H, d, J=1.9 Hz), 7.40 (2H, d, J=8.3 Hz), 7.45 (2H, d, J=8.3 Hz), 8.12 (1H, t, J=1.9 Hz).

Reference Example 94

5-Bromo-2-({(E)-3-[4-(diethoxymethyl)phenyl]prop-2-en-1-yl}oxy)pyridine $^1$H-NMR (CDCl$_3$) δ: 1.23 (6H, t, J=7.1 Hz), 3.48-3.64 (4H, m), 4.96 (2H, d, J=6.1 Hz), 5.49 (1H, s), 6.43 (1H, dt, J=15.9, 6.1 Hz), 6.69-6.74 (2H, m), 7.38-7.44 (4H, m), 7.65 (1H, ddd, J=8.8, 2.4, 0.7 Hz), 8.20 (1H, d, J=2.4 Hz).

Reference Example 95

1-(Diethoxymethyl)-4-{(E)-3-[4-(propan-2-yl)phenoxy]prop-1-en-1-yl}benzene $^1$H-NMR (CDCl$_3$) δ: 1.22-1.25 (12H, m), 2.81-2.92 (1H, m), 3.49-3.65 (4H, m), 4.68 (2H, dd, J=5.7, 1.2 Hz), 5.49 (1H, s), 6.42 (1H, dt, J=16.0, 5.7 Hz), 6.72 (1H, d, J=16.0 Hz), 6.89 (2H, dt, J=9.4, 2.5 Hz), 7.15 (2H, dt, J=9.4, 2.5 Hz), 7.39-7.44 (4H, m).

Reference Example 96

2-({(E)-3-[4-(Diethoxymethyl)phenyl]prop-2-en-1-yl}oxy)-5-methylpyridine $^1$H-NMR (CDCl$_3$) δ: 1.23 (6H, t, J=7.1 Hz), 2.25 (3H, s), 3.49-3.64 (4H, m), 4.97 (2H, dd, J=6.1, 1.5 Hz), 5.49 (1H, s), 6.47 (1H, dt, J=16.0, 6.0 Hz), 6.69-6.75 (2H, m), 7.38-7.44 (5H, m), 7.96-7.97 (1H, m).

Reference Example 97

1-(Diethoxymethyl)-4-(3-phenoxypropyl)benzene $^1$H-NMR (CDCl$_3$) δ: 1.24 (6H, t, J=7.1 Hz), 2.07-2.14 (2H, m), 2.82 (2H, t, J=7.7 Hz), 3.50-3.66 (4H, m), 3.96 (2H, t, J=6.3 Hz), 5.48 (1H, s), 6.88-6.96 (3H, m), 7.21 (2H, d, J=8.1 Hz), 7.25-7.31 (2H, m), 7.39 (2H, d, J=8.1 Hz).

Reference Example 98

2-Chloro-5-{3-[4-(diethoxymethyl)phenyl]propoxy}pyridine $^1$H-NMR (CDCl$_3$) δ: 1.27 (6H, t, J=7.1 Hz), 2.10-2.17 (2H, m), 2.84 (2H, t, J=7.6 Hz), 3.52-3.69 (4H, m), 4.00 (2H, t, J=6.2 Hz), 5.50 (1H, s), 7.17-7.26 (4H, m), 7.43 (2H, d, J=8.1 Hz), 8.07 (1H, dd, J=3.1, 0.6 Hz).

Reference Example 99

1-(Diethoxymethyl)-4-[(E)-2-methyl-3-(4-methylphenoxy)prop-1-en-1-yl]benzene $^1$H-NMR (CDCl$_3$) δ: 1.24 (6H, t, J=7.1 Hz), 1.96 (3H, d, J=1.2 Hz), 2.29 (3H, s), 3.50-3.67 (4H, m), 4.54 (2H, s), 5.50 (1H, s), 6.62 (1H, brs), 6.87 (2H, dt, J=9.1, 2.4 Hz), 7.09 (2H, d, J=8.3 Hz), 7.29 (2H, d, J=8.3 Hz), 7.44 (2H, d, J=8.3 Hz).

Reference Example 100 tert-Butyl 4-[4-(2-hydroxyethyl)benzyl]piperazine-1-carboxylate (1.44 g), 2-hydroxy-5-methylpyridine (0.737 g), tri-n-butylphosphine (1.76 mL), 1,1'-(azodicarbonyl)-dipiperidine (1.70 g), and THF (16.5 mL) were mixed in a 20 mL process vial. The vial was sealed, and the reaction mixture was heated with microwaves to 55° C. for 10 minutes. The reaction mixture was concentrated under reduced pressure. The residue was purified by silica gel column chromatography (n-hexane/AcOEt =10/1 to 3/10) to give tert-butyl 4-(4-{2-[(5-methylpyridin-2-yl)oxy]ethyl}benzyl)piperazine-1-carboxylate as a pale yellow amorphous (1.01 g).

$^1$H-NMR (CDCl$_3$) δ: 1.45 (9H, s), 2.22 (3H, s), 2.37 (4H, t, J=4.9 Hz), 3.06 (2H, t, J=7.1 Hz), 3.42 (4H, t, J =4.9 Hz), 3.47 (2H, s), 4.46 (2H, t, J=7.1 Hz), 6.63 (1H, d, J=8.3 Hz), 7.22-7.24 (4H, m), 7.36 (1H, dd, J=8.5, 2.4 Hz), 7.93 (1H, s).

The following compound was produced in the same manner as in Reference Example 100 using appropriate starting materials.

Reference Example 101 tert-Butyl 4-(4-{2-[(6-methylpyridin-3-yl)oxy]ethyl}benzyl)piperazine-1-carboxylate $^1$H-NMR (CDCl$_3$) δ: 1.45 (9H, s), 2.39 (4H, t, J=4.9 Hz), 2.48 (3H, s), 3.08 (2H, t, J=7.1 Hz), 3.42 (4H, t, J=4.9 Hz), 3.49 (2H, s), 4.18 (2H, t, J=7.1 Hz), 7.05-7.11 (2H, m), 7.20-7.22 (2H, m), 7.24-7.26 (2H, m), 8.16 (1H, d, J=2.7 Hz).

Reference Example 102

To a toluene (99 mL) solution of 4-bromo-2-fluorobenzaldehyde (10.00 g) was added ethylene glycol (3.30 mL) and toluenesulfonic acid (849 mg), then the resultant mixture was refluxed for 8 hours. The mixture was poured into saturated aqueous NaHCO$_3$, and extracted with AcOEt. The organic layer was washed with water and saturated aqueous NaCl, dried over anhydrous Na$_2$SO$_4$, and evaporated. The residue was purified by silica gel column chromatography (n-hexane/AcOEt=99/1 to 95/5) to afford 2-(4-bromo-2-fluorophenyl)-1,3-dioxolane as a colorless oil (11.046 g).

$^1$H-NMR (CDCl$_3$) δ: 4.02-4.06 (2H, m), 4.11-4.15 (2H, m), 6.03 (1H, s), 7.25-7.32 (2H, m), 7.40-7.42 (1H, m).

Reference Example 103

To a THF (40 mL) solution of 2-(4-bromo-2-fluorophenyl)-1,3-dioxolane (3.29 g) was added Mg (406 mg) and I$_2$ (135 mg), then the resultant mixture was refluxed for 5 hours. After cooling to 0° C., the reaction mixture was added ethylene oxide (12.5 mL, 1.1 M in THF), then the resultant mixture was stirred at 50° C. for 3 hours. The reaction mixture was added ethylene oxide (12.5 mL, 1.1 M in THF), the resultant mixture was stirred at 50° C. over night. The mixture was poured into saturated aqueous NH$_4$Cl, and extracted with AcOEt. The organic layer was washed with water and saturated aqueous NaCl, dried over anhydrous Na$_2$SO$_4$, and evaporated. The residue was purified by silica gel column chromatography (n-hexane/AcOEt=99/1 to 4/1) to afford a colorless oil. To a THF (10 mL) solution of that colorless oil and PPh$_3$ (857 mg) and alpha,alpha,alpha-trifluoro-p-cresol (530 mg) were added DEAD (1.486 mL, 2.2 M in toluene) at 0° C., then the resultant mixture was stirred at room temperature over night. The reaction mixture was evaporated, to the residue was added n-hexane/AcOEt (4/1), then the mixture was filtered, and the filtrate was evaporated. The residue was purified by silica gel column chromatography (n-hexane/AcOEt=1/0 to 9/1) to afford 2-(2-fluoro-4-{2-[4-(trifluoromethyl)phenoxy]ethyl}phenyl)-1,3-dioxolane as a colorless oil (0.552 g).

$^1$H-NMR (CDCl$_3$) δ: 3.11 (2H, t, J=6.7 Hz), 4.03-4.21 (6H, m), 6.07 (1H, s), 6.93 (2H, d, J=8.5 Hz), 7.01 (1H, d, J=11.0 Hz), 7.08 (1H, d, J=7.8 Hz), 7.46-7.54 (3H, m).

Reference Example 104 tert-Butyl 4-{4-[2-(4-iodophenoxy)ethyl]benzyl}piperazine-1-carboxylate (209 mg), potassium cyclopropyltrifluoroborate (86 mg), Pd(OAc)$_2$ (6 mg), di(1-adamantyl)-n-butyl-phosphine (13 mg), Cs$_2$CO$_3$ (391 mg), and toluene/water (10:1) (3.3 mL) were mixed in a 5 mL process vial. The vial was sealed, and the reaction mixture was heated with microwaves to 130° C. for 1 hour. After filtration through a Celite pad, the solvent was removed under reduced pressure. The residue was purified by silica gel column chromatography (n-hexane/AcOEt=1/0 to 0/1) to give tert-butyl 4-{4-[2-(4-cyclopropylphenoxy)ethyl]benzyl}piperazine-1-carboxylate as a pale yellow solid (40 mg).

$^1$H-NMR (CDCl$_3$) δ: 0.57-0.62 (2H, m), 0.85-0.90 (2H, m), 1.45 (9H, s), 1.81-1.86 (1H, m), 2.37 (4H, t, J=5.0 Hz), 3.06 (2H, t, J=7.1 Hz), 3.42 (4H, t, J=5.0 Hz), 3.47 (2H, s), 4.13 (2H, t, J=7.1 Hz), 6.78-6.81 (2H, m), 6.97-7.00 (2H, m), 7.21-7.26 (4H, m).

Reference Example 105

To a THF (100 mL) solution of 1-bromo-4-[2-(4-fluorophenoxy)ethyl]benzene (3.05 g) was added 1.6 M solution of n-BuLi in n-hexane (6.80 mL) dropwise at −70° C. under an argon atmosphere. After stirring for 30 minutes, DMF (1.20 mL) was slowly added at −70° C. The resultant mixture was stirred and slowly warmed to −40° C. for 3 hours. The reaction mixture was quenched by addition of saturated aqueous NH$_4$Cl, and extracted with AcOEt. The organic layer was washed with water, saturated aqueous NaCl, dried over anhydrous MgSO$_4$, and concentrated under reduced pressure. The residue was purified by silica gel column chromatography (n-hexane/AcOEt=9/1 to 1/1) to afford 4-[2-(4-fluorophenoxy)ethyl]benzaldehyde as a light yellow solid (1.63 g).

$^1$H-NMR (DMSO-d$_6$) δ: 3.13 (2H, t, J=6.6 Hz), 4.22 (2H, t, J=6.6 Hz), 6.90-6.98 (2H, m), 7.05-7.15 (2H, m), 7.56 (2H, d, J=8.2 Hz), 7.86 (2H, d, J=8.2 Hz), 9.98 (1H, s).

The following compounds were produced in the same manner as in Reference Example 105 using appropriate starting materials.

Reference Example 106

4-{2-[4-(Propan-2-yl)phenoxy]ethyl}benzaldehyde $^1$H-NMR (CDCl$_3$) δ: 1.24 (6H, d, J=6.9 Hz), 2.85 (1H, septet, J=6.9 Hz), 3.16 (2H, t, J=6.6 Hz), 4.20 (2H, t, J=6.6 Hz), 6.77-6.88 (2H, m), 7.08-7.17 (2H, m), 7.42-7.49 (2H, m), 7.79-7.87 (2H, m), 9.99 (1H, s).

Reference Example 107

4-[2-(4-Methoxyphenoxy)ethyl]benzaldehyde $^1$H-NMR (CDCl$_3$) δ: 3.15 (2H, t, J=6.8 Hz), 3.76 (3H, s), 4.17 (2H, t, J=6.8 Hz), 6.81 (4H, s), 7.45 (2H, d, J=7.9 Hz), 7.82-7.84 (2H, m), 9.99 (1H, s).

Reference Example 108

4-[2-(4-Methylphenoxy)ethyl]benzaldehyde $^1$H-NMR (CDCl$_3$) δ: 2.28 (3H, s), 3.16 (2H, t, J=6.6 Hz), 4.19 (2H, t, J=6.9 Hz), 6.78 (2H, d, J=8.6 Hz), 7.07 (2H, d, J=8.2 Hz), 7.45 (2H, d, J=7.9 Hz), 7.83 (2H, d, J=8.2 Hz), 9.99 (1H, s).

Reference Example 109

4-[2-(4-Ethoxyphenoxy)ethyl]benzaldehyde $^1$H-NMR (CDCl$_3$) δ: 1.38 (3H, t, J=6.9 Hz), 3.15 (2H, t, J=6.9 Hz), 3.97 (2H, q, J=6.9 Hz), 4.17 (2H, t, J=6.9 Hz), 6.81 (4H, s), 7.45 (2H, d, J=8.2 Hz), 7.83 (2H, d, J=8.2 Hz), 9.99 (1H, s).

Reference Example 110

4-[1-(4-Methylphenoxy)propan-2-yl]benzaldehyde $^1$H-NMR (CDCl$_3$) δ: 1.42 (3H, d, J=7.1 Hz), 2.27 (3H, s), 3.27-3.36 (1H, m), 4.01 (1H, dd, J=9.2, 6.7 Hz), 4.07 (1H, dd, J=9.2, 6.7 Hz), 6.76 (2H, d, J=8.5 Hz), 7.06 (2H, d, J=8.5 Hz), 7.45 (2H, d, J=8.2 Hz), 7.84 (2H, dt, J=8.2, 1.7 Hz), 9.99 (1H, s).

Reference Example 111

4-[(E)-4-(4-Methylphenoxy)but-2-en-2-yl]benzaldehyde $^1$H-NMR (CDCl$_3$) δ: 2.16 (3H, d, J=1.0 Hz), 2.30 (3H, s), 4.73-4.75 (2H, m), 6.17-6.21 (1H, m), 6.85 (2H, dt, J=9.1, 2.4

Hz), 7.10 (2H, d, J=8.3 Hz), 7.58 (2H, dt, J=8.5, 1.8 Hz), 7.84 (2H, dt, J=8.5, 1.8 Hz), 10.00 (1H, s).

Reference Example 112

4-[2-(4-Chlorophenoxy)ethyl]-3-fluorobenzaldehyde $^1$H-NMR (CDCl$_3$) δ: 3.20 (2H, t, J=6.6 Hz), 4.19 (2H, t, J=6.6 Hz), 6.80 (2H, d, J=8.8 Hz), 7.22 (2H, d, J=8.8 Hz), 7.48-7.49 (1H, m), 7.56 (1H, d, J=9.8 Hz), 7.63 (1H, d, J=7.6 Hz), 9.96 (1H, d, J=1.5 Hz).

Reference Example 113

To a THF (44 mL) solution of tert-butyl 4-(4-bromo-2-fluorobenzyl)piperazine-1-carboxylate (8.445 g) was added slowly n-BuLi (11.31 mL, 2.6 M in hexane) at −78° C., then the resultant mixture was stirred for 0.5 hour. To the mixture was added slowly DMF (1.927 mL) at −78° C. After stirring for 1 hour at −78° C., then the mixture was stirred at room temperature over night. The mixture was poured into saturated aqueous NH$_4$Cl, and extracted with AcOEt. The organic layer was washed with water and saturated aqueous NaCl, dried over anhydrous Na$_2$SO$_4$, and evaporated. The residue was purified by silica gel column chromatography (n-hexane/AcOEt=9/1 to 2/1) to afford a colorless oil. To a MeOH (13 mL) solution of that colorless oil was added NaBH$_4$ (0.200 g) at 0° C., then the resultant mixture was stirred for 5 hours. To the reaction mixture was added saturated aqueous NaHCO$_3$, and extracted with AcOEt. The organic layer was washed with saturated aqueous NaCl, dried over anhydrous Na$_2$SO$_4$, and concentrated under reduced pressure. The residue was purified by silica gel column chromatography (n-hexane/AcOEt=3/1 to 1/1) to afford tert-butyl 4-[2-fluoro-4-(hydroxymethyl)benzyl]piperazine-1-carboxylate as a colorless oil (0.500 g).

$^1$H-NMR (CDCl$_3$) δ: 1.45 (9H, s), 1.70-1.80 (1H, m), 2.41-2.42 (4H, m), 3.42-3.43 (4H, m), 3.58 (2H, s), 4.69 (2H, s), 7.06-7.12 (2H, m), 7.33-7.37 (1H, m).

Reference Example 114

To a THF (53 mL) solution of tert-butyl 4-(4-bromo-2-fluorobenzyl)piperazine-1-carboxylate (5.331 g) was added slowly n-BuLi (11.48 mL, 2.6 M in hexane) at −78° C., then the resultant mixture was stirred for 0.5 hour. To the mixture was added slowly DMF (1.681 mL) at −78° C., then the resultant mixture was stirred for 2 hours. The mixture was poured into saturated aqueous NH$_4$Cl, and extracted with AcOEt. The organic layer was washed with water and saturated aqueous NaCl, dried over anhydrous Na$_2$SO$_4$, and evaporated. The residue was purified by silica gel column chromatography (n-hexane/AcOEt=95/5 to 67/33) to afford a colorless oil. To a CH$_2$Cl$_2$ (25 mL) solution of that colorless oil and tert-butyl 1-piperazinecarboxylate (3.42 g) were added NaBH(OAc)$_3$ (5.310 g) at 0° C. The resultant mixture was stirred at room temperature over night. To the reaction mixture was added saturated aqueous NaHCO$_3$, and extracted with CH$_2$Cl$_2$. The organic layer was washed with saturated aqueous NaCl, dried over anhydrous MgSO$_4$, and concentrated under reduced pressure. The residue was purified by silica gel column chromatography (n-hexane/AcOEt=67/33 to 33/67) to afford a colorless oil. To a THF (25 mL) solution of that colorless oil was added TBAF (25.05 mL, 1.0 M in THF) at 0° C. The resultant mixture was stirred at room temperature for 1 hour. After cooling to 0° C., the reaction mixture was diluted with AcOEt and water. The organic layer was washed with saturated aqueous NaCl, dried over anhydrous Na$_2$SO$_4$, and concentrated under reduced pressure. The residue was purified by silica gel column chromatography (n-hexane/AcOEt=67/33 to 1/4) to afford tert-butyl 4-[3-fluoro-4-(hydroxymethyl)benzyl]piperazine-1-carboxylate as a colorless oil (2.303 g).

$^1$H-NMR (CDCl$_3$) δ: 1.45 (9H, s), 1.78-1.80 (1H, m), 2.37-2.38 (4H, m), 3.42-3.43 (4H, m), 3.49 (2H, s), 4.74 (2H, s), 7.05-7.10 (2H, m), 7.33-7.38 (1H, m).

Reference Example 115

To a solution of {4-[2-(4-methylphenoxy)propyl]phenyl}methanol (0.725 g) in THF (20 mL) were added CCl$_4$ (2.3 mL) and PPh$_3$ (1.640 g) at room temperature under an Ar atmosphere. The mixture was heated at reflux for 6.5 hours, and then cooled to room temperature, and evaporated under reduced pressure. The residue was purified by silica gel column chromatography (n-hexane/AcOEt=5/1) to afford 1-[4-(chloromethyl)phenyl]propan-2-yl 4-methylphenyl ether (0.696 g) as a colorless oil.

$^1$H-NMR (CDCl$_3$) δ: 1.28 (3H, d, J=6.1 Hz), 2.27 (3H, s), 2.81 (1H, dd, J=13.7, 6.6 Hz), 3.07 (1H, dd, J=13.7, 6.1 Hz), 4.47-4.55 (1H, m), 4.57 (2H, s), 6.78 (2H, dt, J=9.1, 2.5 Hz), 7.06 (2H, d, J=8.5 Hz), 7.23 (2H, d, J=8.3 Hz), 7.31 (2H, d, J=8.3 Hz).

The following compounds were produced in the same manner as in Reference Example 115 using appropriate starting materials.

Reference Example 116

2-[4-(Chloromethyl)-2-methylphenyl]ethyl 4-methylphenyl ether $^1$H-NMR (CDCl$_3$) δ: 2.28 (3H, s), 2.37 (3H, s), 3.09 (2H, t, J=7.3 Hz), 4.11 (2H, t, J=7.3 Hz), 4.55 (2H, s), 6.79 (2H, dt, J=9.2, 2.6 Hz), 7.07 (2H, dd, J=8.8, 0.5 Hz), 7.16-7.23 (3H, m).

Reference Example 117

2-[4-(Chloromethyl)-2-methylphenyl]ethyl 4-fluorophenyl ether $^1$H-NMR (CDCl$_3$) δ: 2.37 (3H, s), 3.09 (2H, t, J=7.2 Hz), 4.09 (2H, t, J=7.2 Hz), 4.55 (2H, s), 6.79-6.84 (2H, m), 6.92-6.99 (2H, m), 7.17-7.22 (3H, m).

Reference Example 118

(E)-3-[4-(Chloromethyl)-2-methylphenyl]prop-2-en-1-yl 4-methylphenyl ether $^1$H-NMR (CDCl$_3$) δ: 2.29 (3H, s), 2.34 (3H, s), 4.55 (2H, s), 4.69 (2H, dd, J=5.9, 1.5 Hz), 6.30 (1H, dt, J=15.9, 5.9 Hz), 6.86 (2H, dt, J=9.3, 2.5 Hz), 6.91 (1H, d, J=15.9 Hz), 7.09 (2H, d, J=8.8 Hz), 7.17-7.20 (2H, m), 7.46 (1H, d, J=7.8 Hz).

Reference Example 119

(E)-3-[4-(Chloromethyl)-3-methylphenyl]prop-2-en-1-yl 4-methylphenyl ether $^1$H-NMR (CDCl$_3$) δ: 2.29 (3H, s), 2.42 (3H, s), 4.60 (2H, s), 4.67 (2H, dd, J=5.7, 1.6 Hz), 6.41 (1H, dt, J=16.0, 5.7 Hz), 6.68 (1H, d, J=16.0 Hz), 6.85 (2H, dt, J=9.2, 2.4 Hz), 7.09 (2H, d, J=8.8 Hz), 7.21-7.35 (3H, m).

Reference Example 120

1-(Chloromethyl)-2-methyl-4-[2-(4-methylphenoxy)ethyl]benzene $^1$H-NMR (CDCl$_3$) δ: 2.28 (3H, s), 2.42 (3H, s), 3.04 (2H, t, J=7.2 Hz), 4.13 (2H, t, J=7.2 Hz), 4.60 (2H, s), 6.79 (2H, dt, J=9.3, 2.6 Hz), 7.06-7.12 (4H, m), 7.24 (1H, brs).

Reference Example 121

To a CH$_3$CN (250 mL) solution of piperazine-1-carboxylic acid tert-butyl ester (19.8 g) and alpha,alpha-dichloro-p-xylene (18.6 g) was added DIPEA (18.5 mL) under a N$_2$ atmosphere, then the resultant mixture was stirred at room temperature for 3 days. The reaction mixture was poured into saturated aqueous NaHCO$_3$ (600 mL) and extracted with AcOEt (900 mL). The organic layer was washed with saturated aqueous NaCl (300 mL), dried over anhydrous MgSO$_4$, and concentrated under reduced pressure. The residue was purified by silica gel column chromatography (n-hexane/AcOEt=3/1) to afford tert-butyl 4-[4-(chloromethyl)benzyl]piperazine-1-carboxylate (16.3 g) as a white powder.

$^1$H-NMR (CDCl$_3$) δ: 1.45 (9H, s), 2.36-2.39 (4H, m), 3.40-3.44 (4H, m), 3.50 (2H, s), 4.58 (2H, s), 7.26-7.36 (4H, m).

The following compounds were produced in the same manner as in Reference Example 121 using appropriate starting materials.

Reference Example 122 tert-Butyl 4-{4-[2-(4-methylphenoxy)propyl]benzyl}piperazine-1-carboxylate $^1$H-NMR (CDCl$_3$) δ: 1.28 (3H, d, J=6.1 Hz), 1.45 (9H, s), 2.27 (3H, s), 2.36 (4H, t, J=4.9 Hz), 2.78 (1H, dd, J=13.7, 6.7 Hz), 3.06 (1H, dd, J=13.7, 6.1 Hz), 3.41 (4H, t, J=4.9 Hz), 3.47 (2H, s), 4.47-4.54 (1H, m), 6.77 (2H, dt, J=9.4, 2.6 Hz), 7.05 (2H, dd, J=8.7, 0.6 Hz), 7.18 (2H, d, J=8.3 Hz), 7.22 (2H, d, J=8.3 Hz).

Reference Example 123 tert-Butyl 4-{3-methyl-4-[2-(4-methylphenoxy)ethyl]benzyl}piperazine-1-carboxylate $^1$H-NMR (CDCl$_3$) δ: 1.45 (9H, s), 2.28 (3H, s), 2.35 (3H, s), 2.38 (4H, t, J=5.0 Hz), 3.08 (2H, t, J=7.4 Hz), 3.41-3.46 (6H, m), 4.10 (2H, t, J=7.4 Hz), 6.79 (2H, dt, J=9.1, 2.4 Hz), 7.05-7.11 (4H, m), 7.16 (1H, d, J=7.6 Hz).

Reference Example 124 tert-Butyl 4-{4-[2-(4-fluorophenoxy)ethyl]-3-methylbenzyl}piperazine-1-carboxylate $^1$H-NMR (CDCl$_3$) δ: 1.45 (9H, s), 2.35 (3H, s), 2.37 (4H, J=5.0 Hz), 3.07 (2H, t, J=7.3 Hz), 3.42 (4H, t, J=5.0 Hz), 3.45 (2H, s), 4.09 (2H, t, J=7.3 Hz), 6.79-6.85 (2H, m), 6.92-6.99 (2H, m), 7.09-7.17 (3H, m).

Reference Example 125 tert-Butyl 4-{2-methyl-4-[2-(4-methylphenoxy)ethyl]benzyl}piperazine-1-carboxylate $^1$H-NMR (CDCl$_3$) δ: 1.45 (9H, s), 2.28 (3H, s), 2.34 (3H, s), 2.37 (4H, t, J=4.9 Hz), 3.03 (2H, t, J=7.2 Hz), 3.39 (4H, t, J=4.9 Hz), 3.43 (2H, s), 4.13 (2H, t, J=7.2 Hz), 6.80 (2H, dt, J=9.2, 2.5 Hz), 6.98-7.07 (4H, m), 7.17 (1H, d, J=7.6 Hz).

Reference Example 126

To a solution of tert-butyl 4-[4-(chloromethyl)benzyl]piperazine-1-carboxylate (4.00 g) in DMF (25 mL) were added 4-isopropoxyphenol (2.81 g) and K$_2$CO$_3$ (3.40 g) at room temperature, then the reaction mixture was stirred for 2 days. The reaction mixture was diluted with H$_2$O, and extracted with AcOEt. The organic layer was washed with water and saturated aqueous NaCl, dried over anhydrous Na$_2$SO$_4$, and concentrated under reduced pressure. The residue was purified by silica gel column chromatography (n-hexane/AcOEt=3/1 to 1/1) to afford tert-butyl 4-(4-{[4-(propan-2-yloxy)phenoxy]methyl}benzyl)piperazine-1-carboxylate as a colorless solid (5.42 g).

$^1$H-NMR (CDCl$_3$) δ: 1.30 (6H, d, J=5.9 Hz), 1.45 (9H, s), 2.39 (4H, t, J=4.9 Hz), 3.42 (4H, t, J=4.9 Hz), 3.51 (2H, s), 4.42 (1H, septet, J=5.9 Hz), 4.99 (2H, s), 6.80-6.96 (4H, m), 7.29-7.43 (4H, m).

The following compounds were produced in the same manner as in Reference Example 126 using appropriate starting materials.

Reference Example 127 tert-Butyl 4-{4-[(4-chlorophenoxy)methyl]benzyl}piperazine-1-carboxylate $^1$H-NMR (CDCl$_3$) δ: 1.45 (9H, s), 2.38 (4H, t, J=4.9 Hz), 3.42 (4H, t, J=4.9 Hz), 3.51 (2H, s), 5.01 (2H, s), 6.86-6.93 (2H, m), 7.20-7.26 (2H, m), 7.31-7.39 (4H, m).

Reference Example 128 tert-Butyl 4-(4-{[4-(propan-2-yl)phenoxy]methyl}benzyl)piperazine-1-carboxylate $^1$H-NMR (CDCl$_3$) δ: 1.22 (6H, d, J=6.9 Hz), 1.45 (9H, s), 2.38 (4H, t, J=4.9 Hz), 2.86 (1H, septet, J=6.9 Hz), 3.42 (4H, t, J=4.9 Hz), 3.51 (2H, s), 5.01 (2H, s), 6.89-6.94 (2H, m), 7.13-7.17 (2H, m), 7.32 (2H, d, J=8.2 Hz), 7.38 (2H, d, J=8.2 Hz).

Reference Example 129 tert-Butyl 4-(4-{[4-(1H-pyrrol-1-yl)phenoxy]methyl}benzyl)piperazine-1-carboxylate $^1$H-NMR (CDCl$_3$) δ: 1.46 (9H, s), 2.39 (4H, t, J=5.0 Hz), 3.43 (4H, t, J=5.0 Hz), 3.52 (2H, s), 5.06 (2H, s), 6.31-6.33 (2H, m), 6.99-7.04 (4H, m), 7.31 (2H, d, J=8.9 Hz), 7.35 (2H, d, J=8.2 Hz), 7.40 (2H, d, J=8.2 Hz).

Reference Example 130 tert-Butyl 4-{4-[(4-fluorophenoxy)methyl]benzyl}piperazine-1-carboxylate $^1$H-NMR (DMSO-d$_6$) δ: 1.39 (9H, s), 2.29 (4H, t, J=4.9 Hz), 3.28-3.31 (4H, m), 3.47 (2H, s), 5.05 (2H, s), 6.98-7.05 (2H, m), 7.07-7.15 (2H, m), 7.31 (2H, d, J=7.9 Hz), 7.39 (2H, d, J=7.9 Hz).

Reference Example 131 tert-Butyl 4-{4-[(4-methoxyphenoxy)methyl]benzyl}piperazine-1-carboxylate $^1$H-NMR (CDCl$_3$) δ: 1.45 (9H, s), 2.38 (4H, t, J=4.9 Hz), 3.42 (4H, t, J=4.9 Hz), 3.51 (2H, s), 3.77 (3H, s), 4.99 (2H, s), 6.75-6.96 (4H, m), 7.29-7.43 (4H, m).

Reference Example 132 tert-Butyl 4-{4-[(4-ethoxyphenoxy)methyl]benzyl}piperazine-1-carboxylate $^1$H-NMR (CDCl$_3$) δ: 1.38 (3H, t, J=6.9 Hz), 1.45 (9H, s), 2.38 (4H, t, J=4.9 Hz), 3.42 (4H, t, J=4.9 Hz), 3.51 (2H, s), 3.97 (2H, q, J=6.9 Hz), 4.99 (2H, s), 6.70-6.95 (4H, m), 7.28-7.43 (4H, m).

Reference Example 133 tert-Butyl 4-{4-[(1,3-benzodioxol-5-yloxy)methyl]benzyl}piperazine-1-carboxylate $^1$H-NMR (CDCl$_3$) δ: 1.45 (9H, s), 2.38 (4H, t, J=4.9 Hz), 3.42 (4H, t, J=4.9 Hz), 3.51 (2H, s), 4.96 (2H, s), 5.91 (2H, s), 6.39 (1H, dd, J=8.6, 2.3 Hz), 6.56 (1H, d, J=2.3 Hz), 6.70 (1H, d, J=8.6 Hz), 7.30-7.38 (4H, m).

Reference Example 134 tert-Butyl 4-{4-[2-(4-fluorophenyl)-2-oxoethoxy]benzyl}piperazine-1-carboxylate $^1$H-NMR (CDCl$_3$) δ: 1.45 (9H, s), 2.35 (4H, t, J=5.3 Hz), 3.35-3.48 (6H, m), 5.20 (2H, s), 6.83-6.93 (2H, m), 7.12-7.27 (4H, m), 8.00-8.10 (2H, m).

Reference Example 135 tert-Butyl 4-{4-[2-(4-chlorophenoxy)ethoxy]benzyl}piperazine-1-carboxylate $^1$H-NMR (CDCl$_3$) δ: 1.45 (9H, s), 2.36 (4H, t, J=4.9 Hz), 3.41 (4H, t, J=4.9 Hz), 3.44 (2H, s), 4.25-4.30 (4H, m), 6.84-6.90 (4H, m), 7.21-7.26 (4H, m).

Reference Example 136 tert-Butyl 4-{4-[2-(4-methylphenoxy)ethoxy]benzyl}piperazine-1-carboxylate $^1$H-NMR (CDCl$_3$) δ: 1.45 (9H, s), 2.29 (3H, s), 2.36 (4H, brs), 3.41 (4H, t, J=4.9 Hz), 3.45 (2H, s), 4.30 (4H, s), 6.85 (2H, d, J=8.5 Hz), 6.90 (2H, d, J=8.5 Hz), 7.09 (2H, d, J=8.5 Hz), 7.22 (2H, d, J=8.5 Hz).

Reference Example 137 tert-Butyl 4-{4-[2-(4-ethoxyphenoxy)ethoxy]benzyl}piperazine-1-carboxylate $^1$H-NMR (CDCl$_3$) δ: 1.38 (3H, t, J=7.0 Hz), 1.45 (9H, s), 2.35 (4H, t, J=4.9 Hz), 3.41 (4H, t, J=4.9 Hz), 3.43 (2H, s), 3.97 (2H, q, J=7.0 Hz), 4.24-4.28 (4H, m), 6.81-6.90 (6H, m), 7.20-7.22 (2H, m).

Reference Example 138 tert-Butyl 4-{4-[2-(4-methoxyphenoxy)ethoxy]benzyl}piperazine-1-carboxylate $^1$H-NMR (CDCl$_3$) δ: 1.45 (9H, s), 2.35 (4H, t, J=4.9 Hz), 3.40-3.43 (6H, m), 3.74 (3H, s), 4.23-4.27 (4H, m), 6.81-6.84 (2H, m), 6.86-6.90 (4H, m), 7.21 (2H, d, J=8.8 Hz).

Reference Example 139 tert-Butyl 4-{4-[(1-ethoxy-2-methyl-1-oxopropan-2-yl)oxy]-3-fluorobenzyl}piperazine-1-carboxylate $^1$H-NMR (CDCl$_3$) δ: 1.29 (3H, t, J=7.2 Hz), 1.45 (9H, s), 1.57 (6H, s), 2.34-2.37 (4H, m), 3.41-3.43 (6H, m), 4.25 (2H, q, J=7.2 Hz), 6.91-6.92 (2H, m), 7.07 (1H, d, J=12.2 Hz).

Reference Example 140

Ethyl 4-[(4-methylphenoxy)acetyl]benzoate $^1$H-NMR (CDCl$_3$) δ: 1.42 (3H, t, J=7.1 Hz), 2.28 (3H, s), 4.42 (2H, q, J=7.1 Hz), 5.23 (2H, s), 6.82-6.86 (2H, m), 7.06-7.10 (2H, m), 8.04-8.06 (2H, m), 8.14-8.16 (2H, m).

Reference Example 141

To a DMF (10 mL) solution of tert-butyl 4-[4-(2-hydroxyethyl)benzyl]piperazine-1-carboxylate (1.000 g) was added NaH (112 mg, 60% in mineral oil) at 0° C., then the resultant mixture was stirred for 1 hour. To the mixture was added 2-fluoro-6-methylpyridine (0.419 mL), then the resultant mixture was stirred at 70° C. over night. The mixture was poured into water, and extracted with AcOEt. The organic layer was washed with water and saturated aqueous NaCl, dried over anhydrous Na$_2$SO$_4$, and evaporated. The residue was purified by silica gel column chromatography (n-hexane/AcOEt=4/1 to 1/1) to afford tert-butyl 4-(4-{2-[(6-methylpyridin-2-yl)oxy]ethyl}benzyl)piperazine-1-carboxylate as a pale yellow amorphous powder (350 mg).

$^1$H-NMR (CDCl$_3$) δ: 1.45 (9H, s), 2.37-2.38 (4H, m), 2.42 (3H, s), 3.06 (2H, t, J=7.2 Hz), 3.41-3.42 (4H, m), 3.48 (2H, s), 4.48 (2H, t, J=7.2 Hz), 6.50 (1H, d, J=8.1 Hz), 6.69 (1H, d, J=7.1 Hz), 7.24-7.26 (4H, m), 7.42-7.44 (1H, m).

The following compounds were produced in the same manner as in Reference Example 141 using appropriate starting materials.

Reference Example 142 tert-Butyl 4-(4-{[(4-fluorobenzyl)oxy]methyl}benzyl)piperazine-1-carboxylate $^1$H-NMR (DMSO-d$_6$) δ: 1.38 (9H, s), 2.29 (4H, t, J=4.9 Hz), 3.30 (4H, t, J=4.9 Hz), 3.46 (2H, s), 4.50 (2H, s), 4.50 (2H, s), 7.14-7.22 (2H, m), 7.25-7.33 (4H, m), 7.36-7.42 (2H, m).

Reference Example 143 tert-Butyl 4-[4-({[4-(propan-2-yl)benzyl]oxy}methyl)benzyl]piperazine-1-carboxylate $^1$H-NMR (CDCl$_3$) δ: 1.25 (6H, d, J=6.9 Hz), 1.45 (9H, s), 2.37 (4H, t, J=4.9 Hz), 2.91 (1H, septet, J=6.9 Hz), 3.42 (4H, t, J=4.9 Hz), 3.50 (2H, s), 4.53 (2H, s), 4.53 (2H, s), 7.20-7.34 (8H, m).

Reference Example 144 tert-Butyl 4-[4-(2-{[5-(trifluoromethyl)pyridin-2-yl]oxy}ethyl)benzyl]piperazine-1-carboxylate $^1$H-NMR (CDCl$_3$) δ: 1.45 (9H, s), 2.37 (4H, t, J=5.1 Hz), 3.08 (2H, t, J=7.1 Hz), 3.42 (4H, t, J=5.1 Hz), 3.48 (2H, s), 4.57 (2H, t, J=7.1 Hz), 6.80 (1H, d, J=8.9 Hz), 7.21-7.27 (4H, m), 7.75 (1H, dd, J=8.9, 2.5 Hz), 8.42 (1H, brs).

Reference Example 145 tert-Butyl 4-{4-[2-(4-nitrophenoxy)ethyl]benzyl}piperazine-1-carboxylate $^1$H-NMR (CDCl$_3$) δ: 1.45 (9H, s), 2.38 (4H, t, J=4.9 Hz), 3.11-3.14 (2H, m), 3.42 (4H, t, J=4.9 Hz), 3.49 (2H, brs), 4.24-4.27 (2H, m), 6.94 (2H, d, J=9.3 Hz), 7.23 (2H, d, J=8.3 Hz), 7.28 (2H, d, J=8.8 Hz), 8.19 (2H, d, J=9.3 Hz).

Reference Example 146

To a dioxane (10 mL) solution of 4-bromo-2-chlorophenol (207 mg) were added n-butyl acrylate (0.158 mL), N-methyldicyclohexylamine (0.236 mL), tri-tert-butylphosphonium tetrafluoroborate (12 mg), and tris(dibenzylideneacetone)dipalladium (0) (18 mg) under a N$_2$ atmosphere. The resultant mixture was refluxed over night. After cooling, the reaction mixture was filtered off on Celite, and the filtrate was concentrated under reduced pressure. The residue was purified by silica gel column chromatography (n-hexane/AcOEt=4/1 to 2/1) to afford butyl (E)-3-(3-chloro-4-hydroxyphenyl)prop-2-enoate (244 mg) as a colorless oil.

$^1$H-NMR (CDCl$_3$) δ: 0.96 (3H, t, J=7.8 Hz), 1.36-1.49 (2H, m), 1.62-1.74 (2H, m), 4.20 (2H, t, J=6.9 Hz), 5.84 (1H, s), 6.31 (1H, d, J=15.6 Hz), 7.02 (1H, d, J=8.2 Hz), 7.36 (1H, dd, J=8.7, 2.3 Hz), 7.52 (1H, d, J=1.8 Hz), 7.55 (1H, d, J=16.0 Hz).

The following compounds were produced in the same manner as in Reference Example 146 using appropriate starting materials.

Reference Example 147

Butyl (E)-3-(4-hydroxy-3-methylphenyl)prop-2-enoate $^1$H-NMR (CDCl$_3$) δ: 0.96 (3H, t, J=7.3 Hz), 1.42-1.46 (2H, m), 1.63-1.73 (2H, m), 2.26 (3H, s), 4.20 (2H, t, J=6.6 Hz), 5.01 (1H, s), 6.29 (1H, d, J=16.2 Hz), 6.77 (1H, d, J=8.2 Hz), 7.25-7.32 (2H, m), 7.60 (1H, d, J=16.2 Hz).

Reference Example 148

Butyl (E)-3-(4-hydroxy-2-methylphenyl)prop-2-enoate $^1$H-NMR (CDCl$_3$) δ: 0.96 (3H, t, J=7.3 Hz), 1.37-1.50 (2H, m), 1.64-1.74 (2H, m), 2.38 (3H, s), 4.21 (2H, t, J=6.6 Hz), 5.41-5.44 (1H, m), 6.26 (1H, d, J=15.8 Hz), 6.67-6.71 (2H, m), 7.47-7.50 (1H, m), 7.91 (1H, d, J=15.8 Hz).

Reference Example 149

Butyl (E)-3-(3-fluoro-4-hydroxyphenyl)prop-2-enoate $^1$H-NMR (CDCl$_3$) δ: 0.96 (3H, t, J=7.3 Hz), 1.39-1.48 (2H, m), 1.65-1.72 (2H, m), 4.20 (2H, t, J=6.6 Hz), 5.51 (1H, s), 6.30 (1H, d, J=16.1 Hz), 6.99-7.03 (1H, m), 7.21-7.29 (2H, m), 7.57 (1H, d, J=16.1 Hz).

Reference Example 150

Butyl (E)-3-[4-({[tert-butyl(dimethyl)silyl]oxy}methyl)-2-methylphenyl]prop-2-enoate $^1$H-NMR (CDCl$_3$) δ: 0.10 (6H, s), 0.95 (9H, s), 0.97 (3H, t, J=8.1 Hz), 1.40-1.49 (2H, m), 1.66-1.73 (2H, m), 2.43 (3H, s), 4.21 (2H, t, J=6.6 Hz), 4.71 (2H, s), 6.35 (1H, d, J=15.9 Hz), 7.15-7.18 (2H, m), 7.53 (1H, d, J=7.8 Hz), 7.96 (1H, d, J=15.9 Hz).

Reference Example 151

Butyl (E)-3-[4-({[tert-butyl(dimethyl)silyl]oxy}methyl)-3-methylphenyl]prop-2-enoate $^1$H-NMR (CDCl$_3$) δ: 0.11 (6H, s), 0.95 (9H, s), 0.97 (3H, t, J=7.2 Hz), 1.39-1.49 (2H, m), 1.65-1.72 (2H, m), 2.27 (3H, s), 4.20 (2H, t, J=6.7 Hz), 4.70 (2H, s), 6.41 (1H, d, J=16.1 Hz), 7.29 (1H, brs), 7.37 (1H, dd, J=7.9, 1.6 Hz), 7.45 (1H, d, J=7.9 Hz), 7.65 (1H, d, J=16.1 Hz).

Reference Example 152

To a DMF (30 mL) solution of 2-chloro-4-bromo-6-methylphenol (4.90 g) were added 2-chloro-5-nitropyridine (3.58 g) and K$_2$CO$_3$ (3.12 g) at room temperature. After stirring at 50° C. for 3 hours, the solvent was removed under reduced pressure. To the residue was added water, and extracted with AcOEt. The organic layer was washed with water, saturated aqueous NaCl, dried over anhydrous Na$_2$SO$_4$, and concentrated under reduced pressure to give 2-(4-bromo-2-chloro-6-methylphenoxy)-5-nitropyridine as a brown solid (7.59 g).

$^1$H-NMR (CDCl$_3$) δ: 2.17 (3H, s), 7.16 (1H, d, J=8.8 Hz), 7.36-7.37 (1H, m), 7.48-7.49 (1H, m), 8.53 (1H, dd, J=8.8, 2.8 Hz), 8.98 (1H, d, J=2.8 Hz).

The following compounds were produced in the same manner as in Reference Example 152 using appropriate starting materials.

Reference Example 153

Butyl (E)-3-{3-methyl-4-[(5-nitropyridin-2-yl)oxy]phenyl}prop-2-enoate $^1$H-NMR (CDCl$_3$) δ: 0.97 (3H, t, J=7.3 Hz), 1.38-1.52 (2H, m), 1.65-1.75 (2H, m), 2.18 (3H, s), 4.22 (2H, q, J=6.6 Hz), 6.42 (1H, d, J=15.8 Hz), 7.07-7.11 (2H, m), 7.43-7.48 (2H, m), 7.67 (1H, d, J=16.2 Hz), 8.48-8.53 (1H, m), 9.02 (1H, d, J=3.0 Hz).

Reference Example 154

Ethyl (E)-3-({3-methoxy-4-[(5-nitropyridin-2-yl)oxy]phenyl}prop-2-enoate $^1$H-NMR (CDCl$_3$) δ: 1.36 (3H, t, J=7.1 Hz), 3.78 (3H, s), 4.28 (2H, q, J=7.2 Hz), 6.42 (1H, d, J=16.1 Hz), 7.09 (1H, d, J=9.3 Hz), 7.16-7.22 (3H, m), 7.68 (1H, d, J=16.1 Hz), 8.49 (1H, dd, J=9.0, 2.7 Hz), 9.00 (1H, d, J=2.9 Hz).

Reference Example 155

3,5-Dimethoxy-4-[(5-nitropyridin-2-yl)oxy]benzaldehyde $^1$H-NMR (CDCl$_3$) δ: 3.87 (6H, s), 7.17 (1H, d, J=9.0 Hz), 7.24 (2H, s), 8.50 (1H, dd, J=9.0, 2.7 Hz), 8.96 (1H, d, J=2.7 Hz), 9.96 (1H, brs).

Reference Example 156

Butyl (E)-3-{2-methyl-4-[(5-nitropyridin-2-yl)oxy]phenyl}prop-2-enoate $^1$H-NMR (CDCl$_3$) δ: 0.97 (3H, t, J=7.3 Hz), 1.38-1.51 (2H, m), 1.63-1.76 (2H, m), 2.46 (3H, s), 4.22 (2H, t, J=6.9 Hz), 6.36 (1H, d, J=15.8 Hz), 7.00-7.08 (3H, m), 7.62-7.66 (1H, m), 7.94 (1H, d, J=15.8 Hz), 8.50 (1H, dd, J=8.9, 2.6 Hz), 9.05 (1H, d, J=2.6 Hz).

Reference Example 157

Methyl 2-[4-(propan-2-yl)phenoxy]quinoline-6-carboxylate $^1$H-NMR (CDCl$_3$) δ: 1.30 (6H, d, J=6.9 Hz), 2.97 (1H, septet, J=6.9 Hz), 3.97 (3H, s), 7.10-7.22 (3H, m), 7.24-7.34 (2H, m), 7.81 (1H, d, J=8.9 Hz), 8.19 (1H, d, J=8.9 Hz), 8.20 (1H, dd, J=8.9, 2.0 Hz), 8.51 (1H, d, J=2.0 Hz).

Reference Example 158

Methyl 2-(4-methoxyphenoxy)quinoline-6-carboxylate $^1$H-NMR (CDCl$_3$) δ: 3.85 (3H, s), 3.97 (3H, s), 6.92-7.01 (2H, m), 7.12 (1H, d, J=8.6 Hz), 7.15-7.22 (2H, m), 7.79 (1H, d, J=8.9 Hz), 8.18 (1H, d, J=8.9 Hz), 8.21 (1H, dd, J=8.9, 2.0 Hz), 8.50 (1H, d, J=1.6 Hz).

Reference Example 159

Butyl (E)-3-{3-chloro-4-[(5-nitropyridin-2-yl)oxy]phenyl}prop-2-enoate $^1$H-NMR (CDCl$_3$) δ: 0.97 (3H, t, J=7.3 Hz), 1.38-1.51 (2H, m), 1.66-1.76 (2H, m), 4.23 (2H, t, J=6.8 Hz), 6.44 (1H, d, J=16.1 Hz), 7.17 (1H, d, J=9.8 Hz), 7.26 (1H, d, J=8.3 Hz), 7.51 (1H, dd, J=8.3, 2.0 Hz), 7.64 (1H, d, J=16.1 Hz), 7.67 (1H, d, J=2.0 Hz), 8.54 (1H, dd, J=8.8, 2.4 Hz), 9.00 (1H, d, J=2.9 Hz).

Reference Example 160

Butyl (E)-3-{3-fluoro-4-[(5-nitropyridin-2-yl)oxy]phenyl}prop-2-enoate $^1$H-NMR (CDCl$_3$) δ: 0.97 (3H, t, J=7.3 Hz), 1.40-1.49 (2H, m), 1.67-1.74 (2H, m), 4.23 (2H, t, J=6.8 Hz), 6.42 (1H, d, J=15.6 Hz), 7.17 (1H, d, J=9.3 Hz), 7.27 (1H, t, J=8.1 Hz), 7.37-7.41 (2H, m), 7.64 (1H, d, J=16.1 Hz), 8.54 (1H, dd, J=9.0, 2.7 Hz), 9.01 (1H, d, J=2.9 Hz).

Reference Example 161

Ethyl 6-[(5-nitropyridin-2-yl)oxy]naphthalene-2-carboxylate $^1$H-NMR (CDCl$_3$) δ: 1.46 (3H, t, J=7.1 Hz), 4.46 (2H, q, J=7.2 Hz), 7.14 (1H, dd, J=9.0, 0.5 Hz), 7.36 (1H, dd, J=8.9, 2.3 Hz), 7.67 (1H, d, J=2.4 Hz), 7.86 (1H, d, J=8.8 Hz), 8.04 (1H, d, J=9.0 Hz), 8.11 (1H, dd, J=8.7, 1.6 Hz), 8.53 (1H, dd, J=9.0, 2.7 Hz), 8.65 (1H, d, J=0.5 Hz), 9.05 (1H, dd, J=2.9, 0.5 Hz).

Reference Example 162

3,5-Dimethyl-4-[(5-nitropyridin-2-yl)oxy]benzaldehyde $^1$H-NMR (CDCl$_3$) δ: 2.18 (6H, s), 7.15 (1H, d, J=9.0 Hz), 7.69 (2H, s), 8.54 (1H, dd, J=9.0, 2.7 Hz), 8.98 (1H, d, J=2.7 Hz), 9.98 (1H, brs).

Reference Example 163

2-(4-Bromo-5-chloro-2-methylphenoxy)-5-nitropyridine $^1$H-NMR (CDCl$_3$) δ: 2.11 (3H, s), 7.09 (1H, d, J=9.0 Hz), 7.20 (1H, s), 7.56 (1H, s), 8.51 (1H, dd, J=9.0, 2.9 Hz), 9.01 (1H, d, J=2.9 Hz).

Reference Example 164

2-(4-Bromo-2-chloro-5-methylphenoxy)-5-nitropyridine $^1$H-NMR (CDCl$_3$) δ: 2.40 (3H, s), 7.11-7.14 (2H, m), 7.67 (1H, s), 8.52 (1H, dd, J=9.0, 2.7 Hz), 9.00 (1H, d, J=2.7 Hz).

Reference Example 165

To a THF (39 mL) suspension of LiAlH$_4$ (0.15 g) was slowly added methyl 2-(4-methoxyphenoxy)quinoline-6-carboxylate (1.22 g) at 0° C., then the resultant mixture was stirred over night at room temperature. The reaction mixture was acidified with 6 M aqueous HCl, and extracted with AcOEt. The organic layer was washed with water and saturated aqueous NaCl, dried over anhydrous Na$_2$SO$_4$, and concentrated under reduced pressure to afford [2-(4-methoxyphenoxy)quinolin-6-yl]methanol (1.11 g) as a pale yellow amorphous powder.

$^1$H-NMR (CDCl$_3$) δ: 1.89 (1H, brs), 3.84 (3H, s), 4.84 (2H, s), 6.91-6.99 (2H, m), 7.05 (1H, d, J=8.6 Hz), 7.13-7.22 (2H, m), 7.59 (1H, dd, J=8.6, 2.0 Hz), 7.73 (1H, brs), 7.78 (1H, d, J=8.6 Hz), 8.08 (1H, d, J=8.6 Hz).

The following compounds were produced in the same manner as in Reference Example 165 using appropriate starting materials.

Reference Example 166

{2-[4-(Propan-2-yl)phenoxy]quinolin-6-yl}methanol $^1$H-NMR (CDCl$_3$) δ: 1.29 (6H, d, J=6.9 Hz), 1.65 (1H, brs), 2.96 (1H, septet, J=6.9 Hz), 4.84 (2H, s), 7.05 (1H, d, J=8.9 Hz), 7.13-7.20 (2H, m), 7.24-7.31 (2H, m), 7.60 (1H, dd, J=8.6, 2.0 Hz), 7.71-7.75 (1H, m), 7.80 (1H, d, J=8.9 Hz), 8.08 (1H, d, J=8.9 Hz).

Reference Example 167

1-[4-(Hydroxymethyl)phenyl]-2-(4-methylphenoxy)ethanol $^1$H-NMR (CDCl$_3$) δ: 1.63 (1H, t, J=5.4 Hz), 2.29 (3H, s), 2.77 (1H, d, J=2.6 Hz), 3.97 (1H, dd, J=9.8, 9.0 Hz), 4.08 (1H, dd, J=9.8, 3.2 Hz), 4.72 (2H, d, J=5.4 Hz), 5.12 (1H, dt, J=9.0, 2.6 Hz), 6.80-6.83 (2H, m), 7.06-7.10 (2H, m), 7.40 (2H, d, J=8.1 Hz), 7.46 (2H, d, J=8.1 Hz).

Reference Example 168 tert-Butyl 4-{3-fluoro-4-[(1-hydroxy-2-methylpropan-2-yl)oxy]benzyl}piperazine-1-carboxylate $^1$H-NMR (CDCl$_3$) δ: 1.29 (6H, s), 1.46 (9H, s), 2.33-2.37 (5H, m), 3.43-3.44 (6H, m), 3.58-3.60 (2H, m), 6.99-7.01 (2H, m), 7.10 (1H, d, J=11.2 Hz).

Reference Example 169

To a solution of (E)-ethyl 3-(4-(diethoxymethyl)phenyl)acrylate (1.400 g) in toluene (10 mL) was added DIBAH (1 M solution in toluene) (10 mL) at −20° C. under an Ar atmosphere. The mixture was stirred at −20° C. for 1 hour. To the mixture was added MeOH, and then the mixture was heated to room temperature. To the mixture was added water, and the mixture was extracted with AcOEt. The organic layer was washed with saturated aqueous NaCl, dried over anhydrous Na$_2$SO$_4$, and concentrated under reduced pressure. The residue was purified by silica gel column chromatography (n-hexane/AcOEt=1/1) to afford (E)-3-[4-(diethoxymethyl)phenyl]prop-2-en-1-ol (1.120 g) as a colorless oil.

$^1$H-NMR (CDCl$_3$) δ: 1.24 (6H, t, J=7.1 Hz), 1.42 (1H, t, J=6.0 Hz), 3.49-3.65 (4H, m), 4.33 (2H, td, J=6.0, 1.5 Hz), 5.49 (1H, s), 6.38 (1H, dt, J=16.1, 6.0 Hz), 6.62 (1H, dt, J=16.1, 1.5 Hz), 7.38 (2H, dd, J=6.6, 1.8 Hz), 7.43 (2H, dd, J=6.6, 1.8 Hz).

The following compounds were produced in the same manner as in Reference Example 169 using appropriate starting materials.

Reference Example 170

(E)-3-[4-({[tert-Butyl(dimethyl)silyl]oxy}methyl)-2-methylphenyl]prop-2-en-1-ol $^1$H-NMR (CDCl$_3$) δ: 0.10 (6H, s), 0.94 (9H, s), 1.42 (1H, t, J=6.0 Hz), 2.35 (3H, s), 4.32-4.36 (2H, m), 4.69 (2H, s), 6.25 (1H, dt, J=15.9, 5.8 Hz), 6.81 (1H, d, J=15.9 Hz), 7.10-7.13 (2H, m), 7.42 (1H, d, J=8.1 Hz).

Reference Example 171

(E)-3-[4-({[tert-Butyl(dimethyl)silyl]oxy}methyl)-3-methylphenyl]prop-2-en-1-ol $^1$H-NMR (CDCl$_3$) δ: 0.10 (6H, s), 0.94 (9H, s), 1.40-1.43 (1H, m), 2.26 (3H, s), 4.30-4.33 (2H, m), 4.69 (2H, s), 6.34 (1H, dt, J=15.9, 5.9 Hz), 6.58 (1H, dt, J=15.9, 1.3 Hz), 7.16 (1H, d, J=1.7 Hz), 7.22 (1H, dd, J=8.1, 1.7 Hz), 7.36 (1H, d, J=8.1 Hz).

Reference Example 172

(E)-3-[4-(Diethoxymethyl)phenyl]-2-methylprop-2-en-1-ol $^1$H-NMR (CDCl$_3$) δ: 1.24 (6H, t, J=7.0 Hz), 1.50 (1H, t, J=6.1 Hz), 1.90 (3H, d, J=1.0 Hz), 3.51-3.67 (4H, m), 4.19 (2H, d, J=6.1 Hz), 5.50 (1H, s), 6.52 (1H, brs), 7.28 (2H, d, J=8.3 Hz), 7.44 (2H, d, J=8.3 Hz).

Reference Example 173

To a CH$_2$Cl$_2$ (38 mL) solution of [2-(4-methoxyphenoxy)quinolin-6-yl]methanol (1.11 g) and iodobenzene diacetate (1.33 g) was added 2,2,6,6-tetramethyl-1-piperidinyloxy radical (61.0 mg), then the resultant mixture was stirred over night at room temperature. The reaction mixture was quenched by addition of saturated aqueous Na$_2$S$_2$O$_3$ and NaHCO$_3$, and extracted with CH$_2$Cl$_2$. The organic layer was washed with water and saturated aqueous NaCl, dried over anhydrous Na$_2$SO$_4$, and concentrated under reduced pressure. The residue was purified by silica gel column chromatography (n-hexane/AcOEt=10/1 to 5/1) to afford 2-(4-methoxyphenoxy)quinoline-6-carbaldehyde (1.08 g) as a colorless solid.

$^1$H-NMR (CDCl$_3$) δ: 3.86 (3H, s), 6.92-7.02 (2H, m), 7.13-7.23 (3H, m), 7.85 (1H, d, J=8.6 Hz), 8.08 (1H, dd, J=8.6, 1.6 Hz), 8.23 (1H, d, J=8.9 Hz), 8.26 (1H, d, J=2.0 Hz), 10.13 (1H, s).

The following compounds were produced in the same manner as in Reference Example 173 using appropriate starting materials.

Reference Example 174

2-[4-(Propan-2-yl)phenoxy]quinoline-6-carbaldehyde $^1$H-NMR (CDCl$_3$) δ: 1.30 (6H, d, J=6.9 Hz), 2.98 (1H, septet, J=6.9 Hz), 7.14-7.22 (3H, m), 7.27-734 (2H, m), 7.88 (1H, d, J=8.6 Hz), 8.09 (1H, dd, J=8.6, 2.0 Hz), 8.24 (1H, d, J=8.9 Hz), 8.27 (1H, d, J=2.0 Hz), 10.13 (1H, s).

Reference Example 175

4-[(4-Methylphenoxy)acetyl]benzaldehyde $^1$H-NMR (CDCl$_3$) δ: 2.28 (3H, s), 5.23 (2H, s), 6.82-6.85 (2H, m), 7.07-7.10 (2H, m), 7.98-8.01 (2H, m), 8.13-8.16 (2H, m), 10.11 (1H, s).

Reference Example 176

To a solution of 1-(diethoxymethyl)-4-[(E)-3-(4-methylphenoxy)prop-1-en-1-yl]benzene (1.270 g) in THF (20 mL) was added 6 M HCl (4 mL) at room temperature. The mixture was stirred at room temperature for 0.5 hour. To the mixture was added 5 M NaOH (4 mL), and the mixture was evaporated under reduced pressure. To the residue was added saturated aqueous NaHCO$_3$, and the mixture was extracted with AcOEt. The organic layer was washed with saturated aqueous NaCl, dried over anhydrous Na$_2$SO$_4$, and concentrated under reduced pressure to afford 4-[(E)-3-(4-methylphenoxy)prop-1-en-1-yl]benzaldehyde (0.942 g) as a colorless solid.

$^1$H-NMR (CDCl$_3$) δ: 2.30 (3H, s), 4.72 (2H, dd, J=5.4, 1.8 Hz), 6.58 (1H, dt, J=16.2, 5.4 Hz), 6.80 (1H, dt, J=16.2, 1.8 Hz), 6.86 (2H, dt, J=9.2, 2.4 Hz), 7.10 (2H, d, J=8.3 Hz), 7.55 (2H, d, J=8.3 Hz), 7.84 (2H, dt, J=8.3, 1.7 Hz), 9.99 (1H, s).

The following compounds were produced in the same manner as in Reference Example 176 using appropriate starting materials.

Reference Example 177

4-[(E)-3-(4-Fluorophenoxy)prop-1-en-1-yl]benzaldehyde $^1$H-NMR (CDCl$_3$) δ: 4.70 (2H, dd, J=5.4, 1.7 Hz), 6.56 (1H, dt, J=16.3, 5.4 Hz), 6.79 (1H, dt, J=16.3, 1.7 Hz), 6.88-6.93 (2H, m), 6.97-7.03 (2H, m), 7.56 (2H, d, J=8.3 Hz), 7.85 (2H, dt, J=8.3, 1.7 Hz), 9.99 (1H, s).

Reference Example 178

4-[(E)-3-Phenoxyprop-1-en-1-yl]benzaldehyde $^1$H-NMR (CDCl$_3$) δ: 4.75 (2H, dd, J=5.4, 1.7 Hz), 6.59 (1H, dt, J=16.1, 5.4 Hz), 6.81 (1H, d, J=16.1 Hz), 6.95-7.00 (3H, m), 7.29-7.39 (2H, m), 7.56 (2H, d, J=8.3 Hz), 7.83-7.86 (2H, m), 9.99 (1H, s).

Reference Example 179

4-[(E)-3-(4-Methoxyphenoxy)prop-1-en-1-yl]benzaldehyde $^1$H-NMR (CDCl$_3$) δ: 3.78 (3H, s), 4.69 (2H, dd, J=5.4, 1.5 Hz), 6.59 (1H, dt, J=16.1, 5.4 Hz), 6.79 (1H, d, J=16.1 Hz), 6.83-6.93 (4H, m), 7.55 (2H, d, J=8.3 Hz), 7.83-7.85 (2H, m), 9.99 (1H, s).

Reference Example 180

4-{(E)-3-[4-(Propan-2-yl)phenoxy]prop-1-en-1-yl}benzaldehyde $^1$H-NMR (CDCl$_3$) δ: 1.23 (6H, d, J=7.1 Hz), 2.82-2.93 (1H, m), 4.72 (2H, dd, J=5.3, 1.7 Hz), 6.58 (1H, dt, J=16.1, 5.3 Hz), 6.80 (1H, d, J=16.1 Hz), 6.88-6.92 (2H, m), 7.15-7.18 (2H, m), 7.56 (2H, d, J=8.2 Hz), 7.84 (2H, d, J=8.2 Hz), 9.99 (1H, s).

Reference Example 181

4-{(E)-3-[(6-Chloropyridin-3-yl)oxy]prop-1-en-1-yl}benzaldehyde $^1$H-NMR (CDCl$_3$) δ: 4.78 (2H, dd, J=5.3, 1.6 Hz), 6.53 (1H, dt, J=16.1, 5.3 Hz), 6.80 (1H, d, J=16.1 Hz), 7.25 (2H, d, J=2.0 Hz), 7.56 (2H, d, J=8.1 Hz), 7.85-7.87 (2H, m), 8.13 (1H, t, J=1.8 Hz), 10.00 (1H, s).

Reference Example 182

4-{(E)-3-[(5-Bromopyridin-2-yl)oxy]prop-1-en-1-yl}benzaldehyde $^1$H-NMR (CDCl$_3$) δ: 5.01 (2H, dd, J=5.7, 1.3 Hz), 6.60 (1H, dt, J=15.9, 5.7 Hz), 6.72-6.79 (2H, m), 7.55 (2H, d, J=8.2 Hz), 7.68 (1H, dd, J=8.8, 2.4 Hz), 7.84 (2H, d, J=8.2 Hz), 8.21 (1H, d, J=2.4 Hz), 9.99 (1H, s).

Reference Example 183

4-{(E)-3-[(5-Methylpyridin-2-yl)oxy]prop-1-en-1-yl}benzaldehyde $^1$H-NMR (CDCl$_3$) δ: 2.26 (3H, s), 5.02 (2H, dd, J=5.6, 1.5 Hz), 6.63 (1H, dt, J=16.0, 5.6 Hz), 6.72 (1H, d, J=8.6 Hz), 6.78 (1H, d, J=16.0 Hz), 7.42 (1H, ddd, J=8.6, 2.5, 0.5 Hz), 7.55 (2H, d, J=8.3 Hz), 7.83 (2H, dt, J=8.3, 1.7 Hz), 7.96-7.97 (1H, m), 9.98 (1H, s).

Reference Example 184

4-[(E)-3-Hydroxyprop-1-en-1-yl]benzaldehyde $^1$H-NMR (CDCl$_3$) δ: 1.68 (1H, brs), 4.39 (2H, s), 6.53 (1H, dt, J=15.9, 5.3 Hz), 6.70 (1H, dt, J=15.9, 1.7 Hz), 7.53 (2H, d, J=8.2 Hz), 7.83 (2H, dt, J=8.2, 1.7 Hz), 9.98 (1H, s).

Reference Example 185

4-(3-Phenoxypropyl)benzaldehyde $^1$H-NMR (CDCl$_3$) δ: 1.56-1.58 (1H, m), 2.13-2.15 (2H, m), 2.91 (2H, t, J=7.6 Hz), 3.97 (2H, t, J=6.1 Hz), 6.87-6.91 (2H, m), 6.93-6.96 (1H, m), 7.26-7.31 (2H, m), 7.38 (2H, d, J=8.2 Hz), 7.81 (2H, d, J=8.2 Hz), 9.98 (1H, s).

Reference Example 186

4-{3-[(6-Chloropyridin-3-yl)oxy]propyl}benzaldehyde $^1$H-NMR (CDCl$_3$) δ: 2.12-2.19 m), 2.91 (2H, t, J=7.6 Hz), 4.00 (2H, t, J=6.1 Hz), 7.16 (1H, J=8.8, 3.0 Hz), 7.22 (1H, d, J=8.8 Hz), 7.37 (2H, d, J=8.0 Hz), 7.82 (2H, d, J=8.0 Hz), 8.04 (1H, d, J=3.0 Hz), 9.98 (1H, s).

Reference Example 187

4-[(E)-2-Methyl-3-(4-methylphenoxy)prop-1-en-1-yl]benzaldehyde $^1$H-NMR (CDCl$_3$) δ: 1.99 (3H, d, J=1.2 Hz), 2.30 (3H, s), 4.56 (2H, s), 6.68 (1H, brs), 6.87 (2H, dt, J=9.2, 2.6 Hz), 7.10 (2H, dd, J=8.7, 0.6 Hz), 7.45 (2H, d, J=8.3 Hz), 7.85 (2H, dt, J=8.3, 1.7 Hz), 9.99 (1H, s).

Reference Example 188

To a solution of 3-[4-(diethoxymethyl)phenyl]propan-1-ol (3.00 g), p-cresol (1.63 g), and triphenylphosphine (4.95 g) in THF (25 mL) was added 2.2 M solution of DEAD in toluene (8.58 mL). After stirring at room temperature for 2 hours, to the reaction mixture was added H₂O, and extracted with AcOEt. The organic layer was washed with saturated aqueous NaCl, dried over anhydrous Na₂SO₄, and concentrated under reduced pressure. The residue was purified by silica gel column chromatography (n-hexane/AcOEt=1/0 to 9/1) to afford a colorless oil (0.751 g). To a solution of that colorless oil (0.751 g) in THF (30 mL) was added 6 M aqueous HCl (0.492 mL). After stirring at room temperature for 1 hour, to the reaction mixture was added 5 M aqueous NaOH, and the solvent was removed under reduced pressure. To the residue was added saturated aqueous NaHCO₃, and extracted with AcOEt. The organic layer was washed with saturated aqueous NaCl, dried over anhydrous Na₂SO₄, and concentrated under reduced pressure. The residue was purified by silica gel column chromatography (n-hexane/AcOEt=9/1 to 4/1) to afford 4-[3-(4-methylphenoxy)propyl]benzaldehyde as a colorless oil (0.497 g).

¹H-NMR (CDCl₃) δ: 2.08-2.15 (2H, m), 2.29 (3H, s), 2.90 (2H, t, J=7.6 Hz), 3.94 (2H, t, J=6.1 Hz), 6.79 (2H, dt, J=9.2, 2.4 Hz), 7.06-7.10 (2H, m), 7.38 (2H, d, J=8.1 Hz), 7.81 (2H, dt, J=8.1, 1.7 Hz), 9.98 (1H, s).

The following compounds were produced in the same manner as in Reference Example 188 using appropriate starting materials.

Reference Example 189

{4-[2-(4-Fluorophenoxy)ethyl]-3-methylphenyl}methanol

¹H-NMR (CDCl₃) δ: 1.54 (1H, brs), 2.38 (3H, s), 3.09 (2H, t, J=7.3 Hz), 4.09 (2H, t, J=7.3 Hz), 4.65 (2H, s), 6.79-6.84 (2H, m), 6.92-6.99 (2H, m), 7.15-7.23 (3H, m).

Reference Example 190

4-[2-(4-Fluorophenoxy)propyl]benzaldehyde

¹H-NMR (CDCl₃) δ: 1.30 (3H, d, J=6.1 Hz), 2.94 (1H, dd, J=13.8, 5.6 Hz), 3.11 (1H, dd, J=13.8, 6.7 Hz), 4.46-4.54 (1H, m), 6.76-6.81 (2H, m), 6.91-6.97 (2H, m), 7.41 (2H, d, J=8.3 Hz), 7.82 (2H, d, J=8.3 Hz), 9.98 (1H, s).

Reference Example 191

{2-Methyl-4-[2-(4-methylphenoxy)ethyl]phenyl}methanol

¹H-NMR (CDCl₃) δ: 1.46 (1H, brs), 2.28 (3H, s), 2.36 (3H, s), 3.04 (2H, t, J=7.2 Hz), 4.13 (2H, t, J=7.2 Hz), 4.68 (2H, d, J=4.9 Hz), 6.79 (2H, dt, J=9.2, 2.6 Hz), 7.07 (2H, dd, J=8.8, 0.7 Hz), 7.11-7.13 (2H, m), 7.29 (1H, d, J=7.3 Hz).

The following compounds were produced in the same manner as in Reference Example 1 using appropriate starting materials.

Reference Example 192 tert-Butyl 4-{4-[2-(4-methoxyphenyl)ethoxy]benzyl}piperazine-1-carboxylate

¹H-NMR (CDCl₃) δ: 1.45 (9H, s), 2.35 (4H, t, J=5.0 Hz), 3.00-3.05 (2H, m), 3.39-3.43 (4H, m), 3.48 (2H, s), 3.79 (3H, s), 4.09-4.14 (2H, m), 6.84 (2H, d, J=8.6 Hz), 6.85 (2H, d, J=8.6 Hz), 7.20 (4H, d, J=8.6 Hz).

Reference Example 193 tert-Butyl 4-{4-[2-(4-methylphenyl)ethoxy]benzyl}piperazine-1-carboxylate

¹H-NMR (CDCl₃) δ: 1.44 (9H, s), 2.30-2.38 (7H, m), 3.04 (2H, t, J=7.3 Hz), 3.36-3.45 (6H, m), 4.13 (2H, t, J=7.3 Hz), 6.79-6.88 (2H, m), 7.08-7.25 (6H, m).

Reference Example 194 tert-Butyl 4-(4-{2-[4-(propan-2-yl)phenyl]ethoxy}benzyl)piperazine-1-carboxylate ¹H-NMR (CDCl₃) δ: 1.24 (6H, d, J=6.9 Hz), 1.45 (9H, s), 2.35 (4H, t, J=4.9 Hz), 2.89 (1H, septet, J=6.9 Hz), 3.06 (2H, t, J=7.3 Hz), 3.36-3.47 (6H, m), 4.15 (2H, t, J=7.3 Hz), 6.79-6.88 (2H, m), 7.15-7.25 (6H, m).

Reference Example 195 tert-Butyl 4-{4-[2-(4-fluorophenoxy)ethyl]benzyl}piperazine-1-carboxylate

¹H-NMR (CDCl₃) δ: 1.45 (9H, s), 2.38 (4H, t, J=4.9 Hz), 3.07 (2H, t, J=6.9 Hz), 3.41 (4H, t, J=4.9 Hz), 3.49 (2H, s), 4.14 (2H t, J=6.9 Hz), 6.77-6.87 (2H, m), 6.90-7.00 (2H, m), 7.22 (2H, d, J=8.2 Hz), 7.26 (2H, d, J=8.2 Hz).

Reference Example 196 tert-Butyl 4-{4-[3-(4-fluorophenoxy)propyl]benzyl}piperazine-1-carboxylate

¹H-NMR (CDCl₃) δ: 1.45 (9H, s), 2.03-2.13 (2H, m), 2.37 (4H, t, J=5.0 Hz), 2.79 (2H, t, J=7.6 Hz), 3.42 (4H, t, J=5.1 Hz), 3.48 (2H, s), 3.92 (2H, t, J=6.3 Hz), 6.78-6.87 (2H, m), 6.91-7.01 (2H, m), 7.15 (2H, d, J=8.2 Hz), 7.23 (2H, d, J=8.1 Hz).

Reference Example 197 tert-Butyl 4-(4-{3-[4-(propan-2-yl)phenoxy]propyl}benzyl)piperazine-1-carboxylate ¹H-NMR (CDCl₃) δ: 1.22 (6H, d, J=6.9 Hz), 1.45 (9H, s), 2.03-2.13 (2H, m), 2.37 (4H, t, J=5.0 Hz), 2.79 (2H, t, J=7.6 Hz), 2.80-2.93 (1H, m), 3.42 (4H, t, J=5.0 Hz), 3.47 (2H, s), 3.94 (2H, t, J=6.3 Hz), 6.83 (2H, d, J=8.7 Hz), 7.13 (2H, d, J=8.4 Hz), 7.16 (2H, d, J=8.2 Hz), 7.22 (2H, d, J=8.2 Hz).

Reference Example 198 tert-Butyl 4-{[2-(4-methoxyphenoxy)quinolin-6-yl]methyl}piperazine-1-carboxylate ¹H-NMR (CDCl₃) δ: 1.45 (9H, s), 2.41 (4H, t, J=4.6 Hz), 3.44 (4H, t, J=4.6 Hz), 3.63 (2H, s), 3.85 (3H, s), 6.91-6.99 (2H, m), 7.04 (1H, d, J=8.6 Hz), 7.12-7.22 (2H, m), 7.60 (1H, dd, J=8.6, 2.0 Hz), 7.63-7.68 (1H, m), 7.75 (1H, d, J=8.2 Hz), 8.06 (1H, d, J=8.9 Hz).

Reference Example 199 tert-Butyl 4-({2-[4-(propan-2-yl)phenoxy]quinolin-6-yl}methyl)piperazine-1-carboxylate ¹H-NMR (CDCl₃) δ: 1.29 (6H, d, J=6.9 Hz), 1.45 (9H, s), 2.42 (4H, t, J=4.9 Hz), 2.96 (1H, septet, J=6.9 Hz), 3.44 (4H, t, J=4.6 Hz), 3.64 (2H, s), 7.04 (1H, d, J=8.6 Hz), 7.12-7.20 (2H, m), 7.22-7.31 (2H, m), 7.55-7.68 (2H, m), 7.78 (1H, d, J=8.6 Hz), 8.07 (1H, d, J=8.9 Hz).

Reference Example 200 tert-Butyl 4-(4-{2-[4-(propan-2-yl)phenoxy]ethyl}benzyl)-1,4-diazepane-1-carboxylate ¹H-NMR (CDCl₃) δ: 1.21 (6H, d, J=6.8 Hz), 1.45-1.46 (9H, m), 1.75-1.88 (2H, m), 2.58-2.66 (4H, m), 2.85 (1H, septet, J=6.8 Hz), 3.07 (2H, t, J=7.1 Hz), 3.42-3.51 (4H, m), 3.62 (2H, s), 4.14 (2H, t, J=7.1 Hz), 6.81-6.85 (2H, m), 7.11-7.14 (2H, m), 7.21-7.27 (4H, m).

Reference Example 201 tert-Butyl 4-{4-[1-(4-methylphenoxy)propan-2-yl]benzyl}piperazine-1-carboxylate

¹H-NMR (CDCl₃) δ: 1.39 (3H, d, J=6.8 Hz), 1.45 (9H, s), 2.27 (3H, s), 2.38 (4H, t, J=5.0 Hz), 3.16-3.25 (1H, m), 3.42 (4H, t, J=5.0 Hz), 3.48 (2H, s), 3.91 (1H, dd, J=9.3, 7.8 Hz), 4.05 (1H, dd, J=9.3, 6.0 Hz), 6.78 (2H, dt, J=9.2, 2.6 Hz), 7.05 (2H, dd, J=8.7, 0.6 Hz), 7.23 (2H, d, J=8.3 Hz), 7.26 (2H, d, J=8.3 Hz).

Reference Example 202 tert-Butyl 4-[4-(2-{methyl[4-(propan-2-yl)phenyl]amino}ethyl)benzyl]piperazine-1-carboxylate ¹H-NMR (CDCl₃) δ: 1.22 (6H, d, J=6.8 Hz), 1.45 (9H, s), 2.38 (4H, t, J=4.9 Hz), 2.77-2.89 (3H, m), 2.89 (3H, s), 3.42 (4H, t, J=4.9 Hz), 3.48 (2H, s), 3.49-3.58 (2H, m), 6.66-6.71 (2H, m), 7.08-7.14 (2H, m), 7.14-7.19 (2H, m), 7.21-7.26 (2H, m).

Reference Example 203 tert-Butyl 4-(4-{2-[(4-fluorophenyl)(methyl)amino]ethyl}benzyl)piperazine-1-carboxylate ¹H-NMR (CDCl₃) δ: 1.45 (9H, s), 2.37 (4H, t, J=4.9 Hz), 2.81 (2H, t, J=7.8 Hz), 2.86 (3H, s), 3.42 (4H, t, J=4.9 Hz), 3.48 (2H, s), 3.48-3.55 (2H, m), 6.60-6.69 (2H, m), 6.90-6.98 (2H, m), 7.13 (2H, d, J=7.8 Hz), 7.23 (2H, d, J=7.8 Hz).

Reference Example 204 tert-Butyl 4-{4-[(4-methylphenoxy)acetyl]benzyl}piperazine-1-carboxylate

¹H-NMR (CDCl₃) δ: 1.46 (9H, s), 2.28 (3H, s), 2.39 (4H, t, J=5.0 Hz), 3.44 (4H, t, J=5.0 Hz), 3.56 (2H, s), 5.22 (2H, s), 6.83-6.86 (2H, m), 7.06-7.10 (2H, m), 7.46 (2H, d, J=8.3 Hz), 7.95-7.98 (2H, m).

Reference Example 205 tert-Butyl 4-{4-[(E)-3-(4-methylphenoxy)prop-1-en-1-yl]benzyl}piperazine-1-carboxylate ¹H-NMR (CDCl₃) δ: 1.45 (9H, s), 2.29 (3H, s), 2.37 (4H, t, J=4.9 Hz), 3.42 (4H, t, J=4.9 Hz), 3.49 (2H, s), 4.67 (2H, dd, J=5.8, 1.5 Hz), 6.40 (1H, dt, J=16.0, 5.8 Hz), 6.71 (1H, d, J=16.0 Hz), 6.86 (2H, dt, J=9.3, 2.5 Hz), 7.09 (2H, d, J=8.3 Hz), 7.27 (2H, d, J=8.1 Hz), 7.36 (2H, d, J=8.1 Hz).

Reference Example 206 tert-Butyl 4-(4-{2-[4-(dimethylamino)phenoxy]ethyl}benzyl)piperazine-1-carboxylate ¹H-NMR (CDCl₃) δ: 1.45 (9H, s), 2.38-2.39 (4H, m), 2.86 (6H, s), 3.05 (2H, t, J=7.1 Hz), 3.42-3.43 (4H, m), 3.48 (2H, s), 4.12 (2H, t, J=7.1 Hz), 6.73 (2H, d, J=9.0 Hz), 6.83 (2H, d, J=9.0 Hz), 7.22-7.23 (4H, m).

Reference Example 207 tert-Butyl (3S)-3-[(4-{2-[4-(propan-2-yl)phenoxy]ethyl}benzyl)amino]pyrrolidine-1-carboxylate ¹H-NMR (CDCl₃) δ: 1.22 (6H, d, J=7.1 Hz), 1.45 (9H, s), 1.67-1.72 (1H, m), 1.98-2.03 (1H, m), 2.80-2.87 (1H, m), 3.03-3.07 (2.5H, m), 3.12-3.16 (0.5H, m), 3.32-3.59 (5H, m), 3.73-3.76 (2H, m), 4.12 (2H, t, J=7.1 Hz), 6.79-6.83 (2H, m), 7.09-7.13 (2H, m), 7.21-7.25 (4H, m).

Reference Example 208 tert-Butyl (3S)-3-[methyl(4-{2-[4-(propan-2-yl)phenoxy]ethyl}benzyl)amino]pyrrolidine-1-carboxylate ¹H-NMR (CDCl₃) δ: 1.21 (6H, d, J=7.1 Hz), 1.46 (9H, s), 1.81-1.86 (1H, m), 2.04-2.10 (1H, m), 2.13 (3H, s), 2.80-2.87 (1H, m), 2.98-3.00 (1H, m), 3.06 (2H, t, J=7.1 Hz), 3.18-3.23 (2H, m), 3.43-3.65 (3.5H, m), 3.69-3.72 (0.5H, m), 4.13 (2H, t, J=7.1 Hz), 6.80-6.84 (2H, m), 7.09-7.12 (2H, m), 7.22-7.25 (4H, m).

Reference Example 209 tert-Butyl 4-{4-[(E)-3-phenoxyprop-1-en-1-yl]benzyl}piperazine-1-carboxylate

¹H-NMR (CDCl₃) δ: 1.45 (9H, s), 2.37 (4H, t, J=4.9 Hz), 3.42 (4H, t, J=4.9 Hz), 3.49 (2H, s), 4.70 (2H, dd, J=5.8, 1.5 Hz), 6.41 (1H, dt, J=15.9, 5.8 Hz), 6.72 (1H, d, J=15.9 Hz), 6.94-6.97 (3H, m), 7.26-7.32 (4H, m), 7.36 (2H, d, J=8.3 Hz).

Reference Example 210 tert-Butyl 4-{4-[(E)-3-(4-cyanophenoxy)prop-1-en-1-yl]benzyl}piperazine-1-carboxylate ¹H-NMR (CDCl₃) δ: 1.45 (9H, s), 2.38 (4H, t, J=5.0 Hz), 3.42 (4H, t, J=5.0 Hz), 3.50 (2H, s), 4.75 (2H, dd, J=5.9, 1.5 Hz), 6.36 (1H, dt, J=16.1, 5.9 Hz), 6.72 (1H, d, J=16.1 Hz), 6.98-7.02 (2H, m), 7.29 (2H, d, J=8.2 Hz), 7.36 (2H, d, J=8.2 Hz), 7.58-7.61 (2H, m).

Reference Example 211 tert-Butyl 4-{4-[(E)-3-(4-methoxyphenoxy)prop-1-en-1-yl]benzyl}piperazine-1-carboxylate ¹H-NMR (CDCl₃) δ: 1.45 (9H, s), 2.37 (4H, t, J=4.9 Hz), 3.42 (4H, t, J=4.9 Hz), 3.49 (2H, s), 3.77 (3H, s), 4.65 (2H, dd, J=5.8, 1.2 Hz), 6.39 (1H, dt, J=15.9, 5.8 Hz), 6.70 (1H, d, J=15.9 Hz), 6.82-6.92 (4H, m), 7.27 (2H, d, J=7.6 Hz), 7.36 (2H, d, J=7.6 Hz).

Reference Example 212

(2E)-1-(4-{4-[(1E)-3-(4-Fluorophenoxy)prop-1-en-1-yl]benzyl}piperazin-1-yl)-3-{-4-[(5-hydroxypyridin-2-yl)oxy]-3,5-dimethylphenyl}prop-2-en-1-one ¹H-NMR (CDCl₃) δ: 2.11 (6H, s), 2.48 (4H, t, J=5.0 Hz), 3.53 (2H, s), 3.65-3.75 (4H, m), 4.66 (2H, dd, J=5.9, 1.3 Hz), 5.96 (1H, brs), 6.39 (1H, dt, J=15.9, 5.9 Hz), 6.70-6.79 (3H, m), 6.88-6.92 (2H, m), 6.95-7.00 (2H, m), 7.22-7.26 (3H, m), 7.29 (2H, d, J=8.3 Hz), 7.38 (2H, d, J=8.3 Hz), 7.59 (1H, d, J=15.1 Hz), 7.72 (1H, dd, J=3.1, 0.6 Hz).

Reference Example 213 tert-Butyl 4-{4-[(E)-3-(4-fluorophenoxy)prop-1-en-1-yl]benzyl}piperazine-1-carboxylate ¹H-NMR (CDCl₃) δ: 1.45 (9H, s), 2.38 (4H, t, J=4.9 Hz), 3.42 (4H, t, J=4.9 Hz), 3.49 (2H, s), 4.66 (2H, dd, J=5.7, 1.5 Hz), 6.38 (1H, dt, J=16.0, 5.7 Hz), 6.71 (1H, d, J=16.0 Hz), 6.87-6.92 (2H, m), 6.95-7.01 (2H, m), 7.28 (2H, d, J=8.2 Hz), 7.36 (2H, d, J=8.2 Hz).

Reference Example 214 tert-Butyl 4-{4-[2-(4-fluorophenoxy)propyl]benzyl}piperazine-1-carboxylate

¹H-NMR (CDCl₃) δ: 1.28 (3H, d, J=6.1 Hz), 1.45 (9H, s), 2.37 (4H, t, J=5.0 Hz), 2.80 (1H, dd, J=13.7, 6.6 Hz), 3.04 (1H, dd, J=13.7, 6.1 Hz), 3.42 (4H, t, J=5.0 Hz), 3.47 (2H, s), 4.42-4.50 (1H, m), 6.77-6.82 (2H, m), 6.90-6.96 (2H, m), 7.18 (2H, d, J=8.1 Hz), 7.23 (2H, d, J=8.1 Hz).

Reference Example 215 tert-Butyl 4-(4-{(E)-3-[4-(propan-2-yl)phenoxy]prop-1-en-1-yl}benzyl)piperazine-1-carboxylate ¹H-NMR (CDCl₃) δ: 1.23 (6H, d, J=6.8 Hz), 2.37 (4H, t, J=4.8 Hz), 2.81-2.92 (1H, m), 3.42 (4H, t, J=4.9 Hz), 3.49 (2H, s), 4.67 (2H, dd, J=5.7, 1.2 Hz), 6.40 (1H, dt, J=16.0, 5.7 Hz), 6.71 (1H, d, J=16.0 Hz), 6.87-6.91 (2H, m), 7.13-7.16 (2H, m), 7.26-7.28 (2H, m), 7.36 (2H, d, J=8.3 Hz).

Reference Example 216 tert-Butyl 4-(4-{(E)-3-[(6-chloropyridin-3-yl)oxy]prop-1-en-1-yl}benzyl)piperazine-1-carboxylate ¹H-NMR (CDCl₃) δ: 1.46 (9H, s), 2.38 (4H, t, J=5.0 Hz), 3.42 (4H, t, J=5.0 Hz), 3.50 (2H, s), 4.73 (2H, dd, J=5.9, 1.5 Hz), 6.35 (1H, dt, J=16.0, 5.9 Hz), 6.73 (1H, d, J=16.0 Hz), 7.24 (2H, d, J=1.9 Hz), 7.29 (2H, d, J=8.1 Hz), 7.36 (2H, d, J=8.1 Hz), 8.12 (1H, t, J=1.9 Hz).

Reference Example 217 tert-Butyl 4-(4-{(E)-3-[(6-methylpyridin-3-yl)oxy]prop-1-en-1-yl}benzyl)piperazine-1-carboxylate ¹H-NMR (CDCl₃) δ: 1.45 (9H, s), 2.38 (4H, t, J=5.0 Hz), 2.49 (3H, s), 3.42 (4H, t, J=5.0 Hz), 3.49 (2H, s), 4.72 (2H, dd, J=5.9, 1.5 Hz), 6.38 (1H, dt, J=15.9, 5.9 Hz), 6.72 (1H, d, J=15.9 Hz), 7.07 (1H, d, J=8.5 Hz), 7.16 (1H, dd, J=8.5, 2.8 Hz), 7.28 (2H, d, J=8.1 Hz), 7.36 (2H, d, J=8.1 Hz), 8.25 (1H, d, J=2.8 Hz).

Reference Example 218

9H-Fluoren-9-ylmethyl 4-(4-{(E)-3-[(5-methylpyridin-2-yl)oxy]prop-1-en-1-yl}benzyl)-piperazine-1-carboxylate ¹H-NMR (CDCl₃) δ: 2.25 (3H, s), 2.38 (4H, brs), 3.48-3.49 (6H, m), 4.24 (1H, t, J=6.8 Hz), 4.42 (2H, d, J=6.8 Hz), 4.97 (2H, dd, J=6.1, 1.5 Hz), 6.46 (1H, dt, J=16.0, 6.0 Hz), 6.70-6.74 (2H, m), 7.26-7.32 (4H, m), 7.37-7.42 (5H, m), 7.56 (2H, dd, J=7.3, 0.7 Hz), 7.76 (2H, d, J=7.6 Hz), 7.96-7.97 (1H, m).

Reference Example 219

9H-Fluoren-9-ylmethyl 4-(4-{(E)-3-[(5-bromopyridin-2-yl)oxy]prop-1-en-1-yl}benzyl)-piperazine-1-carboxylate ¹H-NMR (CDCl₃) δ: 2.38 (4H, s), 3.49-3.50 (6H, m), 4.24 (1H, t, J=6.7 Hz), 4.43 (2H, d, J=6.7 Hz), 4.97 (2H, dd, J=6.2, 1.5 Hz), 6.44 (1H, dt, J=16.0, 6.2 Hz), 6.70-6.74 (2H, m), 7.28-7.32 (4H, m), 7.37-7.42 (4H, m), 7.57 (2H, dd, J=7.3, 0.7 Hz), 7.66 (1H, dd, J=8.8, 2.6 Hz), 7.76 (2H, d, J=7.3 Hz), 8.21 (1H, dd, J=2.6, 0.7 Hz).

Reference Example 220 tert-Butyl 4-{4-[(E)-3-hydroxyprop-1-en-1-yl]benzyl}piperazine-1-carboxylate

¹H-NMR (CDCl₃) δ: 1.45 (9H, s), 1.63 (1H, brs), 2.38 (4H, t, J=5.0 Hz), 3.42 (4H, t, J=5.0 Hz), 3.49 (2H, s), 4.32 (2H, d, J=5.6 Hz), 6.36 (1H, dt, J=15.9, 5.6 Hz), 6.61 (1H, d, J=15.9 Hz), 7.25-7.27 (2H, m), 7.34 (2H, d, J=8.1 Hz).

Reference Example 221 tert-Butyl 4-[4-(3-phenoxypropyl)benzyl]piperazine-1-carboxylate

¹H-NMR (CDCl₃) 1.45 (9H, s), 2.06-2.13 (2H, m), 2.37 (4H, t, J=5.0 Hz), 2.80 (2H, t, J=7.7 Hz), 3.42 (4H, t, J=5.0 Hz), 3.47 (2H, s), 3.97 (2H, t, J=6.3 Hz), 6.88-6.95 (3H, m), 7.16 (2H, d, J=8.1 Hz), 7.22 (2H, d, J=8.1 Hz), 7.25-7.30 (2H, m).

Reference Example 222 tert-Butyl 4-(4-{3-[(6-chloropyridin-3-yl)oxy]propyl}benzyl)piperazine-1-carboxylate ¹H-NMR (CDCl₃) δ: 1.45 (9H, s), 2.08-2.15 (2H, m), 2.37 (4H, t, J=5.0 Hz), 2.79 (2H, t, J=7.6 Hz), 3.42 (4H, t, J=5.0 Hz), 3.48 (2H, s), 3.98 (2H, t, J=6.2 Hz), 7.14-7.18 (3H, m), 7.21-7.25 (3H, m), 8.04 (1H, dd, J=3.1, 0.6 Hz).

Reference Example 223 tert-Butyl 4-{4-[2-(4-chlorophenoxy)ethyl]-3-fluorobenzyl}piperazine-1-carboxylate ¹H-NMR (CDCl₃) δ: 1.45 (9H, s), 2.37-2.38 (4H, m), 3.10 (2H, t, J=7.0 Hz), 3.42-3.43 (4H, m), 3.47 (2H, s), 4.14 (2H, t, J=7.0 Hz), 6.81 (2H, d, J=8.8 Hz), 7.03-7.05 (2H, m), 7.20-7.23 (3H, m).

Reference Example 224 tert-Butyl 4-{4-[3-(4-methylphenoxy)propyl]benzyl}piperazine-1-carboxylate

¹H-NMR (CDCl₃) δ: 1.45 (9H, s), 2.06-2.11 (2H, m), 2.28 (3H, s), 2.37 (4H, t, J=5.0 Hz), 2.79 (2H, t, J=7.7 Hz), 3.42 (4H, t, J=5.0 Hz), 3.47 (2H, s), 3.93 (2H, t, J=6.3 Hz), 6.79 (2H, dt, J=9.2, 2.6 Hz), 7.05-7.08 (2H, m), 7.16 (2H, d, J=8.2 Hz), 7.22 (2H, d, J=8.2 Hz).

Reference Example 225

To a THF (10 mL) solution of 2-(2-fluoro-4-{2-[4-(trifluoromethyl)phenoxy]-ethyl}phenyl)-1,3-dioxolane (0.552 g) was added 6 M HCl (0.775 mL) at 0° C., then the resultant mixture was room temperature for 5 hours. The reaction mixture was evaporated to afford a pale yellow oil. To a CH₂Cl₂ (15 mL) solution of that pale yellow oil and tert-Butyl 1-piperazinecarboxylate (0.375 g) were added NaB(OAc)₃ (0.657 g) at 0° C. The resultant mixture was stirred at room temperature for 3 days. To the reaction mixture was added saturated aqueous NaHCO₃, and extracted with CH₂Cl₂. The organic layer was washed with saturated aqueous NaCl, dried over anhydrous MgSO₄, and concentrated under reduced pressure. The residue was purified by silica gel column chromatography (n-hexane/AcOEt=9/1 to 4/1) to afford tert-butyl 4-(2-fluoro-4-{2-[4-(trifluoromethyl)phenoxy]ethyl}benzyl)piperazine-1-carboxylate as a colorless oil (0.511 g).

¹H-NMR (CDCl₃) δ: 1.45 (9H, s), 2.41-2.42 (4H, m), 3.09 (2H, t, J=6.7 Hz), 3.42-3.43 (4H, m), 3.57 (2H, s), 4.20 (2H, t, J=6.7 Hz), 6.93-7.04 (4H, m), 7.29-7.31 (1H, m), 7.53 (2H, d, J=8.5 Hz).

Reference Example 226

To a solution of tert-butyl 4-[4-(2-{(4-methoxyphenyl)[(2-nitrophenyl)sulfonyl]-amino}ethyl)benzyl]piperazine-1-carboxylate in DMF (35 mL) was added mercaptoacetic acid (1.35 mL) and LiOH (1.63 g) at room temperature, then the reaction mixture was stirred over night. The reaction mixture was added mercaptoacetic acid (1.35 mL) and LiOH (1.63 g), and stirred for 5 hours. The reaction mixture was diluted with H₂O, and extracted with AcOEt. The organic layer was washed with water and saturated aqueous NaCl, dried over anhydrous Na₂SO₄, and concentrated under reduced pressure. The residue was purified by silica gel column chromatography (n-hexane/AcOEt=1/1 to 1/2) to afford tert-butyl 4-(4-{2-[(4-methoxyphenyl)amino]ethyl}benzyl)piperazine-1-carboxylate as a pale yellow amorphous (5.96 g).

¹H-NMR (CDCl₃) δ: 1.45 (9H, s), 2.38 (4H, t, J=4.9 Hz), 2.85-2.93 (2H, m), 3.45 (2H, t, J=7.1 Hz), 3.42 (4H, t, J=4.9 Hz), 3.48 (2H, s), 3.75 (3H, s), 6.55-6.61 (2H, m), 6.75-6.81 (2H, m), 7.16 (2H, d, J=8.1 Hz), 7.23-7.30 (2H, m).

The following compounds were produced in the same manner as in Reference Example 226 using appropriate starting materials.

Reference Example 227 tert-Butyl 4-[4-(2-{[4-(propan-2-yl)phenyl]amino}ethyl)benzyl]piperazine-1-carboxylate ¹H-NMR (CDCl₃) δ: 1.20 (6H, d, J=6.8 Hz), 1.45 (9H, s), 2.38 (4H, t, J=4.9 Hz), 2.80 (1H, septet, J=6.8 Hz), 2.90 (2H, t, J=6.8 Hz), 3.37 (2H, t, J=7.1 Hz), 3.42 (4H, t, J=4.9 Hz), 3.48 (2H, s), 3.57 (1H, brs), 6.52-6.59 (2H, m), 7.01-7.08 (2H, m), 7.14-7.21 (2H, m), 7.22-7.28 (2H, m).

Reference Example 228 tert-Butyl 4-(4-{2-[(4-fluorophenyl)amino]ethyl}benzyl)piperazine-1-carboxylate

¹H-NMR (CDCl₃) δ: 1.45 (9H, s), 2.38 (4H, t, J=4.9 Hz), 2.88 (2H, t, J=7.1 Hz), 3.34 (2H, t, J=7.1 Hz), 3.42 (4H, t, J=4.9 Hz), 3.48 (2H, s), 6.49-6.57 (2H, m), 6.82-6.92 (2H, m), 7.13-7.20 (2H, m), 7.22-7.27 (2H, m).

Reference Example 229 tert-Butyl 4-{[4-(2-{[4-(propan-2-yl)phenyl]amino}ethyl)phenyl]amino}piperidine-1-carboxylate ¹H-NMR (CDCl₃) δ: 1.20 (6H, d, J=6.8 Hz), 1.25-1.39 (2H, m), 1.47 (9H, s), 1.98-2.08 (2H, m), 2.75-2.84 (3H, m), 2.92 (2H, t, J=11.5 Hz), 3.31 (2H, t, J=6.8 Hz), 3.35-3.60 (3H, m), 3.95-4.10 (2H, m), 6.52-6.60 (4H, m), 7.00-7.09 (4H, m).

Reference Example 230

To a solution of 3-[4-(diethoxymethyl)phenyl]propan-1-ol (2.27 g), 5-hydroxy-2-methylpyridine (1.25 g), and triphenylphosphine (3.00 g) in THF (19 mL) was added 2.2 M solution of DEAD in toluene (5.20 mL). After stirring at room temperature for 1 hour, to the reaction mixture was added H₂O, and extracted with AcOEt. The organic layer was washed with saturated aqueous NaCl, dried over anhydrous Na₂SO₄, and concentrated under reduced pressure. The residue was purified by silica gel column chromatography (n-hexane/AcOEt=17/3 to 13/7) to afford a colorless oil (3.86 g). To a solution of that colorless oil (3.86 g) in THF (50 mL) was added 6 M aqueous HCl (1.59 mL). After stirring at room temperature for 30 minutes, to the reaction mixture was added 5 M aqueous NaOH, and the solvent was removed under reduced pressure. To the residue was added saturated aqueous NaHCO₃, and extracted with AcOEt. The organic layer was washed with saturated aqueous NaCl, dried over anhydrous Na₂SO₄, and concentrated under reduced pressure. The residue was purified by silica gel column chromatography (n-hexane/AcOEt=3/1 to 13/7) to afford a colorless oil (2.93 g). To a solution of that colorless oil (2.93 g) in (CH₂Cl)₂ (95 mL) was added tert-butyl piperazine-1-carboxylate (1.95 g) and NaBH(OAc)₃ (4.45 g). After stirring at room temperature for 37 hours, to the reaction mixture was added saturated aqueous NaHCO₃, and extracted with AcOEt. The organic layer was washed with saturated aqueous NaCl, dried over anhydrous Na₂SO₄, and concentrated under reduced pressure. The residue was purified by silica gel column chromatography (n-hexane/AcOEt=3/1 to 1/1) to afford tert-butyl 4-(4-{3-[(6-methylpyridin-3-yl)oxy]propyl}benzyl)piperazine-1-carboxylate as a colorless oil (1.37 g).

¹H-NMR (CDCl₃) δ: 1.45 (9H, s), 2.06-2.13 (2H, m), 2.37 (4H, t, J=5.0 Hz), 2.49 (3H, s), 2.79 (2H, t, J=7.7 Hz), 3.42 (4H, t, J=5.0 Hz), 3.47 (2H, s), 3.97 (2H, t, J=6.3 Hz), 7.04 (1H, d, J=8.4 Hz), 7.09 (1H, dd, J=8.4, 2.9 Hz), 7.15 (2H, d, J=8.2 Hz), 7.23 (2H, d, J=8.2 Hz), 8.18 (1H, dd, J=2.9, 0.7 Hz).

Reference Example 231

To an EtOH (25 mL) solution of tert-butyl 4-{4-[2-(4-fluorophenoxy)ethyl]-benzyl}piperazine-1-carboxylate (2.36 g) was added 6 M HCl (9.49 mL) at room temperature. After stirring at 40° C. for 3 hours, the solvent was removed under reduced pressure. The resulting precipitate was collected by filtration, and dissolved in water. The solution was alkalified with 5 M NaOH, and extracted with $CH_2Cl_2$. The organic layer was washed with saturated aqueous NaCl, dried over anhydrous $MgSO_4$, and concentrated under reduced pressure to afford 1-{4-[2-(4-fluorophenoxy)ethyl]benzyl}piperazine as a colorless oil (1.47 g).

$^1$H-NMR (CDCl$_3$) δ: 1.67 (1H, brs), 2.41 (4H, m), 2.88 (4H, t, J=4.6 Hz), 3.06 (2H, t, J=6.9 Hz), 3.47 (2H, s), 4.12 (2H, t, J=6.9 Hz), 6.78-6.86 (2H, m), 6.90-7.00 (2H, m), 7.21 (2H, d, J=7.9 Hz), 7.27 (2H, d, J=7.9 Hz).

The following compounds were produced in the same manner as in Reference Example 231 using appropriate starting materials.

Reference Example 232

1-{4-[2-(4-Methoxyphenyl)ethoxy]benzyl}piperazine $^1$H-NMR (CDCl$_3$) δ: 2.38 (4H, brs), 2.52 (1H, brs), 2.87 (4H, t, J=5.0 Hz), 3.00-3.05 (2H, m), 3.41 (2H, s), 3.79 (3H, s), 4.12 (2H, t, J=7.3 Hz), 6.84 (2H, d, J=8.6 Hz), 6.85 (2H, d, J=8.6 Hz), 7.18-7.21 (4H, m).

Reference Example 233

1-(4-{[4-(Propan-2-yl)phenoxy]methyl}benzyl)piperazine $^1$H-NMR (CDCl$_3$) δ: 1.22 (6H, d, J=6.9 Hz), 1.68 (1H, brs), 2.41 (4H, m), 2.81-2.90 (5H, m), 3.49 (2H, s), 5.01 (2H, s), 6.88-6.93 (2H, m), 7.13-7.17 (2H, m), 7.33 (2H, d, J=8.2 Hz), 7.38 (2H, d, J=8.2 Hz).

Reference Example 234

1-(4-{[4-(1H-Pyrrol-1-yl)phenoxy]methyl}benzyl)piperazine $^1$H-NMR (CDCl$_3$) δ: 2.41 (4H, brs), 2.87-2.90 (4H, m), 3.50 (2H, s), 5.06 (2H, s), 6.31-6.32 (2H, m), 6.99-7.03 (4H, m), 7.30 (2H, d, J=8.9 Hz), 7.35 (2H, d, J=8.9 Hz), 7.39 (2H, d, J=8.6 Hz).

Reference Example 235

1-{4-[(4-Fluorophenoxy)methyl]benzyl}piperazine $^1$H-NMR (DMSO-d$_6$) δ: 2.26-2.28 (5H, m), 2.67 (4H, t, J=4.6 Hz), 3.41 (2H, s), 5.04 (2H, s), 6.98-7.05 (2H, m), 7.07-7.15 (2H, m), 7.29 (2H, d, J=7.9 Hz), 7.38 (2H, d, J=7.9 Hz).

Reference Example 236

1-(4-{[(4-Fluorobenzyl)oxy]methyl}benzyl)piperazine $^1$H-NMR (DMSO-d$_6$) δ: 2.26-2.36 (5H, m), 2.67 (4H, t, J=4.9 Hz), 3.40 (2H, s), 4.49 (2H, s), 4.49 (2H, s), 7.14-7.21 (2H, m), 7.24-7.31 (4H, m), 7.36-7.42 (2H, m).

Reference Example 237

1-[4-({[4-(Propan-2-yl)benzyl]oxy}methyl)benzyl]piperazine $^1$H-NMR (CDCl$_3$) δ: 1.24 (6H, d, J=6.9 Hz), 1.71-1.78 (1H, m), 2.41 (4H, brs), 2.86-2.96 (5H, m), 3.48 (2H, s), 4.53 (2H, s), 4.53 (2H, s), 7.20-7.31 (8H, m).

Reference Example 238

1-{4-[2-(4-Methoxyphenoxy)ethyl]benzyl}piperazine $^1$H-NMR (CDCl$_3$) δ: 1.74 (1H, brs), 2.41 (4H, m), 2.89 (4H, t, J=4.9 Hz), 3.05 (2H, t, J=7.3 Hz), 3.47 (2H, s), 3.76 (3H, s), 4.11 (2H, t, J=7.3 Hz), 6.79-6.85 (4H, m), 7.20-7.28 (4H, m).

Reference Example 239

1-(4-{2-[4-(Propan-2-yl)phenoxy]ethyl}benzyl)piperazine $^1$H-NMR (CDCl$_3$) δ: 1.21 (6H, d, J=6.9 Hz), 1.68 (1H, brs), 2.41 (4H, m), 2.79-2.90 (5H, m), 3.06 (2H, t, J=6.9 Hz), 3.46 (2H, s), 4.14 (2H, t, J=6.9 Hz), 6.80-6.85 (2H, m), 7.10-7.14 (2H, m), 7.20-7.27 (4H, m).

Reference Example 240

1-{4-[2-(4-Methylphenoxy)ethyl]benzyl}piperazine $^1$H-NMR (CDCl$_3$) δ: 1.67 (1H, brs), 2.28 (3H, s), 2.41 (4H, brs), 2.88 (4H, t, J=4.9 Hz), 3.06 (2H, t, J=6.9 Hz), 3.47 (2H, s), 4.13 (2H, t, J=6.9 Hz), 6.79 (2H, d, J=8.6 Hz), 7.06 (2H, d, J=8.6 Hz), 7.20-7.28 (4H, m).

Reference Example 241

1-{4-[2-(4-Chlorophenoxy)ethyl]benzyl}piperazine $^1$H-NMR (CDCl$_3$) δ: 2.42 (4H, brs), 2.52 (1H, brs), 2.90 (4H, t, J=5.0 Hz), 3.03-3.08 (2H, m), 3.47 (2H, s), 4.09-4.14 (2H, m), 6.85 (2H, d, J=9.2 Hz), 7.17-7.22 (4H, m), 7.26 (2H, d, J=8.2 Hz).

Reference Example 242

1-{4-[2-(4-Bromophenoxy)ethyl]benzyl}piperazine $^1$H-NMR (CDCl$_3$) δ: 2.44-2.45 (4H, m), 2.91 (4H, t, J=5.0 Hz), 3.03-3.09 (2H, m), 3.47 (2H, s), 4.09-4.14 (2H, m), 6.74-6.78 (2H, m), 7.21 (2H, d, J=7.9 Hz), 7.26 (2H, d, J=7.9 Hz), 7.33-7.36 (2H, m).

Reference Example 243

1-[4-(2-{[5-(Trifluoromethyl)pyridin-2-yl]oxy}ethyl)benzyl]piperazine $^1$H-NMR (CDCl$_3$) δ: 2.41 (4H, brs), 2.89 (4H, t, J=4.8 Hz), 3.08 (2H, t, J=7.1 Hz), 3.47 (2H, s), 4.57 (2H, t, J=7.1 Hz), 6.80 (1H, d, J=8.6 Hz), 7.20-7.29 (4H, m), 7.75 (1H, dd, J=9.2, 2.6 Hz), 8.41-8.43 (1H, m).

Reference Example 244

1-{4-[2-(3-Methylphenoxy)ethyl]benzyl}piperazine $^1$H-NMR (CDCl$_3$) δ: 1.59 (1H, brs), 2.31 (3H, s), 2.34-2.47 (4H, m), 2.88 (4H, t, J=4.9 Hz), 3.07 (2H, t, J=7.3 Hz), 3.47 (2H, s), 4.14 (2H, t, J=7.3 Hz), 6.66-6.79 (3H, m), 7.10-7.30 (5H, m).

Reference Example 245

1-(4-{2-[3-(Propan-2-yl)phenoxy]ethyl}benzyl)piperazine $^1$H-NMR (CDCl$_3$) δ: 1.23 (6H, d, J=6.9 Hz), 1.61 (1H, brs), 2.30-2.50 (4H, m), 2.77-2.96 (5H, m), 3.08 (2H, t, J=7.3 Hz), 3.47 (2H, s), 4.16 (2H, t, J=7.3 Hz), 6.71 (1H, dd, J=8.2, 2.6 Hz), 6.75-6.85 (2H, m), 7.14-7.31 (5H, m).

Reference Example 246

1-{4-[2-(3-Methoxyphenoxy)ethyl]benzyl}piperazine $^1$H-NMR (CDCl$_3$) δ: 1.85 (1H, brs), 2.30-2.58 (4H, m), 2.88 (4H, t, J=4.9 Hz), 3.07 (2H, t, J=7.3 Hz), 3.47 (2H, s), 3.77 (3H, s), 4.14 (2H, t, J=7.3 Hz), 6.44-6.54 (3H, m), 7.16 (1H, t, J=8.2 Hz), 7.20-7.30 (4H, m).

Reference Example 247

1-{4-[2-(3,4-Dimethylphenoxy)ethyl]benzyl}piperazine $^1$H-NMR (CDCl$_3$) δ: 2.18 (3H, s), 2.22 (3H, s), 2.82-2.55 (4H, m), 2.90 (4H, t, J=4.9 Hz), 3.06 (2H, t, J=7.3 Hz), 3.47 (2H, s), 4.12 (2H, t, J=7.3 Hz), 6.64 (1H, dd, J=8.2, 2.6 Hz), 6.71 (1H, d, J=2.6 Hz), 7.01 (1H, d, J=8.2 Hz), 7.15-7.30 (4H, m).

Reference Example 248

1-{4-[2-(4-tert-Butylphenoxy)ethyl]benzyl}piperazine $^1$H-NMR (CDCl$_3$) δ: 1.29 (9H, s), 1.76 (1H, s), 2.40 (4H, brs), 2.88 (4H, t, J=4.9 Hz), 3.06 (2H, t, J=6.9 Hz), 3.46 (2H, s), 4.14 (2H, t, J=6.9 Hz), 6.80-6.86 (2H, m), 7.20-7.31 (6H, m).

Reference Example 249

1-{4-[3-(4-Fluorophenoxy)propyl]benzyl}piperazine $^1$H-NMR (CDCl$_3$) δ: 1.45 (1H, s), 2.03-2.13 (2H, m), 2.41 (4H, brs), 2.78 (2H, t, J=7.6 Hz), 2.88 (4H, t, J=4.9 Hz), 3.46 (2H, s), 3.92 (2H, t, J=6.3 Hz), 6.79-6.86 (2H, m), 6.91-7.00 (2H, m), 7.15 (2H, d, J=8.1 Hz), 7.24 (2H, d, J=8.1 Hz).

Reference Example 250

1-(4-{3-[4-(Propan-2-yl)phenoxy]propyl}benzyl)piperazine $^1$H-NMR (CDCl$_3$) δ: 1.22 (6H, d, J=6.9 Hz), 1.45 (1H, s), 2.03-2.13 (2H, m), 2.41 (4H, brs), 2.78 (2H, t, J=7.6 Hz), 2.80-2.90 (1H, m), 2.88 (4H, t, J=4.9 Hz), 3.46 (2H, s), 3.94 (2H, t, J=6.3 Hz), 6.83 (2H, d, J=8.7 Hz), 7.13 (2H, d, J=8.7 Hz), 7.15 (2H, d, J=8.2 Hz), 7.23 (2H, d, J=8.1 Hz).

Reference Example 251

1-{4-[2-(4-Methylphenoxy)ethyl]benzyl}piperazine dihydrochloride $^1$H-NMR (DMSO-c4) δ: 2.22 (3H, s), 3.04 (2H, t, J=6.6 Hz), 3.01-3.80 (8H, m), 4.16 (2H, t, J=6.8 Hz), 4.33 (2H, s), 6.82 (2H, d, J=8.6 Hz), 7.07 (2H, d, J=8.6 Hz), 7.40 (2H, d, J=7.9 Hz), 7.57 (2H, d, J=7.6 Hz), 9.67 (1H, s), 12.14 (1H, s).

Reference Example 252

1-{4-[2-(2-Methylphenoxy)ethyl]benzyl}piperazine $^1$H-NMR (CDCl$_3$) δ: 2.19 (3H, s), 2.47 (4H, s), 2.74 (1H, s), 2.94 (4H, t, J=4.8 Hz), 3.09 (2H, t, J=6.8 Hz), 3.48 (2H, s), 4.16 (2H, t, J=6.4 Hz), 6.77-6.86 (2H, m), 7.09-7.15 (2H, m), 7.25 (4H, s).

Reference Example 253

1-{4-[2-(4-Butylphenoxy)ethyl]benzyl}piperazine $^1$H-NMR (CDCl$_3$) δ: 0.91 (3H, t, J=7.3 Hz), 1.26-1.40 (2H, m), 1.50-1.61 (2H, m), 2.40 (4H, s), 2.54 (2H, t, J=7.7 Hz), 2.88 (4H, t, J=4.9 Hz), 3.06 (2H, t, J=7.1 Hz), 3.46 (2H, s), 4.13 (2H, t, J=7.1 Hz), 6.78-6.83 (2H, m), 7.04-7.10 (2H, m), 7.20-7.28 (4H, m).

Reference Example 254

1-{4-[2-(4-Fluorophenoxy)ethyl]benzyl}piperazine dihydrochloride $^1$H-NMR (DMSO-d$_6$) δ: 3.05 (2H, t, J=6.6 Hz), 3.12-3.60 (8H, m), 4.19 (2H, t, J=6.6 Hz), 4.31 (2H, s), 6.90-6.98 (2H, m), 7.06-7.15 (2H, m), 7.41 (2H, d, J=7.9 Hz), 7.56 (2H, d, J=7.9 Hz), 9.56 (1H, brs), 12.01 (1H, brs).

Reference Example 255

1-{4-[2-(1,3-Benzodioxol-5-yloxy)ethyl]benzyl}piperazine $^1$H-NMR (CDCl$_3$) δ: 1.59 (1H, brs), 2.40 (4H, m), 2.88 (4H, t, J=4.9 Hz), 3.04 (2H, t, J=6.9 Hz), 3.46 (2H, s), 4.08 (2H, t, J=6.9 Hz), 5.90 (2H, s), 6.31 (1H, dd, J=8.6, 2.6 Hz), 6.48 (1H, d, J=2.6 Hz), 6.68 (1H, d, J=8.6 Hz), 7.20 (2H, d, J=8.2 Hz), 7.27 (2H, d, J=8.2 Hz).

Reference Example 256

1-{4-[2-(2-Chlorophenoxy)ethyl]benzyl}piperazine dihydrochloride $^1$H-NMR (DMSO-d$_6$) δ: 3.09 (2H, t, J=6.3 Hz), 3.34-3.52 (10H, m), 4.22-4.34 (2H, m), 6.93 (1H, t, J=7.6 Hz), 7.14 (1H, d, J=7.9 Hz), 7.24-7.31 (1H, m), 7.38-7.46 (3H, m), 7.56 (2H, d, J=6.9 Hz), 9.61 (2H, s).

Reference Example 257

2-[4-(piperazin-1-ylmethyl)phenyl]ethanol dihydrochloride $^1$H-NMR (DMSO-$d_6$) δ: 2.75 (2H, t, J=6.9 Hz), 2.92-3.42 (7H, m), 3.62 (2H, t, J=6.9 Hz), 4.11-4.45 (4H, m), 7.29 (2H, d, J=7.3 Hz), 7.52 (2H, d, J=5.0 Hz), 9.85 (2H, s), 12.20 (1H, s).

Reference Example 258

1-{4-[2-(2,3-Dimethylphenoxy)ethyl]benzyl}piperazine dihydrochloride $^1$H-NMR (DMSO-$d_6$) δ: 2.01 (3H, s), 2.18 (3H, s), 3.08 (2H, t, J=6.3 Hz), 3.21-3.55 (8H, m), 4.15 (2H, t, J=6.3 Hz), 4.33 (2H, s), 6.73 (1H, d, J=7.3 Hz), 6.78 (1H, d, J=8.3 Hz), 7.01 (1H, t, J=7.8 Hz), 7.42 (2H, d, J=7.8 Hz), 7.57 (2H, d, J=6.8 Hz), 9.65 (2H, s), 12.07 (1H, s).

Reference Example 259

1-{4-[2-(3,5-Dimethylphenoxy)ethyl]benzyl}piperazine dihydrochloride $^1$H-NMR (DMSO-$d_6$) δ: 2.21 (6H, s), 3.04 (2H, t, J=6.3 Hz), 3.22-3.59 (8H, m), 4.15 (2H, t, J=6.6 Hz), 4.35 (2H, s), 6.53-6.57 (3H, m), 7.40 (2H, d, J=7.8 Hz), 7.59 (2H, d, J=7.8 Hz), 9.80 (2H, s), 12.00-12.31 (1H, m).

Reference Example 260

1-{4-[2-(3-Ethoxyphenoxy)ethyl]benzyl}piperazine dihydrochloride $^1$H-NMR (DMSO-$d_6$) δ: 1.29 (3H, t, J=6.8 Hz), 2.90-3.80 (10H, m), 3.98 (2H, q, J=6.8 Hz), 4.19 (2H, t, J=6.8 Hz), 4.35 (2H, brs), 6.44-6.54 (3H, m), 7.15 (1H, t, J=8.1 Hz), 7.41 (2H, d, J=7.8 Hz), 7.57 (2H, d, J=6.6 Hz), 9.65 (1H, brs), 12.11 (1H, brs).

Reference Example 261

6-{2-[4-(piperazin-1-ylmethyl)phenyl]ethoxy}quinoline dihydrochloride $^1$H-NMR (DMSO-$d_6$) δ: 3.20 (2H, t, J=6.6 Hz), 3.31-3.86 (8H, m), 4.38 (2H, s), 4.43 (2H, t, J=6.6 Hz), 7.48 (2H, d, J=8.3 Hz), 7.59 (2H, dd, J=33.2, 7.8 Hz), 7.73-7.80 (2H, m), 7.97 (1H, dd, J=8.1, 5.1 Hz), 8.31 (1H, d, J=9.3 Hz), 8.92 (1H, d, J=7.8 Hz), 9.08 (1H, d, J=4.4 Hz), 9.86 (2H, s), 12.27 (1H, s).

Reference Example 262

1-{4-[2-(4-Nitrophenoxy)ethyl]benzyl}piperazine $^1$H-NMR (CDCl$_3$) δ: 2.75 (4H, t, J=4.9 Hz), 3.12 (2H, t, J=6.8 Hz), 3.20-3.22 (4H, m), 3.55 (2H, s), 4.26 (2H, t, J=6.8 Hz), 6.94 (2H, d, J=9.2 Hz), 7.24 (4H, brs), 8.18 (2H, d, J=9.5 Hz).

Reference Example 263

1-{4-[(1,3-Benzodioxol-5-yloxy)methyl]benzyl}piperazine $^1$H-NMR (CDCl$_3$) δ: 1.68 (1H, brs), 2.41 (4H, brs), 2.88 (4H, t, J=4.9 Hz), 3.49 (2H, s), 4.96 (2H, s), 5.91 (2H, s), 6.39 (1H, dd, J=8.5, 2.4 Hz), 6.56 (1H, d, J=2.4 Hz), 6.70 (1H, d, J=8.5 Hz), 7.30-7.39 (4H, m).

Reference Example 264

1-{4-[2-(3,4-Dichlorophenoxy)ethyl]benzyl}piperazine dihydrochloride $^1$H-NMR (DMSO-$d_6$) δ: 3.07 (2H, t, J=6.5 Hz), 3.23-3.56 (8H, m), 4.26 (2H, t, J=6.6 Hz), 4.36 (2H, s), 6.97 (1H, dd, J=8.9, 2.6 Hz), 7.25 (1H, d, J=2.4 Hz), 7.41 (2H, d, J=7.8 Hz), 7.51 (1H, d, J=9.0 Hz), 7.61 (2H, d, J=7.6 Hz), 9.92 (2H, s), 12.28 (1H, s).

Reference Example 265

1-{4-[2-(4-Fluoro-3-methylphenoxy)ethyl]benzyl}piperazine dihydrochloride $^1$H-NMR (DMSO-$d_6$) δ: 2.19 (3H, d, J=2.0 Hz), 3.04 (2H, t, J=6.9 Hz), 3.11-3.61 (8H, m), 4.16 (2H, t, J=6.9 Hz), 4.34 (2H, brs), 6.72-6.77 (1H, m), 6.85 (1H, dd, J=6.2, 3.1 Hz), 7.00-7.04 (1H, m), 7.40 (2H, d, J=8.1 Hz), 7.57 (2H, d, J=6.1 Hz), 9.65 (2H, brs), 12.11 (1H, brs).

Reference Example 266

1-{4-[2-(3-Methylphenoxy)ethyl]benzyl}piperazine dihydrochloride $^1$H-NMR (DMSO-$d_6$) δ: 2.26 (3H, s), 3.06 (2H, t, J=6.6 Hz), 3.10-3.60 (8H, m), 4.18 (2H, t, J=6.8 Hz), 4.34 (2H, s), 6.71-6.75 (3H, m), 7.15 (1H, t, J=7.6 Hz), 7.41 (2H, d, J=7.8 Hz), 7.57 (2H, d, J=7.3 Hz), 9.63 (1H, s), 12.10 (1H, s).

Reference Example 267

1-{4-[2-(4-Chlorophenoxy)ethoxy]benzyl}piperazine dihydrochloride $^1$H-NMR (DMSO-$d_6$) δ: 2.95-3.61 (10H, m), 4.26-4.33 (4H, m), 7.00-7.07 (4H, m), 7.33-7.37 (2H, m), 7.54 (2H, brs), 9.53 (2H, brs), 11.87 (1H, brs).

Reference Example 268

1-[4-(4-Chlorophenoxy)benzyl]piperazine dihydrochloride $^1$H-NMR (DMSO-$d_6$) δ: 3.26-3.40 (8H, m), 4.35 (2H, s), 7.09 (4H, dd, J=8.4, 5.5 Hz), 7.47 (2H, d, J=8.8 Hz), 7.66 (2H, d, J=8.1 Hz), 9.71 (2H, s), 12.12 (1H, s).

Reference Example 269

1-{4-[2-(4-Methylphenoxy)ethoxy]benzyl}piperazine dihydrochloride $^1$H-NMR (DMSO-$d_6$) δ: 2.23 (3H, s), 2.93-3.60 (10H, m), 4.27-4.33 (4H, m), 6.85-6.88 (2H, m), 7.08-7.14 (4H, m), 7.54-7.56 (2H, m), 9.59 (2H, brs), 11.92 (1H, brs).

Reference Example 270

1-{4-[2-(5,6,7,8-Tetrahydronaphthalen-2-yloxy)ethyl]benzyl}piperazine dihydrochloride ¹H-NMR (DMSO-d₆) δ: 1.67-1.70 (4H, m), 2.61-2.66 (4H, m), 3.03 (2H, t, J=6.7 Hz), 3.29-3.45 (8H, m), 4.14 (2H, t, J=6.7 Hz), 4.34 (2H, brs), 6.58-6.61 (1H, m), 6.65 (1H, dd, J=8.3, 2.7 Hz), 6.93 (1H, d, J=8.5 Hz), 7.40 (2H, d, J=8.1 Hz), 7.56-7.58 (2H, m), 9.65 (2H, brs), 12.10 (1H, brs).

Reference Example 271

1-{4-[2-(2,3-Dihydro-1H-inden-5-yloxy)ethyl]benzyl}piperazine dihydrochloride

¹H-NMR (DMSO-d₆) δ: 1.94-1.99 (2H, m), 2.76-2.80 (4H, m), 3.04 (2H, t, J=6.6 Hz), 3.29-3.44 (8H, m), 4.16 (2H, t, J=6.6 Hz), 4.34 (2H, brs), 6.67 (1H, dd, J=8.2, 2.3 Hz), 6.80 (1H, d, J=2.0 Hz), 7.08 (1H, d, J=8.1 Hz), 7.40 (2H, d, J=7.3 Hz), 7.58 (2H, d, J=7.8 Hz), 9.76 (2H, brs), 12.17 (1H, brs).

Reference Example 272

1-(4-{2-[4-(Propan-2-yl)phenoxy]ethyl}benzyl)-1,4-diazepane

¹H-NMR (CDCl₃) δ: 1.21 (6H, d, J=6.8 Hz), 1.70-1.79 (3H, m), 2.63-2.69 (4H, m), 2.81-2.91 (3H, m), 2.96 (2H, t, J=6.1 Hz), 3.07 (2H, t, J=7.1 Hz), 3.63 (2H, s), 4.14 (2H, t, J=7.1 Hz), 6.81-6.85 (2H, m), 7.11-7.13 (2H, m), 7.22 (2H, d, J=8.1 Hz), 7.28 (2H, d, J=8.1 Hz).

Reference Example 273

1-(Biphenyl-4-ylmethyl)piperazine dihydrochloride

¹H-NMR (DMSO-d₆) δ: 3.20-3.58 (8H, m), 4.40 (2H, s), 7.40 (1H, t, J=7.2 Hz), 7.49 (2H, t, J=7.6 Hz), 7.68-7.78 (6H, m), 9.78 (2H, s), 12.31 (1H, s).

Reference Example 274

1-{4-[4-(Propan-2-yl)phenoxy]benzyl}piperazine dihydrochloride

¹H-NMR (DMSO-d₆) δ: 1.21 (6H, d, J=6.8 Hz), 2.85-2.96 (1H, m), 3.16-3.48 (8H, m), 4.33 (2H, s), 6.98 (2H, d, J=8.5 Hz), 7.02 (2H, d, J=8.5 Hz), 7.29 (2H, d, J=8.3 Hz), 7.61-7.62 (2H, m), 9.69 (2H, s), 12.07 (1H, s).

Reference Example 275

1-{4-[2-(Naphthalen-2-yloxy)ethyl]benzyl}piperazine dihydrochloride

¹H-NMR (DMSO-d₆) δ: 3.13-3.71 (10H, m), 4.32-4.35 (4H, m), 7.15 (1H, dd, J=8.9, 2.6 Hz), 7.32-7.36 (2H, m), 7.43-7.47 (3H, m), 7.61 (2H, d, J=7.1 Hz), 7.79-7.83 (3H, m), 9.73 (2H, brs), 12.18 (1H, brs).

Reference Example 276

1-(4-{2-[(6-Bromopyridin-3-yl)oxy]ethyl}benzyl)piperazine dihydrochloride

¹H-NMR (DMSO-d₆) δ: 3.08 (2H, t, J=6.7 Hz), 3.17-3.47 (8H, m), 4.31 (2H, t, J=6.7 Hz), 4.36 (2H, brs), 7.40-7.42 (3H, m), 7.54 (1H, d, J=8.5 Hz), 7.59-7.61 (2H, m), 8.12 (1H, d, J=3.2 Hz), 9.85 (2H, brs), 12.26 (1H, brs).

Reference Example 277

1-(4-Fluorophenyl)-2-[4-(piperazin-1-ylmethyl)phenoxy]ethanone dihydrochloride

¹H-NMR (DMSO-d₆) δ: 2.90-3.70 (8H, m), 4.29 (2H, s), 5.62 (2H, s), 7.05 (2H, d, J=8.5 Hz), 7.43 (2H, t, J=8.8 Hz), 7.53 (2H, d, J=7.6 Hz), 8.10-8.14 (2H, m), 9.52 (1H, s), 11.82 (1H, s).

Reference Example 278

1-(4-{2-[4-(piperazin-1-ylmethyl)phenyl]ethoxy}phenyl)ethanone

¹H-NMR (CDCl₃) δ: 2.46 (4H, brs), 2.54 (3H, s), 2.93 (4H, t, J=4.9 Hz), 2.99 (1H, brs), 3.10 (2H, t, J=7.1 Hz), 3.48 (2H, s), 4.22 (2H, t, J=7.1 Hz), 6.90-6.93 (2H, m), 7.22-7.28 (4H, m), 7.90-7.93 (2H, m).

Reference Example 279

1-(4-{2-[(5-Chloropyridin-2-yl)oxy]ethyl}benzyl)piperazine dihydrochloride

¹H-NMR (DMSO-d₆) δ: 3.06 (2H, t, J=6.8 Hz), 3.17-3.56 (8H, m), 4.35 (2H, s), 4.46 (2H, t, J=6.8 Hz), 6.85 (1H, dd, J=8.8, 0.5 Hz), 7.38 (2H, d, J=8.1 Hz), 7.59 (2H, d, J=7.8 Hz), 7.79 (1H, dd, J=8.8, 2.7 Hz), 8.20 (1H, t, J=1.5 Hz), 9.87 (2H, brs), 12.26 (1H, brs).

Reference Example 280

1-{4-[2-(Pyridin-2-yloxy)ethyl]benzyl}piperazine dihydrochloride

¹H-NMR (DMSO-d₆) δ: 3.08 (2H, t, J=6.8 Hz), 3.28-3.66 (8H, m), 4.37 (2H, s), 4.50 (2H, t, J=6.8 Hz), 6.86 (1H, dd, J=5.0, 4.3 Hz), 7.00-7.02 (1H, m), 7.40 (2H, d, J=8.1 Hz), 7.61 (2H, d, J=8.1 Hz), 7.74-7.78 (1H, m), 8.15-8.19 (1H, m), 9.96 (2H, brs), 12.28 (1H, brs).

Reference Example 281

1-{4-[2-(4-Cyclopropylphenoxy)ethyl]benzyl}piperazine dihydrochloride

¹H-NMR (DMSO-d₆) δ: 0.53-0.57 (2H, m), 0.82-0.88 (2H, m), 1.80-1.87 (1H, m), 3.04 (2H, t, J=6.7 Hz), 3.17-3.50 (8H, m), 4.16 (2H, t, J=6.7 Hz), 4.34 (2H, brs), 6.79-6.83 (2H, m), 6.97-6.99 (2H, m), 7.40 (2H, d, J=7.8 Hz), 7.55 (2H, brs), 9.55 (2H, brs), 12.03 (1H, brs).

Reference Example 282

1-{2-Fluoro-4-[(4-fluorophenoxy)methyl]benzyl}piperazine dihydrochloride

¹H-NMR (DMSO-d₆) δ: 3.25-3.46 (8H, m), 4.31 (2H, s), 5.14 (2H, s), 7.02-7.07 (2H, m), 7.11-7.18 (2H, m), 7.36-7.43 (2H, m), 7.73 (1H, s), 9.56 (2H, s).

Reference Example 283

N-Methyl-N-{2-[4-(piperazin-1-ylmethyl)phenyl]ethyl}-4-(propan-2-yl)aniline $^1$H-NMR (CDCl$_3$) δ: 1.22 (6H, d, J=7.1 Hz), 1.69 (1H, brs), 2.32-2.57 (4H, m), 2.77-2.93 (10H, m), 3.45-3.55 (4H, m), 6.66-6.72 (2H, m), 7.08-7.14 (2H, m), 7.14-7.19 (2H, m), 7.21-7.28 (2H, m).

Reference Example 284

1-{3-Fluoro-4-[(4-propylphenoxy)methyl]benzyl}piperazine dihydrochloride $^1$H-NMR (DMSO-d$_6$) δ: 0.87 (3H, t, J=7.3 Hz), 1.53-1.56 (2H, m), 2.67-3.35 (8H, m), 3.80-3.87 (2H, m), 4.32-4.34 (2H, m), 5.10 (2H, s), 6.93 (2H, d, J=8.5 Hz), 7.11 (2H, d, J=8.5 Hz), 7.42-7.60 (3H, br m), 9.51 (2H, s), 12.27 (1H, s).

Reference Example 285

1-{3-Fluoro-4-[(4-fluorophenoxy)methyl]benzyl}piperazine dihydrochloride $^1$H-NMR (DMSO-d$_6$) δ: 3.13-3.48 (8H, m), 4.28-4.30 (2H, m), 5.13 (2H, s), 7.04-7.07 (2H, m), 7.13-7.16 (2H, m), 7.44-7.46 (1H, m), 7.61-7.64 (2H, m), 9.44-9.47 (2H, m), 12.17-12.20 (1H, m).

Reference Example 286

1-(3-Fluoro-4-{[4-(propan-2-yloxy)phenoxy]methyl}benzyl)piperazine $^1$H-NMR (CDCl$_3$) δ: 1.30 (6H, d, J=6.1 Hz), 2.40-2.43 (4H, m), 2.89-2.90 (4H, m), 3.47 (2H, s), 4.39-4.45 (1H, m), 5.05 (2H, s), 6.83 (2H, d, J=9.0 Hz), 6.90 (2H, d, J=9.0 Hz), 7.10 (2H, d, J=9.5 Hz), 7.42 (1H, t, J=7.6 Hz).

Reference Example 287

N-{2-[4-(piperazin-1-ylmethyl)phenyl]ethyl}-4-(propan-2-yl)aniline trihydrochloride $^1$H-NMR (DMSO-d$_6$) δ: 1.20 (6H, d, J=6.8 Hz), 2.91 (1H, septet, J=6.8 Hz), 3.00-4.20 (13H, m), 4.37 (2H, s), 7.36 (4H, t, J=7.8 Hz), 7.43 (2H, d, J=7.8 Hz), 7.61 (2H, d, J=8.1 Hz), 9.89 (2H, brs), 12.27 (1H, brs).

Reference Example 288

4-Fluoro-N-methyl-N-{2-[4-(piperazin-1-ylmethyl)phenyl]ethyl}aniline trihydrochloride $^1$H-NMR (DMSO-d$_6$) δ: 2.60-4.60 (18H, m), 7.20-7.70 (8H, m), 9.88 (2H, brs), 12.27 (1H, brs).

Reference Example 289

4-Fluoro-N-{2-[4-(piperazin-1-ylmethyl)phenyl]ethyl}aniline trihydrochloride $^1$H-NMR (DMSO-d$_6$) δ: 2.98 (2H, t, J=8.1 Hz), 3.10-3.60 (14H, m), 7.17 (4H, brs), 7.36 (2H, d, J=8.3 Hz), 7.58 (2H, d, J=8.1 Hz), 9.67 (2H, brs), 12.11 (1H, brs).

Reference Example 290

1-(4-{2-[(6-Chloropyridin-3-yl)oxy]ethyl}benzyl)piperazine dihydrochloride $^1$H-NMR (DMSO-d$_6$) δ: 3.08 (2H, t, J=6.6 Hz), 3.24-3.43 (8H, m), 4.30-4.33 (4H, m), 7.40-7.43 (3H, m), 7.47-7.51 (1H, m), 7.57-7.59 (2H, m), 8.12 (1H, dd, J=3.2, 0.5 Hz), 9.72 (2H, brs), 12.18 (1H, brs).

Reference Example 291

1-(4-{2-[(5-Methylpyridin-2-yl)oxy]ethyl}benzyl)piperazine dihydrochloride $^1$H-NMR (DMSO-d$_6$) δ: 2.21 (3H, s), 3.06 (2H, t, J=6.8 Hz), 3.25 (2H, brs), 3.41-3.62 (4H, m), 4.36-4.47 (6H, m), 6.78 (1H, d, J=8.5 Hz), 7.39 (2H, d, J=8.3 Hz), 7.59-7.61 (3H, m), 7.99 (1H, dd, J=1.6, 0.9 Hz), 9.83 (2H, brs), 12.23 (1H, brs).

Reference Example 292

1-(4-{2-[(6-Methylpyridin-3-yl)oxy]ethyl}benzyl)piperazine dihydrochloride $^1$H-NMR (DMSO-d$_6$) δ: 2.61 (3H, s), 3.11 (2H, t, J=6.7 Hz), 3.24-3.74 (8H, m), 4.33 (2H, brs), 4.42 (2H, t, J=6.7 Hz), 7.42 (2H, d, J=8.1 Hz), 7.58-7.60 (2H, m), 7.71 (1H, dd, J=8.8, 2.9 Hz), 7.97-7.99 (1H, m), 8.46 (1H, d, J=2.7 Hz), 9.65 (2H, brs), 11.53 (1H, brs).

Reference Example 293

1-(4-Methylphenyl)-2-[4-(piperazin-1-ylmethyl)phenoxy]ethanone dihydrochloride $^1$H-NMR (DMSO-d$_6$) δ: 2.41 (3H, s), 2.90-3.65 (8H, m), 4.30 (2H, brs), 5.59 (2H, s), 7.03 (2H, d, J=8.8 Hz), 7.39 (2H, d, J=7.8 Hz), 7.53 (2H, d, J=7.1 Hz), 7.92-7.95 (2H, m), 9.58 (1H, brs), 11.92 (1H, brs).

Reference Example 294

1-(4-{2-[(5-Bromopyridin-2-yl)oxy]ethyl}benzyl)piperazine dihydrochloride $^1$H-NMR (DMSO-d$_6$) δ: 3.06 (2H, t, J=6.8 Hz), 3.40-3.53 (8H, m), 4.33 (2H, brs), 4.46 (2H, t, J=6.8 Hz), 6.81 (1H, dd, J=8.8, 0.5 Hz), 7.38 (2H, d, J=7.8 Hz), 7.54-7.56 (2H, m), 7.89 (1H, dd, J=8.8, 2.7 Hz), 8.28 (1H, dd, J=2.7, 0.5 Hz), 9.59 (2H, brs), 12.06 (1H, brs).

Reference Example 295

4-Methoxy-N-{2-[4-(piperazin-1-ylmethyl)phenyl]ethyl}aniline trihydrochloride $^1$H-NMR (DMSO-d$_6$) δ: 3.00-3.70 (15H, m), 3.77 (3H, s), 4.33 (2H, brs), 7.00-7.10 (2H, m), 7.35 (2H, d, J=8.1 Hz), 7.40-7.51 (2H, m), 7.57 (2H, d, J=7.6 Hz), 9.64 (2H, brs).

Reference Example 296

1-(4-{2-[(6-Methylpyridin-2-yl)oxy]ethyl}benzyl)piperazine dihydrochloride $^1$H-NMR (DMSO-d$_6$) δ: 2.39 (3H, s), 3.07 (2H, t, J=6.8 Hz), 3.24-3.27 (2H, m), 3.43-3.46 (6H, m), 4.37 (2H, s), 4.46

(2H, t, J=6.8 Hz), 6.66 (1H, d, J=8.1 Hz), 6.87 (1H, d, J=7.3 Hz), 7.41 (2H, d, J=7.8 Hz), 7.60-7.66 (3H, m), 9.85 (2H, s), 12.25 (1H, s).

Reference Example 297

1-(4-{2-[(6-Methoxypyridin-3-yl)oxy]ethyl}benzyl)piperazine dihydrochloride $^1$H-NMR (DMSO-d$_6$) δ: 3.05 (2H, t, J=6.7 Hz), 3.32-3.57 (8H, m), 3.78 (3H, s), 4.22 (2H, t, J=6.7 Hz), 4.35 (2H, brs), 6.75 (1H, dd, J=9.0, 0.5 Hz), 7.39-7.41 (3H, m), 7.58-7.60 (2H, m), 7.85 (1H, d, J=2.7 Hz), 9.76 (2H, brs), 12.20 (1H, brs).

Reference Example 298

6-Chloro-2-{2-[4-(piperazin-1-ylmethyl)phenyl]ethoxy}-1,3-benzoxazole dihydrochloride $^1$H-NMR (DMSO-d$_6$) δ: 3.03 (2H, t, J=7.1 Hz), 3.22-3.57 (8H, m), 4.07 (2H, t, J=7.1 Hz), 4.32 (2H, brs), 7.19 (1H, d, J=8.3 Hz), 7.24 (1H, dd, J=8.3, 2.0 Hz), 7.31 (2H, d, J=8.1 Hz), 7.51-7.53 (3H, m), 9.75 (2H, brs), 12.14 (1H, brs).

Reference Example 299

2-(4-Methylphenoxy)-1-[4-(piperazin-1-ylmethyl)phenyl]ethanone dihydrochloride $^1$H-NMR (DMSO-d$_6$) δ: 2.23 (3H, s), 2.85-3.70 (10H, m), 4.42 (1H, s), 5.52 (2H, s), 6.84-6.87 (2H, m), 7.08 (2H, dd, J=8.8, 0.5 Hz), 7.80 (2H, d, J=8.1 Hz), 8.08 (2H, d, J=8.3 Hz), 9.51 (1H, brs), 12.32 (1H, brs).

Reference Example 300

1-{4-[2-(4-Ethoxyphenoxy)ethoxy]benzyl}piperazine dihydrochloride $^1$H-NMR (DMSO-d$_6$) δ: 1.31 (3H, t, J=6.9 Hz), 3.18-3.79 (8H, m), 3.96 (2H, q, J=6.9 Hz), 4.25-4.34 (6H, m), 6.85-6.93 (4H, m), 7.07 (2H, d, J=8.8 Hz), 7.57-7.59 (2H, m), 9.70 (2H, brs), 12.05 (1H, brs).

Reference Example 301

1-{4-[2-(4-Methoxyphenoxy)ethoxy]benzyl}piperazine dihydrochloride $^1$H-NMR (DMSO-d$_6$) δ: 3.23-3.50 (8H, m), 3.70 (3H, s), 4.24-4.26 (2H, m), 4.30-4.32 (4H, m), 6.87-6.92 (4H, m), 7.06 (2H, d, J=8.8 Hz), 7.59 (2H, d, J=8.5 Hz), 9.93 (2H, brs), 12.20 (1H, brs).

Reference Example 302

1-{4-[(E)-3-(4-Methylphenoxy)prop-1-en-1-yl]benzyl}piperazine dihydrochloride $^1$H-NMR (DMSO-d$_6$) δ: 2.23 (3H, s), 3.20-3.43 (8H, m), 4.35 (2H, brs), 4.70 (2H, dd, J=5.6, 1.1 Hz), 6.58 (1H, dt, J=16.1, 5.6 Hz), 6.77 (1H, d, J=16.1 Hz), 6.88 (2H, dt, J=9.1, 2.5 Hz), 7.09 (2H, d, J=8.3 Hz), 7.55-7.58 (4H, m), 9.60 (2H, brs), 12.10 (1H, brs).

Reference Example 303

2-{2-[4-(piperazin-1-ylmethyl)phenyl]ethoxy}-1,3-benzothiazole dihydrochloride $^1$H-NMR (DMSO-d$_6$) δ: 2.99 (2H, t, J=7.4 Hz), 3.22-3.43 (8H, m), 4.18 (2H, t, J=7.4 Hz), 4.30 (2H, brs), 7.16-7.20 (1H, m), 7.31-7.37 (4H, m), 7.53 (2H, d, J=6.8 Hz), 7.64 (1H, dd, J=7.7, 0.9 Hz), 9.70 (2H, brs), 12.10 (1H, brs).

Reference Example 304

2-Methyl-5-{2-[4-(piperazin-1-ylmethyl)phenyl]ethoxy}-1,3-benzothiazole dihydrochloride $^1$H-NMR (DMSO-d$_6$) δ: 2.77 (3H, s), 3.11 (2H, t, J=6.6 Hz), 3.29-3.58 (8H, m), 4.30 (2H, t, J=6.6 Hz), 4.38 (2H, brs), 7.03 (1H, dd, J=8.8, 2.4 Hz), 7.44-7.46 (3H, m), 7.62-7.67 (2H, m), 7.89 (1H, d, J=8.8 Hz), 9.81 (2H, brs), 12.18 (1H, s).

Reference Example 305

(3S)—N-Methyl-N-(4-{2-[4-(propan-2-yl)phenoxy]ethyl}benzyl)pyrrolidin-3-amine dihydrochloride $^1$H-NMR (DMSO-d$_6$) δ: 1.16 (6H, d, J=7.1 Hz), 2.33-2.46 (2H, m), 2.60 (3H, s), 2.78-2.85 (1H, m), 3.06 (2H, t, J=6.7 Hz), 3.20 (1H, brs), 3.47-3.66 (3H, m), 3.99-4.02 (1H, m), 4.16-4.19 (3H, m), 4.44-4.51 (1H, m), 6.83-6.86 (2H, m), 7.12-7.14 (2H, m), 7.41 (2H, d, J=8.1 Hz), 7.56-7.58 (2H, m), 9.66 (1H, brs), 9.77 (1H, brs), 11.76 (1H, brs).

Reference Example 306

1-{4-[(E)-3-Phenoxyprop-1-en-1-yl]benzyl}piperazine $^1$H-NMR (CDCl$_3$) δ: 2.40 (4H, brs), 2.87 (4H, t, J=4.9 Hz), 3.47 (2H, s), 4.69 (2H, dd, J=5.8, 1.2 Hz), 6.40 (1H, dt, J=15.9, 5.8 Hz), 6.72 (1H, d, J=15.9 Hz), 6.93-6.97 (3H, m), 7.26-7.32 (4H, m), 7.35-7.37 (2H, m).

Reference Example 307

N-{4-[2-(4-Fluorophenoxy)ethyl]phenyl}piperidin-4-amine $^1$H-NMR (CDCl$_3$) δ: 1.24-1.37 (2H, m), 1.63 (1H, brs), 2.01-2.10 (2H, m), 2.66-2.76 (2H, m), 2.96 (2H, t, J=7.3 Hz), 3.11 (2H, dt, J=13.2, 3.6 Hz), 3.28-3.60 (2H, m), 4.06 (2H, t, J=7.3 Hz), 6.51-6.61 (2H, m), 6.78-6.86 (2H, m), 6.90-7.00 (2H, m), 7.02-7.09 (2H, m).

Reference Example 308

N-[4-(2-{[4-(Propan-2-yl)phenyl]amino}ethyl)phenyl]piperidin-4-amine $^1$H-NMR (CDCl$_3$) δ: 1.20 (6H, d, J=6.8 Hz), 1.27-1.39 (2H, m), 1.77 (1H, brs), 2.03-2.12 (2H, m), 2.67-2.85 (5H, m), 3.13 (2H, dt, J=12.9, 3.7 Hz), 3.26-3.68 (5H, m), 6.51-6.61 (4H, m), 6.99-7.07 (4H, m).

Reference Example 309

N-{4-[2-(4-Methylphenoxy)ethyl]phenyl}piperidin-4-amine dihydrochloride $^1$H-NMR (DMSO-d$_6$) δ: 1.78-1.96 (2H, m), 2.02-2.12 (2H, m), 2.22 (3H, s), 2.90 (2H, q, J=11.5 Hz), 3.00 (2H, t, J=6.8

Hz), 3.26-3.38 (2H, m), 3.40-4.10 (3H, m), 4.13 (2H, t, J=6.8 Hz), 6.78-6.84 (2H, m), 7.04-7.10 (2H, m), 7.16-7.44 (4H, m), 8.86-8.99 (1H, m), 9.16-9.29 (1H, m).

Reference Example 310

3-[4-(piperazin-1-ylmethyl)phenyl]propan-1-ol dihydrochloride $^1$H-NMR (DMSO-d$_6$) δ: 1.69-1.76 (2H, m), 2.64 (2H, t, J=7.7 Hz), 3.40-3.57 (10H, m), 4.35 (2H, s), 7.26-7.31 (2H, m), 7.55-7.59 (2H, m), 9.85 (2H, brs), 12.10 (1H, brs).

Reference Example 311

4-({(E)-3-[4-(piperazin-1-ylmethyl)phenyl]prop-2-en-1-yl}oxy)benzonitrile dihydrochloride $^1$H-NMR (DMSO-d$_6$) δ: 3.41 (8H, brs), 4.36 (2H, s), 4.86 (2H, dd, J=5.7, 1.1 Hz), 6.60 (1H, dt, J=16.0, 5.7 Hz), 6.82 (1H, d, J=16.0 Hz), 7.16-7.20 (2H, m), 7.57 (2H, d, J=8.2 Hz), 7.62 (2H, d, J=8.2 Hz), 7.77-7.81 (2H, m), 9.73 (2H, brs).

Reference Example 312

1-{4-[(E)-3-(4-Methoxyphenoxy)prop-1-en-1-yl]benzyl}piperazine dihydrochloride $^1$H-NMR (DMSO-d$_6$) δ: 3.40 (8H, brs), 3.70 (3H, s), 4.34 (2H, brs), 4.68 (2H, dd, J=5.6, 1.1 Hz), 6.58 (1H, dt, J=16.1, 5.6 Hz), 6.78 (1H, d, J=16.1 Hz), 6.85-6.89 (2H, m), 6.92-6.96 (2H, m), 7.55-7.61 (4H, m), 9.62 (2H, brs).

Reference Example 313

1-{4-[(E)-3-(4-Fluorophenoxy)prop-1-en-1-yl]benzyl}piperazine dihydrochloride $^1$H-NMR (DMSO-d$_6$) δ: 3.38 (8H, brs), 4.32 (2H, s), 4.72 (2H, dd, J=5.6, 1.0 Hz), 6.58 (1H, dt, J=16.1, 5.6 Hz), 6.79 (1H, d, J=16.1 Hz), 7.04-7.99 (2H, m), 7.10-7.16 (2H, m), 7.56-7.59 (4H, m), 9.55 (2H, brs), 12.04 (1H, brs).

Reference Example 314

1-(4-{(E)-3-[4-(Propan-2-yl)phenoxy]prop-1-en-1-yl}benzyl)piperazine dihydrochloride $^1$H-NMR (DMSO-d$_6$) δ: 1.17 (6H, d, J=7.1 Hz), 2.78-2.88 (1H, m), 3.38 (8H, brs), 4.32 (2H, s), 4.71 (2H, d, J=5.2 Hz), 6.59 (1H, dt, J=16.0, 5.2 Hz), 6.78 (1H, d, J=16.0 Hz), 6.91 (2H, d, J=8.5 Hz), 7.15 (2H, d, J=8.5 Hz), 7.55-7.61 (4H, m), 9.58 (2H, brs), 12.03 (1H, brs).

Reference Example 315

1-(4-{(E)-3-[(6-Chloropyridin-3-yl)oxy]prop-1-en-1-yl}benzyl)piperazine dihydrochloride $^1$H-NMR (DMSO-d$_6$) δ: 3.41 (8H, brs), 4.36 (2H, s), 4.85 (2H, dd, J=5.7, 1.2 Hz), 6.59 (1H, dt, J=16.0, 5.7 Hz), 6.82 (1H, d, J=16.0 Hz), 7.45 (1H, dd, J=8.8, 0.5 Hz), 7.54-7.64 (5H, m), 8.19 (1H, d, J=3.2 Hz), 9.74 (2H, brs), 12.19 (1H, brs).

Reference Example 316

4-{(E)-3-[(6-Methylpyridin-3-yl)oxy]prop-1-en-1-yl}benzaldehyde $^1$H-NMR (CDCl$_3$) δ: 2.50 (3H, s), 4.76 (2H, dd, J=5.3, 1.6 Hz), 6.55 (1H, dt, J=16.3, 5.3 Hz), 6.80 (1H, d, J=16.3 Hz), 7.08 (1H, d, J=8.5 Hz), 7.17 (1H, dd, J=8.5, 2.9 Hz), 7.56 (2H, d, J=8.3 Hz), 7.85 (2H, dt, J=8.3, 1.7 Hz), 8.26 (1H, d, J=2.9 Hz), 10.00 (1H, s).

Reference Example 317

1-(4-{(E)-3-[(6-Methylpyridin-3-yl)oxy]prop-1-en-1-yl}benzyl)piperazine dihydrochloride $^1$H-NMR (DMSO-d$_6$) δ: 2.59-2.71 (3H, m), 3.46 (8H, brs), 4.37 (2H, s), 4.97 (2H, d, J=5.6 Hz), 6.60 (1H, dt, J=16.0, 5.6 Hz), 6.86 (1H, d, J=16.0 Hz), 7.58 (2H, d, J=8.3 Hz), 7.63 (2H, d, J=8.3 Hz), 7.79 (1H, d, J=9.0 Hz), 8.11 (1H, dd, J=9.0, 2.8 Hz), 8.53 (1H, d, J=2.8 Hz), 9.74 (2H, brs), 12.12 (1H, brs).

Reference Example 318

(E)-3-[4-(piperazin-1-ylmethyl)phenyl]prop-2-en-1-ol dihydrochloride $^1$H-NMR (DMSO-d$_6$) δ: 3.43 (8H, brs), 4.14 (2H, dd, J=4.8, 1.7 Hz), 4.33 (2H, s), 6.47 (1H, dt, J=16.0, 4.8 Hz), 6.59 (1H, d, J=16.0 Hz), 7.50 (2H, d, J=8.2 Hz), 7.57 (2H, d, J=8.2 Hz), 9.61 (2H, brs), 11.98 (1H, brs).

Reference Example 319

1-[4-(3-Phenoxypropyl)benzyl]piperazine dihydrochloride $^1$H-NMR (DMSO-d$_6$) δ: 2.00-2.07 (2H, m), 2.78 (2H, t, J=7.8 Hz), 3.41 (8H, brs), 3.98 (2H, t, J=6.3 Hz), 4.31 (2H, s), 6.91-6.94 (3H, m), 7.26-7.34 (4H, m), 7.54 (2H, d, J=8.1 Hz), 9.59 (2H, brs), 11.91 (1H, brs).

Reference Example 320

2-(4-{2-[4-(piperazin-1-ylmethyl)phenyl]ethoxy}phenyl)ethanol dihydrochloride $^1$H-NMR (DMSO-d$_6$) δ: 2.64 (2H, t, J=7.2 Hz), 3.05 (2H, t, J=6.6 Hz), 3.24-3.55 (9H, m), 4.19-4.30 (5H, m), 6.83 (2H, d, J=8.5 Hz), 7.10 (2H, d, J=8.5 Hz), 7.40 (2H, d, J=7.8 Hz), 7.56-7.59 (2H, m), 9.82 (2H, s), 12.23 (1H, s).

Reference Example 321

1-(4-{3-[(6-Chloropyridin-3-yl)oxy]propyl}benzyl)piperazine dihydrochloride $^1$H-NMR (DMSO-d$_6$) δ: 2.01-2.08 (2H, m), 2.77 (2H, t, J=7.7 Hz), 3.40-3.45 (8H, m), 4.07 (2H, t, J=6.2 Hz), 4.33 (2H, hrs), 7.32 (2H, d, J=8.0 Hz), 7.42 (1H, dd, J=8.8, 0.6 Hz), 7.49 (1H, dd, J=8.8, 3.2 Hz), 7.56 (2H, d, J=8.0 Hz), 8.12 (1H, dd, J=3.2, 0.6 Hz), 9.73 (2H, brs), 12.10 (1H, brs).

Reference Example 322

1-(4-{3-[(6-Methylpyridin-3-yl)oxy]propyl}benzyl)piperazine dihydrochloride $^1$H-NMR (DMSO-d$_6$) δ: 2.04-2.11 (2H, m), 2.66 (3H, s), 2.79 (2H, t, J=7.6 Hz), 3.39-3.47 (8H, m), 4.19 (2H, t, J=6.2 Hz), 4.35 (2H, s), 7.33 (2H, d, J=8.2 Hz), 7.58 (2H, d, J=8.2 Hz), 7.79 (1H, d, J=8.8 Hz), 8.09 (1H, dd, J=8.8, 2.9 Hz), 8.48 (1H, d, J=2.9 Hz), 9.93 (2H, brs), 12.20 (1H, brs).

Reference Example 323

1-{4-[2-(4-Chlorophenoxy)ethyl]-3-fluorobenzyl}piperazine dihydrochloride $^1$H-NMR (DMSO-d$_6$) δ: 3.07-3.43 (10H, m), 4.23-4.31 (4H, m), 6.96 (2H, d, J=9.0 Hz), 7.31 (2H, d, J=9.0 Hz), 7.44-7.49 (3H, m), 9.75 (2H, s), 12.33 (1H, s).

Reference Example 324

1-(2-Fluoro-4-{2-[4-(trifluoromethyl)phenoxy]ethyl}benzyl)piperazine dihydrochloride $^1$H-NMR (DMSO-d$_6$) δ: 3.12 (2H, t, J=6.5 Hz), 3.21-3.49 (7H, m), 3.95-3.97 (1H, m), 4.32-4.34 (4H, m), 7.13 (2H, d, J=8.5 Hz), 7.29-7.34 (2H, m), 7.64 (3H, d, J=8.8 Hz), 9.60 (2H, s), 12.18-12.20 (1H, m).

Reference Example 325

1-{4-[3-(4-Methylphenoxy)propyl]benzyl}piperazine dihydrochloride $^1$H-NMR (DMSO-d$_6$) δ: 1.97-2.04 (2H, m), 2.22 (3H, s), 2.76 (2H, t, J=7.7 Hz), 3.40 (8H, brs), 3.93 (2H, t, J=6.2 Hz), 4.32 (2H, brs), 6.82 (2H, d, J=8.5 Hz), 7.07 (2H, d, J=8.5 Hz), 7.32 (2H, d, J=7.8 Hz), 7.55 (2H, d, J=7.8 Hz), 9.70 (2H, brs), 12.07 (1H, brs).

Reference Example 326

To a solution of tert-butyl 4-(4-{[4-(propan-2-yloxy)phenoxy]methyl}benzyl)-piperazine-1-carboxylate (5.42 g) in CH$_2$Cl$_2$ (41 mL) was added TFA (10 mL) at room temperature, then the reaction mixture was stirred for 8 hours. The reaction mixture was basified with 5 M aqueous NaOH, and extracted with CH$_2$Cl$_2$. The organic layer was washed with water and saturated aqueous NaCl, dried over anhydrous Na$_2$SO$_4$, and concentrated under reduced pressure to afford 1-(4-{[4-(propan-2-yloxy)phenoxy]methyl}benzyl)piperazine as a colorless solid (5.73 g).

$^1$H-NMR (CDCl$_3$) δ: 1.30 (6H, d, J=5.9 Hz), 1.73 (1H, brs), 2.35-2.47 (4H, m), 2.88 (4H, t, J=4.9 Hz), 3.49 (2H, s), 4.42 (1H, septet, J=5.9 Hz), 4.98 (2H, s), 6.78-6.93 (4H, m), 7.29-7.43 (4H, m).

The following compounds were produced in the same manner as in Reference Example 326 using appropriate starting materials.

Reference Example 327

1-{4-[(4-Chlorophenoxy)methyl]benzyl}piperazine $^1$H-NMR (CDCl$_3$) δ: 1.65 (1H, brs), 2.42 (4H, brs), 2.89 (4H, t, J=4.9 Hz), 3.49 (2H, s), 5.01 (2H, s), 6.86-6.93 (2H, m), 7.20-7.26 (2H, m), 7.31-7.39 (4H, m).

Reference Example 328

1-{4-[2-(4-Methylphenyl)ethoxy]benzyl}piperazine $^1$H-NMR (CDCl$_3$) δ: 1.80 (1H, brs), 2.33 (3H, s), 2.35-2.45 (4H, m), 2.87 (4H, t, J=4.9 Hz), 3.05 (2H, t, J=7.3 Hz), 3.41 (2H, s), 4.13 (2H, t, J=7.3 Hz), 6.79-6.88 (2H, m), 7.08-7.28 (6H, m).

Reference Example 329

1-(4-{2-[4-(Propan-2-yl)phenyl]ethoxy}benzyl)piperazine $^1$H-NMR (CDCl$_3$) δ: 1.24 (6H, d, J=6.9 Hz), 1.94 (1H, brs), 2.33-2.43 (4H, m), 2.80-2.92 (5H, m), 3.06 (2H, t, J=7.3 Hz), 3.41 (2H, s), 4.14 (2H, t, J=7.3 Hz), 6.79-6.88 (2H, m), 7.15-7.28 (6H, m).

Reference Example 330

1-{4-[(4-Methoxyphenoxy)methyl]benzyl}piperazine $^1$H-NMR (CDCl$_3$) δ: 1.91 (1H, brs), 2.35-2.50 (4H, m), 2.89 (4H, t, J=4.6 Hz), 3.50 (2H, s), 3.77 (3H, s), 4.99 (2H, s), 6.78-6.93 (4H, m), 7.30-7.43 (4H, m).

Reference Example 331

1-{4-[(4-Ethoxyphenoxy)methyl]benzyl}piperazine $^1$H-NMR (CDCl$_3$) δ: 1.39 (3H, t, J=6.9 Hz), 2.18 (1H, brs), 2.38-2.50 (4H, m), 2.90 (4H, t, J=4.9 Hz), 3.50 (2H, s), 3.98 (2H, q, J=6.9 Hz), 4.99 (2H, s), 6.78-6.93 (4H, m), 7.30-7.43 (4H, m).

Reference Example 332

1-(4-{2-[4-(Propan-2-yloxy)phenoxy]ethyl}benzyl)piperazine $^1$H-NMR (CDCl$_3$) δ: 1.29 (6H, d, J=5.9 Hz), 1.86 (1H, brs), 2.33-2.52 (4H, m), 2.88 (4H, t, J=4.9 Hz), 3.05 (2H, t, J=7.3 Hz), 3.46 (2H, s), 4.11 (2H, t, J=7.3 Hz), 4.40 (1H, septet, J=5.9 Hz), 6.81 (4H, s), 7.18-7.34 (4H, m).

Reference Example 333

1-{4-[2-(4-Ethoxyphenoxy)ethyl]benzyl}piperazine $^1$H-NMR (CDCl$_3$) δ: 1.38 (3H, t, J=6.9 Hz), 1.69 (1H, brs), 2.34-2.50 (4H, m), 2.88 (4H, t, J=4.9 Hz), 3.05 (2H, t, J=6.9

Hz), 3.47 (2H, s), 3.97 (2H, q, J=6.9 Hz), 4.11 (2H, t, J=6.9 Hz), 6.81 (4H, s), 7.16-7.30 (4H, m).

Reference Example 334

1-{-4-[2-(3-Chlorophenoxy)ethyl]benzyl}piperazine $^1$H-NMR (CDCl$_3$) δ: 1.61 (1H, brs), 2.34-2.48 (4H, m), 2.88 (4H, t, J=4.9 Hz), 3.07 (2H, t, J=6.9 Hz), 3.47 (2H, s), 4.14 (2H, t, J=6.9 Hz), 6.72-6.83 (1H, m), 6.85-6.95 (2H, m), 7.10-7.30 (5H, m).

Reference Example 335

4-{2-[4-(piperazin-1-ylmethyl)phenyl]ethoxy}benzonitrile trifluoroacetate $^1$H-NMR (DMSO-d$_6$) δ: 2.92-3.14 (6H, m), 3.22-3.45 (4H, m), 4.01 (2H, brs), 4.31 (2H, t, J=6.6 Hz), 7.11 (2H, d, J=8.2 Hz), 7.38 (4H, s), 7.76 (2H, d, J=8.2 Hz), 9.03 (1H, brs).

Reference Example 336

1-(4-{2-[4-(Methylsulfonyl)phenoxy]ethyl}benzyl)piperazine trifluoroacetate $^1$H-NMR (DMSO-d$_6$) δ: 2.93-3.13 (6H, m), 3.15 (3H, s), 3.27 (4H, brs), 4.04 (2H, brs), 4.33 (2H, t, J=6.9 Hz), 7.16 (2H, d, J=8.9 Hz), 7.39 (4H, s), 7.83 (2H, d, J=8.9 Hz), 9.09 (2H, brs).

Reference Example 337

1-{4-[2-(4-Iodophenoxy)ethyl]benzyl}piperazine trifluoroacetate $^1$H-NMR (DMSO-d$_6$) δ: 2.93-3.11 (6H, m), 3.32 (4H, brs), 3.99 (2H, brs), 4.18 (2H, t, J=6.9 Hz), 6.78 (2H, d, J=8.9 Hz), 7.36 (4H, s), 7.58 (2H, d, J=8.9 Hz), 8.99 (2H, brs), 11.12 (1H, brs).

Reference Example 338

6-(piperazin-1-ylmethyl)-2-[4-(propan-2-yl)phenoxy]quinoline $^1$H-NMR (CDCl$_3$) δ: 1.29 (6H, d, J=6.9 Hz), 1.68 (1H, brs), 2.45 (4H, brs), 2.90 (4H, t, J=4.6 Hz), 2.95 (1H, septet, J=6.9 Hz), 3.62 (2H, s), 7.03 (1H, d, J=8.7 Hz), 7.12-7.19 (2H, m), 7.24-7.30 (2H, m), 7.62 (1H, dd, J=6.9, 1.8 Hz), 7.67 (1H, s), 7.77 (1H, d, J=8.7 Hz), 8.07 (1H, d, J=8.7 Hz).

Reference Example 339

2-(4-Methoxyphenoxy)-6-(piperazin-1-ylmethyl)quinoline $^1$H-NMR (CDCl$_3$) δ: 1.58 (1H, brs), 2.44 (4H, brs), 2.89 (4H, t, J=4.5 Hz), 3.61 (2H, s), 3.84 (3H, s), 6.91-6.99 (2H, m), 7.02 (1H, d, J=9.2 Hz), 7.13-7.20 (2H, m), 7.61 (1H, dd, J=8.2 Hz), 7.64-7.69 (1H, m), 7.74 (1H, d, J=8.7 Hz), 8.06 (1H, d, J=9.2 Hz).

Reference Example 340

1-{4-[2-(4-Methylphenoxy)propyl]benzyl}piperazine $^1$H-NMR (CDCl$_3$) δ: 1.27 (3H, d, J=6.1 Hz), 2.27 (3H, s), 2.40 (4H, brs), 2.78 (1H, dd, J=13.7, 6.6 Hz), 2.88 (4H, t, J=4.9 Hz), 3.07 (1H, dd, J=13.7, 5.9 Hz), 3.45 (2H, s), 4.47-4.54 (1H, m), 6.78 (2H, dt, J=9.4, 2.6 Hz), 7.05 (2H, dd, J=8.7, 0.6 Hz), 7.18 (2H, d, J=8.1 Hz), 7.23 (2H, d, J=8.1 Hz).

Reference Example 341

1-{4-[1-(4-Methylphenoxy)propan-2-yl]benzyl}piperazine $^1$H-NMR (CDCl$_3$) δ: 1.39 (3H, d, J=7.1 Hz), 2.27 (3H, s), 2.41 (4H, brs), 2.88 (4H, t, J=4.9 Hz), 3.17-3.25 (1H, m), 3.47 (2H, s), 3.91 (1H, dd, J=9.2, 7.8 Hz), 4.05 (1H, dd, J=9.2, 5.7 Hz), 6.78 (2H, d, J=8.8 Hz), 7.05 (2H, d, J=8.8 Hz), 7.22 (2H, d, J=8.3 Hz), 7.27 (2H, d, J=8.3 Hz).

Reference Example 342

1-{4-[(E)-3-Methoxyprop-1-en-1-yl]benzyl}piperazine $^1$H-NMR (CDCl$_3$) δ: 2.42 (4H, brs), 2.89 (4H, t, J=4.9 Hz), 3.39 (3H, s), 3.47 (2H, s), 4.09 (2H, dd, J=6.1, 1.5 Hz), 6.26 (1H, dt, J=16.1, 6.1 Hz), 6.60 (1H, d, J=16.1 Hz), 7.27 (2H, d, J=8.3 Hz), 7.34 (2H, d, J=8.3 Hz).

Reference Example 343

1-{3-Methyl-4-[2-(4-methylphenoxy)ethyl]benzyl}piperazine $^1$H-NMR (CDCl$_3$) δ: 2.28 (3H, s), 2.35 (3H, s), 2.40 (4H, brs), 2.88 (4H, t, J=4.9 Hz), 3.07 (2H, t, J=7.4 Hz), 3.43 (2H, s), 4.10 (2H, t, J=7.4 Hz), 6.79 (2H, dt, J=9.3, 2.5 Hz), 7.05-7.12 (4H, m), 7.16 (1H, d, J=7.8 Hz).

Reference Example 344

1-{4-[2-(4-Fluorophenoxy)ethyl]-3-methylbenzyl}piperazine $^1$H-NMR (CDCl$_3$) δ: 2.35 (3H, s), 2.41 (4H, brs), 2.89 (4H, t, J=4.9 Hz), 3.07 (2H, t, J=7.3 Hz), 3.44 (2H, s), 4.09 (2H, t, J=7.3 Hz), 6.79-6.85 (2H, m), 6.92-7.00 (2H, m), 7.09-7.16 (3H, m).

Reference Example 345

N,N-Dimethyl-4-{2-[4-(piperazin-1-ylmethyl)phenyl]ethoxy}aniline $^1$H-NMR (CDCl$_3$) δ: 2.39-2.42 (4H, m), 2.86-2.88 (10H, m), 3.05 (2H, t, J=7.2 Hz), 3.46 (2H, s), 4.11 (2H, t, J=7.2 Hz), 6.72-6.73 (2H, m), 6.82-6.84 (2H, m), 7.21-7.27 (4H, m).

Reference Example 346

1-{4-[2-(4-Fluorophenoxy)propyl]benzyl}piperazine $^1$H-NMR (CDCl$_3$) δ: 1.28 (3H, d, J=6.1 Hz), 2.39 (4H, brs), 2.79 (1H, dd, J=13.7, 6.6 Hz), 2.88 (4H, t, J=4.9 Hz), 3.04

(1H, dd, J=13.7, 6.1 Hz), 3.46 (2H, s), 4.41-4.49 (1H, m), 6.77-6.82 (2H, m), 6.90-6.96 (2H, m), 7.17 (2H, d, J=8.1 Hz), 7.24 (2H, d, J=8.1 Hz).

Reference Example 347

1-{2-Methyl-4-[2-(4-methylphenoxy)ethyl]benzyl}piperazine $^1$H-NMR (CDCl$_3$) δ: 2.28 (3H, s), 2.35 (3H, s), 2.40 (4H, brs), 2.85 (4H, t, J=4.9 Hz), 3.03 (2H, t, J=7.2 Hz), 3.41 (2H, s), 4.12 (2H, t, J=7.2 Hz), 6.80 (2H, dt, J=9.3, 2.5 Hz), 7.00-7.08 (4H, m), 7.19 (1H, d, J=7.6 Hz).

Reference Example 348

2-[2-Fluoro-4-(piperazin-1-ylmethyl)phenoxy]-2-methylpropan-1-ol $^1$H-NMR (CDCl$_3$) δ: 1.28 (6H, s), 1.89-1.93 (2H, m), 2.39-2.42 (4H, m), 2.89-2.90 (4H, m), 3.43 (2H, s), 3.59 (2H, s), 6.98-7.00 (2H, m), 7.10 (1H, d, J=12.0 Hz).

Reference Example 349

To a solution of 9H-fluoren-9-ylmethyl 4-(4-{(E)-3-[(5-bromopyridin-2-yl)oxy]-prop-1-en-1-yl}benzyl)piperazine-1-carboxylate (0.604 g) in CH$_2$Cl$_2$ (10 mL) was added piperidine (0.196 mL). After stirring at room temperature for 1 hour, to the reaction mixture was added piperidine (0.784 mL) and stirred at room temperature for 4 hours. Then to the reaction mixture was added saturated aqueous NH$_4$Cl and CH$_2$Cl$_2$. The organic layer was washed with saturated aqueous NH$_4$Cl and saturated aqueous NaCl, dried over anhydrous Na$_2$SO$_4$, and concentrated under reduced pressure. The residue was washed with Et$_2$O to afford 1-(4-{(E)-3-[(5-bromopyridin-2-yl)oxy]prop-1-en-1-yl}benzyl)piperazine as a white powder (0.282 g).

$^1$H-NMR (CDCl$_3$) δ: 2.72 (4H, t, J=4.8 Hz), 3.19 (4H, t, J=4.8 Hz), 3.54 (2H, s), 4.96 (2H, d, J=6.1 Hz), 6.42 (1H, dt, J=15.9, 6.1 Hz), 6.68-6.72 (2H, m), 7.23-7.26 (2H, m), 7.36 (2H, d, J=8.1 Hz), 7.65 (1H, dd, J=8.7, 2.5 Hz), 8.20 (1H, d, J=2.5 Hz).

The following compound was produced in the same manner as in Reference Example 349 using appropriate starting materials.

Reference Example 350

1-(4-{(E)-3-[(5-Methylpyridin-2-yl)oxy]prop-1-en-1-yl}benzyl)piperazine $^1$H-NMR (CDCl$_3$) δ: 2.25 (3H, s), 2.74 (4H, t, J=4.8 Hz), 3.21 (4H, t, J=4.9 Hz), 3.54 (2H, s), 4.96 (2H, dd, J=6.0, 1.2 Hz), 6.45 (1H, dt, J=15.9, 6.0 Hz), 6.69-6.72 (2H, m), 7.23 (2H, d, J=8.2 Hz), 7.36 (2H, d, J=8.2 Hz), 7.40 (1H, ddd, J=8.5, 2.4, 0.5 Hz), 7.96-7.97 (1H, m).

Reference Example 351

To an EtOH (500 mL) solution of butyl (E)-3-{3-chloro-4-[(5-nitropyridin-2-yl)oxy]phenyl}prop-2-enoate (45.4 g) and tin powder (57.3 g) was slowly added conc. HCl (36.6 mL) at 0° C., then the resultant mixture was stirred at room temperature for 1 hour. The reaction mixture was neutralized with 5 M aqueous NaOH, and the mixture was filtered off on Celite. The filtrate was evaporated and water was added to the residue, and the mixture was extracted with AcOEt. The organic layer was washed with water and saturated aqueous NaCl, dried over anhydrous Na$_2$SO$_4$, and concentrated under reduced pressure. The residue was purified by silica gel column chromatography (n-hexane/AcOEt=2/1) to afford butyl (E)-3-{4-[(5-amino-pyridin-2-yl)oxy]-3-chlorophenyl}prop-2-enoate (39.9 g) as a pale yellow solid.

$^1$H-NMR (CDCl$_3$) δ: 0.97 (3H, t, J=7.3 Hz), 1.38-1.50 (2H, m), 1.64-1.74 (2H, m), 3.58 (2H, brs), 4.21 (2H, t, J=6.8 Hz), 6.37 (1H, d, J=16.1 Hz), 6.85 (1H, d, J=7.8 Hz), 7.08-7.15 (2H, m), 7.39 (1H, dd, J=8.3, 2.0 Hz), 7.55-7.67 (3H, m).

The following compounds were produced in the same manner as in Reference Example 351 using appropriate starting materials.

Reference Example 352

Ethyl (E)-3-{4-[(5-aminopyridin-2-yl)oxy]-3-methoxyphenyl}prop-2-enoate $^1$H-NMR (CDCl$_3$) δ: 1.34 (3H, t, J=7.1 Hz), 3.50 (2H, s), 3.83 (3H, s), 4.27 (2H, q, J=7.2 Hz), 6.36 (1H, d, J=15.6 Hz), 6.82 (1H, d, J=8.8 Hz), 7.03-7.14 (4H, m), 7.65 (2H, dd, J=9.5, 6.6 Hz).

Reference Example 353

Butyl (E)-3-{4-[(5-aminopyridin-2-yl)oxy]-3-methylphenyl}prop-2-enoate $^1$H-NMR (CDCl$_3$) δ: 0.96 (3H, t, J=7.3 Hz), 1.37-1.51 (2H, m), 1.64-1.74 (2H, m), 2.24 (3H, s), 3.55 (2H, brs), 4.20 (2H, q, J=6.6 Hz), 6.35 (1H, d, J=15.8 Hz), 6.76 (1H, d, J=8.6 Hz), 6.93 (1H, d, J=8.2 Hz), 7.09 (1H, dd, J=8.6, 3.0 Hz), 7.31-7.35 (1H, m), 7.41 (1H, brs), 7.63 (1H, d, J=15.8 Hz), 7.69 (1H, d, J=3.0 Hz).

Reference Example 354

Butyl (E)-3-{4-[(5-aminopyridin-2-yl)oxy]-3-chloro-5-methylphenyl}prop-2-enoate $^1$H-NMR (CDCl$_3$) δ: 0.97 (3H, t, J=7.3 Hz), 1.39-1.48 (2H, m), 1.65-1.72 (2H, m), 2.19 (3H, s), 3.47 (2H, brs), 4.20 (2H, t, J=6.6 Hz), 6.37 (1H, d, J=15.9 Hz), 6.82 (1H, d, J=8.5 Hz), 7.10-7.13 (1H, m), 7.31-7.32 (1H, m), 7.46 (1H, d, J=1.7 Hz), 7.56-7.60 (2H, m).

Reference Example 355

Ethyl (E)-3-{4-[(5-aminopyridin-2-yl)oxy]-3,5-dimethoxyphenyl}prop-2-enoate $^1$H-NMR (CDCl$_3$) δ: 1.35 (3H, t, J=7.2 Hz), 3.41 (2H, brs), 3.79 (6H, s), 4.27 (2H, q, J=7.2 Hz), 6.38 (1H, d, J=15.9 Hz), 6.82 (2H, s), 6.85 (1H, d, J=8.8 Hz), 7.08 (1H, dd, J=8.5, 2.9 Hz), 7.58 (1H, d, J=2.9 Hz), 7.64 (1H, d, J=15.9 Hz).

Reference Example 356

Butyl (E)-3-{4-[(5-aminopyridin-2-yl)oxy]-2-methylphenyl}prop-2-enoate $^1$H-NMR (CDCl$_3$) δ: 0.96 (3H, t, J=7.3 Hz), 1.37-1.50 (2H, m), 1.64-1.74 (2H, m), 2.40 (3H, s), 3.58 (2H, brs), 4.20 (2H, t, J=6.6 Hz), 6.29 (1H, d, J=15.8 Hz), 6.80 (1H, d, J=8.9 Hz), 6.86-6.90 (2H, m), 7.10 (1H, dd, J=8.6, 3.0 Hz), 7.53-7.56 (1H, m), 7.73 (1H, dd, J=3.0 Hz), 7.92 (1H, d, J=15.8 Hz).

Reference Example 357

6-(4-Bromo-2-chloro-6-methylphenoxy)pyridin-3-amine $^1$H-NMR (CDCl$_3$) δ: 2.16 (3H, s), 3.46 (2H, brs), 6.80 (1H, dd, J=8.6, 0.5 Hz), 7.10 (1H, dd, J=8.8, 3.2 Hz), 7.25-7.33 (1H, m), 7.43 (1H, dd, J=2.3, 0.5 Hz), 7.56 (1H, dd, J=2.9, 0.5 Hz).

Reference Example 358

Butyl (E)-3-{4-[(5-aminopyridin-2-yl)oxy]-3-fluorophenyl}prop-2-enoate $^1$H-NMR (CDCl$_3$) δ: 0.97 (3H, t, J=7.3 Hz), 1.39-1.49 (2H, m), 1.66-1.73 (2H, m), 3.54 (2H, s), 4.21 (2H, t, J=6.6 Hz), 6.36 (1H, d, J=16.1 Hz), 6.86 (1H, d, J=8.3 Hz), 7.12 (1H, dd, J=9.0, 2.7 Hz), 7.17 (1H, t, J=8.1 Hz), 7.26-7.35 (2H, m), 7.59-7.64 (2H, m).

Reference Example 359

Ethyl (E)-3-{4-[(5-aminopyridin-2-yl)oxy]-3,5-dimethylphenyl}prop-2-enoate $^1$H-NMR (CDCl$_3$) δ: 1.34 (3H, t, J=7.1 Hz), 2.12 (6H, s), 3.44 (2H, brs), 4.26 (2H, t, J=7.1 Hz), 6.36 (1H, d, J=16.1 Hz), 6.70 (1H, d, J=8.8 Hz), 7.08 (1H, dd, J=8.6, 2.9 Hz), 7.26 (2H, s), 7.61-7.65 (2H, m).

Reference Example 360

To a solution of ethyl 6-[(5-nitropyridin-2-yl)oxy]naphthalene-2-carboxylate (23.3 g) in EtOH (460 mL) was added Pd/C (0.367 g) under a H$_2$ atmosphere. Then the reaction mixture was warmed to 50° C., and stirred for 7.5 hours. The reaction mixture was filtered off on celite, and the filtrate was concentrated under reduced pressure. The residual solid was dried under reduced pressure at 60° C. to afford ethyl 6-[(5-aminopyridin-2-yl)oxy]naphthalene-2-carboxylate as a pale brown powder (19.6 g).

$^1$H-NMR (CDCl$_3$) δ: 1.44 (3H, t, J=7.2 Hz), 3.60 (2H, s), 4.43 (2H, q, J=7.2 Hz), 6.87 (1H, dd, J=8.5, 0.5 Hz), 7.14 (1H, dd, J=8.5, 3.2 Hz), 7.32 (1H, dd, J=8.9, 2.3 Hz), 7.41 (1H, d, J=2.2 Hz), 7.74 (1H, d, J=8.5 Hz), 7.76 (1H, dd, J=2.9, 0.5 Hz), 7.93 (1H, d, J=9.0 Hz), 8.03 (1H, dd, J=8.5, 1.7 Hz), 8.57 (1H, s).

Reference Example 361

To a solution of 2-(4-bromo-2-chloro-5-methylphenoxy)-5-nitropyridine (10.0 g) in AcOEt (150 mL) was added 5% Pt/C (1.00 g) at 0° C. After stirring at room temperature for 5 hours under a hydrogen atmosphere, the reaction mixture was filtered off using celite, and the filtrate was concentrated under reduced pressure to give 6-(4-bromo-2-chloro-5-methyl-phenoxy)pyridin-3-amine as a pink solid (9.13 g).

$^1$H-NMR (CDCl$_3$) δ: 2.33 (3H, s), 3.51 (2H, brs), 6.80-6.83 (1H, m), 7.01 (1H, s), 7.10 (1H, dd, J=8.5, 2.9 Hz), 7.60 (1H, s), 7.63-7.64 (1H, m).

The following compounds were produced in the same manner as in Reference Example 361 using appropriate starting materials.

Reference Example 362

6-(4-Bromo-5-chloro-2-methylphenoxy)pyridin-3-amine $^1$H-NMR (CDCl$_3$) δ: 2.16 (3H, s), 3.53 (2H, brs), 6.76 (1H, d, J=8.5 Hz), 7.05 (1H, s), 7.08-7.13 (1H, m), 7.46 (1H, s), 7.66 (1H, d, J=2.9 Hz).

Reference Example 363 tert-Butyl 4-{4-[2-(4-aminophenoxy)ethyl]benzyl}piperazine-1-carboxylate $^1$H-NMR (CDCl$_3$) δ: 1.45 (9H, s), 2.38 (4H, t, J=4.9 Hz), 3.02-3.06 (2H, m), 3.41-3.43 (6H, m), 3.48 (2H, brs), 4.07-4.11 (2H, m), 6.62 (2H, d, J=8.8 Hz), 6.73 (2H, d, J=8.8 Hz), 7.22 (2H, d, J=8.3 Hz), 7.25 (2H, d, J=8.8 Hz).

Reference Example 364

To a THF (400 mL) solution of butyl (E)-3-{4-[(5-aminopyridin-2-yl)oxy]-3-chlorophenyl}prop-2-enoate (30.0 g) was slowly added H$_2$SO$_4$ (6.92 mL) at 0° C. After stirring for 10 minutes, n-pentyl nitrite (17.3 mL) was slowly added to the reaction mixture. Then the resultant mixture was stirred at 0° C. for 1 hour. The resulting precipitate was collected by filtration and dried under reduced pressure to afford a diazonium salt as a pale yellow powder. To acetic acid (400 mL) was slowly added the above diazonium salt at 100° C., then the resultant mixture was stirred at 100° C. for 3 hours. After cooling, the solvent was evaporated and the residue was neutralized with 5 M aqueous NaOH, and the mixture was extracted with AcOEt. The organic layer was washed with water and saturated aqueous NaCl, dried over anhydrous Na$_2$SO$_4$, and concentrated under reduced pressure. The residue was purified by silica gel column chromatography (n-hexane/AcOEt=2/1) to afford butyl (E)-3-{3-chloro-4-[(5-hydroxypyridin-2-yl)oxy]phenyl}prop-2-enoate (14.8 g) as a brown oil.

$^1$H-NMR (CDCl$_3$) δ: 0.97 (3H, t, J=7.3 Hz), 1.38-1.50 (2H, m), 1.64-1.74 (2H, m), 4.21 (2H, t, J=6.8 Hz), 6.26 (1H, brs), 6.37 (1H, d, J=16.1 Hz), 6.90 (1H, d, J=8.8 Hz), 7.12 (1H, d, J=8.8 Hz), 7.28 (1H, dd, J=8.8, 2.9 Hz), 7.40 (1H, dd, J=8.3, 2.0 Hz), 7.54-7.62 (2H, m), 7.75 (1H, d, J=2.4 Hz).

The following compounds were produced in the same manner as in Reference Example 364 using appropriate starting materials.

Reference Example 365

Butyl (E)-3-{3-chloro-4-[(5-hydroxypyridin-2-yl)oxy]-5-methylphenyl}prop-2-enoate $^1$H-NMR (CDCl$_3$) δ: 0.97 (3H, t, J=7.3 Hz), 1.41-1.46 (2H, m), 1.66-1.72 (2H, m), 2.19 (3H, s), 4.21 (2H, t, J=6.6 Hz), 5.59 (1H, s), 6.37 (1H, d, J=16.2 Hz), 6.87 (1H, d, J=8.9 Hz), 7.24-7.31 (2H, m), 7.45 (1H, d, J=2.0 Hz), 7.56 (1H, d, J=15.8 Hz), 7.67 (1H, d, J=3.0 Hz).

Reference Example 366

Butyl (E)-3-{-4-[(5-hydroxypyridin-2-yl)oxy]-2-methylphenyl}prop-2-enoate $^1$H-NMR (CDCl$_3$) δ: 0.96 (3H, t, J=7.3 Hz), 1.39-1.48 (2H, m), 1.65-1.72 (2H, m), 2.37 (3H, s), 4.21 (2H, t, J=6.8 Hz), 6.29 (1H, d, J=16.1 Hz), 6.81-6.87 (3H, m), 7.24-7.27 (1H, m), 7.52-7.54 (1H, m), 7.68 (1H, brs), 7.83 (1H, d, J=3.4 Hz), 7.90 (1H, d, J=16.1 Hz).

Reference Example 367

Ethyl (E)-3-{4-[(5-hydroxypyridin-2-yl)oxy]-3-methoxyphenyl}prop-2-enoate $^1$H-NMR (CDCl$_3$) δ: 1.35 (3H, t, J=7.1 Hz), 3.79 (3H, s), 4.27 (2H, q, J=7.1 Hz), 6.36 (1H, d, J=15.6 Hz), 6.45-6.75 (1H, m), 6.83 (1H, d, J=8.8 Hz), 7.04-7.13 (3H, m), 7.22 (1H, dd, J=8.8, 2.9 Hz), 7.61-7.73 (2H, m).

Reference Example 368

Ethyl (E)-3-{4-[(5-hydroxypyridin-2-yl)oxy]phenyl}prop-2-enoate $^1$H-NMR(CDCl$_3$) δ: 1.34 (3H, t, J=7.2 Hz), 4.27 (2H, q, J=7.2 Hz), 6.35 (1H, brs), 6.35 (1H, d, J=16.1 Hz), 6.87 (1H, d, J=8.8 Hz), 7.06 (2H, dt, J=9.2, 2.4 Hz), 7.27 (1H, dd, J=8.8, 3.1 Hz), 7.51 (2H, dt, J=9.2, 2.4 Hz), 7.65 (1H, d, J=16.1 Hz), 7.85 (1H, dd, J=3.2, 0.5 Hz).

Reference Example 369

Butyl (E)-3-{4-[(5-hydroxypyridin-2-yl)oxy]-3-methylphenyl}prop-2-enoate $^1$H-NMR (CDCl$_3$) δ: 0.96 (3H, t, J=7.3 Hz), 1.39-1.48 (2H, m), 1.65-1.72 (2H, m), 2.21 (3H, s), 4.21 (2H, t, J=6.9 Hz), 6.35 (1H, d, J=15.6 Hz), 6.77 (1H, d, J=8.7 Hz), 6.92 (1H, d, J=8.2 Hz), 7.24 (1H, dd, J=8.9, 3.0 Hz), 7.32 (1H, dd, J=8.5, 2.1 Hz), 7.40 (1H, d, J=1.8 Hz), 7.44 (1H, s), 7.62 (1H, d, J=16.0 Hz), 7.78 (1H, d, J=2.7 Hz).

Reference Example 370

Butyl (E)-3-{3-fluoro-4-[(5-hydroxypyridin-2-yl)oxy]phenyl}prop-2-enoate $^1$H-NMR (CDCl$_3$) δ: 0.97 (3H, t, J=7.3 Hz), 1.39-1.49 (2H, m), 1.66-1.73 (2H, m), 4.21 (2H, t, J=6.7 Hz), 5.20 (1H, s), 6.37 (1H, d, J=16.1 Hz), 6.93 (1H, d, J=8.8 Hz), 7.20 (1H, t, J=8.1 Hz), 7.27-7.35 (3H, m), 7.61 (1H, d, J=15.9 Hz), 7.75 (1H, d, J=3.2 Hz).

Reference Example 371

6-(4-Bromo-2-chloro-6-methylphenoxy)pyridin-3-ol $^1$H-NMR (CDCl$_3$) δ: 2.15 (3H, s), 6.24 (1H, brs), 6.84 (1H, d, J=8.8 Hz), 7.22-7.29 (2H, m), 7.38-7.43 (1H, m), 7.63 (1H, d, J=3.2 Hz).

Reference Example 372

Ethyl (E)-3-{4-[(5-hydroxypyridin-2-yl)oxy]-3,5-dimethylphenyl}prop-2-enoate $^1$H-NMR (CDCl$_3$) δ: 1.34 (3H, t, J=7.1 Hz), 2.09 (6H, s), 4.26 (2H, t, J=7.1 Hz), 6.34 (1H, d, J=15.9 Hz), 6.66 (1H, d, J=8.8 Hz), 7.19-7.26 (3H, m), 7.57-7.61 (2H, m), 7.66 (1H, d, J=2.2 Hz).

Reference Example 373

Ethyl 6-[(5-hydroxypyridin-2-yl)oxy]naphthalene-2-carboxylate $^1$H-NMR (DMSO-d$_6$) δ: 1.37 (3H, t, J=7.1 Hz), 4.38 (2H, q, J=7.2 Hz), 7.03 (1H, dd, J=8.7, 0.6 Hz), 7.33-7.37 (2H, m), 7.51 (1H, d, J=2.4 Hz), 7.77 (1H, dd, J=3.2, 0.5 Hz), 7.92-7.98 (2H, m), 8.16 (1H, d, J=9.3 Hz), 8.61 (1H, d, J=0.7 Hz), 9.82 (1H, brs).

Reference Example 374

6-(4-Bromo-2-chloro-5-methylphenoxy)pyridin-3-ol $^1$H-NMR (DMSO-d$_6$) δ: 2.30 (3H, s), 6.96 (1H, d, J=8.8 Hz), 7.23 (1H, s), 7.30 (1H, dd, J=8.8, 2.9 Hz), 7.63 (1H, d, J=2.9 Hz), 7.79 (1H, s), 9.66 (1H, s).

Reference Example 375

6-(4-Bromo-5-chloro-2-methylphenoxy)pyridin-3-ol $^1$H-NMR (DMSO-d$_6$) δ: 2.09 (3H, s), 6.95 (1H, d, J=8.8 Hz), 7.22 (1H, s), 7.30 (1H, dd, J=8.8, 3.2 Hz), 7.66 (1H, d, J=3.2 Hz), 7.71 (1H, s), 9.67 (1H, s).

Reference Example 376

Ethyl (E)-3-{4-[(5-hydroxypyridin-2-yDoxy]-3,5-dimethoxyphenyl}prop-2-enoate $^1$H-NMR (DMSO-d$_6$) δ: 1.27 (3H, t, J=7.1 Hz), 3.72 (6H, s), 4.20 (2H, q, J=7.1 Hz), 6.72 (1H, d, J=16.1 Hz), 6.79 (1H, d, J=8.8 Hz), 7.14 (2H, s), 7.21 (1H, dd, J=8.8, 2.9 Hz), 7.51 (1H, d, J=2.7 Hz), 7.64 (1H, d, J=16.1 Hz), 9.38 (1H, s).

Reference Example 377

To a 1,4-dioxane (10 mL) solution of 2-(4-bromo-2-chloro-6-methylphenoxy)-5-nitropyridine (1.00 g) and butyl acrylate (0.480 mL) were added N,N-dicyclohexylmethylamine (0.655 mL), tri-tert-butylphosphine tetrafluoroborate (34 mg) and tris(dibenzylideneacetone)dipalladium (0) (40 mg) at room temperature. The resultant mixture was stirred at 70° C. under a nitrogen atmosphere for 4 hours. To the reaction mixture was added water, and extracted with AcOEt. The organic layer was washed with saturated aqueous NaCl, dried over anhydrous MgSO$_4$, and concentrated under reduced pressure. The residue was purified by silica gel column chromatography (n-hexane/AcOEt=9/1 to 1/1) to afford butyl (E)-3-{3-chloro-5-methyl-4-[(5-nitropyridin-2-yl)oxy]phenyl}prop-2-enoate as a yellow powder (1.05 g).

$^1$H-NMR (CDCl$_3$) δ: 0.97 (3H, t, J=7.3 Hz), 1.39-1.49 (2H, m), 1.66-1.73 (2H, m), 2.20 (3H, s), 4.22 (2H, t, J=6.8 Hz), 6.42 (1H, d, J=16.1 Hz), 7.17 (1H, d, J=9.0 Hz), 7.36-7.37 (1H, m), 7.50 (1H, d, J=2.0 Hz), 7.59 (1H, d, J=16.1 Hz), 8.54 (1H, dd, J=9.0, 2.9 Hz), 8.98-8.99 (1H, m).

The following compounds were produced in the same manner as in Reference Example 377 using appropriate starting materials.

Reference Example 378

Butyl (E)-3-{5-chloro-4-[(5-hydroxypyridin-2-yl)oxy]-2-methylphenyl}prop-2-enoate $^1$H-NMR (CDCl$_3$) δ: 0.97 (3H, t, J=7.6 Hz), 1.39-1.48 (2H, m), 1.66-1.73 (2H, m), 2.37 (3H, s), 4.21 (2H, t, J=6.6 Hz), 5.38 (1H, brs), 6.32 (1H, d, J=15.9 Hz), 6.90 (1H, d, J=8.8 Hz), 6.97 (1H, s), 7.26-7.29 (1H, m), 7.62 (1H, s), 7.77 (1H, d, J=2.9 Hz), 7.84 (1H, d, J=15.9 Hz).

Reference Example 379

Butyl (E)-3-{2-chloro-4-[(5-hydroxypyridin-2-yl)oxy]-5-methylphenyl}prop-2-enoate $^1$H-NMR (CDCl$_3$) δ: 0.97 (3H, t, J=7.3 Hz), 1.39-1.49 (2H, m), 1.66-1.73 (2H, m), 2.20 (3H, s), 4.22 (2H, t, J=6.8 Hz), 5.23-5.30 (1H, m), 6.38 (1H, d, J=15.9 Hz), 6.87 (1H, d, J=8.8 Hz), 7.01 (1H, s), 7.28 (1H, dd, J=8.8, 2.9 Hz), 7.51 (1H, s), 7.82 (1H, d, J=2.9 Hz), 8.02 (1H, d, J=15.9 Hz).

Reference Example 380

To a DMF (50 mL) solution of 6-(4-bromo-2-chloro-6-methylphenoxy)pyridin-3-ol (5.00 g) were added imidazole (1.41 g) and TBDMSCl (2.87 g) at room temperature. After stirring at room temperature for 5 hours, to the reaction mixture was added saturated aqueous NaHCO$_3$, and extracted with AcOEt. The organic layer was washed with water, saturated aqueous NaCl, dried over anhydrous Na$_2$SO$_4$, and concentrated under reduced pressure. The residue was purified by silica gel column chromatography (n-hexane/AcOEt=9/1 to 2/1) to give 2-(4-bromo-2-chloro-6-methylphenoxy)-5-{[tert-butyl(dimethyl)silyl]oxy}pyridine as a colorless oil (6.16 g).

$^1$H-NMR (CDCl$_3$) δ: 0.18 (6H, s), 0.97 (9H, s), 2.15 (3H, s), 6.86 (1H, dd, J=8.8, 0.7 Hz), 7.21 (1H, dd, J=8.8, 2.9 Hz), 7.30-7.31 (1H, m), 7.43-7.44 (1H, m), 7.65-7.67 (1H, m).

Reference Example 381

A THF (15 mL) solution of bis(pinacolato)diboron (3.03 g), copper(I) chloride (0.032 g), 4,5-bis(diphenylphosphino)-9,9-dimethylxanthene (0.188 g) and sodium tert-butoxide (0.063 g) was stirred at room temperature for 30 minutes under an argon atmosphere. To the mixture were added 2-(trimethylsilyl)ethyl but-2-ynoate (2.00 g) and MeOH (0.878 mL) in order. After stirring for 5 hours at room temperature, the mixture was filtered through a pad of Celite and the filtrate was concentrated under reduced pressure. The residue was purified by silica gel column chromatography (n-hexane/AcOEt=19/1 to 9/1) to afford 2-(trimethylsilyl)ethyl (Z)-3-(4,4,5,5-tetramethyl-1,3,2-dioxaborolan-2-yl)but-2-enoate as a colorless oil (2.86 g).

$^1$H-NMR (CDCl$_3$) δ: 0.05 (9H, s), 0.94-1.06 (2H, m), 1.28 (12H, s), 2.17 (3H, d, J=2.0 Hz), 4.15-4.26 (2H, m), 6.42 (1H, d, J=1.6 Hz).

Reference Example 382

A mixture of ethyl (E)-2-methyl-3-{[(trifluoromethyl)sulfonyl]oxy}but-2-enoate (2.00 g), bis(pinacolato)diboron (2.02 g), dichlorobis(triphenylphosphine) palladium (II) (0.15 g), triphenylphosphine (0.11 g) and potassium tert-butoxide (1.44 g) in toluene (40 mL) was stirred at 50° C. for 2 hours under an argon atmosphere. The mixture was filtered through a pad of Celite and the filtrate was concentrated under reduced pressure. The residue was purified by silica gel column chromatography (n-hexane/AcOEt=99/1 to 19/1) to afford ethyl (Z)-2-methyl-3-(4,4,,5,5-tetramethyl-1,3,2-dioxaborolan-2-yl)but-2-enoate as a colorless oil (0.91 g).

$^1$H-NMR (CDCl$_3$) δ: 1.28 (12H, s), 1.30 (3H, t, J=7.3 Hz), 1.87 (3H, q, J=1.6 Hz), 2.10 (3H, q, J=1.6 Hz), 4.22 (2H, q, J=7.3 Hz).

Reference Example 383

To a solution of 6-(4-bromo-2-chloro-6-methylphenoxy)pyridin-3-ol (5.00 g) in CH$_2$Cl$_2$-THF (70 mL, 5:2) were added 3,4-dihydro-2H-pyran (4.35 mL) and PPTS (200 mg) at room temperature. After stirring at room temperature for 95 hours, the solvent was removed under reduced pressure. To the residue was added saturated aqueous NaHCO$_3$, and extracted with AcOEt. The organic layer was washed with saturated aqueous NaCl, dried over anhydrous Na$_2$SO$_4$, and concentrated under reduced pressure. The residue was purified by silica gel column chromatography (n-hexane/AcOEt=4/1 to 1/1) to give 2-(4-bromo-2-chloro-6-methylphenoxy)-5-(tetrahydro-2H-pyran-2-yloxy)pyridine as a yellow oil (6.30 g).

$^1$H-NMR (CDCl$_3$) δ: 1.51-2.01 (6H, m), 2.16 (3H, s), 3.57-3.62 (1H, m), 3.86-3.94 (1H, m), 5.28 (1H, t, J=3.2 Hz), 6.88-6.92 (1H, m), 7.30-7.31 (1H, m), 7.43-7.52 (2H, m), 7.87-7.89 (1H, m).

The following compound was produced in the same manner as in Reference Example 105 using appropriate starting materials.

Reference Example 384

3-Chloro-5-methyl-4-{[5-(tetrahydro-2H-pyran-2-yloxy)pyridin-2-yl]oxy}benzaldehyde $^1$H-NMR (CDCl$_3$) δ: 1.58-1.99 (6H, m), 2.26 (3H, s), 3.58-3.62 (1H, m), 3.86-3.92 (1H, m), 5.28-5.30 (1H, m), 6.96 (1H, d, J=9.0 Hz), 7.49 (1H, dd, J=9.0, 2.9 Hz), 7.70-7.71 (1H, m), 7.82 (1H, d, J=1.7 Hz), 7.86 (1H, d, J=2.9 Hz), 9.92 (1H, s).

Reference Example 385

To a THF (100 mL) solution of triethyl phosphonoacetate (44.0 mL) was slowly added NaH (60% dispersion in mineral oil, 8.8 g) at 0° C. After stirring for 1 hour, a THF (200 mL) solution of 3,5-dimethyl-4-[(5-nitropyridin-2-yl)oxy]benzaldehyde (54.5 g) was added to the reaction mixture. After stirring at room temperature for 2 hours, AcOEt and H$_2$O were added to the reaction mixture. The resulting precipitate was collected to give ethyl (E)-3-{3,5-dimethyl-4-[(5-nitropyridin-2-yl)oxy]phenyl}prop-2-enoate as a white powder (40.9 g).

$^1$H-NMR (CDCl$_3$) δ: 1.35 (3H, t, J=7.1 Hz), 2.12 (6H, s), 4.27 (2H, t, J=7.1 Hz), 6.40 (1H, d, J=16.1 Hz), 7.09 (1H, d, J=9.0 Hz), 7.31 (2H, s), 7.64 (1H, d, J=15.9 Hz), 8.51 (1H, dd, J=9.0, 2.2 Hz), 9.01 (1H, d, J=2.4 Hz).

The following compounds were produced in the same manner as in Reference Example 385 using appropriate starting materials.

Reference Example 386

Ethyl (E)-3-{3,5-dimethoxy-4-[(5-nitropyridin-2-yl)oxy]phenyl}prop-2-enoate $^1$H-NMR (CDCl$_3$) δ: 1.36 (3H, t, J=7.1 Hz), 3.81 (6H, s), 4.29 (2H, q, J=7.1 Hz), 6.42 (1H, d, J=16.2 Hz), 6.84 (2H, s), 7.13 (1H, d, J=8.9 Hz), 7.66 (1H, d, J=16.2 Hz), 8.48 (1H, dd, J=9.1, 2.8 Hz), 8.99 (1H, d, J=3.0 Hz).

Reference Example 387

Ethyl (E)-3-(3-chloro-5-methyl-4-{[5-(tetrahydro-2H-pyran-2-yloxy)pyridin-2-yl]oxy}phenyl)-2-methylprop-2-enoate $^1$H-NMR (CDCl$_3$) δ: 1.35 (3H, t, J=7.1 Hz), 1.55-1.74 (3H, m), 1.82-1.89 (2H, m), 1.91-2.02 (1H, m), 2.13 (3H, d, J=1.5 Hz), 2.20 (3H, s), 3.56-4.64 (1H, m), 3.85-3.96 (1H, m), 4.27 (2H, q, J=7.1 Hz), 5.29 (1H, t, J=3.3 Hz), 6.91 (1H, dd, J=8.9, 0.5 Hz), 7.20 (1H, d, J=2.0 Hz), 7.35 (1H, d, J=2.1 Hz), 7.46 (1H, dd, J=8.9, 3.1 Hz), 7.55-7.60 (1H, m), 7.91 (1H, d, J=2.4 Hz).

Reference Example 388

To a solution of ethyl (E)-3-(3-chloro-5-methyl-4-{[5-(tetrahydro-2H-pyran-2-yloxy)pyridin-2-yl]oxy}phenyl)-2-methylprop-2-enoate (2.58 g) in EtOH (40 mL) was added p-toluenesulfonic acid (1.14 g) at room temperature, then the reaction mixture was stirred for 1 hour. The reaction mixture was concentrated under reduced pressure. The residue was diluted with H$_2$O, and extracted with AcOEt. The organic layer was washed with water and saturated aqueous NaCl, dried over anhydrous Na$_2$SO$_4$, and concentrated under reduced pressure. The residue was purified by silica gel column chromatography (n-hexane/AcOEt=10/1 to 2/1) to afford ethyl (E)-3-{3-chloro-4-[(5-hydroxypyridin-2-yl)oxy]-5-methylphenyl}-2-methylprop-2-enoate as a colorless amorphous (1.98 g).
$^1$H-NMR (CDCl$_3$) δ: 1.35 (3H, t, J=7.1 Hz), 2.13 (3H, d, J=1.5 Hz), 2.20 (3H, s), 4.27 (2H, q, J=7.1 Hz), 4.59 (1H, s), 6.90 (1H, d, J=8.8 Hz), 7.18-7.22 (1H, m), 7.26-7.31 (1H, m), 7.35 (1H, d, J=2.0 Hz), 7.56-7.59 (1H, m), 7.72 (1H, d, J=3.2 Hz).

Reference Example 389

To a DMF (40 mL) solution of butyl (E)-3-{4-[(5-hydroxypyridin-2-yl)oxy]-2-methylphenyl}prop-2-enoate (3.54 g) was added NaH (60% in oil) (467 mg) at 0 °C. After stirring for 10 minutes, 1-(bromomethyl)-4-methylbenzene (2.10 g) was added, and the resultant mixture was stirred at room temperature for 3.5 hours. To the reaction mixture was added saturated aqueous NH$_4$Cl, and extracted with AcOEt. The organic layer was washed with water, saturated aqueous NaCl, dried over anhydrous Na$_2$SO$_4$, and concentrated under reduced pressure. The residue was purified by silica gel column chromatography (n-hexane/AcOEt =9/1 to 3/1) to afford butyl (E)-3-[2-methyl-4-({5-[(4-methylbenzyl)oxy]pyridin-2-yl}oxy)phenyl]prop-2-enoate as a yellow solid (4.72 g).
$^1$H-NMR (CDCl$_3$) δ: 0.97 (3H, t, J=7.3 Hz), 1.41-1.47 (2H, m), 1.65-1.73 (2H, m), 2.36 (3H, s), 2.41 (3H, s), 4.20 (2H, t, J=6.8 Hz), 5.03 (2H, s), 6.30 (1H, d, J=15.6 Hz), 6.87-6.93 (3H, m), 7.20 (2H, d, J=7.8 Hz), 7.30 (2H, d, J =7.8 Hz), 7.34 (1H, dd, J=9.0, 3.2 Hz), 7.55-7.57 (1H, m), 7.90-7.94 (2H, m).

The following compounds were produced in the same manner as in Reference Example 389 using appropriate starting materials.

Reference Example 390

Butyl (E)-3-[3-chloro-5-methyl-4-({5-[(4-methylbenzyl)oxy]pyridin-2-yl}oxy)phenyl]prop-2-enoate $^1$H-NMR (CDCl$_3$) δ: 0.97 (3H, t, J=7.4 Hz), 1.37-1.51 (2H, m), 1.64-1.75 m), 2.20 (3H, s), 2.36 (3H, s), 4.21 (2H, t, J=6.8 Hz), 4.99 (2H, s), 6.38 (1H, d, J=16.2 Hz), 6.93 (1H, d, J=8.9 Hz), 7.19 (2H, d, J=8.2 Hz), 7.26-7.38 (4H, m), 7.47 (1H, d, J=2.0 Hz), 7.58 (1H, d, J=16.2 Hz), 7.79 (1H, d, J=3.0 Hz).

Reference Example 391

Butyl (E)-3-[3-chloro-4-({5-[(2-fluorobenzyl)oxy]pyridin-2-yl}oxy)-5-methylphenyl]prop-2-enoate $^1$H-NMR (CDCl$_3$) δ: 0.97 (3H, t, J=7.4 Hz), 1.38-1.49 (2H, m), 1.64-1.75 (2H, m), 2.20 (3H, s), 4.21 (2H, t, J=6.6 Hz), 5.10 (2H, s), 6.38 (1H, d, J=16.2 Hz), 6.95 (1H, d, J=8.9 Hz), 7.02-7.21 (2H, m), 7.28-7.35 (2H, m), 7.39 (1H, dd, J=8.9, 3.3 Hz), 7.43-7.50 (2H, m), 7.58 (1H, d, J=15.8 Hz), 7.82 (1H, d, J=3.0 Hz).

Reference Example 392

Butyl (E)-3-[3-chloro-4-({5-[(2-chlorobenzyl)oxy]pyridin-2-yl}oxy)-5-methylphenyl]prop-2-enoate $^1$H-NMR (CDCl$_3$) δ: 0.97 (3H, t, J=7.3 Hz), 1.41-1.47 (2H, m), 1.64-1.74 (2H, m), 2.20 (3H, s), 4.21 (2H, t, J=6.6 Hz), 5.14 (2H, s), 6.38 (1H, d, J=15.8 Hz), 6.95 (1H, d, J=8.9 Hz), 7.26-7.32 (3H, m), 7.38-7.42 (2H, m), 7.47-7.61 (3H, m), 7.82 (1H, d, J=2.6 Hz).

Reference Example 393

Butyl (E)-3-[4-({5-[(2-chlorobenzyl)oxy]pyridin-2-yl}oxy)-2-methylphenyl]prop-2-enoate $^1$H-NMR (CDCl$_3$) δ: 0.97 (3H, t, J=7.3 Hz), 1.41-1.47 (2H, m), 1.66-1.71 (2H, m), 2.42 (3H, s), 4.21 (2H, t, J=6.8 Hz), 5.18 (2H, s), 6.31 (1H, d, J=15.6 Hz), 6.86-6.93 (3H, m), 7.26-7.33 (2H, m), 7.36-7.42 (2H, m), 7.52-7.58 (2H, m), 7.91-7.96 (2H, m).

Reference Example 394

Ethyl (E)-3-[4-({5-[(2-chlorobenzyl)oxy]pyridin-2-yl}oxy)-3-methoxyphenyl]prop-2-enoate $^1$H-NMR (CDCl$_3$) δ: 1.32 (3H, t, J=7.1 Hz), 3.77 (3H, s), 4.25 (2H, q, J=7.1 Hz), 5.11 (2H, s), 6.38 (1H, d, J=16.1 Hz), 6.91 (1H, d, J=8.8 Hz), 7.07-7.14 (3H, m), 7.21-7.28 (2H, m), 7.33-7.37 (2H, m), 7.48-7.51 (1H, m), 7.65 (1H, d, J=16.1 Hz), 7.86 (1H, d, J=2.9 Hz).

Reference Example 395

Butyl (E)-3-[3-chloro-4-({5-[(2-chlorobenzyl)oxy]pyridin-2-yl}oxy)phenyl]prop-2-enoate $^1$H-NMR (CDCl$_3$) δ: 0.97 (3H, t, J=7.3 Hz), 1.37-1.50 (2H, m), 1.64-1.75 (2H, m), 4.21 (2H, t, J=6.8 Hz), 5.17 (2H, s), 6.38 (1H, d, J=16.1 Hz), 6.98 (1H, d, J=9.0 Hz), 7.17 (1H, d, J=8.3 Hz), 7.25-7.32 (2H, m), 7.37-7.45 (3H, m), 7.48-7.55 (1H, m), 7.56-7.66 (2H, m), 7.88 (1H, d, J=3.2 Hz).

Reference Example 396

Ethyl (E)-3-[4-({5-[(2-chlorobenzyl)oxy]pyridin-2-yl}oxy)phenyl]prop-2-enoate $^1$H-NMR (CDCl$_3$) δ: 1.34 (3H, t, J=7.2 Hz), 4.26 (2H, q, J=7.2 Hz), 5.18 (2H, s), 6.36 (1H, d, J=15.9 Hz), 6.93 (1H, d, J=8.8 Hz), 7.10 (2H, d, J=8.8 Hz), 7.28-7.31 (2H, m), 7.37-7.43 (2H, m), 7.52-7.54 (3H, m), 7.67 (1H, d, J=15.9 Hz), 7.96 (1H, d, J=2.9 Hz).

Reference Example 397

2-(4-Bromo-2-chloro-6-methylphenoxy)-5-[(2-chlorobenzyl)oxy]pyridine

¹H-NMR (CDCl₃) δ: 2.16 (3H, s), 5.14 (2H, s), 6.93 (1H, d, J=9.0 Hz), 7.26-7.35 (3H, m), 7.36-7.42 (2H, m), 7.44 (1H, d, J=2.4 Hz), 7.49-7.55 (1H, m), 7.81 (1H, d, J=2.9 Hz).

Reference Example 398

Ethyl (E)-3-[3-chloro-4-({5-[(2-chlorobenzyl)oxy]pyridin-2-yl}oxy)-5-methylphenyl]-2-methylprop-2-enoate ¹H-NMR (CDCl₃) δ: 1.35 (3H, t, J=7.1 Hz), 2.13 (3H, d, J=1.5 Hz), 2.21 (3H, s), 4.27 (2H, q, J=7.1 Hz), 5.15 (2H, s), 6.94 (1H, dd, J=9.0, 0.5 Hz), 7.17-7.22 (1H, m), 7.25-7.33 (2H, m), 7.35 (1H, d, J=2.2 Hz), 7.37-7.44 (2H, m), 7.50-7.55 (1H, m), 7.55-7.60 (1H, m), 7.83 (1H, d, J=2.9 Hz).

Reference Example 399

2-(Trimethylsilyl)ethyl (E)-3-[3-chloro-5-methyl-4-({5-[(4-methylbenzyl)oxy]pyridin-2-yl}oxy)phenyl]but-2-enoate ¹H-NMR (CDCl₃) δ: 0.07 (9H, s), 1.01-1.09 (2H, m), 2.21 (3H, s), 2.36 (3H, s), 2.55 (3H, d, J=1.2 Hz), 4.21-4.29 (2H, m), 6.09-6.14 (1H, m), 6.82-7.45 (8H, m), 7.75-7.84 (1H, m).

Reference Example 400

2-(4-Bromo-2-chloro-6-methylphenoxy)-5-[(4-methylbenzyl)oxy]pyridine

¹H-NMR (CDCl₃) δ: 2.16 (3H, s), 2.36 (3H, s), 4.99 (2H, s), 6.91 (1H, d, J=8.5 Hz), 7.19 (2H, d, J=7.8 Hz), 7.26-7.34 (3H, m), 7.35 (1H, dd, J=9.0, 3.2 Hz), 7.44 (1H, dd, J=2.4, 0.5 Hz), 7.78 (1H, dd, J=8.5, 2.9 Hz).

Reference Example 401

Ethyl (E)-3-[3-chloro-5-methyl-4-({5-[(4-methylbenzyl)oxy]pyridin-2-yl}oxy)phenyl]-2-methylprop-2-enoate ¹H-NMR (CDCl₃) δ: 1.35 (3H, t, J=7.1 Hz), 2.13 (3H, d, J=1.5 Hz), 2.20 (3H, s), 2.36 (3H, s), 4.27 (2H, q, J=7.1 Hz), 4.99 (2H, s), 6.91 (1H, dd, J=9.0, 0.5 Hz), 7.16-7.22 (3H, m), 7.27-7.32 (2H, m), 7.33-7.37 (2H, m), 7.55-7.61 (1H, m), 7.80 (1H, d, J=2.4 Hz).

Reference Example 402

Butyl (E)-3-{3-chloro-5-methyl-4-[(5-{[4-(trifluoromethyl)benzyl]oxy}pyridin-2-yl)oxy]phenyl}prop-2-enoate ¹H-NMR (CDCl₃) δ: 0.97 (3H, t, J=7.3 Hz), 1.42-1.46 (2H, m), 1.66-1.73 (2H, m), 2.20 (3H, s), 4.21 (2H, t, J=6.6 Hz), 5.09 (2H, s), 6.38 (1H, d, J=15.9 Hz), 6.96 (1H, d, J=9.0 Hz), 7.33 (1H, s), 7.38 (1H, dd, J=8.9, 3.1 Hz), 7.47 (1H, d, J=1.7 Hz), 7.52 (2H, d, J=8.5 Hz), 7.58 (1H, d, J=15.9 Hz), 7.64 (2H, d, J=8.3 Hz), 7.78 (1H, d, J=2.9 Hz).

Reference Example 403

Ethyl (E)-3-[4-({5-[(2-chlorobenzyl)oxy]pyridin-2-yl}oxy)-3,5-dimethylphenyl]prop-2-enoate ¹H-NMR (CDCl₃) δ: 1.34 (3H, t, J=7.2 Hz), 2.13 (6H, s), 4.26 (2H, q, J=7.1 Hz), 5.13 (2H, s), 6.37 (1H, d, J=15.9 Hz), 6.83 (1H, d, J=9.0 Hz), 7.26-7.31 (4H, m), 7.36 (1H, dd, J=8.9, 3.1 Hz), 7.38-7.40 (1H, m), 7.51-7.53 (1H, m), 7.63 (1H, d, J=15.9 Hz), 7.84 (1H, d, J=2.9 Hz).

Reference Example 404

Ethyl (E)-3-[3,5-dimethyl-4-({5-[(4-methylbenzyl)oxy]pyridin-2-yl}oxy)phenyl]prop-2-enoate ¹H-NMR (CDCl₃) δ: 1.34 (3H, t, J=7.0 Hz), 2.12 (6H, s), 2.35 (3H, s), 4.26 (2H, q, J=7.0 Hz), 4.98 (2H, s), 6.36 (1H, d, J=16.1 Hz), 6.81 (1H, d, J=8.8 Hz), 7.19 (2H, d, J=7.6 Hz), 7.27-7.34 (5H, m), 7.63 (1H, d, J=15.9 Hz), 7.82 (1H, d, J=2.0 Hz).

Reference Example 405

Ethyl (E)-3-[4-({5-[(4-fluorobenzyl)oxy]pyridin-2-yl}oxy)-3,5-dimethylphenyl]prop-2-enoate ¹H-NMR (CDCl₃) δ: 1.34 (3H, t, J=7.1 Hz), 2.12 (6H, s), 4.26 (2H, q, J=7.1 Hz), 4.99 (2H, s), 6.36 (1H, d, J=16.1 Hz), 6.83 (1H, d, J=9.0 Hz), 7.05-7.09 (2H, m), 7.27 (2H, brs), 7.32 (1H, dd, J=9.0, 3.2 Hz), 7.36-7.40 (2H, m), 7.63 (1H, d, J=16.1 Hz), 7.81 (1H, d, J=3.2 Hz).

Reference Example 406

Ethyl (E)-3-[4-({5-[(4-methoxybenzyl)oxy]pyridin-2-yl}oxy)-3,5-dimethylphenyl]prop-2-enoate ¹H-NMR (CDCl₃) δ: 1.34 (3H, t, J=7.2 Hz), 2.12 (6H, s), 3.81 (3H, s), 4.26 (2H, q, J=7.2 Hz), 4.95 (2H, s), 6.36 (1H, d, J=15.9 Hz), 6.81 (1H, d, J=8.8 Hz), 6.91 (2H, dt, J=9.3, 2.4 Hz), 7.27 (2H, brs), 7.31-7.34 (3H, m), 7.63 (1H, d, J=15.9 Hz), 7.82 (1H, d, J=2.9 Hz).

Reference Example 407

Ethyl (E)-3-[4-({5-[(4-cyanobenzyl)oxy]pyridin-2-yl}oxy)-3,5-dimethylphenyl]prop-2-enoate ¹H-NMR (CDCl₃) δ: 1.34 (3H, t, J=7.1 Hz), 2.12 (6H, s), 4.26 (2H, q, J=7.1 Hz), 5.09 (2H, s), 6.37 (1H, d, J=15.9 Hz), 6.85 (1H, d, J=9.0 Hz), 7.27 (2H, s), 7.34 (1H, dd, J=8.9, 3.1 Hz), 7.52 (2H, d, J=8.3 Hz), 7.63 (1H, d, J=15.9 Hz), 7.68 (2H, d, J=8.3 Hz), 7.80 (1H, d, J=2.9 Hz).

Reference Example 408

Butyl (E)-3-[3-chloro-4-({5-[(4-fluorobenzyl)oxy]pyridin-2-yl}oxy)phenyl]prop-2-enoate ¹H-NMR (CDCl₃) δ: 0.97 (3H, t, J=7.3 Hz), 1.37-1.50 (2H, m), 1.64-1.74 (2H, m), 4.21 (2H, t, J=6.6 Hz), 5.02 (2H, s), 6.38 (1H, d, J=15.9 Hz), 6.96 (1H, d, J=8.8 Hz), 7.03-7.12

(2H, m), 7.16 (1H, d, J=8.5 Hz), 7.32-7.46 (4H, m), 7.56-7.66 (2H, m), 7.85 (1H, d, J=3.2 Hz).

Reference Example 409

Butyl (E)-3-[5-chloro-4-({5-[(2-chlorobenzyl)oxy]pyridin-2-yl}oxy)-2-methylphenyl]prop-2-enoate $^1$H-NMR (CDCl$_3$) δ: 0.97 (3H, t, J=7.6 Hz), 1.39-1.48 (2H, m), 1.66-1.73 (2H, m), 2.38 (3H, s), 4.21 (2H, t, J=7.1 Hz), 5.16 (2H, s), 6.32 (1H, d, J=15.9 Hz), 6.96 (1H, d, J=8.8 Hz), 7.00 (1H, s), 7.27-7.32 (2H, m), 7.38-7.43 (2H, m), 7.51-7.54 (1H, m), 7.63 (1H, s), 7.84 (1H, d, J=15.9 Hz), 7.89 (1H, d, J=3.2 Hz).

Reference Example 410

Butyl (E)-3-[5-chloro-2-methyl-4-({5-[(4-methylbenzyl)oxy]pyridin-2-yl}oxy)phenyl]prop-2-enoate $^1$H-NMR (CDCl$_3$) δ: 0.97 (3H, t, J=7.3 Hz), 1.39-1.49 (2H, m), 1.66-1.73 (2H, m), 2.36 (3H, s), 2.38 (3H, s), 4.21 (2H, t, J=6.6 Hz), 5.01 (2H, s), 6.32 (1H, d, J=15.9 Hz), 6.93 (1H, d, J=8.8 Hz), 6.98 (1H, s), 7.19 (2H, d, J=8.1 Hz), 7.29 (2H, d, J=8.1 Hz), 7.36 (1H, dd, J=8.8, 2.9 Hz), 7.63 (1H, s), 7.84 (1H, d, J=15.9 Hz), 7.87 (1H, d, J=2.9 Hz).

Reference Example 411

Butyl (E)-3-[2-chloro-4-({5-[(2-chlorobenzyl)oxy]pyridin-2-yl}oxy)-5-methylphenyl]prop-2-enoate $^1$H-NMR (CDCl$_3$) δ: 0.97 (3H, t, J=7.6 Hz), 1.40-1.49 (2H, m), 1.66-1.73 (2H, m), 2.20 (3H, s), 4.22 (2H, t, J=6.9 Hz), 5.17 (2H, s), 6.39 (1H, d, J=15.9 Hz), 6.91 (1H, d, J=8.8 Hz), 7.04 (1H, s), 7.26-7.33 (2H, m), 7.38-7.42 (2H, m), 7.51-7.54 (2H, m), 7.92 (1H, d, J=3.2 Hz), 8.02 (1H, d, J=15.9 Hz).

Reference Example 412

Butyl (E)-3-[2-chloro-5-methyl-4-({5-[(4-methylbenzyl)oxy]pyridin-2-yl}oxy)phenyl]prop-2-enoate $^1$H-NMR (CDCl$_3$) δ: 0.97 (3H, t, J=7.3 Hz), 1.41-1.49 (2H, m), 1.66-1.73 (2H, m), 2.20 (3H, s), 2.36 (3H, s), 4.21 (2H, t, J=6.6 Hz), 5.02 (2H, s), 6.38 (1H, d, J=15.9 Hz), 6.89 (1H, d, J=9.0 Hz), 7.02 (1H, s), 7.19 (2H, d, J=7.8 Hz), 7.30 (2H, d, J=7.8 Hz), 7.35 (1H, dd, J=9.0, 2.9 Hz), 7.51 (1H, s), 7.90 (1H, d, J=2.9 Hz), 8.02 (1H, d, J=15.9 Hz).

Reference Example 413

Ethyl (E)-3-[3,5-dimethyl-4-({5-[(6-methylpyridin-2-yl)methoxy]pyridin-2-yl}oxy)phenyl]prop-2-enoate $^1$H-NMR (CDCl$_3$) δ: 1.34 (3H, t, J=7.1 Hz), 2.12 (6H, s), 2.56 (3H, s), 4.26 (2H, q, J=7.1 Hz), 5.12 (2H, s), 6.36 (1H, d, J=16.1 Hz), 6.83 (1H, d, J=9.0 Hz), 7.09 (1H, d, J=7.6 Hz), 7.28-7.30 (3H, m), 7.37 (1H, dd, J=8.9, 2.9 Hz), 7.60-7.64 (2H, m), 7.84 (1H, d, J=2.9 Hz).

Reference Example 414

Ethyl (E)-3-[4-({5-[(2-cyanobenzyl)oxy]pyridin-2-yl}oxy)-3,5-dimethoxyphenyl]prop-2-enoate $^1$H-NMR (CDCl$_3$) δ: 1.38 (3H, t, J=7.1 Hz), 3.83 (6H, s), 4.30 (2H, q, J=7.1 Hz), 5.25 (2H, s), 6.41 (1H, d, J=15.9 Hz), 6.85 (2H, s), 7.00 (1H, d, J=8.8 Hz), 7.42 (1H, dd, J=8.8, 2.9 Hz), 7.45-7.49 (1H, m), 7.63-7.69 (3H, m), 7.73 (1H, d, J=7.8 Hz), 7.85 (1H, d, J=2.9 Hz).

Reference Example 415

Ethyl (E)-3-[4-({5-[(4-cyanobenzyl)oxy]pyridin-2-yl}oxy)-3,5-dimethoxyphenyl]prop-2-enoate $^1$H-NMR (CDCl$_3$) δ: 1.35 (3H, t, J=7.1 Hz), 3.79 (6H, s), 4.28 (2H, q, J=7.1 Hz), 5.09 (2H, s), 6.39 (1H, d, J=15.9 Hz), 6.83 (2H, s), 6.97 (1H, d, J=9.0 Hz), 7.33 (1H, dd, J=9.0, 2.9 Hz), 7.52 (2H, d, J=8.3 Hz), 7.62-7.69 (3H, m), 7.77 (1H, d, J=2.9 Hz).

Reference Example 416

Ethyl (E)-3-(3,5-dimethyl-4-{[5-(pyridin-4-ylmethoxy)pyridin-2-yl]oxy}phenyl)prop-2-enoate $^1$H-NMR (CDCl$_3$) δ: 1.34 (3H, t, J=7.2 Hz), 2.12 (6H, s), 4.26 (2H, q, J=7.1 Hz), 5.06 (2H, s), 6.37 (1H, d, J=15.9 Hz), 6.85 (1H, d, J=8.8 Hz), 7.27 (2H, d, J=4.9 Hz), 7.32-7.36 (3H, m), 7.63 (1H, d, J=16.1 Hz), 7.80 (1H, d, J=2.9 Hz), 8.63 (2H, d, J=5.6 Hz).

Reference Example 417

Butyl (E)-3-[3-chloro-4-({5-[(4-cyanobenzyl)oxy]pyridin-2-yl}oxy)phenyl]prop-2-enoate $^1$H-NMR (CDCl$_3$) δ: 0.97 (3H, t, J=7.3 Hz), 1.37-1.50 (2H, m), 1.64-1.74 (2H, m), 4.21 (2H, t, J=7.3 Hz), 5.12 (2H, s), 6.38 (1H, d, J=15.9 Hz), 6.99 (1H, dd, J=9.0, 0.5 Hz), 7.17 (1H, d, J=8.5 Hz), 7.38 (1H, dd, J=9.0, 3.2 Hz), 7.43 (1H, dd, J=8.5, 2.2 Hz), 7.51-7.56 (2H, m), 7.58-7.65 (2H, m), 7.65-7.72 (2H, m), 7.83 (1H, dd, J=3.2, 0.5 Hz).

Reference Example 418

Ethyl (E)-3-(4-{[5-(1,3-benzothiazol-6-ylmethoxy)pyridin-2-yl]oxy}-3,5-dimethoxyphenyl)prop-2-enoate $^1$H-NMR (CDCl$_3$) δ: 1.35 (3H, t, J=7.1 Hz), 3.79 (6H, s), 4.28 (2H, q, J=7.1 Hz), 5.19 (2H, s), 6.38 (1H, d, J=15.9 Hz), 6.82 (2H, s), 6.96 (1H, d, J=9.0 Hz), 7.36 (1H, dd, J=8.8, 2.7 Hz), 7.55 (1H, d, J=8.3 Hz), 7.64 (1H, d, J=16.1 Hz), 7.82 (1H, d, J=2.9 Hz), 8.03 (1H, s), 8.14 (1H, d, J=8.5 Hz), 9.01 (1H, s).

Reference Example 419

Butyl (E)-3-[5-chloro-4-({5-[(4-cyanobenzyl)oxy]pyridin-2-yl}oxy)-2-methylphenyl]prop-2-enoate $^1$H-NMR (CDCl$_3$) δ: 0.97 (3H, t, J=7.3 Hz), 1.41-1.48 (2H, m), 1.67-1.71 (2H, m), 2.39 (3H, s), 4.21 (2H, t, J=6.6 Hz), 5.11 (2H, s), 6.32 (1H, d, J=15.9 Hz), 6.96-6.98 (1H, m), 7.00 (1H, s), 7.37 (1H, dd, J=9.0, 3.2 Hz), 7.52-7.54 (2H, m), 7.63 (1H, s), 7.66-7.70 (2H, m), 7.82-7.86 (2H, m).

Reference Example 420

Butyl (E)-3-[2-chloro-4-({5-[(4-cyanobenzyl)oxy]pyridin-2-yl}oxy)-5-methylphenyl]prop-2-enoate $^1$H-NMR (CDCl$_3$) δ: 0.97 (3H, t, J=7.3 Hz), 1.40-1.49 (2H, m), 1.66-1.73 (2H, m), 2.19 (3H, s), 4.22 (2H, t, J=6.8 Hz), 5.13 (2H, s), 6.39 (1H, d, J=15.9 Hz), 6.92 (1H, d, J=8.8 Hz), 7.04 (1H, s), 7.37 (1H, dd, J=8.8, 3.2 Hz), 7.52-7.55 (3H, m), 7.68-7.70 (2H, m), 7.88 (1H, d, J=3.2 Hz), 8.02 (1H, d, J=15.9 Hz).

Reference Example 421

Ethyl (E)-3-(3,5-dimethyl-4-{[5-(1,3-thiazol-5-yl-methoxy)pyridin-2-yl]oxy}phenyl)prop-2-enoate $^1$H-NMR (CDCl$_3$) δ: 1.34 (3H, t, J=7.1 Hz), 2.12 (6H, s), 4.26 (2H, q, J=7.1 Hz), 5.25 (2H, d, J=0.7 Hz), 6.37 (1H, d, J=15.9 Hz), 6.85 (1H, dd, J=8.8, 0.5 Hz), 7.27 (2H, d, J=0.5 Hz), 7.34 (1H, dd, J=8.8, 2.9 Hz), 7.63 (1H, d, J=16.1 Hz), 7.83 (1H, dd, J=2.0, 0.5 Hz), 7.87 (1H, d, J=0.7 Hz), 8.83 (1H, d, J=0.7 Hz).

Reference Example 422

Ethyl (E)-3-(3,5-dimethyl-4-{[5-(1,3-thiazol-4-yl-methoxy)pyridin-2-yl]oxy}phenyl)prop-2-enoate $^1$H-NMR (CDCl$_3$) δ: 1.33 (3H, d, J=7.1 Hz), 2.12 (6H, s), 4.26 (2H, t, J=7.1 Hz), 5.23 (2H, s), 6.36 (1H, d, J=15.9 Hz), 6.82-6.85 (1H, m), 7.27 (2H, s), 7.37-7.40 (2H, m), 7.63 (1H, d, J=15.9 Hz), 7.85-7.86 (1H, m), 8.83-8.85 (1H, m).

Reference Example 423

Butyl (E)-3-{3-chloro-4-[(5-{[4-(difluoromethoxy)benzyl]oxy}pyridin-2-yl)oxy]-5-methylphenyl}prop-2-enoate $^1$H-NMR (CDCl$_3$) δ: 0.97 (3H, t, J=7.3 Hz), 1.39-1.49 (2H, m), 1.66-1.73 (2H, m), 2.20 (3H, s), 4.21 (2H, t, J=6.6 Hz), 5.01 (2H, s), 6.38 (1H, d, J=16.1 Hz), 6.51 (1H, t, J=73.7 Hz), 6.95 (1H, d, J=8.8 Hz), 7.14 (2H, d, J=8.5 Hz), 7.33 (1H, brs), 7.37 (1H, dd, J=8.8, 2.9 Hz), 7.41 (2H, d, J=8.5 Hz), 7.47 (1H, brs), 7.58 (1H, d, J=16.1 Hz), 7.78 (1H, d, J=2.9 Hz).

Reference Example 424

To a solution of 2-(4-bromo-2-chloro-6-methylphenoxy)-5-{[tert-butyl(dimethyl)-silyl]oxy}pyridine (1.00 g) in 1,4-dioxane (23.3 mL) were added 2 M aqueous K$_2$CO$_3$ (2.33 mL) and Pd(PPh$_3$)$_4$ (81 mg) under a N$_2$ atmosphere, then the reaction mixture was stirred over night at 50° C. Then the reaction mixture was added Pd(PPh$_3$)$_4$ (81 mg) and stirred at 80° C. for 6 hours. The reaction mixture was concentrated under reduced pressure, and diluted with AcOEt. The mixture was filtered off on celite, and the filtrate was concentrated under reduced pressure. The residue was purified by silica gel column chromatography (n-hexane/AcOEt=10/1 to 4/1) to afford 2-(trimethylsilyl)ethyl (E)-3-{4-[(5-{[tert-butyl(dimethyl)silyl]oxy}pyridin-2-yl)oxy]-3-chloro-5-methylphenyl}but-2-enoate as a colorless oil (0.630 g).

$^1$H-NMR (CDCl$_3$) δ: 0.07 (9H, s), 0.18 (6H, s), 0.97 (9H, s), 1.00-1.10 (2H, m), 2.20 (3H, s), 2.54 (3H, d, J=1.2 Hz), 4.22-4.29 (2H, m), 6.08-6.13 (1H, m), 6.87 (1H, dd, J=8.8, 0.7 Hz), 7.22 (1H, d, J=8.8, 2.9 Hz), 7.24-7.30 (1H, m), 7.38-7.44 (1H, m), 7.69 (1H, dd, J=2.9, 0.5 Hz).

The following compounds were produced in the same manner as in Reference Example 424 using appropriate starting materials.

Reference Example 425

2-(Trimethylsilyl)ethyl (E)-3-[3-chloro-4-({5-[(2-chlorobenzyl)oxy]pyridin-2-yl}oxy)-5-methylphenyl]but-2-enoate $^1$H-NMR (CDCl$_3$) δ: 0.07 (9H, s), 1.01-1.09 (2H, m), 2.21 (3H, s), 2.55 (3H, d, J=1.2 Hz), 4.21-4.29 (2H, m), 5.15 (2H, s), 6.09-6.12 (1H, m), 6.95 (1H, dd, J=8.8, 0.5 Hz), 7.25-7.32 (3H, m), 7.36-7.43 (3H, m), 7.49-7.55 (1H, m), 7.83 (1H, d, J=2.7 Hz).

Reference Example 426

Ethyl (E)-3-[3-chloro-5-methyl-4-({5-[(4-methyl-benzyl)oxy]pyridin-2-yl}oxy)phenyl]-2-methylbut-2-enoate $^1$H-NMR (CDCl$_3$) δ: 1.35 (3H, t, J=7.1 Hz), 1.79-1.84 (3H, m), 2.18 (3H, s), 2.22-2.25 (3H, m), 2.36 (3H, s), 4.26 (2H, q, J=7.1 Hz), 5.00 (2H, s), 6.88 (1H, dd, J=8.8, 0.5 Hz), 6.94 (1H, dd, J=2.2, 0.7 Hz), 7.08 (1H, dd, J=2.0, 0.5 Hz), 7.19 (2H, d, J=7.6 Hz), 7.29 (2H, d, J=8.1 Hz), 7.35 (1H, dd, J=8.8, 3.2 Hz), 7.82 (1H, dd, J=3.0, 0.5 Hz).

Reference Example 427

Ethyl (E)-3-[3-chloro-4-({5-[(2-chlorobenzyl)oxy]pyridin-2-yl}oxy)-5-methylphenyl]-2-methylbut-2-enoate $^1$H-NMR (CDCl$_3$) δ: 1.35 (3H, t, J=7.1 Hz), 1.79-1.84 (3H, m), 2.19 (3H, s), 2.20-2.25 (3H, m), 4.26 (2H, q, J=7.1 Hz), 5.15 (2H, s), 6.91 (1H, dd, J=8.8, 0.5 Hz), 6.94 (1H, dd, J=2.2, 0.5 Hz), 7.08 (1H, dd, J=2.2, 0.5 Hz), 7.25-7.35 (2H, m), 7.35-7.43 (2H, m), 7.50-7.55 (1H, m), 7.85 (1H, dd, J=2.9, 0.5 Hz).

Reference Example 428

To a solution of 2-(trimethylsilyl)ethyl (E)-3-{4-[(5-{[tert-butyl(dimethyl)silyl]-oxy}pyridin-2-yl)oxy]-3-chloro-5-methylphenyl}but-2-enoate (0.630 g) in EtOH (12 mL) was added PPTS (0.296 g) at room temperature, then the reaction mixture was stirred for 4 days. The reaction mixture was warmed to 60° C., and stirred over night. The reaction mixture was concentrated under reduced pressure. The residue was diluted with pH 7 phosphate buffer, and extracted with AcOEt. The organic layer was washed with water and saturated aqueous NaCl, dried over anhydrous Na$_2$SO$_4$, and concentrated under reduced pressure. The residue was purified by silica gel column chromatography (n-hexane/AcOEt=8/1 to 2/1) to afford 2-(trimethylsilyl)ethyl (E)-3-{3-chloro-4-[(5-hydroxypyridin-2-yl)oxy]-5-methylphenyl}but-2-enoate as a colorless oil (0.490 g).

$^1$H-NMR (CDCl$_3$) δ: 0.07 (9H, s), 1.01-1.09 (2H, m), 2.20 (3H, s), 2.54 (3H, d, J=1.5 Hz), 4.21-4.29 (2H, m), 4.94 (1H, s), 6.09-6.12 (1H, m), 6.89 (1H, d, J=8.8 Hz), 7.26-7.30 (2H, m), 7.39 (1H, d, J=1.7 Hz), 7.70 (1H, dd, J=3.0, 0.5 Hz).

The following compounds were produced in the same manner as in Reference Example 20 using appropriate starting materials.

Reference Example 429

Butyl (E)-3-[3-chloro-4-({5-[2-(4-chlorophenyl)ethoxy]pyridin-2-yl}oxy)-5-methylphenyl]prop-2-enoate ¹H-NMR (CDCl₃) δ: 0.97 (3H, t, J=7.3 Hz), 1.41-1.47 (2H, m), 1.64-1.74 (2H, m), 2.19 (3H, s), 3.04 (2H, t, J=6.6 Hz), 4.13 (2H, t, J=6.4 Hz), 4.21 (2H, t, J=6.6 Hz), 6.38 (1H, d, J=15.8 Hz), 6.91 (1H, d, J=8.9 Hz), 7.18-7.21 (2H, m), 7.28-7.31 (4H, m), 7.46 (1H, d, J=2.0 Hz), 7.58 (1H, d, J=15.8 Hz), 7.71 (1H, d, J=3.0 Hz).

Reference Example 430

Butyl (E)-3-[3-chloro-5-methyl-4-({5-[2-(4-methylphenyl)ethoxy]pyridin-2-yl}oxy)phenyl]prop-2-enoate ¹H-NMR (CDCl₃) δ: 0.97 (3H, t, J=7.4 Hz), 1.39-1.46 (2H, m), 1.64-1.74 (2H, m), 2.19 (3H, s), 2.33 (3H, s), 3.04 (2H, t, J=7.1 Hz), 4.13 (2H, t, J=6.9 Hz), 4.21 (2H, t, J=6.8 Hz), 6.38 (1H, d, J=15.8 Hz), 6.90 (1H, d, J=8.9 Hz), 7.12-7.16 (4H, m), 7.28-7.32 (2H, m), 7.46 (1H, d, J=2.0 Hz), 7.58 (1H, d, J=15.8 Hz), 7.72 (1H, d, J=3.3 Hz).

Reference Example 431

Butyl (E)-3-[3-chloro-4-({5-[2-(3,4-dichlorophenyl)ethoxy]pyridin-2-yl}oxy)-5-methylphenyl]prop-2-enoate ¹H-NMR (CDCl₃) δ: 0.97 (3H, t, J=7.3 Hz), 1.37-1.52 (2H, m), 1.64-1.74 (2H, m), 2.19 (3H, s), 3.03 (2H, t, J=6.4 Hz), 4.13 (2H, t, J=6.6 Hz), 4.21 (2H, t, J=6.6 Hz), 6.38 (1H, d, J=15.8 Hz), 6.92 (1H, d, J=8.9 Hz), 7.10 (1H, dd, J=8.2, 2.0 Hz), 7.27-7.32 (2H, m), 7.36-7.38 (2H, m), 7.46 (1H, d, J=2.0 Hz), 7.58 (1H, d, J=16.2 Hz), 7.71 (1H, d, J=3.0 Hz).

Reference Example 432

To an EtOH (50 mL) solution of butyl (E)-3-[2-methyl-4-({5-[(4-methylbenzyl)-oxy]pyridin-2-yl}oxy)phenyl]prop-2-enoate (4.67 g) was added 5 M NaOH (3.25 mL) at room temperature. After stirring for 14 hours, 5 M NaOH (1.08 mL) and water (25 mL) were added, and then the reaction mixture was refluxed for 2 hours. The solvent was removed under reduced pressure. The residue was dissolved in water, and neutralized with 6 M HCl at 0° C. The resulting precipitate was collected by filtration and dried to afford (E)-3-[2-methyl-4-({5-[(4-methylbenzyl)oxy]pyridin-2-yl}oxy)phenyl]prop-2-enoic acid as a colorless solid (4.06 g).

¹H-NMR (DMSO-d₆) δ: 2.30 (3H, s), 2.36 (3H, s), 5.09 (2H, s), 6.37 (1H, d, J=15.9 Hz), 6.88 (1H, dd, J=8.5, 2.7 Hz), 6.94 (1H, d, J=2.7 Hz), 7.04 (1H, d, J=9.0 Hz), 7.20 (2H, d, J=7.8 Hz), 7.34 (2H, d, J=7.8 Hz), 7.58 (1H, dd, J=9.0, 3.2 Hz), 7.72 (1H, d, J=8.5 Hz), 7.77 (1H, d, J=15.9 Hz), 7.95 (1H, d, J=3.2 Hz), 12.39 (1H, brs).

The following compounds were produced in the same manner as in Reference Example 432 using appropriate starting materials.

Reference Example 433

(E)-3-[3-Chloro-4-({5-[2-(4-chlorophenyl)ethoxy]pyridin-2-yl}oxy)-5-methylphenyl]prop-2-enoic acid ¹H-NMR (DMSO-d₆) δ: 2.10 (3H, s), 3.02 (2H, t, J=6.6 Hz), 4.20 (2H, t, J=6.8 Hz), 6.57 (1H, d, J=16.2 Hz), 7.06 (1H, d, J=8.9 Hz), 7.34-7.37 (4H, m), 7.50-7.55 (2H, m), 7.64 (1H, d, J=1.6 Hz), 7.73 (1H, d, J=3.0 Hz), 7.75 (1H, d, J=2.0 Hz), 12.43 (1H, brs).

Reference Example 434

(E)-3-[3-Chloro-5-methyl-4-({5-[2-(4-methylphenyl)ethoxy]pyridin-2-yl}oxy)phenyl]prop-2-enoic acid ¹H-NMR (DMSO-d₆) δ: 2.10 (3H, s), 2.26 (3H, s), 2.97 (2H, t, J=6.9 Hz), 4.17 (2H, t, J=6.9 Hz), 6.56 (1H, d, J=16.2 Hz), 7.06 (1H, d, J=8.9 Hz), 7.10 (2H, d, J=7.9 Hz), 7.19 (2H, d, J=7.9 Hz), 7.49-7.57 (2H, m), 7.64 (1H, d, J=1.6 Hz), 7.73 (1H, d, J=3.0 Hz), 7.75 (1H, d, J=2.0 Hz), 12.45 (1H, brs).

Reference Example 435

(E)-3-[3-Chloro-4-({5-[2-(3,4-dichlorophenyl)ethoxy]pyridin-2-yl}oxy)-5-methylphenyl]prop-2-enoic acid ¹H-NMR (DMSO-d₆) δ: 2.10 (3H, s), 3.04 (2H, t, J=6.6 Hz), 4.22 (2H, t, J=6.6 Hz), 6.57 (1H, d, J=15.8 Hz), 7.07 (1H, d, J=8.9 Hz), 7.33 (1H, dd, J=8.4, 2.1 Hz), 7.51-7.58 (3H, m), 7.63-7.64 (2H, m), 7.74-7.75 (2H, m), 12.45 (1H, brs).

Reference Example 436

(E)-3-[3-Chloro-5-methyl-4-({5-[(4-methylbenzyl)oxy]pyridin-2-yl}oxy)phenyl]prop-2-enoic acid ¹H-NMR (DMSO-d₆) δ: 2.10 (3H, s), 2.30 (3H, s), 5.05 (2H, s), 6.57 (1H, d, J=15.8 Hz), 7.09 (1H, d, J=8.9 Hz), 7.20 (2H, d, J=7.9 Hz), 7.33 (2H, d, J=7.9 Hz), 7.52-7.61 (2H, m), 7.65 (1H, d, J=1.3 Hz), 7.76 (1H, d, J=2.0 Hz), 7.80 (1H, d, J=3.0 Hz), 12.45 (1H, s).

Reference Example 437

(E)-3-[3-Chloro-4-({5-[(2-fluorobenzyl)oxy]pyridin-2-yl}oxy)-5-methylphenyl]prop-2-enoic acid ¹H-NMR (CDCl₃) δ: 2.21 (4H, s), 5.11 (2H, s), 6.37 (1H, d, J=16.2 Hz), 6.97 (1H, d, J=8.9 Hz), 7.04-7.22 (2H, m), 7.29-7.49 (5H, m), 7.64 (1H, d, J=15.8 Hz), 7.82 (1H, d, J=3.0 Hz).

Reference Example 438

(E)-3-[3-Chloro-4-({5-[(2-chlorobenzyl)oxy]pyridin-2-yl}oxy)-5-methylphenyl]prop-2-enoic acid ¹H-NMR (CDCl₃) δ: 2.22 (3H, s), 5.15 (2H, s), 6.36 (1H, d, J=15.8 Hz), 6.98 (1H, d, J=8.9 Hz), 7.26-7.35 (3H, m), 7.37-7.44 (2H, m), 7.49-7.54 (2H, m), 7.64 (1H, d, J=15.8 Hz), 7.83 (1H, d, J=2.6 Hz).

Reference Example 439

(E)-3-[4-({5-[(2-Chlorobenzyl)oxy]pyridin-2-yl}oxy)-3-methoxyphenyl]prop-2-enoic acid ¹H-NMR (CDCl₃) δ: 3.82 (3H, s), 5.16 (2H, s), 6.36 (1H, d, J=15.9 Hz), 6.96 (1H, d, J=8.8 Hz), 7.11-7.20 (3H, m), 7.26-7.32 (3H, m), 7.37-7.43 (2H, m), 7.51-7.55 (1H, m), 7.72 (1H, d, J=15.9 Hz), 7.89 (1H, d, J=2.9 Hz).

Reference Example 440

(E)-3-[3-Chloro-4-({5-[(2-chlorobenzyl)oxy]pyridin-2-yl}oxy)phenyl]prop-2-enoic acid $^1$H-NMR (DMSO-d$_6$) δ: 5.19 (2H, s), 6.58 (1H, d, J=15.9 Hz), 7.14 (1H, d, J=8.8 Hz), 7.25 (1H, d, J=8.5 Hz), 7.37-7.44 (2H, m), 7.48-7.74 (5H, m), 7.93 (1H, d, J=3.2 Hz), 7.95 (1H, d, J=2.0 Hz).

Reference Example 441

(E)-3-[4-({5-[(2-Chlorobenzyl)oxy]pyridin-2-yl}oxy)-2-methylphenyl]prop-2-enoic acid $^1$H-NMR (DMSO-d$_6$) δ: 2.37 (3H, s), 5.20 (2H, s), 6.38 (1H, d, J=15.6 Hz), 6.90 (1H, dd, J=8.3, 2.4 Hz), 6.96 (1H, d, J=2.4 Hz), 7.07 (1H, d, J=8.8 Hz), 7.38-7.46 (2H, m), 7.51-7.55 (1H, m), 7.61-7.65 (2H, m), 7.73 (1H, d, J=8.3 Hz), 7.82 (1H, d, J=15.6 Hz), 8.01 (1H, d, J=2.9 Hz), 12.40 (1H, brs).

Reference Example 442

(E)-3-[4-({5-[(2-Chlorobenzyl)oxy]pyridin-2-yl}oxy)phenyl]prop-2-enoic acid $^1$H-NMR (CDCl$_3$) δ: 5.19 (2H, s), 6.37 (1H, d, J=15.9 Hz), 6.95 (1H, d, J=8.8 Hz), 7.12 (2H, dt, J=9.0, 2.3 Hz), 7.29-7.32 (2H, m), 7.38-7.43 (2H, m), 7.52-7.55 (1H, m), 7.56 (2H, d, J=8.8 Hz), 7.76 (1H, d, J=15.9 Hz), 7.97 (1H, d, J=3.2 Hz).

Reference Example 443

(E)-3-[3-Chloro-5-methyl-4-({5-[(4-methylbenzyl)oxy]pyridin-2-yl}oxy)phenyl]-2-methylprop-2-enoic acid $^1$H-NMR (DMSO-d$_6$) δ: 2.05 (3H, d, J=1.5 Hz), 2.12 (3H, s), 2.30 (3H, s), 5.05 (2H, s), 7.09 (1H, dd, J=9.0, 0.5 Hz), 7.19 (2H, d, J=7.8 Hz), 7.33 (2H, d, J=8.1 Hz), 7.38 (1H, d, J=2.0 Hz), 7.48 (1H, d, J=2.0 Hz), 7.52-7.56 (1H, m), 7.58 (1H, dd, J=8.8, 3.2 Hz), 7.81 (1H, dd, J=3.2, 0.5 Hz), 12.61 (1H, brs).

Reference Example 444

(E)-3-[3-Chloro-4-({5-[(2-chlorobenzyl)oxy]pyridin-2-yl}oxy)-5-methylphenyl]-2-methylbut-2-enoic acid $^1$H-NMR (DMSO-d$_6$) δ: 1.73 (3H, d, J=1.7 Hz), 2.11 (3H, s), 2.18-2.23 (3H, m), 5.17 (2H, s), 7.09 (1H, d, J=9.0 Hz), 7.12-7.15 (1H, m), 7.21 (1H, d, J=2.0 Hz), 7.35-7.45 (2H, m), 7.48-7.55 (1H, m), 7.59-7.66 (2H, m), 7.88 (1H, d, J=3.2 Hz), 12.51 (1H, brs).

Reference Example 445

(E)-3-[3-Chloro-5-methyl-4-({5-[(4-methylbenzyl)oxy]pyridin-2-yl}oxy)phenyl]-2-methylbut-2-enoic acid $^1$H-NMR (DMSO-d$_6$) δ: 1.71-1.75 (3H, m), 2.10 (3H, s), 2.17-2.22 (3H, m), 2.30 (3H, s), 5.05 (2H, s), 7.06 (1H, dd, J=9.0, 0.5 Hz), 7.09-7.14 (1H, m), 7.17-7.23 (3H, m), 7.33 (2H, d, J=8.1 Hz), 7.58 (1H, dd, J=9.0, 3.2 Hz), 7.81 (1H, dd, J=2.9, 0.5 Hz), 12.55 (1H, brs).

Reference Example 446

(E)-3-[3-Chloro-4-({5-[(2-chlorobenzyl)oxy]pyridin-2-yl}oxy)-5-methylphenyl]-2-methylprop-2-enoic acid $^1$H-NMR (DMSO-d$_6$) δ: 2.05 (3H, d, J=1.5 Hz), 2.13 (3H, s), 5.17 (2H, s), 7.12 (1H, dd, J=9.0, 0.5 Hz), 7.36-7.46 (3H, m), 7.46-7.57 (3H, m), 7.58-7.67 (2H, m), 7.86 (1H, dd, J=3.2, 0.5 Hz), 12.62 (1H, brs).

Reference Example 447

(E)-3-{3-Chloro-5-methyl-4-[(5-{[4-(trifluoromethyl)benzyl]oxy}pyridin-2-yl)oxy]phenyl}prop-2-enoic acid $^1$H-NMR (DMSO-d$_6$) δ: 2.10 (3H, s), 5.23 (2H, s), 6.58 (1H, d, J=16.1 Hz), 7.13 (1H, d, J=8.8 Hz), 7.55 (1H, d, J=15.9 Hz), 7.62-7.69 (4H, m), 7.77-7.79 (3H, m), 7.84 (1H, d, J=3.2 Hz), 12.49 (1H, s).

Reference Example 448

(E)-3-[4-({5-[(2-Chlorobenzyl)oxy]pyridin-2-yl}oxy)-3,5-dimethylphenyl]prop-2-enoic acid $^1$H-NMR (DMSO-d$_6$) δ: 2.04 (6H, s), 5.16 (2H, s), 6.47 (1H, d, J=15.9 Hz), 7.02 (1H, d, J=9.0 Hz), 7.39-7.41 (2H, m), 7.45 (2H, brs), 7.49-7.53 (2H, m), 7.60-7.63 (2H, m), 7.85 (1H, d, J=2.9 Hz).

Reference Example 449

(E)-3-[3,5-Dimethyl-4-({5-[(4-methylbenzyl)oxy]pyridin-2-yl}oxy)phenyl]prop-2-enoic acid $^1$H-NMR (DMSO-d$_6$) δ: 2.03 (6H, s), 2.30 (3H, s), 5.04 (2H, s), 6.47 (1H, d, J=15.9 Hz), 6.98 (1H, d, J=8.5 Hz), 7.19 (2H, d, J=7.1 Hz), 7.32 (2H, d, J=7.1 Hz), 7.43 (2H, brs), 7.50 (1H, d, J=16.1 Hz), 7.55 (1H, d, J=8.8 Hz), 7.80 (1H, brs).

Reference Example 450

(E)-3-[4-({5-[(4-Fluorobenzyl)oxy]pyridin-2-yl}oxy)-3,5-dimethylphenyl]prop-2-enoic acid $^1$H-NMR (CDCl$_3$) δ: 2.13 (6H, s), 4.99 (2H, s), 6.35 (1H, d, J=16.1 Hz), 6.86 (1H, d, J=9.0 Hz), 7.04-7.10 (2H, m), 7.29 (2H, brs), 7.33-7.40 (3H, m), 7.68 (1H, d, J=16.1 Hz), 7.82 (1H, d, J=3.2 Hz).

Reference Example 451

(E)-3-[4-({5-[(4-Methoxybenzyl)oxy]pyridin-2-yl}oxy)-3,5-dimethylphenyl]prop-2-enoic acid $^1$H-NMR (CDCl$_3$) δ: 2.14 (6H, s), 3.82 (3H, s), 4.96 (2H, s), 6.35 (1H, d, J=15.9 Hz), 6.85 (1H, d, J=9.0 Hz), 6.91 (2H, dt, J=9.2, 2.4 Hz), 7.29 (2H, brs), 7.31-7.36 (3H, m), 7.68 (1H, d, J=15.9 Hz), 7.82 (1H, d, J=2.9 Hz).

Reference Example 452

(E)-3-[4-({5-[(4-Cyanobenzyl)oxy]pyridin-2-yl}oxy)-3,5-dimethylphenyl]prop-2-enoic acid $^1$H-NMR (CDCl$_3$) δ: 2.13 (6H, s), 5.10 (2H, s), 6.35 (1H, d, J=16.1 Hz), 6.89 (1H, d, J=8.8 Hz), 7.26-7.29 (3H, m), 7.36

(1H, dd, J=8.9, 3.1 Hz), 7.53 (2H, d, J=8.3 Hz), 7.67-7.69 (3H, m), 7.80 (1H, d, J=2.9 Hz).

Reference Example 453

(E)-3-[3-Chloro-4-({5-[(4-fluorobenzyl)oxy]pyridin-2-yl}oxy)phenyl]prop-2-enoic acid $^1$H-NMR (DMSO-d$_6$) δ: 5.12 (2H, s), 6.57 (1H, d, J=16.1 Hz), 7.12 (1H, d, J=8.8 Hz), 7.18-7.28 (3H, m), 7.47-7.66 (4H, m), 7.69 (1H, dd, J=8.5, 2.2 Hz), 7.90 (1H, d, J=2.9 Hz), 7.95 (1H, d, J=2.0 Hz), 12.49 (1H, brs).

Reference Example 454

(E)-3-[5-Chloro-2-methyl-4-({5-[(4-methylbenzyl)oxy]pyridin-2-yl}oxy)phenyl]prop-2-enoic acid $^1$H-NMR (DMSO-d$_6$) δ: 2.30 (3H, s), 2.35 (3H, s), 5.08 (2H, s), 6.51 (1H, d, J=15.9 Hz), 7.08 (1H, d, J=8.8 Hz), 7.12 (1H, s), 7.20 (2H, d, J=7.8 Hz), 7.33 (2H, d, J=7.8 Hz), 7.59 (1H, dd, J=9.0, 2.2 Hz), 7.71 (1H, d, J=15.9 Hz), 7.87 (1H, d, J=2.7 Hz), 7.90 (1H, s), 12.48 (1H, brs).

Reference Example 455

(E)-3-[5-Chloro-4-({5-[(2-chlorobenzyl)oxy]pyridin-2-yl}oxy)-2-methylphenyl]prop-2-enoic acid $^1$H-NMR (DMSO-d$_6$) δ: 2.35 (3H, s), 5.19 (2H, s), 6.51 (1H, d, J=15.9 Hz), 7.11 (1H, d, J=9.0 Hz), 7.14 (1H, s), 7.37-7.43 (2H, m), 7.50-7.54 (1H, m), 7.59-7.66 (2H, m), 7.71 (1H, d, J=15.9 Hz), 7.91-7.93 (2H, m), 12.49 (1H, s).

Reference Example 456

(E)-3-[2-Chloro-4-({5-[(2-chlorobenzyl)oxy]pyridin-2-yl}oxy)-5-methylphenyl]prop-2-enoic acid $^1$H-NMR (CDCl$_3$) δ: 2.13 (3H, s), 5.20 (2H, s), 6.58 (1H, d, J=15.9 Hz), 7.11 (1H, d, J=8.8 Hz), 7.16 (1H, s), 7.37-7.43 (2H, m), 7.50-7.54 (1H, m), 7.60-7.66 (2H, m), 7.82 (1H, d, J=15.9 Hz), 7.92 (1H, s), 7.96-7.97 (1H, m), 12.55 (1H, brs).

Reference Example 457

(E)-3-{4-[(5-Hydroxypyridin-2-yl)oxy]-3,5-dimethylphenyl}prop-2-enoic acid $^1$H-NMR (DMSO-d$_6$) δ: 2.03 (6H, s), 6.45 (1H, d, J=15.9 Hz), 6.87 (1H, d, J=8.8 Hz), 7.27 (1H, dd, J=8.8, 2.9 Hz), 7.44 (2H, s), 7.52 (1H, d, J=15.9 Hz), 7.55 (1H, d, J=2.9 Hz), 9.49 (1H, s), 12.32 (1H, s).

Reference Example 458

(E)-3-{4-[(5-Hydroxypyridin-2-yl)oxy]-2-methylphenyl}prop-2-enoic acid $^1$H-NMR (DMSO-d$_6$) δ: 2.36 (3H, s), 6.36 (1H, d, J=15.9 Hz), 6.85 (1H, dd, J=8.5, 2.0 Hz), 6.90 (1H, d, J=2.0 Hz), 6.94 (1H, d, J=8.8 Hz), 7.30 (1H, dd, J=8.7, 3.1 Hz), 7.71 (1H, d, J=8.5 Hz), 7.75-7.78 (2H, m), 9.76 (1H, s), 12.37 (1H, s).

Reference Example 459

(E)-3-[4-({5-[(4-Cyanobenzyl)oxy]pyridin-2-yl}oxy)-3,5-dimethoxyphenyl]prop-2-enoic acid $^1$H-NMR (DMSO-d$_6$) δ: 3.72 (6H, s), 5.21 (2H, s), 6.61 (1H, d, J=15.9 Hz), 6.93 (1H, d, J=8.8 Hz), 7.11 (2H, s), 7.52 (1H, dd, J=8.8, 2.9 Hz), 7.58 (1H, d, J=15.9 Hz), 7.64 (2H, d, J=8.1 Hz), 7.77 (1H, d, J=2.9 Hz), 7.87 (2H, d, J=8.1 Hz), 12.36 (1H, s).

Reference Example 460

(E)-3-[4-({5-[(2-Cyanobenzyl)oxy]pyridin-2-yl}oxy)-3,5-dimethoxyphenyl]prop-2-enoic acid $^1$H-NMR (DMSO-d$_6$) δ: 3.73 (6H, s), 5.24 (2H, s), 6.61 (1H, d, J=16.1 Hz), 6.95 (1H, d, J=8.8 Hz), 7.11 (2H, s), 7.54-7.61 (3H, m), 7.72-7.78 (2H, m), 7.81 (1H, d, J=2.9 Hz), 7.91 (1H, d, J=7.6 Hz), 12.35 (1H, s).

Reference Example 461

(E)-3-(3,5-Dimethyl-4-{[5-(pyridin-4-ylmethoxy)pyridin-2-yl]oxy}phenyl)prop-2-enoic acid $^1$H-NMR (DMSO-d$_6$) δ: 2.03 (6H, s), 5.18 (2H, s), 6.46 (1H, d, J=16.1 Hz), 7.02 (1H, d, J=9.0 Hz), 7.43-7.45 (4H, m), 7.52 (1H, d, J=16.1 Hz), 7.60 (1H, dd, J=9.0, 2.9 Hz), 7.83 (1H, d, J=2.9 Hz), 8.58 (2H, d, J=5.9 Hz), 12.33 (1H, s).

Reference Example 462

(E)-3-[3,5-Dimethyl-4-({5-[(6-methylpyridin-2-yl)methoxy]pyridin-2-yl}oxy)phenyl]prop-2-enoic acid $^1$H-NMR (DMSO-d$_6$) δ: 2.03 (6H, s), 2.59 (3H, s), 5.25 (2H, s), 6.46 (1H, d, J=15.9 Hz), 7.04 (1H, d, J=9.0 Hz), 7.44-7.47 (3H, m), 7.52-7.55 (2H, m), 7.63 (1H, dd, J=9.0, 2.9 Hz), 7.85 (1H, d, J=2.9 Hz), 8.01 (1H, brs).

Reference Example 463

(E)-3-[3-Chloro-4-({5-[(4-cyanobenzyl)oxy]pyridin-2-yl}oxy)phenyl]prop-2-enoic acid $^1$H-NMR (DMSO-d$_6$) δ: 5.25 (2H, s), 6.57 (1H, d, J=15.9 Hz), 7.13 (1H, d, J=9.0 Hz), 7.23 (1H, d, J=8.5 Hz), 7.50-7.73 (4H, m), 7.84-7.95 (5H, m), 12.45 (1H, brs).

Reference Example 464

(E)-3-(4-{[5-(1,3-Benzothiazol-6-ylmethoxy)pyridin-2-yl]oxy}-3,5-dimethoxyphenyl)prop-2-enoic acid $^1$H-NMR (DMSO-d$_6$) δ: 3.72 (6H, s), 5.26 (2H, s), 6.61 (1H, d, J=15.9 Hz), 6.93 (1H, d, J=9.0 Hz), 7.11 (2H, s), 7.54 (1H, dd, J=9.0, 2.9 Hz), 7.59 (1H, d, J=15.9 Hz), 7.61-7.63

(1H, m), 7.81 (1H, d, J=2.9 Hz), 8.10 (1H, d, J=8.5 Hz), 8.26 (1H, s), 9.41 (1H, s), 12.36 (1H, s).

Reference Example 465

(E)-3-[2-Chloro-5-methyl-4-({5-[(4-methylbenzyl)oxy]pyridin-2-yl}oxy)phenyl]prop-2-enoic acid $^1$H-NMR (DMSO-d$_6$) δ: 2.12 (3H, s), 2.30 (3H, s), 5.09 (2H, s), 6.58 (1H, d, J=15.9 Hz), 7.08 (1H, d, J=8.8 Hz), 7.14 (1H, s), 7.20 (2H, d, J=8.1 Hz), 7.33 (2H, d, J=8.1 Hz), 7.59 (1H, dd, J=8.8, 2.9 Hz), 7.82 (1H, d, J=15.9 Hz), 7.91-7.92 (2H, m), 12.57 (1H, s).

Reference Example 466

(E)-3-[2-Chloro-4-({5-[(4-cyanobenzyl)oxy]pyridin-2-yl}oxy)-5-methylphenyl]prop-2-enoic acid $^1$H-NMR (DMSO-d$_6$) δ: 2.12 (3H, s), 5.26 (2H, s), 6.59 (1H, d, J=15.9 Hz), 7.11 (1H, d, J=8.8 Hz), 7.15 (1H, s), 7.62-7.66 (3H, m), 7.82 (1H, d, J=15.9 Hz), 7.88 (2H, d, J=8.5 Hz), 7.92 (1H, s), 7.94 (1H, d, J=2.9 Hz), 12.58 (1H, s).

Reference Example 467

(E)-3-[5-Chloro-4-({5-[(4-cyanobenzyl)oxy]pyridin-2-yl}oxy)-2-methylphenyl]prop-2-enoic acid $^1$H-NMR (DMSO-d$_6$) δ: 2.35 (3H, s), 5.25 (2H, s), 6.51 (1H, d, J=15.9 Hz), 7.10-7.13 (2H, m), 7.61-7.66 (3H, m), 7.71 (1H, d, J=15.9 Hz), 7.86-7.90 (4H, m), 12.49 (1H, s).

Reference Example 468

(E)-3-(3,5-Dimethyl-4-{[5-(1,3-thiazol-5-yl-methoxy)pyridin-2-yl]oxy}phenyl)prop-2-enoic acid $^1$H-NMR (DMSO-d$_6$) δ: 2.03 (6H, s), 5.39 (2H, d, J=0.5 Hz), 6.46 (1H, d, J=16.1 Hz), 7.01 (1H, dd, J=9.0, 0.5 Hz), 7.46 (2H, s), 7.52 (1H, d, J=15.9 Hz), 7.60 (1H, dd, J=9.0, 3.2 Hz), 7.83 (1H, dd, J=3.2, 0.5 Hz), 8.00 (1H, d, J=0.7 Hz), 9.13 (1H, d, J=0.7 Hz), 12.35 (1H, brs).

Reference Example 469

(E)-3-(3,5-Dimethyl-4-{[5-(1,3-thiazol-4-yl-methoxy)pyridin-2-yl]oxy}phenyl)prop-2-enoic acid $^1$H-NMR (DMSO-d$_6$) δ: 2.03 (6H, s), 5.22 (2H, s), 6.46 (1H, d, J=15.9 Hz), 7.01 (1H, d, J=9.0 Hz), 7.45 (2H, s), 7.52 (1H, d, J=15.9 Hz), 7.61 (1H, dd, J=9.0, 3.2 Hz), 7.83 (1H, d, J=2.0 Hz), 7.84 (1H, d, J=3.2 Hz), 9.12 (1H, d, J=2.0 Hz), 12.33 (1H, s).

Reference Example 470

(E)-3-{3-Chloro-4-[(5-{[4-(difluoromethoxy)benzyl]oxy}pyridin-2-yl)oxy]-5-methylphenyl}-prop-2-enoic acid $^1$H-NMR (DMSO-d$_6$) δ: 2.10 (3H, s), 5.10 (2H, s), 6.57 (1H, d, J=15.9 Hz), 7.10 (1H, d, J=8.8 Hz), 7.20 (2H, d, J=8.3 Hz), 7.24 (1H, t, J=74.1 Hz), 7.50-7.57 (3H, m), 7.60 (1H, dd, J=8.8, 2.9 Hz), 7.65 (1H, brs), 7.75 (1H, brs), 7.81 (1H, d, J=2.9 Hz), 12.45 (1H, s).

Reference Example 471

To a DMF (40 mL) solution of butyl (E)-3-{3-fluoro-4-[(5-hydroxypyridin-2-yl)oxy]phenyl}prop-2-enoate (3.82 g) and 2-chlorobenzyl chloride (1.6 mL) was added sodium hydride (60% w/w in oil, 0.60 g) at 0° C., and stirred at room temperature for 3 hours. The reaction mixture was quenched by addition of saturated NH$_4$Cl (90 mL), and extracted with AcOEt. The organic layer was washed with water, saturated aqueous NaCl, dried over anhydrous Na$_2$SO$_4$, and evaporated. The residue was purified by silica gel column chromatography (n-hexane/AcOEt=19/1 to 9/1) to afford (E)-3-[4-({5-[(2-Chlorobenzyl)oxy]pyridin-2-yl}oxy)-3-fluorophenyl]prop-2-enoic acid butyl ester (3.53 g).

To an EtOH (40 mL) solution of the ester was added 5 M NaOH (6.9 mL), and stirred for 2.5 hours at 50° C., then EtOH was evaporated. The residue was dissolved in water, and acidified with 6 M HCl. The resulting precipitate was collected by filtration and dried to afford (E)-3-[4-({5-[(2-Chlorobenzyl)oxy]pyridin-2-yl}oxy)-3-fluorophenyl]prop-2-enoic acid as a white powder (2.78 g).

$^1$H-NMR (DMSO-d$_6$) δ: 5.19 (2H, s), 6.57 (1H, d, J=16.1 Hz), 7.15 (1H, d, J=8.8 Hz), 7.30 (1H, t, J=8.3 Hz), 7.37-7.44 (2H, m), 7.51-7.57 (3H, m), 7.60-7.63 (1H, m), 7.65 (1H, dd, J=8.9, 3.1 Hz), 7.76 (1H, dd, J=12.0, 2.0 Hz), 7.92 (1H, d, J=2.9 Hz).

The following compounds were produced in the same manner as in Reference Example 471 using appropriate starting materials.

Reference Example 472

(E)-3-[3-Chloro-4-({5-[(3-chloro-2-fluorobenzyl)oxy]pyridin-2-yl}oxy)-5-methylphenyl]prop-2-enoic acid $^1$H-NMR (DMSO-d$_6$) δ: 2.11 (3H, s), 5.20 (2H, s), 6.58 (1H, dd, J=15.9, 0.7 Hz), 7.13 (1H, d, J=9.0 Hz), 7.28 (1H, t, J=7.9 Hz), 7.55 (2H, t, J=7.9 Hz), 7.60-7.67 (3H, m), 7.77 (1H, d, J=1.5 Hz), 7.85 (1H, d, J=2.9 Hz), 12.50 (1H, s).

Reference Example 473

(E)-3-[3-Chloro-4-({5-[(2,3-difluorobenzyl)oxy]pyridin-2-yl}oxy)-5-methylphenyl]prop-2-enoic acid $^1$H-NMR (DMSO-d$_6$) δ: 2.11 (3H, s), 5.21 (2H, s), 6.58 (1H, d, J=15.9 Hz), 7.13 (1H, d, J=9.0 Hz), 7.23-7.28 (1H, m), 7.39 (1H, t, J=6.8 Hz), 7.43-7.49 (1H, m), 7.55 (1H, d, J=16.1 Hz), 7.64-7.67 (2H, m), 7.77 (1H, d, J=1.7 Hz), 7.85 (1H, d, J=3.2 Hz), 12.48 (1H, s).

Reference Example 474

(E)-3-[3-Methyl-4-({5-[(4-methylbenzyl)oxy]pyridin-2-yl}oxy)phenyl]prop-2-enoic acid $^1$H-NMR (DMSO-d$_6$) δ: 2.12 (3H, s), 2.31 (3H, s), 5.08 (2H, s), 6.46 (1H, d, J=15.9 Hz), 6.96 (1H, d, J=8.3 Hz), 7.02 (1H, d, J=9.0 Hz), 7.20 (2H, d, J=8.1 Hz), 7.33 (2H, d, J=8.1 Hz), 7.50-7.59 (3H, m), 7.64 (1H, d, J=2.0 Hz), 7.88 (1H, d, J=3.2 Hz), 12.36 (1H, s).

Reference Example 475

(E)-3-[4-({5-[(2,3-Dichlorobenzyl)oxy]pyridin-2-yl}oxy)-3-methylphenyl]prop-2-enoic acid $^1$H-NMR (DMSO-d$_6$) δ: 2.13 (3H, s), 5.23 (2H, s), 6.47 (1H, d, J=15.9 Hz), 6.99 (1H, d, J=8.3 Hz), 7.05 (1H, d, J=9.0

Hz), 7.43 (1H, t, J=7.9 Hz), 7.51-7.57 (2H, m), 7.60-7.68 (4H, m), 7.94 (1H, d, J=3.2 Hz), 12.24 (1H, s).

Reference Example 476

(E)-3-[4-({5-[(2-Chlorobenzyl)oxy]pyridin-2-yl}oxy)-3-methylphenyl]prop-2-enoic acid $^1$H-NMR (DMSO-d$_6$) δ: 2.13 (3H, s), 5.19 (2H, s), 6.47 (1H, d, J=16.1 Hz), 6.99 (1H, d, J=8.3 Hz), 7.05 (1H, d, J=8.8 Hz), 7.37-7.44 (2H, m), 7.52-7.58 (3H, m), 7.61-7.65 (3H, m), 7.93 (1H, d, J=2.9 Hz), 12.38 (1H, s).

Reference Example 477

6-({5-[(2-Chlorobenzyl)oxy]pyridin-2-yl}oxy)naphthalene-2-carboxylic acid $^1$H-NMR (DMSO-d$_6$) δ: 5.22 (2H, s), 7.16 (1H, dd, J=8.8, 0.5 Hz), 7.37-7.45 (3H, m), 7.51-7.56 (1H, m), 7.60 (1H, d, J=2.2 Hz), 7.62-7.66 (1H, m), 7.68 (1H, dd, J=8.8, 3.2 Hz), 7.93 (1H, d, J=8.8 Hz), 7.97 (1H, dd, J=8.5, 1.5 Hz), 8.03 (1H, dd, J=3.2, 0.5 Hz), 8.15 (1H, d, J=9.0 Hz), 8.61 (1H, d, J=0.7 Hz), 13.03 (1H, brs).

Reference Example 478

(E)-3-[3-Chloro-4-({5-[(4-cyanobenzyl)oxy]pyridin-2-yl}oxy)-5-methylphenyl]prop-2-enoic acid $^1$H-NMR (CDCl$_3$) δ: 2.21 (3H, s), 5.10 (2H, s), 6.09-6.33 (1H, m), 6.37 (1H, d, J=16.1 Hz), 6.96-7.01 (1H, m), 7.34 (1H, s), 7.38-7.41 (1H, m), 7.48-7.54 (3H, m), 7.64 (1H, d, J=16.1 Hz), 7.68-7.85 (3H, m).

Reference Example 479

6-({5-[(2,3-Difluorobenzyl)oxy]pyridin-2-yl}oxy)naphthalene-2-carboxylic acid $^1$H-NMR (DMSO-d$_6$) δ: 3.36 (1H, brs), 5.26 (2H, s), 7.15 (1H, dd, J=8.8, 0.5 Hz), 7.24-7.30 (1H, m), 7.36 (1H, dd, J=8.8, 2.4 Hz), 7.39-7.51 (2H, m), 7.58 (1H, d, J=2.4 Hz), 7.68 (1H, dd, J=8.8, 3.2 Hz), 7.89 (1H, d, J=9.0 Hz), 7.98 (1H, dd, 8.5, 1.7 Hz), 8.02 (1H, dd, J=3.2, 0.5 Hz), 8.12 (1H, d, J=9.3 Hz), 8.58 (1H, d, J=0.7 Hz).

Reference Example 480

(E)-3-[4-({5-[(2,3-Difluorobenzyl)oxy]pyridin-2-yl}oxy)-3-fluorophenyl]prop-2-enoic acid $^1$H-NMR (DMSO-d$_6$) δ: 5.23 (2H, s), 6.57 (1H, d, J=15.9 Hz), 7.14 (1H, d, J=9.0 Hz), 7.23-7.32 (2H, m), 7.37-7.41 (1H, m), 7.42-7.49 (1H, m), 7.54 (1H, dd, J=8.2, 1.8 Hz), 7.58 (1H, d, J=16.1 Hz), 7.66 (1H, dd, J=9.0, 3.2 Hz), 7.77 (1H, dd, J=12.0, 2.0 Hz), 7.92 (1H, d, J=2.7 Hz), 12.47 (1H, brs).

Reference Example 481

(E)-3-[4-({5-[(2,4-Difluorobenzyl)oxy]pyridin-2-yl}oxy)-3-fluorophenyl]prop-2-enoic acid $^1$H-NMR (DMSO-d$_6$) Es: 5.14 (2H, s), 6.57 (1H, d, J=16.1 Hz), 7.11-7.16 (2H, m), 7.27-7.34 (2H, m), 7.54 (1H, dd, J=8.3, 1.7 Hz), 7.59 (1H, d, J=15.9 Hz), 7.62-7.67 (2H, m), 7.77 (1H, dd, J=12.0, 2.0 Hz), 7.91 (1H, d, J=2.9 Hz), 12.46 (1H, brs).

Reference Example 482

(E)-3-[4-({5-[(3,4-Difluorobenzyl)oxy]pyridin-2-yl}oxy)-3-fluorophenyl]prop-2-enoic acid $^1$H-NMR (DMSO-d$_6$) δ: 5.12 (2H, s), 6.57 (1H, d, J=15.9 Hz), 7.13 (1H, dd, J=9.0, 0.5 Hz), 7.27-7.34 (2H, m), 7.46 (1H, dt, J=14.8, 5.4 Hz), 7.52-7.64 (4H, m), 7.77 (1H, dd, J=12.0, 2.0 Hz), 7.89 (1H, dd, J=3.2, 0.5 Hz), 12.45 (1H, brs).

Reference Example 483

(E)-3-[4-({5-[(4-Cyanobenzyl)oxy]pyridin-2-yl}oxy)-3-fluorophenyl]prop-2-enoic acid $^1$H-NMR (DMSO-d$_6$) δ: 5.25 (2H, s), 6.56 (1H, d, J=16.1 Hz), 7.14 (1H, d, J=8.8 Hz), 7.29 (1H, t, J=8.3 Hz), 7.50-7.66 (5H, m), 7.77 (1H, dd, J=12.0, 2.0 Hz), 7.87-7.90 (3H, m), 12.46 (1H, s).

Reference Example 484

To a THF (50 mL) solution of butyl (E)-3-{4-[(5-aminopyridin-2-yl)oxy]-3-chloro-5-methylphenyl}prop-2-enoate (5.00 g) were added sulfuric acid (1.1 mL) and n-pentyl nitrite (2.44 g) at 0° C. After stirring for 1 hour, the resulting precipitate was collected by filtration and dried under reduced pressure to afford a diazonium salt as a pale brown powder (6.45 g).

To acetic acid (100 mL) was added an acetic acid (50 mL) solution of the diazonium salt (6.45 g) at 100-110° C. After stirring for 1 hour, acetic acid was evaporated. K$_2$CO$_3$ (9.58 g) was added to an EtOH (50 mL) solution of the residue at room temperature. After stirring over night, EtOH was evaporated. To the residue were added water and AcOEt, and the mixture was acidified with 1 M HCl. The organic layer was washed with saturated NaHCO$_3$, saturated aqueous NaCl, dried over anhydrous Na$_2$SO$_4$, and evaporated. The residue was purified by silica gel column chromatography (n-hexane/AcOEt=7/3 to 1/1) to afford (E)-3-{3-chloro-4-[(5-hydroxypyridin-2-yl)oxy]-5-methylphenyl}prop-2-enoic acid butyl ester (4.73 g).

To a MeOH (10 mL) solution of the ester (4.73 g) was added 5 M NaOH (2 mL), and stirred for 1 hour at 50° C., then MeOH was evaporated. The residue was dissolved in water, and acidified with 6 M HCl. The resulting precipitate was collected by filtration and dried to afford (E)-3-{3-chloro-4-[(5-hydroxypyridin-2-yl)oxy]-5-methylphenyl}prop-2-enoic acid as a pale yellow powder (3.77 g).

$^1$H-NMR (DMSO-d$_6$) δ: 2.10 (3H, s), 6.56 (1H, d, J=16.2 Hz), 6.96 (1H, d, J=8.9 Hz), 7.30 (1H, dd, J=8.9, 3.0 Hz), 7.52 (1H, d, J=10.2 Hz), 7.53 (1H, d, J=15.8 Hz), 7.63 (1H, d, J=1.6 Hz), 7.74 (1H, d, J=2.0 Hz), 9.58 (1H, s), 12.45 (1H, brs).

The following compounds were produced in the same manner as in Reference Example 15 using appropriate starting materials.

Reference Example 485

(E)-3-[3-Chloro-4-({5-[(2-chlorobenzyl)oxy]pyridin-2-yl}oxy)-5-methylphenyl]but-2-enoic acid $^1$H-NMR (DMSO-d$_6$) δ: 2.13 (3H, s), 2.45-2.54 (3H, m), 5.17 (2H, s), 6.14-6.18 (1H, m), 7.12 (1H, d, J=8.8 Hz), 7.36-7.45 (2H, m), 7.48-7.54 (2H, m), 7.54-7.58 (2H, m), 7.60-7.70 (1H, m), 7.85 (1H, d, J=2.9 Hz), 12.32 (1H, brs).

Reference Example 486

(E)-3-[3-Chloro-5-methyl-4-({5-[(4-methylbenzyl)oxy]pyridin-2-yl}oxy)phenyl]but-2-enoic acid $^1$H-NMR (DMSO-d$_6$) δ: 2.11 (3H, s), 2.30 (3H, s), 2.48 (3H, d, J=1.5 Hz), 5.05 (2H, s), 6.14-6.18 (1H, m), 7.09 (1H, dd, J=9.0, 0.5 Hz), 7.19 (2H, d, J=7.8 Hz), 7.33 (2H, d, J=8.1 Hz), 7.47-7.52 (1H, m), 7.54-7.57 (1H, m), 7.58 (1H, dd, J=9.0, 3.2 Hz), 7.79 (1H, dd, J=3.2, 0.5 Hz), 12.31 (1H, brs).

Reference Example 487

To a DMF (26 mL) solution of (E)-3-{4-[(5-hydroxypyridin-2-yl)oxy]-3,5-dimethylphenyl}prop-2-enoic acid (1.300 g) and 1-{4-[2-(4-chlorophenoxy)ethyl]benzyl}-piperazine hydrochloride (2.116 g) were added HOBT (0.070 g), WSC (1.310 g), and Et$_3$N (1.905 mL) at room temperature, then the resultant mixture was stirred at room temperature over night. The mixture was poured into water, and extracted with AcOEt. The organic layer was washed with water and saturated aqueous NaCl, dried over anhydrous Na$_2$SO$_4$, and evaporated. The residue was purified by silica gel column chromatography (n-hexane/AcOEt=1/1 to 1/0 and then AcOEt/MeOH=4/1) to afford (E)-1-(4-{4-[2-(4-chlorophenoxy)ethyl]benzyl}piperazin-1-yl)-3-{4-[(5-hydroxypyridin-2-yl)oxy]-3,5-dimethylphenyl}prop-2-en-1-one as a pale yellow amorphous powder (2.57 g).

$^1$H-NMR (CDCl$_3$) δ: 2.09 (6H, s), 2.47-2.48 (4H, m), 3.07 (2H, t, J=7.0 Hz), 3.52 (2H, s), 3.64-3.66 (2H, m), 3.73-3.76 (2H, m), 4.13 (2H, t, J=7.0 Hz), 6.70 (1H, d, J=8.8 Hz), 6.75 (1H, d, J=15.4 Hz), 6.81 (2H, d, J=9.0 Hz), 7.21-7.26 (10H, m), 7.57 (1H, d, J=15.4 Hz), 7.72 (1H, d, J=2.7 Hz).

The following compounds were produced in the same manner as in Reference Example 487 using appropriate starting materials.

Reference Example 488

(E)-3-{3-Chloro-4-[(5-hydroxypyridin-2-yl)oxy]-5-methylphenyl}-1-[4-(4-methylbenzyl)piperazin-1-yl]prop-2-en-1-one $^1$H-NMR (CDCl$_3$) δ: 2.17 (3H, s), 2.35 (3H, s), 2.48 (4H, t, J=4.9 Hz), 3.50 (2H, s), 3.63-3.73 (4H, m), 6.39 (1H, s), 6.77 (1H, d, J=15.5 Hz), 6.86 (1H, d, J=8.9 Hz), 7.14-7.20 (4H, m), 7.24-7.28 (2H, m), 7.41 (1H, d, J=2.0 Hz), 7.54 (1H, d, J=15.2 Hz), 7.67 (1H, d, J=3.0 Hz).

Reference Example 489

(E)-3-{3-Chloro-4-[(5-hydroxypyridin-2-yl)oxy]-5-methylphenyl}-1-(4-{4-[2-(4-fluorophenoxy)ethyl]benzyl}piperazin-1-yl)prop-2-en-1-one $^1$H-NMR (CDCl$_3$) δ: 2.16 (3H, s), 2.48 (4H, t, J=4.6 Hz), 3.07 (2H, t, J=6.9 Hz), 3.52 (2H, s), 3.64-3.74 (4H, m), 4.13 (2H, t, J=6.9 Hz), 6.78-6.81 (4H, m), 6.93-6.96 (2H, m), 7.22-7.28 (6H, m), 7.38 (1H, d, J=2.0 Hz), 7.53 (1H, d, J=15.5 Hz), 7.66 (1H, d, J=3.0 Hz).

Reference Example 490

(E)-3-{3-Chloro-4-[(5-hydroxypyridin-2-yl)oxy]-5-methylphenyl}-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=6.9 Hz), 2.18 (3H, s), 2.48 (4H, t, J=4.8 Hz), 2.85 (1H, septet, J=6.9 Hz), 3.08 (2H, t, J=6.9 Hz), 3.52 (2H, s), 3.64-3.74 (4H, m), 4.15 (2H, t, J=6.9 Hz), 6.10 (1H, s), 6.75-6.88 (4H, m), 7.13 (2H, d, J=8.9 Hz), 7.26-7.28 (6H, m), 7.41 (1H, d, J=2.0 Hz), 7.55 (1H, d, J=15.2 Hz), 7.68 (1H, d, J=3.0 Hz).

Reference Example 491

(E)-3-{3-Chloro-4-[(5-hydroxypyridin-2-yl)oxy]-5-methylphenyl}-1-(4-{4-[2-(4-methylphenoxy)ethyl]benzyl}piperazin-1-yl)prop-2-en-1-one $^1$H-NMR (CDCl$_3$) δ: 2.18 (3H, s), 2.28 (3H, s), 2.48 (4H, t, J=4.8 Hz), 3.08 (2H, t, J=7.1 Hz), 3.52 (2H, s), 3.65-3.75 (4H, m), 4.15 (2H, t, J=7.1 Hz), 5.97 (1H, s), 6.75-6.81 (3H, m), 6.87 (1H, d, J=8.9 Hz), 7.07 (2H, d, J=8.6 Hz), 7.24-7.29 (6H, m), 7.42 (1H, s), 7.55 (1H, d, J=15.2 Hz), 7.68 (1H, d, J=3.0 Hz).

Reference Example 492

(E)-3-{3-Chloro-4-[(5-hydroxypyridin-2-yl)oxy]-5-methylphenyl}-1-(4-{4-[2-(4-methoxyphenoxy)ethyl]benzyl}piperazin-1-yl)prop-2-en-1-one $^1$H-NMR (CDCl$_3$) δ: 2.17 (3H, s), 2.48 (4H, t, J=4.8 Hz), 3.07 (2H, t, J=6.9 Hz), 3.52 (2H, s), 3.64-3.76 (4H, m), 3.70 (3H, s), 4.12 (2H, t, J=6.9 Hz), 6.76-6.84 (5H, m), 7.24-7.27 (8H, m), 7.40 (1H, d, J=2.0 Hz), 7.54 (1H, d, J=15.2 Hz), 7.67 (1H, d, J=3.0 Hz).

Reference Example 493

(E)-3-{3-Chloro-4-[(5-hydroxypyridin-2-yl)oxy]-5-methylphenyl}-1-(4-{4-[2-(4-chlorophenoxy)ethyl]benzyl}piperazin-1-yl)prop-2-en-1-one $^1$H-NMR (DMSO-d$_6$) δ: 2.09 (3H, s), 2.35 (2H, s), 2.41 (2H, s), 3.01 (2H, t, J=6.8 Hz), 3.49 (2H, s), 3.56 (2H, s), 3.72 (2H, s), 4.18 (2H, t, J=6.8 Hz), 6.94-6.98 (3H, m), 7.24-7.32 (8H, m), 7.43 (1H, d, J=15.4 Hz), 7.55 (1H, dd, J=2.9, 0.5 Hz), 7.61 (1H, d, J=2.0 Hz), 7.81 (1H, d, J=2.2 Hz), 9.57 (1H, s).

Reference Example 494 tert-Butyl 4-{(E)-3-[3-chloro-4-({5-[(2-chlorobenzyl)oxy]pyridin-2-yl}oxy)-5-methylphenyl]prop-2-enoyl}piperazine-1-carboxylate $^1$H-NMR (CDCl$_3$) δ: 1.48 (9H, s), 2.20 (3H, s), 3.49-3.70 (8H, m), 5.14 (2H, s), 6.79 (1H, d, J=15.4 Hz), 6.94-6.96 (1H, m), 7.25-7.32 (3H, m), 7.38-7.41 (2H, m), 7.47 (1H, d, J=2.2 Hz), 7.51-7.53 (1H, m), 7.60 (1H, d, J=15.4 Hz), 7.81-7.82 (1H, m).

Reference Example 495 tert-Butyl 4-{(E)-3-[3-chloro-5-methyl-4-({5-[(4-methylbenzyl)oxy]pyridin-2-yl}oxy)phenyl]-prop-2-enoyl}piperazine-1-carboxylate $^1$H-NMR (CDCl$_3$) δ: 1.49 (9H, s), 2.20 (3H, s), 2.36 (3H, s), 3.49-3.72 (8H, m), 4.99 (2H, s), 6.79 (1H, d, J=15.4 Hz), 6.91-6.93 (1H, m), 7.19 (2H, d, J=7.8 Hz), 7.28-7.30 (3H, m), 7.36 (1H, dd, J=8.9, 3.1 Hz), 7.47 (1H, d, J=2.0 Hz), 7.60 (1H, d, J=15.4 Hz), 7.79-7.80 (1H, m).

Reference Example 496

(E)-1-(4-{4-[2-(4-Fluorophenoxy)ethyl]benzyl}piperazin-1-yl)-3-{4-[(5-hydroxypyridin-2-yl)oxy]-2-methylphenyl}prop-2-en-1-one $^1$H-NMR (CDCl$_3$) δ: 2.31 (3H, s), 2.48-2.50 (4H, m), 3.07 (2H, t, J=7.0 Hz), 3.52 (2H, s), 3.64-3.66 (2H, m), 3.75-3.77 (2H, m), 4.12-4.14 (2H, m), 6.69 (1H, d, J=15.4 Hz), 6.79-6.87 (5H, m), 6.94-6.96 (2H, m), 7.25-7.26 (5H, m), 7.48 (1H, d, J=8.5 Hz), 7.85-7.89 (3H, m).

Reference Example 497 tert-Butyl (3R)-4-{(E)-3-[3-chloro-5-methyl-4-({5-[(4-methylbenzyl)oxy]pyridin-2-yl}oxy)phenyl]prop-2-enoyl}-3-methylpiperazine-1-carboxylate $^1$H-NMR (CDCl$_3$) δ: 1.25-1.27 (3H, m), 1.48 (9H, s), 2.19 (3H, s), 2.35 (3H, s), 2.90-4.88 (7H, m), 4.98 (2H, s), 6.77 (1H, d, J=15.4 Hz), 6.92 (1H, d, J=8.8 Hz), 7.18 (2H, d, J=7.8 Hz), 7.27-7.29 (3H, m), 7.35 (1H, dd, J=8.8, 2.9 Hz), 7.46 (1H, d, J=2.0 Hz), 7.59 (1H, d, J=15.4 Hz), 7.79 (1H, d, J=2.9 Hz).

Reference Example 498 tert-Butyl (3S)-4-{(E)-3-[3-chloro-5-methyl-4-({5-[(4-methylbenzyl)oxy]pyridin-2-yl}oxy)phenyl]prop-2-enoyl}-3-methylpiperazine-1-carboxylate $^1$H-NMR (CDCl$_3$) δ: 1.25-1.27 (3H, m), 1.48 (9H, s), 2.19 (3H, s), 2.35 (3H, s), 2.89-4.87 (7H, m), 4.98 (2H, s), 6.77 (1H, d, J=15.4 Hz), 6.91-6.93 (1H, m), 7.18 (2H, d, J=7.8 Hz), 7.28-7.30 (3H, m), 7.36 (1H, dd, J=8.8, 2.9 Hz), 7.46 (1H, d, J=2.2 Hz), 7.59 (1H, d, J=15.4 Hz), 7.78-7.79 (1H, m).

Reference Example 499 tert-Butyl (2S)-4-{(E)-3-[3-chloro-5-methyl-4-({5-[(4-methylbenzyl)oxy]pyridin-2-yl}oxy)phenyl]prop-2-enoyl}-2-methylpiperazine-1-carboxylate $^1$H-NMR (CDCl$_3$) δ: 1.16 (3H, d, J=6.6 Hz), 1.48 (9H, s), 2.20 (3H, s), 2.35 (3H, s), 2.78 (3H, m), 3.79-3.97 (2H, m), 4.35-4.62 (2H, m), 4.98 (2H, s), 6.72-6.83 (1H, m), 6.92 (1H, d, J=8.8 Hz), 7.18 (2H, d, J=7.8 Hz), 7.28-7.30 (3H, m), 7.36 (1H, dd, J=8.8, 2.9 Hz), 7.46 (1H, brs), 7.62 (1H, d, J=15.4 Hz), 7.79 (1H, d, J=2.9 Hz).

Reference Example 500 tert-Butyl 5-{(E)-3-[3-chloro-5-methyl-4-({5-[(4-methylbenzyl)oxy]pyridin-2-yl}oxy)phenyl]prop-2-enoyl}-1,2,5-oxadiazepane-2-carboxylate $^1$H-NMR (CDCl$_3$) δ: 1.49 (9H, s), 2.20 (3H, s), 2.36 (3H, s), 3.77-3.90 (6H, m), 4.06-4.10 (2H, m), 4.99 (2H, s), 6.72-6.80 (1H, m), 6.92 (1H, d, J=8.8 Hz), 7.19 (2H, d, J=7.8 Hz), 7.28-7.30 (3H, m), 7.36 (1H, dd, J=8.8, 2.9 Hz), 7.46-7.47 (1H, m), 7.61-7.66 (1H, m), 7.80 (1H, d, J=2.9 Hz).

Reference Example 501 tert-Butyl 4-{(E)-3-[4-({5-[(4-fluorobenzyl)oxy]pyridin-2-yl}oxy)-3,5-dimethylphenyl]prop-2-enoyl}piperazine-1-carboxylate $^1$H-NMR (CDCl$_3$) δ: 1.49 (9H, s), 2.13 (6H, s), 3.49 (4H, brs), 3.65-3.69 (4H, m), 4.99 (2H, s), 6.78 (1H, d, J=15.4 Hz), 6.82 (1H, dd, J=9.0, 0.5 Hz), 7.04-7.10 (2H, m), 7.26 (2H, brs), 7.32 (1H, dd, J=9.0, 3.2 Hz), 7.35-7.40 (2H, m), 7.64 (1H, d, J=15.4 Hz), 7.81 (1H, dd, J=3.2, 0.5 Hz).

Reference Example 502 tert-Butyl 4-[(E)-3-{4-[(5-hydroxypyridin-2-yl)oxy]-3,5-dimethylphenyl}prop-2-enoyl]piperazine-1-carboxylate $^1$H-NMR (CDCl$_3$) δ: 1.49 (9H, s), 2.12 (6H, s), 3.49 (4H, brs), 3.65-3.70 (4H, m), 6.74-6.79 (2H, m), 7.23-7.25 (3H, m), 7.62 (1H, d, J=15.4 Hz), 7.73 (1H, d, J=3.2 Hz).

Reference Example 503 tert-Butyl 5-{(E)-3-[4-({5-[(4-cyanobenzyl)oxy]pyridin-2-yl}oxy)-3,5-dimethylphenyl]prop-2-enoyl}-1,2,5-oxadiazepane-2-carboxylate $^1$H-NMR (CDCl$_3$) δ: 1.49 (9H, s), 2.12 (6H, s), 3.78-3.90 (6H, m), 4.06-4.11 (2H, m), 5.09 (2H, s), 6.75 (1H, t, J=14.9 Hz), 6.85 (1H, d, J=9.0 Hz), 7.25-7.27 (2H, m), 7.34 (1H, dd, J=9.0, 3.1 Hz), 7.52 (2H, d, J=8.3 Hz), 7.65-7.69 (3H, m), 7.79-7.80 (1H, m).

Reference Example 504

To a solution of (E)-3-[4-(chloromethyl)-3-methylphenyl]prop-2-en-1-yl 4-methylphenyl ether (0.180 g) and (E)-3-{4-[(5-hydroxypyridin-2-yl)oxy]-3,5-dimethylphenyl}-1-(piperazin-1-yl)prop-2-en-1-one (0.222 g) in DMF (2 mL) was added KHCO$_3$ (0.063 g) at room temperature under an Ar atmosphere. The mixture was heated at 100° C. for 3 hours, and then cooled to room temperature, and evaporated under reduced pressure. To the residue was added saturated aqueous NaHCO$_3$, and the mixture was extracted with AcOEt. The organic layer was washed with saturated aqueous NaCl, dried over anhydrous Na$_2$SO$_4$. The residue was purified by silica gel column chromatography (AcOEt) to afford (2E)-3-{4-[(5-hydroxypyridin-2-yl)oxy]-3,5-dimethylphenyl}-1-(4-{2-methyl-4-[(1E)-3-(4-methylphenoxy)prop-1-en-1-yl]benzyl}piperazin-1-yl)prop-2-en-1-one (0.286 g) as a colorless powder.

$^1$H-NMR (CDCl$_3$) δ: 2.11 (6H, s), 2.29 (3H, s), 2.37 (3H, s), 2.48 (4H, t, J=4.2 Hz), 3.47 (2H, s), 3.62 (2H, brs), 3.72 (2H, brs), 4.67 (2H, dd, J=5.8, 1.4 Hz), 5.46 (1H, brs), 6.40 (1H, dt, J=16.0, 5.8 Hz), 6.68 (1H, dt, J=16.0, 1.4 Hz), 6.75 (1H, d, J=8.8 Hz), 6.78 (1H, d, J=15.4 Hz), 6.86 (2H, dt, J=9.3, 2.6 Hz), 7.09 (2H, d, J=8.3 Hz), 7.20-7.25 (6H, m), 7.60 (1H, d, J=15.4 Hz), 7.73 (1H, d, J=3.2 Hz).

The following compound was produced in the same manner as in Reference Example 231 using appropriate starting materials.

Reference Example 505

(E)-3-{4-[(5-Hydroxypyridin-2-yl)oxy]-3,5-dimethylphenyl}-1-(piperazin-1-yl)prop-2-en-1-one $^1$H-NMR (CDCl$_3$) δ: 2.11 (6H, s), 2.92 (4H, t, J=5.1 Hz), 3.65-3.71 (4H, m), 6.72 (1H, d, J=8.8 Hz), 6.77 (1H, d, J=15.4 Hz), 7.21-7.24 (3H, m), 7.59 (1H, d, J=15.4 Hz), 7.71 (1H, dd, J=3.2, 0.5 Hz).

The following compound was produced in the same manner as in Reference Example 326 using appropriate starting materials.

Reference Example 506

(E)-3-[3-Chloro-4-({5-[(2-chlorobenzyl)oxy]pyridin-2-yl}oxy)-5-methylphenyl]-1-(piperazin-1-yl)prop-2-en-1-one $^1$H-NMR (CDCl$_3$) δ: 1.67 (1H, s), 2.20 (3H, s), 2.91 (4H, t, J=5.1 Hz), 3.62-3.70 (4H, m), 5.14 (2H, s), 6.81 (1H, d, J=15.4 Hz), 6.93-6.95 (1H, m), 7.25-7.31 (3H, m), 7.36-7.42 (2H, m), 7.46 (1H, d, J=2.2 Hz), 7.50-7.54 (1H, m), 7.58 (1H, d, J=15.4 Hz), 7.81-7.82 (1H, m).

Reference Example 507

(E)-3-[3-Chloro-5-methyl-4-({5-[(4-methylbenzyl)oxy]pyridin-2-yl}oxy)phenyl]-1-(piperazin-1-yl)prop-2-en-1-one $^1$H-NMR (CDCl$_3$) δ: 2.19 (3H, s), 2.36 (3H, s), 2.90-2.92 (4H, m), 3.63-3.73 (4H, m), 4.99 (2H, s), 6.81 (1H, d, J=15.4 Hz), 6.91 (1H, dd, J=8.8, 0.5 Hz), 7.19 (2H, d, J=7.8 Hz), 7.28-7.30 (3H, m), 7.36 (1H, dd, J=8.9, 2.9 Hz), 7.46 (1H, d, J=2.0 Hz), 7.58 (1H, d, J=15.4 Hz), 7.79 (1H, d, J=2.9 Hz).

Reference Example 508

(E)-3-[3-Chloro-5-methyl-4-({5-[(4-methylbenzyl)oxy]pyridin-2-yl}oxy)phenyl]-1-[(2S)-2-methylpiperazin-1-yl]prop-2-en-1-one $^1$H-NMR (CDCl$_3$) δ: 1.35 (3H, d, J=6.6 Hz), 1.59 (1H, brs), 2.19 (3H, s), 2.35 (3H, s), 2.70-4.98 (9H, m), 6.79 (1H, d, J=15.4 Hz), 6.90-6.92 (1H, m), 7.18 (2H, d, J=7.6 Hz), 7.28-7.30 (3H, m), 7.35 (1H, dd, J=9.0, 3.2 Hz), 7.46 (1H, d, J=2.2 Hz), 7.57 (1H, d, J=15.4 Hz), 7.79-7.80 (1H, m).

Reference Example 509

(E)-3-[3-Chloro-5-methyl-4-({5-[(4-methylbenzyl)oxy]pyridin-2-yl}oxy)phenyl]-1-[(2R)-2-methylpiperazin-1-yl]prop-2-en-1-one $^1$H-NMR (CDCl$_3$) δ: 1.35 (3H, d, J=6.4 Hz), 1.64 (1H, brs), 2.19 (3H, s), 2.35 (3H, s), 2.70-4.98 (9H, m), 6.79 (1H, d, J=15.4 Hz), 6.90-6.93 (1H, m), 7.18 (2H, d, J=7.8 Hz), 7.28-7.30 (3H, m), 7.35 (1H, dd, J=9.0, 3.2 Hz), 7.46 (1H, d, J=2.2 Hz), 7.58 (1H, d, J=15.4 Hz), 7.79-7.80 (1H, m).

Reference Example 510

(E)-3-[3-Chloro-5-methyl-4-({5-[(4-methylbenzyl)oxy]pyridin-2-yl}oxy)phenyl]-1-[(3S)-3-methylpiperazin-1-yl]prop-2-en-1-one $^1$H-NMR (CDCl$_3$) δ: 1.13 (3H, d, J=5.4 Hz), 1.64 (1H, brs), 2.19 (3H, s), 2.35-2.43 (3.5H, m), 2.77-2.87 (3H, m), 3.06-3.09 (1H, m), 3.17-3.24 (0.5H, m), 3.88-3.98 (1H, m), 4.57-4.61 (1H, m), 4.98 (2H, s), 6.80 (1H, d, J=15.4 Hz), 6.91 (1H, d, J=8.8 Hz), 7.19 (2H, d, J=7.8 Hz), 7.28-7.30 (3H, m), 7.35 (1H, dd, J=8.8, 2.9 Hz), 7.46 (1H, brs), 7.57 (1H, d, J=15.4 Hz), 7.79 (1H, d, J=2.9 Hz).

Reference Example 511

(E)-3-[3-Chloro-5-methyl-4-({5-[(4-methylbenzyl)oxy]pyridin-2-yl}oxy)phenyl]-1-(1,2,5-oxadiazepan-5-yl)prop-2-en-1-one $^1$H-NMR (CDCl$_3$) δ: 2.19 (3H, s), 2.36 (3H, s), 3.16-3.19 (2H, m), 3.76-3.97 (6H, m), 4.98 (2H, s), 6.74-6.82 (1H, m), 6.92 (1H, d, J=9.0 Hz), 7.19 (2H, d, J=8.1 Hz), 7.28-7.30 (3H, m), 7.36 (1H, dd, J=9.0, 2.9 Hz), 7.45-7.47 (1H, m), 7.60-7.66 (1H, m), 7.79 (1H, d, J=2.9 Hz).

Reference Example 512

(E)-3-[4-({5-[(4-Fluorobenzyl)oxy]pyridin-2-yl}oxy)-3,5-dimethylphenyl]-1-(piperazin-1-yl)prop-2-en-1-one $^1$H-NMR (CDCl$_3$) δ: 2.12 (6H, s), 2.91 (4H, t, J=5.1 Hz), 3.65-3.71 (4H, m), 4.99 (2H, s), 6.80 (1H, d, J=15.4 Hz), 6.81 (1H, dd, J=9.0, 0.6 Hz), 7.04-7.10 (2H, m), 7.24-7.27 (2H, m), 7.32 (1H, dd, J=9.0, 3.1 Hz), 7.35-7.40 (2H, m), 7.62 (1H, d, J=15.4 Hz), 7.81 (1H, dd, J=3.1, 0.6 Hz).

Reference Example 513

4-{[(6-{2,6-Dimethyl-4-[(E)-3-(1,2,5-oxadiazepan-5-yl)-3-oxoprop-1-en-1-yl]phenoxy}pyridin-3-yl)oxy]methyl}benzonitrile $^1$H-NMR (CDCl$_3$) δ: 2.12 (6H, s), 3.18 (2H, t, J=5.4 Hz), 3.77-3.97 (6H, m), 5.09 (2H, s), 5.84 (1H, brs), 6.78 (1H, t, J=15.4 Hz), 6.84 (1H, d, J=9.0 Hz), 7.25-7.26 (2H, m), 7.33 (1H, dd, J=9.0, 3.1 Hz), 7.52 (2H, d, J=8.5 Hz), 7.66-7.70 (3H, m), 7.80 (1H, d, J=2.7 Hz).

Example 1

To a solution of (E)-3-[4-({5-[(4-methoxybenzyl)oxy]pyridin-2-yl}oxy)-3,5-dimethylphenyl]prop-2-enoic acid (0.122 g) and 1-{4-[(E)-3-(4-methylphenoxy)prop-1-en-1-yl]benzyl}piperazine dihydrochloride (0.119 g) in DMF (2 mL) were added Et$_3$N (0.08 mL), WSC (0.070 g), and HOBT (0.055 g) at room temperature under an Ar atmosphere. The mixture was stirred at room temperature for 14 hours, and evaporated under reduced pressure. To the residue was added saturated aqueous NaHCO$_3$, and the mixture was extracted with AcOEt. The organic layer was washed with saturated aqueous NaCl, dried over anhydrous Na$_2$SO$_4$, and concentrated under reduced pressure. The residue was purified by silica gel column chromatography (AcOEt). The resulting powder was crystallized from EtOH (10 mL) to give (2E)-3-[4-({5-[(4-methoxybenzyl)oxy]pyridin-2-yl}oxy)-3,5-dimethylphenyl]-1-(4-{4-[(1E)-3-(4-methylphenoxy)prop-1-en-1-yl]benzyl}piperazin-1-yl)prop-2-en-1-one (0.195 g) as a colorless powder.

mp: 130-132° C.

$^1$H-NMR (CDCl$_3$) δ: 2.12 (6H, s), 2.29 (3H, s), 2.48 (4H, t, J=4.9 Hz), 3.52 (2H, s), 3.65 (2H, brs), 3.74 (2H, brs), 3.81 (3H, s), 4.68 (2H, dd, J=5.9, 1.5 Hz), 4.95 (2H, s), 6.41 (1H, dt, J=16.1, 5.9 Hz), 6.72 (1H, d, J=16.1 Hz), 6.78 (1H, d, J=15.4 Hz), 6.79 (1H, dd, J=8.8, 0.7 Hz), 6.86 (2H, dt, J=9.3, 2.6 Hz), 6.91 (2H, dt, J=9.3, 2.6 Hz), 7.09 (2H, dd, J=8.8, 0.7 Hz), 7.25-7.34 (7H, m), 7.38 (2H, d, J=8.3 Hz), 7.61 (1H, d, J=15.4 Hz), 7.82 (1H, d, J=2.7 Hz).

The following compounds were produced in the same manner as in Example 1 using appropriate starting materials.

Example 2

(2E)-3-[4-({5-[(4-Fluorobenzyl)oxy]pyridin-2-yl}oxy)-3,5-dimethylphenyl]-1-(4-{4-[(1E)-3-(4-methylphenoxy)prop-1-en-1-yl]benzyl}piperazin-1-yl)prop-2-en-1-one mp: 136-138° C.
¹H-NMR (CDCl₃) δ: 2.12 (6H, s), 2.29 (3H, s), 2.48 (4H, t, J=4.8 Hz), 3.52 (2H, s), 3.65-3.74 (4H, m), 4.68 (2H, dd, J=5.9, 1.5 Hz), 4.98 (2H, s), 6.41 (1H, dt, J=16.0, 5.9 Hz), 6.72 (1H, d, J=16.0 Hz), 6.78 (1H, d, J=15.4 Hz), 6.81 (1H, d, J=9.0 Hz), 6.86 (2H, dt, J=9.1, 2.5 Hz), 7.04-7.10 (4H, m), 7.25-7.26 (2H, m), 7.29 (2H, d, J=8.3 Hz), 7.32 (1H, dd, J=9.0, 3.2 Hz), 7.36-7.39 (4H, m), 7.61 (1H, d, J=15.4 Hz), 7.81 (1H, d, J=3.2 Hz).

Example 3

(2E)-3-[3-Chloro-5-methyl-4-({5-[(4-methylbenzyl)oxy]pyridin-2-yl}oxy)phenyl]-1-(4-{4-[(1E)-3-(4-methylphenoxy)prop-1-en-1-yl]benzyl}piperazin-1-yl)prop-2-en-1-one mp: 152° C.
¹H-NMR (CDCl₃) δ: 2.19 (3H, s), 2.29 (3H, s), 2.36 (3H, s), 2.48 (4H, t, J=5.1 Hz), 3.53 (2H, s), 3.64 (2H, brs), 3.74 (2H, brs), 4.68 (2H, dd, J=5.7, 1.3 Hz), 4.98 (2H, s), 6.41 (1H, dt, J=16.0, 5.7 Hz), 6.72 (1H, d, J=16.0 Hz), 6.79 (1H, d, J=15.4 Hz), 6.86 (2H, dt, J=9.2, 2.6 Hz), 6.91 (1H, d, J=8.8 Hz), 7.09 (2H, d, J=8.8 Hz), 7.19 (2H, d, J=8.1 Hz), 7.28-7.29 (5H, m), 7.33-7.39 (3H, m), 7.45 (1H, d, J=2.0 Hz), 7.57 (1H, d, J=15.4 Hz), 7.79 (1H, d, J=2.9 Hz).

Example 4

(2E)-3-[4-({5-[(4-Methoxybenzyl)oxy]pyridin-2-yl}oxy)-3,5-dimethylphenyl]-1-(4-{4-[(1E)-3-phenoxyprop-1-en-1-yl]benzyl}piperazin-1-yl)prop-2-en-1-one ¹H-NMR (CDCl₃) δ: 2.21 (6H, s), 2.48 (4H, t, J=4.8 Hz), 3.53 (2H, s), 3.65-3.74 (4H, m), 3.81 (3H, s), 4.70 (2H, dd, J=5.7, 1.3 Hz), 4.94 (2H, s), 6.42 (1H, dt, J=16.1, 5.7 Hz), 6.71-6.80 (3H, m), 6.89-6.92 (2H, m), 6.94-6.98 (3H, m), 7.25 (2H, s), 7.28-7.34 (7H, m), 7.38 (2H, d, J=8.3 Hz), 7.61 (1H, d, J=15.4 Hz), 7.82 (1H, d, J=2.9 Hz).

Example 5

4-{[(6-{2,6-Dimethyl-4-[(1E)-3-oxo-3-(4-{4-[(1E)-3-phenoxyprop-1-en-1-yl]benzyl}piperazin-1-yl)prop-1-en-1-yl]phenoxy}pyridin-3-yl)oxy]methyl}benzonitrile ¹H-NMR (CDCl₃) δ: 2.11 (6H, s), 2.48 (4H, t, J=4.8 Hz), 3.53 (2H, s), 3.65-3.74 (4H, m), 4.71 (2H, dd, J=5.7, 1.3 Hz), 5.09 (2H, s), 6.43 (1H, dt, J=16.1, 5.7 Hz), 6.71-6.85 (3H, m), 6.94-6.98 (3H, m), 7.25-7.34 (7H, m), 7.38 (2H, d, J=8.1 Hz), 7.51-7.53 (2H, m), 7.61 (1H, d, J=15.4 Hz), 7.67-7.70 (2H, m), 7.79-7.80 (1H, m).

Example 6

(2E)-3-[4-({5-[(4-Fluorobenzyl)oxy]pyridin-2-yl}oxy)-3,5-dimethylphenyl]-1-(4-{4-[(1E)-3-phenoxyprop-1-en-1-yl]benzyl}piperazin-1-yl)prop-2-en-1-one ¹H-NMR (CDCl₃) δ: 2.12 (6H, s), 2.48 (4H, t, J=4.8 Hz), 3.53 (2H, s), 3.65-3.74 (4H, m), 4.71 (2H, d, J=5.7 Hz), 4.98 (2H, s), 6.42 (1H, dt, J=16.1, 5.7 Hz), 6.71-6.82 (3H, m), 6.94-6.98 (3H, m), 7.04-7.10 (2H, m), 7.25-7.33 (7H, m), 7.36-7.39 (4H, m), 7.61 (1H, d, J=15.4 Hz), 7.81 (1H, d, J=3.2 Hz).

Example 7

4-{[(6-{2-Chloro-4-[(1E)-3-(4-{4-[(1E)-3-(4-methoxyphenoxy)prop-1-en-1-yl]benzyl}piperazin-1-yl)-3-oxoprop-1-en-1-yl]-6-methylphenoxy}pyridin-3-yl)oxy]methyl}benzonitrile ¹H-NMR (CDCl₃) δ: 2.18 (3H, s), 2.47 (4H, t, J=4.9 Hz), 3.51 (2H, s), 3.63-3.76 (7H, m), 4.64 (2H, dd, J=5.8, 1.5 Hz), 5.08 (2H, s), 6.39 (1H, dt, J=16.0, 5.8 Hz), 6.70 (1H, d, J=16.0 Hz), 6.76-6.85 (3H, m), 6.87-6.90 (2H, m), 6.94 (1H, dd, J=8.8, 0.5 Hz), 7.26-7.28 (3H, m), 7.34-7.37 (3H, m), 7.44 (1H, d, J=2.2 Hz), 7.50-7.57 (3H, m), 7.65-7.68 (2H, m), 7.747-7.754 (1H, m).

Example 8

4-{[(2E)-3-{4-[(4-{(2E)-3-[3-Chloro-4-({5-[(4-cyanobenzyl)oxy]pyridin-2-yl}oxy)-5-methylphenyl]prop-2-enoyl}piperazin-1-yl)methyl]phenyl}prop-2-en-1-yl]oxy}benzonitrile ¹H-NMR (CDCl₃) δ: 2.19 (3H, s), 2.48 (4H, t, J=4.9 Hz), 3.54 (2H, s), 3.65-3.74 (4H, m), 4.76 (2H, dd, J=5.8, 1.5 Hz), 5.09 (2H, s), 6.38 (1H, dt, J=15.9, 5.8 Hz), 6.74 (1H, d, J=15.9 Hz), 6.80 (1H, d, J=15.4 Hz), 6.95-7.02 (3H, m), 7.29-7.31 (3H, m), 7.35-7.39 (3H, m), 7.45 (1H, d, J=2.0 Hz), 7.51-7.62 (5H, m), 7.67-7.69 (2H, m), 7.76 (1H, d, J=2.9 Hz).

Example 9

(2E)-3-[3-Chloro-4-({5-[(2-chlorobenzyl)oxy]pyridin-2-yl}oxy)-5-methylphenyl]-1-(4-{4-[(1E)-3-(4-fluorophenoxy)prop-1-en-1-yl]benzyl}piperazin-1-yl)prop-2-en-1-one mp: 112.7-113.3° C.

Example 10

4-({[6-(2-Chloro-6-methyl-4-{(1E)-3-oxo-3-[4-(4-{(1E)-3-[4-(propan-2-yl)phenoxy]prop-1-en-1-yl}benzyl)piperazin-1-yl]prop-1-en-1-yl}phenoxy)pyridin-3-yl]oxy}methyl)benzonitrile ¹H-NMR (CDCl₃) δ: 1.23 (6H, d, J=6.8 Hz), 2.19 (3H, s), 2.48 (4H, t, J=4.8 Hz), 2.81-2.92 (1H, m), 3.53 (2H, s), 3.64-3.75 (4H, m), 4.68 (2H, dd, J=5.8, 1.5 Hz), 5.09 (2H, s), 6.42 (1H, dt, J=16.0, 5.8 Hz), 6.72 (1H, d, J=16.0 Hz), 6.80

(1H, d, J=15.4 Hz), 6.88-6.91 (2H, m), 6.95 (1H, d, J=8.8 Hz), 7.13-7.17 (2H, m), 7.28-7.30 (3H, m), 7.35-7.39 (3H, m), 7.45 (1H, d, J=2.0 Hz), 7.52 (2H, d, J=8.5 Hz), 7.57 (1H, d, J=15.4 Hz), 7.67-7.70 (2H, m), 7.77 (1H, d, J=2.9 Hz).

Example 11

4-({[6-(2-Chloro-4-{(1E)-3-[4-(4-{(1E)-3-[(6-chloropyridin-3-yl)oxy]prop-1-en-1-yl}benzyl)piperazin-1-yl]-3-oxoprop-1-en-1-yl}-6-methylphenoxy)pyridin-3-yl]oxy}methyl)benzonitrile $^1$H-NMR (CDCl$_3$) δ: 2.19 (3H, s), 2.48 (4H, t, J=5.0 Hz), 3.54 (2H, s), 3.65-3.75 (4H, m), 4.74 (2H, dd, J=5.9, 1.2 Hz), 5.09 (2H, s), 6.36 (1H, dt, J=15.9, 5.9 Hz), 6.73 (1H, d, J=15.9 Hz), 6.80 (1H, d, J=15.5 Hz), 6.96 (1H, d, J=8.8 Hz), 7.238-7.243 (2H, m), 7.29-7.31 (3H, m), 7.36-7.39 (3H, m), 7.45 (1H, d, J=2.0 Hz), 7.51-7.53 (2H, m), 7.57 (1H, d, J=15.5 Hz), 7.67-7.69 (2H, m), 7.76 (1H, d, J=2.9 Hz), 8.12 (1H, t, J=1.8 Hz).

Example 12

4-({[6-(2-Chloro-6-methyl-4-{(1E)-3-[4-(4-{(1E)-3-[(6-methylpyridin-3-yl)oxy]prop-1-en-1-yl}benzyl)piperazin-1-yl]-3-oxoprop-1-en-1-yl}phenoxy)pyridin-3-yl]oxy}methyl)benzonitrile $^1$H-NMR (CDCl$_3$) δ: 2.19 (3H, s), 2.47-2.49 (7H, m), 3.53 (2H, s), 3.65-3.74 (4H, m), 4.72 (2H, dd, J=5.9, 1.2 Hz), 5.09 (2H, s), 6.39 (1H, dt, J=15.9, 5.9 Hz), 6.73 (1H, d, J=15.9 Hz), 6.80 (1H, d, J=15.4 Hz), 6.95 (1H, d, J=9.0 Hz), 7.07 (1H, d, J=8.5 Hz), 7.17 (1H, dd, J=8.5, 2.9 Hz), 7.29 (3H, d, J=7.6 Hz), 7.35-7.39 (3H, m), 7.45 (1H, d, J=2.0 Hz), 7.51-7.59 (3H, m), 7.68 (2H, d, J=8.1 Hz), 7.76 (1H, d, J=3.2 Hz), 8.25 (1H, d, J=2.9 Hz).

Example 13

4-({[6-(4-{(1E)-3-[4-(4-{(1E)-3-[(5-Bromopyridin-2-yl)oxy]prop-1-en-1-yl}benzyl)piperazin-1-yl]-3-oxoprop-1-en-1-yl}-2-chloro-6-methylphenoxy)pyridin-3-yl]oxy}methyl)benzonitrile $^1$H-NMR (CDCl$_3$) δ: 2.19 (3H, s), 2.48 (4H, t, J=5.0 Hz), 3.53 (2H, s), 3.64-3.75 (4H, m), 4.97 (2H, dd, J=6.1, 1.2 Hz), 5.10 (2H, s), 6.44 (1H, dt, J=15.9, 6.1 Hz), 6.71-6.73 (2H, m), 6.80 (1H, d, J=15.4 Hz), 6.96 (1H, d, J=8.8 Hz), 7.26-7.30 (3H, m), 7.36-7.39 (3H, m), 7.46 (1H, d, J=2.0 Hz), 7.52 (2H, d, J=8.1 Hz), 7.57 (1H, d, J=15.4 Hz), 7.65-7.70 (3H, m), 7.77 (1H, d, J=2.9 Hz), 8.21 (1H, d, J=2.4 Hz).

Example 14

4-({[6-(2-Chloro-6-methyl-4-{(1E)-3-[4-(4-{(1E)-3-[(5-methylpyridin-2-yl)oxy]prop-1-en-1-yl}benzyl)piperazin-1-yl]-3-oxoprop-1-en-1-yl}phenoxy)pyridin-3-yl]oxy}methyl)benzonitrile $^1$H-NMR (CDCl$_3$) δ: 2.19 (3H, s), 2.25 (3H, s), 2.48 (4H, t, J=4.6 Hz), 3.52 (2H, s), 3.64-3.74 (4H, m), 4.97 (2H, dd, J=6.1, 1.2 Hz), 5.09 (2H, s), 6.46 (1H, dt, J=15.9, 6.1 Hz), 6.69-6.74 (2H, m), 6.80 (1H, d, J=15.4 Hz), 6.95 (1H, d, J=9.0 Hz), 7.26-7.29 (3H, m), 7.35-7.42 (4H, m), 7.45 (1H, d, J=2.2 Hz), 7.51-7.59 (3H, m), 7.68 (2H, dt, J=8.2, 1.8 Hz), 7.77 (1H, d, J=2.9 Hz), 7.96-7.97 (1H, m).

Example 15

(E)-3-[3-Chloro-5-methyl-4-({5-[(4-methylbenzyl)oxy]pyridin-2-yl}oxy)phenyl]-1-(4-{4-[(4-chlorophenoxy)methyl]benzyl}piperazin-1-yl)prop-2-en-1-one mp: 168.4-169.1° C.
$^1$H-NMR (DMSO-d$_6$) δ: 2.09 (3H, s), 2.30 (3H, s), 2.36-2.42 (4H, m), 3.52 (2H, s), 3.57 (2H, brs), 3.73 (2H, brs), 5.05 (2H, s), 5.08 (2H, s), 7.02-7.09 (3H, m), 7.18-7.46 (12H, m), 7.56-7.62 (2H, m), 7.79-7.83 (2H, m).

Example 16

(E)-3-[3-Chloro-4-({5-[(2-chlorobenzyl)oxy]pyridin-2-yl}oxy)-5-methylphenyl]-1-(4-{4-[(4-chlorophenoxy)methyl]benzyl}piperazin-1-yl)prop-2-en-1-one mp: 167.1-167.6° C.
$^1$H-NMR (DMSO-d$_6$) δ: 2.10 (3H, s), 2.39 (4H, brs), 3.52 (2H, s), 3.56 (2H, brs), 3.72 (2H, brs), 5.08 (2H, s), 5.16 (2H, s), 7.03 (2H, d, J=8.9 Hz), 7.11 (1H, d, J=8.9 Hz), 7.26-7.53 (11H, m), 7.60-7.66 (3H, m), 7.84-7.85 (2H, m).

Example 17

(E)-3-[3-Chloro-4-({5-[(2-chlorobenzyl)oxy]pyridin-2-yl}oxy)-5-methylphenyl]-1-[4-(4-{[4-(propan-2-yl)phenoxy]methyl}benzyl)piperazin-1-yl]prop-2-en-1-one $^1$H-NMR (CDCl$_3$) δ: 1.22 (6H, d, J=6.8 Hz), 2.19 (3H, s), 2.49 (4H, t, J=4.9 Hz), 2.86 (1H, septet, J=6.8 Hz), 3.54 (2H, s), 3.64 (2H, brs), 3.74 (2H, brs), 5.03 (2H, s), 5.14 (2H, s), 6.80 (1H, d, J=15.6 Hz), 6.91-6.95 (3H, m), 7.15 (2H, d, J=8.8 Hz), 7.26-7.41 (9H, m), 7.45-7.47 (1H, m), 7.50-7.54 (1H, m), 7.57 (1H, d, J=15.6 Hz), 7.81 (1H, d, J=2.9 Hz).

Example 18

(E)-3-[3-Chloro-5-methyl-4-({5-[(4-methylbenzyl)oxy]pyridin-2-yl}oxy)phenyl]-1-[4-(4-{[4-(propan-2-yl)phenoxy]methyl}benzyl)piperazin-1-yl]prop-2-en-1-one $^1$H-NMR (CDCl$_3$) δ: 1.22 (6H, d, J=6.8 Hz), 2.19 (3H, s), 2.35 (3H, s), 2.49 (4H, t, J=4.9 Hz), 2.86 (1H, septet, J=6.8 Hz), 3.54 (2H, s), 3.64 (2H, brs), 3.74 (2H, brs), 4.98 (2H, s), 5.03 (2H, s), 6.80 (1H, d, J=15.6 Hz), 6.90-6.93 (3H, m), 7.13-7.20 (4H, m), 7.28-7.30 (3H, m), 7.33-7.37 (3H, m), 7.40 (2H, d, J=7.8 Hz), 7.45 (1H, d, J=2.0 Hz), 7.57 (1H, d, J=15.6 Hz), 7.79 (1H, d, J=3.4 Hz).

Example 19

(E)-3-[3-Chloro-4-({5-[(2-chlorobenzyl)oxy]pyridin-2-yl}oxy)-5-methylphenyl]-1-(4-{4-[(4-fluorophenoxy)methyl]benzyl}piperazin-1-yl)prop-2-en-1-one mp: 152.3-153.9° C.
$^1$H-NMR (DMSO-d$_6$) δ: 2.10 (3H, s), 2.35-2.43 (4H, m), 3.52 (2H, s), 3.56 (2H, brs), 3.73 (2H, brs), 5.06 (2H, s), 5.16 (2H, s), 6.99-7.04 (2H, m), 7.10-7.15 (3H, m), 7.27-7.45 (8H, m), 7.49-7.55 (1H, m), 7.59-7.65 (3H, m), 7.83-7.85 (2H, m).

Example 20

(E)-3-[3-Chloro-5-methyl-4-({5-[(4-methylbenzyl)oxy]pyridin-2-yl}oxy)phenyl]-1-(4-{4-[(4-fluorophenoxy)methyl]benzyl}piperazin-1-yl)prop-2-en-1-one mp: 153.2-153.9° C.
$^1$H-NMR (DMSO-d$_6$) δ: 2.09 (3H, s), 2.30 (3H, s), 2.35-2.43 (4H, m), 3.52 (2H, s), 3.56 (2H, brs), 3.72 (2H, brs), 5.05 (2H, s), 5.06 (2H, s), 7.00-7.14 (5H, m), 7.19 (2H, d, J=8.1 Hz), 7.27-7.35 (5H, m), 7.40-7.45 (3H, m), 7.58 (1H, dd, J=8.6, 3.2 Hz), 7.62 (1H, d, J=1.7 Hz), 7.79 (1H, d, J=3.2 Hz), 7.82 (1H, d, J=1.7 Hz).

Example 21

(E)-3-[4-({5-[(2-Chlorobenzyl)oxy]pyridin-2-yl}oxy)-2-methylphenyl]-1-[4-(4-[4-(propan-2-yloxy)phenoxy]methyl)benzyl)piperazin-1-yl]prop-2-en-1-one $^1$H-NMR (CDCl$_3$) δ: 1.31 (6H, d, J=6.1 Hz), 2.41 (3H, s), 2.49 (4H, brs), 3.54 (2H, s), 3.64 (2H, brs), 3.75 (2H, brs), 4.42 (1H, septet, J=6.1 Hz), 5.00 (2H, s), 5.17 (2H, s), 6.71 (1H, d, J=15.4 Hz), 6.81-6.86 (2H, m), 6.88-6.93 (5H, m), 7.26-7.43 (8H, m), 7.51-7.54 (2H, m), 7.90 (1H, d, J=15.4 Hz), 7.95 (1H, d, J=3.2 Hz).

Example 22

(E)-3-[4-({5-[(2-Chlorobenzyl)oxy]pyridin-2-yl}oxy)-3-methoxyphenyl]-1-[4-(4-{[4-(propan-2-yloxy)phenoxy]methyl}benzyl)piperazin-1-yl]prop-2-en-1-one $^1$H-NMR (CDCl$_3$) δ: 1.31 (6H, d, J=6.1 Hz), 2.51-2.53 (4H, m), 3.57 (2H, s), 3.65-3.67 (2H, m), 3.75-3.77 (2H, m), 3.81 (3H, s), 4.40-4.45 (1H, m), 5.00 (2H, s), 5.15 (2H, s), 6.76-6.93 (6H, m), 7.05-7.19 (3H, m), 7.26-7.40 (8H, m), 7.50-7.54 (1H, m), 7.64 (1H, d, J=15.4 Hz), 7.87 (1H, d, J=2.9 Hz).

Example 23

(E)-3-[3-Chloro-4-({5-[(3-chloro-2-fluorobenzyl)oxy]pyridin-2-yl}oxy)-5-methylphenyl]-1-[4-(4-{[4-(propan-2-yloxy)phenoxy]methyl}benzyl)piperazin-1-yl]prop-2-en-1-one $^1$H-NMR (CDCl$_3$) δ: 1.31 (6H, d, J=6.1 Hz), 2.19 (3H, s), 2.49 (4H, t, J=5.0 Hz), 3.55 (2H, s), 3.65 (2H, s), 3.75 (2H, s), 4.42 (1H, septet, J=6.1 Hz), 5.00 (2H, s), 5.11 (2H, s), 6.79-6.85 (3H, m), 6.88-6.92 (2H, m), 6.95 (1H, d, J=8.8 Hz), 7.12 (1H, td, J=7.8, 1.0 Hz), 7.29 (1H, d, J=2.0 Hz), 7.33-7.41 (7H, m), 7.46 (1H, d, J=2.0 Hz), 7.57 (1H, d, J=15.4 Hz), 7.80 (1H, d, J=2.9 Hz).

Example 24

(E)-1-(4-{4-[(1,3-Benzodioxol-5-yloxy)methyl]benzyl}piperazin-1-yl)-3-[3-chloro-5-methyl-4-({5-[(4-methylbenzyl)oxy]pyridin-2-yl}oxy)phenyl]prop-2-en-1-one mp: 149.0-151.2° C.
$^1$H-NMR (DMSO-d$_6$) δ: 2.09 (3H, s), 2.30 (3H, s), 2.35-3.42 (4H, m), 3.52 (2H, s), 3.56 (2H, brs), 3.72 (2H, brs), 5.00 (2H, s), 5.05 (2H, s), 5.95 (2H, s), 6.44 (1H, dd, J=8.3, 2.7 Hz), 6.70 (1H, d, J=2.7 Hz), 6.81 (1H, d, J=8.3 Hz), 7.07 (1H, d, J=9.0 Hz), 7.19 (2H, d, J=8.1 Hz), 7.27-7.34 (5H, m), 7.38-7.45 (3H, m), 7.58 (1H, dd, J=9.0, 3.2 Hz), 7.62 (1H, d, J=1.7 Hz), 7.79 (1H, d, J=3.2 Hz), 7.82 (1H, d, J=1.7 Hz).

Example 25

(E)-3-[4-({5-[(2-Chlorobenzyl)oxy]pyridin-2-yl}oxy)phenyl]-1-[4-(4-{[4-(propan-2-yl)phenoxy]methyl}benzyl)piperazin-1-yl]prop-2-en-1-one $^1$H-NMR (CDCl$_3$) δ: 1.23 (6H, d, J=7.1 Hz), 2.49 (4H, t, J=4.8 Hz), 2.83-2.90 (1H, m), 3.54 (2H, s), 3.65-3.75 (4H, m), 5.03 (2H, s), 5.18 (2H, s), 6.79 (1H, d, J=15.4 Hz), 6.91-6.94 (3H, m), 7.09 (2H, d, J=8.5 Hz), 7.15 (2H, d, J=8.5 Hz), 7.28-7.42 (8H, m), 7.51-7.54 (3H, m), 7.65 (1H, d, J=15.4 Hz), 7.95 (1H, d, J=3.2 Hz).

Example 26

(E)-3-[4-({5-[(2-Chlorobenzyl)oxy]pyridin-2-yl}oxy)-3-fluorophenyl]-1-[4-(4-{[4-(propan-2-yloxy)phenoxy]methyl}benzyl)piperazin-1-yl]prop-2-en-1-one $^1$H-NMR (CDCl$_3$) δ: 1.31 (6H, d, J=6.1 Hz), 2.49 (4H, t, J=4.8 Hz), 3.55 (2H, s), 3.64 (2H, s), 3.75 (2H, s), 4.42 (1H, septet, J=6.1 Hz), 5.00 (2H, s), 5.16 (2H, s), 6.78-6.93 (5H, m), 6.97 (1H, d, J=8.8 Hz), 7.19 (1H, t, J=8.1 Hz), 7.26-7.41 (10H, m), 7.52 (1H, t, J=4.6 Hz), 7.61 (1H, d, J=15.1 Hz), 7.86 (1H, d, J=2.9 Hz).

Example 27

(E)-3-[2-Methyl-4-({5-[(4-methylbenzyl)oxy]pyridin-2-yl}oxy)phenyl]-1-[4-(4-{[4-(propan-2-yl)phenoxy]methyl}benzyl)piperazin-1-yl]prop-2-en-1-one $^1$H-NMR (CDCl$_3$) δ: 1.22 (6H, d, J=6.8 Hz), 2.36 (3H, s), 2.40 (3H, s), 2.48 (4H, brs), 2.86 (1H, septet, J=6.8 Hz), 3.54 (2H, s), 3.63-3.75 (4H, m), 5.02 (4H, s), 6.71 (1H, d, J=15.1 Hz), 6.86-6.93 (5H, m), 7.13-7.17 (2H, m), 7.19 (2H, d, J=7.8 Hz), 7.29-7.35 (5H, m), 7.40 (2H, d, J=8.3 Hz), 7.51-7.53 (1H, m), 7.88-7.93 (2H, m).

Example 28

(E)-3-[3-Chloro-4-({5-[(2-chlorobenzyl)oxy]pyridin-2-yl}oxy)-5-methylphenyl]-1-[4-(4-{[(4-fluorobenzyl)oxy]methyl}benzyl)piperazin-1-yl]prop-2-en-1-one $^1$H-NMR (CDCl$_3$) δ: 2.19 (3H, s), 2.48 (4H, t, J=4.9 Hz), 3.54 (2H, s), 3.64-3.74 (4H, m), 4.53 (2H, s), 4.54 (2H, s), 5.14 (2H, s), 6.80 (1H, d, J=15.4 Hz), 6.94 (1H, d, J=8.8 Hz), 7.02-7.06 (2H, m), 7.26-7.41 (11H, m), 7.46 (1H, brs), 7.51-7.53 (1H, m), 7.57 (1H, d, J=15.4 Hz), 7.81 (1H, d, J=2.9 Hz).

Example 29

(E)-3-[3-Chloro-5-methyl-4-({5-[(4-methylbenzyl)oxy]pyridin-2-yl}oxy)phenyl]-1-[4-(4-{[(4-fluorobenzyl)oxy]methyl}benzyl)piperazin-1-yl]prop-2-en-1-one $^1$H-NMR (CDCl$_3$) δ: 2.18 (3H, s), 2.35 (3H, s), 2.48 (4H, t, J=4.9 Hz), 3.54 (2H, s), 3.64-3.74 (4H, m), 4.53 (2H, s), 4.54

(2H, s), 4.98 (2H, s), 6.79 (1H, d, J=15.4 Hz), 6.91 (1H, d, J=8.8 Hz), 7.01-7.07 (2H, m), 7.19 (2H, d, J=7.8 Hz), 7.28-7.37 (10H, m), 7.45 (1H, d, J=2.0 Hz), 7.57 (1H, d, J=15.4 Hz), 7.79 (1H, d, J=3.2 Hz).

Example 30

(E)-3-[3-Chloro-4-({5-[(2-chlorobenzyl)oxy]pyridin-2-yl}oxy)-5-methylphenyl]-1-{4-[4-({[4-(propan-2-yl)benzyl]oxy}methyl)benzyl]piperazin-1-yl}prop-2-en-1-one $^1$H-NMR (CDCl$_3$) δ: 1.24 (6H, d, J=7.1 Hz), 2.19 (3H, s), 2.48 (4H, t, J=4.9 Hz), 2.90 (1H, septet, J=7.1 Hz), 3.53 (2H, s), 3.64-3.74 (4H, m), 4.53 (2H, s), 4.54 (2H, s), 5.14 (2H, s), 6.79 (1H, d, J=15.4 Hz), 6.94 (1H, d, J=8.8 Hz), 7.21 (2H, d, J=8.1 Hz), 7.27-7.41 (11H, m), 7.45 (1H, d, J=2.0 Hz), 7.50-7.53 (1H, m), 7.56 (1H, d, J=15.4 Hz), 7.81 (1H, d, J=2.9 Hz).

Example 31

(E)-3-[3-Chloro-5-methyl-4-({5-[(4-methylbenzyl)oxy]pyridin-2-yl}oxy)phenyl]-1-{4-[4-({[4-(propan-2-yl)benzyl]oxy}methyl)benzyl]piperazin-1-yl}prop-2-en-1-one $^1$H-NMR (CDCl$_3$) δ: 1.24 (6H, d, J=6.8 Hz), 2.18 (3H, s), 2.35 (3H, s), 2.48 (4H, t, J=4.9 Hz), 2.90 (1H, septet, J=6.8 Hz), 3.53 (2H, s), 3.63-3.74 (4H, m), 4.53 (2H, s), 4.54 (2H, s), 4.98 (2H, s), 6.79 (1H, d, J=15.4 Hz), 6.91 (1H, d, J=8.8 Hz), 7.17-7.36 (14H, m), 7.45 (1H, d, J=2.0 Hz), 7.56 (1H, d, J=15.4 Hz), 7.79 (1H, d, J=3.2 Hz).

Example 32

4-{[(6-{2-Chloro-4-[(E)-3-(4-{2-fluoro-4-[(4-fluorophenoxy)methyl]benzyl}piperazin-1-yl)-3-oxoprop-1-en-1-yl]-6-methylphenoxy}pyridin-3-yl)oxy]methyl}benzonitrile $^1$H-NMR (CDCl$_3$) δ: 2.19 (3H, s), 2.54-2.58 (4H, m), 3.64-3.68 (4H, m), 3.74-3.77 (2H, m), 5.01 (2H, s), 5.09 (2H, s), 6.79 (1H, d, J=15.4 Hz), 6.88-7.01 (5H, m), 7.12-7.18 (2H, m), 7.28 (1H, s), 7.35-7.40 (2H, m), 7.45 (1H, s), 7.51-7.58 (3H, m), 7.68 (2H, d, J=8.1 Hz), 7.77 (1H, d, J=2.9 Hz).

Example 33

(E)-3-[3-Chloro-5-methyl-4-({5-[(4-methylbenzyl)oxy]pyridin-2-yl}oxy)phenyl]-1-(4-{2-fluoro-4-[(4-fluorophenoxy)methyl]benzyl}piperazin-1-yl)prop-2-en-1-one $^1$H-NMR (CDCl$_3$) δ: 2.18 (3H, s), 2.35 (3H, s), 2.54-2.58 (4H, m), 3.65-3.68 (4H, m), 3.74-3.77 (2H, m), 4.98 (2H, s), 5.00 (2H, s), 6.78 (1H, d, J=15.1 Hz), 6.88-6.92 (3H, m), 6.96-7.00 (2H, m), 7.12-7.20 (4H, m), 7.26-7.30 (3H, m), 7.34-7.40 (2H, m), 7.44 (1H, d, J=1.2 Hz), 7.55 (1H, d, J=15.4 Hz), 7.79 (1H, d, J=2.9 Hz).

Example 34

4-{[(6-{2-Chloro-4-[(E)-3-(4-{3-fluoro-4-[(4-propylphenoxy)methyl]benzyl}-yl)-3-oxoprop-1-en-1-yl]-6-methylphenoxy}pyridin-3-yl)oxy]methyl}benzonitrile $^1$H-NMR (CDCl$_3$) δ: 0.93 (3H, t, J=7.3 Hz), 1.56-1.66 (2H, m), 2.19 (3H, s), 2.48-2.49 (4H, m), 2.52-2.54 (2H, m), 3.53 (2H, s), 3.64-3.66 (2H, m), 3.74-3.77 (2H, m), 5.09 (4H, s), 6.80 (1H, d, J=15.4 Hz), 6.91 (2H, d, J=8.5 Hz), 6.95 (1H, d, J=8.8 Hz), 7.08-7.13 (4H, m), 7.29 (1H, s), 7.37 (1H, dd, J=9.0, 2.9 Hz), 7.44-7.48 (2H, m), 7.52 (2H, d, J=8.1 Hz), 7.57 (1H, d, J=15.4 Hz), 7.68 (2H, d, J=8.3 Hz), 7.77 (1H, d, J=2.9 Hz).

Example 35

(E)-3-[3-Chloro-5-methyl-4-({5-[(4-methylbenzyl)oxy]pyridin-2-yl}oxy)phenyl]-1-(4-{3-fluoro-4-[(4-fluorophenoxy)methyl]benzyl}piperazin-1-yl)prop-2-en-1-one mp: 133.0-133.4° C.

Example 36

(E)-3-[3-Chloro-4-({5-[(2-chlorobenzyl)oxy]pyridin-2-yl}oxy)-5-methylphenyl]-1-(4-{3-fluoro-4-[(4-fluorophenoxy)methyl]benzyl}piperazin-1-yl)prop-2-en-1-one $^1$H-NMR (CDCl$_3$) δ: 2.20 (3H, s), 2.48-2.49 (4H, m), 3.53 (2H, s), 3.64-3.67 (2H, m), 3.74-3.77 (2H, m), 5.07 (2H, s), 5.14 (2H, s), 6.80 (1H, d, J=15.4 Hz), 6.90-7.01 (5H, m), 7.12 (2H, d, J=9.3 Hz), 7.26-7.31 (3H, m), 7.38-7.46 (4H, m), 7.50-7.53 (1H, m), 7.58 (1H, d, J=15.4 Hz), 7.81 (1H, d, J=2.9 Hz).

Example 37

(E)-3-[3-Chloro-5-methyl-4-({5-[(4-methylbenzyl)oxy]pyridin-2-yl}oxy)phenyl]-1-(4-{3-fluoro-4-[(4-propylphenoxy)methyl]benzyl}piperazin-1-yl)prop-2-en-1-one $^1$H-NMR (CDCl$_3$) δ: 0.93 (3H, t, J=7.3 Hz), 1.56-1.64 (2H, m), 2.19 (3H, s), 2.35 (3H, s), 2.48-2.49 (4H, m), 2.53 (2H, t, J=7.7 Hz), 3.53 (2H, s), 3.64-3.66 (2H, m), 3.74-3.76 (2H, m), 4.98 (2H, s), 5.09 (2H, s), 6.80 (1H, d, J=15.4 Hz), 6.91 (3H, d, J=8.1 Hz), 7.10 (2H, d, J=5.9 Hz), 7.12 (2H, d, J=6.1 Hz), 7.18 (2H, d, J=7.8 Hz), 7.27-7.30 (3H, m), 7.35 (1H, dd, J=8.9, 3.1 Hz), 7.43-7.48 (2H, m), 7.57 (1H, d, J=15.4 Hz), 7.79 (1H, d, J=2.9 Hz).

Example 38

4-{[(6-{2-Chloro-4-[(E)-3-(4-{3-fluoro-4-[(4-fluorophenoxy)methyl]benzyl}piperazin-1-yl)-3-oxoprop-1-en-1-yl]-6-methylphenoxy}pyridin-3-yl)oxy]methyl}benzonitrile $^1$H-NMR (CDCl$_3$) δ: 2.19 (3H, s), 2.48-2.50 (4H, m), 3.54 (2H, s), 3.64-3.67 (2H, m), 3.74-3.77 (2H, m), 5.08 (2H, s), 5.09 (2H, s), 6.80 (1H, d, J=15.4 Hz), 6.90-7.01 (5H, m), 7.12 (2H, d, J=9.3 Hz), 7.29 (1H, s), 7.37 (1H, dd, J=8.9, 3.1 Hz), 7.42-7.47 (2H, m), 7.52 (2H, d, J=8.1 Hz), 7.57 (1H, d, J=15.4 Hz), 7.68 (2H, d, J=8.1 Hz), 7.76 (1H, d, J=2.9 Hz).

Example 39

(E)-3-[3-Chloro-4-({5-[(2-chlorobenzyl)oxy]pyridin-2-yl}oxy)-5-methylphenyl]-1-[4-(3-fluoro-4-{[4-(propan-2-yloxy)phenoxy]methyl}benzyl)piperazin-1-yl]prop-2-en-1-one $^1$H-NMR (CDCl$_3$) δ: 1.31 (6H, d, J=5.9 Hz), 2.20 (3H, s), 2.48-2.49 (4H, m), 3.53 (2H, s), 3.64-3.67 (2H, m), 3.74-3.77

(2H, m), 4.39-4.46 (1H, m), 5.06 (2H, s), 5.14 (2H, s), 6.78-6.85 (3H, m), 6.91 (2H, d, J=9.0 Hz), 6.94 (1H, d, J=9.0 Hz), 7.11 (2H, d, J=9.0 Hz), 7.27-7.31 (3H, m), 7.38-7.41 (2H, m), 7.43-7.48 (2H, m), 7.50-7.53 (1H, m), 7.58 (1H, d, J=15.4 Hz), 7.82 (1H, d, J=2.7 Hz).

Example 40

4-({[6-(2-Chloro-4-{(E)-3-[4-(3-fluoro-4-{[4-(propan-2-yloxy)phenoxy]methyl}benzyl)piperazin-1-yl]-3-oxoprop-1-en-1-yl}-6-methylphenoxy)pyridin-3-yl]oxy}methyl)benzonitrile $^1$H-NMR (CDCl$_3$) δ: 1.31 (6H, d, J=6.1 Hz), 2.19 (3H, s), 2.48-2.49 (4H, m), 3.53 (2H, s), 3.64-3.66 (2H, m), 3.74-3.76 (2H, m), 4.39-4.45 (1H, m), 5.06 (2H, s), 5.09 (2H, s), 6.78-6.86 (3H, m), 6.91 (2H, d, J=9.3 Hz), 6.95 (1H, d, J=9.0 Hz), 7.10 (1H, s), 7.12 (1H, s), 7.29 (1H, s), 7.37 (1H, dd, J=8.9, 3.1 Hz), 7.43-7.47 (2H, m), 7.52 (2H, d, J=8.3 Hz), 7.57 (1H, d, J=15.1 Hz), 7.68 (2H, d, J=8.3 Hz), 7.76 (1H, d, J=2.9 Hz).

Example 41

(E)-3-[5-Chloro-4-({5-[(2-chlorobenzyl)oxy]pyridin-2-yl}oxy)-2-methylphenyl]-1-[4-(4-{[4-(propan-2-yl)phenoxy]methyl}benzyl)piperazin-1-yl]prop-2-en-1-one $^1$H-NMR (CDCl$_3$) δ: 1.22 (6H, d, J=6.8 Hz), 2.37 (3H, s), 2.50 (4H, t, J=4.9 Hz), 2.86 (1H, septet, J=6.8 Hz), 3.55 (2H, s), 3.65-3.75 (4H, m), 5.03 (2H, s), 5.16 (2H, s), 6.73 (1H, d, J=15.4 Hz), 6.91-6.96 (3H, m), 6.99 (1H, s), 7.15 (2H, d, J=8.5 Hz), 7.26-7.35 (4H, m), 7.38-7.41 (4H, m), 7.51-7.53 (1H, m), 7.59 (1H, s), 7.83 (1H, d, J=15.4 Hz), 7.88 (1H, d, J=2.9 Hz).

Example 42

4-{[(6-{4-[(E)-3-(4-{4-[(4-Chlorophenoxy)methyl]benzyl}piperazin-1-yl)-3-oxoprop-1-en-1-yl]-2,6-dimethylphenoxy}pyridin-3-yl)oxy]methyl}benzonitrile $^1$H-NMR (CDCl$_3$) δ: 2.11 (6H, s), 2.48-2.49 (4H, m), 3.55 (2H, s), 3.64-3.67 (2H, m), 3.73-3.76 (2H, m), 5.03 (2H, s), 5.09 (2H, s), 6.78 (1H, d, J=15.4 Hz), 6.84 (1H, d, J=8.8 Hz), 6.90 (2H, d, J=9.0 Hz), 7.23-7.25 (4H, m), 7.31-7.40 (5H, m), 7.52 (2H, d, J=8.1 Hz), 7.61 (1H, d, J=15.4 Hz), 7.68 (2H, d, J=8.1 Hz), 7.79 (1H, d, J=2.9 Hz).

Example 43

4-({[6-(2,6-Dimethyl-4-{(E)-3-oxo-3-[4-(4-{[4-(propan-2-yloxy)phenoxy]methyl}benzyl)piperazin-1-yl]prop-1-en-1-yl}phenoxy)pyridin-3-yl]oxy}methyl)benzonitrile $^1$H-NMR (CDCl$_3$) δ: 1.31 (6H, d, J=6.1 Hz), 2.11 (6H, s), 2.47-2.50 (4H, m), 3.54 (2H, s), 3.64-3.66 (2H, m), 3.73-3.76 (2H, m), 4.41-4.43 (1H, m), 5.00 (2H, s), 5.09 (2H, s), 6.78 (1H, d, J=15.4 Hz), 6.82-6.84 (3H, m), 6.90 (2H, d, J=9.0 Hz), 7.25-7.26 (2H, m), 7.31-7.35 (3H, m), 7.40 (2H, d, J=8.1 Hz), 7.52 (2H, d, J=8.3 Hz), 7.61 (1H, d, J=15.4 Hz), 7.68 (2H, d, J=8.3 Hz), 7.80 (1H, d, J=2.9 Hz).

Example 44

(E)-3-[2-Chloro-4-({5-[(2-chlorobenzyl)oxy]pyridin-2-yl}oxy)-5-methylphenyl]-1-[4-(4-{[4-(propan-2-yl)phenoxy]methyl}benzyl)piperazin-1-yl]prop-2-en-1-one $^1$H-NMR (CDCl$_3$) δ: 1.22 (6H, d, J=6.8 Hz), 2.19 (3H, s), 2.48-2.50 (4H, m), 2.86 (1H, septet, J=6.8 Hz), 3.55 (2H, s), 3.64-3.75 (4H, m), 5.03 (2H, s), 5.17 (2H, s), 6.79 (1H, d, J=15.4 Hz), 6.89-6.93 (3H, m), 7.03 (1H, s), 7.13-7.17 (2H, m), 7.27-7.42 (8H, m), 7.46 (1H, s), 7.51-7.54 (1H, m), 7.91-7.95 (2H, m).

Example 45

(E)-3-[2-Chloro-5-methyl-4-({5-[(4-methylbenzyl)oxy]pyridin-2-yl}oxy)phenyl]-1-[4-(4-{[4-(propan-2-yl)phenoxy]methyl}benzyl)piperazin-1-yl]prop-2-en-1-one $^1$H-NMR (DMSO-d$_6$) δ: 1.16 (6H, d, J=6.8 Hz), 2.12 (3H, s), 2.30 (3H, s), 2.37-2.43 (4H, m), 2.82 (1H, septet, J=6.8 Hz), 3.52 (2H, s), 3.57-3.72 (4H, m), 5.04 (2H, s), 5.08 (2H, s), 6.90-6.93 (2H, m), 7.07 (1H, d, J=9.0 Hz), 7.11 (1H, s), 7.12-7.16 (2H, m), 7.20 (2H, d, J=7.8 Hz), 7.27 (1H, d, J=15.4 Hz), 7.32-7.34 (4H, m), 7.40 (2H, d, J=7.8 Hz), 7.59 (1H, dd, J=9.0, 3.2 Hz), 7.75 (1H, d, J=15.4 Hz), 7.91 (1H, d, J=3.2 Hz), 7.97 (1H, s).

Example 46

(E)-3-[5-Chloro-2-methyl-4-({5-[(4-methylbenzyl)oxy]pyridin-2-yl}oxy)phenyl]-1-[4-(4-{[4-(propan-2-yl)phenoxy]methyl}benzyl)piperazin-1-yl]prop-2-en-1-one $^1$H-NMR (CDCl$_3$) δ: 1.22 (6H, d, J=6.8 Hz), 2.36 (3H, s), 2.37 (3H, s), 2.49 (4H, t, J=4.9 Hz), 2.86 (1H, septet, J=6.8 Hz), 3.55 (2H, s), 3.65-3.75 (4H, m), 5.01 (2H, s), 5.03 (2H, s), 6.72 (1H, d, J=15.4 Hz), 6.90-6.94 (3H, m), 6.97 (1H, s), 7.13-7.17 (2H, m), 7.19 (2H, d, J=7.8 Hz), 7.29 (2H, d, J=7.8 Hz), 7.33-7.37 (3H, m), 7.40 (2H, d, J=8.3 Hz), 7.59 (1H, s), 7.81-7.87 (2H, m).

Example 47

4-({[6-(5-Chloro-2-methyl-4-{(E)-3-oxo-3-[4-(4-{[4-(propan-2-yl)phenoxy]methyl}benzyl)piperazin-1-yl]prop-1-en-1-yl}phenoxy)pyridin-3-yl]oxy}methyl)benzonitrile $^1$H-NMR (CDCl$_3$) δ: 1.22 (6H, d, J=6.8 Hz), 2.19 (3H, s), 3.49 (4H, brs), 2.86 (1H, septet, J=6.8 Hz), 3.55 (2H, s), 3.64-3.75 (4H, m), 5.03 (2H, s), 5.12 (2H, s), 6.79 (1H, d, J=15.4 Hz), 6.90-6.93 (3H, m), 7.03 (1H, s), 7.13-7.17 (2H, m), 7.33-7.41 (5H, m), 7.46 (1H, s), 7.53 (2H, d, J=8.3 Hz), 7.68-7.70 (2H, m), 7.87 (1H, d, J=3.2 Hz), 7.93 (1H, d, J=15.4 Hz).

Example 48

4-({[6-(2-Chloro-5-methyl-4-{(E)-3-oxo-3-[4-(4-{[4-(propan-2-yl)phenoxy]methyl}benzyl)piperazin-1-yl]prop-1-en-1-yl}phenoxy)pyridin-3-yl]oxy}methyl)benzonitrile $^1$H-NMR (CDCl$_3$) δ: 1.22 (6H, d, J=6.8 Hz), 2.37 (3H, s), 2.49 (4H, t, J=4.9 Hz), 2.86 (1H, septet, J=6.8 Hz), 3.55 (2H, s), 3.64-3.75 (4H, m), 5.03 (2H, s), 5.11 (2H, s), 6.73 (1H, d, J=15.4 Hz), 6.90-6.93 (2H, m), 6.95-6.99 (2H, m), 7.13-7.17 (2H, m), 7.33-7.41 (5H, m), 7.51-7.53 (2H, m), 7.59 (1H, s), 7.67-7.70 (2H, m), 7.81-7.85 (2H, m).

Example 49

(E)-3-(3,5-Dimethyl-4-{[5-(1,3-thiazol-4-ylmethoxy)pyridin-2-yl]oxy}phenyl)-1-[4-(4-{[4-(propan-2-yl)phenoxy]methyl}benzyl)piperazin-1-yl]prop-2-en-1-one $^1$H-NMR (CDCl$_3$) δ: 1.22 (6H, d, J=6.8 Hz), 2.12 (6H, s), 2.49 (4H, t, J=4.9 Hz), 2.86 (1H, septet, J=6.8 Hz), 3.54 (2H, s), 3.65-3.75 (4H, m), 5.03 (2H, s), 5.23 (2H, s), 6.77-6.83 (2H, m), 6.90-6.94 (2H, m), 7.13-7.18 (2H, m), 7.25 (2H, s), 7.33-7.42 (6H, m), 7.61 (1H, d, J=15.4 Hz), 7.86 (1H, d, J=2.9 Hz), 8.83 (1H, d, J=2.2 Hz).

Example 50

(E)-3-[3-Chloro-5-methyl-4-({5-[(4-methylbenzyl)oxy]pyridin-2-yl}oxy)phenyl]-2-methyl-1-[4-(4-{[4-(propan-2-yl)phenoxy]methyl}benzyl)piperazin-1-yl]prop-2-en-1-one $^1$H-NMR (CDCl$_3$) δ: 1.22 (6H, d, J=6.8 Hz), 2.11 (3H, d, J=1.5 Hz), 2.18 (3H, s), 2.36 (3H, s), 2.46 (4H, brs), 2.86 (1H, septet, J=6.8 Hz), 3.55 (2H, s), 3.61 (4H, brs), 4.99 (2H, s), 5.03 (2H, s), 6.41 (2H, s), 6.88-6.95 (3H, m), 7.09 (1H, d, J=1.7 Hz), 7.11-7.21 (4H, m), 7.24-7.42 (7H, m), 7.80 (1H, d, J=2.9 Hz).

Example 51

(E)-3-[3-Chloro-5-methyl-4-({5-[(4-methylbenzyl)oxy]pyridin-2-yl}oxy)phenyl]-1-[4-(4-{[4-(propan-2-yl)phenoxy]methyl}benzyl)piperazin-1-yl]but-2-en-1-one $^1$H-NMR (CDCl$_3$) δ: 1.22 (6H, d, J=6.8 Hz), 2.19 (3H, s), 2.22 (3H, d, J=1.0 Hz), 2.36 (3H, s), 2.45 (4H, dt, J=17.6, 4.9 Hz), 2.87 (1H, septet, J=6.8 Hz), 3.50-3.58 (4H, m), 3.72 (2H, t, J=4.9 Hz), 4.99 (2H, s), 5.03 (2H, s), 6.24 (1H, d, J=1.2 Hz), 6.89-6.95 (3H, m), 7.11-7.21 (4H, m), 7.24-7.31 (3H, m), 7.31-7.43 (6H, m), 7.80 (1H, d, J=2.7 Hz).

Example 52

(E)-3-[3-Chloro-4-({5-[(2-chlorobenzyl)oxy]pyridin-2-yl}oxy)-5-methylphenyl]-1-[4-(4-{[4-(propan-2-yloxy)phenoxy]methyl}benzyl)piperazin-1-yl]prop-2-en-1-one $^1$H-NMR (CDCl$_3$) δ: 1.30 (6H, d, J=6.4 Hz), 2.20 (3H, s), 2.49 (4H, t, J=4.9 Hz), 3.55 (2H, s), 3.59-3.79 (4H, m), 4.42 (1H, septet, J=6.4 Hz), 5.00 (2H, s), 5.14 (2H, s), 6.77-6.86 (3H, m), 6.88-6.97 (3H, m), 7.24-7.42 (9H, m), 7.46 (1H, d, J=2.0 Hz), 7.49-7.54 (1H, m), 7.57 (1H, d, J=15.1 Hz), 7.81 (1H, d, J=3.4 Hz).

Example 53

(E)-3-[3-Chloro-4-({5-[(2-chlorobenzyl)oxy]pyridin-2-yl}oxy)-5-methylphenyl]-1-(4-{-4-[(4-methoxyphenoxy)methyl]benzyl}piperazin-1-yl)prop-2-en-1-one $^1$H-NMR (CDCl$_3$) δ: 2.20 (3H, s), 2.49 (4H, t, J=4.9 Hz), 3.55 (2H, s), 3.60-3.80 (7H, m), 5.01 (2H, s), 5.14 (2H, s), 6.77-6.87 (3H, m), 6.89-6.97 (3H, m), 7.24-7.42 (9H, m), 7.46 (1H, d, J=2.0 Hz), 7.49-7.54 (1H, m), 7.57 (1H, d, J=15.1 Hz), 7.81 (1H, d, J=2.9 Hz).

Example 54

(E)-3-[3-Chloro-4-({5-[(2-chlorobenzyl)oxy]pyridin-2-yl}oxy)-5-methylphenyl]-1-(4-{4-[(4-ethoxyphenoxy)methyl]benzyl}piperazin-1-yl)prop-2-en-1-one $^1$H-NMR (CDCl$_3$) δ: 1.39 (3H, t, J=6.8 Hz), 2.20 (3H, s), 2.49 (4H, t, J=4.9 Hz), 3.55 (2H, s), 3.60-3.82 (4H, m), 3.98 (2H, q, J=6.8 Hz), 5.00 (2H, s), 5.14 (2H, s), 6.78-6.86 (3H, m), 6.88-6.98 (3H, m), 7.24-7.42 (9H, m), 7.46 (1H, d, J=2.0 Hz), 7.48-7.54 (1H, m), 7.57 (1H, d, J=15.1 Hz), 7.81 (1H, d, J=3.4 Hz).

Example 55

(E)-3-[3-Chloro-4-({5-[(2-chlorobenzyl)oxy]pyridin-2-yl}oxy)phenyl]-1-[4-(4-{[4-(propan-2-yloxy)phenoxy]methyl}benzyl)piperazin-1-yl]prop-2-en-1-one $^1$H-NMR (CDCl$_3$) δ: 1.30 (6H, d, J=6.1 Hz), 2.49 (4H, t, J=4.9 Hz), 3.55 (2H, s), 3.60-3.80 (4H, m), 4.42 (1H, septet, J=6.1 Hz), 5.00 (2H, s), 5.16 (2H, s), 6.77-6.86 (3H, m), 6.88-6.92 (2H, m), 6.97 (1H, dd, J=9.0, 0.5 Hz), 7.15 (1H, d, J=8.5 Hz), 7.27-7.38 (4H, m), 7.37-7.43 (5H, m), 7.48-7.55 (1H, m), 7.56-7.64 (2H, m), 7.88 (1H, d, J=2.9 Hz).

Example 56

(E)-3-[3-Chloro-4-({5-[(2-chlorobenzyl)oxy]pyridin-2-yl}oxy)-5-methylphenyl]-1-[4-(4-{[4-(1H-pyrrol-1-yl)phenoxy]methyl}benzyl)piperazin-1-yl]prop-2-en-1-one $^1$H-NMR (CDCl$_3$) δ: 2.20 (3H, s), 2.50 (4H, t, J=4.9 Hz), 3.56 (2H, s), 3.60-3.80 (4H, m), 5.08 (2H, s), 5.14 (2H, s), 6.32 (2H, t, J=2.2 Hz), 6.80 (1H, d, J=15.4 Hz), 6.94 (1H, d, J=8.8 Hz), 6.99-7.06 (4H, m), 7.25-7.33 (5H, m), 7.36-7.44 (6H, m), 7.46 (1H, d, J=2.0 Hz), 7.49-7.54 (1H, m), 7.57 (1H, d, J=15.4 Hz), 7.81 (1H, d, J=2.9 Hz).

Example 57

(E)-3-[3-Chloro-4-({5-[(2-chlorobenzyl)oxy]pyridin-2-yl}oxy)-5-methylphenyl]-2-methyl-1-[4-(4-{[4-(propan-2-yl)phenoxy]methyl}benzyl)piperazin-1-yl]prop-2-en-1-one $^1$H-NMR (CDCl$_3$) δ: 1.22 (6H, d, J=6.8 Hz), 2.11 (3H, d, J=1.7 Hz), 2.19 (3H, s), 2.46 (4H, brs), 2.87 (1H, septet, J=7.1 Hz), 3.55 (2H, s), 3.62 (4H, brs), 5.03 (2H, s), 5.14 (2H, s), 6.41 (1H, d, J=1.5 Hz), 6.86-6.96 (3H, m), 7.10 (1H, d, J=2.0 Hz), 7.11-7.18 (2H, m), 7.24-7.42 (9H, m), 7.49-7.56 (1H, m), 7.83 (1H, d, J=2.9 Hz).

Example 58

(E)-3-[3-Chloro-5-methyl-4-({5-[(4-methylbenzyl)oxy]pyridin-2-yl}oxy)phenyl]-2-methyl-1-[4-(4-{[4-(propan-2-yl)phenoxy]methyl}benzyl)piperazin-1-yl]but-2-en-1-one ¹H-NMR (CDCl₃) δ: 1.22 (6H, d, J=6.8 Hz), 1.80 (3H, d, J=1.5 Hz), 1.96 (3H, d, J=1.5 Hz), 2.17 (3H, s), 2.36 (3H, s), 2.40-2.56 (4H, m), 2.87 (1H, septet, J=6.8 Hz), 3.52 (2H, t, J=4.9 Hz), 3.55 (2H, s), 3.73 (2H, brs), 4.99 (2H, s), 5.03 (2H, s), 6.86-6.94 (3H, m), 6.98 (1H, d, J=1.5 Hz), 7.09-7.21 (5H, m), 7.24-7.42 (7H, m), 7.81 (1H, d, J=2.9 Hz).

Example 59

(E)-3-[3-Chloro-4-({5-[(2-chlorobenzyl)oxy]pyridin-2-yl}oxy)-5-methylphenyl]-2-methyl-1-[4-(4-{[4-(propan-2-yl)phenoxy]methyl}benzyl)piperazin-1-yl]but-2-en-1-one ¹H-NMR (CDCl₃) δ: 1.22 (6H, d, J=6.8 Hz), 1.80 (3H, d, J=1.5 Hz), 1.96 (3H, d, J=1.5 Hz), 2.18 (3H, s), 2.40-2.56 (4H, m), 2.87 (1H, septet, J=6.8 Hz), 3.52 (2H, t, J=4.9 Hz), 3.55 (2H, s), 3.73 (2H, brs), 5.03 (2H, s), 5.15 (2H, s), 6.88-6.94 (3H, m), 6.95-7.00 (1H, m), 7.11 (1H, d, J=2.2 Hz), 7.13-7.18 (2H, m), 7.24-7.43 (8H, m), 7.50-7.55 (1H, m), 7.84 (1H, d, J=2.9 Hz).

Example 60

(E)-3-[3-Chloro-4-({5-[(2-chlorobenzyl)oxy]pyridin-2-yl}oxy)-5-methylphenyl]-1-[4-(4-{[4-(propan-2-yl)phenoxy]methyl}benzyl)piperazin-1-yl]but-2-en-1-one ¹H-NMR (CDCl₃) δ: 1.22 (6H, d, J=7.1 Hz), 2.20 (3H, s), 2.23 (3H, d, J=0.7 Hz), 2.40-2.51 (4H, m), 2.87 (1H, septet, J=7.1 Hz), 3.50-3.57 (4H, m), 3.72 (2H, brs), 5.03 (2H, s), 5.14 (2H, s), 6.24 (1H, d, J=1.2 Hz), 6.90-6.97 (3H, m), 7.12-7.18 (2H, m), 7.24-7.42 (10H, m), 7.49-7.55 (1H, m), 7.83 (1H, d, J=3.2 Hz).

Example 61

(E)-3-[3-Chloro-4-({5-[(2-fluorobenzyl)oxy]pyridin-2-yl}oxy)-5-methylphenyl]-1-(4-{-4-[2-(3,4-dichlorophenoxy)ethyl]benzyl}piperazin-1-yl)prop-2-en-1-one ¹H-NMR (CDCl₃) δ: 2.19 (3H, s), 2.47-2.49 (4H, m), 3.08 (2H, t, J=7.0 Hz), 3.53 (2H, s), 3.63-3.66 (2H, m), 3.73-3.76 (2H, m), 4.13 (2H, t, J=7.0 Hz), 5.10 (2H, s), 6.74 (1H, dd, J=8.9, 2.8 Hz), 6.80 (1H, d, J=15.4 Hz), 6.94 (1H, dd, J=8.8, 0.5 Hz), 6.98 (1H, d, J=2.9 Hz), 7.06-7.11 (1H, m), 7.17 (1H, td, J=7.5, 1.1 Hz), 7.22-7.33 (7H, m), 7.39 (1H, dd, J=9.0, 3.2 Hz), 7.45-7.49 (2H, m), 7.57 (1H, d, J=−15.4 Hz), 7.81 (1H, t, J=1.6 Hz).

Example 62

(E)-3-[3-Chloro-5-methyl-4-({5-[(4-methylbenzyl)oxy]pyridin-2-yl}oxy)phenyl]-1-(4-{4-[2-(3,4-dichlorophenoxy)ethyl]benzyl}piperazin-1-yl)prop-2-en-1-one ¹H-NMR (CDCl₃) δ: 2.19 (3H, s), 2.36 (3H, s), 2.47-2.49 (4H, m), 3.08 (2H, t, J=7.0 Hz), 3.53 (2H, s), 3.63-3.66 (2H, m), 3.73-3.76 (2H, m), 4.13 (3H, t, J=7.0 Hz), 4.98 (2H, s), 6.74 (1H, dd, J=8.9, 2.8 Hz), 6.80 (1H, d, J=15.4 Hz), 6.92 (1H, d, J=8.8 Hz), 6.98 (1H, d, J=2.9 Hz), 7.19 (2H, d, J=7.8 Hz), 7.23 (2H, d, J=8.1 Hz), 7.26-7.31 (6H, m), 7.36 (1H, dd, J=8.9, 3.1 Hz), 7.45 (1H, d, J=2.2 Hz), 7.57 (1H, d, J=15.4 Hz), 7.79 (1H, d, J=2.9 Hz).

Example 63

(E)-1-(4-{4-[2-(4-Chlorophenoxy)ethyl]benzyl}piperazin-1-yl)-3-[2-methyl-4-({5-[(4-methylbenzyl)oxy]pyridin-2-yl}oxy)phenyl]prop-2-en-1-one mp: 124.5-124.8° C.

Example 64

(E)-3-[3-Chloro-4-({5-[2-(4-chlorophenyl)ethoxy]pyridin-2-yl}oxy)-5-methylphenyl]-1-[4-(4-{2-[4-(propan-2-yl)phenoxy]ethyl}benzyl)piperazin-1-yl]prop-2-en-1-one ¹H-NMR (CDCl₃) δ: 1.22 (6H, d, J=6.9 Hz), 2.18 (3H, s), 2.48 (4H, t, J=4.9 Hz), 2.85 (1H, septet, J=6.9 Hz), 3.04-3.08 (4H, m), 3.52 (2H, s), 3.65-3.74 (4H, m), 4.13-4.15 (4H, m), 6.78-6.83 (3H, m), 6.90 (1H, d, J=8.9 Hz), 7.13 (2H, d, J=8.9 Hz), 7.19 (2H, d, J=8.6 Hz), 7.25-7.29 (8H, m), 7.45 (1H, d, J=1.6 Hz), 7.56 (1H, d, J=15.5 Hz), 7.71 (1H, d, J=3.3 Hz).

Example 65

(E)-3-[3-Chloro-5-methyl-4-({5-[2-(4-methylphenyl)ethoxy]pyridin-2-yl}oxy)phenyl]-1-(4-{2-(4-fluorophenoxy)ethyl]benzyl}piperazin-1-yl)prop-2-en-1-one ¹H-NMR (CDCl₃) δ: 2.18 (3H, s), 2.33 (3H, s), 2.48 (4H, t, J=4.9 Hz), 3.03 (2H, t, J=6.9 Hz), 3.08 (2H, t, J=6.9 Hz), 3.52 (2H, s), 3.65-3.74 (4H, m), 4.12 (2H, t, J=6.9 Hz), 4.13 (2H, t, J=6.9 Hz), 6.78-6.83 (3H, m), 6.88-6.99 (3H, m), 7.12-7.16 (4H, m), 7.22-7.30 (6H, m), 7.45 (1H, d, J=2.0 Hz), 7.57 (1H, d, J=15.5 Hz), 7.72 (1H, d, J=3.0 Hz).

Example 66

(E)-3-[3-Chloro-5-methyl-4-({5-[(4-methylbenzyl)oxy]pyridin-2-yl}oxy)phenyl]-1-(4-{-4-[2-(2-methylphenoxy)ethyl]benzyl}piperazin-1-yl)prop-2-en-1-one ¹H-NMR (CDCl₃) δ: 2.19 (3H, s), 2.19 (3H, s), 2.36 (3H, s), 2.48 (4H, t, J=4.9 Hz), 3.11 (2H, t, J=6.8 Hz), 3.52 (2H, s), 3.64-3.74 (4H, m), 4.17 (2H, t, J=6.6 Hz), 4.98 (2H, s), 6.77-6.88 (3H, m), 6.91 (1H, d, J=8.9 Hz), 7.10-7.20 (4H, m), 7.26-7.31 (7H, m), 7.36 (1H, dd, J=8.9, 3.0 Hz), 7.45 (1H, d, J=2.0 Hz), 7.57 (1H, d, J=15.2 Hz), 7.79 (1l3, d, J=3.0 Hz).

Example 67

(E)-1-(4-{4-[2-(4-Butylphenoxy)ethyl]benzyl}piperazin-1-yl)-3-[3-chloro-5-methyl-4-({5[(4-methylbenzyl)oxy]pyridin-2-yl}oxy)phenyl]prop-2-en-1-one $^1$H-NMR (CDCl$_3$) δ: 0.91 (3H, t, J=7.4 Hz), 1.26-1.40 (2H, m), 1.50-1.61 (2H, m), 2.19 (3H, s), 2.36 (3H, s), 2.46-2.57 (6H, m), 3.08 (2H, t, J=7.1 Hz), 3.52 (2H, s), 3.64-3.74 (4H, m), 4.15 (2H, t, J=6.9 Hz), 4.98 (2H, s), 6.77-6.83 (3H, m), 6.91 (1H, d, J=8.9 Hz), 7.05-7.10 (2H, m), 7.19 (2H, d, J=7.9 Hz), 7.23-7.31 (7H, m), 7.36 (1H, dd, J=8.9, 3.0 Hz), 7.45 (1H, d, J=2.0 Hz), 7.57 (1H, d, J=15.5 Hz), 7.79 (1H, d, J=3.0 Hz).

Example 68

(E)-3-[3-Chloro-4-({5-[(2-chlorobenzyl)oxy]pyridin-2-yl}oxy)-5-methylphenyl]-1-[4-(4-{2-[3-(propan-2-yl)phenoxy]ethyl}benzyl)piperazin-1-yl]prop-2-en-1-one $^1$H-NMR (CDCl$_3$) δ: 1.23 (6H, d, J=6.9 Hz), 2.19 (3H, s), 2.46-2.50 (4H, m), 2.81-2.91 (1H, m), 3.09 (2H, t, J=7.1 Hz), 3.52 (2H, s), 3.62-3.66 (2H, m), 3.72-3.76 (2H, m), 4.17 (2H, t, J=7.1 Hz), 5.13 (2H, s), 6.68-6.75 (1H, m), 6.76-6.85 (3H, m), 6.94 (1H, d, J=8.9 Hz), 7.16-7.28 (8H, m), 7.36-7.61 (5H, m), 7.81 (1H, d, J=2.6 Hz).

Example 69

(E)-1-(4-{4-[2-(1,3-Benzodioxol-5-yloxy)ethyl]benzyl}piperazin-1-yl)-3-[3-chloro-4-({5-[2-chlorobenzyl)oxy]pyridin-2-yl}oxy)-5-methylphenyl]prop-2-en-1-one $^1$H-NMR (CDCl$_3$) δ: 2.19 (3H, s), 2.48 (4H, t, J=4.9 Hz), 3.05 (2H, t, J=6.9 Hz), 3.52 (2H, s), 3.64 (2H, brs), 3.74 (2H, brs), 4.09 (2H, t, J=6.9 Hz), 5.14 (2H, s), 5.90 (2H, s), 6.31 (1H, dd, J=8.7, 2.3 Hz), 6.48 (1H, d, J=2.3 Hz), 6.69 (1H, d, J=8.7 Hz), 6.80 (1H, d, J=15.6 Hz), 6.94 (1H, d, J=9.2 Hz), 7.22-7.32 (7H, m), 7.38-7.41 (2H, m), 7.45 (1H, d, J=1.8 Hz), 7.52 (1H, m), 7.57 (1H, d, J=15.6 Hz), 7.81 (1H, d, J=2.7 Hz).

Example 70

(E)-1-(4-{4-[2-(1,3-Benzodioxol-5-yloxy)ethyl]benzyl}piperazin-1-yl)-3-[3-chloro-5-methyl-4-({5-[(4-methylbenzyl)oxy]pyridin-2-yl}oxy)phenyl]prop-2-en-1-one $^1$H-NMR (CDCl$_3$) δ: 2.19 (3H, s), 2.35 (3H, s), 2.48 (4H, t, J=4.9 Hz), 3.05 (2H, t, J=6.9 Hz), 3.52 (2H, s), 3.64 (2H, brs), 3.74 (2H, brs), 4.09 (2H, t, J=6.9 Hz), 4.98 (2H, s), 5.90 (2H, s), 6.31 (1H, dd, J=8.7, 2.3 Hz), 6.48 (1H, d, J=2.3 Hz), 6.68 (1H, d, J=8.7 Hz), 6.79 (1H, d, J=15.6 Hz), 6.91 (1H, d, J=9.2 Hz), 7.19 (2H, d, J=9.2 Hz), 7.22-7.30 (7H, m), 7.35 (1H, dd, J=9.2, 3.2 Hz), 7.45 (1H, d, J=2.3 Hz), 7.56 (1H, d, J=15.6 Hz), 7.79 (1H, d, J=3.2 Hz).

Example 71

(E)-3-[3-Chloro-4-({5-[(2-chlorobenzyl)oxy]pyridin-2-yl}oxy)-5-methylphenyl]-1-(4-({4-[2-(3,4-dimethylphenoxy]ethyl]benzyl}piperazin-1-yl)prop-2-en-1-one $^1$H-NMR (CDCl$_3$) δ: 2.18 (3H, s), 2.19 (3H, s), 2.22 (3H, s), 2.49-2.52 (4H, m), 3.07 (2H, t, J=6.9 Hz), 3.55 (2H, s), 3.64-3.67 (2H, m), 3.74-3.77 (2H, m), 4.13 (2H, t, J=6.9 Hz), 5.13 (2H, s), 6.64 (1H, dd, J=8.2, 2.3 Hz), 6.71 (1H, d, J=1.8 Hz), 6.80 (1H, d, J=15.1 Hz), 6.94 (1H, d, J=8.7 Hz), 7.01 (1H, d, J=8.2 Hz), 7.23-7.31 (7H, m), 7.37-7.58 (5H, m), 7.81 (1H, d, J=3.2 Hz).

Example 72

(E)-3-[3-Chloro-4-({5-[(2-chlorobenzyl)oxy]pyridin-2-yl}oxy)-5-methylphenyl]-1-(4-{4-[2-(3-methoxyphenoxy)ethyl]benzyl}piperazin-1-yl)prop-2-en-1-one $^1$H-NMR (CDCl$_3$) δ: 2.19 (3H, s), 2.50-2.53 (4H, m), 3.09 (2H, t, J=7.1 Hz), 3.55 (2H, s), 3.65-3.67 (2H, m), 3.73-3.79 (5H, m), 4.16 (2H, t, J=7.1 Hz), 5.14 (2H, s), 6.45-6.52 (3H, m), 6.79 (1H, d, J=15.1 Hz), 6.95 (1H, d, J=8.7 Hz), 7.17 (1H, t, J=8.2 Hz), 7.24-7.30 (7H, m), 7.37-7.46 (3H, m), 7.51-7.58 (2H, m), 7.82 (1H, d, J=2.7 Hz).

Example 73

(E)-3-[3-Chloro-4-({5-[(2-chlorobenzyl)oxy]pyridin-2-yl}oxy)-5-methylphenyl]-1-(4-{2-(2-chlorophenoxy)ethyl]benzyl}piperazin-1-yl)prop-2-en-1-one $^1$H-NMR (CDCl$_3$) δ: 2.19 (3H, s), 2.47-2.50 (4H, m), 3.15 (2H, t, J=6.9 Hz), 3.53 (2H, s), 3.63-3.66 (2H, m), 3.73-3.76 (2H, m), 4.22 (2H, t, J=6.9 Hz), 5.14 (2H, s), 6.80 (1H, d, J=15.1 Hz), 6.85-6.91 (2H, m), 6.95 (1H, d, J=9.2 Hz), 7.18 (1H, t, J=7.1 Hz), 7.26-7.32 (7H, m), 7.33-7.42 (3H, m), 7.45 (1H, s), 7.51-7.59 (2H, m), 7.81 (1H, d, J=2.7 Hz).

Example 74

(E)-3-[3-Chloro-5-methyl-4-({5-[(4-methylbenzyl)oxy]pyridin-2-yl}oxy)phenyl]-1-(4-{4-[2-(4-iodophenoxy)ethyl]benzyl}piperazin-1-yl)prop-2-en-1-one mp: 125.8-126.2° C.

$^1$H-NMR (CDCl$_3$) δ: 2.19 (3H, s), 2.36 (3H, s), 2.48 (4H, t, J=4.9 Hz), 3.06-3.10 (2H, m), 3.52 (2H, s), 3.65 (2H, brs), 3.74 (2H, brs), 4.11-4.15 (2H, m), 4.98 (2H, brs), 6.67 (2H, d, J=8.8 Hz), 6.80 (1H, d, J=15.6 Hz), 6.92 (1H, d, J=8.8 Hz), 7.19 (2H, d, J=8.3 Hz), 7.24 (2H, d, J=7.8 Hz), 7.26-7.28 (3H, m), 7.29 (2H, d, J=7.8 Hz), 7.34-7.37 (1H, m), 7.45 (1H, d, J=2.0 Hz), 7.54 (2H, d, J=8.8 Hz), 7.55-7.59 (1H, m), 7.78 (1H, d, J=2.9 Hz).

Example 75

(E)-3-[3-Chloro-4-({5-[(2-chlorobenzyl)oxy]pyridin-2-yl}oxy)-5-methylphenyl]-1-(4-{4-[2-(4-iodophenoxy)ethyl]benzyl}piperazin-1-yl)prop-2-en-1-one $^1$H-NMR (CDCl$_3$) δ: 2.19 (3H, s), 2.48 (4H, t, J=4.9 Hz), 3.06-3.10 (2H, m), 3.52 (2H, s), 3.64 (2H, brs), 3.74 (2H, brs), 4.11-4.15 (2H, m), 5.14 (2H, brs), 6.67 (2H, d, J=8.8 Hz), 6.80 (1H, d, J=15.1 Hz), 6.95 (1H, d, J=8.8 Hz), 7.22-7.32 (7H, m), 7.38-7.41 (2H, m), 7.46 (1H, d, J=2.0 Hz), 7.51-7.59 (4H, m), 7.81 (1H, d, J=3.4 Hz).

Example 76

(E)-3-[3-Chloro-4-({5-[(2-chlorobenzyl)oxy]pyridin-2-yl}oxy)-5-methylphenyl]-1-(4-{4-[2-(4-chlorophenoxy)ethyl]benzyl}piperazin-1-yl)prop-2-en-1-one $^1$H-NMR (CDCl$_3$) δ: 2.20 (3H, s), 2.47-2.50 (4H, m), 3.08 (2H, t, J=6.8 Hz), 3.53 (2H, s), 3.64-3.66 (2H, m), 3.73-3.76 (2H, m), 4.14 (2H, t, J=6.8 Hz), 5.14 (2H, s), 6.76-6.85 (3H, m), 6.95 (1H, d, J=8.8 Hz), 7.21-7.29 (9H, m), 7.38-7.59 (5H, m), 7.81 (1H, d, J=2.9 Hz).

Example 77

(E)-3-[3-Chloro-4-({5-[(2-chlorobenzyl)oxy]pyridin-2-yl}oxy)-5-methylphenyl]-1-(4-{4-[2-(3-chlorophenoxy)ethyl]benzyl}piperazin-1-yl)prop-2-en-1-one $^1$H-NMR (CDCl$_3$) δ: 2.19 (3H, s), 2.47-2.49 (4H, m), 3.08 (2H, t, J=6.8 Hz), 3.52 (2H, s), 3.63-3.65 (2H, m), 3.73-3.76 (2H, m), 4.15 (2H, t, J=6.8 Hz), 5.13 (2H, s), 6.76-6.83 (2H, m), 6.88-6.95 (3H, m), 7.17 (1H, t, J=8.3 Hz), 7.22-7.30 (7H, m), 7.37-7.41 (2H, m), 7.45 (1H, s), 7.50-7.53 (1H, m), 7.57 (1H, d, J=15.6 Hz), 7.81 (1H, d, J=2.9 Hz).

Example 78

(E)-3-[3-Chloro-4-({5-[(2-chlorobenzyl)oxy]pyridin-2-yl}oxy)-5-methylphenyl]-1-(4-{4-[2-(quinolin-6-yloxy)ethyl]benzyl}piperazin-1-yl)prop-2-en-1-one $^1$H-NMR (CDCl$_3$) δ: 2.19 (3H, s), 2.47-2.51 (4H, m), 3.17 (2H, t, J=7.1 Hz), 3.53 (2H, s), 3.64-3.66 (2H, m), 3.73-3.76 (2H, m), 4.30 (2H, t, J=7.1 Hz), 5.13 (2H, s), 6.81 (1H, d, J=15.1 Hz), 6.94 (1H, d, J=8.8 Hz), 7.06 (1H, d, J=2.9 Hz), 7.26-7.41 (11H, m), 7.45-7.61 (3H, m), 7.81 (1H, d, J=2.9 Hz), 7.98-8.03 (2H, m), 8.74-8.78 (1H, m).

Example 79

(E)-3-[3-Chloro-4-({5-[(2-chlorobenzyl)oxy]pyridin-2-yl}oxy)-5-methylphenyl]-1-(4-{4-[2-(2,3-dimethylphenoxy)ethyl]benzyl}piperazin-1-yl)prop-2-en-1-one $^1$H-NMR (CDCl$_3$) δ: 2.12 (3H, s), 2.19 (3H, s), 2.25 (3H, s), 2.47-2.48 (4H, m), 3.10 (2H, t, J=7.2 Hz), 3.52 (2H, s), 3.63-3.65 (2H, m), 3.73-3.76 (2H, m), 4.15 (2H, t, J=7.2 Hz), 5.14 (2H, s), 6.68 (1H, d, J=8.3 Hz), 6.76 (1H, d, J=7.6 Hz), 6.80 (1H, d, J=15.4 Hz), 6.94 (1H, d, J=8.8 Hz), 7.02 (1H, t, J=7.9 Hz), 7.25-7.31 (7H, m), 7.38-7.41 (2H, m), 7.45-7.59 (3H, m), 7.81 (1H, d, J=2.9 Hz).

Example 80

(E)-3-[3-Chloro-4-({5-[(2-chlorobenzyl)oxy]pyridin-2-yl}oxy)-5-methylphenyl]-1-(4-{4-[2-(3-methylphenoxy)ethyl]benzyl}piperazin-1-yl)prop-2-en-1-one $^1$H-NMR (CDCl$_3$) δ: 2.19 (3H, s), 2.31 (3H, s), 2.47-2.48 (4H, m), 3.08 (2H, t, J=7.1 Hz), 3.52 (2H, s), 3.63-3.65 (2H, m), 3.73-3.75 (2H, m), 4.15 (2H, t, J=7.1 Hz), 6.68-6.83 (4H, m), 6.94 (1H, d, J=9.0 Hz), 7.15 (1H, t, J=7.7 Hz), 7.22-7.30 (7H, m), 7.36-7.41 (2H, m), 7.44-7.60 (3H, m), 7.81 (1H, d, J=2.9 Hz).

Example 81

(E)-3-[3-Chloro-4-({5-[(2-chlorobenzyl)oxy]pyridin-2-yl}oxy)-5-methylphenyl]-1-(4-{4-[2-(3,5-dimethylphenoxy)ethyl]benzyl}piperazin-1-yl)prop-2-en-1-one $^1$H-NMR (CDCl$_3$) δ: 2.19 (3H, s), 2.27 (6H, s), 2.48-2.49 (4H, m), 3.07 (2H, t, J=7.1 Hz), 3.52 (2H, s), 3.63-3.65 (2H, m), 3.73-3.76 (2H, m), 4.14 (2H, t, J=7.1 Hz), 5.13 (2H, s), 6.53 (2H, s), 6.59 (1H, s), 6.80 (1H, d, J=15.6 Hz), 6.94 (1H, d, J=8.8 Hz), 7.26-7.31 (7H, m), 7.38-7.59 (5H, m), 7.81 (1H, d, J=2.9 Hz).

Example 82

(E)-3-[4-({5-[(2-Chlorobenzyl)oxy]pyridin-2-yl}oxy)-3-fluorophenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=7.1 Hz), 2.48 (4H, t, J=4.9 Hz), 2.85 (1H, septet, J=7.1 Hz), 3.08 (2H, t, J=7.0 Hz), 3.52 (2H, s), 3.64 (2H, s), 3.75 (2H, s), 4.15 (2H, t, J=7.2 Hz), 5.16 (2H, s), 6.79 (1H, d, J=15.4 Hz), 6.83 (2H, d, J=8.8 Hz), 6.97 (1H, d, J=9.0 Hz), 7.13 (2H, d, J=8.8 Hz), 7.19 (1H, t, J=8.1 Hz), 7.24-7.35 (8H, m), 7.38-7.41 (2H, m), 7.50-7.53 (1H, m), 7.61 (1H, d, J=15.4 Hz), 7.86 (1H, d, J=3.2 Hz).

Example 83

(E)-3-[4-({5-[(2-Chlorobenzyl)oxy]pyridin-2-yl}oxy)-3-methoxyphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.55-2.56 (4H, m), 2.82-2.87 (1H, m), 3.07 (2H, t, J=7.0 Hz), 3.59 (2H, s), 3.67-3.69 (2H, m), 3.76-3.79 (2H, m), 3.80 (3H, s), 4.14 (3H, t, J=6.3 Hz), 5.15 (2H, s), 6.77 (1H, d, J=15.4 Hz), 6.83 (2H, d, J=8.5 Hz), 6.91 (1H, d, J=8.8 Hz), 7.06-7.15 (5H, m), 7.22-7.32 (6H, m), 7.34-7.42 (2H, m), 7.49-7.54 (1H, m), 7.63 (1H, d, J=15.4 Hz), 7.87 (1H, d, J=2.9 Hz).

Example 84

(E)-3-[4-({5-[(2-Chlorobenzyl)oxy]pyridin-2-yl}oxy)-3-methoxyphenyl]-1-(4-{4-[2-(3-methylphenoxy)ethyl]benzyl}piperazin-1-yl)prop-2-en-1-one $^1$H-NMR (CDCl$_3$) δ: 2.31 (3H, s), 2.52-2.54 (4H, m), 3.08 (2H, t, J=7.0 Hz), 3.56 (2H, s), 3.66-3.68 (2H, m), 3.75-3.78 (2H, m), 3.80 (3H, s), 4.15 (2H, t, J=7.0 Hz), 5.15 (2H, s), 6.68-6.80 (4H, m), 6.92 (1H, d, J=8.8 Hz), 7.06-7.18 (4H, m), 7.25-7.32 (6H, m), 7.33-7.42 (2H, m), 7.50-7.53 (1H, m), 7.63 (1H, d, J=15.4 Hz), 7.87 (1H, d, J=2.9 Hz).

Example 85

(E)-3-[4-({5-[(2-Chlorobenzyl)oxy]pyridin-2-yl}oxy)-3-methoxyphenyl]-1-(4-{4-[2-(4-fluorophenoxy)ethyl]benzyl}piperazin-1-yl)prop-2-en-1-one $^1$H-NMR (CDCl$_3$) δ: 2.46-2.49 (4H, m), 3.07 (2H, t, J=7.0 Hz), 3.52 (2H, s), 3.64-3.66 (2H, m), 3.73-3.76 (2H, m), 3.80 (3H, s), 4.12 (2H, t, J=7.0 Hz), 5.14 (2H, s), 6.77-6.84 (3H, m), 6.89-6.97 (3H, m), 7.07-7.15 (3H, m), 7.23-7.30 (6H, m), 7.33-7.41 (2H, m), 7.49-7.54 (1H, m), 7.64 (1H, d, J=15.4 Hz), 7.86 (1H, d, J=2.9 Hz).

Example 86

(E)-3-[4-({5-[(2-Chlorobenzyl)oxy]pyridin-2-yl}oxy)-3-methoxyphenyl]-1-(4-{4-[2-(4-methylphenoxy)ethyl]benzyl}piperazin-1-yl)prop-2-en-1-one $^1$H-NMR (CDCl$_3$) δ: 2.28 (3H, s), 2.48-2.49 (4H, m), 3.08 (2H, t, J=7.1 Hz), 3.52 (2H, s), 3.64-3.66 (2H, m), 3.74-3.76 (2H, m), 3.81 (3H, s), 4.14 (2H, t, J=7.1 Hz), 5.15 (2H, s), 6.76-6.82 (3H, m), 6.92 (1H, d, J=8.8 Hz), 7.06-7.10 (4H, m), 7.13-7.16 (1H, m), 7.24-7.31 (6H, m), 7.34-7.41 (2H, m), 7.50-7.54 (1H, m), 7.64 (1H, d, J=15.4 Hz), 7.87 (1H, d, J=2.9 Hz).

Example 87

(E)-3-[4-({5-[(2-Chlorobenzyl)oxy]pyridin-2-yl}oxy)-2-methylphenyl]-1-(4-{4-[2-(4-fluorophenoxy)ethyl]benzyl}piperazin-1-yl)prop-2-en-1-one $^1$H-NMR (CDCl$_3$) δ: 2.40 (3H, s), 2.48 (4H, t, J=4.6 Hz), 3.07 (2H, t, J=7.1 Hz), 3.52 (2H, s), 3.63 (2H, brs), 3.75 (2H, brs), 4.13 (2H, t, J=7.1 Hz), 5.17 (2H, s), 6.71 (1H, d, J=15.1 Hz), 6.80-6.85 (2H, m), 6.89-6.99 (5H, m), 7.23-7.33 (6H, m), 7.36-7.42 (2H, m), 7.51-7.53 (2H, m), 7.90 (1H, d, J=15.1 Hz), 7.94 (1H, d, J=3.2 Hz).

Example 88

(E)-3-[4-({5-[2-Chlorobenzyl)oxy]pyridin-2-yl}oxy)-2-methylphenyl]-1-(4-{4-[2-(4-methylphenoxy)ethyl]benzyl}piperazin-1-yl)prop-2-en-1-one $^1$H-NMR (CDCl$_3$) δ: 2.27 (3H, s), 2.40 (3H, s), 2.48 (4H, brs), 3.07 (2H, t, J=7.1 Hz), 3.51 (2H, s), 3.63 (2H, brs), 3.75 (2H, brs), 4.14 (2H, t, J=7.1 Hz), 5.17 (2H, s), 6.71 (1H, d, J=15.1 Hz), 6.79 (2H, d, J=8.8 Hz), 6.89-6.91 (3H, m), 7.06 (2H, d, J=8.8 Hz), 7.22-7.42 (8H, m), 7.51-7.53 (2H, m), 7.90 (1H, d, J=15.1 Hz), 7.94 (1H, d, J=3.2 Hz).

Example 89

(E)-3-[4-({5-[(2-Chlorobenzyl)oxy]pyridin-2-yl}oxy)-2-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=6.8 Hz), 2.40 (3H, s), 2.48 (4H, brs), 2.85 (1H, septet, J=6.8 Hz), 3.08 (2H, t, J=7.1 Hz), 3.51 (2H, s), 3.63 (2H, brs), 3.75 (2H, brs), 4.15 (2H, t, J=7.1 Hz), 5.17 (2H, s), 6.71 (1H, d, J=15.1 Hz), 6.83 (2H, d, J=8.5 Hz), 6.89-6.91 (3H, m), 7.13 (2H, d, J=8.5 Hz), 7.22-7.42 (8H, m), 7.51-7.53 (2H, m), 7.90 (1H, d, J=15.1 Hz), 7.94 (1H, d, J=2.9 Hz).

Example 90

(E)-3-[3-Chloro-4-({5-[(3-chloro-2-fluorobenzyl)oxy]pyridin-2-yl}oxy)-5-methylphenyl]-1-(4-{2-(4-methylphenoxy)ethyl]benzyl}piperazin-1-yl)prop-2-en-1-one mp: 127.3-128.5° C.

Example 91

(E)-3-[3-Chloro-4-({5-[(3-chloro-2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.48 (4H, t, J=4.8 Hz), 3.08 (2H, t, J=7.1 Hz), 3.53 (2H, s), 3.65 (2H, s), 3.74 (2H, s), 4.13 (2H, t, J=7.2 Hz), 5.11 (2H, s), 6.78-6.85 (3H, m), 6.93-6.99 (3H, m), 7.12 (1H, td, J=7.9, 1.1 Hz), 7.23-7.29 (5H, m), 7.36-7.41 (3H, m), 7.46 (1H, d, J=2.0 Hz), 7.57 (1H, d, J=15.4 Hz), 7.80 (1H, d, J=2.9 Hz).

Example 92

(E)-3-[3-Chloro-4-({5-[(3-chloro-2-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.19 (3H, s), 2.48 (4H, t, J=4.9 Hz), 2.85 (1H, septet, J=6.8 Hz), 3.08 (2H, t, J=7.1 Hz), 3.52 (2H, s), 3.64 (2H, s), 3.74 (2H, s), 4.15 (2H, t, J=7.0 Hz), 5.10 (2H, s), 6.78-6.85 (3H, m), 6.95 (1H, d, J=9.0 Hz), 7.09-7.15 (3H, m), 7.24-7.29 (5H, m), 7.37-7.40 (3H, m), 7.46 (1H, d, J=1.7 Hz), 7.57 (1H, d, J=15.4 Hz), 7.80 (1H, d, J=3.2 Hz).

Example 93

(E)-3-[3-Chloro-4-({5-[(2,3-difluorobenzyl)oxy]pyridin-2-yl}oxy)-5-methylphenyl]-1-(4-{2-(4-methylphenoxy)ethyl]benzyl}piperazin-1-yl)prop-2-en-1-one $^1$H-NMR (CDCl$_3$) δ: 2.19 (3H, s), 2.28 (3H, s), 2.48 (4H, t, J=4.9 Hz), 3.08 (2H, t, J=7.1 Hz), 3.52 (2H, s), 3.65 (2H, s), 3.75 (2H, s), 4.15 (2H, t, J=7.1 Hz), 5.11 (2H, s), 6.78-6.82 (3H, m), 6.95 (1H, d, J=8.8 Hz), 7.07 (2H, d, J=8.8 Hz), 7.09-7.19 (2H, m), 7.22-7.29 (6H, m), 7.38 (1H, dd, J=8.9, 3.1 Hz), 7.46 (1H, d, J=1.7 Hz), 7.57 (1H, d, J=15.1 Hz), 7.81 (1H, d, J=3.2 Hz).

Example 94

(E)-3-[3-Chloro-4-({5-[(2,3-difluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.19 (3H, s), 2.48 (4H, t, J=4.9 Hz), 2.85 (1H, septet, J=7.1 Hz), 3.08 (2H, t, J=7.0 Hz), 3.52 (2H, s), 3.65 (2H, s), 3.75 (2H, s), 4.16 (2H, d, J=7.1 Hz), 5.11 (2H, s), 6.78-6.85 (3H, m), 6.95 (1H, d, J=9.0 Hz), 7.10-7.17 (4H, m), 7.22-7.29 (6H, m), 7.38 (1H, dd, J=8.9, 3.1 Hz), 7.46 (1H, d, J=1.7 Hz), 7.57 (1H, d, J=15.4 Hz), 7.81 (1H, d, J=3.2 Hz).

Example 95

(E)-3-[4-({5-[(2-Chlorobenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=7.1 Hz), 2.48 (4H, t, J=4.9 Hz), 2.80-2.90 (1H, m), 3.08 (2H, t, J=7.1 Hz), 3.52

(2H, s), 3.64 (2H, brs), 3.74 (2H, brs), 4.15 (2H, t, J=7.1 Hz), 5.18 (2H, s), 6.79 (1H, d, J=15.4 Hz), 6.83 (2H, d, J=8.5 Hz), 6.92 (1H, d, J=9.0 Hz), 7.08 (2H, d, J=8.8 Hz), 7.13 (2H, d, J=8.8 Hz), 7.23-7.31 (6H, m), 7.37-7.42 (2H, m), 7.51-7.54 (3H, m), 7.65 (1H, d, J=15.4 Hz), 7.95 (1H, d, J=3.2 Hz).

Example 96

(E)-3-[4-({5-[(2-Chlorobenzyl)oxy]pyridin-2-yl}oxy)-3-methoxyphenyl]-1-(4-{4-[2-(4-chlorophenoxy)ethyl]benzyl}piperazin-1-yl)prop-2-en-1-one $^1$H-NMR (CDCl$_3$) δ: 2.47-2.48 (4H, m), 3.08 (2H, t, J=7.0 Hz), 3.52 (2H, s), 3.64-3.66 (2H, m), 3.73-3.76 (2H, m), 3.80 (3H, s), 4.13 (2H, t, J=7.0 Hz), 5.14 (2H, s), 6.76-6.83 (3H, m), 6.92 (1H, d, J=8.8 Hz), 7.07-7.16 (3H, m), 7.20-7.31 (8H, m), 7.34-7.41 (2H, m), 7.50-7.53 (1H, m), 7.64 (1H, d, J=15.4 Hz), 7.86 (1H, d, J=2.9 Hz).

Example 97

(E)-3-[3-Chloro-4-({5-[(2-chlorobenzyl)oxy]pyridin-2-yl}oxy)-5-methylphenyl]-1-(4-{4-[2-(3,4-dichlorophenoxy)ethyl]benzyl}piperazin-1-yl)prop-2-en-1-one $^1$H-NMR (CDCl$_3$) δ: 2.19 (3H, s), 2.47-2.49 (4H, m), 3.08 (2H, t, J=6.8 Hz), 3.52 (2H, s), 3.63-3.66 (2H, m), 3.73-3.76 (2H, m), 4.13 (2H, t, J=6.8 Hz), 5.14 (2H, s), 6.72-6.83 (2H, m), 6.93-6.99 (2H, m), 7.22-7.32 (8H, m), 7.37-7.47 (3H, m), 7.50-7.53 (1H, m), 7.57 (1H, d, J=15.4 Hz), 7.81 (1H, d, J=2.9 Hz).

Example 98

(E)-3-[3-Chloro-5-methyl-4-({5-[(4-methylbenzyl)oxy]pyridin-2-yl}oxy)phenyl]-1-(4-{4-[2-(4-chlorophenoxy)ethyl]benzyl}piperazin-1-yl)prop-2-en-1-one $^1$H-NMR (CDCl$_3$) δ: 2.19 (3H, s), 2.36 (3H, s), 2.47-2.49 (4H, m), 3.08 (2H, t, J=7.0 Hz), 3.52 (2H, s), 3.63-3.66 (2H, m), 3.73-3.76 (2H, m), 4.14 (2H, t, J=7.0 Hz), 4.98 (2H, s), 6.77-6.85 (3H, m), 6.92 (1H, d, J=9.0 Hz), 7.17-7.30 (11H, m), 7.36 (1H, dd, J=8.9, 3.1 Hz), 7.45 (1H, s), 7.57 (1H, d, J=15.4 Hz), 7.79 (1H, d, J=2.9 Hz).

Example 99

(E)-3-[3-Chloro-4-({5-[(2-chlorobenzyl)oxy]pyridin-2-yl}oxy)-5-methylphenyl]-1-(4-{4-[2-(4-nitrophenoxy)ethyl]benzyl}piperazin-1-yl)prop-2-en-1-one $^1$H-NMR (CDCl$_3$) δ: 2.19 (3H, s), 2.48 (4H, brs), 3.14 (2H, t, J=6.8 Hz), 3.53 (2H, s), 3.65 (2H, brs), 3.74 (2H, brs), 4.27 (2H, d, J=6.8 Hz), 5.14 (2H, brs), 6.80 (1H, d, J=15.4 Hz), 6.95 (2H, d, J=9.0 Hz), 7.24-7.32 (9H, m), 7.38-7.41 (2H, m), 7.46 (1H, d, J=1.7 Hz), 7.51-7.53 (1H, m), 7.57 (1H, d, J=15.4 Hz), 7.81 (1H, d, J=2.9 Hz), 8.19 (2H, d, J=9.0 Hz).

Example 100

(E)-3-[3-Chloro-5-methyl-4-({5-[(4-methylbenzyl)oxy]pyridin-2-yl}oxy)phenyl]-1-(4-{4-[2-(4-nitrophenoxy)ethyl]benzyl}piperazin-1-yl)prop-2-en-1-one $^1$H-NMR (CDCl$_3$) δ: 2.19 (3H, s), 2.36 (3H, s), 2.48 (4H, brs), 3.14 (2H, t, J=6.8 Hz), 3.53 (2H, s), 3.65 (2H, brs), 3.74 (2H, brs), 4.27 (2H, d, J=6.8 Hz), 4.98 (2H, brs), 6.80 (1H, d, J=15.4 Hz), 6.92 (1H, d, J=8.8 Hz), 6.94 (2H, d, J=9.3 Hz), 7.19 (2H, d, J=7.8 Hz), 7.25 (2H, d, J=7.8 Hz), 7.28-7.30 (5H, m), 7.36 (1H, dd, J=8.8, 2.9 Hz), 7.45 (1H, d, J=2.2 Hz), 7.57 (1H, d, J=15.4 Hz), 7.79 (1H, d, J=2.9 Hz), 8.19 (2H, d, J=9.3 Hz).

Example 101

(E)-1-(4-{4-[2-(4-Methoxyphenoxy)ethyl]benzyl}piperazin-1-yl)-3-[3-methyl-4-({5-[(4-methylbenzyl)oxy]pyridin-2-yl}oxy)phenyl]prop-2-en-1-one $^1$H-NMR (CDCl$_3$) δ: 2.21 (3H, s), 2.36 (3H, s), 2.48 (4H, t, J=5.0 Hz), 3.07 (2H, t, J=7.1 Hz), 3.52 (2H, s), 3.60-3.85 (7H, m), 4.13 (2H, t, J=7.1 Hz), 5.01 (2H, s), 6.76-6.86 (6H, m), 6.97 (1H, d, J=8.3 Hz), 7.19 (2H, d, J=7.8 Hz), 7.23-7.35 (8H, m), 7.40 (1H, s), 7.63 (1H, d, J=15.4 Hz), 7.88 (1H, d, J=2.9 Hz).

Example 102

(E)-3-[3-Methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one $^1$H-NMR (CDCl$_3$) δ: 2.21 (3H, s), 2.28 (3H, s), 2.36 (3H, s), 2.48 (4H, t, J=5.0 Hz), 3.08 (2H, t, J=7.1 Hz), 3.52 (2H, s), 3.65 (2H, s), 3.74 (2H, s), 4.15 (2H, t, J=7.1 Hz), 5.01 (2H, s), 6.76-6.82 (3H, m), 6.84 (1H, dd, J=8.9, 0.6 Hz), 6.97 (1H, d, J=8.3 Hz), 7.07 (2H, dd, J=8.7, 0.6 Hz), 7.19 (2H, d, J=7.8 Hz), 7.23-7.35 (8H, m), 7.40 (1H, d, J=2.0 Hz), 7.63 (1H, d, J=15.4 Hz), 7.88 (1H, dd, J=3.2, 0.5 Hz).

Example 103

(E)-3-[3-Methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=7.1 Hz), 2.21 (3H, s), 2.36 (3H, s), 2.48 (4H, t, J=5.0 Hz), 2.85 (1H, septet, J=7.1 Hz), 3.08 (2H, t, J=7.1 Hz), 3.52 (2H, s), 3.65 (2H, s), 3.74 (2H, s), 4.15 (2H, t, J=7.1 Hz), 5.01 (2H, s), 6.78 (1H, d, J=15.4 Hz), 6.82-6.85 (3H, m), 6.97 (1H, d, J=8.3 Hz), 7.11-7.15 (2H, m), 7.19 (2H, d, J=7.6 Hz), 7.23-7.35 (8H, m), 7.40 (1H, s), 7.63 (1H, d, J=15.4 Hz), 7.88 (1H, d, J=2.9 Hz).

Example 104

(E)-3-[4-({5-[(2,3-Dichlorobenzyl)oxy]pyridin-2-yl}oxy)-3-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.21 (3H, s), 2.48 (4H, t, J=5.0 Hz), 2.85 (1H, septet, J=7.1 Hz), 3.08 (2H, t, J=7.1 Hz), 3.52 (2H, s), 3.65 (2H, s), 3.75 (2H, s), 4.15 (2H, t, J=7.1 Hz), 5.16 (2H, s), 6.79 (1H, d, J=15.4 Hz), 6.82-6.85 (2H, m), 6.88 (1H, d, J=8.8 Hz), 6.99 (1H, d, J=8.3 Hz), 7.11-7.15 (2H, m), 7.23-7.27 (5H, m), 7.34-7.37 (2H, m), 7.41 (1H, d, J=2.0 Hz), 7.45 (2H, d, J=7.8 Hz), 7.63 (1H, d, J=15.4 Hz), 7.89 (1H, d, J=3.2 Hz).

Example 105

(E)-3-[4-({5-[(2,3-Dichlorobenzyl)oxy]pyridin-2-yl}oxy)-3-methylphenyl]-1-(4-{4-[2-(4-methylphenoxy)ethyl]benzyl}piperazin-1-yl)prop-2-en-1-one ¹H-NMR (CDCl₃) δ: 2.21 (3H, s), 2.28 (3H, s), 2.48 (4H, t, J=4.9 Hz), 3.08 (2H, t, J=7.1 Hz), 3.52 (2H, s), 3.65 (2H, s), 3.74 (2H, s), 4.14 (2H, t, J=7.0 Hz), 5.16 (2H, s), 6.77-6.81 (3H, m), 6.88 (1H, d, J=8.8 Hz), 6.99 (1H, d, J=8.3 Hz), 7.07 (2H, d, J=8.5 Hz), 7.23-7.28 (5H, m), 7.34-7.37 (2H, m), 7.41 (1H, s), 7.45 (2H, d, J=7.8 Hz), 7.63 (1H, d, J=15.4 Hz), 7.89 (1H, d, J=3.2 Hz).

Example 106

(E)-3-[4-({5-[(2-Chlorobenzyl)oxy]pyridin-2-yl}oxy)-3-methylphenyl]-1-(4-{4-[2-(4-methylphenoxy)ethyl]benzyl}piperazin-1-yl)prop-2-en-1-one ¹H-NMR (CDCl₃) δ: 2.22 (3H, s), 2.28 (3H, s), 2.48 (4H, t, J=5.1 Hz), 3.08 (2H, t, J=7.1 Hz), 3.52 (2H, s), 3.65-3.74 (4H, m), 4.14 (2H, t, J=7.1 Hz), 5.16 (2H, s), 6.76-6.81 (3H, m), 6.87 (1H, d, J=8.8 Hz), 6.98 (1H, d, J=8.3 Hz), 7.07 (2H, d, J=8.8 Hz), 7.23-7.32 (6H, m), 7.34-7.42 (4H, m), 7.50-7.55 (1H, m), 7.63 (1H, d, J=15.6 Hz), 7.91 (1H, d, J=3.4 Hz).

Example 107

(E)-3-[4-({5-[(2-Chlorobenzyl)oxy]pyridin-2-yl}oxy)-3-methylphenyl]-1-(4-{4-[2-(4-fluorophenoxy)ethyl]benzyl}piperazin-1-yl)prop-2-en-1-one ¹H-NMR (CDCl₃) δ: 2.22 (3H, s), 2.48 (4H, t, J=4.9 Hz), 3.08 (2H, t, J=7.1 Hz), 3.52 (2H, s), 3.65-3.74 (4H, m), 4.13 (2H, t, J=7.1 Hz), 5.16 (2H, s), 6.77-6.89 (4H, m), 6.92-6.99 (3H, m), 7.23-7.30 (6H, m), 7.32-7.42 (4H, m), 7.51-7.54 (1H, m), 7.63 (1H, d, J=15.1 Hz), 7.90 (1H, d, J=2.9 Hz).

Example 108

(E)-3-[4-({5-[(2-Chlorobenzyl)oxy]pyridin-2-yl}oxy)-3-methylphenyl]-1-[4-(4-{2-[4-(propan-2-yl)phenoxy]ethyl}benzyl)piperazin-1-yl]prop-2-en-1-one ¹H-NMR (CDCl₃) δ: 1.22 (6H, d, J=6.8 Hz), 2.22 (3H, s), 2.48 (4H, t, J=4.9 Hz), 2.85 (1H, septet, J=6.8 Hz), 3.08 (2H, t, J=7.1 Hz), 3.52 (2H, s), 3.65 (2H, s), 3.75 (2H, s), 4.15 (2H, t, J=7.1 Hz), 5.16 (2H, s), 6.79 (1H, d, J=15.1 Hz), 6.82-6.88 (3H, m), 6.98 (1H, d, J=8.3 Hz), 7.11-7.15 (2H, m), 7.24-7.32 (5H, m), 7.34-7.41 (5H, m), 7.50-7.55 (1H, m), 7.63 (1H, d, J=15.1 Hz), 7.91 (1H, d, J=3.4 Hz).

Example 109

(E)-3-[4-({5-[(2-Chlorobenzyl)oxy]pyridin-2-yl}oxy)-3-methylphenyl]-1-(4-{4-[2-(3-methylphenoxy)ethyl]benzyl}piperazin-1-yl)prop-2-en-1-one ¹H-NMR (CDCl₃) δ: 2.22 (3H, s), 2.32 (3H, s), 2.48 (4H, t, J=4.9 Hz), 3.09 (2H, t, J=7.1 Hz), 3.52 (2H, s), 3.65 (2H, s), 3.75 (2H, s), 4.16 (2H, t, J=7.1 Hz), 5.16 (2H, s), 6.70-6.81 (4H, m), 6.87 (1H, d, J=8.8 Hz), 6.98 (1H, d, J=8.3 Hz), 7.15 (1H, t, J=7.8 Hz), 7.24-7.41 (10H, m), 7.51-7.54 (1H, m), 7.63 (1H, d, J=15.1 Hz), 7.91 (1H, d, J=3.4 Hz).

Example 110

(E)-3-[4-({5-[(2-Chlorobenzyl)oxy]pyridin-2-yl}oxy)-3-fluorophenyl]-1-(4-{4-[2-(4-methylphenoxy)ethyl]benzyl}piperazin-1-yl)prop-2-en-1-one ¹H-NMR (CDCl₃) δ: 2.28 (3H, s), 2.48 (4H, t, J=4.9 Hz), 3.08 (2H, t, J=7.0 Hz), 3.52 (2H, s), 3.64 (2H, s), 3.75 (2H, s), 4.15 (2H, t, J=7.2 Hz), 5.16 (2H, s), 6.77-6.84 (3H, m), 6.97 (1H, d, J=9.0 Hz), 7.07 (2H, d, J=8.5 Hz), 7.15-7.45 (11H, m), 7.47-7.56 (1H, m), 7.60 (1H, d, J=2.9 Hz), 7.86 (1H, d, J=15.4 Hz).

Example 111

(E)-3-[4-({5-[(2-Chlorobenzyl)oxy]pyridin-2-yl}oxy)-3-fluorophenyl]-1-(4-{4-[2-(4-fluorophenoxy)ethyl]benzyl}piperazin-1-yl)prop-2-en-1-one ¹H-NMR (CDCl₃) δ: 2.48 (4H, t, J=4.9 Hz), 3.08 (2H, t, J=7.0 Hz), 3.52 (2H, s), 3.64 (2H, s), 3.75 (2H, s), 4.13 (2H, t, J=7.2 Hz), 5.16 (2H, s), 6.77-6.84 (3H, m), 6.93-6.98 (3H, m), 7.19 (1H, t, J=8.1 Hz), 7.23-7.35 (8H, m), 7.38-7.41 (2H, m), 7.50-7.53 (1H, m), 7.61 (1H, d, J=15.4 Hz), 7.86 (1H, d, J=3.2 Hz).

Example 112

(E)-3-[4-({5-[(2-Chlorobenzyl)oxy]pyridin-2-yl}oxy)-3-fluorophenyl]-1-(4-{4-[2-(3-methylphenoxy)ethyl]benzyl}piperazin-1-yl)prop-2-en-1-one ¹H-NMR (CDCl₃) δ: 2.32 (3H, s), 2.48 (4H, t, J=5.0 Hz), 3.09 (2H, t, J=7.1 Hz), 3.52 (2H, s), 3.64 (2H, s), 3.75 (2H, s), 4.16 (2H, t, J=7.1 Hz), 5.16 (2H, s), 6.69-6.77 (3H, m), 6.79 (1H, d, J=15.4 Hz), 6.97 (1H, d, J=9.0 Hz), 7.13-7.21 (2H, m), 7.24-7.35 (8H, m), 7.38-7.41 (2H, m), 7.50-7.53 (1H, m), 7.61 (1H, d, J=15.4 Hz), 7.86 (1H, d, J=2.9 Hz).

Example 113

(E)-1-(4-{4-[2-(4-Fluorophenoxy)ethyl]benzyl}piperazin-1-yl)-3-[2-methyl-4-({5-[(4-methylbenzyl)oxy]pyridin-2-yl}oxy)phenyl]prop-2-en-1-one mp: 124.3-125.0° C.
¹H-NMR (CDCl₃) δ: 3.26 (3H, s), 2.40 (3H, s), 2.48 (4H, t, J=4.9 Hz), 3.07 (2H, t, J=7.1 Hz), 3.52 (2H, s), 3.52-3.63 (4H, m), 4.13 (2H, t, J=7.1 Hz), 5.02 (2H, s), 6.70 (1H, d, J=15.1 Hz), 6.80-6.99 (7H, m), 7.19 (2H, d, J=7.8 Hz), 7.23-7.35 (7H, m), 7.50-7.53 (1H, m), 7.88-7.93 (2H, m).

Example 114

(E)-3-[2-Methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one ¹H-NMR (CDCl₃) δ: 2.27 (3H, s), 2.36 (3H, s), 2.40 (3H, s), 2.47 (4H, t, J=4.6 Hz), 3.07 (2H, t, J=7.1 Hz), 3.51 (2H, s), 3.63-3.74 (4H, m), 4.14 (2H, t, J=7.1 Hz), 5.02 (2H, s), 6.70 (1H, d, J=15.1 Hz), 6.78-6.81 (2H, m), 6.86-6.91 (3H, m), 7.05-7.07 (2H, m), 7.19 (2H, d, J=7.8 Hz), 7.23-7.28 (4H, m), 7.30 (2H, d, J=8.1 Hz), 7.33 (1H, dd, J=8.8, 3.2 Hz), 7.05-7.53 (1H, m), 7.90 (1H, d, J=15.1 Hz), 7.92 (1H, d, J=3.2 Hz).

Example 115

(E)-3-[2-Methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=7.1 Hz), 2.36 (3H, s), 2.40 (3H, s), 2.47 (4H, brs), 2.85 (1H, septet, J=7.1 Hz), 3.08 (2H, t, J=7.1 Hz), 3.51 (2H, s), 3.63-3.74 (4H, m), 4.15 (2H, t, J=7.1 Hz), 5.02 (2H, s), 6.70 (1H, d, J=15.1 Hz), 6.81-6.85 (2H, m), 6.86-6.91 (3H, m), 7.11-7.14 (2H, m), 7.19 (2H, d, J=7.8 Hz), 7.23-7.35 (7H, m), 7.50-7.53 (1H, m), 7.88-7.93 (2H, m).

Example 116

(E)-1-(4-{4-[2-(4-Acetylphenoxy)ethyl]benzyl}piperazin-1-yl)-3-[3-chloro-4-({5-[(2-chlorobenzyl)oxy]pyridin-2-yl}oxy)-5-methylphenyl]prop-2-en-1-one $^1$H-NMR (CDCl$_3$) δ: 2.19 (3H, s), 2.48 (4H, t, J=4.9 Hz), 2.55 (3H, s), 3.12 (2H, t, J=7.1 Hz), 3.52 (2H, s), 3.64-3.74 (4H, m), 4.24 (2H, t, J=7.1 Hz), 5.14 (2H, s), 6.80 (1H, d, J=15.1 Hz), 6.91-6.95 (3H, m), 7.24-7.31 (7H, m), 7.38-7.41 (2H, m), 7.45-7.46 (1H, m), 7.50-7.53 (1H, m), 7.57 (1H, d, J=15.1 Hz), 7.81 (1H, d, J=2.9 Hz), 7.91 (2H, d, J=8.3 Hz).

Example 117

(E)-1-(4-{4-[2-(4-Acetylphenoxy)ethyl]benzyl}piperazin-1-yl)-3-[3-chloro-5-methyl-4-({5[(4-methylbenzyl)oxy]pyridin-2-yl}oxy)phenyl]prop-2-en-1-one $^1$H-NMR (CDCl$_3$) δ: 2.18 (3H, s), 2.35 (3H, s), 2.48 (4H, t, J=4.9 Hz), 2.55 (3H, s), 3.12 (2H, t, J=7.1 Hz), 3.53 (2H, s), 3.64-3.74 (4H, m), 4.13 (2H, t, J=7.1 Hz), 4.98 (2H, s), 6.80 (1H, d, J=15.4 Hz), 6.90-6.94 (3H, m), 7.19 (2H, d, J=7.8 Hz), 7.24-7.30 (7H, m), 7.35 (1H, dd, J=8.8, 3.2 Hz), 7.45 (1H, d, J=2.2 Hz), 7.57 (1H, d, J=15.4 Hz), 7.79 (1H, d, J=3.2 Hz), 7.90-7.94 (2H, m).

Example 118

(E)-3-[3-Chloro-5-methyl-4-({5-[(4-methylbenzyl)oxy]pyridin-2-yl}oxy)phenyl]-1-(4-{4-[2-(4-methylphenoxy)propyl]benzyl}piperazin-1-yl)prop-2-en-1-one $^1$H-NMR (CDCl$_3$) δ: 1.29 (3H, d, J=6.1 Hz), 2.19 (3H, s), 2.28 (3H, s), 2.36 (3H, s), 2.47 (4H, t, J=5.0 Hz), 2.80 (1H, dd, J=13.7, 6.6 Hz), 3.07 (1H, dd, J=13.7, 5.9 Hz), 3.51 (2H, s), 3.64 (2H, brs), 3.74 (2H, brs), 4.48-4.55 (1H, m), 4.98 (2H, s), 6.76-6.81 (3H, m), 6.91 (1H, d, J=9.0 Hz), 7.06 (2H, dd, J=8.7, 0.6 Hz), 7.18-7.30 (9H, m), 7.35 (1H, dd, J=9.0, 3.1 Hz), 7.45 (1H, d, J=2.0 Hz), 7.56 (1H, d, J=15.4 Hz), 7.79 (1H, d, J=3.1 Hz).

Example 119

(E)-3-[3-Chloro-5-methyl-4-({5-[(4-methylbenzyl)oxy]pyridin-2-yl}oxy)phenyl]-1-(4-{4-[1-(4-methylphenoxy)propan-2-yl]benzyl}piperazin-1-yl)prop-2-en-1-one $^1$H-NMR (CDCl$_3$) δ: 1.40 (3H, d, J=7.1 Hz), 2.19 (3H, s), 2.27 (3H, s), 2.36 (3H, s), 2.48 (4H, t, J=5.0 Hz), 3.18-3.27 (1H, m), 3.52 (2H, s), 3.64 (2H, brs), 3.74 (2H, brs), 3.93 (1H, dd, J=9.3, 7.8 Hz), 4.06 (1H, dd, J=9.3, 5.9 Hz), 4.98 (2H, s), 6.76-6.82 (3H, m), 6.91 (1H, d, J=9.0 Hz), 7.06 (2H, d, J=8.3 Hz), 7.19 (2H, d, J=7.8 Hz), 7.23-7.30 (7H, m), 7.35 (1H, dd, J=9.0, 3.1 Hz), 7.45 (1H, d, J=2.2 Hz), 7.57 (1H, d, J=15.4 Hz), 7.79 (1H, d, J=3.1 Hz).

Example 120

(E)-3-[3-Chloro-4-({5-[(2-chlorobenzyl)oxy]pyridin-2-yl}oxy)-5-methylphenyl]-1-(4-{4-[1-(4-methylphenoxy)propan-2-yl]benzyl}piperazin-1-yl)prop-2-en-1-one $^1$H-NMR (CDCl$_3$) δ: 1.40 (3H, d, J=7.1 Hz), 2.19 (3H, s), 2.27 (3H, s), 2.49 (4H, t, J=5.1 Hz), 3.20-3.25 (1H, m), 3.52 (2H, s), 3.65 (2H, brs), 3.74 (2H, brs), 3.93 (1H, dd, J=9.3, 7.7 Hz), 4.06 (1H, dd, J=9.3, 5.9 Hz), 5.14 (2H, s), 6.78 (2H, d, J=8.5 Hz), 6.80 (1H, d, J=15.4 Hz), 6.94 (1H, d, J=9.0 Hz), 7.06 (2H, d, J=8.1 Hz), 7.22-7.32 (7H, m), 7.38-7.41 (2H, m), 7.45 (1H, d, J=2.0 Hz), 7.51-7.53 (1H, m), 7.57 (1H, d, J=15.4 Hz), 7.82 (1H, d, J=3.2 Hz).

Example 121

(E)-3-[3-Chloro-4-({5-[(2-chlorobenzyl)oxy]pyridin-2-yl}oxy)-5-methylphenyl]-1-(4-{4-[2-(4-methylphenoxy)propyl]benzyl}piperazin-1-yl)prop-2-en-1-one $^1$H-NMR (CDCl$_3$) δ: 1.28 (3H, d, J=6.1 Hz), 2.19 (3H, s), 2.27 (3H, s), 2.47 (4H, t, J=5.0 Hz), 2.80 (1H, dd, J=13.7, 6.3 Hz), 3.07 (1H, dd, J=13.7, 5.9 Hz), 3.51 (2H, s), 3.64 (2H, brs), 3.74 (2H, brs), 4.48-4.55 (1H, m), 5.14 (2H, s), 6.77-6.81 (3H, m), 6.94 (1H, dd, J=8.8, 0.5 Hz), 7.06 (2H, dd, J=8.7, 0.6 Hz), 7.20 (2H, d, J=8.1 Hz), 7.24 (2H, d, J=8.1 Hz), 7.27-7.31 (3H, m), 7.38-7.41 (2H, m), 7.45 (1H, d, J=2.2 Hz), 7.51-7.53 (1H, m), 7.56 (1H, d, J=15.4 Hz), 7.81 (1H, d, J=2.7 Hz).

Example 122

(E)-3-[3-Chloro-4-({5-[(2-chlorobenzyl)oxy]pyridin-2-yl}oxy)-5-methylphenyl]-1-[4-(4-{2-[4-(propan-2-yl)phenoxy]ethyl}benzyl)-1,4-diazepan-1-yl]prop-2-en-1-one $^1$H-NMR (CDCl$_3$) δ: 1.20-1.26 (6H, m), 1.91-1.93 (2H, m), 2.19-2.21 (3H, m), 2.63-2.67 (2H, m), 2.72-2.76 (2H, m), 2.80-2.89 (1H, m), 3.05-3.10 (2H, m), 3.62 (2H, s), 3.67-3.77 (4H, m), 4.12-4.17 (2H, m), 5.14 (2H, s), 6.74-6.86 (3H, m), 6.94 (1H, d, J=8.8 Hz), 7.11-7.15 (2H, m), 7.22-7.32 (7H, m), 7.37-7.41 (2H, m), 7.44-7.48 (1H, m), 7.50-7.55 (1H, m), 7.58-7.64 (1H, m), 7.82 (1H, d, J=2.9 Hz).

Example 123

(E)-3-[3-Chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)-1,4-diazepan-1-yl]prop-2-en-1-one $^1$H-NMR (CDCl$_3$) δ: 1.20-1.23 (6H, m), 1.88-1.96 (2H, m), 2.19-2.20 (3H, m), 2.35 (3H, s), 2.63-2.67 (2H, m), 2.72-2.76 (2H, m), 2.80-2.89 (1H, m), 3.05-3.10 (2H, m), 3.62 (2H, s), 3.66-3.77 (4H, m), 4.09-4.17 (2H, m), 4.98 (2H, s), 6.74-6.86 (3H, m), 6.91 (1H, d, J=8.8 Hz), 7.11-7.14 (2H, m), 7.16-7.30 (9H, m), 7.35 (1H, dd, J=8.8, 3.2 Hz), 7.45 (1H, dd, J=8.5, 2.2 Hz), 7.58-7.63 (1H, m), 7.79 (1H, d, J=2.9 Hz).

Example 124

4-({[6-(2-Chloro-6-methyl-4-{(E)-3-oxo-3-[4-(4-{2-[4-(propan-2-yl)phenoxy]ethyl}benzyl)piperazin-1-yl]prop-1-en-1-yl}phenoxy)pyridin-3-yl]oxy}methyl)benzonitrile $^1$H-NMR (CDCl$_3$) δ: 1.22 (6H, d, J=7.1 Hz), 2.19 (3H, s), 2.47-2.49 (4H, m), 2.81-2.88 (1H, m), 3.08 (2H, t, J=7.0 Hz), 3.52 (2H, s), 3.63-3.65 (2H, m), 3.73-3.75 (2H, m), 4.15 (2H, t, J=7.0 Hz), 5.09 (2H, s), 6.78-6.84 (3H, m), 6.95 (1H, d, J=8.8 Hz), 7.13 (2H, d, J=8.5 Hz), 7.25-7.27 (4H, m), 7.27-7.30 (1H, m), 7.37 (1H, dd, J=8.9, 3.1 Hz), 7.45 (1H, s), 7.52 (2H, d, J=8.1 Hz), 7.56 (1H, d, J=15.4 Hz), 7.68 (2H, d, J=8.3 Hz), 7.76 (1H, d, J=2.9 Hz).

Example 125

4-{[(6-{2-Chloro-6-methyl-4-[(E)-3-(4-{2-[4-methylphenoxy)ethyl]benzyl}piperazin-1-yl)-3-oxo-prop-1-en-1-yl]phenoxy}pyridin-3-yl)oxy]methyl}benzonitrile $^1$H-NMR (CDCl$_3$) δ: 2.19 (3H, s), 2.27 (3H, s), 2.47-2.48 (4H, m), 3.07 (2H, t, J=7.0 Hz), 3.52 (2H, s), 3.63-3.65 (2H, m), 3.73-3.75 (2H, m), 4.14 (2H, t, J=7.0 Hz), 5.08 (2H, s), 6.78-6.82 (3H, m), 6.95 (1H, d, J=8.8 Hz), 7.06 (2H, d, J=8.5 Hz), 7.25-7.29 (5H, m), 7.36 (1H, dd, J=8.9, 3.1 Hz), 7.45 (1H, s), 7.51 (2H, d, J=8.1 Hz), 7.56 (1H, d, J=15.4 Hz), 7.67 (2H, d, J=8.1 Hz), 7.76 (1H, d, J=2.9 Hz).

Example 126

[6-({5-[(2-Chlorobenzyl)oxy]pyridin-2-yl}oxy)naphthalen-2-yl][4-(4-{2-[4-(propan-2-yl)phenoxy]ethyl}benzyl)piperazin-1-yl]methanone $^1$H-NMR (CDCl$_3$) δ: 1.21 (6H, d, J=6.8 Hz), 2.41-2.54 (4H, m), 2.84 (1H, septet, J=6.8 Hz), 3.07 (2H, t, J=7.1 Hz), 3.49-3.83 (4H, m), 3.52 (2H, s), 4.14 (2H, t, J=7.1 Hz), 5.19 (2H, s), 6.81-6.84 (2H, m), 6.96 (1H, d, J=9.0 Hz), 7.10-7.14 (2H, m), 7.22-7.33 (7H, m), 7.39-7.42 (2H, m), 7.47 (1H, dd, J=8.3, 1.5 Hz), 7.49 (1H, d, J=2.2 Hz), 7.52-7.55 (1H, m), 7.76 (1H, d, J=8.5 Hz), 7.85-7.88 (2H, m), 7.96 (1H, d, J=3.2 Hz).

Example 127

[6-({5-[(2,3-Difluorobenzyl)oxy]pyridin-2-yl}oxy)naphthalen-2-yl][4-(4-{2-[4-(propan-2-yl)phenoxy]ethyl}benzyl)piperazin-1-yl]methanone $^1$H-NMR (CDCl$_3$) δ: 1.21 (6H, d, J=6.8 Hz), 2.41-2.53 (4H, m), 2.84 (1H, septet, J=6.8 Hz), 3.07 (2H, t, J=7.1 Hz), 3.48 (2H, brs), 3.52 (2H, s), 3.83 (2H, brs), 4.14 (2H, t, J=7.1 Hz), 5.16 (2H, s), 6.81-6.84 (2H, m), 6.95-7.00 (1H, m), 7.09-7.18 (4H, m), 7.23-7.27 (5H, m), 7.32 (1H, dd, J=8.9, 2.3 Hz), 7.40 (1H, dd, J=8.9, 3.1 Hz), 7.47 (1H, dd, J=8.4, 1.6 Hz), 7.49 (1H, d, J=2.2 Hz), 7.77 (1H, d, J=8.5 Hz), 7.86-7.89 (2H, m), 7.95 (1H, dd, J=3.2, 0.5 Hz).

Example 128

(E)-3-[4-({5-[(4-Methoxybenzyl)oxy]pyridin-2-yl}oxy)-3,5-dimethylphenyl]-1-(4-{4-[1-(4-methylphenoxy)propan-2-yl]benzyl}piperazin-1-yl)prop-2-en-1-one $^1$H-NMR (CDCl$_3$) δ: 1.40 (3H, d, J=6.8 Hz), 2.12 (6H, s), 2.27 (3H, s), 2.48 (4H, t, J=5.0 Hz), 3.18-3.29 (1H, m), 3.52 (2H, s), 3.66 (2H, brs), 3.74 (2H, brs), 3.81 (3H, s), 3.92 (1H, dd, J=9.3, 7.7 Hz), 4.06 (1H, dd, J=9.3, 5.9 Hz), 4.95 (2H, s), 6.76-6.80 (4H, m), 6.91 (2H, dt, J=9.1, 2.7 Hz), 7.06 (2H, d, J=8.5 Hz), 7.23-7.34 (9H, m), 7.61 (1H, d, J=15.4 Hz), 7.82 (1H, d, J=3.2 Hz).

Example 129

(E)-3-[4-({5-[(4-Fluorobenzyl)oxy]pyridin-2-yl}oxy)-3,5-dimethylphenyl]-1-(4-{4-[1-(4-methylphenoxy)propan-2-yl]benzyl}piperazin-1-yl)prop-2-en-1-one $^1$H-NMR (CDCl$_3$) δ: 1.40 (3H, d, J=7.1 Hz), 2.12 (6H, s), 2.27 (3H, s), 2.48 (4H, t, J=4.6 Hz), 3.18-3.27 (1H, m), 3.52 (2H, s), 3.66 (2H, brs), 3.75 (2H, brs), 3.91-3.95 (1H, m), 4.06 (1H, dd, J=9.2, 6.2 Hz), 4.99 (2H, s), 6.77-6.82 (4H, m), 7.05-7.09 (4H, m), 7.24-7.33 (7H, m), 7.36-7.39 (2H, m), 7.61 (1H, d, J=15.4 Hz), 7.81 (1H, d, J=2.9 Hz).

Example 130

(E)-3-[3,5-Dimethyl-4-({5-[(4-methylbenzyl)oxy]pyridin-2-yl}oxy)phenyl]-1-(4-{4-[2-(4-fluorophenoxy)ethyl]benzyl}piperazin-1-yl)prop-2-en-1-one $^1$H-NMR (CDCl$_3$) δ: 2.12 (6H, s), 2.35 (3H, s), 2.48 (4H, t, J=4.6 Hz), 3.08 (2H, t, J=7.0 Hz), 3.52 (2H, s), 3.65 (2H, brs), 3.74 (2H, brs), 4.13 (2H, t, J=7.0 Hz), 4.98 (2H, s), 6.76-6.84 (4H, m), 6.95 (2H, t, J=8.5 Hz), 7.19 (2H, d, J=7:8 Hz), 7.24-7.33 (9H, m), 7.60 (1H, d, J=15.4 Hz), 7.82 (1H, d, J=2.9 Hz).

Example 131

(E)-3-[4-({5-[(2-Chlorobenzyl)oxy]pyridin-2-yl}oxy)-3,5-dimethylphenyl]-1-(4-{4-[2-(4-methoxyphenoxy)ethyl]benzyl}piperazin-1-yl)prop-2-en-1-one $^1$H-NMR (CDCl$_3$) δ: 2.12 (6H, s), 2.48 (4H, s), 3.07 (2H, t, J=7.0 Hz), 3.52 (2H, s), 3.65 (2H, brs), 3.76 (5H, brs), 4.12 (2H, q, J=6.8 Hz), 5.13 (2H, s), 6.76-6.83 (6H, m), 7.26-7.29 (8H, m), 7.36 (1H, dd, J=9.0, 2.7 Hz), 7.39-7.41 (1H, m), 7.51-7.52 (1H, m), 7.60 (1H, d, J=15.1 Hz), 7.84 (1H, d, J=2.4 Hz).

Example 132

(E)-3-[3,5-Dimethyl-4-({5-[(4-methylbenzyl)oxy]pyridin-2-yl}oxy)phenyl]-1-(4-{4-[2-(4-methoxyphenoxy)ethyl]benzyl}piperazin-1-yl)prop-2-en-1-one $^1$H-NMR (CDCl$_3$) δ: 2.12 (6H, s), 2.35 (3H, s), 2.48 (4H, t, J=4.6 Hz), 3.05-08 (2H, m), 3.52 (3H, s), 3.65 (2H, brs), 3.76 (4H, brs), 4.11-4.15 (2H, m), 4.98 (2H, s), 6.76-6.86 (5H, m), 7.18 (2H, d, J=7.8 Hz), 7.24-7.33 (10H, m), 7.60 (1H, d, J=15.4 Hz), 7.82 (1H, d, J=2.9 Hz).

Example 133

(E)-3-[4-({5-[(2-Chlorobenzyl)oxy]pyridin-2-yl}oxy)-3,5-dimethylphenyl]-1-(4-{4-[2-(4-fluorophenoxy)ethyl]benzyl}piperazin-1-yl)prop-2-en-1-one $^1$H-NMR (CDCl$_3$) δ: 2.12 (6H, s), 2.48 (4H, t, J=4.6 Hz), 3.07 (2H, t, J=7.0 Hz), 3.52 (2H, s), 3.65 (2H, brs), 3.74 (2H, brs), 4.13 (2H, t, J=7.0 Hz), 5.13 (2H, s), 6.78 (1H, d, J=15.6 Hz), 6.80-6.84 (3H, m), 6.93-6.97 (2H, m), 7.23-7.31 (8H, m), 7.34-7.37 (1H, m), 7.38-7.40 (1H, m), 7.51-7.53 (1H, m), 7.61 (1H, d, J=15.4 Hz), 7.84 (1H, d, J=2.9 Hz).

Example 134

(E)-3-[4-({5-[(4-Methoxybenzyl)oxy]pyridin-2-yl}oxy)-3,5-dimethylphenyl]-1-(4-{4-[2-(4-methylphenoxy)propyl]benzyl}piperazin-1-yl)prop-2-en-1-one $^1$H-NMR (CDCl$_3$) δ: 1.28 (3H, d, J=6.1 Hz), 2.12 (6H, s), 2.27 (3H, s), 2.47 (4H, t, J=4.9 Hz), 2.80 (1H, dd, J=13.8, 6.5 Hz), 3.07 (1H, dd, J=13.8, 6.1 Hz), 3.50 (2H, s), 3.65 (2H, brs), 3.74 (2H, brs), 3.81 (3H, s), 4.48-4.55 (1H, m), 4.95 (2H, s), 6.76-6.80 (4H, m), 6.91 (2H, dt, J=9.2, 2.3 Hz), 7.06 (2H, d, J=8.8 Hz), 7.19-7.34 (9H, m), 7.60 (1H, d, J=15.4 Hz), 7.82 (1H, d, J=2.9 Hz).

Example 135

(E)-3-[4-({5-[(4-Fluorobenzyl)oxy]pyridin-2-yl}oxy)-3,5-dimethylphenyl]-1-(4-{4-[2-(4-methylphenoxy)propyl]benzyl}piperazin-1-yl)prop-2-en-1-one $^1$H-NMR (CDCl$_3$) δ: 1.29 (3H, d, J=6.1 Hz), 2.12 (6H, s), 2.28 (3H, s), 2.47 (4H, t, J=4.9 Hz), 2.80 (1H, dd, J=13.7, 6.6 Hz), 3.07 (1H, dd, J=13.7, 6.1 Hz), 3.51 (2H, s), 3.65 (2H, brs), 3.74 (2H, brs), 4.48-4.56 (1H, m), 4.98 (2H, s), 6.76-6.82 (4H, m), 7.04-7.10 (4H, m), 7.19-7.28 (6H, m), 7.32 (1H, dd, J=9.0, 3.2 Hz), 7.36-7.39 (2H, m), 7.61 (1H, d, J=15.4 Hz), 7.81 (1H, d, J=3.2 Hz).

Example 136

(E)-3-[5-Chloro-4-({5-[(2-chlorobenzyl)oxy]pyridin-2-yl}oxy)-2-methylphenyl]-1-(4-{4-[2-(4-methylphenoxy)ethyl]benzyl}piperazin-1-yl)prop-2-en-1-one $^1$H-NMR (CDCl$_3$) δ: 2.27 (3H, s), 2.37 (3H, s), 2.49 (4H, t, J=4.9 Hz), 3.08 (2H, t, J=7.1 Hz), 3.52 (2H, s), 3.65-3.75 (4H, m), 4.14 (2H, t, J=7.1 Hz), 5.16 (2H, s), 6.72 (1H, d, J=15.1 Hz), 6.78-6.81 (2H, m), 6.95-6.96 (1H, m), 6.99 (1H, s), 7.05-7.08 (1H, m), 7.23-7.32 (7H, m), 7.37-7.41 (2H, m), 7.51-7.53 (1H, m), 7.58 (1H, s), 7.83 (1H, d, J=15.1 Hz), 7.88-7.89 (1H, m).

Example 137

(E)-3-[5-Chloro-4-({5-[(2-chlorobenzyl)oxy]pyridin-2-yl}oxy)-2-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=7.1 Hz), 2.37 (3H, s), 2.49 (4H, t, J=4.9 Hz), 2.85 (1H, septet, J=7.1 Hz), 3.08 (2H, t, J=7.1 Hz), 3.52 (2H, s), 3.65-3.74 (4H, m), 4.15 (2H, t, J=7.1 Hz), 5.16 (2H, s), 6.72 (1H, d, J=15.4 Hz), 6.82-6.84 (2H, m), 6.95 (1H, d, J=8.8 Hz), 6.99 (1H, s), 7.11-7.14 (2H, m), 7.23-7.32 (6H, m), 7.37-7.41 (2H, m), 7.51-7.53 (1H, m), 7.58 (1H, s), 7.83 (1H, d, J=15.4 Hz), 7.88 (1H, d, J=3.2 Hz).

Example 138

(E)-3-[5-Chloro-4-({5-[(2-chlorobenzyl)oxy]pyridin-2-yl}oxy)-2-methylphenyl]-1-(4-{4-[2-(4-fluorophenoxy)ethyl]benzyl}piperazin-1-yl)prop-2-en-1-one $^1$H-NMR (CDCl$_3$) δ: 2.27 (3H, s), 2.49 (4H, brs), 3.07 (2H, t, J=6.8 Hz), 3.52 (2H, s), 3.65-3.74 (4H, m), 4.13 (2H, t, J=7.1 Hz), 5.16 (2H, s), 6.72 (1H, d, J=15.4 Hz), 6.81-6.84 (2H, m), 6.93-6.99 (4H, m), 7.23-7.31 (6H, m), 7.38-7.40 (2H, m), 7.50-7.53 (1H, m), 7.58 (1H, s), 7.83 (1H, d, J=15.4 Hz), 7.88 (1H, d, J=2.7 Hz).

Example 139

(E)-3-[5-Chloro-2-methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=6.8 Hz), 2.35 (3H, s), 2.36 (3H, s), 2.48 (4H, t, J=4.9 Hz), 2.85 (1H, septet, J=6.8 Hz), 3.08 (2H, t, J=7.1 Hz), 3.52 (2H, s), 3.64-3.74 (4H, m), 4.15 (2H, t, J=7.1 Hz), 5.01 (2H, s), 6.72 (1H, d, J=15.1 Hz), 6.81-6.85 (2H, m), 6.91-6.93 (1H, m), 6.97 (1H, s), 7.11-7.14 (2H, m), 7.19 (2H, d, J=7.8 Hz), 7.23-7.30 (6H, m), 7.34-7.37 (1H, m), 7.58 (1H, s), 7.83 (1H, d, J=15.1 Hz), 7.86 (1H, d, J=2.7 Hz).

Example 140

(E)-3-[5-Chloro-2-methyl-4-({5-[(4-methylbenzyl)oxy]pyridin-2-yl}oxy)phenyl]-1-(4-{4-[2-(4-methylphenoxy)ethyl]benzyl})piperazin-1-yl)prop-2-en-1-one $^1$H-NMR (CDCl$_3$) δ: 2.27 (3H, s), 2.35 (3H, s), 2.36 (3H, s), 2.48 (4H, t, J=4.9 Hz), 3.07 (2H, t, J=7.1 Hz), 3.52 (2H, s), 3.64-3.74 (4H, m), 4.14 (2H, t, J=7.1 Hz), 5.10 (2H, s), 6.72 (1H, d, J=15.1 Hz), 6.78-6.81 (2H, m), 6.91-6.94 (1H, m), 6.97 (1H, s), 7.05-7.08 (2H, m), 7.19 (2H, d, J=7.8 Hz), 7.23-7.30 (6H, m), 7.35 (1H, dd, J=8.8, 2.9 Hz), 7.58 (1H, s), 7.82 (1H, d, J=15.1 Hz), 7.86 (1H, d, J=2.7 Hz).

Example 141

(E)-3-[5-Chloro-2-methyl-4-({5-[(4-methylbenzyl)oxy]pyridin-2-yl}oxy)phenyl]-1-(4-{4-[2-(4-fluorophenoxy)ethyl]benzyl}piperazin-1-yl)prop-2-en-1-one $^1$H-NMR (DMSO-d$_6$) δ: 2.30 (3H, s), 2.32 (3H, s), 2.35-2.40 (4H, m), 3.00 (2H, t, J=6.8 Hz), 3.48 (2H, s), 3.56-3.72 (4H, m), 4.16 (2H, t, J=6.8 Hz), 5.07 (2H, s), 6.91-6.96 (2H, m), 7.05-7.12 (4H, m), 7.18-7.29 (7H, m), 7.33 (2H, d, J=8.1 Hz), 7.56-7.64 (2H, m), 7.86-7.87 (1H, m), 8.01 (1H, s).

Example 142

(E)-3-[3-Chloro-4-({5[(2-chlorobenzyl)oxy]pyridin-2-yl}oxy)-5-methylphenyl]-1-[4-(4-{2-[4-(propan-2-yloxy)phenoxy]ethyl}benzyl)piperazin-1-yl]prop-2-en-1-one $^1$H-NMR (CDCl$_3$) δ: 1.30 (6H, d, J=6.1 Hz), 2.19 (3H, s), 2.49 (4H, d, J=4.6 Hz), 3.07 (2H, t, J=7.0 Hz), 3.52 (2H, s), 3.64 (2H, brs), 3.74 (2H, brs), 4.10-4.15 (2H, m), 4.38-4.44 (1H, m), 5.14 (2H, s), 6.70-6.82 (5H, m), 6.94 (1H, d, J=9.0 Hz), 7.23-7.31 (7H, m), 7.38-7.41 (2H, m), 7.45 (1H, s), 7.51-7.53 (1H, m), 7.57 (1H, d, J=15.4 Hz), 7.81 (1H, d, J=2.9 Hz).

Example 143

(E)-3-[3,5-Dimethyl-4-({5-[(4-methylbenzyl)oxy]pyridin-2-yl}oxy)phenyl]-1-[4-(4-{2-[4-(propan-2-yloxy)phenoxy]ethyl}benzyl)piperazin-1-yl]prop-2-en-1-one $^1$H-NMR (CDCl$_3$) δ: 1.30 (6H, d, J=6.1 Hz), 2.12 (6H, s), 2.35 (3H, s), 2.48 (4H, t, J=4.6 Hz), 3.07 (2H, t, J=7.1 Hz), 3.52 (2H, s), 3.65 (2H, brs), 3.74 (2H, brs), 4.12 (2H, t, J=7.1 Hz), 4.38-4.44 (1H, m), 4.98 (2H, s), 6.76-6.82 (6H, m), 7.19 (2H, d, J=7.8 Hz), 7.24-7.33 (9H, m), 7.61 (1H, d, J=15.1 Hz), 7.82 (1H, d, J=2.9 Hz).

Example 144

(E)-3-[3-Chloro-5-methyl-4-({5-[(4-methylbenzyl)oxy]pyridin-2-yl}oxy)phenyl]-1-[4-(4-{2-[4-(propan-2-yloxy)phenoxy]ethyl}benzyl)piperazin-1-yl]prop-2-en-1-one $^1$H-NMR (CDCl$_3$) δ: 1.30 (6H, d, J=6.1 Hz), 2.19 (3H, s), 2.36 (3H, s), 2.49 (4H, d, J=4.4 Hz), 3.07 (2H, t, J=7.1 Hz), 3.52 (2H, s), 3.64 (2H, brs), 3.74 (2H, brs), 4.12 (2H, t, J=7.0 Hz), 4.38-4.44 (1H, m), 4.98 (2H, s), 6.78-6.82 (5H, m), 6.92 (1H, d, J=8.8 Hz), 7.19 (2H, d, J=7.8 Hz), 7.23-7.31 (7H, m), 7.35 (1H, dd, J=8.9, 3.1 Hz), 7.45 (1H, s), 7.57 (1H, d, J=15.4 Hz), 7.79 (1H, d, J=2.9 Hz).

Example 145

(E)-3-[4-({5-[(2-Chlorobenzyl)oxy]pyridin-2-yl}oxy)-3,5-dimethylphenyl]-1-[4-(4-{2-[4-(propan-2-yloxy)phenoxy]ethyl}benzyl)piperazin-1-yl]prop-2-en-1-one $^1$H-NMR (CDCl$_3$) δ: 1.30 (6H, d, J=5.9 Hz), 2.12 (6H, s), 2.48 (4H, t, J=4.6 Hz), 3.07 (2H, t, J=7.1 Hz), 3.52 (2H, s), 3.65 (2H, brs), 3.74 (2H, brs), 4.12 (2H, t, J=7.1 Hz), 4.38-4.44 (1H, m), 5.13 (2H, s), 6.77-6.83 (6H, m), 7.25-7.31 (8H, m), 7.35 (1H, dd, J=8.9, 3.1 Hz), 7.39-7.41 (1H, m), 7.51-7.53 (1H, m), 7.61 (1H, d, J=15.4 Hz), 7.84 (1H, d, J=2.9 Hz).

Example 146

4-{[(6-{4-[(E)-3-(4-{4-[2-(4-Chlorophenoxy)ethyl]benzyl}piperazin-1-yl)-3-oxoprop-1-en-1-yl]-2,6-dimethylphenoxy}pyridin-3-yl)oxy]methyl}benzonitrile $^1$H-NMR (CDCl$_3$) δ: 2.11 (6H, s), 2.47-2.48 (4H, m), 3.08 (2H, t, J=7.0 Hz), 3.52 (2H, s), 3.64-3.66 (2H, m), 3.73-3.75 (2H, m), 4.14 (3H, t, J=7.0 Hz), 5.09 (2H, s), 6.79-6.82 (4H, m), 7.20-7.28 (8H, m), 7.33 (1H, dd, J=8.9, 3.1 Hz), 7.52 (2H, d, J=8.1 Hz), 7.60 (1H, d, J=15.4 Hz), 7.68 (2H, d, J=8.1 Hz), 7.79 (1H, d, J=2.9 Hz).

Example 147

(E)-3-[2-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.48 (4H, t, J=4.9 Hz), 3.07 (2H, t, J=7.1 Hz), 3.52 (2H, s), 3.65-3.74 (4H, m), 4.13 (2H, t, J=4.9 Hz), 5.17 (2H, s), 6.76-6.84 (3H, m), 6.89-6.97 (3H, m), 7.03 (1H, s), 7.23-7.32 (6H, m), 7.37-7.42 (2H, m), 7.45 (1H, s), 7.51-7.53 (1H, m), 7.90-7.94 (2H, m).

Example 148

(E)-3-[2-Chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one $^1$H-NMR (DMSO-d$_6$) δ: 2.12 (3H, s), 2.21 (3H, s), 2.30 (3H, s), 2.35-2.42 (4H, m), 2.99 (2H, t, J=6.8 Hz), 3.49 (2H, s), 3.57-3.71 (4H, m), 4.13 (2H, t, J=6.8 Hz), 5.08 (2H, s), 6.79-6.83 (2H, m), 7.05-7.08 (3H, m), 7.11 (1H, s), 7.20 (2H, d, J=7.8 Hz), 7.24-7.29 (5H, m), 7.33 (2H, d, J=7.8 Hz), 7.59 (1H, dd, J=9.0, 3.2 Hz), 7.75 (1H, d, J=15.4 Hz), 7.90 (1H, d, J=3.2 Hz), 7.97 (1H, s).

Example 149

(E)-3-[2-Chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)prop-2-en-1-one $^1$H-NMR (DMSO-d$_6$) δ: 2.12 (3H, s), 2.30 (3H, s), 2.35-2.41 (4H, m), 3.00 (2H, t, J=6.8 Hz), 3.49 (2H, s), 3.57-3.71 (4H, m), 4.16 (2H, t, J=6.8 Hz), 5.08 (2H, s), 6.91-6.96 (2H, m), 7.06-7.12 (4H, m), 7.20 (2H, d, J=7.8 Hz), 7.24-7.29 (5H, m), 7.33 (2H, d, J=7.8 Hz), 7.59 (1H, dd, J=9.0, 3.2 Hz), 7.75 (1H, d, J=15.4 Hz), 7.90-7.91 (1H, m), 7.97 (1H, s).

Example 150

(E)-3-[2-Chloro-4-({5-[(2-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one $^1$H-NMR (CDCl$_3$) δ: 2.19 (3H, s), 2.27 (3H, s), 2.48 (4H, t, J=4.9 Hz), 3.07 (2H, t, J=7.1 Hz), 3.52 (2H, s), 3.64-3.74 (4H, m), 4.14 (2H, t, J=7.1 Hz), 5.17 (2H, s), 6.76-6.81 (3H, m), 6.89-6.91 (1H, m), 7.03-7.07 (3H, m), 7.23-7.33 (6H, m), 7.37-7.42 (2H, m), 7.45 (1H, s), 7.51-7.53 (1H, m), 7.90-7.94 (2H, m).

Example 151

(E)-3-[2-Chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=6.8 Hz), 2.19 (3H, s), 2.36 (3H, s), 2.48 (4H, t, J=4.9 Hz), 2.85 (1H, septet, J=6.8

Hz), 3.07 (2H, t, J=7.1 Hz), 3.52 (2H, s), 3.64-3.74 (4H, m), 4.15 (2H, t, J=7.1 Hz), 5.02 (2H, s), 6.78 (1H, d, J=15.4 Hz), 6.83 (2H, d, J=8.3 Hz), 6.87 (1H, d, J=8.8 Hz), 7.01 (1H, s), 7.12 (2H, d, J=8.5 Hz), 7.19 (2H, d, J=8.1 Hz), 7.23-7.31 (6H, m), 7.34 (1H, dd, J=9.0, 3.2 Hz), 7.44 (1H, s), 7.89-7.94 (2H, m).

Example 152

(E)-3-[2-Chloro-4-({5-[(2-chlorobenzyl)oxy]pyridin-2-yl}oxy)-5-methylphenyl]-1-[4-(4-{2-[4-(propan-2-ypphenoxy]ethyl}benzyl)piperazin-1-yl]prop-2-en-1-one $^1$H-NMR (CDCl$_3$) δ: 1.21 (6H, d, J=6.8 Hz), 2.19 (3H, s), 2.48 (4H, t, J=4.9 Hz), 2.85 (1H, septet, J=6.8 Hz), 3.07 (2H, t, J=7.1 Hz), 3.52 (2H, s), 3.64-3.74 (4H, m), 4.15 (2H, t, J=7.1 Hz), 5.17 (2H, s), 6.76-6.85 (3H, m), 6.89-6.91 (1H, m), 7.03 (1H, s), 7.11-7.15 (2H, m), 7.23-7.32 (6H, m), 7.37-7.42 (2H, m), 7.45 (1H, s), 7.51-7.54 (1H, m), 7.90-7.94 (2H, m).

Example 153

4-{[(6-{4-[(E)-3-(4-{2-[4-(3,5-Dimethylphenoxy)ethyl]benzyl}piperazin-1-yl)-3-oxoprop-1-en-1-yl]-2,6-dimethylphenoxy}pyridin-3-yl)oxy]methyl}benzonitrile $^1$H-NMR (CDCl$_3$) δ: 2.11 (6H, s), 2.27 (6H, s), 2.47-2.48 (4H, m), 3.07 (2H, t, J=7.0 Hz), 3.51 (2H, s), 3.64-3.66 (2H, m), 3.73-3.75 (2H, m), 4.14 (2H, t, J=7.0 Hz), 5.08 (2H, s), 6.53 (2H, s), 6.58 (1H, s), 6.79 (1H, d, J=15.4 Hz), 6.83 (1H, d, J=8.9 Hz), 7.25-7.27 (6H, m), 7.33 (1H, dd, J=8.9, 3.1 Hz), 7.51 (2H, d, J=8.3 Hz), 7.61 (1H, d, J=15.4 Hz), 7.67 (2H, d, J=8.3 Hz), 7.79 (1H, d, J=3.1 Hz).

Example 154

4-{[(6-{2,6-Dimethyl-4-[(E)-3-oxo-3-(4-{4-[2-(quinolin-6-yloxy)ethyl]benzyl}piperazin-1-yl)prop-1-en-1-yl]phenoxy}pyridin-3-yl)oxy]methyl}benzonitrile $^1$H-NMR (CDCl$_3$) δ: 2.11 (6H, s), 2.47-2.49 (4H, m), 3.17 (2H, t, J=7.0 Hz), 3.53 (2H, s), 3.64-3.67 (2H, m), 3.73-3.75 (2H, m), 4.30 (2H, t, J=7.0 Hz), 5.08 (2H, s), 6.79 (1H, d, J=15.1 Hz), 6.83 (1H, d, J=9.0 Hz), 7.06 (1H, d, J=2.4 Hz), 7.25 (1H, s), 7.29-7.34 (6H, m), 7.37 (1H, dd, J=9.3, 2.9 Hz), 7.51 (2H, d, J=8.1 Hz), 7.61 (1H, d, J=15.1 Hz), 7.67 (2H, d, J=8.1 Hz), 7.79 (1H, d, J=2.9 Hz), 7.98-8.00 (2H, m), 8.75 (1H, dd, J=4.2, 1.2 Hz).

Example 155

2-({[6-(2,6-Dimethoxy-4-{(E)-3-oxo-3-[4-(4-{2-[3-(propan-2-yl)phenoxy]ethyl}benzyl)-piperazin-1-yl]prop-1-en-1-yl}phenoxy)pyridin-3-yl]oxy}methyl)benzonitrile $^1$H-NMR (CDCl$_3$) Et: 1.23 (6H, d, J=6.8 Hz), 2.49 (4H, s), 2.83-2.90 (1H, m), 3.09 (2H, t, J=7.1 Hz), 3.53 (2H, s), 3.66 (2H, brs), 3.76 (2H, brs), 3.80 (4H, s), 4.17 (2H, t, J=7.0 Hz), 5.22 (2H, s), 6.72 (1H, d, J=8.1 Hz), 6.76-6.83 (5H, m), 6.97 (1H, d, J=8.8 Hz), 7.19 (1H, t, J=7.9 Hz), 7.26-7.27 (6H, m), 7.38 (1H, dd, J=9.0, 2.9 Hz), 7.42-7.46 (1H, m), 7.60-7.64 (3H, m), 7.70 (1H, d, J=7.8 Hz), 7.82 (1H, d, J=2.7 Hz).

Example 156

2-{[(6-{4-[(E)-3-(4-{2-[4-(4-Fluorophenoxy)ethyl]benzyl}piperazin-1-yl)-3-oxoprop-1-en-1-yl]-2,6-dimethoxyphenoxy}pyridin-3-yl)oxy]methyl}benzonitrile $^1$H-NMR (CDCl$_3$) δ: 2.49 (4H, brs), 3.08 (2H, t, J=7.0 Hz), 3.53 (2H, s), 3.66 (2H, brs), 3.76 (2H, brs), 3.80 (6H, s), 4.13 (2H, t, J=7.0 Hz), 5.22 (2H, s), 6.76-6.84 (5H, m), 6.93-6.98 (3H, m), 7.26 (4H, brs), 7.38 (1H, dd, J=9.0, 2.9 Hz), 7.43-7.46 (1H, m), 7.60-7.64 (3H, m), 7.70 (1H, d, J=7.8 Hz), 7.82 (1H, d, J=2.7 Hz).

Example 157

4-{[(6-{4-[(E)-3-(4-{2-[4-(4-Fluorophenoxy)ethyl]benzyl}piperazin-1-yl)-3-oxoprop-1-en-1-yl]-2,6-dimethoxyphenoxy}pyridin-3-yl)oxy]methyl}benzonitrile $^1$H-NMR (CDCl$_3$) δ: 2.49 (4H, brs), 3.08 (2H, t, J=7.0 Hz), 3.53 (2H, s), 3.66 (2H, brs), 3.76 (2H, brs), 3.79 (6H, s), 4.13 (2H, t, J=7.1 Hz), 5.08 (2H, s), 6.77 (1H, d, J=15.4 Hz), 6.79 (2H, s), 6.82 (2H, dd, J=9.0, 4.4 Hz), 6.93-6.97 (3H, m), 7.23-7.29 (4H, m), 7.32 (1H, dd, J=9.0, 2.9 Hz), 7.52 (2H, d, J=8.3 Hz), 7.61 (1H, d, J=15.1 Hz), 7.67 (2H, d, J=8.3 Hz), 7.77 (1H, d, J=2.9 Hz).

Example 158

4-({[6-(2,6-Dimethoxy-4-{(E)-3-oxo-3-[4-(4-{2-[3-(propan-2-yl)phenoxy]ethyl}benzyl)-piperazin-1-yl]prop-1-en-1-yl}phenoxy)pyridin-3-yl]oxy}methyl)benzonitrile $^1$H-NMR (CDCl$_3$) δ: 1.23 (6H, d, J=6.8 Hz), 2.49 (4H, s), 2.82-2.88 (1H, m), 3.09 (2H, t, J=7.1 Hz), 3.53 (2H, s), 3.66 (2H, brs), 3.76 (2H, brs), 3.79 (4H, s), 4.17 (2H, t, J=7.1 Hz), 5.08 (2H, s), 6.72 (1H, d, J=8.1 Hz), 6.76-6.83 (5H, m), 6.96 (1H, d, J=9.0 Hz), 7.19 (1H, t, J=7.8 Hz), 7.26-7.27 (4H, m), 7.32 (1H, dd, J=9.0, 2.9 Hz), 7.52 (2H, d, J=8.1 Hz), 7.61 (1H, d, J=15.4 Hz), 7.67 (2H, d, J=8.1 Hz), 7.77 (1H, d, J=2.9 Hz).

Example 159

(E)-3-[4-({5-[(4-Fluorobenzyl)oxy]pyridin-2-yl}oxy)-3,5-dimethylphenyl]-1-(4-{3-methyl-4-[2-(4-methylphenoxy)ethyl]benzyl}piperazin-1-yl)prop-2-en-1-one $^1$H-NMR (CDCl$_3$) δ: 2.12 (6H, s), 2.28 (3H, s), 2.37 (3H, s), 2.48 (4H, t, J=5.0 Hz), 3.09 (2H, t, J=7.4 Hz), 3.49 (2H, s), 3.65-3.74 (4H, m), 4.11 (2H, t, J=7.4 Hz), 4.98 (2H, s), 6.76-6.82 (4H, m), 7.05-7.12 (6H, m), 7.18 (1H, d, J=7.6 Hz), 7.25-7.26 (2H, m), 7.32 (1H, dd, J=8.9, 3.1 Hz), 7.36-7.39 (2H, m), 7.61 (1H, d, J=15.4 Hz), 7.81 (1H, d, J=3.1 Hz).

Example 160

(E)-3-[3-Chloro-5-methyl-4-({5-[(4-methylbenzyl)oxy]pyridin-2-yl}oxy)phenyl]-1-(4-{3-methyl-4-[2-(4-methylphenoxy)ethyl]benzyl}piperazin-1-yl)prop-2-en-1-one $^1$H-NMR (CDCl$_3$) δ: 2.19 (3H, s), 2.28 (3H, s), 2.36 (3H, s), 2.37 (3H, s), 2.48 (4H, t, J=4.9 Hz), 3.09 (2H, t, J=7.3 Hz), 3.49 (2H, s), 3.65-3.74 (4H, m), 4.12 (2H, t, J=7.3 Hz), 4.98 (2H, s), 6.78-6.81 (3H, m), 6.91 (1H, dd, J=8.9, 0.6 Hz), 7.06-7.12 (4H, m), 7.17-7.20 (3H, m), 7.28-7.30 (3H, m), 7.35 (1H, dd, J=8.9, 3.1 Hz), 7.45 (1H, d, J=2.2 Hz), 7.56 (1H, d, J=15.4 Hz), 7.79 (1H, dd, J=3.1, 0.6 Hz).

Example 161

(E)-1-(4-{4-[2-(3,4-Dimethylphenoxy)ethyl]benzyl}piperazin-1-yl)-3-(3,5-dimethyl-4-{[5-(pyridin-4-ylmethoxy)pyridin-2-yl]oxy}phenyl)prop-2-en-1-one $^1$H-NMR (CDCl$_3$) δ: 2.12 (6H, s), 2.18 (3H, s), 2.22 (3H, s), 2.47-2.49 (4H, m), 3.07 (2H, t, J=7.0 Hz), 3.52 (2H, s), 3.64-3.66 (2H, m), 3.73-3.76 (2H, m), 4.14 (2H, t, J=7.0 Hz), 5.05 (2H, s), 6.64 (1H, dd, J=8.1, 2.4 Hz), 6.71 (1H, d, J=2.0 Hz), 6.79 (1H, d, J=15.4 Hz), 6.83 (1H, d, J=9.0 Hz), 7.01 (1H, d, J=8.3 Hz), 7.26-7.27 (6H, m), 7.32-7.35 (3H, m), 7.61 (1H, d, J=15.1 Hz), 7.80 (1H, d, J=2.9 Hz), 8.62 (2H, d, J=5.6 Hz).

Example 162

4-{[(6-{5-Chloro-2-methyl-4-[(E)-3-(4-{4-[2-(4-methylphenoxy)ethyl]benzyl}piperazin-1-yl)-3-oxoprop-1-en-1-yl]phenoxy}pyridin-3-yl)oxy]methyl}benzonitrile $^1$H-NMR (CDCl$_3$) δ: 2.18 (3H, s), 2.27 (3H, s), 2.48 (4H, t, J=4.9 Hz), 3.07 (2H, t, J=7.1 Hz), 3.52 (2H, s), 3.64-3.74 (4H, m), 4.14 (2H, t, J=7.1 Hz), 5.12 (2H, s), 6.77-6.81 (3H, m), 6.90-6.92 (1H, m), 7.03 (1H, s), 7.05-7.08 (2H, m), 7.23-7.28 (4H, m), 7.36 (1H, dd, J=9.0, 3.2 Hz), 7.45 (1H, s), 7.53 (2H, d, J=8.5 Hz), 7.68-7.70 (2H, m), 7.87 (1H, d, J=3.2 Hz), 7.92 (1H, d, J=15.4 Hz).

Example 163

4-{[(6-{2-Chloro-4-[(E)-3-(4-{4-[2-(4-fluorophenoxy)ethyl]benzyl}piperazin-1-yl)-3-oxoprop-1-en-1-yl]-5-methylphenoxy}pyridin-3-yl)oxy]methyl}benzonitrile $^1$H-NMR (CDCl$_3$) δ: 2.37 (3H, s), 2.49 (4H, t, J=4.9 Hz), 3.07 (2H, t, J=7.1 Hz), 3.53 (2H, s), 3.65-3.75 (4H, m), 4.13 (2H, t, J=7.1 Hz), 5.11 (2H, s), 6.73 (1H, d, J=15.4 Hz), 6.80-6.85 (2H, m), 6.92-6.99 (4H, m), 7.23-7.28 (4H, m), 7.36 (1H, dd, J=9.0, 3.2 Hz), 7.52 (2H, d, J=8.5 Hz), 7.58 (1H, s), 7.67-7.70 (2H, m), 7.81-7.85 (2H, m).

Example 164

4-{[(6-{5-Chloro-4-[(E)-3-(4-{4-[2-(4-fluorophenoxy)ethyl]benzyl}piperazin-1-yl)-3-oxoprop-1-en-1-yl]-2-methylphenoxy}pyridin-3-yl)oxy]methyl}benzonitrile $^1$H-NMR (CDCl$_3$) δ: 2.18 (3H, s), 2.48 (4H, t, J=4.9 Hz), 3.07 (2H, t, J=7.1 Hz), 3.52 (2H, s), 3.64-3.74 (4H, m), 4.13 (2H, t, J=7.1 Hz), 5.12 (2H, s), 6.77-6.85 (3H, m), 6.90-6.99 (3H, m), 7.03 (1H, s), 7.23-7.28 (4H, m), 7.36 (1H, dd, J=9.0, 3.2 Hz), 7.45 (1H, s), 7.52-7.54 (2H, m), 7.68-7.71 (2H, m), 7.87 (1H, d, J=3.2 Hz), 7.92 (1H, d, J=15.4 Hz).

Example 165

4-({[6-(2-Chloro-5-methyl-4-{(E)-3-oxo-3-[4-(4-{2-[4-(propan-2-yl)phenoxy]ethyl}benzyl)-piperazin-1-yl]prop-1-en-1-yl}phenoxy)pyridin-3-yl]oxy}methyl)benzonitrile $^1$H-NMR (CDCl$_3$) δ: 1.21 (6H, d, J=7.1 Hz), 2.37 (3H, s), 2.48 (4H, t, J=4.9 Hz), 2.85 (1H, septet, J=7.1 Hz), 3.08 (2H, t, J=7.1 Hz), 3.52 (2H, s), 3.64-3.75 (4H, m), 4.15 (2H, t, J=7.1 Hz), 5.11 (2H, s), 6.73 (1H, d, J=15.4 Hz), 6.81-6.85 (2H, m), 6.96 (1H, dd, J=8.8, 0.5 Hz), 6.99 (1H, s), 7.11-7.14 (2H, m), 7.23-7.28 (4H, m), 7.36 (1H, dd, J=8.8, 3.2 Hz), 7.51-7.53 (2H, m), 7.58 (1H, s), 7.67-7.70 (2H, m), 7.81-7.85 (2H, m).

Example 166

4-({[6-(5-Chloro-2-methyl-4-{(E)-3-oxo-3-[4-(4-{2-[4-(propan-2-yl)phenoxy]ethyl}benzyl)-piperazin-1-yl]prop-1-en-1-yl}phenoxy)pyridin-3-yl]oxy}methyl)benzonitrile $^1$H-NMR (CDCl$_3$) δ: 1.21 (6H, d, J=6.8 Hz), 2.18 (3H, s), 2.48 (4H, t, J=4.9 Hz), 2.85 (1H, septet, J=6.8 Hz), 3.08 (2H, t, J=7.1 Hz), 3.52 (2H, s), 3.64-3.75 (4H, m), 4.15 (2H, t, J=7.1 Hz), 5.12 (2H, s), 6.77-6.85 (3H, m), 6.90-6.92 (1H, m), 7.03 (1H, s), 7.11-7.14 (2H, m), 7.23-7.28 (4H, m), 7.36 (1H, dd, J=9.0, 3.2 Hz), 7.45 (1H, s), 7.52-7.54 (2H, m), 7.68-7.71 (2H, m), 7.86-7.87 (1H, m), 7.92 (1H, d, J=15.4 Hz).

Example 167

4-{[(6-{2-Chloro-5-methyl-4-[(E)-3-(4-{4-[2-(4-methylphenoxy)ethyl]benzyl}piperazin-1-yl)-3-oxoprop-1-en-1-yl]phenoxy}pyridin-3-yl)oxy]methyl}benzonitrile $^1$H-NMR (CDCl$_3$) δ: 2.27 (3H, s), 2.37 (3H, s), 2.49 (4H, t, J=4.9 Hz), 3.08 (2H, t, J=7.1 Hz), 3.52 (2H, s), 3.64-3.75 (4H, m), 4.14 (2H, t, J=7.1 Hz), 5.11 (2H, s), 6.73 (1H, d, J=15.1 Hz), 6.78-6.81 (2H, m), 6.96 (1H, d, J=8.8 Hz), 6.99 (1H, s), 7.05-7.08 (2H, m), 7.23-7.28 (4H, m), 7.36 (1H, dd, J=8.8, 3.2 Hz), 7.52 (2H, d, J=8.1 Hz), 7.58 (1H, s), 7.67-7.69 (2H, m), 7.81-7.85 (2H, m).

Example 168

(E)-1-(4-{4-[2-(2-Chlorophenoxy)ethyl]benzyl}piperazin-1-yl)-3-[3,5-dimethyl-4-({5-[(6-methylpyridin-2-yl)methoxy]pyridin-2-yl}oxy)phenyl]prop-2-en-1-one $^1$H-NMR (CDCl$_3$) δ: 2.11 (6H, s), 2.47-2.48 (4H, m), 2.55 (3H, s), 3.14 (2H, t, J=7.0 Hz), 3.52 (2H, s), 3.64-3.66 (2H, m), 3.73-3.75 (2H, m), 4.21 (2H, t, J=7.0 Hz), 5.12 (2H, s), 6.78-6.81 (2H, m), 6.85-6.89 (2H, m), 7.08 (1H, d, J=7.8 Hz), 7.16-7.18 (1H, m), 7.24-7.30 (7H, m), 7.33-7.37 (2H, m), 7.58-7.63 (2H, m), 7.84 (1H, d, J=2.9 Hz).

Example 169

(E)-1-(4-{4-[2-(3-Chlorophenoxy)ethyl]
benzyl}piperazin-1-yl)-3-(3,5-dimethyl-4-{[5-(pyridin-4-ylmethoxy)pyridin-2-yl]oxy}phenyl)prop-2-en-1-one ¹H-NMR (CDCl₃) δ: 2.11 (6H, s), 2.47-2.49 (4H, m), 3.08 (2H, t, J=7.0 Hz), 3.52 (2H, s), 3.64-3.67 (2H, m), 3.73-3.75 (2H, m), 4.15 (2H, t, J=7.0 Hz), 5.05 (2H, s), 6.79-6.83 (3H, m), 6.89-6.91 (2H, m), 7.16-7.18 (1H, m), 7.25-7.27 (6H, m), 7.32-7.35 (3H, m), 7.61 (1H, d, J=15.4 Hz), 7.80 (1H, d, J=2.9 Hz), 8.62 (2H, d, J=5.9 Hz).

Example 170

(E)-3-(4-{[5-(1,3-Benzothiazol-6-ylmethoxy)pyridin-2-yl]oxy}-3,5-dimethoxyphenyl)-1-[4-(4-{2-[4-(propan-2-yloxy)phenoxy]ethyl}benzyl)piperazin-1-yl]prop-2-en-1-one ¹H-NMR (CDCl₃) δ: 1.30 (6H, d, J=6.1 Hz), 2.49 (4H, s), 3.07 (2H, t, J=7.0 Hz), 3.52 (2H, s), 3.65 (2H, brs), 3.75 (2H, brs), 3.79 (6H, s), 4.12 (2H, t, J=7.0 Hz), 4.41 (1H, septet, J=6.1 Hz), 5.18 (2H, s), 6.75-6.79 (3H, m), 6.81 (4H, s), 6.95 (1H, d, J=8.8 Hz), 7.26 (4H, brs), 7.35 (1H, dd, J=8.8, 2.9 Hz), 7.54 (1H, d, J=8.5 Hz), 7.61 (1H, d, J=15.4 Hz), 7.82 (1H, d, J=2.9 Hz), 8.02 (1H, s), 8.14 (1H, d, J=8.5 Hz), 9.01 (1H, s).

Example 171

(E)-3-[4-({5-[4-Fluorobenzyl)oxy]pyridin-2-yl}oxy)-3,5-dimethylphenyl]-1-(4-{4-[2-(4-fluorophenoxy)ethyl]-3-methylbenzyl}piperazin-1-yl)prop-2-en-1-one ¹H-NMR (CDCl₃) δ: 2.12 (6H, s), 2.37 (3H, s), 2.48 (4H, t, J=4.8 Hz), 3.09 (2H, t, J=7.3 Hz), 3.49 (2H, s), 3.66-3.73 (4H, m), 4.10 (2H, t, J=7.3 Hz), 4.99 (2H, s), 6.76-6.85 (4H, m), 6.93-7.00 (2H, m), 7.05-7.13 (4H, m), 7.18 (1H, d, J=7.6 Hz), 7.25-7.26 (2H, m), 7.32 (1H, dd, J=8.9, 3.1 Hz), 7.36-7.39 (2H, m), 7.61 (1H, d, J=15.4 Hz), 7.81 (1H, d, J=3.1 Hz).

Example 172

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]-3-methylbenzyl}piperazin-1-yl)prop-2-en-1-one ¹H-NMR (CDCl₃) δ: 2.19 (3H, s), 2.36 (3H, s), 2.37 (3H, s), 2.48 (4H, t, J=5.0 Hz), 3.09 (2H, t, J=7.3 Hz), 3.49 (2H, s), 3.64-3.74 (4H, m), 4.10 (2H, t, J=7.3 Hz), 4.99 (2H, s), 6.78-6.84 (3H, m), 6.90-7.00 (3H, m), 7.10-7.13 (2H, m), 7.17-7.20 (3H, m), 7.28-7.30 (3H, m), 7.35 (1H, dd, J=8.9, 3.1 Hz), 7.45 (1H, d, J=2.2 Hz), 7.57 (1H, d, J=15.4 Hz), 7.79 (1H, d, J=3.1 Hz).

Example 173

(E)-3-(4-{[5-(1,3-Benzothiazol-6-ylmethoxy)pyridin-2-yl]oxy}-3,5-dimethoxyphenyl)-1-(4-{4-[2-(4-fluorophenoxy)ethyl]benzyl}piperazin-1-yl)prop-2-en-1-one ¹H-NMR (CDCl₃) δ: 2.49 (4H, t, J=4.8 Hz), 3.08 (2H, t, J=7.1 Hz), 3.53 (2H, s), 3.66 (2H, brs), 3.75 (2H, brs), 3.79 (6H, s), 4.13 (2H, t, J=7.1 Hz), 5.18 (2H, s), 6.75-6.79 (3H, m), 6.81-6.84 (2H, m), 6.93-6.98 (3H, m), 7.24 (2H, d, J=8.1 Hz), 7.27 (2H, d, J=8.1 Hz), 7.35 (1H, dd, J=9.0, 2.9 Hz), 7.54 (1H, d, J=8.5 Hz), 7.61 (1H, d, J=15.4 Hz), 7.82 (1H, d, J=2.9 Hz), 8.02 (1H, s), 8.14 (1H, d, J=8.5 Hz), 9.01 (1H, s).

Example 174

(E)-1-(4-{4-[2-(4-tert-Butylphenoxy)ethyl]
benzyl}piperazin-1-yl)-3-[4-({5-[3,4-difluorobenzyl)oxy]pyridin-2-yl}oxy)-3-fluorophenyl]prop-2-en-1-one ¹H-NMR (CDCl₃) δ: 1.29 (9H, s), 2.48 (4H, t, J=5.0 Hz), 3.08 (2H, t, J=7.0 Hz), 3.52 (2H, s), 3.63-3.74 (4H, m), 4.16 (2H, t, J=7.1 Hz), 4.99 (2H, s), 6.79 (1H, d, J=15.4 Hz), 6.82-6.86 (2H, m), 6.96 (1H, dd, J=9.0, 0.5 Hz), 7.10-7.37 (13H, m), 7.60 (1H, d, J=15.4 Hz), 7.81 (1H, dd, J=3.1, 0.6 Hz).

Example 175

4-({[6-(2,6-Dimethyl-4-{(E)-3-[4-(4-{2-[6-methylpyridin-2-yl)oxy]ethyl}benzyl)piperazin-1-yl]-3-oxoprop-1-en-1-yl}phenoxy)pyridin-3-yl]oxy}methyl)benzonitrile ¹H-NMR (CDCl₃) δ: 2.11 (6H, s), 2.43 (3H, s), 2.47-2.48 (4H, m), 3.08 (2H, t, J=7.2 Hz), 3.51 (2H, s), 3.64-3.66 (2H, m), 3.73-3.75 (2H, m), 4.49 (2H, t, J=7.2 Hz), 5.09 (2H, s), 6.51 (1H, d, J=8.3 Hz), 6.69-6.70 (1H, m), 6.79 (1H, d, J=15.4 Hz), 6.83 (1H, d, J=8.9 Hz), 7.25-7.26 (6H, m), 7.33 (1H, dd, J=8.9, 2.9 Hz), 7.43-7.45 (1H, m), 7.52 (2H, d, J=8.1 Hz), 7.60 (1H, d, J=15.4 Hz), 7.68 (2H, d, J=8.1 Hz), 7.80 (1H, d, J=2.9 Hz).

Example 176

(E)-3-[4-({5-[(3,4-Difluorobenzyl)oxy]pyridin-2-yl}oxy)-3-fluorophenyl]-1-(4-{4-[(4-methylphenoxy)acetyl]benzyl}piperazin-1-yl)prop-2-en-1-one mp: 152.9-154.3° C.

Example 177

(E)-3-[3-Chloro-4-({5-[(2-chlorobenzyl)oxy]pyridin-2-yl}oxy)-5-methylphenyl]-1-(4-{4-[(4-methylphenoxy)acetyl]benzyl}piperazin-1-yl)prop-2-en-1-one ¹H-NMR (CDCl₃) δ: 2.20 (3H, s), 2.28 (3H, s), 2.50 (4H, t, J=5.0 Hz), 3.60 (2H, s), 3.67-3.76 (4H, m), 5.14 (2H, s), 5.22 (2H, s), 6.80 (1H, d, J=15.4 Hz), 6.83-6.87 (2H, m), 6.95 (1H, dd, J=9.0, 0.5 Hz), 7.08 (2H, dd, J=8.7, 0.6 Hz), 7.25-7.32 (3H, m), 7.38-7.41 (2H, m), 7.46-7.53 (4H, m), 7.58 (1H, d, J=15.4 Hz), 7.81 (1H, dd, J=2.9, 0.5 Hz), 7.97-8.00 (2H, m).

Example 178

(E)-1-(4-{4-[2-(4-Fluorophenoxy)ethyl]-3-methylbenzyl}piperazin-1-yl)-3-[4-({5-[(4-methoxybenzyl)oxy]pyridin-2-yl}oxy)-3,5-dimethylphenyl]prop-2-en-1-one ¹H-NMR (CDCl₃) δ: 2.12 (6H, s), 2.37 (3H, s), 2.48 (4H, t, J=4.9 Hz), 3.09 (2H, t, J=7.3 Hz), 3.49 (2H, s), 3.66 (2H, brs), 3.74 (2H, brs), 3.81 (3H, s), 4.10 (2H, t, J=7.3 Hz), 4.95 (2H, s), 6.76-6.85 (4H, m), 6.89-7.00 (4H, m), 7.10-7.13 (2H, m), 7.18 (1H, d, J=7.8 Hz), 7.25-7.26 (2H, m), 7.30-7.34 (3H, m), 7.61 (1H, d, J=15.4 Hz), 7.82 (1H, d, J=2.9 Hz).

Example 179

4-{[(6-{2-Fluoro-4-[(E)-3-(4-{4-[(4-methylphenoxy)acetyl]benzyl}piperazin-1-yl)-3-oxoprop-1-en-1-yl]phenoxy}pyridin-3-yl)oxy]methyl}benzonitrile mp: 137.1-137.9° C.

Example 180

4-({[6-(2-Fluoro-4-{(E)-3-oxo-3-[4-(4-{2-[4-(propan-2-yl)phenoxy]ethyl}benzyl)piperazin-1-yl]prop-1-en-1-yl}phenoxy)pyridin-3-yl]oxy}methyl)benzonitrile $^1$H-NMR (CDCl$_3$) δ: 1.22 (6H, d, J=7.1 Hz), 2.48 (4H, t, J=5.0 Hz), 2.85 (1H, septet, J=7.1 Hz), 3.08 (2H, t, J=7.1 Hz), 3.52 (2H, s), 3.63-3.74 (4H, m), 4.15 (2H, t, J=7.1 Hz), 5.11 (2H, s), 6.79 (1H, d, J=15.4 Hz), 6.82-6.85 (2H, m), 6.97 (1H, dd, J=8.9, 0.6 Hz), 7.11-7.15 (2H, m), 7.19 (1H, t, J=8.1 Hz), 7.23-7.38 (7H, m), 7.51-7.54 (2H, m), 7.60 (1H, d, J=15.4 Hz), 7.67-7.70 (2H, m), 7.81 (1H, dd, J=3.2, 0.5 Hz).

Example 181

(E)-3-(3,5-Dimethyl-4-{[5-(1,3-thiazol-4-ylmethoxy)pyridin-2-yl]oxy}phenyl)-1-(4-{4-[2-(4-methylphenoxy)ethyl]benzyl}piperazin-1-yl)prop-2-en-1-one $^1$H-NMR (CDCl$_3$) δ: 2.12 (6H, s), 2.27 (3H, s), 2.46-2.49 (4H, m), 3.07 (2H, t, J=7.1 Hz), 3.52 (2H, s), 3.65-3.74 (4H, m), 4.14 (2H, t, J=7.1 Hz), 5.22 (2H, s), 6.76-6.83 (4H, m), 7.05-7.08 (2H, m), 7.23-7.28 (6H, m), 7.36-7.41 (2H, m), 7.60 (1H, d, J=15.4 Hz), 7.86 (1H, d, J=3.2 Hz), 8.83 (1H, d, J=2.2 Hz).

Example 182

(E)-3-(3,5-Dimethyl-4-{[5-(1,3-thiazol-4-ylmethoxy)pyridin-2-yl]oxy}phenyl)-1-(4-{4-[2-(4-fluorophenoxy)ethyl]benzyl}piperazin-1-yl)prop-2-en-1-one $^1$H-NMR (CDCl$_3$) δ: 2.12 (6H, s), 2.47 (4H, t, J=4.9 Hz), 3.07 (2H, t, J=7.1 Hz), 3.52 (2H, s), 3.65-3.74 (4H, m), 4.13 (2H, t, J=7.1 Hz), 5.22 (2H, s), 6.76-6.84 (4H, m), 6.92-6.97 (2H, m), 7.23-7.28 (6H, m), 7.36-7.40 (2H, m), 7.60 (1H, d, J=15.4 Hz), 7.86 (1H, d, J=2.9 Hz), 8.83-8.84 (1H, m).

Example 183

(E)-3-(3,5-Dimethyl-4-{[5-(1,3-thiazol-4-ylmethoxy)pyridin-2-yl]oxy}phenyl)-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=6.8 Hz), 2.12 (6H, s), 2.47 (4H, t, J=4.9 Hz), 2.85 (1H, septet, J=6.8 Hz), 3.08 (2H, t, J=7.1 Hz), 3.51 (2H, s), 3.65-3.74 (4H, m), 4.15 (2H, t, J=7.1 Hz), 5.22 (2H, s), 6.77-6.85 (4H, m), 7.11-7.15 (2H, m), 7.23-7.28 (6H, m), 7.36-7.41 (2H, m), 7.61 (1H, d, J=15.4 Hz), 7.86 (1H, dd, J=3.2, 2.7 Hz), 8.83 (1H, d, J=2.0 Hz).

Example 184

(E)-3-[4-({5-[(4-Methoxybenzyl)oxy]pyridin-2-yl}oxy)-3,5-dimethylphenyl]-1-(4-{3-methyl-4-[2-(4-methylphenoxy)ethyl]benzyl}piperazin-1-yl)prop-2-en-1-one $^1$H-NMR (CDCl$_3$) δ: 2.12 (6H, s), 2.28 (3H, s), 2.37 (3H, s), 2.48 (4H, t, J=4.9 Hz), 3.09 (2H, t, J=7.4 Hz), 3.49 (2H, s), 3.66 (2H, brs), 3.75 (2H, brs), 3.81 (3H, s), 4.11 (2H, t, J=7.4 Hz), 4.95 (2H, s), 6.76-6.82 (4H, m), 6.91 (2H, dt, J=9.1, 2.4 Hz), 7.06-7.13 (4H, m), 7.18 (1H, d, J=7.6 Hz), 7.25-7.26 (2H, m), 7.30-7.34 (3H, m), 7.61 (1H, d, J=15.1 Hz), 7.82 (1H, d, J=2.9 Hz).

Example 185

4-{[(6-{4-[(E)-3-(4-{4-[2-(4-Fluorophenoxy)ethyl]-3-methylbenzyl}piperazin-1-yl)-3-oxoprop-1-en-1-yl]-2,6-dimethylphenoxy}pyridin-3-yl)oxy]methyl}benzonitrile $^1$H-NMR (CDCl$_3$) δ: 2.11 (6H, s), 2.37 (3H, s), 2.48 (4H, t, J=5.0 Hz), 3.09 (2H, t, J=7.3 Hz), 3.65 (2H, brs), 3.75 (2H, brs), 4.10 (2H, t, J=7.3 Hz), 5.09 (2H, s), 6.76-6.85 (4H, m), 6.93-6.98 (2H, m), 7.10-7.13 (2H, m), 7.18 (1H, d, J=7.6 Hz), 7.25-7.26 (4H, m), 7.33 (1H, dd, J=8.9, 3.1 Hz), 7.52 (2H, d, J=8.5 Hz), 7.61 (1H, d, J=15.4 Hz), 7.68 (2H, d, J=8.5 Hz), 7.79 (1H, d, J=3.1 Hz).

Example 186

(E)-3-{3-Chloro-4-[(5-{[4-(difluoromethoxy)benzyl]oxy}pyridin-2-yl)oxy]-5-methylphenyl}-1-(4-{4-[2-(4-methylphenoxy)ethyl]benzyl}piperazin-1-yl)prop-2-en-1-one $^1$H-NMR (CDCl$_3$) δ: 2.19 (3H, s), 2.28 (3H, s), 2.47-2.49 (4H, m), 3.06-3.09 (2H, m), 3.52 (2H, s), 3.64 (2H, brs), 3.74 (2H, brs), 4.11-4.16 (2H, m), 5.00 (2H, s), 6.51 (1H, t, J=73.8 Hz), 6.80 (1H, d, J=15.3 Hz), 6.80 (2H, d, J=8.3 Hz), 6.93 (1H, d, J=8.8 Hz), 7.07 (2H, d, J=8.3 Hz), 7.14 (2H, d, J=8.3 Hz), 7.26 (4H, brs), 7.28 (1H, brs), 7.36 (1H, dd, J=8.8, 2.9 Hz), 7.40 (2H, d, J=8.3 Hz), 7.45 (1H, brs), 7.56 (1H, d, J=15.3 Hz), 7.78 (1H, d, J=2.9 Hz).

Example 187

(E)-1-(4-{4-[2-(4-Fluorophenoxy)propyl]benzyl}piperazin-1-yl)-3-[4-({5-[(4-methoxybenzyl)oxy]pyridin-2-yl}oxy)-3,5-dimethylphenyl]prop-2-en-1-one $^1$H-NMR (CDCl$_3$) δ: 1.29 (3H, d, J=6.1 Hz), 2.12 (6H, s), 2.46 (4H, t, J=4.9 Hz), 2.81 (1H, dd, J=13.7, 6.3 Hz), 3.05 (1H, dd, J=13.7, 6.1 Hz), 3.51 (2H, s), 3.64-3.74 (4H, m), 3.81 (3H, s), 4.43-4.51 (1H, m), 4.95 (2H, s), 6.76-6.82 (4H, m), 6.90-6.96 (4H, m), 7.19 (2H, d, J=8.1 Hz), 7.24-7.26 (4H, m), 7.30-7.34 (3H, m), 7.61 (1H, d, J=15.4 Hz), 7.82 (1H, d, J=3.2 Hz).

Example 188

(E)-3-[4-({5-[(4-Fluorobenzyl)oxy]pyridin-2-yl}oxy)-3,5-dimethylphenyl]-1-(4-{4-[2-(4-fluorophenoxy)propyl]benzyl}piperazin-1-yl)prop-2-en-1-one ¹H-NMR (CDCl₃) δ: 1.29 (3H, d, J=6.1 Hz), 2.12 (6H, s), 2.47 (4H, t, J=5.0 Hz), 2.81 (1H, dd, J=13.7, 6.3 Hz), 3.05 (1H, dd, J=13.7, 6.1 Hz), 3.51 (2H, s), 3.65 (2H, brs), 3.74 (2H, brs), 4.43-4.51 (1H, m), 4.98 (2H, s), 6.76-6.82 (4H, m), 6.91-6.95 (2H, m), 7.05-7.09 (2H, m), 7.19 (2H, d, J=8.1 Hz), 7.24-7.26 (4H, m), 7.32 (1H, dd, J=8.9, 3.1 Hz), 7.36-7.40 (2H, m), 7.61 (1H, d, J=15.4 Hz), 7.81 (1H, d, J=3.1 Hz).

Example 189

(E)-3-[4-({5-[(4-Fluorobenzyl)oxy]pyridin-2-yl}oxy)-3,5-dimethylphenyl]-1-(4-{2-methyl-4-[2-(4-methylphenoxy)ethyl]benzyl}piperazin-1-yl)prop-2-en-1-one ¹H-NMR (CDCl₃) δ: 2.12 (6H, s), 2.28 (3H, s), 2.36 (3H, s), 2.47 (4H, t, J=5.0 Hz), 3.04 (2H, t, J=7.2 Hz), 3.47 (2H, s), 3.63 (2H, brs), 3.71 (2H, brs), 4.14 (2H, t, J=7.2 Hz), 4.99 (2H, s), 6.79 (1H, d, J=15.6 Hz), 6.79-6.82 (2H, m), 7.05-7.09 (5H, m), 7.19 (1H, d, J=7.3 Hz), 7.25-7.26 (4H, m), 7.32 (1H, dd, J=8.9, 3.1 Hz), 7.36-7.39 (2H, m), 7.61 (1H, d, J=15.6 Hz), 7.81 (1H, d, J=3.1 Hz).

Example 190

(E)-3-[4-({5-[(4-Methoxybenzyl)oxy]pyridin-2-yl}oxy)-3,5-dimethylphenyl]-1-(4-{2-methyl-4-[2-(4-methylphenoxy)ethyl]benzyl}piperazin-1-yl)prop-2-en-1-one ¹H-NMR (CDCl₃) δ: 2.12 (6H, s), 2.28 (3H, s), 2.37 (3H, s), 2.48 (4H, t, J=4.9 Hz), 3.04 (2H, t, J=7.3 Hz), 3.47 (2H, s), 3.63 (2H, brs), 3.71 (2H, brs), 3.81 (3H, s), 4.14 (2H, t, J=7.3 Hz), 4.95 (2H, s), 6.77-6.82 (3H, m), 6.91 (2H, dt, J=9.3, 2.4 Hz), 7.06-7.09 (3H, m), 7.19 (1H, d, J=7.6 Hz), 7.25-7.26 (4H, m), 7.30-7.34 (3H, m), 7.61 (1H, d, J=15.4 Hz), 7.82 (1H, d, J=2.7 Hz).

Example 191

4-({[6-(2-Chloro-4-{(E)-3-[4-(4-{2-[4-(2-hydroxyethyl)phenoxy]ethyl}benzyl)piperazin-1-yl]-3-oxoprop-1-en-1-yl}-6-methylphenoxy)pyridin-3-yl]oxy}methyl)benzonitrile ¹H-NMR (CDCl₃) δ: 1.74-1.76 (1H, m), 2.19 (3H, s), 2.47-2.49 (4H, m), 2.80 (2H, t, J=6.5 Hz), 3.08 (2H, t, J=7.1 Hz), 3.52 (2H, s), 3.63-3.65 (2H, m), 3.73-3.75 (2H, m), 3.81 (2H, t, J=6.5 Hz), 4.15 (2H, t, J=7.1 Hz), 5.09 (2H, s), 6.80-6.84 (3H, m), 6.95 (1H, d, J=8.8 Hz), 7.13 (2H, d, J=8.3 Hz), 7.25-7.27 (5H, m), 7.36-7.38 (1H, m), 7.45-7.58 (4H, m), 7.68 (2H, d, J=8.1 Hz), 7.76 (1H, d, J=2.7 Hz).

Example 192

4-{[(6-{2-Chloro-6-methyl-4-[(E)-3-oxo-3-{4-[4-(2-[5-(trifluoromethyl)pyridin-2-yl]oxy}-ethyl)benzyl]piperazin-1-yl}prop-1-en-1-yl]phenoxy}pyridin-3-yl)oxy]methyl}benzonitrile ¹H-NMR (CDCl₃) δ: 2.19 (3H, s), 2.48 (4H, t, J=5.0 Hz), 3.09 (2H, t, J=7.1 Hz), 3.52 (2H, s), 3.64-3.74 (4H, m), 4.58 (2H, t, J=7.1 Hz), 5.09 (2H, s), 6.79 (1H, d, J=5.1 Hz), 6.82 (1H, d, J=1.5 Hz), 6.96 (1H, dd, J=9.0, 0.5 Hz), 7.24-7.29 (5H, m), 7.37 (1H, dd, J=8.9, 3.1 Hz), 7.45 (1H, d, J=2.2 Hz), 7.51-7.59 (3H, m), 7.68 (2H, dt, J=8.2, 1.7 Hz), 7.74-7.77 (2H, m), 8.42-8.43 (1H, m).

Example 193

4-{[(6-{4[(E)-3-(4-{4-[2-(4-Chlorophenoxy)ethyl]-3-fluorobenzyl}piperazin-1-yl)-3-oxoprop-1-en-1-yl]-2,6-dimethylphenoxy}pyridin-3-yl)oxy]methyl}benzonitrile ¹H-NMR (CDCl₃) δ: 2.11 (6H, s), 2.47-2.48 (4H, m), 3.11 (2H, t, J=7.0 Hz), 3.51 (2H, s), 3.65-3.67 (2H, m), 3.73-3.76 (2H, m), 4.15 (2H, t, J=7.0 Hz), 5.09 (2H, s), 6.79-6.82 (4H, m), 7.04-7.07 (2H, m), 7.21-7.25 (5H, m), 7.33 (1H, dd, J=8.9, 3.1 Hz), 7.52 (2H, d, J=8.1 Hz), 7.61 (1H, d, J=15.1 Hz), 7.68 (2H, d, J=8.1 Hz), 7.79 (1H, d, J=2.9 Hz).

Example 194

4-({[6-(4-{(E)-3-[4-(2-Fluoro-4-{2-[4-(trifluoromethyl)phenoxy]ethyl}benzyl)piperazin-1-yl]-3-oxoprop-1-en-1-yl}-2,6-dimethylphenoxy)pyridin-3-yl]oxy}methyl)benzonitrile ¹H-NMR (CDCl₃) δ: 2.11 (6H, s), 2.51-2.53 (4H, m), 3.10 (2H, t, J=6.7 Hz), 3.61 (2H, s), 3.65-3.67 (2H, m), 3.73-3.76 (2H, m), 4.21 (2H, t, J=6.7 Hz), 5.09 (2H, s), 6.78-6.83 (2H, m), 6.96-7.03 (4H, m), 7.27-7.32 (4H, m), 7.52-7.53 (4H, m), 7.60 (1H, d, J=15.1 Hz), 7.67 (2H, d, J=8.1 Hz), 7.79 (1H, d, J=2.9 Hz).

Example 195

(E)-3-[3-Chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)prop-2-en-1-one ¹H-NMR (CDCl₃) δ: 2.10 (3H, d, J=1.5 Hz), 2.18 (3H, s), 2.28 (3H, s), 2.36 (3H, s), 2.45 (4H, brs), 3.08 (2H, t, J=7.1 Hz), 3.52 (2H, s), 3.54-3.75 (4H, brs), 4.14 (2H, t, J=7.1 Hz), 4.99 (2H, s), 6.41 (1H, d, J=1.5 Hz), 6.77-6.93 (2H, m), 6.90 (1H, dd, J=9.0, 0.5 Hz), 7.02-7.11 (3H, m), 7.18 (2H, d, J=7.6 Hz), 7.22-7.31 (7H, m), 7.35 (1H, dd, J=9.0, 2.9 Hz), 7.80 (1H, dd, J=2.9, 0.5 Hz).

Example 196

(E)-3-[3-Chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]but-2-en-1-one ¹H-NMR (CDCl₃) δ: 1.21 (6H, d, J=6.8 Hz), 2.19 (3H, s), 2.22 (3H, d, J=1.2 Hz), 2.36 (3H, s), 2.44 (4H, dt, J=17.3, 4.9 Hz), 2.85 (1H, septet, J=6.8 Hz), 3.08 (2H, t, J=7.1 Hz), 3.51 (2H, t, J=4.9 Hz), 3.53 (2H, t, J=4.9 Hz), 3.72 (2H, t, J=4.9 Hz), 4.15 (2H, t, J=7.1 Hz), 4.99 (2H, s), 6.23 (1H, d, J=1.0 Hz), 6.80-6.88 (2H, m), 6.91 (1H, dd, J=8.8, 0.5 Hz), 7.09-7.15

(2H, m), 7.18 (2H, d, J=7.8 Hz), 7.22-7.31 (7H, m), 7.32-7.39 (2H, m), 7.80 (1H, d, J=2.4 Hz).

Example 197

(E)-3-[3-Chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)but-2-en-1-one $^1$H-NMR (CDCl$_3$) δ: 2.19 (3H, s), 2.22 (3H, d, J=1.2 Hz), 2.28 (3H, s), 2.36 (3H, s), 2.44 (4H, dt, J=17.1, 4.9 Hz), 3.08 (2H, t, J=7.1 Hz), 3.51 (2H, s), 3.53 (2H, t, J=4.9 Hz), 3.72 (2H, t, J=4.9 Hz), 4.14 (2H, t, J=7.1 Hz), 4.98 (2H, s), 6.23 (1H, d, J=1.2 Hz), 6.76-6.82 (2H, m), 6.91 (1H, dd, J=8.8, 0.5 Hz), 7.04-7.09 (2H, m), 7.18 (2H, d, J=7.8 Hz), 7.21-7.31 (7H, m), 7.33-7.39 (2H, m), 7.80 (1H, dd, J=2.9, 0.5 Hz).

Example 198

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)but-2-en-1-one $^1$H-NMR (CDCl$_3$) δ: 2.19 (3H, s), 2.22 (3H, d, J=1.2 Hz), 2.36 (3H, s), 2.44 (4H, dt, J=16.7, 4.9 Hz), 3.08 (2H, t, J=7.1 Hz), 3.52 (2H, s), 3.53 (2H, t, J=4.9 Hz), 3.72 (2H, t, J=4.9 Hz), 4.13 (2H, t, J=7.1 Hz), 4.99 (2H, s), 6.23 (1H, d, J=1.0 Hz), 6.79-6.87 (2H, m), 6.89-7.01 (3H, m), 7.16-7.31 (9H, m), 7.32-7.39 (2H, m), 7.80 (1H, dd, J=2.9, 0.5 Hz).

Example 199

(E)-3-[3-Chloro-4-({5-[(2-chlorobenzyl)oxy]pyridin-2-yl}oxy)phenyl]-1-(4-{4-[2-(3-methylphenoxy)ethyl]benzyl}piperazin-1-yl)prop-2-en-1-one $^1$H-NMR (CDCl$_3$) δ: 2.32 (3H, s), 2.48 (4H, t, J=4.9 Hz), 3.08 (2H, t, J=7.1 Hz), 3.52 (2H, s), 3.599-3.80 (4H, m), 4.16 (2H, t, J=7.1 Hz), 5.16 (2H, s), 6.67-6.84 (4H, m), 6.97 (1H, dd, J=8.8, 0.5 Hz), 7.12-7.18 (2H, m), 7.24-7.32 (6H, m), 7.36-7.42 (3H, m), 7.48-7.55 (1H, m), 7.58-7.63 (2H, m), 7.87 (1H, d, J=2.7 Hz).

Example 200

(E)-3-[3-Chloro-4-({5-[(2-chlorobenzyl)oxy]pyridin-2-yl}oxy)phenyl]-1-(4-{4-[2-(4-fluorophenoxy)ethyl]benzyl}piperazin-1-yl)prop-2-en-1-one $^1$H-NMR (CDCl$_3$) δ: 2.48 (4H, t, J=4.9 Hz), 3.08 (2H, t, J=7.1 Hz), 3.52 (2H, s), 3.59-3.80 (4H, m), 4.13 (2H, t, J=7.1 Hz), 5.16 (2H, s), 6.78-6.86 (3H, m), 6.91-7.00 (3H, m), 7.15 (1H, d, J=8.3 Hz), 7.22-7.34 (6H, m), 7.36-7.43 (3H, m), 7.48-7.55 (1H, m), 7.56-7.63 (2H, m), 7.87 (1H, d, J=2.9 Hz).

Example 201

(E)-3-[3-Chloro-4-({5-[(2-chlorobenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=7.1 Hz), 2.48 (4H, t, J=4.9 Hz), 2.85 (1H, septet, J=7.1 Hz), 3.08 (2H, t, J=7.1 Hz), 3.52 (2H, s), 3.60-3.80 (4H, m), 4.15 (2H, t, J=7.1 Hz), 5.16 (2H, s), 6.77-6.88 (3H, m), 6.97 (1H, d, J=8.5 Hz), 7.10-7.18 (3H, m), 7.23-7.33 (6H, m), 7.37-7.44 (3H, m), 7.49-7.56 (1H, m), 7.66-7.64 (2H, m), 7.87 (1H, d, J=2.9 Hz).

Example 202

(E)-3-[3-Chloro-4-({5-[(2-chlorobenzyl)oxy]pyridin-2-yl}oxy)phenyl]-1-(4-{4-[2-(4-methylphenoxy)ethyl]benzyl}piperazin-1-yl)prop-2-en-1-one $^1$H-NMR (CDCl$_3$) δ: 2.28 (3H, s), 2.48 (4H, t, J=4.9 Hz), 3.08 (2H, t, J=7.1 Hz), 3.52 (2H, s), 3.60-3.80 (4H, m), 4.15 (2H, t, J=7.1 Hz), 5.16 (2H, s), 6.77-6.84 (3H, m), 6.97 (1H, d, J=9.0 Hz), 7.04-7.10 (2H, m), 7.15 (1H, d, J=8.5 Hz), 7.23-7.33 (6H, m), 7.37-7.43 (3H, m), 7.48-7.55 (1H, m), 7.56-7.64 (2H, m), 7.88 (1H, d, J=3.2 Hz).

Example 203

(E)-3-[3-Chloro-4-({5-[(2-chlorobenzyl)oxy]pyridin-2-yl}oxy)-5-methylphenyl]-1-(4-{4-[2-(3-ethoxyphenoxy)ethyl]benzyl}piperazin-1-yl)prop-2-en-1-one $^1$H-NMR (CDCl$_3$) δ: 1.40 (3H, t, J=7.1 Hz), 2.19 (3H, s), 2.48 (4H, t, J=4.9 Hz), 3.08 (2H, t, J=7.1 Hz), 3.52 (2H, s), 3.60-3.80 (4H, m), 4.00 (2H, q, J=7.1 Hz), 4.14 (2H, q, J=7.7 Hz), 5.14 (2H, s), 6.43-6.52 (3H, m), 6.80 (1H, d, J=15.4 Hz), 6.94 (1H, d, J=8.8 Hz), 7.10-7.60 (13H, m), 7.81 (1H, d, J=2.9 Hz).

Example 204

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)-2-methylprop-2-en-1-one $^1$H-NMR (CDCl$_3$) δ: 2.09-2.13 (3H, m), 2.18 (3H, s), 2.36 (3H, s), 2.45 (4H, brs), 3.07 (2H, t, J=6.8 Hz), 3.52 (2H, s), 3.62 (4H, brs), 4.13 (2H, q, J=7.1 Hz), 4.99 (2H, s), 6.41 (1H, brs), 6.79-6.86 (2H, m), 6.88-6.99 (3H, m), 7.09 (1H, s), 7.19 (2H, d, J=7.8 Hz), 7.24-7.32 (7H, m), 7.32-7.38 (1H, m), 7.80 (1H, d, J=2.9 Hz).

Example 205

(E)-3-[3-Chloro-4-({5-[(2-chlorobenzyl)oxy]pyridin-2-yl}oxy)-5-methylphenyl]-2-methyl-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=6.8 Hz), 2.10 (3H, d, J=1.7 Hz), 2.18 (3H, s), 2.45 (4H, brs), 2.85 (1H, septet, J=6.8 Hz), 3.08 (2H, t, J=7.1 Hz), 3.52 (2H, s), 3.61 (4H, brs), 4.15 (2H, t, J=7.3 Hz), 5.14 (2H, s), 6.39-6.43 (1H, m), 6.80-6.86 (2H, m), 6.93 (1H, dd, J=9.0, 0.5 Hz), 7.06-7.15 (3H, m), 7.24-7.32 (7H, m), 7.37-7.42 (2H, m), 7.49-7.55 (1H, m), 7.83 (1H, dd, J=3.2, 0.5 Hz).

Example 206

(E)-3-[3-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)-2-methylprop-2-en-1-one $^1$H-NMR (CDCl$_3$) δ: 2.11 (3H, d, J=1.7 Hz), 2.18 (3H, s), 2.45 (4H, brs), 3.08 (2H, t, J=7.1 Hz), 3.52 (2H, s), 3.62 (4H, brs), 4.13 (2H, t, J=7.1 Hz), 5.14 (2H, s), 6.39-6.43 (1H, m), 6.79-6.86 (2H, m), 6.91-7.00 (3H, m), 7.08-7.11 (1H, m), 7.24-7.32 (7H, m), 7.36-7.42 (2H, m), 7.49-7.55 (1H, m), 7.83 (1H, d, J=3.2 Hz).

Example 207

(E)-3-[3-Chloro-4-({5-[(2-chlorobenzyl)oxy]pyridin-2-yl}oxy)-5-methylphenyl]-2-methyl-1-(4-{4-[2-(4-methylphenoxy)ethyl]benzyl}piperazin-1-yl)prop-2-en-1-one $^1$H-NMR (CDCl$_3$) δ: 2.10 (3H, d, J=1.5 Hz), 2.18 (3H, s), 2.28 (3H, s), 2.45 (4H, brs), 3.08 (2H, t, J=7.1 Hz), 3.52 (2H, s), 3.62 (4H, brs), 4.14 (2H, t, J=7.1 Hz), 5.14 (2H, s), 6.39-6.43 (1H, m), 6.77-6.83 (2H, m), 6.93 (1H, d, J=9.0 Hz), 7.03-7.12 (3H, m), 7.24-7.32 (7H, m), 7.36-7.42 (2H, m), 7.49-7.56 (1H, m), 7.83 (1H, d, J=3.2 Hz).

Example 208

(E)-3-[3-Chloro-5-methyl-4-({5-[(4-methylbenzyl)oxy]pyridin-2-yl}oxy)phenyl]-2-methyl-1-[4-(4-{2-[4-(propan-2-yl)phenoxy]ethyl}benzyl)piperazin-1-yl]but-2-en-1-one $^1$H-NMR (CDCl$_3$) δ: 2.10 (3H, d, J=1.5 Hz), 2.18 (3H, s), 2.28 (3H, s), 2.45 (4H, brs), 3.08 (2H, t, J=7.1 Hz), 3.52 (2H, s), 3.62 (4H, brs), 4.14 (2H, t, J=7.1 Hz), 5.14 (2H, s), 6.39-6.43 (1H, m), 6.77-6.83 (2H, m), 6.93 (1H, d, J=9.0 Hz), 7.03-7.12 (3H, m), 7.24-7.32 (7H, m), 7.36-7.42 (2H, m), 7.49-7.56 (1H, m), 7.83 (1H, d, J=3.2 Hz).

Example 209

(E)-3-[3-Chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)but-2-en-1-one $^1$H-NMR (CDCl$_3$) δ: 1.80 (3H, d, J=1.5 Hz), 1.95 (3H, d, J=1.5 Hz), 2.17 (3H, s), 2.28 (3H, s), 2.36 (3H, s), 2.40-2.55 (4H, m), 3.08 (2H, t, J=7.1 Hz), 3.49-3.54 (4H, m), 3.73 (2H, brs), 4.14 (2H, t, J=7.1 Hz), 4.99 (2H, s), 6.76-6.82 (2H, m), 6.88 (1H, dd, J=8.8, 0.5 Hz), 6.96-6.99 (1H, m), 7.00-7.08 (2H, m), 7.10 (1H, d, J=1.7 Hz), 7.15-7.32 (8H, m), 7.35 (1H, dd, J=8.8, 2.9 Hz), 7.81 (1H, d, J=2.7 Hz).

Example 210

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)-2-methylbut-2-en-1-one $^1$H-NMR (CDCl$_3$) δ: 1.80 (3H, d, J=1.5 Hz), 1.95 (3H, d, J=1.5 Hz), 2.17 (3H, s), 2.36 (3H, s), 2.40-2.56 (4H, m), 3.08 (2H, t, J=7.1 Hz), 3.49-3.55 (4H, m), 3.73 (2H, brs), 4.13 (2H, t, J=7.1 Hz), 4.99 (2H, s), 6.79-6.86 (2H, m), 6.88 (1H, dd, J=8.8, 0.5 Hz), 6.91-7.00 (3H, m), 7.10 (1H, d, J=1.5 Hz), 7.19 (2H, d, J=7.8 Hz), 7.24-7.32 (6H, m), 7.35 (1H, dd, J=8.8, 3.2 Hz), 7.81 (1H, dd, J=2.9, 0.5 Hz).

Example 211

(E)-3-[3-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)-2-methylbut-2-en-1-one $^1$H-NMR (CDCl$_3$) δ: 1.80 (3H, d, J=1.5 Hz), 1.96 (3H, d, J=1.5 Hz), 2.18 (3H, s), 2.40-2.55 (4H, m), 3.08 (2H, t, J=7.1 Hz), 3.49-3.55 (4H, m), 3.73 (2H, brs), 4.13 (2H, t, J=7.1 Hz), 5.15 (2H, s), 6.79-6.86 (2H, m), 6.89-7.00 (4H, m), 7.11 (1H, d, J=2.0 Hz), 7.24-7.32 (6H, m), 7.36-7.43 (2H, m), 7.49-7.55 (1H, m), 7.84 (1H, d, J=3.2 Hz).

Example 212

(E)-3-[3-Chloro-4-({5-[(2-chlorobenzyl)oxy]pyridin-2-yl}oxy)-5-methylphenyl]-2-methyl-1-[4-(4-{2-[4-(propan-2-yl)phenoxy]ethyl}benzyl)piperazin-1-yl]but-2-en-1-one $^1$H-NMR (CDCl$_3$) δ: 1.21 (6H, d, J=6.8 Hz), 1.80 (3H, d, J=1.5 Hz), 1.96 (3H, d, J=1.5 Hz), 2.17 (3H, s), 2.38-2.56 (4H, m), 2.85 (1H, septet, J=6.8 Hz), 3.08 (2H, t, J=7.1 Hz), 3.49-3.55 (4H, m), 3.74 (2H, brs), 4.15 (2H, t, J=7.1 Hz), 5.15 (2H, s), 6.80-6.87 (2H, m), 6.91 (1H, d, J=8.8 Hz), 6.98 (1H, d, J=1.5 Hz), 7.09-7.16 (3H, m), 7.24-7.32 (6H, m), 7.35-7.43 (2H, m), 7.49-7.55 (1H, m), 7.84 (1H, d, J=2.9 Hz).

Example 213

(E)-3-[3-Chloro-4-({5-[(2-chlorobenzyl)oxy]pyridin-2-yl}oxy)-5-methylphenyl]-2-methyl-1-(4-{4-[2-(4-methylphenoxy)ethyl]benzyl}piperazin-1-yl)but-2-en-1-one $^1$H-NMR (CDCl$_3$) δ: 1.80 (3H, d, J=1.5 Hz), 1.95 (3H, d, J=1.5 Hz), 2.18 (3H, s), 2.28 (3H, s), 2.38-2.55 (4H, m), 3.08 (2H, t, J=7.1 Hz), 3.49-3.55 (4H, m), 3.73 (2H, brs), 4.14 (2H, t, J=7.1 Hz), 5.25 (2H, s), 6.78-6.82 (2H, m), 6.91 (1H, d, J=8.8 Hz), 6.96-6.99 (1H, m), 7.03-7.09 (2H, m), 7.10 (1H, d, J=2.0 Hz), 7.24-7.32 (6H, m), 7.35-7.43 (2H, m), 7.49-7.55 (1H, m), 7.84 (1H, d, J=2.9 Hz).

Example 214

(E)-3-[3-Chloro-4-({5-[(2-chlorobenzyl)oxy]pyridin-2-yl}oxy)-5-methylphenyl]-1-(4-{4-[2-(4-methylphenoxy)ethyl]benzyl}piperazin-1-yl)but-2-en-1-one $^1$H-NMR (CDCl$_3$) δ: 2.19 (3H, s), 2.22 (3H, d, J=1.0 Hz), 2.28 (3H, s), 2.44 (4H, dt, J=17.3, 4.9 Hz), 3.08 (2H, t, J=7.1 Hz), 3.49-3.56 (4H, m), 3.66-3.76 (2H, m), 4.14 (2H, t, J=7.1 Hz), 5.14 (2H, s), 6.24 (1H, d, J=1.0 Hz), 6.76-6.82 (2H, m), 6.94 (1H, d, J=9.0 Hz), 7.06 (2H, d, J=8.3 Hz), 7.23-7.32 (7H, m), 7.34-7.42 (3H, m), 7.49-7.55 (1H, m), 7.82 (1H, d, J=2.7 Hz).

Example 215

(E)-3-[3-Chloro-4-({5-[(2-chlorobenzyl)oxy]pyridin-2-yl}oxy)-5-methylphenyl]-1-(4-{4-[2-(4-chlorophenoxy)ethyl]benzyl}piperazin-1-yl)but-2-en-1-one $^1$H-NMR (CDCl$_3$) δ: 2.19 (3H, s), 2.22 (3H, d, J=0.7 Hz), 2.44 (4H, dt, J=16.8, 5.1 Hz), 3.08 (2H, t, J=7.1 Hz), 3.49-

3.56 (4H, m), 3.66-3.77 (2H, m), 4.14 (2H, t, J=7.1 Hz), 5.14 (2H, s), 6.24 (1H, s), 6.79-6.85 (2H, m), 6.94 (1H, d, J=9.0 Hz), 7.20-7.32 (9H, m), 7.34-7.42 (3H, m), 7.50-7.55 (1H, m), 7.82 (1H, d, J=3.2 Hz).

Example 216

(E)-3-[3-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)but-2-en-1-one $^1$H-NMR (CDCl$_3$) δ: 2.19 (3H, s), 2.22 (3H, d, J=1.0 Hz), 2.44 (41, dt, J=16.6, 4.5 Hz), 3.08 (2H, t, J=7.1 Hz), 3.49-3.57 (4H, m), 3.68-3.76 (2H, m), 4.13 (2H, t, J=7.1 Hz), 5.14 (2H, s), 6.24 (1H, d, J=1.2 Hz), 6.80-6.87 (2H, m), 6.91-7.00 (3H, m), 7.20-7.32 (7H, m), 7.34-7.42 (3H, m), 7.49-7.54 (1H, m), 7.82 (1H, d, J=3.2 Hz).

Example 217

(E)-3-[3-Chloro-4-({5-[(2-chlorobenzyl)oxy]pyridin-2-yl}oxy)-5-methylphenyl]-1-(4-{4-[2-(4-methoxyphenoxy)ethyl]benzyl}piperazin-1-yl)but-2-en-1-one $^1$H-NMR (CDCl$_3$) δ: 2.19 (3H, s), 2.22 (3H, d, J=1.0 Hz), 2.44 (4H, dt, J=16.4, 4.6 Hz), 3.07 (2H, t, J=7.1 Hz), 3.49-3.57 (4H, m), 3.68-3.74 (2H, m), 3.76 (3H, s), 4.12 (2H, t, J=7.1 Hz), 5.14 (2H, s), 6.24 (1H, s), 6.79-6.87 (4H, m), 6.94 (1H, d, J=8.8 Hz), 7.34-7.43 (7H, m), 7.34-7.42 (3H, m), 7.49-7.55 (1H, m), 7.82 (1H, d, J=3.2 Hz).

Example 218

(E)-3-[3-Chloro-4-({5-[(2-chlorobenzyl)oxy]pyridin-2-yl}oxy)-5-methylphenyl]-1-[4-(4-{2-[4-(propan-2-yl)phenoxy]ethyl}benzyl)piperazin-1-yl]but-2-en-1-one $^1$H-NMR (CDCl$_3$) δ: 1.21 (6H, d, J=6.8 Hz), 2.19 (3H, s), 2.22 (3H, d, J=1.0 Hz), 2.40-2.50 (4H, m), 2.85 (1H, septet, J=7.1 Hz), 3.08 (2H, t, J=7.1 Hz), 3.49-3.56 (4H, m), 3.68-3.75 (2H, m), 4.15 (2H, t, J=7.1 Hz), 5.14 (2H, s), 6.23 (1H, d, J=1.2 Hz), 6.80-6.86 (2H, m), 6.94 (1H, d, J=9.0 Hz), 7.10-7.16 (2H, m), 7.20-7.32 (7H, m), 7.34-7.42 (3H, m), 7.49-7.54 (1H, m), 7.82 (1H, d, J=2.9 Hz).

Example 219

(E)-3-[3-Chloro-4-({5-[(4-fluorobenzyl)oxy]pyridin-2-yl}oxy)phenyl]-1-(4-{4-[2-(4-fluorophenoxy)ethyl]benzyl}piperazin-1-yl)prop-2-en-1-one $^1$H-NMR (CDCl$_3$) δ: 2.48 (4H, t, J=4.9 Hz), 3.08 (2H, t, J=7.1 Hz), 3.52 (2H, s), 3.60-3.80 (4H, m), 4.13 (2H, t, J=7.1 Hz), 5.01 (2H, s), 6.77-6.86 (3H, m), 6.90-7.00 (3H, m), 7.02-7.10 (2H, m), 7.15 (1H, d, J=8.5 Hz), 7.22-7.32 (4H, m), 7.32-7.42 (4H, m), 7.56-7.63 (2H, m), 7.84 (1H, d, J=3.2 Hz).

Example 220

(E)-3-[3-Chloro-4-({5-[(4-fluorobenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=6.8 Hz), 2.48 (4H, t, J=4.9 Hz), 2.85 (1H, septet, J=6.8 Hz), 3.08 (2H, t, J=7.1 Hz), 3.52 (2H, s), 3.60-3.80 (4H, m), 4.15 (2H, t, J=7.1 Hz), 5.01 (2H, s), 6.77-6.87 (3H, m), 6.95 (1H, d, J=8.8 Hz), 7.03-7.17 (5H, m), 7.22-7.29 (4H, m), 7.34-7.42 (4H, m), 7.56-7.63 (2H, m), 7.84 (1H, d, J=2.9 Hz).

Example 221

(E)-3-[3-Chloro-4-({5-[(4-fluorobenzyl)oxy]pyridin-2-yl}oxy)phenyl]-1-(4-{4-[2-(4-methylphenoxy)ethyl]benzyl}piperazin-1-yl)prop-2-en-1-one $^1$H-NMR (CDCl$_3$) δ: 2.28 (3H, s), 2.48 (4H, t, J=4.9 Hz), 3.08 (2H, t, J=7.1 Hz), 3.52 (2H, s), 3.60-3.80 (4H, m), 4.15 (2H, t, J=7.1 Hz), 5.01 (2H, s), 6.76-6.84 (3H, m), 6.95 (1H, dd, J=9.0, 0.5 Hz), 7.03-7.11 (4H, m), 7.15 (1H, d, J=8.3 Hz), 7.22-7.30 (4H, m), 7.33-7.42 (4H, m), 7.56-7.62 (2H, m), 7.84 (1H, d, J=2.7 Hz).

Example 222

4-{[(6-{2-Chloro-4-[(E)-3-(4-{4-[2-(3-ethoxyphenoxy)ethyl]benzyl}piperazin-1-yl)-3-oxoprop-1-en-1-yl]phenoxy}pyridin-3-yl)oxy]methyl}benzonitrile $^1$H-NMR (CDCl$_3$) δ: 1.39 (3H, t, J=7.1 Hz), 2.48 (4H, t, J=4.9 Hz), 3.08 (2H, t, J=7.1 Hz), 3.52 (2H, s), 3.60-3.80 (4H, m), 4.00 (2H, q, J=7.1 Hz), 4.15 (2H, t, J=7.1 Hz), 5.11 (2H, s), 6.44-6.51 (3H, m), 6.80 (1H, d, J=15.4 Hz), 6.97 (1H, dd, J=8.8, 0.5 Hz), 7.11-7.18 (2H, m), 7.22-7.30 (4H, m), 7.34-7.42 (2H, m), 7.49-7.55 (2H, m), 7.56-7.62 (2H, m), 7.67-7.71 (2H, m), 7.82 (1H, dd, J=2.9, 0.5 Hz).

Example 223

4-{[(6-{2-Chloro-4-[(E)-3-(4-{4-[2-(3-methoxyphenoxy)ethyl]benzyl}piperazin-1-yl)-3-oxoprop-1-en-1-yl]phenoxy}pyridin-3-yl)oxy]methyl}benzonitrile $^1$H-NMR (CDCl$_3$) δ: 2.48 (4H, t, J=4.9 Hz), 3.09 (2H, t, J=7.1 Hz), 3.52 (2H, s), 3.60-3.80 (4H, m), 3.78 (3H, s), 4.16 (2H, t, J=7.1 Hz), 5.11 (2H, s), 6.45-6.53 (3H, m), 6.80 (1H, d, J=15.4 Hz), 6.97 (1H, dd, J=9.0, 0.5 Hz), 7.13-7.20 (2H, m), 7.22-7.30 (4H, m), 7.34-7.42 (2H, m), 7.50-7.55 (2H, m), 7.56-7.62 (2H, m), 7.64-7.72 (2H, m), 7.82 (1H, dd, J=2.9, 0.5 Hz).

Example 224

(E)-3-[3-Chloro-4-({5-[(4-fluorobenzyl)oxy]pyridin-2-yl}oxy)phenyl]-1-(4-{4-[2-(3-ethoxyphenoxy)ethyl]benzyl}piperazin-1-yl)prop-2-en-1-one $^1$H-NMR (CDCl$_3$) δ: 1.40 (3H, t, J=7.1 Hz), 2.48 (4H, t, J=4.9 Hz), 3.08 (2H, t, J=7.1 Hz), 3.52 (2H, s), 3.60-3.80 (4H, m), 4.00 (2H, q, J=7.1 Hz), 4.15 (2H, t, J=7.1 Hz), 5.01 (2H, s), 6.44-6.51 (3H, m), 6.80 (1H, d, J=15.4 Hz), 6.95 (1H, d, J=8.8 Hz), 7.02-7.11 (2H, m), 7.11-7.18 (2H, m), 7.22-7.30 (4H, m), 7.33-7.42 (4H, m), 7.56-7.63 (2H, m), 7.84 (1H, d, J=2.9 Hz).

Example 225

(E)-3-(3,5-Dimethyl-4-{[5-(1,3-thiazol-5-ylmethoxy)pyridin-2-yl]oxy}phenyl)-1-(4-{4-[2-(3-ethoxyphenoxy)ethyl]benzyl}piperazin-1-yl)prop-2-en-1-one $^1$H-NMR (CDCl$_3$) δ: 1.40 (3H, t, J=7.1 Hz), 2.11 (6H, s), 2.48 (4H, t, J=4.9 Hz), 3.08 (2H, t, J=7.1 Hz), 3.52 (2H, s), 3.60-3.80 (4H, m), 4.00 (2H, q, J=7.1 Hz), 4.15 (2H, t, J=7.1 Hz), 5.25 (2H, d, J=0.7 Hz), 6.44-6.51 (3H, m), 6.78 (1H, d, J=15.4 Hz), 6.83 (1H, d, J=9.0 Hz), 7.15 (1H, t, J=8.1 Hz), 7.23-7.29 (6H, m), 7.33 (1H, dd, J=9.0, 3.2 Hz), 7.60 (1H, d, J=15.4 Hz), 7.83 (1H, d, J=2.9 Hz), 7.87 (1H, d, J=0.7 Hz), 8.83 (1H, d, J=0.5 Hz).

Example 226

(E)-3-(3,5-Dimethyl-4-{[5-(1,3-thiazol-5-yl-methoxy)pyridin-2-yl]oxy}phenyl)-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=6.8 Hz), 2.11 (6H, s), 2.48 (4H, t, J=4.9 Hz), 2.85 (1H, septet, J=6.8 Hz), 3.08 (2H, t, J=7.1 Hz), 3.52 (2H, s), 2.60-3.80 (4H, m), 4.15 (2H, t, J=7.1 Hz), 5.25 (2H, s), 6.78 (1H, d, J=15.4 Hz), 6.81-6.86 (3H, m), 7.10-7.16 (2H, m), 7.23-7.30 (6H, m), 7.33 (1H, dd, J=9.0, 3.2 Hz), 7.60 (1H, d, J=15.4 Hz), 7.83 (1H, d, J=3.2 Hz), 7.87 (1H, s), 8.83 (1H, s).

Example 227

(E)-3-(3,5-Dimethyl-4-{[5-(1,3-thiazol-5-yl-methoxy)pyridin-2-yl]oxy}phenyl)-1-(4-{4-[2-(4-methylphenoxy)ethyl]benzyl}piperazin-1-yl)prop-2-en-1-one $^1$H-NMR (CDCl$_3$) δ: 2.11 (6H, s), 2.28 (3H, s), 2.48 (4H, t, J=4.9 Hz), 3.08 (2H, t, J=7.1 Hz), 3.52 (2H, s), 3.60-3.80 (4H, m), 4.15 (2H, t, J=7.1 Hz), 5.25 (2H, d, J=0.7 Hz), 6.75-6.85 (4H, m), 7.04-7.10 (2H, m), 7.24-7.30 (6H, m), 7.33 (1H, dd, J=9.0, 3.2 Hz), 7.60 (1H, d, J=15.4 Hz), 7.83 (1H, d, J=2.7 Hz), 7.87 (1H, d, J=0.7 Hz), 8.83 (1H, d, J=0.5 Hz).

Example 228

(E)-3-(3,5-Dimethyl-4-{[5-(1,3-thiazol-5-yl-methoxy)pyridin-2-yl]oxy}phenyl)-1-(4-{4-[2-(4-fluorophenoxy)ethyl]benzyl}piperazin-1-yl)prop-2-en-1-one $^1$H-NMR (CDCl$_3$) δ: 2.12 (6H, s), 2.48 (4H, t, J=4.9 Hz), 3.08 (2H, t, J=7.1 Hz), 3.52 (2H, s), 3.60-3.80 (4H, m), 4.13 (2H, t, J=7.1 Hz), 5.25 (2H, d, J=0.7 Hz), 6.78 (1H, d, J=15.4 Hz), 6.81-6.86 (3H, m), 6.92-6.99 (2H, m), 7.22-7.30 (6H, m), 7.33 (1H, dd, J=9.0, 3.2 Hz), 7.60 (1H, d, J=15.4 Hz), 7.80-7.85 (1H, m), 7.87 (1H, d, J=0.7 Hz), 8.83 (1H, d, J=0.7 Hz).

Example 229

(E)-3-(3,5-Dimethyl-4-{[5-(1,3-thiazol-5-yl-methoxy)pyridin-2-yl]oxy}phenyl)-1-[4-(4-{2-[4-(propan-2-yloxy)phenoxy]ethyl}benzyl)piperazin-1-yl]prop-2-en-1-one $^1$H-NMR (CDCl$_3$) δ: 1.29 (6H, d, J=5.9 Hz), 2.11 (6H, s), 2.48 (4H, t, J=4.9 Hz), 3.07 (2H, t, J=7.1 Hz), 3.52 (2H, s), 3.60-3.80 (4H, m), 4.12 (2H, t, J=7.1 Hz), 4.41 (1H, septet, J=5.9 Hz), 5.25 (2H, d, J=0.7 Hz), 6.78 (1H, d, J=15.4 Hz), 6.81-6.85 (5H, m), 7.24-7.30 (6H, m), 7.33 (1H, dd, J=9.0, 3.2 Hz), 7.60 (1H, d, J=15.4 Hz), 7.83 (1H, d, J=3.2 Hz), 7.87 (1H, d, J=0.7 Hz), 8.83 (1H, d, J=0.5 Hz).

Example 230

(E)-3-[3-Chloro-5-methyl-4-({5-[(4-methylbenzyl)oxy]pyridin-2-yl}oxy)phenyl]-1-(4-{4-[3-(4-fluorophenoxy)propyl]benzyl}piperazin-1-yl)prop-2-en-1-one mp: 132.9-133.6° C.
$^1$H-NMR (CDCl$_3$) δ: 2.07-2.11 (2H, m), 2.18 (3H, s), 2.35 (3H, s), 2.48 (4H, t, J=4.9 Hz), 2.80 (2H, t, J=7.3 Hz), 3.51 (2H, s), 3.64-3.74 (4H, m), 3.92 (2H, t, J=6.4 Hz), 4.98 (2H, s), 6.77-6.85 (3H, m), 6.90-6.99 (3H, m), 7.16-7.20 (4H, m), 7.23-7.30 (5H, m), 7.34-7.37 (1H, m), 7.45 (1H, d, J=2.2 Hz), 7.56 (1H, d, J=15.4 Hz), 7.79-7.80 (1H, m).

Example 231

(E)-3-[3-Chloro-5-methyl-4-({5-[(4-methylbenzyl)oxy]pyridin-2-yl}oxy)phenyl]-1-[4-(4-{3-[4-(propan-2-yl)phenoxy]propyl}benzyl)piperazin-1-yl]prop-2-en-1-one mp: 108.6-109.2° C.
$^1$H-NMR (CDCl$_3$) δ: 1.22 (6H, d, J=6.8 Hz), 2.07-2.11 (2H, m), 2.18 (3H, s), 2.35 (3H, s), 2.47 (4H, t, J=4.9 Hz), 2.80 (2H, t, J=7.6 Hz), 2.85 (1H, septet, J=6.8 Hz), 3.51 (2H, s), 3.64-3.74 (4H, m), 3.95 (2H, t, J=6.4 Hz), 4.98 (2H, s), 6.77-6.85 (3H, m), 6.91 (1H, d, J=9.0 Hz), 7.11-7.15 (2H, m), 7.17-7.20 (4H, m), 7.23-7.30 (5H, m), 7.35 (1H, dd, J=9.0, 2.9 Hz), 7.45 (1H, d, J=2.0 Hz), 7.56 (1H, d, J=15.4 Hz), 7.79 (1H, d, J=2.9 Hz).

Example 232

(E)-3-[3-Chloro-4-({5-[(2-chlorobenzyl)oxy]pyridin-2-yl}oxy)-5-methylphenyl]-1-(4-{4-[3-(4-fluorophenoxy)propyl]benzyl}piperazin-1-yl)prop-2-en-1-one mp: 110.6-112.3° C.
$^1$H-NMR (CDCl$_3$) δ: 2.07-2.11 (2H, m), 2.19 (3H, s), 2.48 (4H, t, J=4.9 Hz), 2.80 (2H, t, J=7.3 Hz), 3.51 (2H, s), 3.64-3.74 (4H, m), 3.92 (2H, t, J=6.4 Hz), 5.14 (2H, s), 6.78-6.85 (3H, m), 6.93-6.99 (3H, m), 7.17 (2H, d, J=8.3 Hz), 7.23-7.30 (5H, m), 7.37-7.41 (2H, m), 7.45 (1H, d, J=2.0 Hz), 7.50-7.53 (1H, m), 7.57 (1H, d, J=15.4 Hz), 7.81-7.82 (1H, m).

Example 233

(E)-3-[3-Chloro-4-({5-[(2-chlorobenzyl)oxy]pyridin-2-yl}oxy)-5-methylphenyl]-1-[4-(4-{3-[4-(propan-2-yl)phenoxy]propyl}benzyl)piperazin-1-yl]prop-2-en-1-one $^1$H-NMR (CDCl$_3$) δ: 1.22 (6H, d, J=6.8 Hz), 2.07-2.11 (2H, m), 2.19 (3H, s), 2.48 (4H, t, J=4.9 Hz), 2.80 (2H, t, J=7.6 Hz), 2.85 (1H, septet, J=6.8 Hz), 3.51 (2H, s), 3.64-3.74 (4H, m), 3.95 (2H, t, J=6.4 Hz), 5.14 (2H, s), 6.78-6.85 (3H, m), 6.94 (1H, d, J=9.0 Hz), 7.13 (2H, d, J=8.8 Hz), 7.18 (2H, d, J=7.8 Hz), 7.23-7.31 (5H, m), 7.37-7.40 (2H, m), 7.45 (1H, d, J=2.0 Hz), 7.50-7.53 (1H, m), 7.57 (1H, d, J=15.4 Hz), 7.81 (1H, d, J=2.9 Hz).

Example 234

4-{[(6-{2-Chloro-6-methyl-4-[(E)-3-oxo-3-{4-[4-(3-phenoxypropyl)benzyl]piperazin-1-yl}prop-1-en-1-yl]phenoxy}pyridin-3-yl)oxy]methyl}benzonitrile $^1$H-NMR (CDCl$_3$) δ: 2.11 (2H, tt, J=6.9, 6.9 Hz), 2.19 (3H, s), 2.48 (4H, t, J=4.8 Hz), 2.81 (2H, t, J=6.9 Hz), 3.51 (2H, s), 3.64-3.74 (4H, m), 3.97 (2H, t, J=6.9 Hz), 5.09 (2H, s), 6.80 (1H, d, J=15.4 Hz), 6.89-6.96 (4H, m), 7.18 (2H, d, J=7.8 Hz), 7.23-7.30 (5H, m), 7.37 (1H, ddd, J=8.9, 3.1, 1.0 Hz), 7.45 (1H, s), 7.51-7.58 (3H, m), 7.68 (2H, d, J=7.8 Hz), 7.76 (1H, d, J=2.9 Hz).

Example 235

4-{[(6-{2-Chloro-4-[(E)-3-(4-{4-[3-(4-fluorophenoxy)propyl]benzyl}piperazin-1-yl)-3-oxoprop-1-en-1-yl]-6-methylphenoxy}pyridin-3-yl)oxy]methyl}benzonitrile ¹H-NMR (CDCl₃) δ: 2.06-2.13 (2H, m), 2.19 (3H, s), 2.48 (4H, t, J=4.9 Hz), 2.80 (2H, t, J=7.6 Hz), 3.52 (2H, s), 3.65-3.75 (4H, m), 3.93 (2H, t, J=6.2 Hz), 5.10 (2H, s), 6.78-6.85 (3H, m), 6.93-7.00 (3H, m), 7.18 (2H, d, J=8.2 Hz), 7.25 (2H, d, J=8.2 Hz), 7.29 (1H, d, J=2.0 Hz), 7.37 (1H, dd, J=9.0, 3.2 Hz), 7.45 (1H, d, J=2.2 Hz), 7.52 (2H, dd, J=7.9, 0.6 Hz), 7.57 (1H, d, J=15.4 Hz), 7.69 (2H, dt, J=8.2, 1.7 Hz), 7.77 (1H, dd, J=3.2, 0.5 Hz).

Example 236

4-({[6-(2-Chloro-4-{(E)-3-[4-(4-{3-[(6-chloropyridin-3-yl)oxy]propyl}benzyl)piperazin-1-yl]-3-oxoprop-1-en-1-yl}-6-methylphenoxy)pyridin-3-yl]oxy}methyl)benzonitrile ¹H-NMR (CDCl₃) δ: 2.09-2.16 (2H, m), 2.19 (3H, s), 2.48 (4H, t, J=4.9 Hz), 2.81 (2H, t, J=7.6 Hz), 3.52 (2H, s), 3.64-3.74 (4H, m), 3.99 (2H, t, J=6.2 Hz), 5.09 (2H, s), 6.80 (1H, d, J=15.4 Hz), 6.95 (1H, d, J=8.8 Hz), 7.15-7.18 (3H, m), 7.21-7.26 (3H, m), 7.29 (1H, d, J=1.5 Hz), 7.37 (1H, dd, J=8.9, 3.1 Hz), 7.45 (1H, d, J=2.0 Hz), 7.52 (2H, d, J=8.3 Hz), 7.57 (1H, d, J=15.4 Hz), 7.67-7.69 (2H, m), 7.76 (1H, d, J=3.2 Hz), 8.03 (1H, d, J=2.9 Hz).

Example 237

4-({[6-(2-Chloro-6-methyl-4-{(E)-3-[4-(4-{3-[(6-methylpyridin-3-yl)oxy]propyl}benzyl)-piperazin-1-yl]-3-oxoprop-1-en-1-yl}phenoxy)pyridin-3-yl]oxy}methyl)benzonitrile ¹H-NMR (CDCl₃) δ: 2.07-2.14 (2H, m), 2.19 (3H, s), 2.47-2.49 (7H, m), 2.81 (2H, t, J=7.6 Hz), 3.51 (2H, s), 3.64-3.74 (4H, m), 3.98 (2H, t, J=6.2 Hz), 5.09 (2H, s), 6.80 (1H, d, J=15.4 Hz), 6.95 (1H, dd, J=8.9, 0.6 Hz), 7.05 (1H, d, J=8.3 Hz), 7.09 (1H, dd, J=8.5, 2.9 Hz), 7.17 (2H, d, J=8.1 Hz), 7.24 (2H, d, J=8.3 Hz), 7.29 (1H, t, J=1.1 Hz), 7.37 (1H, dd, J=8.9, 3.1 Hz), 7.45 (1H, d, J=2.2 Hz), 7.51-7.59 (3H, m), 7.68 (2H, dt, J=8.2, 1.8 Hz), 7.76 (1H, dd, J=3.2, 0.5 Hz), 8.18 (1H, dd, J=2.9, 0.7 Hz).

Example 238

4-{[(6-{2-Chloro-6-methyl-4-[(E)-3-(4-{4-[3-(4-methylphenoxy)propyl]benzyl}piperazin-1-yl)-3-oxoprop-1-en-1-yl]phenoxy}pyridin-3-yl)oxy]methyl}benzonitrile ¹H-NMR (CDCl₃) δ: 2.05-2.12 (2H, m), 2.19 (3H, s), 2.28 (3H, s), 2.48 (4H, t, J=5.0 Hz), 2.80 (2H, t, J=7.6 Hz), 3.51 (2H, s), 3.64-3.74 (4H, m), 3.94 (2H, t, J=6.2 Hz), 5.09 (2H, s), 6.78-6.82 (3H, m), 6.95 (1H, d, J=9.0 Hz), 7.07 (2H, d, J=8.4 Hz), 7.18 (2H, d, J=8.1 Hz), 7.24 (2H, d, J=8.1 Hz), 7.29 (1H, d, J=1.7 Hz), 7.37 (1H, dd, J=8.9, 3.2 Hz), 7.45 (1H, d, J=2.0 Hz), 7.51-7.58 (3H, m), 7.68 (2H, dt, J=8.4, 1.7 Hz), 7.77 (1H, d, J=3.2 Hz).

Example 239

4-({[6-(2-Chloro-6-methyl-4-{(E)-3-oxo-3-[4-(4-{3-[4-(propan-2-yl)phenoxy]propyl}benzyl)-piperazin-1-yl]prop-1-en-1-yl}phenoxy)pyridin-3-yl]oxy}methyl)benzonitrile ¹H-NMR (CDCl₃) δ: 1.22 (3H, s), 1.23 (3H, s), 2.06-2.13 (2H, m), 2.19 (3H, s), 2.48 (4H, t, J=4.9 Hz), 2.78-2.91 (3H, m), 3.51 (2H, s), 3.64-3.74 (4H, m), 3.95 (2H, t, J=6.3 Hz), 5.09 (2H, s), 6.78-6.85 (3H, m), 6.95 (1H, dd, J=9.0, 0.5 Hz), 7.13 (2H, dt, J=9.4, 2.4 Hz), 7.18 (2H, d, J=8.1 Hz), 7.24 (2H, d, J=8.1 Hz), 7.29 (1H, d, J=2.0 Hz), 7.37 (1H, dd, J=9.0, 3.1 Hz), 7.45 (1H, d, J=2.0 Hz), 7.51-7.59 (3H, m), 7.68 (2H, dt, J=8.3, 1.7 Hz), 7.77 (1H, dd, J=3.1, 0.5 Hz).

Example 240

(E)-3-[3-Chloro-5-methyl-4-({5-[(4-methylbenzyl)oxy]pyridin-2-yl}oxy)phenyl]-1-[4-({4-[2-(4-methylphenoxy)ethyl]phenyl}amino)piperidin-1-yl]prop-2-en-1-one ¹H-NMR (CDCl₃) δ: 1.36-1.49 (2H, m), 2.10-2.21 (5H, m), 2.28 (3H, s), 2.36 (3H, s), 2.93-3.07 (3H, m), 3.22-3.60 (3H, m), 4.00-4.11 (3H, m), 4.50-4.64 (1H, m), 4.98 (2H, s), 6.56-6.62 (2H, m), 6.76-6.82 (2H, m), 6.83 (1H, d, J=15.4 Hz), 6.92 (1H, dd, J=9.0, 0.5 Hz), 7.20-7.12 (4H, m), 7.18 (2H, d, J=7.8 Hz), 7.24-7.31 (3H, m), 7.35 (1H, dd, J=9.0, 3.2 Hz), 7.46 (1H, d, J=2.2 Hz), 7.57 (1H, d, J=15.1 Hz), 7.79 (1H, dd, J=2.9, 0.5 Hz).

Example 241

(E)-3-[3-Chloro-5-methyl-4-({5-[(4-methylbenzyl)oxy]pyridin-2-yl}oxy)phenyl]-1-[4-({4-[2-(4-fluorophenoxy)ethyl]phenyl}amino)piperidin-1-yl]prop-2-en-1-one ¹H-NMR (CDCl₃) δ: 1.34-1.48 (2H, m), 2.10-2.20 (5H, m), 2.35 (3H, s), 2.92-3.07 (3H, m), 3.20-3.39 (1H, m), 3.42-3.60 (2H, m), 4.00-4.11 (3H, m), 4.48-4.64 (1H, m), 4.98 (2H, s), 6.56-6.62 (2H, m), 6.78-6.88 (3H, m), 6.90-6.99 (3H, m), 7.06-7.12 (2H, m), 7.18 (2H, d, J=7.8 Hz), 7.26-7.31 (3H, m), 7.35 (1H, dd, J=9.0, 3.2 Hz), 7.46 (1H, d, J=2.2 Hz), 7.57 (1H, d, J=15.4 Hz), 7.79 (1H, dd, J=2.4, 0.5 Hz).

Example 242

(E)-3-[3-Chloro-5-methyl-4-({5-[(4-methylbenzyl)oxy]pyridin-2-yl}oxy)phenyl]-1-{4-[4-(2-{[4-(propan-2-yl)phenyl]amino}ethyl)benzyl]piperazin-1-yl}prop-2-en-1-one ¹H-NMR (CDCl₃) δ: 1.20 (6H, d, J=6.8 Hz), 2.19 (3H, s), 2.35 (3H, s), 2.49 (4H, t, J=4.9 Hz), 2.80 (1H, septet, J=6.8 Hz), 2.90 (2H, t, J=7.1 Hz), 3.38 (2H, t, J=7.1 Hz), 3.52 (2H, s), 3.60-3.82 (5H, m), 4.98 (2H, s), 6.54-6.60 (2H, m), 6.79 (1H, d, J=15.4 Hz), 6.91 (1H, dd, J=8.8, 0.5 Hz), 7.01-7.08 (2H, m), 7.16-7.22 (4H, m), 7.25-7.30 (5H, m), 7.35 (1H, dd, J=9.0, 3.2 Hz), 7.45 (1H, d, J=2.0 Hz), 7.56 (1H, d, J=15.4 Hz), 7.79 (1H, dd, J=3.2, 0.5 Hz).

Example 243

(E)-3-[3-Chloro-4-({5-[(2-chlorobenzyl)oxy]pyridin-2-yl}oxy)-5-methylphenyl]-1-{4-[4-(2-{[4-(propan-2-yl)phenyl]amino}ethyl)benzyl]piperazin-1-yl}prop-2-en-1-one ¹H-NMR (CDCl₃) δ: 1.20 (6H, d, J=7.1 Hz), 2.19 (3H, s), 2.49 (4H, t, J=4.9 Hz), 2.80 (1H, septet, J=7.1 Hz), 2.91 (2H, t, J=7.1 Hz), 3.38 (2H, t, J=7.1 Hz), 3.52 (2H, s), 3.52-3.80 (5H, m), 5.14 (2H, s), 6.54-6.60 (2H, m), 6.80 (1H, d, J=15.4 Hz), 6.94 (1H, dd, J=8.8, 0.5 Hz), 7.01-7.08 (2H, m), 7.16-7.22 (2H, m), 7.22-7.32 (5H, m), 7.36-7.42 (2H, m), 7.45 (1H, d, J=2.0 Hz), 7.48-7.54 (1H, m), 7.56 (1H, d, J=15.4 Hz), 7.81 (1H, dd, J=3.2, 0.5 Hz).

Example 244

(E)-3-[3-Chloro-5-methyl-4-({5-[(4-methylbenzyl)oxy]pyridin-2-yl}oxy)phenyl]-1-{4-[4-(2-{methyl[4-(propan-2-yl)phenyl]amino}ethyl)benzyl]piperazin-1-yl}prop-2-en-1-one ¹H-NMR (CDCl₃) δ: 1.22 (6H, d, J=7.1 Hz), 2.19 (3H, s), 2.35 (3H, s), 2.48 (4H, t, J=4.9 Hz), 2.76-2.90 (6H, m), 3.49-3.56 (4H, m), 3.60-3.80 (4H, m), 4.98 (2H, s), 6.66-6.72 (2H, m), 6.79 (1H, d, J=15.4 Hz), 6.91 (1H, dd, J=9.0, 0.5 Hz), 7.08-7.14 (2H, m), 7.15-7.21 (4H, m), 7.24-7.32 (5H, m), 7.35 (1H, dd, J=8.8, 3.2 Hz), 7.45 (1H, d, J=2.2 Hz), 7.56 (1H, d, J=15.4 Hz), 7.78 (1H, dd, J=3.2, 0.5 Hz).

Example 245

(E)-3-[3-Chloro-4-({5-[(2-chlorobenzyl)oxy]pyridin-2-yl}oxy)-5-methylphenyl]-1-[4-(4-{2-[(4-fluorophenyl)(methyl)amino]ethyl}benzyl)piperazin-1-yl]prop-2-en-1-one ¹H-NMR (CDCl₃) δ: 2.19 (3H, s), 2.47 (4H, t, J=4.9 Hz), 2.78-2.90 (5H, m), 3.48-3.55 (4H, m), 3.60-3.80 (4H, m), 5.14 (2H, s), 6.60-6.67 (2H, m), 6.80 (1H, d, J=15.4 Hz), 6.90-6.98 (3H, m), 7.15 (2H, d, J=8.1 Hz), 7.22-7.31 (5H, m), 7.36-7.42 (2H, m), 7.45 (1H, d, J=2.0 Hz), 7.49-7.55 (1H, m), 7.56 (1H, d, J=15.1 Hz), 7.81 (1H, d, J=3.2 Hz).

Example 246

(E)-3-[3-Chloro-4-({5-[(2-chlorobenzyl)oxy]pyridin-2-yl}oxy)-5-methylphenyl]-1-[4-(4-{2-[(4-fluorophenyl)amino]ethyl}benzyl)piperazin-1-yl]prop-2-en-1-one ¹H-NMR (CDCl₃) δ: 2.19 (3H, s), 2.49 (4H, t, J=4.9 Hz), 2.90 (2H, t, J=7.1 Hz), 3.36 (2H, t, J=7.1 Hz), 3.50-3.80 (7H, m), 5.14 (2H, s), 6.51-6.56 (2H, m), 6.79 (1H, d, J=15.4 Hz), 6.85-6.91 (2H, m), 6.94 (1H, d, J=9.0 Hz), 7.18 (2H, d, J=8.1 Hz), 7.24-7.31 (5H, m), 7.35-7.41 (2H, m), 7.45 (1H, d, J=1.7 Hz), 7.49-7.54 (1H, m), 7.56 (1H, d, J=15.4 Hz), 7.81 (1H, d, J=3.2 Hz).

Example 247

(E)-3-[3-Chloro-5-methyl-4-({5-[(4-methylbenzyl)oxy]pyridin-2-yl}oxy)phenyl]-1-[4-(4-{2-[(4-fluorophenyl)(methyl)amino]ethyl}benzyl)piperazin-1-yl]prop-2-en-1-one ¹H-NMR (CDCl₃) δ: 2.19 (3H, s), 2.36 (3H, s), 2.47 (4H, t, J=4.9 Hz), 2.78-2.90 (5H, m), 3.47-3.55 (4H, m), 3.60-3.80 (4H, m), 4.98 (2H, s), 6.60-6.66 (2H, m), 6.79 (1H, d, J=15.4 Hz), 6.88-6.98 (3H, m), 7.12-7.21 (4H, m), 7.20-7.32 (5H, m), 7.35 (1H, dd, J=9.0, 3.2 Hz), 7.45 (1H, d, J=2.0 Hz), 7.56 (1H, d, J=15.4 Hz), 7.79 (1H, d, J=2.9 Hz).

Example 248

(E)-3-[3-Chloro-5-methyl-4-({5-[(4-methylbenzyl)oxy]pyridin-2-yl}oxy)phenyl]-1-[4-(4-{2-[(4-fluorophenyl)amino]ethyl}benzyl)piperazin-1-yl]prop-2-en-1-one ¹H-NMR (CDCl₃) δ: 2.19 (3H, s), 2.35 (3H, s), 2.49 (4H, t, J=4.9 Hz), 2.90 (2H, t, J=6.8 Hz), 3.36 (2H, t, J=6.8 Hz), 3.50-3.80 (7H, m), 4.98 (2H, s), 6.50-6.58 (2H, m), 6.79 (1H, d, J=15.4 Hz), 6.84-6.94 (3H, m), 7.18 (4H, d, J=7.8 Hz), 7.24-7.31 (5H, m), 7.35 (1H, dd, J=9.0, 3.2 Hz), 7.45 (1H, d, J=1.7 Hz), 7.56 (1H, d, J=15.1 Hz), 7.79 (1H, d, J=2.9 Hz).

Example 249

(E)-3-[3-Chloro-4-({5-[(4-fluorobenzyl)oxy]pyridin-2-yl}oxy)phenyl]-1-[4-(4-{2-[(4-fluorophenyl)amino]ethyl}benzyl)piperazin-1-yl]prop-2-en-1-one ¹H-NMR (CDCl₃) δ: 2.49 (4H, t, J=4.9 Hz), 2.90 (2H, t, J=6.8 Hz), 3.36 (2H, t, J=7.1 Hz), 3.49-3.80 (7H, m), 5.01 (2H, s), 6.50-6.58 (2H, m), 6.80 (1H, d, J=15.4 Hz), 6.84-6.92 (2H, m), 6.95 (1H, dd, J=8.8, 0.5 Hz), 7.04-7.11 (2H, m), 7.15 (1H, d, J=8.3 Hz), 7.18 (2H, d, J=8.1 Hz), 7.24-7.30 (2H, m), 7.33-7.42 (4H, m), 7.56-7.63 (2H, m), 7.84 (1H, dd, J=3.2, 0.5 Hz).

Example 250

4-({[6-(2-Chloro-4-{(E)-3-[4-(4-{2-[(4-fluorophenyl)amino]ethyl}benzyl)piperazin-1-yl]-3-oxoprop-1-en-1-yl}phenoxy)pyridin-3-yl]oxy}methyl)benzonitrile ¹H-NMR (CDCl₃) δ: 2.49 (4H, t, J=4.9 Hz), 2.90 (2H, t, J=6.8 Hz), 3.36 (2H, t, J=7.1 Hz), 3.49-3.80 (7H, m), 5.11 (2H, s), 6.50-6.57 (2H, m), 6.80 (1H, d, J=15.4 Hz), 6.85-6.92 (2H, m), 6.97 (1H, dd, J=8.8, 0.5 Hz), 7.12-7.21 (3H, m), 7.24-7.30 (2H, m), 7.33-7.43 (2H, m), 7.49-7.55 (2H, m), 7.57-7.62 (2H, m), 7.66-7.71 (2H, m), 7.82 (1H, d, J=2.9 Hz).

Example 251

4-({[6-(2-Chloro-4-{(E)-3-[4-(4-{2-[(4-methoxyphenyl)amino]ethyl}benzyl)piperazin-1-yl]-3-oxoprop-1-en-1-yl}phenoxy)pyridin-3-yl]oxy}methyl)benzonitrile ¹H-NMR (CDCl₃) δ: 2.49 (4H, t, J=4.9 Hz), 2.90 (2H, t, J=6.8 Hz), 3.36 (2H, t, J=7.1 Hz), 3.43 (1H, brs), 3.52 (2H, s), 3.60-3.80 (7H, m), 5.11 (2H, s), 6.55-6.61 (2H, m), 6.75-6.84 (3H, m), 6.97 (1H, d, J=8.8 Hz), 7.15 (1H, d, J=8.3 Hz), 7.18 (2H, d, J=8.1 Hz), 7.24-7.30 (2H, m), 7.35-7.42 (2H, m), 7.52 (2H, d, J=15.6 Hz), 7.55-7.63 (2H, m), 7.66-7.71 (2H, m), 7.82 (1H, d, J=3.2 Hz).

Example 252

(E)-3-[3-Chloro-4-({5-[(4-fluorobenzyl)oxy]pyridin-2-yl}oxy)phenyl]-1-[4-(4-{2-[(4-methoxyphenyl)amino]ethyl}benzyl)piperazin-1-yl]prop-2-en-1-one ¹H-NMR (CDCl₃) δ: 2.49 (4H, t, J=4.9 Hz), 2.90 (2H, t, J=6.8 Hz), 3.36 (2H, t, J=7.1 Hz), 3.40-3.60 (3H, m), 3.60-

3.80 (7H, m), 5.01 (2H, s), 6.56-6.62 (2H, m), 6.75-6.84 (3H, m), 6.95 (1H, d, J=9.0 Hz), 7.04-7.11 (2H, m), 7.15 (1H, d, J=8.5 Hz), 7.18 (2H, d, J=8.1 Hz), 7.24-7.30 (2H, m), 7.33-7.42 (4H, m), 7.56-7.63 (2H, m), 7.84 (1H, d, J=3.2 Hz).

Example 253

(E)-3-[3-Chloro-5-methyl-4-({5-[(4-methylbenzyl)oxy]pyridin-2-yl}oxy)phenyl]-1-[4-(4-{2-[(4-methoxyphenyl)amino]ethyl}benzyl)piperazin-1-yl]prop-2-en-1-one $^1$H-NMR (CDCl$_3$) δ: 2.19 (3H, s), 2.36 (3H, s), 2.49 (4H, t, J=4.9 Hz), 2.90 (2H, t, J=6.8 Hz), 3.36 (2H, t, J=7.1 Hz), 3.40-3.50 (3H, m), 3.60-3.80 (7H, m), 4.98 (2H, s), 6.56-6.61 (2H, m), 6.76-6.82 (3H, m), 6.91 (1H, d, J=8.8 Hz), 7.18 (4H, d, J=8.1 Hz), 7.24-7.31 (5H, m), 7.35 (1H, dd, J=9.0, 3.2 Hz), 7.45 (1H, d, J=2.2 Hz), 7.56 (1H, d, J=15.4 Hz), 7.79 (1H, d, J=2.9 Hz).

Example 254

(E)-3-[3-Chloro-5-methyl-4-({5-[(4-methylbenzyl)oxy]pyridin-2-yl}oxy)phenyl]-1-(4-{[4-(2-{[4-(propan-2-yl)phenyl]amino}ethyl)phenyl]amino}piperidin-1-yl)prop-2-en-1-one $^1$H-NMR (CDCl$_3$) δ: 1.20 (6H, d, J=6.8 Hz), 1.32-1.48 (2H, m), 2.10-2.22 (5H, m), 2.35 (3H, s), 2.75-2.85 (3H, m), 2.90-3.10 (1H, m), 3.22-3.38 (3H, m), 3.41-3.60 (3H, m), 4.00-4.11 (1H, m), 4.49-4.67 (1H, m), 4.98 (2H, s), 6.53-6.62 (4H, m), 6.84 (1H, d, J=15.4 Hz), 6.92 (1H, d, J=8.8 Hz), 7.01-7.08 (4H, m), 7.18 (2H, d, J=7.8 Hz), 7.26-7.31 (3H, m), 7.35 (1H, dd, J=9.0, 3.2 Hz), 7.46 (1H, d, J=2.2 Hz), 7.57 (1H, d, J=15.4 Hz), 7.79 (1H, d, J=3.2 Hz).

Example 255

(E)-3-[3-Chloro-4-({5-[(2-chlorobenzyl)oxy]pyridin-2-yl}oxy)-5-methylphenyl]-1-(4-{[2-(4-methoxyphenoxy)quinolin-6-yl]methyl}piperazin-1-yl)prop-2-en-1-one $^1$H-NMR (CDCl$_3$) δ: 2.19 (3H, s), 2.52 (4H, t, J=5.0 Hz), 3.60-3.80 (6H, m), 3.85 (3H, s), 5.14 (2H, s), 6.80 (1H, d, J=15.6 Hz), 6.91-6.98 (3H, m), 7.05 (1H, d, J=8.7 Hz), 7.13-7.21 (2H, m), 7.22-7.32 (2H, m), 7.36-7.42 (2H, m), 7.46 (1H, d, J=1.8 Hz), 7.48-7.69 (4H, m), 7.76 (1H, d, J=8.2 Hz), 7.81 (1H, d, J=3.2 Hz), 8.02 (1H, s), 8.07 (1H, d, J=8.7 Hz).

Example 256

(E)-3-[3-Chloro-4-({5-[(2-chlorobenzyl)oxy]pyridin-2-yl}oxy)-5-methylphenyl]-1-[4-({2-[4-(propan-2-yl)phenoxy]quinolin-6-yl}methyl)piperazin-1-yl]prop-2-en-1-one $^1$H-NMR (CDCl$_3$) δ: 1.29 (6H, d, J=6.9 Hz), 2.53 (4H, t, J=5.0 Hz), 2.96 (1H, septet, J=6.9 Hz), 3.60-3.82 (6H, m), 5.14 (2H, s), 6.80 (1H, d, J=15.6 Hz), 6.94 (1H, d, J=8.7 Hz), 7.05 (1H, d, J=8.7 Hz), 7.12-7.19 (2H, m), 7.24-7.32 (5H, m), 7.36-7.42 (2H, m), 7.46 (1H, d, J=1.8 Hz), 7.49-7.54 (1H, m), 7.57 (1H, d, J=15.6 Hz), 7.63 (1H, dd, J=8.7, 1.8 Hz), 7.67 (1H, s), 7.76-7.84 (2H, m), 8.08 (1H, d, J=8.7 Hz).

Example 257

4-{[(6-{2-Chloro-4-[(E)-3-(4-{[2-(4-methoxyphenoxy)quinolin-6-yl]methyl}piperazin-1-yl)-3-oxoprop-1-en-1-yl]phenoxy}pyridin-3-yl)oxy]methyl}benzonitrile $^1$H-NMR (CDCl$_3$) δ: 2.52 (4H, t, J=4.9 Hz), 3.60-3.80 (6H, m), 3.84 (3H, s), 5.11 (2H, s), 6.80 (1H, d, J=15.6 Hz), 6.92-6.99 (3H, m), 7.04 (1H, d, J=8.8 Hz), 7.12-7.20 (3H, m), 7.34-7.42 (2H, m), 7.49-7.55 (2H, m), 7.57-7.64 (3H, m), 7.65-7.71 (3H, m), 7.76 (1H, d, J=8.8 Hz), 7.82 (1H, d, J=2.9 Hz), 8.07 (1H, d, J=8.8 Hz).

Example 258

(E)-3-[3-Chloro-4-({5-[(2-chlorobenzyl)oxy]pyridin-2-yl}oxy)-5-methylphenyl]-1-(4-{4-[2-(4-fluorophenyl)-2-oxoethoxy]benzyl}piperazin-1-yl)prop-2-en-1-one $^1$H-NMR (CDCl$_3$) δ: 2.19 (3H, s), 2.46 (4H, t, J=4.9 Hz), 3.47 (2H, s), 3.63-3.73 (4H, m), 5.14 (2H, s), 5.22 (2H, s), 6.80 (1H, d, J=15.4 Hz), 6.88-6.92 (2H, m), 6.95 (1H, d, J=8.8 Hz), 7.15-7.21 (2H, m), 7.23-7.32 (5H, m), 7.38-7.41 (2H, m), 7.45 (1H, d, J=2.2 Hz), 7.51-7.53 (1H, m), 7.57 (1H, d, J=15.4 Hz), 7.81 (1H, d, J=2.9 Hz), 8.04-8.09 (2H, m).

Example 259

(E)-3-[4-({5-[(3,4-Difluorobenzyl)oxy]pyridin-2-yl}oxy)-3-fluorophenyl]-1-(4-{2-(4-methylphenyl)-2-oxoethoxy]benzyl}piperazin-1-yl)prop-2-en-1-one mp: 117.5-118.4° C.

Example 260

(E)-3-[4-({5-[(2,3-Dichlorobenzyl)oxy]pyridin-2-yl}oxy)-3-methylphenyl]-1-(4-{4-[2-(4-methylphenyl)-2-oxoethoxy]benzyl}piperazin-1-yl)prop-2-en-1-one $^1$H-NMR (CDCl$_3$) δ: 2.21 (3H, s), 2.43-2.46 (7H, m), 3.47 (2H, s), 3.63-3.73 (4H, m), 5.16 (2H, s), 5.25 (2H, s), 6.78 (1H, d, J=15.4 Hz), 6.87-6.92 (3H, m), 6.98 (1H, d, J=8.3 Hz), 7.21-7.27 (3H, m), 7.30 (2H, d, J=8.1 Hz), 7.34-7.37 (2H, m), 7.41 (1H, d, J=2.0 Hz), 7.45 (2H, d, J=8.1 Hz), 7.63 (1H, d, J=15.4 Hz), 7.89-7.93 (3H, m).

Example 261

4-{[(6-{2-Fluoro-4-[(E)-3-(4-{4-[2-(4-methylphenyl)-2-oxoethoxy]benzyl}piperazin-1-yl)-3-oxoprop-1-en-1-yl]phenoxy}pyridin-3-yl)oxy]methyl}benzonitrile mp: 140.3-141.4° C.

Example 262

(E)-1-[4-(4-Chlorobenzyl)piperazin-1-yl]-3-[3-chloro-5-methyl-4-({5-[2-(4-methylphenyl)-ethoxy]pyridin-2-yl}oxy)phenyl]prop-2-en-1-one mp: 142.2-142.9° C.

Example 263

(E)-1-[4-(4-Chlorobenzyl)piperazin-1-yl]-3-[3-chloro-4-({5-[2-(3,4-dichlorophenyl)ethoxy]-pyridin-2-yl}oxy)-5-methylphenyl]prop-2-en-1-one $^1$H-NMR (CDCl$_3$) δ: 2.18 (3H, s), 2.47 (4H, t, J=4.9 Hz), 3.03 (2H, t, J=6.4 Hz), 3.50 (2H, s), 3.65-3.74 (4H, m), 4.13 (2H, t, J=6.4 Hz), 6.79 (1H, d, J=15.5 Hz), 6.91 (1H, d, J=8.9 Hz), 7.10 (1H, dd, J=8.2, 2.0 Hz), 7.28-7.32 (6H, m), 7.37-7.38 (2H, m), 7.45 (1H, d, J=2.0 Hz), 7.57 (1H, d, J=15.2 Hz), 7.71 (1H, d, J=3.0 Hz).

Example 264

(E)-3-[3-Chloro-4-({5-[(2-chlorobenzyl)oxy]pyridin-2-yl}oxy)-5-methylphenyl]-1-{4-[4-(2-hydroxyethyl)benzyl]piperazin-1-yl}prop-2-en-1-one $^1$H-NMR (CDCl$_3$) δ: 1.40-1.43 (1H, m), 2.20 (3H, s), 2.47-2.50 (4H, m), 2.88 (2H, t, J=6.6 Hz), 3.52 (2H, s), 3.63-3.66 (2H, m), 3.73-3.76 (2H, m), 3.85-3.90 (2H, m), 5.14 (2H, s), 6.80 (1H, d, J=15.6 Hz), 6.95 (1H, d, J=8.8 Hz), 7.19-7.32 (7H, m), 7.38-7.59 (5H, m), 7.81 (1H, d, J=2.9 Hz).

Example 265

(E)-3-[3-Chloro-4-({5-[(2-chlorobenzyl)oxy]pyridin-2-yl}oxy)-5-methylphenyl]-1-{4-[4-(4-chlorophenoxy)benzyl]piperazin-1-yl}prop-2-en-1-one $^1$H-NMR (CDCl$_3$) δ: 2.19 (3H, s), 2.47-2.51 (4H, m), 3.52 (2H, s), 3.64-3.67 (2H, m), 3.74-3.77 (2H, m), 5.13 (2H, s), 6.81 (1H, d, J=15.4 Hz), 6.92-6.99 (5H, m), 7.25-7.31 (7H, m), 7.38-7.40 (2H, m), 7.46 (1H, d, J=1.5 Hz), 7.50-7.53 (1H, m), 7.58 (1H, d, J=15.4 Hz), 7.81 (1H, d, J=2.9 Hz).

Example 266

(E)-3-[3-Chloro-5-methyl-4-({5-[(4-methylbenzyl)oxy]pyridin-2-yl}oxy)phenyl]-1-{4-[4-(4-chlorophenoxy)benzyl]piperazin-1-yl}prop-2-en-1-one $^1$H-NMR (CDCl$_3$) δ: 2.19 (3H, s), 2.35 (3H, s), 2.48-2.49 (4H, m), 3.52 (2H, s), 3.64-3.67 (2H, m), 3.74-3.76 (2H, m), 4.98 (2H, s), 6.80 (1H, d, J=15.4 Hz), 6.91-6.97 (5H, m), 7.17-7.20 (2H, m), 7.26-7.30 (7H, m), 7.36 (1H, dd, J=8.9, 3.1 Hz), 7.46 (1H, d, J=1.2 Hz), 7.57 (1H, d, J=15.4 Hz), 7.79 (1H, d, J=2.9 Hz).

Example 267

(E)-1-[4-(Biphenyl-4-ylmethyl)piperazin-1-yl]-3-[3-chloro-4-({5-[(2-chlorobenzyl)oxy]pyridin-2-yl}oxy)-5-methylphenyl]prop-2-en-1-one $^1$H-NMR (CDCl$_3$) δ: 2.19 (3H, s), 2.52-2.53 (4H, m), 3.59 (2H, s), 3.66-3.68 (2H, m), 3.76-3.78 (2H, m), 5.14 (2H, s), 6.81 (1H, d, J=15.4 Hz), 6.94 (1H, d, J=9.0 Hz), 7.25-7.47 (11H, m), 7.50-7.62 (6H, m), 7.81 (1H, d, J=2.9 Hz).

Example 268

(E)-1-[4-(Biphenyl-4-ylmethyl)piperazin-1-yl]-3-[3-chloro-5-methyl-4-({5-[(4-methylbenzyl)-oxy]pyridin-2-yl}oxy)phenyl]prop-2-en-1-one $^1$H-NMR (CDCl$_3$) δ: 2.19 (3H, s), 2.35 (3H, s), 2.52-2.53 (4H, m), 3.59 (2H, s), 3.65-3.68 (2H, m), 3.76-3.78 (2H, m), 4.98 (2H, s), 6.81 (1H, d, J=15.4 Hz), 6.91 (1H, d, J=8.8 Hz), 7.18 (2H, d, J=7.8 Hz), 7.26-7.46 (10H, m), 7.55-7.62 (5H, m), 7.79 (1H, d, J=2.9 Hz).

Example 269

(E)-3-[3-Chloro-5-methyl-4-({5-[(4-methylbenzyl)oxy]pyridin-2-yl}oxy)phenyl]-1-(4-{4-[4-(propan-2-yl)phenoxy]benzyl}piperazin-1-yl)prop-2-en-1-one $^1$H-NMR (CDCl$_3$) δ: 1.25 (6H, d, J=6.8 Hz), 2.19 (3H, s), 2.35 (3H, s), 2.48-2.49 (4H, m), 2.87-2.94 (1H, m), 3.51 (2H, s), 3.64-3.66 (2H, m), 3.74-3.76 (2H, m), 4.98 (2H, s), 6.81 (1H, d, J=15.4 Hz), 6.90-6.98 (5H, m), 7.17-7.21 (4H, m), 7.25-7.30 (5H, m), 7.35 (1H, dd, J=8.9, 3.1 Hz), 7.46 (1H, d, J=1.0 Hz), 7.57 (1H, d, J=15.4 Hz), 7.79 (1H, d, J=2.9 Hz).

Example 270

4-{[(6-{2-Chloro-6-methyl-4-[(E)-3-oxo-3-(4-{4-[4-(propan-2-yl)phenoxy]benzyl}piperazin-1-yl)prop-1-en-1-yl]phenoxy}pyridin-3-yl)oxy]methyl}benzonitrile $^1$H-NMR (CDCl$_3$) δ: 1.25 (6H, d, J=6.8 Hz), 2.19 (3H, s), 2.53-2.57 (4H, m), 2.88-2.93 (1H, m), 3.57 (2H, s), 3.66-3.69 (2H, m), 3.76-3.78 (2H, m), 5.09 (2H, s), 6.80 (1H, d, J=15.4 Hz), 6.92-6.97 (5H, m), 7.19 (2H, d, J=8.3 Hz), 7.24-7.30 (3H, m), 7.37 (1H, dd, J=8.9, 3.1 Hz), 7.45 (1H, d, J=1.5 Hz), 7.52 (2H, d, J=8.1 Hz), 7.56 (1H, d, J=15.4 Hz), 7.68 (2H, d, J=8.1 Hz), 7.77 (1H, d, J=2.9 Hz).

Example 271

(E)-3-[4-({5-[(2,4-Difluorobenzyl)oxy]pyridin-2-yl}oxy)-3-fluorophenyl]-1-[4-(4-{2-[4-(propan-2-yl)phenyl]ethoxy}benzyl)piperazin-1-yl]prop-2-en-1-one $^1$H-NMR (CDCl$_3$) δ: 1.22 (6H, d, J=6.8 Hz), 2.48 (4H, t, J=5.0 Hz), 2.85 (1H, septet, J=7.1 Hz), 3.08 (2H, t, J=7.1 Hz), 3.52 (2H, s), 3.63-3.75 (4H, m), 4.15 (2H, t, J=7.0 Hz), 5.06 (2H, s), 6.79 (1H, d, J=15.4 Hz), 6.82-6.88 (3H, m), 6.88-6.93 (1H, m), 6.96 (1H, dd, J=8.8, 0.5 Hz), 7.11-7.15 (2H, m), 7.19 (1H, t, J=8.1 Hz), 7.23-7.30 (5H, m), 7.33 (1H, dd, J=11.4, 2.1 Hz), 7.37 (1H, dd, J=8.9, 3.1 Hz), 7.41-7.47 (1H, m), 7.60 (1H, d, J=15.4 Hz), 7.84 (1H, dd, J=3.2, 0.5 Hz).

Example 272

(E)-3-[4-({5-[(2,3-Difluorobenzyl)oxy]pyridin-2-yl}oxy)-3-fluorophenyl]-1-[4-(4-{2-[4-(propan-2-yl)phenyl]ethoxy}benzyl)piperazin-1-yl]prop-2-en-1-one $^1$H-NMR (CDCl$_3$) δ: 1.22 (6H, d, J=7.1 Hz), 2.48 (4H, t, J=5.0 Hz), 2.85 (1H, septet, J=7.1 Hz), 3.08 (2H, t, J=7.1 Hz), 3.52 (2H, s), 3.64-3.74 (4H, m), 4.15 (2H, t, J=7.0 Hz), 5.13 (2H, s), 6.79 (1H, d, J=15.6 Hz), 6.82-6.85 (2H, m), 6.97 (1H, d, J=9.0 Hz), 7.08-7.30 (11H, m), 7.33 (1H, dd, J=11.2, 2.0 Hz), 7.38 (1H, dd, J=8.9, 3.1 Hz), 7.60 (1H, d, J=15.4 Hz), 7.85 (1H, d, J=3.2 Hz).

Example 273

4-({[6-(2-Chloro-4-{(E)-3-[4-(4-chlorobenzyl)piperazin-1-yl]-3-oxoprop-1-en-1-yl}-6-methylphenoxy)pyridin-3-yl]oxy}methyl)benzonitrile $^1$H-NMR (CDCl$_3$) δ: 2.19 (3H, s), 2.46-2.47 (4H, m), 3.50 (2H, s), 3.63-3.66 (2H, m), 3.73-3.75 (2H, m), 5.09 (2H, s), 6.80 (1H, d, J=15.4 Hz), 6.96 (1H, d, J=9.0 Hz), 7.26-7.32 (5H, m), 7.37 (1H, dd, J=8.9, 3.1 Hz), 7.45 (1H, d, J=1.2 Hz), 7.52 (2H, d, J=8.1 Hz), 7.57 (1H, d, J=15.4 Hz), 7.68 (2H, d, J=8.3 Hz), 7.76 (1H, d, J=2.9 Hz).

Example 274

4-({[6-(2-Chloro-6-methyl-4-{(E)-3-[4-(4-methylbenzyl)piperazin-1-yl]-3-oxoprop-1-en-1-yl}phenoxy)pyridin-3-yl]oxy}methyl)benzonitrile $^1$H-NMR (CDCl$_3$) δ: 2.19 (3H, s), 2.34 (3H, s), 2.47-2.48 (4H, m), 3.50 (2H, s), 3.64-3.68 (2H, m), 3.71-3.73 (2H, m), 5.09 (2H, s), 6.80 (1H, d, J=15.4 Hz), 6.95 (1H, d, J=8.8 Hz), 7.14 (2H, d, J=7.8 Hz), 7.21 (2H, d, J=7.8 Hz), 7.29 (1H, s), 7.37 (1H, dd, J=9.0, 2.9 Hz), 7.47-7.55 (4H, m), 7.67 (2H, d, J=8.1 Hz), 7.76 (1H, d, J=2.7 Hz).

Example 275

(2E)-3-[3-Chloro-5-methyl-4-({5-[(4-methylbenzyl)oxy]pyridin-2-yl}oxy)phenyl]-1-(4-{4-[(1E)-3-methoxyprop-1-en-1-yl]benzyl}piperazin-1-yl)prop-2-en-1-one $^1$H-NMR (CDCl$_3$) δ: 2.19 (3H, s), 2.36 (3H, s), 2.48 (4H, t, J=5.0 Hz), 3.39 (3H, s), 3.52 (2H, s), 3.64 (2H, brs), 3.73 (2H, brs), 4.10 (2H, dd, J=6.1, 1.5 Hz), 4.98 (2H, s), 6.28 (1H, dt, J=16.1, 6.1 Hz), 6.61 (1H, d, J=16.1 Hz), 6.79 (1H, d, J=15.4 Hz), 6.91 (1H, dd, J=8.9, 0.6 Hz), 7.19 (2H, d, J=7.8 Hz), 7.27-7.30 (5H, m), 7.34-7.37 (3H, m), 7.45 (1H, d, J=2.0 Hz), 7.56 (1H, d, J=15.4 Hz), 7.79 (1H, dd, J=3.2, 0.6 Hz).

Example 276

4-({[6-(2,6-Dimethyl-4-{(E)-3-[4-(4-methylbenzyl)piperazin-1-yl]-3-oxoprop-1-en-1-yl}phenoxy)pyridin-3-yl]oxy}methyl)benzonitrile $^1$H-NMR (CDCl$_3$) δ: 2.11 (6H, s), 2.35 (3H, s), 2.47-2.48 (4H, m), 3.50 (2H, s), 3.63-3.66 (2H, m), 3.72-3.75 (2H, m), 5.09 (2H, s), 6.78 (11H, d, J=15.4 Hz), 6.83 (1H, d, J=8.8 Hz), 7.14 (2H, d, J=7.8 Hz), 7.21 (2H, d, J=8.1 Hz), 7.25-7.26 (2H, m), 7.33 (1H, dd, J=8.9, 3.1 Hz), 7.52 (2H, d, J=8.1 Hz), 7.60 (1H, d, J=15.4 Hz), 7.68 (2H, d, J=8.1 Hz), 7.80 (1H, d, J=2.9 Hz).

Example 277

4-{[(6-{4-[(E)-3-{4-[4-(4-Chlorophenoxy)benzyl]piperazin-1-yl}-3-oxoprop-1-en-1-yl]-2,6-dimethylphenoxy}pyridin-3-yl)oxy]methyl}benzonitrile $^1$H-NMR (CDCl$_3$) δ: 2.12 (6H, s), 2.48-2.49 (4H, m), 3.52 (2H, s), 3.65-3.68 (2H, m), 3.74-3.76 (2H, m), 5.09 (2H, s), 6.79 (1H, d, J=15.4 Hz), 6.84 (1H, d, J=8.8 Hz), 6.94-6.96 (4H, m), 7.25-7.35 (7H, m), 7.52 (2H, d, J=8.1 Hz), 7.61 (1H, d, J=15.4 Hz), 7.68 (2H, d, J=8.1 Hz), 7.79 (1H, d, J=2.9 Hz).

Example 278

(2E)-3-[4-({5-[(4-Fluorobenzyl)oxy]pyridin-2-yl}oxy)-3,5-dimethylphenyl]-1-(4-{4-[(1E)-3-methoxyprop-1-en-1-yl]benzyl}piperazin-1-yl)prop-2-en-1-one $^1$H-NMR (CDCl$_3$) δ: 2.12 (6H, s), 2.48 (4H, t, J=4.8 Hz), 3.39 (3H, s), 3.52 (2H, s), 3.65 (2H, brs), 3.73 (2H, brs), 4.10 (2H, dd, J=6.0, 1.3 Hz), 4.98 (2H, s), 6.28 (1H, dt, J=15.9, 6.0 Hz), 6.61 (1H, d, J=15.9 Hz), 6.78 (1H, d, J=15.4 Hz), 6.81 (1H, d, J=8.8 Hz), 7.04-7.09 (2H, m), 7.24-7.39 (9H, m), 7.61 (1H, d, J=15.4 Hz), 7.81 (1H, d, J=2.9 Hz).

Example 279

4-({[6-(4-{(E)-3-[4-(Biphenyl-4-ylmethyl)piperazin-1-yl]-3-oxoprop-1-en-1-yl}-2,6-dimethylphenoxy)pyridin-3-yl]oxy}methyl)benzonitrile $^1$H-NMR (CDCl$_3$) δ: 2.11 (6H, s), 2.52-2.53 (4H, m), 3.58 (2H, s), 3.66-3.69 (2H, m), 3.75-3.78 (2H, m), 5.08 (2H, s), 6.79-6.83 (2H, m), 7.25 (2H, s), 7.31-7.36 (2H, m), 7.39-7.46 (4H, m), 7.52 (2H, d, J=8.3 Hz), 7.58-7.61 (5H, m), 7.68 (2H, d, J=8.1 Hz), 7.79 (1H, d, J=2.9 Hz).

Example 280

4-{[(6-{4-[(E)-3-{4-[4-(2-Hydroxyethyl)benzyl]piperazin-1-yl}-3-oxoprop-1-en-1-yl]-2,6-dimethylphenoxy}pyridin-3-yl)oxy]methyl}benzonitrile $^1$H-NMR (CDCl$_3$) δ: 1.40-1.41 (1H, m), 2.11 (6H, s), 2.47-2.49 (4H, m), 2.87 (2H, t, J=6.5 Hz), 3.52 (2H, s), 3.64-3.66 (2H, m), 3.73-3.75 (2H, m), 3.87-3.88 (2H, m), 5.09 (2H, s), 6.78 (1H, d, J=15.4 Hz), 6.84 (1H, d, J=8.9 Hz), 7.20 (2H, d, J=8.1 Hz), 7.26-7.28 (4H, m), 7.33 (1H, dd, J=8.9, 2.9 Hz), 7.52 (2H, d, J=8.1 Hz), 7.61 (1H, d, J=15.4 Hz), 7.68 (2H, d, J=8.1 Hz), 7.79 (1H, d, J=2.9 Hz).

Example 281

(E)-3-(3,5-Dimethyl-4-{[5-(pyridin-4-ylmethoxy)pyridin-2-yl]oxy}phenyl)-1-{4-[4-(2-hydroxyethyl)benzyl]piperazin-1-yl}prop-2-en-1-one $^1$H-NMR (CDCl$_3$) δ: 1.42-1.45 (1H, m), 2.12 (6H, s), 2.47-2.49 (4H, m), 2.88 (2H, t, J=6.5 Hz), 3.52 (2H, s), 3.64-3.66 (2H, m), 3.73-3.75 (2H, m), 3.87-3.88 (2H, m), 5.06 (2H, s), 6.78 (1H, d, J=15.4 Hz), 6.84 (1H, d, J=8.8 Hz), 7.20 (2H, d, J=8.1 Hz), 7.26-7.28 (4H, m), 7.33-7.34 (3H, m), 7.61 (1H, d, J=15.4 Hz), 7.80 (1H, d, J=2.9 Hz), 8.62 (2H, d, J=5.9 Hz).

Example 282

(2E)-3-[4-({5-[(4-Methoxybenzyl)oxy]pyridin-2-yl}oxy)-3,5-dimethylphenyl]-1-(4-{4-[(1E)-3-methoxyprop-1-en-1-yl]benzyl}piperazin-1-yl)prop-2-en-1-one $^1$H-NMR (CDCl$_3$) δ: 2.12 (6H, s), 2.48 (4H, t, J=5.0 Hz), 3.39 (3H, s), 3.52 (2H, s), 3.66 (2H, brs), 3.74 (2H, brs), 3.81

(3H, s), 4.10 (2H, dd, J=6.2, 1.5 Hz), 4.95 (2H, s), 6.28 (1H, dt, J=15.9, 6.2 Hz), 6.61 (1H, d, J=15.9 Hz), 6.76-6.80 (2H, m), 6.91 (2H, dt, J=9.1, 2.4 Hz), 7.24-7.37 (9H, m), 7.61 (1H, d, J=15.1 Hz), 7.82 (1H, d, J=2.7 Hz).

Example 283

(E)-3-[4-({5-[(2-Chlorobenzyl)oxy]pyridin-2-yl}oxy)-3-methoxyphenyl]-1-{4-[4-(2-hydroxyethyl)benzyl]piperazin-1-yl}prop-2-en-1-one $^1$H-NMR (CDCl$_3$) δ: 2.15-2.18 (1H, m), 2.46-2.48 (4H, m), 2.85 (2H, t, J=6.7 Hz), 3.50 (2H, s), 3.63-3.65 (2H, m), 3.72-3.75 (2H, m), 3.79 (3H, s), 3.84 (2H, t, J=6.7 Hz), 5.14 (2H, s), 6.79 (1H, d, J=15.4 Hz), 6.90-6.91 (1H, m), 7.08-7.14 (3H, m), 7.19 (2H, d, J=8.1 Hz), 7.26-7.29 (4H, m), 7.34-7.40 (2H, m), 7.50-7.52 (1H, m), 7.63 (1H, d, J=15.4 Hz), 7.86-7.86 (1H, m).

Example 284

(E)-3-{3-Chloro-4-[(5-{[4-(difluoromethoxy)benzyl]oxy}pyridin-2-yl)oxy]-5-methylphenyl}-1-[4-(4-methylbenzyl)piperazin-1-yl]prop-2-en-1-one $^1$H-NMR (CDCl$_3$) δ: 2.19 (3H, s), 2.35 (3H, s), 2.48 (4H, t, J=4.9 Hz), 3.51 (2H, s), 3.64 (2H, brs), 3.74 (2H, brs), 5.01 (2H, s), 6.51 (1H, t, J=73.8 Hz), 6.80 (1H, d, J=15.4 Hz), 6.93 (1H, d, J=8.8 Hz), 7.13-7.15 (4H, m), 7.21 (2H, d, J=7.8 Hz), 7.29 (1H, brs), 7.36 (1H, dd, J=8.8, 2.9 Hz), 7.41 (2H, d, 8.5 Hz), 7.45 (1H, brs), 7.56 (1H, d, J=15.4 Hz), 7.78 (1H, d, J=2.9 Hz).

Example 285

(E)-3-{3-Chloro-4-[(5-{[4-(difluoromethoxy)benzyl]oxy}pyridin-2-yl)oxy]-5-methylphenyl}-1-{4-[4-(propan-2-yloxy)benzyl]piperazin-1-yl}prop-2-en-1-one $^1$H-NMR (CDCl$_3$) δ: 1.34 (6H, d, J=6.1 Hz), 2.19 (3H, s), 2.47 (4H, brs), 3.47 (2H, s), 3.64 (2H, brs), 3.74 (2H, brs), 4.54 (1H, septet, J=6.1 Hz), 5.00 (2H, s), 6.51 (1H, t, J=73.8 Hz), 6.80 (1H, d, J=15.4 Hz), 6.85 (2H, d, J=8.3 Hz), 6.93 (1H, d, J=8.8 Hz), 7.14 (2H, d, J=8.3 Hz), 7.21 (2H, d, J=8.3 Hz), 7.29 (1H, brs), 7.36 (1H, dd, J=8.8, 2.7 Hz), 7.40 (2H, d, J=8.3 Hz), 7.45 (1H, brs), 7.56 (1H, d, J=15.4 Hz), 7.78 (1H, d, J=2.7 Hz).

Example 286

4-{[(6-{2-Chloro-4-[(E)-3-{4-[4-(3-hydroxypropyl)benzyl]piperazin-1-yl}-3-oxoprop-1-en-1-yl]-6-methylphenoxy}pyridin-3-yl)oxy]methyl}benzonitrile $^1$H-NMR (CDCl$_3$) δ: 1.33 (1H, brs), 1.87-1.94 (2H, m), 2.19 (3H, s), 2.48 (4H, t, J=5.0 Hz), 2.71 (2H, t, J=7.8 Hz), 3.51 (2H, s), 3.64-3.74 (6H, m), 5.09 (2H, s), 6.80 (1H, d, J=15.4 Hz), 6.95 (1H, dd, J=9.0, 0.5 Hz), 7.17 (2H, d, J=8.1 Hz), 7.23-7.29 (3H, m), 7.37 (1H, dd, J=8.9, 3.1 Hz), 7.45 (1H, d, J=2.2 Hz), 7.51-7.58 (3H, m), 7.67-7.70 (2H, m), 7.76-7.77 (1H, m).

Example 287

4-{[(6-{2-Chloro-4-[(1E)-3-(4-{4-[(1E)-3-hydroxyprop-1-en-1-yl]benzyl}piperazin-1-yl)-3-oxoprop-1-en-1-yl]-6-methylphenoxy}pyridin-3-yl)oxy]methyl}benzonitrile $^1$H-NMR (CDCl$_3$) δ: 1.52 (1H, brs), 2.19 (3H, s), 2.48 (4H, t, J=4.9 Hz), 3.53 (2H, s), 3.64-3.74 (4H, m), 4.33 (2H, d, J=5.7 Hz), 5.09 (2H, s), 6.37 (1H, dt, J=16.0, 5.7 Hz), 6.62 (1H, d, J=16.0 Hz), 6.80 (1H, d, J=15.6 Hz), 6.96 (1H, d, J=8.8 Hz), 7.26-7.29 (3H, m), 7.35-7.39 (3H, m), 7.45 (1H, d, J=2.0 Hz), 7.51-7.59 (3H, m), 7.68 (2H, d, J=8.1 Hz), 7.77 (1H, d, J=2.9 Hz).

Example 288

4-{[(6-{2-Chloro-4-[(E)-3-(4-{3-fluoro-4-[(1-hydroxy-2-methylpropan-2-yl)oxy]benzyl}-piperazin-1-yl)-3-oxoprop-1-en-1-yl]-6-methylphenoxy}pyridin-3-yl)oxy]methyl}benzonitrile $^1$H-NMR (CDCl$_3$) δ: 1.30 (6H, s), 2.19 (3H, s), 2.47-2.49 (5H, m), 3.49 (2H, s), 3.60 (2H, s), 3.65-3.67 (2H, m), 3.74-3.77 (2H, m), 5.09 (2H, s), 6.81 (1H, d, J=15.4 Hz), 6.94-7.05 (3H, m), 7.12 (1H, d, J=11.0 Hz), 7.28-7.29 (1H, m), 7.36-7.38 (1H, m), 7.44-7.47 (1H, m), 7.53-7.57 (3H, m), 7.68 (2H, d, J=8.1 Hz), 7.76 (1H, d, J=2.9 Hz).

Example 289

To a solution of (E)-3-{3-chloro-5-methyl-4-[(5-{[4-(trifluoromethyl)benzyl]-oxy}pyridin-2-yl)oxy]phenyl}prop-2-enoic acid (139 mg) and 4-{2-[4-(piperazin-1-ylmethyl)-phenyl]ethoxy}benzonitrile trifluoroacetate (131 mg) in DMF (6 mL) was added DEPC (0.073 mL) and Et$_3$N (0.165 mL) at 0° C. After stirring at 0° C. for 1 hour, to the reaction mixture was added H$_2$O, and extracted with AcOEt. The organic layer was washed with saturated aqueous NaCl, dried over anhydrous MgSO$_4$, and concentrated under reduced pressure. The residue was purified by silica gel column chromatography (AcOEt) to give 4-{2-[4-({4-[(E)-3-{3-chloro-5-methyl-4-[(5-{[4-(trifluoromethyl)benzyl]oxy}pyridin-2-yl)oxy]phenyl}prop-2-enoyl]piperazin-1-yl}methyl)phenyl]ethoxy}benzonitrile as a pale yellow amorphous (195 mg).

$^1$H-NMR (CDCl$_3$) δ: 2.19 (3H, s), 2.48 (4H, brs), 3.11 (2H, t, J=7.1 Hz), 3.53 (2H, s), 3.65-3.74 (4H, m), 4.21 (2H, t, J=7.1 Hz), 5.09 (2H, s), 6.81 (1H, d, J=15.4 Hz), 6.92-6.95 (3H, m), 7.25-7.29 (5H, m), 7.37 (1H, dd, J=8.9, 3.1 Hz), 7.45 (1H, d, J=2.0 Hz), 7.51-7.59 (5H, m), 7.64 (2H, d, J=8.1 Hz), 7.78 (1H, d, J=3.2 Hz).

The following compounds were produced in the same manner as in Example 289 using appropriate starting materials.

Example 290

(E)-3-[3-Chloro-5-methyl-4-({5-[(4-methylbenzyl)oxy]pyridin-2-yl}oxy)phenyl]-1-(4-{4-[2-(2,3-dihydro-1H-inden-5-yloxy)ethyl]benzyl}piperazin-1-yl)prop-2-en-1-one $^1$H-NMR (CDCl$_3$) δ: 2.02-2.08 (2H, m), 2.19 (3H, s), 2.36 (3H, s), 2.48 (4H, t, J=5.0 Hz), 2.81-2.88 (4H, m), 3.08 (2H, t, J=7.1 Hz), 3.52 (2H, s), 3.64-3.74 (4H, m), 4.14 (2H, t, J=7.1 Hz), 4.98 (2H, s), 6.69 (1H, dd, J=8.1, 2.4 Hz), 6.79-6.81 (2H, m), 6.92 (1H, d, J=9.0 Hz), 7.10 (1H, d, J=8.1 Hz), 7.19 (2H, d, J=7.8 Hz), 7.23-7.28 (7H, m, J=8.6 Hz), 7.35 (1H, dd, J=8.9, 3.1 Hz), 7.45 (1H, d, J=2.0 Hz), 7.57 (1H, d, J=15.4 Hz), 7.79 (1H, d, J=2.9 Hz).

Example 291

(E)-3-(3-Chloro-5-methyl-4-[(5-{[4-(trifluoromethyl)benzyl]oxy}pyridin-2-yl)oxy]phenyl)-1-(4-{4-[2-(4-methylphenoxy)ethyl]benzyl}piperazin-1-yl)prop-2-en-1-one $^1$H-NMR (CDCl$_3$) δ: 2.18 (3H, s), 2.26 (3H, s), 2.47 (4H, brs), 3.07 (2H, t, J=7.1 Hz), 3.50 (2H, s), 3.63-3.74 (4H, m), 4.13 (2H, t, J=7.1 Hz), 5.06 (2H, s), 6.79-6.82 (3H, m), 6.94 (1H, d, J=8.8 Hz), 7.05 (2H, d, J=8.5 Hz), 7.24-7.27 (5H, m), 7.35 (1H, dd, J=8.9, 3.1 Hz), 7.45 (1H, s), 7.50 (2H, d, J=8.3 Hz), 7.57 (1H, d, J=15.4 Hz), 7.62 (2H, d, J=8.1 Hz), 7.77 (1H, d, J=3.2 Hz).

Example 292

(E)-3-{3-Chloro-5-methyl-4-[(5-{[4-(trifluoromethyl)benzyl]oxy}pyridin-2-yl)oxy]phenyl}-1-(4-{4-[2-(4-chlorophenoxy)ethyl]benzyl}piperazin-1-yl)prop-2-en-1-one $^1$H-NMR (CDCl$_3$) δ: 2.18 (3H, s), 2.47 (4H, t, J=4.9 Hz), 3.07 (2H, t, J=7.0 Hz), 3.51 (2H, s), 3.63-3.74 (4H, m), 4.12 (2H, t, J=7.0 Hz), 5.07 (2H, s), 6.79-6.83 (3H, m), 6.94 (1H, d, J=9.0 Hz), 7.20-7.26 (7H, m), 7.36 (1H, dd, J=8.9, 3.1 Hz), 7.45 (1H, d, J=1.7 Hz), 7.51 (2H, d, J=8.1 Hz), 7.57 (1H, d, J=15.4 Hz), 7.63 (2H, d, J=8.1 Hz), 7.77 (1H, d, J=2.9 Hz).

Example 293

(E)-3-{3-Chloro-5-methyl-4-[(5-{[4-(trifluoromethyl)benzyl]oxy}pyridin-2-yl)oxy]phenyl}-1-(4-{4-[2-(4-iodophenoxy)ethyl]benzyl}piperazin-1-yl)prop-2-en-1-one $^1$H-NMR (CDCl$_3$) δ: 2.18 (3H, s), 2.47 (4H, t, J=4.9 Hz), 3.06 (2H, t, J=7.1 Hz), 3.51 (2H, s), 3.63-3.74 (4H, m), 4.12 (2H, t, J=7.1 Hz), 5.07 (2H, s), 6.64-6.67 (2H, m), 6.81 (1H, d, J=15.4 Hz), 6.94 (1H, d, J=8.8 Hz), 7.22-7.28 (5H, m), 7.36 (1H, dd, J=8.9, 3.1 Hz), 7.45 (1H, d, J=2.0 Hz), 7.50-7.52 (4H, m), 7.57 (1H, d, J=15.4 Hz), 7.63 (2H, d, J=8.3 Hz), 7.77 (1H, d, J=2.9 Hz).

Example 294

(E)-3-{3-Chloro-5-methyl-4-[(5-{[4-(trifluoromethyl)benzyl]oxy}pyridin-2-yl)oxy]phenyl}-1-[4-(4-{2-[4-(propan-2-yl)phenoxy]ethyl}benzyl)piperazin-1-yl]prop-2-en-1-one $^1$H-NMR (CDCl$_3$) δ: 1.21 (6H, d, J=7.1 Hz), 2.18 (3H, s), 2.47 (4H, t, J=4.9 Hz), 2.81-2.88 (1H, m), 3.07 (2H, t, J=7.1 Hz), 3.51 (2H, s), 3.63-3.74 (4H, m), 4.14 (2H, t, J=7.1 Hz), 5.06 (2H, s), 6.80-6.83 (3H, m), 6.94 (1H, d, J=9.0 Hz), 7.12 (2H, d, J=8.8 Hz), 7.25-7.27 (5H, m), 7.36 (1H, dd, J=9.0, 3.2 Hz), 7.45 (1H, d, J=1.7 Hz), 7.50 (2H, d, J=8.1 Hz), 7.57 (1H, d, J=15.4 Hz), 7.63 (2H, d, J=8.1 Hz), 7.77 (1H, d, J=2.9 Hz).

Example 295

(E)-3-{3-Chloro-5-methyl-4-[(5-{[4-(trifluoromethyl)benzyl]oxy}pyridin-2-yl)oxy]phenyl}-1-(4-{4-[2-(5,6,7,8-tetrahydronaphthalen-2-yloxy)ethyl]benzyl}piperazin-1-yl)prop-2-en-1-one $^1$H-NMR (CDCl$_3$) δ: 1.74-1.76 (4H, m), 2.18 (3H, s), 2.47 (4H, t, J=4.9 Hz), 2.67-2.71 (4H, m), 3.06 (2H, t, J=7.1 Hz), 3.51 (2H, s), 3.63-3.74 (4H, m), 4.13 (2H, t, J=7.1 Hz), 5.06 (2H, s), 6.61 (1H, s), 6.66 (1H, dd, J=8.3, 2.4 Hz), 6.81 (1H, d, J=15.4 Hz), 6.93-6.95 (2H, m), 7.25-7.27 (5H, m), 7.36 (1H, dd, J=8.9, 3.1 Hz), 7.45 (1H, s), 7.50 (2H, d, J=8.1 Hz), 7.57 (1H, d, J=15.4 Hz), 7.63 (2H, d, J=8.3 Hz), 7.77 (1H, d, J=3.2 Hz).

Example 296

(E)-3-{3-Chloro-5-methyl-4-[(5-{[4-(trifluoromethyl)benzyl]oxy}pyridin-2-yl)oxy]phenyl}-1-(4-{4-[2-(naphthalen-2-yloxy)ethyl]benzyl}piperazin-1-yl)prop-2-en-1-one $^1$H-NMR (CDCl$_3$) δ: 2.18 (3H, s), 2.46 (4H, brs), 3.15 (2H, t, J=7.1 Hz), 3.51 (2H, s), 3.61-3.74 (4H, m), 4.27 (2H, t, J=7.1 Hz), 5.04 (2H, s), 6.80 (1H, d, J=15.4 Hz), 6.93 (1H, d, J=8.8 Hz), 7.12-7.15 (2H, m), 7.28-7.35 (7H, m), 7.38-7.42 (1H, m), 7.45-7.49 (3H, m), 7.57 (1H, d, J=15.4 Hz), 7.62 (2H, d, J=8.1 Hz), 7.67-7.74 (3H, m), 7.77 (1H, d, J=3.2 Hz).

Example 297

(E)-3-{3-Chloro-5-methyl-4-[(5-{[4-(trifluoromethyl)benzyl]oxy}pyridin-2-yl)oxy]phenyl}-1-(4-{4-[2-(4-methylphenoxy)ethoxy]benzyl}piperazin-1-yl)prop-2-en-1-one $^1$H-NMR (CDCl$_3$) δ: 2.18 (3H, s), 2.28 (3H, s), 2.45 (4H, brs), 3.47 (2H, s), 3.62-3.73 (4H, m), 4.27-4.30 (4H, brs), 5.06 (2H, s), 6.81-6.84 (3H, m), 6.91-6.94 (3H, m), 7.08 (2H, d, J=8.5 Hz), 7.23 (2H, d, J=9.0 Hz), 7.29 (1H, s), 7.36 (1H, dd, J=9.0, 3.2 Hz), 7.47-7.50 (3H, m), 7.57 (1H, d, J=15.4 Hz), 7.63 (2H, d, J=8.1 Hz), 7.77 (1H, d, J=2.9 Hz).

Example 298

(E)-1-[4-(4-{2-[(6-Bromopyridin-3-yl)oxy]ethyl}benzyl)piperazin-1-yl]-3-{3-chloro-5-methyl-4-[(5-{[4-(trifluoromethyl)benzyl]oxy}pyridin-2-yl)oxy]phenyl}prop-2-en-1-one $^1$H-NMR (CDCl$_3$) δ: 2.19 (3H, s), 2.48 (4H, t, J=4.9 Hz), 3.10 (2H, t, J=6.8 Hz), 3.52 (2H, s), 3.65-3.74 (4H, m), 4.19 (2H, t, J=6.8 Hz), 5.08 (2H, s), 6.81 (1H, d, J=15.4 Hz), 6.95 (1H, d, J=9.0 Hz), 7.07 (1H, dd, J=8.5, 3.2 Hz), 7.23-7.30 (5H, m), 7.33 (1H, d, J=8.5 Hz), 7.37 (1H, dd, J=8.9, 3.1 Hz), 7.45 (1H, d, J=2.0 Hz), 7.52 (2H, d, J=8.1 Hz), 7.57 (1H, d, J=15.4 Hz), 7.64 (2H, d, J=8.1 Hz), 7.78 (1H, d, J=2.9 Hz), 8.03 (1H, d, J=3.2 Hz).

Example 299

(E)-3-{3-Chloro-5-methyl-4-[(5-{[4-(trifluoromethyl)benzyl]oxy}pyridin-2-yl)oxy]phenyl}-1-(4-{4-[2-(4-ethoxyphenoxy)ethyl]benzyl}piperazin-1-yl)prop-2-en-1-one $^1$H-NMR (CDCl$_3$) δ: 1.37 (3H, t, J=7.1 Hz), 2.18 (3H, s), 2.47 (4H, t, J=4.9 Hz), 3.06 (2H, t, J=7.1 Hz), 3.51 (2H, s), 3.63-3.74 (4H, m), 3.96 (2H, q, J=7.1 Hz), 4.11 (2H, t, J=7.1 Hz), 5.07 (2H, s), 6.79-6.83 (5H, m), 6.94 (1H, d, J=8.8 Hz), 7.23-7.28 (5H, m), 7.36 (1H, dd, J=8.9, 3.1 Hz), 7.45 (1H, s), 7.51 (2H, d, J=8.1 Hz), 7.57 (1H, d, J=15.4 Hz), 7.63 (2H, d, J=8.3 Hz), 7.77 (1H, d, J=2.9 Hz).

Example 300

(E)-3-{3-Chloro-5-methyl-4-[(5-{[4-(trifluoromethyl)benzyl]oxy}pyridin-2-yl)oxy]phenyl}-1-[4-(4-{2-[4-(methylsulfonyl)phenoxy]ethyl}benzyl)piperazin-1-yl]prop-2-en-1-one $^1$H-NMR (CDCl$_3$) δ: 2.19 (3H, s), 2.47 (4H, brs), 3.01 (3H, s), 3.12 (2H, t, J=7.1 Hz), 3.52 (2H, s), 3.65-3.74 (4H, m), 4.25 (2H, t, J=7.1 Hz), 5.09 (2H, s), 6.83 (1H, d, J=15.4 Hz), 6.95 (1H, d, J=8.8 Hz), 6.99-7.01 (2H, m), 7.24-7.30 (5H, m), 7.38 (1H, dd, J=8.9, 3.1 Hz), 7.46 (1H, d, J=2.0 Hz), 7.52 (2H, d, J=7.8 Hz), 7.57 (1H, d, J=15.4 Hz), 7.64 (2H, d, J=8.1 Hz), 7.78 (1H, d, J=2.7 Hz), 7.83-7.85 (2H, m).

Example 301

(E)-3-{3-Chloro-5-methyl-4-[(5-{[4-(trifluoromethyl)benzyl]oxy}pyridin-2-yl)oxy]phenyl}-1-(4-{4-[2-(4-fluoro-3-methylphenoxy)ethyl]benzyl}piperazin-1-yl)prop-2-en-1-one $^1$H-NMR (CDCl$_3$) δ: 2.18 (3H, s), 2.22 (3H, d, J=1.7 Hz), 2.47 (4H, t, J=4.9 Hz), 3.06 (2H, t, J=7.0 Hz), 3.52 (2H, s), 3.64-3.74 (4H, m), 4.10 (2H, t, J=7.0 Hz), 5.07 (2H, s), 6.62-6.66 (1H, m), 6.68-6.71 (1H, m), 6.81 (1H, d, J=15.4 Hz), 6.87 (1H, t, J=9.0 Hz), 6.94 (1H, d, J=9.0 Hz), 7.23-7.28 (5H, m), 7.36 (1H, dd, J=8.9, 3.1 Hz), 7.45 (1H, d, J=1.7 Hz), 7.51 (2H, d, J=8.1 Hz), 7.57 (1H, d, J=15.4 Hz), 7.63 (2H, d, J=8.1 Hz), 7.77 (1H, d, J=3.2 Hz).

Example 302

(E)-3-{3-Chloro-5-methyl-4-[(5-{[4-(trifluoromethyl)benzyl]oxy}pyridin-2-yl)oxy]phenyl}-1-(4-{4-[2-(4-chlorophenoxy)ethoxy]benzyl}piperazin-1-yl)prop-2-en-1-one $^1$H-NMR (CDCl$_3$) δ: 2.19 (3H, s), 2.46 (4H, t, J=4.9 Hz), 3.48 (2H, s), 3.63-3.73 (4H, m), 4.27-4.31 (4H, m), 5.08 (2H, s), 6.80 (1H, d, J=15.4 Hz), 6.87-6.95 (5H, m), 7.21-7.25 (4H, m), 7.29 (1H, s), 7.36 (1H, dd, J=8.9, 3.1 Hz), 7.45 (1H, d, J=2.2 Hz), 7.51 (2H, d, J=8.1 Hz), 7.57 (1H, d, J=15.4 Hz), 7.63 (2H, d, J=8.1 Hz), 7.78 (1H, d, J=3.2 Hz).

Example 303

(E)-3-{3-Chloro-5-methyl-4-[(5-{[4-(trifluoromethyl)benzyl]oxy}pyridin-2-yl)oxy]phenyl}-1-(4-{4-[2-(4-methylphenyl)ethoxy]benzyl}piperazin-1-yl)prop-2-en-1-one $^1$H-NMR (CDCl$_3$) δ: 2.18 (3H, s), 2.32 (3H, s), 2.45 (4H, t, J=4.9 Hz), 3.05 (2H, t, J=7.1 Hz), 3.46 (2H, s), 3.62-3.73 (4H, m), 4.13 (2H, t, J=7.1 Hz), 5.07 (2H, s), 6.80 (1H, d, J=15.4 Hz), 6.85 (2H, d, J=8.8 Hz), 6.94 (1H, d, J=9.0 Hz), 7.12 (2H, d, J=7.8 Hz), 7.16-7.24 (4H, m), 7.28 (1H, s), 7.36 (1H, dd, J=8.9, 3.1 Hz), 7.45 (1H, d, J=2.0 Hz), 7.51 (2H, d, J=8.1 Hz), 7.56 (1H, d, J=15.4 Hz), 7.63 (2H, d, J=8.1 Hz), 7.77 (1H, d, J=2.9 Hz).

Example 304

(E)-3-{3-Chloro-5-methyl-4-[(5-{[4-(trifluoromethyl)benzyl]oxy}pyridin-2-yl)oxy]phenyl}-1-(4-{4-[2-(4-methoxyphenyl)ethoxy]benzyl}piperazin-1-yl)prop-2-en-1-one $^1$H-NMR (CDCl$_3$) δ: 2.18 (3H, s), 2.45 (4H, t, J=4.9 Hz), 3.03 (2H, t, J=7.1 Hz), 3.46 (2H, s), 3.62-3.73 (4H, m), 3.78 (3H, s), 4.12 (2H, t, J=7.1 Hz), 5.07 (2H, s), 6.80 (1H, d, J=15.4 Hz), 6.82-6.87 (4H, m), 6.94 (1H, d, J=8.8 Hz), 7.18-7.25 (4H, m), 7.28 (1H, s), 7.36 (1H, dd, J=8.8, 3.2 Hz), 7.45 (1H, d, J=2.0 Hz), 7.51 (2H, d, J=8.1 Hz), 7.56 (1H, d, J=15.4 Hz), 7.63 (2H, d, J=8.3 Hz), 7.77 (1H, d, J=2.9 Hz).

Example 305

(E)-3-{3-Chloro-5-methyl-4-[(5-{[4-(trifluoromethyl)benzyl]oxy}pyridin-2-yl)oxy]phenyl}-1-[4-(4-{2-[(5-chloropyridin-2-yl)oxy]ethyl}benzyl)piperazin-1-yl]prop-2-en-1-one $^1$H-NMR (CDCl$_3$) δ: 2.19 (3H, s), 2.47 (4H, t, J=5.0 Hz), 3.06 (2H, t, J=7.1 Hz), 3.51 (2H, s), 3.64-3.74 (4H, m), 4.49 (2H, t, J=7.1 Hz), 5.08 (2H, s), 6.67 (1H, dd, J=8.8, 0.5 Hz), 6.81 (1H, d, J=15.4 Hz), 6.94 (1H, d, J=9.0 Hz), 7.22-7.29 (5H, m), 7.36 (1H, dd, J=9.0, 3.2 Hz), 7.45 (1H, d, J=2.0 Hz), 7.48-7.53 (3H, m), 7.57 (1H, d, J=15.4 Hz), 7.64 (2H, d, J=8.1 Hz), 7.78 (1H, d, J=2.7 Hz), 8.07 (1H, dd, J=2.7, 0.5 Hz).

Example 306

(E)-3-{3-Chloro-5-methyl-4-[(5-{[4-(trifluoromethyl)benzyl]oxy}pyridin-2-yl)oxy]phenyl}-1-(4-{4-[2-(4-cyclopropylphenoxy)ethyl]benzyl}piperazin-1-yl)prop-2-en-1-one $^1$H-NMR (CDCl$_3$) δ: 0.57-0.61 (2H, m), 0.85-0.90 (2H, m), 1.80-1.86 (1H, m), 2.19 (3H, s), 2.47 (4H, t, J=5.0 Hz), 3.06 (2H, t, J=7.1 Hz), 3.51 (2H, s), 3.63-3.74 (4H, m), 4.13 (2H, t, J=7.1 Hz), 5.07 (2H, s), 6.78-6.82 (3H, m), 6.94 (1H, dd, J=8.8, 0.5 Hz), 6.97-7.00 (2H, m), 7.23-7.28 (5H, m), 7.36 (1H, dd, J=8.9, 3.1 Hz), 7.45 (1H, d, J=2.0 Hz), 7.51 (2H, d, J=8.1 Hz), 7.57 (1H, d, J=15.4 Hz), 7.63 (2H, d, J=8.1 Hz), 7.78 (1H, d, J=2.7 Hz).

Example 307

(E)-3-{3-Chloro-5-methyl-4-[(5-{[4-(trifluoromethyl)benzyl]oxy}pyridin-2-yl)oxy]phenyl}-1-(4-{4-[2-(pyridin-2-yloxy)ethyl]benzyl}piperazin-1-yl)prop-2-en-1-one $^1$H-NMR (CDCl$_3$) δ: 2.18 (3H, s), 2.47 (4H, t, J=5.0 Hz), 3.08 (2H, t, J=7.1 Hz), 3.51 (2H, s), 3.63-3.74 (4H, m), 4.52 (2H, t, J=7.1 Hz), 5.08 (2H, s), 6.70-6.73 (1H, m), 6.79-6.85 (2H, m), 6.94 (1H, dd, J=9.0, 0.5 Hz), 7.26-7.29 (5H, m), 7.36 (1H, dd, J=8.9, 3.1 Hz), 7.45 (1H, d, J=2.2 Hz), 7.50-7.59 (4H, m), 7.63 (2H, d, J=8.3 Hz), 7.78 (1H, d, J=2.7 Hz), 8.12-8.14 (1H, m).

Example 308

(E)-1-(4-{4-[2-(4-Bromophenoxy)ethyl]benzyl}piperazin-1-yl)-3-{3-chloro-5-methyl-4-[(5-{[4-(trifluoromethyl)benzyl]oxy}pyridin-2-yl)oxy]phenyl}prop-2-en-1-one $^1$H-NMR (CDCl$_3$) δ: 2.18 (3H, s), 2.47 (4H, t, J=5.0 Hz), 3.07 (2H, t, J=7.0 Hz), 3.51 (2H, s), 3.63-3.74 (4H, m), 4.12

(2H, t, J=7.0 Hz), 5.07 (2H, s), 6.73-6.80 (3H, m), 6.94 (1H, d, J=8.8 Hz), 7.22-7.28 (5H, m), 7.32-7.37 (3H, m), 7.45 (1H, d, J=2.0 Hz), 7.51 (2H, d, J=8.1 Hz), 7.56 (1H, d, J=15.4 Hz), 7.63 (2H, d, J=8.1 Hz), 7.77 (1H, d, J=2.9 Hz).

Example 309

(E)-3-[3-Chloro-5-methyl-4-({5-[(4-methylbenzyl)oxy]pyridin-2-yl}oxy)phenyl]-1-[4-(4-{2-[(5-methylpyridin-2-yl)oxy]ethyl}benzyl)piperazin-1-yl]prop-2-en-1-one $^1$H-NMR (CDCl$_3$) δ: 2.18 (3H, s), 2.22 (3H, s), 2.34 (3H, s), 2.47 (4H, t, J=5.0 Hz), 3.07 (2H, t, J=7.1 Hz), 3.50 (2H, s), 3.63-3.74 (4H, m), 4.47 (2H, t, J=7.1 Hz), 4.97 (2H, s), 6.63 (1H, d, J=8.3 Hz), 6.80 (1H, d, J=15.4 Hz), 6.90 (1H, d, J=8.8 Hz), 7.18 (2H, d, J=8.1 Hz), 7.25-7.29 (7H, m), 7.33-7.38 (2H, m), 7.45 (1H, d, J=2.0 Hz), 7.57 (1H, d, J=15.4 Hz), 7.79 (1H, d, J=2.9 Hz), 7.94 (1H, d, J=2.4 Hz).

Example 310

(E)-3-[3-Chloro-5-methyl-4-({5-[(4-methylbenzyl)oxy]pyridin-2-yl}oxy)phenyl]-1-[4-(4-{2-[(6-chloropyridin-3-yl)oxy]ethyl}benzyl)piperazin-1-yl]prop-2-en-1-one $^1$H-NMR (CDCl$_3$) δ: 2.18 (3H, s), 2.35 (3H, s), 2.48 (4H, brs), 3.10 (2H, t, J=6.7 Hz), 3.52 (2H, s), 3.65-3.74 (4H, m), 4.20 (2H, t, J=6.7 Hz), 4.98 (2H, s), 6.80 (1H, d, J=15.4 Hz), 6.91 (1H, d, J=8.8 Hz), 7.14-7.29 (11H, m), 7.35 (1H, dd, J=8.2, 2.3 Hz), 7.45 (1H, s), 7.56 (1H, d, J=15.4 Hz), 7.79 (1H, d, J=2.2 Hz), 8.03 (1H, d, J=2.0 Hz).

Example 311

(E)-3-[3-Chloro-5-methyl-4-({5-[(4-methylbenzyl)oxy]pyridin-2-yl}oxy)phenyl]-1-[4-(4-{2-[(6-methylpyridin-3-yl)oxy]ethyl}benzyl)piperazin-1-yl]prop-2-en-1-one $^1$H-NMR (CDCl$_3$) δ: 2.19 (3H, s), 2.35 (3H, s), 2.47-2.49 (7H, m), 3.09 (2H, t, J=7.0 Hz), 3.52 (2H, s), 3.64-3.74 (4H, m), 4.19 (2H, t, J=7.0 Hz), 4.98 (2H, s), 6.80 (1H, d, J=15.4 Hz), 6.91 (1H, d, J=8.8 Hz), 7.04 (1H, d, J=4.6 Hz), 7.09 (1H, dd, J=8.4, 2.8 Hz), 7.18 (2H, d, J=7.6 Hz), 7.23-7.29 (7H, m), 7.35 (1H, dd, J=8.9, 3.1 Hz), 7.45 (1H, d, J=2.0 Hz), 7.57 (1H, d, J=15.4 Hz), 7.79 (1H, d, J=2.7 Hz), 8.18 (1H, d, J=2.9 Hz).

Example 312

(E)-1-[4-(4-{2-[(5-Bromopyridin-2-yl)oxy]ethyl}benzyl)piperazin-1-yl]-3-[3-chloro-5-methyl-4-({5-[(4-methylbenzyl)oxy]pyridin-2-yl}oxy)phenyl]prop-2-en-1-one $^1$H-NMR (CDCl$_3$) δ: 2.18 (3H, s), 2.34 (3H, s), 2.47 (4H, t, J=4.9 Hz), 3.06 (2H, t, J=7.1 Hz), 3.51 (2H, s), 3.63-3.74 (4H, m), 4.48 (2H, t, J=7.1 Hz), 4.97 (2H, s), 6.63 (1H, dd, J=8.8, 0.5 Hz), 6.80 (1H, d, J=15.4 Hz), 6.91 (1H, dd, J=8.8, 0.5 Hz), 7.18 (2H, d, J=7.8 Hz), 7.22-7.29 (7H, m), 7.34 (1H, dd, J=8.9, 3.1 Hz), 7.45 (1H, d, J=2.2 Hz), 7.57 (1H, d, J=15.4 Hz), 7.61 (1H, dd, J=8.8, 2.7 Hz), 7.79 (1H, d, J=2.7 Hz), 8.16 (1H, dd, J=2.6, 0.6 Hz).

Example 313

(E)-3-[3-Chloro-5-methyl-4-({5-[(4-methylbenzyl)oxy]pyridin-2-yl}oxy)phenyl]-1-[4-(4-{2-[(6-methoxypyridin-3-yl)oxy]ethyl}benzyl)piperazin-1-yl]prop-2-en-1-one $^1$H-NMR (CDCl$_3$) δ: 2.18 (3H, s), 2.35 (3H, s), 2.47 (4H, t, J=5.0 Hz), 3.07 (2H, t, J=7.0 Hz), 3.52 (2H, s), 3.64-3.74 (4H, m), 3.87 (3H, s), 4.16 (2H, t, J=7.0 Hz), 4.97 (2H, s), 6.66 (1H, d, J=8.8 Hz), 6.80 (1H, d, J=15.4 Hz), 6.91 (1H, d, J=9.0 Hz), 7.17-7.20 (3H, m), 7.23-7.29 (7H, m), 7.35 (1H, dd, J=8.9, 3.2 Hz), 7.45 (1H, d, J=2.2 Hz), 7.57 (1H, d, J=15.4 Hz), 7.79 (2H, t, J=3.2 Hz).

Example 314

(E)-1-[4-(4-{2-[(6-Chloro-1,3-benzoxazol-2-yl)oxy]ethyl}benzyl)piperazin-1-yl]-3-[3-chloro-5-methyl-4-({5-[(4-methylbenzyl)oxy]pyridin-2-yl}oxy)phenyl]prop-2-en-1-one $^1$H-NMR (CDCl$_3$) δ: 2.18 (3H, s), 2.34 (3H, s), 2.38-2.40 (4H, m), 3.04 (2H, t, J=7.1 Hz), 3.47 (2H, s), 3.63-3.73 (4H, m), 4.01 (2H, t, J=7.1 Hz), 4.97 (2H, s), 6.57 (1H, d, J=8.3 Hz), 6.82 (1H, d, J=15.4 Hz), 6.91 (1H, d, J=8.8 Hz), 7.01 (1H, dd, J=8.3, 2.0 Hz), 7.12 (2H, d, J=8.1 Hz), 7.16-7.22 (5H, m), 7.27-7.29 (3H, m), 7.35 (1H, dd, J=8.9, 3.1 Hz), 7.44 (1H, d, J=2.0 Hz), 7.57 (1H, d, J=15.4 Hz), 7.78 (1H, d, J=2.9 Hz).

Example 315

(E)-3-[3-Chloro-5-methyl-4-({5-[(4-methylbenzyl)oxy]pyridin-2-yl}oxy)phenyl]-1-(4-{4-[2-(4-ethoxyphenoxy)ethoxy]benzyl}piperazin-1-yl)prop-2-en-1-one $^1$H-NMR (CDCl$_3$) δ: 1.38 (3H, t, J=7.0 Hz), 2.18 (3H, s), 2.35 (3H, s), 2.46 (4H, t, J=5.0 Hz), 3.48 (2H, s), 3.66-3.73 (4H, m), 3.97 (2H, q, J=7.0 Hz), 4.26-4.29 (4H, m), 4.97 (2H, s), 6.78-6.92 (8H, m), 7.18 (2H, d, J=8.1 Hz), 7.22-7.29 (5H, m), 7.35 (1H, dd, J=8.8, 3.2 Hz), 7.45 (1H, d, J=2.2 Hz), 7.56 (1H, d, J=15.1 Hz), 7.79 (1H, d, J=2.9 Hz).

Example 316

(E)-3-[3-Chloro-5-methyl-4-({5-[(4-methylbenzyl)oxy]pyridin-2-yl}oxy)phenyl]-1-(4-{4-[2-(4-methoxyphenoxy)ethoxy]benzyl}piperazin-1-yl)prop-2-en-1-one $^1$H-NMR (CDCl$_3$) δ: 2.19 (3H, s), 2.36 (3H, s), 2.48 (4H, brs), 3.50 (2H, brs), 3.68-3.74 (7H, m), 4.27-4.32 (4H, m), 4.99 (2H, s), 6.77-6.84 (3H, m), 6.92-6.97 (5H, m), 7.19 (2H, d, J=8.1 Hz), 7.24-7.30 (5H, m), 7.36 (1H, dd, J=8.9, 3.1 Hz), 7.46 (1H, d, J=1.7 Hz), 7.57 (1H, d, J=15.4 Hz), 7.80 (1H, d, J=3.2 Hz).

Example 317

(E)-1-(4-{4-[2-(1,3-Benzothiazol-2-yloxy)ethyl]benzyl}piperazin-1-yl)-3-[3-chloro-5-methyl-4-({5-[(4-methylbenzyl)oxy]pyridin-2-yl}oxy)phenyl]prop-2-en-1-one $^1$H-NMR (CDCl$_3$) δ: 2.18 (3H, s), 2.34 (3H, s), 2.43 (4H, brs), 3.02 (2H, t, J=7.3 Hz), 3.49 (2H, s), 3.64-3.72 (4H, m), 4.14 (2H, t, J=7.3 Hz), 4.97 (2H, s), 6.81 (1H, d, J=15.4 Hz), 6.89-6.93 (2H, m), 7.12-7.18 (5H, m), 7.21-7.29 (6H, m), 7.35 (1H, dd, J=8.9, 3.1 Hz), 7.40 (1H, dd, J=7.8, 1.2 Hz), 7.45 (1H, d, J=2.0 Hz), 7.57 (1H, d, J=15.4 Hz), 7.78 (1H, d, J=2.9 Hz).

Example 318

(E)-3-[3-Chloro-5-methyl-4-({5-[(4-methylbenzyl)oxy]pyridin-2-yl}oxy)phenyl]-1-[4-(4-{2-[(2-methyl-1,3-benzothiazol-5-yl)oxy]ethyl}benzyl)piperazin-1-yl]prop-2-en-1-one $^1$H-NMR (CDCl$_3$) δ: 2.18 (3H, s), 2.35 (3H, s), 2.48 (4H, t, J=4.9 Hz), 2.80 (3H, s), 3.13 (2H, t, J=7.0 Hz), 3.52 (2H, s), 3.64-3.74 (4H, m), 4.25 (2H, t, J=7.0 Hz), 4.98 (2H, s), 6.80 (1H, d, J=15.4 Hz), 6.91 (1H, d, J=9.3 Hz), 6.98 (1H, dd, J=8.8, 2.4 Hz), 7.18 (2H, d, J=7.8 Hz), 7.28-7.29 (7H, m), 7.35 (1H, dd, J=8.9, 3.1 Hz), 7.43-7.46 (2H, m), 7.57 (1H, d, J=15.4 Hz), 7.64 (1H, d, J=8.8 Hz), 7.79 (1H, d, J=2.9 Hz).

Example 319

(E)-3-[3-Chloro-5-methyl-4-({5-[4-methylbenzyl)oxy]pyridin-2-yl}oxy)phenyl]-1-{(3S)-3-[methyl(4-{2-[4-(propan-2-yl)phenoxy]ethyl}benzyl)amino]pyrrolidin-1-yl}prop-2-en-1-one $^1$H-NMR (CDCl$_3$) δ: 1.21 (6H, d, J=6.9 Hz), 1.86-2.03 (1H, m), 2.17-2.19 (7H, m), 2.34 (3H, s), 2.81-2.88 (1H, m), 3.02-3.08 (2.5H, m), 3.15-3.17 (0.5H, m), 3.40-3.64 (4H, m), 3.82-3.91 (1.5H, m), 3.99-4.02 (0.5H, m), 4.14 (2H, t, J=7.1 Hz), 4.96 (2H, s), 6.64 (1H, dd, J=15.4, 8.8 Hz), 6.81-6.84 (2H, m), 6.91 (1H, dd, J=8.8, 2.4 Hz), 7.12 (2H, dd, J=8.5, 2.2 Hz), 7.17 (2H, d, J=7.8 Hz), 7.22-7.30 (7H, m), 7.33-7.36 (1H, m), 7.47 (1H, d, J=1.7 Hz), 7.61 (1H, dd, J=15.4, 4.9 Hz), 7.78-7.80 (1H, m).

Example 320

(E)-3-[3-Chloro-5-methyl-4-({5-[(4-methylbenzyl)oxy]pyridin-2-yl}oxy)phenyl]-1-(4-{4-[2-(4-cyclopropylphenoxy)ethyl]benzyl}piperazin-1-yl)prop-2-en-1-one $^1$H-NMR (CDCl$_3$) δ: 0.58-0.61 (2H, m), 0.86-0.89 (2H, m), 1.81-1.86 (1H, m), 2.18 (3H, s), 2.35 (3H, s), 2.47 (4H, t, J=5.0 Hz), 3.07 (2H, t, J=7.1 Hz), 3.51 (2H, s), 3.64-3.74 (4H, m), 4.13 (2H, t, J=7.1 Hz), 4.98 (2H, s), 6.78-6.82 (3H, m), 6.91 (1H, d, J=9.0 Hz), 6.98-7.00 (2H, m), 7.18 (2H, d, J=7.8 Hz), 7.23-7.29 (7H, m), 7.35 (1H, dd, J=8.9, 3.1 Hz), 7.45 (1H, d, J=2.2 Hz), 7.56 (1H, d, J=15.4 Hz), 7.79 (1H, d, J=2.9 Hz).

Example 321

To a CH$_2$Cl$_2$ (5 mL) solution of (E)-3-[3-chloro-5-methyl-4-({5-[(4-methyl-benzyl)oxy]pyridin-2-yl}oxy)phenyl]prop-2-enoic acid (200 mg) was added N,N-dimethyl-4-{2-[4-(piperazin-1-ylmethyl)phenyl]ethoxy}aniline (191 mg), DCC (151 mg), and DMAP (5.96 mg) at room temperature, then the resultant mixture was stirred over night. The mixture was evaporated. The residue was added AcOEt, then filtered off, and the filtrate was evaporated. The residue was purified by silica gel column chromatography (n-hexane/AcOEt=1/1 to 1/0 and then AcOEt/MeOH=4/1) to afford (E)-3-[3-chloro-5-methyl-4-({5-[(4-methylbenzyl)oxy]-pyridin-2-yl}oxy)phenyl]-1-[4-(4-{2-[4-(dimethylamino)phenoxy]ethyl}benzyl)piperazin-1-yl]prop-2-en-1-one as a pale brown amorphous powder (184 mg).

$^1$H-NMR (DMSO-d$_6$) δ: 2.09 (3H, s), 2.30 (3H, s), 2.34-2.36 (2H, m), 2.40-2.42 (2H, m), 2.78 (6H, s), 2.97 (2H, t, J=7.0 Hz), 3.32 (2H, s), 3.49 (2H, s), 3.55-3.57 (2H, m), 3.70-3.73 (2H, m), 4.08 (2H, t, J=7.0 Hz), 5.05 (2H, s), 6.67-6.69 (2H, m), 6.79-6.81 (2H, m), 7.07 (1H, d, J=9.3 Hz), 7.19 (2H, d, J=7.8 Hz), 7.24-7.34 (7H, m), 7.43 (1H, d, J=15.4 Hz), 7.57-7.59 (1H, m), 7.62-7.62 (1H, m), 7.79-7.82 (2H, m).

Example 322

To a DMF (5 mL) solution of (E)-3-{3-chloro-4-[(5-hydroxypyridin-2-yl)oxy]-5-methylphenyl}-1-(4-{4-[2-(4-methylphenoxy)ethyl]benzyl}piperazin-1-yl)prop-2-en-1-one (479 mg) and 4-methylbenzyl bromide (155 mg) was added sodium hydride (60% w/w in oil, 42 mg) at 0° C., and stirred for 1 hour. The reaction mixture was quenched by addition of saturated aqueous NH$_4$Cl (10 mL), and extracted with AcOEt. The organic layer was washed with water, saturated aqueous NaCl, dried over anhydrous Na$_2$SO$_4$, and evaporated. The residue was purified by silica gel column chromatography (AcOEt/MeOH=1/0 to 9/1) to afford (E)-3-[3-chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one (480 mg).

$^1$H-NMR (CDCl$_3$) δ: 2.18 (3H, s), 2.28 (3H, s), 2.36 (3H, s), 2.48 (4H, t, J=4.9 Hz), 3.08 (2H, t, J=7.1 Hz), 3.52 (2H, s), 3.60-3.80 (4H, m), 4.15 (2H, t, J=7.1 Hz), 4.98 (2H, s), 6.76-6.84 (3H, m), 6.91 (1H, d, J=8.8 Hz), 7.06 (2H, d, J=8.8 Hz), 7.18 (2H, d, J=8.3 Hz), 7.23-7.29 (7H, m), 7.35 (1H, ddd, J=9.0, 3.2, 0.7 Hz), 7.45 (1H, d, J=1.7 Hz), 7.56 (1H, d, J=15.1 Hz), 7.79 (1H, d, J=3.2 Hz).

The following compounds were produced in the same manner as in Example 322 using appropriate starting materials.

Example 323

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.36 (3H, s), 2.48 (4H, t, J=4.8 Hz), 3.08 (2H, t, J=7.1 Hz), 3.53 (2H, s), 3.60-3.80 (4H, m), 4.13 (2H, t, J=7.1 Hz), 4.99 (2H, s), 6.75-6.87 (3H, m), 6.88-6.99 (3H, m), 7.17-7.31 (9H, m), 7.35 (1H, dd, J=8.9, 3.3 Hz), 7.45 (1H, d, J=2.0 Hz), 7.56 (1H, d, J=15.5 Hz), 7.79 (1H, d, J=3.0 Hz).

Example 324

(E)-3-[3-Chloro-4-({5-[(4-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.48 (4H, t, J=4.9 Hz), 3.08 (2H, t, J=7.1 Hz), 3.53 (2H, s), 3.60-3.80 (4H, m), 4.13 (2H, t, J=7.1 Hz), 5.00 (2H, s), 6.77-6.87 (3H, m), 6.90-7.01 (3H, m), 7.21-7.38 (10H, m), 7.45 (1H, d, J=2.0 Hz), 7.57 (1H, d, J=15.2 Hz), 7.77 (1H, d, J=3.0 Hz).

Example 325

(E)-3-[3-Chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.9 Hz), 2.19 (3H, s), 2.36 (3H, s), 2.48 (4H, t, J=4.8 Hz), 2.85 (1H, septet, J=6.9 Hz), 3.08 (2H, t, J=7.1 Hz), 3.52 (2H, s), 3.65-3.73 (4H, m), 4.15 (2H, t, J=7.1 Hz), 4.98 (2H, s), 6.79-6.84 (3H, m), 6.91 (1H, d, J=8.9 Hz), 7.11-7.30 (11H, m), 7.35 (1H, dd, J=8.9, 3.3 Hz), 7.45 (1H, d, J=2.0 Hz), 7.56 (1H, d, J=15.2 Hz), 7.79 (1H, d, J=3.0 Hz).

Example 326

(E)-3-[3-Chloro-4-({5-[(4-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.9 Hz), 2.19 (3H, s), 2.48 (4H, t, J=4.9 Hz), 2.85 (1H, septet, J=6.9 Hz), 3.08 (2H, t, J=6.9 Hz), 3.52 (2H, s), 3.64-3.74 (4H, m), 4.15 (2H, t, J=7.1 Hz), 5.00 (2H, s), 6.77-6.86 (3H, m), 6.93 (1H, d, J=8.9 Hz), 7.13 (2H, d, J=8.6 Hz), 7.28-7.34 (10H, m), 7.45 (1H, d, J=2.0 Hz), 7.57 (1H, d, J=15.5 Hz), 7.77 (1H, d, J=3.0 Hz).

Example 327

(E)-3-{3-Chloro-5-methyl-4-[(5-{[4-(trifluoromethyl)benzyl]oxy}pyridin-2-yl)oxy]phenyl}-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.48 (4H, t, J=4.9 Hz), 3.08 (2H, t, J=7.1 Hz), 3.52 (2H, s), 3.65-3.74 (4H, m), 4.13 (2H, t, J=6.9 Hz), 5.09 (2H, s), 6.79-6.83 (3H, m), 6.92-6.99 (3H, m), 7.24-7.27 (5H, m), 7.37 (1H, dd, J=8.9, 3.0 Hz), 7.45 (1H, d, J=2.0 Hz), 7.53-7.57 (3H, m), 7.65 (2H, d, J=7.9 Hz), 7.78 (1H, d, J=3.0 Hz).

Example 328

(E)-3-[3-Chloro-4-({5-[(4-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.48 (4H, t, J=4.9 Hz), 3.08 (2H, t, J=6.9 Hz), 3.53 (2H, s), 3.59-3.83 (4H, m), 4.13 (2H, t, J=7.1 Hz), 4.99 (2H, s), 6.65-6.87 (3H, m), 6.90-6.99 (3H, m), 7.02-7.11 (2H, m), 7.20-7.30 (5H, m), 7.31-7.41 (3H, m), 7.45 (1H, d, J=2.0 Hz), 7.57 (1H, d, J=15.5 Hz), 7.78 (1H, d, J=3.0 Hz).

Example 329

(E)-3-{3-Chloro-5-methyl-4-[(5-{[4-(propan-2-yl)benzyl]oxy}pyridin-2-yl)oxy]phenyl}-1-(4-{4-[2-(4-fluorophenoxy)ethyl]benzyl}piperazin-1-yl)prop-2-en-1-one $^1$H-NMR (CDCl$_3$) δ: 1.25 (6H, d, J=6.9 Hz), 2.19 (3H, s), 2.48 (4H, t, J=4.9 Hz), 2.91 (1H, septet, J=6.9 Hz), 3.08 (2H, t, J=6.9 Hz), 3.52 (2H, s), 3.65-3.74 (4H, m), 4.13 (2H, t, J=6.9 Hz), 4.99 (2H, s), 6.76-6.85 (3H, m), 6.93-6.96 (3H, m), 7.28-7.34 (10H, m), 7.45 (1H, d, J=2.0 Hz), 7.57 (1H, d, J=15.5 Hz), 7.80 (1H, d, J=3.0 Hz).

Example 330

(E)-3-[3-Chloro-4-({5-[(4-fluorobenzyl)oxy]pyridin-2-yl}oxy)-5-methylphenyl]-1-(4-{4-[2-(4-methylphenoxy)ethyl]benzyl}piperazin-1-yl)prop-2-en-1-one $^1$H-NMR (CDCl$_3$) δ: 2.19 (3H, s), 2.28 (3H, s), 2.48 (4H, t, J=4.8 Hz), 3.08 (2H, t, J=7.1 Hz), 3.52 (2H, s), 3.64-3.74 (4H, m), 4.15 (2H, t, J=7.1 Hz), 4.99 (2H, s), 6.78-6.81 (3H, m), 6.93 (1H, d, J=8.9 Hz), 7.04-7.10 (4H, m), 7.27-7.28 (5H, m), 7.35-7.39 (3H, m), 7.45 (1H, d, J=2.0 Hz), 7.57 (1H, d, J=15.5 Hz), 7.78 (1H, d, J=3.0 Hz).

Example 331

(E)-3-[3-Chloro-4-({5-[(4-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.9 Hz), 2.19 (3H, s), 2.48 (4H, t, J=4.9 Hz), 2.85 (1H, septet, J=6.9 Hz), 3.08 (2H, t, J=7.1 Hz), 3.52 (2H, s), 3.58-3.82 (4H, m), 4.15 (2H, t, J=6.9 Hz), 4.99 (2H, s), 6.72-6.87 (3H, m), 6.93 (1H, d, J=8.9 Hz), 7.01-7.18 (4H, m), 7.22-7.29 (5H, m), 7.32-7.41 (3H, m), 7.45 (1H, d, J=1.6 Hz), 7.57 (1H, d, J=15.5 Hz), 7.78 (1H, d, J=3.0 Hz).

Example 332

(E)-3-(3-Chloro-5-methyl-4-{[5-(pyridin-3-ylmethoxy)pyridin-2-yl]oxy}phenyl)-1-(4-{4-[2-(4-fluorophenoxy)ethyl]benzyl}piperazin-1-yl)prop-2-en-1-one $^1$H-NMR (CDCl$_3$) δ: 2.20 (3H, s), 2.48 (4H, t, J=4.9 Hz), 3.08 (2H, t, J=7.1 Hz), 3.53 (2H, s), 3.65-3.74 (4H, m), 4.13 (2H, t, J=6.9 Hz), 5.05 (2H, s), 6.81-6.83 (3H, m), 6.93-6.97 (3H, m), 7.23-7.31 (5H, m), 7.35-7.38 (2H, m), 7.46 (1H, d, J=2.0 Hz), 7.57 (1H, d, J=15.5 Hz), 7.75 (1H, d, J=7.9 Hz), 7.80 (1H, d, J=3.0 Hz), 8.60 (1H, dd, J=4.8, 1.5 Hz), 8.66 (1H, d, J=2.0 Hz).

Example 333

(E)-3-(3-Chloro-5-methyl-4-{[5-(pyridin-2-ylmethoxy)pyridin-2-yl]oxy}phenyl)-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.48 (4H, t, J=4.8 Hz), 3.08 (2H, t, J=7.1 Hz), 3.53 (2H, s), 3.65-3.74 (4H, m), 4.13 (2H, t, J=6.9 Hz), 5.17 (2H, s), 6.79 (1H, d, J=9.2 Hz), 6.80-6.85 (2H, m), 6.92-6.99 (3H, m), 7.25-7.27 (6H, m), 7.41 (1H, dd, J=8.9, 3.0 Hz), 7.45 (1H, d, J=2.0 Hz), 7.50 (1H, d, J=7.9 Hz), 7.57 (1H, d, J=15.5 Hz), 7.73 (1H, td, J=7.7, 1.8 Hz), 7.82 (1H, d, J=3.0 Hz), 8.59 (1H, d, J=4.6 Hz).

Example 334

(E)-3-[3-Chloro-5-methyl-4-({5-[(4-methylbenzyl)oxy]pyridin-2-yl}oxy)phenyl]-1-(4-{4-[2-(4-methoxyphenoxy)ethyl]benzyl}piperazin-1-yl)prop-2-en-1-one $^1$H-NMR (CDCl$_3$) δ: 2.19 (3H, s), 2.36 (3H, s), 2.48 (4H, t, J=4.9 Hz), 3.07 (2H, t, J=7.1 Hz), 3.52 (2H, s), 3.55-3.83 (7H, m), 4.13 (2H, t, J=7.1 Hz), 4.98 (2H, s), 6.77-6.87 (5H, m), 6.92 (1H, d, J=8.9 Hz), 7.19 (2H, d, J=7.9 Hz), 7.23-7.31 (7H, m), 7.36 (1H, dd, J=8.9, 3.3 Hz), 7.45 (1H, d, J=2.0 Hz), 7.57 (1H, d, J=15.5 Hz), 7.79 (1H, d, J=3.3 Hz).

Example 335

(E)-3-[3-Chloro-4-({5-[(6-chloropyridin-3-yl)methoxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.48 (4H, t, J=4.9 Hz), 3.08 (2H, t, J=7.1 Hz), 3.53 (2H, s), 3.65-3.74 (4H, m), 4.13 (2H, t, J=6.9 Hz), 5.03 (2H, s), 6.78-6.85 (3H, m), 6.94-6.98 (3H, m), 7.24-7.28 (5H, m), 7.35-7.39 (2H, m), 7.46 (1H, d, J=2.0 Hz), 7.57 (1H, d, J=15.5 Hz), 7.73 (1H, dd, J=8.2, 2.6 Hz), 7.78 (1H, d, J=3.0 Hz), 8.43 (1H, d, J=2.3 Hz).

Example 336

(E)-3-(3-Chloro-5-methyl-4-{[5-(pyridin-3-ylmethoxy)pyridin-2-yl]oxy}phenyl)-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.9 Hz), 2.05 (2H, s), 2.19 (3H, s), 2.48 (4H, t, J=4.9 Hz), 2.79-2.91 (1H, m), 3.08 (2H, t, J=7.1 Hz), 3.52 (2H, s), 3.65 (2H, s), 3.74 (2H, s), 4.12 (3H, t, J=10.7 Hz), 5.05 (2H, s), 6.73-6.89 (3H, m), 6.90-6.99 (1H, m), 7.08-7.18 (2H, m), 7.27-7.42 (0H, m), 7.43-7.48 (1H, m), 7.52-7.62 (1H, m), 7.75 (1H, dt, J=7.8, 1.9 Hz), 7.80 (2H, d, J=3.0 Hz), 8.60 (2H, dd, J=4.9, 1.6 Hz), 8.66 (2H, d, J=1.3 Hz).

Example 337

(E)-3-[3-Chloro-4-({5-[(6-chloropyridin-3-yl)methoxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.20-1.25 (6H, m), 2.19 (3H, s), 2.47-2.51 (4H, m), 2.82-2.88 (1H, m), 3.08 (2H, t, J=6.9 Hz), 3.53 (2H, s), 3.65-3.71 (4H, m), 4.07-4.18 (2H, m), 5.03 (2H, s), 6.81-6.86 (3H, m), 6.95 (1H, d, J=9.2 Hz), 7.13 (2H, d, J=8.2 Hz), 7.24-7.28 (3H, m), 7.34-7.39 (3H, m), 7.47 (1H, d, J=2.0 Hz), 7.56 (1H, d, J=15.5 Hz), 7.73-7.78 (2H, m), 8.42 (1H, d, J=2.0 Hz).

Example 338

(E)-3-(3-Chloro-5-methyl-4-{[5-(pyridin-2-ylmethoxy)pyridin-2-yl]oxy}phenyl)-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.9 Hz), 2.19 (3H, s), 2.47-2.49 (4H, m), 2.80-2.90 (1H, m), 3.08 (2H, t, J=7.1 Hz), 3.52 (2H, s), 3.64 (2H, s), 3.74 (2H, s), 4.15 (2H, t, J=7.1 Hz), 5.17 (2H, s), 6.77-6.95 (4H, m), 7.11-7.15 (2H, m), 7.22-7.27 (6H, m), 7.40-7.44 (2H, m), 7.51-7.57 (2H, m), 7.72-7.75 (1H, m), 7.82 (1H, d, J=3.0 Hz), 8.58-8.60 (1H, m).

Example 339

(E)-3-[3-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.47-2.49 (4H, m), 3.08 (2H, t, J=7.1 Hz), 3.52 (2H, s), 3.65 (2H, s), 3.74 (2H, s), 4.13 (2H, t, J=7.1 Hz), 5.14 (2H, s), 6.75-6.87 (3H, m), 6.90-7.01 (3H, m), 7.22-7.26 (3H, m), 7.28-7.32 (3H, m), 7.35-7.43 (2H, m), 7.45 (1H, d, J=2.0 Hz), 7.48-7.61 (3H, m), 7.79-7.84 (1H, m).

Example 340

(E)-3-[3-Chloro-5-methyl-4-({5-[(2-methylbenzyl)oxy]pyridin-2-yl}oxy)phenyl]-1-(4-{4-[2-(4-fluorophenoxy)ethyl]benzyl}piperazin-1-yl)prop-2-en-1-one $^1$H-NMR (CDCl$_3$) δ: 2.20 (3H, s), 2.36 (3H, s), 2.47-2.49 (4H, m), 3.08 (2H, t, J=6.9 Hz), 3.53 (2H, s), 3.63-3.66 (2H, m), 3.72-3.76 (2H, m), 4.13 (2H, t, J=6.9 Hz), 5.01 (2H, s), 6.77-6.89 (3H, m), 6.89-7.00 (3H, m), 7.14-7.25 (4H, m), 7.25-7.27 (3H, m), 7.27-7.31 (1H, m), 7.34-7.41 (2H, m), 7.46 (1H, d, J=2.0 Hz), 7.57 (1H, d, J=15.5 Hz), 7.82 (1H, d, J=2.6 Hz).

Example 341

(E)-3-[3-Chloro-4-({5-[(2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.47-2.49 (4H, m), 3.08 (2H, t, J=7.1 Hz), 3.53 (2H, s), 3.63-3.67 (2H, m), 3.72-3.76 (2H, m), 4.13 (2H, t, J=7.1 Hz), 5.10 (2H, s), 6.77-6.99 (6H, m), 7.02-7.23 (3H, m), 7.23-7.27 (2H, m), 7.29-7.49 (6H, m), 7.57 (1H, d, J=15.2 Hz), 7.82 (1H, d, J=3.0 Hz).

Example 342

(E)-3-[3-Chloro-4-({5-[(2-fluorobenzyl)oxy]pyridin-2-yl}oxy)-5-methylphenyl]-1-(4-{4-[2-(4-methylphenoxy)ethyl]benzyl}piperazin-1-yl)prop-2-en-1-one $^1$H-NMR (CDCl$_3$) δ: 2.19 (3H, s), 2.28 (3H, s), 2.47-2.49 (4H, m), 3.08 (2H, t, J=7.1 Hz), 3.52 (2H, s), 3.63-3.66 (2H, m), 3.72-3.76 (2H, m), 4.15 (2H, t, J=7.1 Hz), 5.10 (2H, s), 6.80 (3H, dd, J=11.9, 3.3 Hz), 6.94 (1H, d, J=8.9 Hz), 7.03-7.20 (4H, m), 7.21-7.41 (7H, m), 7.43-7.51 (2H, m), 7.57 (1H, d, J=15.5 Hz), 7.82 (1H, d, J=3.0 Hz).

Example 343

(E)-3-[3-Chloro-4-({5-[(2-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one $^1$H-NMR (CDCl$_3$) δ: 2.19 (3H, s), 2.28 (3H, s), 2.47-2.49 (4H, m), 3.08 (2H, t, J=7.1 Hz), 3.52 (2H, s), 3.63-3.66 (2H, m), 3.72-3.76 (2H, m), 4.15 (2H, t, J=7.1 Hz), 5.14 (2H, s), 6.79-6.81 (3H, m), 6.94 (1H, d, J=8.9 Hz), 7.07 (2H, d, J=8.2 Hz), 7.23-7.32 (7H, m), 7.39-7.44 (3H, m), 7.53-7.57 (2H, m), 7.81 (1H, d, J=3.0 Hz).

Example 344

(E)-3-[3-Chloro-5-methyl-4-({5-[(2-methylbenzyl)oxy]pyridin-2-yl}oxy)phenyl]-1-(4-{4-[2-(4-methylphenoxy)ethyl]benzyl}piperazin-1-yl)prop-2-en-1-one $^1$H-NMR (CDCl$_3$) δ: 2.20 (3H, s), 2.28 (3H, s), 2.36 (3H, s), 2.47-2.49 (4H, m), 3.08 (2H, t, J=7.1 Hz), 3.52 (2H, s), 3.63-3.66 (2H, m), 3.72-3.76 (2H, m), 4.14 (2H, t, J=7.1 Hz), 5.01 (2H, s), 6.76-6.85 (3H, m), 6.93 (1H, d, J=8.9 Hz), 7.07 (2H, d, J=8.2 Hz), 7.20-7.29 (8H, m), 7.33-7.41 (2H, m), 7.46 (1H, d, J=2.3 Hz), 7.57 (1H, d, J=15.5 Hz), 7.82 (1H, d, J=3.0 Hz).

Example 345

(E)-3-[3-Chloro-5-methyl-4-({5-[(6-methylpyridin-2-yl)methoxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.9 Hz), 2.19 (3H, s), 2.47-2.49 (4H, m), 2.56 (3H, s), 2.80-2.90 (1H, m), 3.08 (2H, t, J=7.1 Hz), 3.52 (2H, s), 3.62-3.66 (2H, m), 3.72-3.76 (2H, m), 4.15 (2H, t, J=7.1 Hz), 5.13 (2H, s), 6.77-6.86 (3H, m), 6.93 (1H, d, J=8.9 Hz), 7.08-7.15 (3H, m), 7.22-7.27 (4H, m), 7.27-7.34 (2H, m), 7.40 (1H, dd, J=8.9, 3.0 Hz), 7.45 (1H, d, J=2.0 Hz), 7.54-7.64 (2H, m), 7.81 (1H, d, J=3.0 Hz).

Example 346

(E)-3-[3-Chloro-4-({5-[(2-fluorobenzyl)oxy]pyridin-2-yl}oxy)-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.9 Hz), 2.19 (3H, s), 2.47-2.49 (4H, m), 2.80-2.90 (1H, m), 3.08 (2H, t, J=7.1 Hz), 152 (2H, s), 3.63-3.66 (2H, m), 3.72-3.76 (2H, m), 4.15 (2H, t, J=7.1 Hz), 5.10 (2H, s), 6.74-6.87 (3H, m), 6.93 (1H, d, J=8.9 Hz), 7.05-7.19 (4H, m), 7.22-7.27 (3H, m), 7.29-7.41 (4H, m), 7.42-7.51 (2H, m), 7.57 (1H, d, J=15.2 Hz), 7.81 (1H, d, J=3.0 Hz).

Example 347

(E)-3-[3-Chloro-5-methyl-4-({5-[(2-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.9 Hz), 2.20 (3H, s), 2.36 (3H, s), 2.45-2.53 (4H, m), 2.80-2.90 (1H, m), 3.08 (2H, t, J=6.9 Hz), 3.52 (2H, s), 3.63-3.67 (2H, m), 3.72-3.76 (2H, m), 4.15 (2H, t, J=6.9 Hz), 5.01 (2H, s), 6.75-6.86 (3H, m), 6.93 (1H, d, J=8.9 Hz), 7.13 (2H, d, J=8.2 Hz), 7.19-7.30 (8H, m), 7.33-7.42 (2H, m), 7.46 (1H, s), 7.57 (1H, d, J=15.5 Hz), 7.82 (1H, d, J=3.0 Hz).

Example 348

(E)-3-[3-Chloro-4-({5-[(2-chlorobenzyl)oxy]pyridin-2-yl}oxy)-5-methylphenyl]-1-(4-{4-[2-(4-methoxyphenoxy)ethyl]benzyl}piperazin-1-yl)prop-2-en-1-one $^1$H-NMR (CDCl$_3$) δ: 2.19 (3H, s), 2.46-2.50 (4H, m), 3.07 (2H, t, J=7.1 Hz), 3.52 (2H, s), 3.63-3.66 (2H, m), 3.73-3.78 (5H, m), 4.13 (2H, t, J=7.1 Hz), 5.14 (2H, s), 6.76-6.85 (5H, m), 6.94 (1H, d, J=8.9 Hz), 7.23-7.32 (7H, m), 7.37-7.60 (5H, m), 7.81 (1H, d, J=2.6 Hz).

Example 349

(E)-3-[3-Chloro-4-({5-[(2-methoxybenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.19 (3H, s), 2.48-2.49 (4H, m), 2.82-2.89 (1H, m), 3.08 (2H, t, J=7.0 Hz), 3.52 (2H, s), 3.63-3.66 (2H, m), 3.73-3.76 (2H, m), 3.84 (3H, s), 4.15 (2H, t, J=7.0 Hz), 5.08 (2H, s), 6.78-6.85 (3H, m), 6.89-6.92 (2H, m), 6.97 (1H, t, J=7.4 Hz), 7.13 (2H, d, J=8.5 Hz), 7.21-7.33 (6H, m), 7.37-7.42 (2H, m), 7.45 (1H, s), 7.57 (1H, d, J=15.4 Hz), 7.82 (1H, d, J=2.9 Hz).

Example 350

(E)-3-[3-Chloro-4-({5-[(2-chloro-4-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.19 (3H, s), 2.48-2.49 (4H, m), 2.81-2.89 (1H, m), 3.08 (2H, t, J=7.1 Hz), 3.52 (2H, s), 3.63-3.66 (2H, m), 3.73-3.75 (2H, m), 4.15-4.18 (2H, m), 5.09 (2H, s), 6.77-6.85 (3H, m), 6.95 (1H, d, J=8.8 Hz), 7.02 (1H, td, J=8.3, 2.4 Hz), 7.11-7.18 (3H, m), 7.23-7.30 (5H, m), 7.38 (1H, dd, J=8.9, 3.1 Hz), 7.45-7.51 (2H, m), 7.57 (1H, d, J=15.4 Hz), 7.80 (1H, d, J=2.9 Hz).

Example 351

2-({[6-(2-Chloro-6-methyl-4-{(E)-3-oxo-3-[4-(4-{2-[4-(propan-2-yl)phenoxy]ethyl}benzyl)-piperazin-1-yl]prop-1-en-1-yl}phenoxy)pyridin-3-yl]oxy}methyl)benzonitrile $^1$H-NMR (CDCl$_3$) δ: 1.22 (6H, d, J=6.8 Hz), 2.19 (3H, s), 2.47-2.49 (4H, m), 2.81-2.88 (1H, m), 3.08 (2H, t, J=7.0 Hz), 3.52 (2H, s), 3.63-3.66 (2H, m), 3.73-3.76 (2H, m), 4.15 (2H, t, J=7.0 Hz), 5.22 (2H, s), 6.77-6.86 (3H, m), 6.96 (1H, d, J=8.8 Hz), 7.13 (2H, d, J=8.5 Hz), 7.20-7.29 (5H, m), 7.41-7.47 (3H, m), 7.57 (1H, d, J=15.4 Hz), 7.64 (2H, d, J=4.2 Hz), 7.71 (1H, d, J=7.6 Hz), 7.82 (1H, d, J=2.9 Hz).

Example 352

(E)-3-[3-Chloro-4-({5-[(3-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.19 (3H, s), 2.48-2.49 (4H, m), 2.81-2.89 (1H, m), 3.08 (2H, t, J=7.0 Hz), 3.52 (2H, s), 3.63-3.66 (2H, m), 3.73-3.76 (2H, m), 4.14-4.18 (2H, m), 5.03 (2H, s), 6.78-6.85 (3H, m), 6.94 (1H, d, J=8.8 Hz), 6.98-7.05 (1H, m), 7.10-7.18 (4H, m), 7.23-7.30 (5H, m), 7.31-7.39 (2H, m), 7.45 (1H, s), 7.57 (1H, d, J=15.4 Hz), 7.78 (1H, d, J=2.9 Hz).

Example 353

(E)-3-[3-Chloro-5-methyl-4-({5-[(3-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.19 (3H, s), 2.36 (3H, s), 2.47-2.49 (4H, m), 2.80-2.89 (1H, m), 3.08 (2H, t, J=7.0 Hz), 3.52 (2H, s), 3.63-3.65 (2H, m), 3.73-3.76 (2H, m), 4.15 (2H, t, J=7.0 Hz), 4.99 (2H, s), 6.77-6.85 (3H, m), 6.92 (1H, d, J=9.0 Hz), 7.11-7.16 (3H, m), 7.18-7.29 (8H, m), 7.37 (1H, dd, J=9.0, 2.9 Hz), 7.45 (1H, s), 7.57 (1H, d, J=15.4 Hz), 7.80 (1H, d, J=2.9 Hz).

Example 354

(E)-3-[3-Chloro-4-({5-[(3-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.19 (3H, s), 2.47-2.49 (4H, m), 2.81-2.89 (1H, m), 3.08 (2H, t, J=7.1 Hz), 3.52 (2H, s), 3.63-3.65 (2H, m), 3.73-3.75 (2H, m), 4.15 (2H, t, J=7.1 Hz), 5.00 (2H, s), 6.78-6.86 (3H, m), 6.94 (1H, d, J=9.0 Hz), 7.13 (2H, d, J=8.5 Hz), 7.24-7.32 (8H, m), 7.36 (1H, dd, J=8.9, 3.1 Hz), 7.41 (1H, s), 7.45-7.46 (1H, m), 7.57 (1H, d, J=15.4 Hz), 7.77 (1H, d, J=2.9 Hz).

Example 355

(E)-3-[3-Chloro-4-({5-[(2-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.9 Hz), 2.20 (3H, s), 2.41-2.54 (4H, m), 2.79-2.91 (1H, m), 3.08 (2H, t, J=6.9 Hz), 3.52 (2H, s), 3.63-3.67 (2H, m), 3.72-3.76 (2H, m), 4.16 (2H, t, J=6.9 Hz), 5.14 (2H, s), 6.77-6.85 (3H, m), 6.94 (1H, d, J=8.9 Hz), 7.13 (2H, d, J=8.6 Hz), 7.25-7.31 (7H, m), 7.36-7.62 (5H, m), 7.82 (1H, d, J=2.6 Hz).

Example 356

(2E)-1-(4-{4-[(1E)-3-(4-Fluorophenoxy)prop-1-en-1-yl]benzyl}piperazin-1-yl)-3-[4-({5-[(4-methoxybenzyl)oxy]pyridin-2-yl}oxy)-3,5-dimethylphenyl]prop-2-en-1-one mp: 136-137° C.
$^1$H-NMR (CDCl$_3$) δ: 2.12 (6H, s), 2.48 (4H, t, J=4.9 Hz), 3.53 (2H, s), 3.66 (2H, brs), 3.74 (2H, brs), 3.81 (3H, s), 4.67 (2H, dd, J=5.9, 1.3 Hz), 4.95 (2H, s), 6.39 (1H, dt, J=15.9, 5.9 Hz), 6.72 (1H, d, J=15.9 Hz), 6.78 (1H, d, J=15.4 Hz), 6.79 (1H, d, J=8.8 Hz), 6.88-6.93 (4H, m), 6.95-7.00 (2H, m), 7.25-7.26 (2H, m), 7.28-7.34 (5H, m), 7.38 (2H, d, J=8.1 Hz), 7.61 (1H, d, J=15.4 Hz), 7.82 (1H, d, J=2.9 Hz).

Example 357

(2E)-3-[4-({5-[(4-Methoxybenzyl)oxy]pyridin-2-yl}oxy)-3,5-dimethylphenyl]-1-(4-{2-methyl-4-[(1E)-3-(4-methylphenoxy)prop-1-en-1-yl]benzyl}piperazin-1-yl)prop-2-en-1-one $^1$H-NMR (CDCl$_3$) δ: 2.12 (6H, s), 2.29 (3H, s), 2.37 (3H, s), 2.47 (4H, t, J=4.9 Hz), 3.47 (2H, s), 3.62-3.75 (4H, m), 3.81 (3H, s), 4.67 (2H, dd, J=5.7, 1.3 Hz), 4.95 (2H, s), 6.40 (1H, dt, J=16.1, 5.7 Hz), 6.68 (1H, d, J=16.1 Hz), 6.77-6.80 (2H, m), 6.86 (2H, dt, J=9.2, 2.4 Hz), 6.91 (2H, dt, J=9.2, 2.4 Hz), 7.09 (2H, d, J=8.8 Hz), 7.21-7.22 (3H, m), 7.25-7.26 (2H, m), 7.30-7.34 (3H, m), 7.61 (1H, d, J=15.4 Hz), 7.82 (1H, d, J=2.9 Hz).

Example 358

(E)-3-{3-Chloro-5-methyl-4-[(5-{[4-(propan-2-yl)benzyl]oxy}pyridin-2-yl)oxy]phenyl}-1-[4-(4-methylbenzyl)piperazin-1-yl]prop-2-en-1-one $^1$H-NMR (CDCl$_3$) δ: 1.24 (6H, d, J=6.9 Hz), 2.18 (3H, s), 2.34 (3H, s), 2.46 (4H, t, J=4.9 Hz), 2.91 (1H, septet, J=6.9 Hz), 3.49 (2H, s), 3.60-3.82 (4H, m), 4.97 (2H, s), 6.80 (1H, d, J=15.5 Hz), 6.91 (1H, d, J=8.9 Hz), 7.09-7.39 (10H, m), 7.45 (1H, d, J=2.0 Hz), 7.56 (1H, d, J=15.5 Hz), 7.79 (1H, d, J=3.0 Hz).

Example 359

(E)-3-[3-Chloro-5-methyl-4-({5-[(4-methylbenzyl)oxy]pyridin-2-yl}oxy)phenyl]-1-[4-(4-methylbenzyl)piperazin-1-yl]prop-2-en-1-one $^1$H-NMR (CDCl$_3$) δ: 2.19 (3H, s), 2.35 (3H, s), 2.35 (3H, s), 2.47 (4H, t, J=4.9 Hz), 3.50 (2H, s), 3.64-3.73 (4H, m), 4.98 (2H, s), 6.79 (1H, d, J=15.5 Hz), 6.91 (1H, dd, J=4.5, 2.2 Hz), 7.13-7.23 (6H, m), 7.27-7.29 (3H, m), 7.35 (1H, dd, J=8.9, 3.3 Hz), 7.45 (1H, d, J=2.0 Hz), 7.56 (1H, d, J=15.5 Hz), 7.79 (1H, d, J=2.6 Hz).

Example 360

To a solution of (E)-3-{3-chloro-4-[(5-hydroxypyridin-2-yl)oxy]-5-methyl-phenyl}-1-(4-{4-[2-(4-chlorophenoxy)ethyl]benzyl}piperazin-1-yl)prop-2-en-1-one (400 mg) was added 3-fluoro-4-methylbenzyl bromide (144 mg) and K$_2$CO$_3$ (134 mg) at room temperature, then the reaction mixture was stirred for 4 hours. The reaction mixture was diluted with H$_2$O and extracted with AcOEt. The organic layer was washed with water and saturated aqueous NaCl, dried over anhydrous Na$_2$SO$_4$, and concentrated under reduced pressure. The residue was purified by silica gel column chromatography (AcOEt) to afford (E)-3-[3-chloro-4-({5-[(3-fluoro-4-methylbenzyl)oxy]pyridin-2-yl}oxy)-5-methylphenyl]-1-(4-{4-[2-(4-chlorophenoxy)ethyl]benzyl}piperazin-1-yl)prop-2-en-1-one as a colorless amorphous (430 mg).
$^1$H-NMR (CDCl$_3$) δ: 2.19 (3H, s), 2.27 (3H, d, J=1.7 Hz), 2.48 (4H, t, J=4.9 Hz), 3.08 (2H, t, J=7.0 Hz), 3.52 (2H, s), 3.64 (2H, s), 3.74 (2H, s), 4.14 (2H, t, J=7.0 Hz), 4.98 (2H, s), 6.78-6.84 (3H, m), 6.93 (1H, dd, J=8.8, 0.5 Hz), 7.16-7.29 (10H, m), 7.35 (1H, dd, J=8.9, 3.1 Hz), 7.45 (1H, d, J=2.2 Hz), 7.57 (1H, d, J=15.4 Hz), 7.77 (1H, d, J=3.2 Hz).

The following compounds were produced in the same manner as in Example 360 using appropriate starting materials.

Example 361

(E)-3-[3-Chloro-4-({5-[(3-fluoro-2-methylbenzyl)oxy]pyridin-2-yl}oxy)-5-methylphenyl]-1-(4-{4-[2-(4-methylphenoxy)ethyl]benzyl}piperazin-1-yl)prop-2-en-1-one $^1$H-NMR (CDCl$_3$) δ: 2.23 (3H, s), 2.29 (3H, d, J=1.7 Hz), 2.31 (3H, s), 2.51 (4H, t, J=4.9 Hz), 3.11 (2H, t, J=7.1 Hz), 3.55 (2H, s), 3.67 (2H, s), 3.77 (2H, s), 4.18 (2H, t, J=7.1 Hz), 5.04 (2H, s), 6.81-6.85 (3H, m), 6.97 (1H, dd, J=9.0, 0.5 Hz), 7.03-7.12 (3H, m), 7.17-7.23 (2H, m), 7.26-7.32 (5H, m), 7.40 (1H, dd, J=8.9, 3.1 Hz), 7.49 (1H, d, J=2.2 Hz), 7.60 (1H, d, J=15.4 Hz), 7.83 (1H, d, J=2.9 Hz).

Example 362

(E)-3-[3-Chloro-4-({5-[(3-fluoro-2-methylbenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.20 (3H, s), 2.27 (3H, d, J=2.0 Hz), 2.48 (4H, t, J=4.9 Hz), 2.81 (1H, septet, J=7.1 Hz), 3.08 (2H, t, J=7.0 Hz), 3.52 (2H, s), 3.64 (2H, s), 3.74 (2H, s), 4.15 (2H, t, J=7.1 Hz), 5.01 (2H, s), 6.78-6.85 (3H, m), 6.94 (1H, d, J=8.8 Hz), 7.00-7.07 (1H, m), 7.11-7.20 (4H, m), 7.24-7.29 (5H, m), 7.37 (1H, dd, J=8.9, 3.1 Hz), 7.46 (1H, d, J=1.7 Hz), 7.57 (1H, d, J=15.4 Hz), 7.80 (1H, d, J=2.9 Hz).

Example 363

(E)-3-[3-Chloro-4-({5-[(3-fluoro-2-methylbenzyl)oxy]pyridin-2-yl}oxy)-5-methylphenyl]-1-(4-{4-[2-(4-chlorophenoxy)ethyl]benzyl}piperazin-1-yl)prop-2-en-1-one $^1$H-NMR (CDCl$_3$) δ: 2.20 (3H, s), 2.27 (3H, d, J=2.0 Hz), 2.49 (4H, t, J=4.9 Hz), 3.08 (2H, t, J=7.1 Hz), 3.53 (2H, s), 3.65 (2H, s), 3.75 (2H, s), 4.13 (2H, t, J=7.1 Hz), 5.01 (2H, s), 6.78-6.85 (3H, m), 6.91-6.99 (3H, m), 7.00-7.07 (1H, m), 7.15-7.18 (2H, m), 7.24-7.30 (5H, m), 7.37 (1H, dd, J=8.9, 3.1 Hz), 7.46 (1H, d, J=2.0 Hz), 7.57 (1H, d, J=15.4 Hz), 7.81 (1H, d, J=3.2 Hz).

Example 364

(E)-3-[3-Chloro-4-({5-[(3-fluoro-2-methylbenzyl)oxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.20 (3H, s), 2.27 (3H, d, J=2.0 Hz), 2.48 (4H, t, J=5.0 Hz), 3.08 (2H, t, J=7.0 Hz), 3.52 (2H, s), 3.65 (2H, s), 3.74 (2H, s), 4.14 (2H, t, J=7.0 Hz), 5.01 (2H, s), 6.78-6.84 (3H, m), 6.95 (1H, dd, J=8.9, 0.6 Hz), 7.00-7.05 (1H, m), 7.15-7.29 (9H, m), 7.37 (1H, dd, J=8.9, 3.1 Hz), 7.46 (1H, d, J=2.0 Hz), 7.57 (1H, d, J=15.4 Hz), 7.80 (1H, dd, J=3.1, 0.6 Hz).

Example 365

(E)-3-[3-Chloro-4-({5-[(3-fluoro-5-methylbenzyl)oxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.35 (3H, s), 2.48 (4H, t, J=5.0 Hz), 3.08 (2H, t, J=7.1 Hz), 3.53 (2H, s), 3.65 (2H, s), 3.74 (2H, s), 4.14 (2H, d, J=7.1 Hz), 4.98 (2H, s), 6.78-6.85 (4H, m), 6.91-6.98 (5H, m), 7.23-7.29 (5H, m), 7.36 (1H, dd, J=9.0, 3.2 Hz), 7.45 (1H, d, J=2.0 Hz), 7.57 (1H, d, J=15.4 Hz), 7.77 (1H, d, J=2.9 Hz).

Example 366

(E)-3-[3-Chloro-4-({5-[(3-fluoro-4-methylbenzyl)oxy]pyridin-2-yl}oxy)-5-methylphenyl]-1-(4-{4-[2-(4-fluorophenoxy)ethyl]benzyl}piperazin-1-yl)prop-2-en-1-one $^1$H-NMR (CDCl$_3$) δ: 2.19 (3H, s), 2.27 (3H, d, J=1.7 Hz), 2.48 (4H, t, J=4.8 Hz), 3.08 (2H, t, J=7.0 Hz), 3.53 (2H, s), 3.64 (2H, s), 3.74 (2H, s), 4.13 (2H, t, J=7.0 Hz), 4.98 (2H, s), 6.78-6.85 (3H, m), 6.92-7.00 (3H, m), 7.05-7.07 (2H, m), 7.18 (1H, t, J=7.7 Hz), 7.23-7.29 (5H, m), 7.35 (1H, dd, J=8.9, 3.1 Hz), 7.45 (1H, d, J=2.2 Hz), 7.57 (1H, d, J=15.4 Hz), 7.77 (1H, dd, J=3.2, 0.5 Hz).

Example 367

(E)-3-[3-Chloro-4-({5-[(3-fluoro-4-methylbenzyl)oxy]pyridin-2-yl}oxy)-5-methylphenyl]-1-(4-{4-[2-(4-methoxyphenoxy)ethyl]benzyl}piperazin-1-yl)prop-2-en-1-one $^1$H-NMR (CDCl$_3$) δ: 2.19 (3H, s), 2.27 (3H, d, J=1.7 Hz), 2.48 (4H, t, J=4.9 Hz), 3.07 (2H, t, J=7.1 Hz), 3.52 (2H, s), 3.60-3.80 (7H, m), 4.13 (2H, t, J=7.1 Hz), 4.98 (2H, s), 6.78-6.86 (5H, m), 6.93 (1H, dd, J=8.8, 0.5 Hz), 7.05-7.07 (2H, m), 7.16-7.20 (1H, m), 7.24-7.29 (5H, m), 7.35 (1H, dd, J=9.0, 3.2 Hz), 7.45 (1H, d, J=2.0 Hz), 7.57 (1H, d, J=15.4 Hz), 7.77 (1H, dd, J=3.2, 0.5 Hz).

Example 368

(E)-3-[3-Chloro-4-({5-[(3-fluoro-5-methylbenzyl)oxy]pyridin-2-yl}oxy)-5-methylphenyl]-1-(4-{4-[2-(4-chlorophenoxy)ethyl]benzyl}piperazin-1-yl)prop-2-en-1-one $^1$H-NMR (CDCl$_3$) δ: 2.19 (3H, s), 2.35 (3H, s), 2.48 (4H, t, J=5.0 Hz), 3.08 (2H, t, J=7.0 Hz), 3.52 (2H, s), 3.64 (2H, s), 3.74 (2H, s), 4.14 (2H, t, J=7.0 Hz), 4.98 (2H, s), 6.78-6.85 (4H, m), 6.91-6.95 (2H, m), 6.98 (1H, s), 7.20-7.29 (7H, m), 7.36 (1H, dd, J=8.9, 3.1 Hz), 7.45 (1H, d, J=2.0 Hz), 7.57 (1H, d, J=15.4 Hz), 7.77 (1H, d, J=2.9 Hz).

Example 369

(E)-3-[3-Chloro-4-({5-[(3-fluoro-5-methylbenzyl)oxy]pyridin-2-yl}oxy)-5-methylphenyl]-1-(4-{4-[2-(4-methoxyphenoxy)ethyl]benzyl}piperazin-1-yl)prop-2-en-1-one $^1$H-NMR (CDCl$_3$) δ: 2.19 (3H, s), 2.36 (3H, s), 2.48 (4H, t, J=4.9 Hz), 3.07 (2H, t, J=7.1 Hz), 3.52 (2H, s), 3.58-3.80 (7H, m), 4.13 (2H, t, J=6.6 Hz), 4.98 (2H, s), 6.78-6.85 (6H, m), 6.90-7.00 (1H, m), 6.98 (1H, s), 7.23-7.29 (6H, m), 7.36 (1H, dd, J=8.8, 3.2 Hz), 7.45 (1H, d, J=1.7 Hz), 7.57 (1H, d, J=15.4 Hz), 7.77 (1H, d, J=2.9 Hz).

Example 370

(E)-3-[3-Chloro-4-({5-[(3-fluoro-4-methylbenzyl)oxy]pyridin-2-yl}oxy)-5-methylphenyl]-1-(4-{4-[2-(4-methylphenoxy)ethyl]benzyl}piperazin-1-yl)prop-2-en-1-one $^1$H-NMR (CDCl$_3$) δ: 2.18 (3H, d, J=4.9 Hz), 2.27-2.28 (6H, m), 2.48 (4H, t, J=4.9 Hz), 3.08 (2H, t, J=7.1 Hz), 3.52 (2H, s), 3.64 (2H, s), 3.75 (2H, s), 4.15 (2H, t, J=7.1 Hz), 4.98 (2H, s), 6.78-6.82 (3H, m), 6.93 (1H, d, J=8.8 Hz), 7.05-7.08 (4H, m), 7.18 (1H, t, J=7.7 Hz), 7.24-7.29 (5H, m), 7.35 (1H, dd, J=8.9, 3.1 Hz), 7.45 (1H, d, J=2.0 Hz), 7.57 (1H, d, J=15.4 Hz), 7.77 (1H, d, J=2.9 Hz).

Example 371

(E)-3-[3-Chloro-4-({5-[(3-fluoro-4-methylbenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=7.1 Hz), 2.19 (3H, s), 2.27 (3H, d, J=1.7 Hz), 2.48 (4H, t, J=4.9 Hz), 2.85 (1H, septet, J=6.8 Hz), 3.08 (2H, t, J=7.1 Hz), 3.52 (2H, s), 3.64 (2H, s), 3.74 (2H, s), 4.15 (2H, t, J=7.0 Hz), 4.98 (2H, s), 6.78-6.85 (3H, m), 6.93 (1H, dd, J=9.0, 0.5 Hz), 7.05-7.07 (2H, m), 7.11-7.15 (2H, m), 7.18 (1H, t, J=7.9 Hz), 7.24-7.29 (5H, m), 7.35 (1H, dd, J=8.9, 3.1 Hz), 7.45 (1H, d, J=2.0 Hz), 7.57 (1H, d, J=15.4 Hz), 7.77 (1H, d, J=2.7 Hz).

Example 372

(E)-3-[3-Chloro-4-({5-[(3-fluoro-5-methylbenzyl)oxy]pyridin-2-yl}oxy)-5-methylphenyl]-1-(4-{4-[2-(4-methylphenoxy)ethyl]benzyl}piperazin-1-yl)prop-2-en-1-one $^1$H-NMR (CDCl$_3$) δ: 2.19 (3H, s), 2.28 (3H, s), 2.35 (3H, d, J=0.5 Hz), 2.48 (4H, t, J=5.0 Hz), 3.08 (2H, t, J=7.1 Hz), 3.52 (2H, s), 3.64 (2H, s), 3.74 (2H, s), 4.15 (2H, t, J=7.1 Hz), 4.98 (2H, s), 6.78-6.85 (4H, m), 6.91-6.98 (3H, m), 7.07 (2H, dd, J=8.7, 0.6 Hz), 7.23-7.29 (5H, m), 7.36 (1H, dd, J=8.9, 3.1 Hz), 7.45 (1H, d, J=2.2 Hz), 7.57 (1H, d, J=15.4 Hz), 7.77-7.78 (1H, m).

Example 373

(E)-3-[3-Chloro-4-({5-[3-fluoro-5-methylbenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=7.1 Hz), 2.19 (3H, s), 2.35 (3H, s), 2.48 (4H, t, J=4.9 Hz), 2.85 (1H, septet, J=7.1 Hz), 3.08 (2H, t, J=7.1 Hz), 3.52 (2H, s), 3.64 (2H, s), 3.74 (2H, s), 4.15 (2H, t, J=7.1 Hz), 4.98 (2H, s), 6.78-6.85 (3H, m), 6.91-6.98 (1H, m), 6.98 (1H, s), 7.13 (2H, d, J=8.3 Hz), 7.24-7.29 (6H, m), 7.36 (1H, dd, J=8.9, 3.1 Hz), 7.45 (1H, d, J=2.0 Hz), 7.57 (1H, d, J=15.4 Hz), 7.77 (1H, d, J=2.9 Hz).

Example 374

(E)-3-[3-Chloro-5-methyl-4-({5-[(2-nitrobenzyl)oxy]pyridin-2-yl}oxy)phenyl]-1-(4-{4-[2-(4-methoxyphenoxy)ethyl]benzyl}piperazin-1-yl)prop-2-en-1-one $^1$H-NMR (CDCl$_3$) δ: 2.20 (3H, s), 2.47-2.49 (4H, m), 3.07 (2H, t, J=7.1 Hz), 3.52 (2H, s), 3.64 (2H, brs), 3.76 (5H, brs), 4.13 (2H, t, J=7.1 Hz), 5.46 (2H, s), 6.80 (1H, d, J=15.6 Hz), 6.82 (2H, d, J=9.6 Hz), 6.84 (2H, d, J=9.6 Hz), 6.96 (1H, d, J=9.0 Hz), 7.26 (4H, s), 7.28 (1H, s), 7.41 (1H, dd, J=9.0, 2.9 Hz), 7.45 (1H, s), 7.51 (1H, t, J=7.8 Hz), 7.57 (1H, d, J=15.4 Hz), 7.68-7.72 (1H, m), 7.82 (1H, d, J=2.9 Hz), 7.86 (1H, d, J=7.6 Hz), 8.16 (1H, d, J=8.1 Hz).

Example 375

(E)-3-[3-Chloro-5-methyl-4-({5-[(2-nitrobenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=6.8 Hz), 2.19 (3H, s), 2.48 (4H, s), 2.85 (1H, qq, J=6.8, 6.8 Hz), 3.08 (2H, t, J=7.1 Hz), 3.52 (2H, s), 3.64 (2H, s), 3.74 (2H, s), 4.15 (2H, t, J=7.1 Hz), 5.46 (2H, s), 6.78-6.84 (3H, m), 6.96 (1H, d, J=9.0 Hz), 7.13 (2H, d, J=8.5 Hz), 7.26 (4H, s), 7.29 (1H, s), 7.41 (1H, dd, J=9.0, 2.9 Hz), 7.45 (1H, s), 7.51 (1H, t, J=7.7 Hz), 7.57 (1H, d, J=15.4 Hz), 7.69-7.72 (1H, m), 7.82 (1H, d, J=2.9 Hz), 7.86 (1H, d, J=7.8 Hz), 8.16 (1H, d, J=8.1 Hz).

Example 376

(E)-3-[3-Chloro-5-methyl-4-({5-[(4-nitrobenzyl)oxy]pyridin-2-yl}oxy)phenyl]-1-(4-{4-[2-(4-methylphenoxy)ethyl]benzyl}piperazin-1-yl)prop-2-en-1-one $^1$H-NMR (CDCl$_3$) δ: 2.19 (3H, s), 2.28 (3H, s), 2.48 (4H, t, J=4.6 Hz), 3.08 (2H, t, J=7.1 Hz), 3.52 (2H, s), 3.64 (2H, brs), 3.74 (2H, brs), 4.15 (2H, t, J=7.1 Hz), 5.14 (2H, s), 6.80 (2H, d, J=8.5 Hz), 6.80 (1H, d, J=15.1 Hz), 6.96 (1H, d, J=9.0 Hz), 7.07 (2H, d, J=8.3 Hz), 7.26 (4H, s), 7.29 (1H, s), 7.38 (1H, dd, J=9.0, 2.9 Hz), 7.45 (1H, s), 7.57 (1H, d, J=15.1 Hz), 7.59 (2H, d, J=8.5 Hz), 7.78 (1H, d, J=2.9 Hz), 8.25 (2H, d, J=8.5 Hz).

Example 377

(E)-3-[3-Chloro-5-methyl-4-({5-[(4-nitrobenzyl)oxy]pyridin-2-yl}oxy)phenyl]-1-[4-(4-{2-[4-(propan-2-yl)phenoxy]ethyl}benzyl)piperazin-1-yl]prop-2-en-1-one $^1$H-NMR (CDCl$_3$) δ: 1.22 (6H, d, J=7.1 Hz), 2.19 (3H, s), 2.47-2.49 (4H, m), 2.82-2.88 (1H, m), 3.08 (2H, t, J=7.1 Hz), 3.52 (2H, brs), 3.64 (2H, brs), 3.74 (2H, brs), 4.15 (2H, t, J=7.1 Hz), 5.14 (2H, s), 6.78-6.84 (3H, m), 6.96 (1H, d, J=8.8 Hz), 7.13 (2H, d, J=8.5 Hz), 7.26 (4H, s), 7.29 (1H, s), 7.38 (1H, dd, J=8.8, 2.9 Hz), 7.45 (1H, s), 7.54-7.60 (3H, m), 7.78 (1H, d, J=2.9 Hz), 8.25 (2H, d, J=8.8 Hz).

Example 378

(E)-3-[3-Chloro-5-methyl-4-({5-[(2-nitrobenzyl)oxy]pyridin-2-yl}oxy)phenyl]-1-(4-{4-[2-(4-methylphenoxy)ethyl]benzyl}piperazin-1-yl)prop-2-en-1-one $^1$H-NMR (CDCl$_3$) δ: 2.19 (3H, s), 2.28 (3H, s), 2.48 (4H, s), 3.08 (2H, t, J=7.1 Hz), 3.52 (2H, s), 3.64 (2H, brs), 3.74 (2H, brs), 4.15 (2H, t, J=7.1 Hz), 5.46 (2H, s), 6.80 (2H, d, J=8.5 Hz), 6.80 (1H, d, J=14.9 Hz), 6.96 (1H, d, J=8.8 Hz), 7.07 (2H, d, J=8.3 Hz), 7.26 (4H, s), 7.28 (1H, s), 7.41 (1H, dd, J=8.8, 2.9 Hz), 7.45 (1H, s), 7.49-7.53 (1H, m), 7.56 (1H, d, J=15.4 Hz), 7.70 (1H, t, J=7.3 Hz), 7.82 (1H, d, J=2.9 Hz), 7.86 (1H, d, J=7.8 Hz), 8.16 (1H, d, J=8.1 Hz).

Example 379

(E)-3-[4-({5-[(3-Fluorobenzyl)oxy]pyridin-2-yl}oxy)-2-methylphenyl]-1-(4-{4-[2-(4-fluorophenoxy)ethyl]benzyl}piperazin-1-yl)prop-2-en-1-one $^1$H-NMR (CDCl$_3$) δ: 2.40 (3H, s), 2.46-2.49 (4H, m), 3.07 (2H, t, J=7.0 Hz), 3.52 (2H, s), 3.62-3.65 (2H, m), 3.73-3.76 (2H, m), 4.13 (2H, t, J=7.0 Hz), 5.06 (2H, s), 6.71 (1H, d, J=15.1 Hz), 6.81-6.84 (2H, m), 6.88-6.97 (5H, m), 7.02 (1H, td, J=8.4, 2.0 Hz), 7.13-7.17 (2H, m), 7.23-7.28 (2H, m), 7.34-7.36 (2H, m), 7.52-7.53 (1H, m), 7.89-7.91 (2H, m).

Example 380

(E)-1-(4-{4-[2-(4-Fluorophenoxy)ethyl]benzyl}piperazin-1-yl)-3-[4-({5-[(2-methoxybenzyl)-oxy]pyridin-2-yl}oxy)-2-methylphenyl]prop-2-en-1-one $^1$H-NMR (CDCl$_3$) δ: 2.40 (3H, s), 2.46-2.49 (4H, m), 3.07 (2H, t, J=7.0 Hz), 3.52 (2H, s), 3.62-3.65 (2H, m), 3.73-3.76 (2H, m), 3.85 (3H, s), 4.13 (2H, t, J=7.0 Hz), 5.12 (2H, s), 6.70 (1H, d, J=15.1 Hz), 6.81-6.99 (9H, m), 7.23-7.33 (5H, m), 7.36 (1H, dd, J=8.8, 2.9 Hz), 7.42 (1H, d, J=7.1 Hz), 7.51-7.52 (1H, m), 7.90 (1H, d, J=15.1 Hz), 7.95 (1H, d, J=3.2 Hz).

Example 381

(E)-1-(4-{4-[2-(4-Fluorophenoxy)ethyl]benzyl}piperazin-1-yl)-3-[2-methyl-4-({5[(3-methylbenzyl)oxy]pyridin-2-yl}oxy)phenyl]prop-2-en-1-one $^1$H-NMR (CDCl$_3$) δ: 2.36 (3H, s), 2.40 (3H, s), 2.46-2.48 (4H, m), 3.07 (2H, t, J=7.0 Hz), 3.51 (2H, s), 3.62-3.64 (2H, m), 3.73-3.76 (2H, m), 4.12 (2H, t, J=7.0 Hz), 5.02 (2H, s), 6.71 (1H, d, J=15.1 Hz), 6.80-6.84 (2H, m), 6.86-6.97 (5H, m), 7.14 (1H, d, J=7.3 Hz), 7.19-7.28 (7H, m), 7.34 (1H, dd, J=8.9, 3.1 Hz), 7.51-7.52 (1H, m), 7.90-7.92 (2H, m).

Example 382

(E)-3-[4-({5-[(2-Chloro-4-fluorobenzyl)oxy]pyridin-2-yl}oxy)-3,5-dimethylphenyl]-1-(4-{4-[2-(4-chlorophenoxy)ethyl]benzyl}piperazin-1-yl)prop-2-en-1-one $^1$H-NMR (CDCl$_3$) δ: 2.12 (6H, s), 2.47-2.48 (4H, m), 3.08 (2H, t, J=7.0 Hz), 3.52 (2H, s), 3.64-3.66 (2H, m), 3.73-3.75 (2H, m), 4.14 (2H, t, J=7.0 Hz), 5.07 (2H, s), 6.79-6.81 (4H, m), 7.01 (1H, td, J=8.3, 2.4 Hz), 7.15 (1H, dd, J=8.3, 2.4 Hz), 7.22-7.26 (8H, m), 7.34 (1H, dd, J=8.9, 3.1 Hz), 7.49 (1H, dd, J=8.5, 6.1 Hz), 7.61 (1H, d, J=15.4 Hz), 7.83 (1H, d, J=2.9 Hz).

Example 383

(E)-3-[4-({5-[(3-Chlorobenzyl)oxy]pyridin-2-yl}oxy)-3,5-dimethylphenyl]-1-(4-{4-[2-(4-chlorophenoxy)ethyl]benzyl}piperazin-1-yl)prop-2-en-1-one $^1$H-NMR (CDCl$_3$) δ: 2.12 (6H, s), 2.47-2.48 (4H, m), 3.07 (2H, t, J=7.0 Hz), 3.52 (2H, s), 3.64-3.66 (2H, m), 3.73-3.75 (2H, m), 4.13 (2H, t, J=7.0 Hz), 4.99 (2H, s), 6.78-6.81 (4H, m), 7.20-7.34 (12H, m), 7.40 (1H, s), 7.61 (1H, d, J=15.4 Hz), 7.80 (1H, d, J=2.9 Hz).

Example 384

To a DMF (5 mL) solution of (E)-3-(3,5-dimethyl-4-{[5-(pyridin-4-ylmethoxy)-pyridin-2-yl]oxy}phenyl)-1-{4-[4-(2-hydroxyethyl)benzyl]piperazin-1-yl}prop-2-en-1-one (400 mg) was added NaH (35.9 mg, 60% in mineral oil) at 0° C., then the resultant mixture was stirred for 1 hour. To the mixture was added 4-chlorobenzyl chloride (0.093 mL) at 0° C., then the resultant mixture was stirred at room temperature for 3 hours. The mixture was poured into saturated aqueous NH$_4$Cl, and extracted with AcOEt. The organic layer was washed with H$_2$O and saturated aqueous NaCl, dried over anhydrous Na$_2$SO$_4$, and evaporated. The residue was purified by silica gel column chromatography (n-hexane/AcOEt=1/1 to 1/0 and then AcOEt/MeOH=4/1) to afford (E)-1-[4-(4-{2-[(4-chlorobenzyl)oxy]ethyl}benzyl)piperazin-1-yl]-3-(3,5-dimethyl-4-{[5-(pyridin-4-ylmethoxy)pyridin-2-yl]oxy}phenyl)prop-2-en-1-one as a pale yellow amorphous powder (91 mg).

$^1$H-NMR (CDCl$_3$) δ: 2.12 (6H, s), 2.48-2.50 (4H, m), 2.92 (2H, t, J=7.0 Hz), 3.53 (2H, s), 3.67-3.69 (4H, m), 3.73-3.76 (2H, m), 4.49 (2H, s), 5.06 (2H, s), 6.78 (1H, d, J=15.4 Hz), 6.84 (1H, d, J=8.8 Hz), 7.18-7.35 (13H, m), 7.61 (1H, d, J=15.4 Hz), 7.80 (1H, d, J=2.9 Hz), 8.62 (2H, d, J=5.6 Hz).

The following compounds were produced in the same manner as in Example 384 using appropriate starting materials.

Example 385

(E)-3-[3-Chloro-4-({5-[(2-chlorobenzyl)oxy]pyridin-2-yl}oxy)-5-methylphenyl]-1-[4-(4-{2-[(4-methylbenzyl)oxy]ethyl}benzyl)piperazin-1-yl]prop-2-en-1-one $^1$H-NMR (CDCl$_3$) δ: 2.19 (3H, s), 2.34 (3H, s), 2.47-2.48 (4H, m), 2.92 (2H, t, J=7.2 Hz), 3.51 (2H, s), 3.63-3.70 (4H, m), 3.73-3.75 (2H, m), 4.49 (2H, s), 5.14 (2H, s), 6.80 (1H, d, J=15.4 Hz), 6.94 (1H, d, J=9.0 Hz), 7.12-7.15 (2H, m), 7.18-7.31 (9H, m), 7.38-7.41 (2H, m), 7.45 (1H, s), 7.49-7.54 (1H, m), 7.57 (1H, d, J=15.4 Hz), 7.81 (1H, d, J=2.9 Hz).

Example 386

(E)-3-[3-Chloro-4-({5-[(2-chlorobenzyl)oxy]pyridin-2-yl}oxy)-5-methylphenyl]-1-[4-(4-{2-[(4-fluorobenzyl)oxy]ethyl}benzyl)piperazin-1-yl]prop-2-en-1-one $^1$H-NMR (CDCl$_3$) δ: 2.19 (3H, s), 2.34 (3H, s), 2.47-2.48 (4H, m), 2.92 (2H, t, J=7.2 Hz), 3.51 (2H, s), 3.63-3.70 (4H, m), 3.73-3.75 (2H, m), 4.49 (2H, s), 5.14 (2H, s), 6.80 (1H, d, J=15.4 Hz), 6.94 (1H, d, J=9.0 Hz), 7.12-7.15 (2H, m), 7.18-7.31 (9H, m), 7.38-7.41 (2H, m), 7.45 (1H, s), 7.49-7.54 (1H, m), 7.57 (1H, d, J=15.4 Hz), 7.81 (1H, d, J=2.9 Hz).

Example 387

(E)-1-[4-(4-{2-[(4-Chlorobenzyl)oxy]ethyl}benzyl) piperazin-1-yl]-3-[3-chloro-4-({5-[(2-chlorobenzyl) oxy]pyridin-2-yl}oxy)-5-methylphenyl]prop-2-en-1-one $^1$H-NMR (CDCl$_3$) δ: 2.19 (3H, s), 2.47-2.49 (4H, m), 2.92 (2H, t, J=7.1 Hz), 3.52 (2H, s), 3.61-3.71 (2H, m), 3.73-3.75 (2H, m), 4.49 (2H, s), 5.14 (2H, s), 6.80 (1H, d, J=15.4 Hz), 6.94 (1H, d, J=9.0 Hz), 7.18-7.31 (11H, m), 7.38-7.41 (2H, m), 7.45 (1H, d, J=1.2 Hz), 7.50-7.54 (1H, m), 7.57 (1H, d, J=15.4 Hz), 7.81 (1H, d, J=2.9 Hz).

Example 388

(E)-3-(3,5-Dimethyl-4-{[5-(pyridin-4-ylmethoxy) pyridin-2-yl]oxy}phenyl)-1-[4-(4-{2-[(4-fluorobenzyl)oxy]ethyl}benzyl)piperazin-1-yl]prop-2-en-1-one $^1$H-NMR (CDCl$_3$) δ: 2.11 (6H, s), 2.48-2.50 (4H, m), 2.92 (2H, t, J=7.0 Hz), 3.53 (2H, s), 3.67-3.69 (4H, m), 3.73-3.76 (2H, m), 4.48 (2H, s), 5.05 (2H, s), 6.78 (1H, d, J=15.4 Hz), 6.83 (1H, d, J=9.0 Hz), 6.99-7.02 (2H, m), 7.18-7.20 (2H, m), 7.25-7.27 (6H, m), 7.33-7.34 (3H, m), 7.61 (1H, d, J=15.4 Hz), 7.80 (1H, d, J=2.9 Hz), 8.62 (2H, d, J=5.9 Hz).

Example 389

(E)-3-(3,5-Dimethyl-4-{[5-(pyridin-4-ylmethoxy) pyridin-2-yl]oxy}phenyl)-1-[4-(4-{2-[(4-methylbenzyl)oxy]ethyl}benzyl)piperazin-1-yl]prop-2-en-1-one $^1$H-NMR (CDCl$_3$) δ: 2.11 (6H, s), 2.33 (3H, s), 2.47-2.48 (4H, m), 2.91 (2H, t, J=7.1 Hz), 3.51 (2H, s), 3.66-3.68 (4H, m), 3.73-3.75 (2H, m), 4.49 (2H, s), 5.04 (2H, s), 6.79 (1H, d, J=15.4 Hz), 6.83 (1H, d, J=9.0 Hz), 7.13 (2H, d, J=7.8 Hz), 7.18-7.26 (8H, m), 7.32-7.35 (3H, m), 7.61 (1H, d, J=15.4 Hz), 7.80 (1H, d, J=2.9 Hz), 8.62 (2H, d, J=5.6 Hz).

Example 390

(E)-3-[3-Chloro-4-({5-[(2-chlorobenzyl)oxy]pyridin-2-yl}oxy)-5-methylphenyl]-1-(4-{4-[2-(cyclopropylmethoxy)ethyl]benzyl}piperazin-1-yl)prop-2-en-1-one $^1$H-NMR (CDCl$_3$) δ: 0.18-0.22 (2H, m), 0.51-0.56 (2H, m), 1.04-1.10 (1H, m), 2.19 (3H, s), 2.46-2.49 (4H, m), 2.91 (2H, t, J=7.3 Hz), 3.30 (2H, d, J=6.8 Hz), 3.51 (2H, s), 3.65-3.67 (4H, m), 3.73-3.75 (2H, m), 5.14 (2H, s), 6.80 (1H, d, J=15.4 Hz), 6.94 (1H, d, J=8.8 Hz), 7.18-7.32 (7H, m), 7.37-7.42 (2H, m), 7.46 (1H, s), 7.51-7.53 (1H, m), 7.57 (1H, d, J=15.4 Hz), 7.81 (1H, d, J=2.9 Hz).

Example 391

To a DMF (7 mL) solution of (E)-3-[3-chloro-4-({5-[(2-chlorobenzyl)oxy]-pyridin-2-yl}oxy)-5-methylphenyl]-1-(piperazin-1-yl)prop-2-en-1-one (0.70 g) and 4-vinylbenzyl chloride (240 μL) was added K$_2$CO$_3$ (291 mg) at room temperature. After stirring at room temperature for 36 hours, to the reaction mixture was added water, and extracted with AcOEt. The organic layer was washed with water, saturated aqueous NaCl, dried over anhydrous Na$_2$SO$_4$, and concentrated under reduced pressure. The residue was purified by silica gel column chromatography (n-hexane/AcOEt=1/1 to 0/1 and then AcOEt/MeOH=19/1) to give (E)-3-[3-chloro-4-({5-[(2-chlorobenzyl)oxy]pyridin-2-yl}oxy)-5-methylphenyl]-1-[4-(4-ethenylbenzyl)-piperazin-1-yl]prop-2-en-1-one as a colorless powder (0.73 g).

$^1$H-NMR (CDCl$_3$) δ: 2.19 (3H, s), 2.48 (4H, t, J=4.9 Hz), 3.53 (2H, s), 3.64-3.74 (4H, m), 5.14 (2H, s), 5.24 (1H, d, J=11.0 Hz), 5.74 (1H, d, J=17.6 Hz), 6.71 (1H, dd, J=17.6, 11.0 Hz), 6.80 (1H, d, J=15.4 Hz), 6.94 (1H, d, J=9.3 Hz), 7.26-7.31 (5H, m), 7.37-7.41 (4H, m), 7.45 (1H, brs), 7.51-7.53 (1H, m), 7.57 (1H, d, J=15.4 Hz), 7.81 (1H, d, J=2.9 Hz).

Example 392

To a CH$_2$Cl$_2$ (5 mL) solution of (E)-3-[3-chloro-5-methyl-4-({5-[(4-methylbenzyl)oxy]pyridin-2-yl}oxy)phenyl]-1-[(3S)-3-methylpiperazin-1-yl]prop-2-en-1-one (0.50 g) and 4-[2-(4-fluorophenoxy)ethyl]benzaldehyde (298 mg) was added NaBH(OAc)$_3$ (323 mg) at room temperature. The resultant mixture was stirred at room temperature for 3 days. To the reaction mixture was added saturated aqueous NaHCO$_3$, and extracted with CH$_2$Cl$_2$. The organic layer was washed with saturated aqueous NaCl, dried over anhydrous Na$_2$SO$_4$, and concentrated under reduced pressure. The residue was purified by silica gel column chromatography (n-hexane/AcOEt=1/1 to 0/1) to give (E)-3-[3-chloro-5-methyl-4-({5-[(4-methylbenzyl)oxy]pyridin-2-yl}oxy)phenyl]-1-[(3S)-4-{4-[2-(4-fluorophenoxy)ethyl]benzyl}-3-methylpiperazin-1-yl]prop-2-en-1-one as a yellow powder (451 mg).

$^1$H-NMR (CDCl$_3$) δ: 1.19 (3H, d, J=6.1 Hz), 2.13-2.19 (4H, m), 2.35 (3H, s), 2.51-2.54 (1H, m), 2.73-2.76 (1H, m), 2.94-3.41 (5H, m), 3.75-3.79 (1H, m), 3.94-4.26 (4H, m), 4.98 (2H, s), 6.75-6.86 (3H, m), 6.90-7.00 (3H, m), 7.18 (2H, d, J=8.1 Hz), 7.22-7.30 (7H, m), 7.35 (1H, dd, J=8.9, 2.9 Hz), 7.43-7.47 (1H, m), 7.56 (1H, d, J=15.4 Hz), 7.79 (1H, d, J=2.9 Hz).

The following compounds were produced in the same manner as in Example 392 using appropriate starting materials.

Example 393

(E)-3-[3-Chloro-5-methyl-4-({5-[(4-methylbenzyl) oxy]pyridin-2-yl}oxy)phenyl]-1-[(2S)-2-methyl-4-{4-[2-(4-methylphenoxy)ethyl]benzyl}piperazin-1-yl]prop-2-en-1-one $^1$H-NMR (CDCl$_3$) δ: 1.37 (3H, brs), 2.03-2.09 (1H, m), 2.18-2.20 (4H, m), 2.27 (3H, s), 2.35 (3H, s), 2.69-4.98 (13H, m), 6.76-6.82 (3H, m), 6.98-6.92 (1H, m), 7.04-7.08 (2H, m), 7.18 (2H, d, J=7.8 Hz), 7.23-7.30 (7H, m), 7.35 (1H, dd, J=9.0, 3.2 Hz), 7.44 (1H, d, J=2.0 Hz), 7.56 (1H, d, J=15.4 Hz), 7.78-7.79 (1H, m).

Example 394

(E)-3-[3-Chloro-5-methyl-4-({5-[(4-methylbenzyl) oxy]pyridin-2-yl}oxy)phenyl]-1-[(2S)-4-{4-[2-(4-fluorophenoxy)ethyl]benzyl}-2-methylpiperazin-1-yl]prop-2-en-1-one $^1$H-NMR (CDCl$_3$) δ: 1.37 (3H, brs), 2.04-2.10 (1H, m), 2.18-2.21 (4H, m), 2.35 (3H, s), 2.69-4.98 (13H, m), 6.76-

6.85 (3H, m), 6.90-6.99 (3H, m), 7.18 (2H, d, J=7.8 Hz), 7.22-7.31 (7H, m), 7.35 (1H, dd, J=9.0, 3.2 Hz), 7.45 (1H, d, J=2.0 Hz), 7.56 (1H, d, J=15.4 Hz), 7.79 (1H, d, J=3.2 Hz).

Example 395

(E)-3-[3-Chloro-5-methyl-4-({5-[(4-methylbenzyl)oxy]pyridin-2-yl}oxy)phenyl]-1-[(2R)-4-{2-(4-fluorophenoxy)ethyl]benzyl}-2-methylpiperazin-1-yl]prop-2-en-1-one ¹H-NMR (CDCl₃) δ: 1.37 (3H, brs), 2.03-2.10 (1H, m), 2.18-2.20 (4H, m), 2.35 (3H, s), 2.69-4.98 (13H, m), 6.76-6.85 (3H, m), 6.90-6.99 (3H, m), 7.18 (2H, d, J=7.8 Hz), 7.22-7.29 (7H, m), 7.35 (1H, dd, J=8.8, 2.9 Hz), 7.45 (1H, d, J=2.2 Hz), 7.56 (1H, d, J=15.4 Hz), 7.79 (1H, d, J=2.9 Hz).

Example 396

(E)-3-[3-Chloro-5-methyl-4-({5-[(4-methylbenzyl)oxy]pyridin-2-yl}oxy)phenyl]-1-[(2R)-2-methyl-4-{4-[2-(4-methylphenoxy)ethyl]benzyl}piperazin-1-yl]prop-2-en-1-one ¹H-NMR (CDCl₃) δ: 1.37 (3H, brs), 2.03-2.09 (1H, m), 2.18-2.20 (4H, m), 2.28 (3H, s), 2.35 (3H, s), 2.69-4.98 (13H, m), 6.76-6.82 (3H, m), 6.91 (1H, d, J=8.8 Hz), 7.06 (2H, d, J=8.3 Hz), 7.18 (2H, d J=7.8 Hz), 7.23-7.31 (7H, m), 7.35 (1H, dd, J=8.8, 2.9 Hz), 7.45 (1H, d, J=2.0 Hz), 7.56 (1H, d, J=15.4 Hz), 7.79 (1H, d, J=2.9 Hz).

Example 397

(E)-3-[3-Chloro-5-methyl-4-({5-[(4-methylbenzyl)oxy]pyridin-2-yl}oxy)phenyl]-1-[(3S)-3-methyl-4-{4-[2-(4-methylphenoxy)ethyl]benzyl}piperazin-1-yl]prop-2-en-1-one ¹H-NMR (CDCl₃) δ: 1.18 (3H, d, J=5.9 Hz), 2.11-2.19 (4H, m), 2.27 (3H, s), 2.35 (3H, s), 2.51-2.53 (1H, m), 2.73-2.76 (1H, m), 2.94-3.41 (5H, m), 3.74-3.78 (1H, m), 3.93-4.27 (4H, m), 4.98 (2H, s), 6.75-6.82 (3H, m), 6.91 (1H, d, J=9.0 Hz), 7.04-7.08 (2H, m), 7.18 (2H, d, J=7.8 Hz), 7.22-7.30 (7H, m), 7.35 (1H, dd, J=9.0, 3.2 Hz), 7.43-7.46 (1H, m), 7.56 (1H, d, J=15.4 Hz), 7.79 (1H, d, J=3.2 Hz).

Example 398

(2E)-3-[3-Chloro-5-methyl-4-({5-[(4-methylbenzyl)oxy]pyridin-2-yl}oxy)phenyl]-1-(4-{4-[(1E)-3-(4-fluorophenoxy)prop-1-en-1-yl]benzyl}piperazin-1-yl)prop-2-en-1-one mp: 142-144° C.
¹H-NMR (CDCl₃) δ: 2.19 (3H, s), 2.36 (3H, s), 2.48 (4H, t, J=5.0 Hz), 3.53 (2H, s), 3.64 (2H, brs), 3.74 (2H, brs), 4.66 (2H, dd, J=5.9, 1.5 Hz), 4.98 (2H, s), 6.39 (1H, dt, J=16.0, 5.9 Hz), 6.72 (1H, d, J=16.0 Hz), 6.79 (1H, d, J=15.4 Hz), 6.87-6.93 (3H, m), 6.95-7.01 (2H, m), 7.19 (2H, d, J=7.6 Hz), 7.28-7.30 (5H, m), 7.34-7.39 (3H, m), 7.45 (1H, d, J=2.2 Hz), 7.57 (1H, d, J=15.4 Hz), 7.79 (1H, dd, J=2.9, 0.5 Hz).

Example 399

(2E)-3-[4-({5-[(4-Fluorobenzyl)oxy]pyridin-2-yl}oxy)-3,5-dimethylphenyl]-1-(4-{4-[(1E)-3-(4-fluorophenoxy)prop-1-en-1-yl]benzyl}piperazin-1-yl)prop-2-en-1-one mp: 101-104° C.
¹H-NMR (CDCl₃) δ: 2.12 (6H, s), 2.48 (4H, t, J=4.9 Hz), 3.53 (2H, s), 3.66 (2H, brs), 3.74 (2H, brs), 4.67 (2H, dd, J=5.8, 1.3 Hz), 4.99 (2H, s), 6.39 (1H, dt, J=16.0, 5.8 Hz), 6.72 (1H, d, J=16.0 Hz), 6.76-6.82 (2H, m), 6.87-6.92 (2H, m), 6.95-7.00 (2H, m), 7.04-7.10 (2H, m), 7.25-7.33 (5H, m), 7.36-7.39 (4H, m), 7.61 (1H, d, J=15.6 Hz), 7.81 (1H, d, J=3.2 Hz).

Example 400

(E)-3-[3-Chloro-5-methyl-4-({5-[(4-methylbenzyl)oxy]pyridin-2-yl}oxy)phenyl]-1-[2-(4-{2-[4-(propan-2-yl)phenoxy]ethyl}benzyl)-1,2,5-oxadiazepan-5-yl]prop-2-en-1-one ¹H-NMR (DMSO-d₆ at 70° C.) δ: 1.16 (6H, d, J=6.8 Hz), 2.10 (3H, s), 2.30 (3H, s), 2.78-2.85 (1H, m), 2.90-3.00 (4H, m), 3.63-3.70 (4H, m), 3.83-3.85 (4H, m), 4.13-4.16 (2H, m), 5.05 (2H, s), 6.81-6.84 (2H, m), 7.02 (1H, d, J=9.0 Hz), 7.10-7.12 (2H, m), 7.17-7.32 (9H, m), 7.44 (1H, d, J=15.1 Hz), 7.54-7.57 (2H, m), 7.75 (1H, brs), 7.78 (1H, d, J=2.9 Hz).

Example 401

4-{[(6-{4-[(E)-3-(2-{4-[2-(4-Fluorophenoxy)ethyl]benzyl})-1,2,5-oxadiazepan-5-yl)-3-oxoprop-1-en-1-yl]-2,6-dimethylphenoxy}pyridin-3-yl)oxy]methyl}benzonitrile ¹H-NMR (CDCl₃) δ: 2.11 (3H, s), 2.12 (3H, s), 2.96-3.08 (4H, m), 3.70-3.86 (8H, m), 4.09-4.14 (2H, m), 5.08 (2H, s), 6.71-6.85 (4H, m), 6.94 (2H, t, J=8.4 Hz), 7.21-7.35 (7H, m), 7.52 (2H, d, J=8.1 Hz), 7.63-7.69 (3H, m), 7.79 (1H, d, J=2.2 Hz).

Example 402

4-{[(6-{4-[(E)-3-(2-{4-[2-(4-Methoxyphenoxy)ethyl]benzyl}-1,2,5-oxadiazepan-5-yl)-3-oxoprop-1-en-1-yl]-2,6-dimethylphenoxy}pyridin-3-yl)oxy]methyl}benzonitrile ¹H-NMR (CDCl₃) δ: 2.11 (3H, s), 2.12 (3H, s), 2.96-3.08 (4H, m), 3.70-3.86 (11H, m), 4.09-4.15 (2H, m), 5.08 (2H, s), 6.75 (1H, t, J=15.8 Hz), 6.82-6.85 (5H, m), 7.21-7.24 (4H, m), 7.28-7.35 (3H, m), 7.52 (2H, d, J=8.3 Hz), 7.64-7.69 (3H, m), 7.80 (1H, d, J=2.9 Hz).

Example 403

(2E)-3-[4-({5-[(4-Fluorobenzyl)oxy]pyridin-2-yl}oxy)-3,5-dimethylphenyl]-1-(4-{4-[(2E)-4-(4-methylphenoxy)but-2-en-2-yl]benzyl}piperazin-1-yl)prop-2-en-1-one ¹H-NMR (CDCl₃) δ: 2.12 (6H, s), 2.14 (3H, d, J=1.5 Hz), 2.29 (3H, s), 2.48 (4H, t, J=4.9 Hz), 3.53 (2H, s), 3.65 (2H, brs), 3.73 (2H, brs), 4.72 (2H, d, J=6.3 Hz), 4.99 (2H, s), 6.05-6.08 (1H, m), 6.78 (1H, d, J=15.4 Hz), 6.81 (1H, d, J=9.0 Hz), 6.85 (2H, dt, J=9.3, 2.5 Hz), 7.05-7.10 (4H, m), 7.25-7.33 (5H, m), 7.36-7.41 (4H, m), 7.61 (1H, d, J=15.4 Hz), 7.81 (1H, d, J=3.2 Hz).

Example 404

(2E)-3-[4-({5-[(4-Fluorobenzyl)oxy]pyridin-2-yl}oxy)-3,5-dimethylphenyl]-1-(4-{4-[(1E)-2-methyl-3-(4-methylphenoxy)prop-1-en-1-yl]benzyl}piperazin-1-yl)prop-2-en-1-one $^1$H-NMR (CDCl$_3$) δ: 1.98 (3H, d, J=1.2 Hz), 2.12 (6H, s), 2.29 (3H, s), 2.49 (4H, t, J=4.9 Hz), 3.53 (2H, s), 3.66 (2H, brs), 3.75 (2H, brs), 4.54 (2H, s), 4.98 (2H, s), 6.61 (1H, brs), 6.79 (1H, d, J=15.4 Hz), 6.81 (1H, dd, J=9.0, 0.5 Hz), 6.87 (2H, dt, J=9.1, 2.4 Hz), 7.04-7.10 (4H, m), 7.25-7.33 (7H, m), 7.36-7.40 (2H, m), 7.61 (1H, d, J=15.4 Hz), 7.81 (1H, dd, J=3.2, 0.5 Hz).

Example 405

(E)-3-[3-Chloro-4-({5-[(2-chlorobenzyl)oxy]pyridin-2-yl}oxy)-5-methylphenyl]-1-(4-{4-[2-(4-ethoxyphenoxy)ethyl]benzyl}piperazin-1-yl)prop-2-en-1-one $^1$H-NMR (CDCl$_3$) δ: 1.38 (3H, t, J=7.1 Hz), 2.19 (3H, s), 2.48 (4H, brs), 3.07 (2H, t, J=7.1 Hz), 3.52 (2H, s), 3.64 (2H, brs), 3.74 (2H, brs), 3.97 (2H, q, J=7.1 Hz), 4.12 (2H, t, J=7.1 Hz), 5.14 (2H, s), 6.78-6.82 (5H, m), 6.94 (1H, d, J=9.0 Hz), 7.23-7.31 (7H, m), 7.38-7.41 (2H, m), 7.45 (1H, brs), 7.51-7.53 (1H, m), 7.57 (1H, d, J=15.4 Hz), 7.82 (1H, d, J=2.9 Hz).

Example 406

(E)-3-[3-Chloro-4-({5-[(2-chlorobenzyl)oxy]pyridin-2-yl}oxy)-5-methylphenyl]-1-(4-{4-[2-(4-methoxyphenyl)ethoxy]benzyl}piperazin-1-yl)prop-2-en-1-one $^1$H-NMR (CDCl$_3$) δ: 2.19 (3H, s), 2.46 (4H, t, J=4.6 Hz), 3.04 (2H, t, J=7.1 Hz), 3.47 (2H, s), 3.63 (2H, brs), 3.73 (2H, brs), 3.80 (3H, s), 4.13 (2H, t, J=7.1 Hz), 5.14 (2H, s), 6.79 (1H, d, J=15.4 Hz), 6.86 (4H, d, J=8.4 Hz), 6.94 (1H, d, J=8.8 Hz), 7.20 (2H, d, J=8.4 Hz), 7.21 (2H, d, J=8.4 Hz), 7.26-7.31 (3H, m), 7.38-7.41 (2H, m), 7.45 (1H, brs), 7.51-7.53 (1H, m), 7.56 (1H, d, J=15.4 Hz), 7.81 (1H, d, J=2.9 Hz).

Example 407

To a solution of (E)-3-[4-({5-[(4-fluorobenzyl)oxy]pyridin-2-yl}oxy)-3,5-dimethylphenyl]-1-(piperazin-1-yl)prop-2-en-1-one (0.328 g) and (E)-3-[4-(chloromethyl)-2-methylphenyl]prop-2-en-1-yl 4-methylphenyl ether (0.204 g) in DMF (2 mL) was added DIPEA (0.13 mL) at room temperature under an Ar atmosphere. The mixture was stirred at room temperature for 20.5 hours, and then heated at 50° C. for 1 hour, and then cooled to room temperature, and evaporated under reduced pressure. To the residue was added saturated aqueous NaHCO$_3$, and the mixture was extracted with AcOEt. The organic layer was washed with saturated aqueous NaCl, dried over anhydrous Na$_2$SO$_4$, and concentrated under reduced pressure. The residue was purified by silica gel column chromatography (AcOEt) to afford (2E)-3-[4-({5-[(4-fluorobenzyl)oxy]pyridin-2-yl}oxy)-3,5-dimethylphenyl]-1-(4-{3-methyl-4-[(1E)-3-(4-methylphenoxy)prop-1-en-1-yl]benzyl}piperazin-1-yl)prop-2-en-1-one (0.370 g) as a colorless oil.

$^1$H-NMR (CDCl$_3$) δ: 2.12 (6H, s), 2.29 (3H, s), 2.34 (3H, s), 2.48 (4H, t, J=4.9 Hz), 3.49 (2H, s), 3.66-3.75 (4H, m), 4.69 (2H, dd, J=5.8, 1.3 Hz), 4.98 (2H, s), 6.29 (1H, dt, J=15.9, 5.8 Hz), 6.78 (1H, d, J=15.4 Hz), 6.81 (1H, d, J=9.0 Hz), 6.87 (2H, dt, J=9.3, 2.6 Hz), 6.92 (1H, d, J=15.9 Hz), 7.05-7.13 (6H, m), 7.25 (2H, brs), 7.32 (1H, dd, J=9.0, 3.1 Hz), 7.36-7.39 (2H, m), 7.44 (1H, d, J=7.8 Hz), 7.61 (1H, d, J=15.4 Hz), 7.81 (1H, d, J=3.1 Hz).

Example 408

To a solution of (E)-3-[3-chloro-5-methyl-4-({5-[(4-methylbenzyl)oxy]pyridin-2-yl}oxy)phenyl]-1-(4-{4-[2-(4-chlorophenoxy)ethyl]benzyl}piperazin-1-yl)prop-2-en-1-one (3.410 g) in EtOH (50 mL) was added 6 M HCl (0.86 mL) at 50° C. The mixture was stirred at room temperature for 16 hours. The resulting precipitate was collected, and crystallized from EtOH (300 mL) and water (100 mL) to give (E)-3-[3-chloro-5-methyl-4-({5-[(4-methylbenzyl)oxy]pyridin-2-yl}oxy)phenyl]-1-(4-{4-[2-(4-chlorophenoxy)ethyl]benzyl}piperazin-1-yl)prop-2-en-1-one hydrochloride (3.060 g) as a colorless powder.

$^1$H-NMR (DMSO-d$_6$) δ: 2.10 (3H, s), 2.30 (3H, s), 3.06-3.58 (6H, m), 3.07 (2H, t, J=6.7 Hz), 4.22 (2H, t, J=6.7 Hz), 4.33 (2H, brs), 4.53-4.57 (2H, m), 5.06 (2H, s), 6.96 (2H, dt, J=9.9, 2.9 Hz), 7.09 (1H, d, J=9.0 Hz), 7.20 (2H, d, J=7.8 Hz), 7.27-7.34 (5H, m), 7.42-7.52 (5H, m), 7.59 (1H, dd, J=9.0, 3.1 Hz), 7.63 (1H, d, J=2.0 Hz), 7.79 (1H, d, J=3.1 Hz), 7.84 (1H, d, J=2.0 Hz), 10.82 (1H, s).

The following compounds were produced in the same manner as in Example 408 using appropriate starting materials.

Example 409

(E)-3-[3-Chloro-4-({5-[(2-fluorobenzyl)oxy]pyridin-2-yl}oxy)-5-methylphenyl]-1-(4-{4-[2-(3,4-dichlorophenoxy)ethyl]benzyl}piperazin-1-yl)prop-2-en-1-one hydrochloride mp: 186.6-189.0° C.

Example 410

(E)-3-[3-Chloro-5-methyl-4-({5-[(4-methylbenzyl)oxy]pyridin-2-yl}oxy)phenyl]-1-(4-{4-[2-(3,4-dichlorophenoxy)ethyl]benzyl}piperazin-1-yl)prop-2-en-1-one hydrochloride mp: 215.1-215.5° C.

Example 411

(E)-3-[3-Chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)prop-2-en-1-one hydrochloride mp: 134.7-136.4° C.

Example 412

(E)-3-[3-Chloro-4-({5-[(2-chlorobenzyl)oxy]pyridin-2-yl}oxy)-5-methylphenyl]-1-[4-(4-{2-[(4-methylbenzyl)oxy]ethyl}benzyl)piperazin-1-yl]prop-2-en-1-one hydrochloride mp: 200.7-201.4° C.

Example 413

(E)-3-[3-Chloro-4-({5-[(2-chlorobenzyl)oxy]pyridin-2-yl}oxy)-5-methylphenyl]-1-[4-(4-{2-[(4-fluorobenzyl)oxy]ethyl}benzyl)piperazin-1-yl]prop-2-en-1-one hydrochloride mp: 183.8-184.2° C.

Example 414

(E)-1-[4-(4-{2-[(4-Chlorobenzyl)oxy]ethyl}benzyl)piperazin-1-yl]-3-[3-chloro-4-({5-[(2-chlorobenzyl)oxy]pyridin-2-yl}oxy)-5-methylphenyl]prop-2-en-1-one hydrochloride mp: 189.4-190.5° C.

Example 415

(E)-3-[3-Chloro-4-({5-[(3-fluoro-2-methylbenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 175.1-176.7° C.

Example 416

(E)-3-[3-Chloro-4-({5-[(3-fluoro-2-methylbenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride mp: 192.8-193.8° C.

Example 417

(E)-3-[3-Chloro-4-({5-[(3-fluoro-2-methylbenzyl)oxy]pyridin-2-yl}oxy)-5-methylphenyl]-1-(4-{4-[2-(4-chlorophenoxy)ethyl]benzyl}piperazin-1-yl)prop-2-en-1-one hydrochloride mp: 175.1-176.7° C.

Example 418

(E)-3-[2-Methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride mp: 180.2-182.7° C. (dec.)

Example 419

(E)-3-[3-Chloro-4-({5-[(3-fluoro-5-methylbenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride mp: 196.6-198.0° C.

Example 420

(E)-3-[3-Chloro-4-({5-[3-fluoro-5-methylbenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 185.2-186.4° C.

Example 421

(E)-3-[3-Chloro-4-({5-[(3-fluoro-5-methylbenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride mp: 207.4-207.9° C.

Example 422

(E)-3-[3-Chloro-4-({5-[(3-fluoro-5-methylbenzyl)oxy]pyridin-2-yl}oxy)-5-methylphenyl]-1-(4-{4-[2-(4-chlorophenoxy)ethyl]benzyl}piperazin-1-yl)prop-2-en-1-one hydrochloride mp: 199.8-201.6° C.

Example 423

(E)-3-[3-Chloro-4-({5-[(3-fluoro-5-methylbenzyl)oxy]pyridin-2-yl}oxy)-5-methylphenyl]-1-(4-{4-[2-(4-methoxyphenoxy)ethyl]benzyl}piperazin-1-yl)prop-2-en-1-one hydrochloride mp: 186.7-187.8° C.

Example 424

(E)-3-[3-Chloro-4-({5-[(3-fluoro-4-methylbenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride mp: 224.7-225.8° C.

Example 425

(E)-3-[3-Chloro-4-({5-[3-fluoro-4-methylbenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 207.9-208.3° C.

Example 426

(E)-3-[3-Chloro-4-({5-[3-fluoro-4-methylbenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride mp: 225.4-225.9° C.

Example 427

(E)-3-[3-Chloro-4-({5-[(3-fluoro-4-methylbenzyl)oxy]pyridin-2-yl}oxy)-5-methylphenyl]-1-(4-{4-[2-(4-chlorophenoxy)ethyl]benzyl}piperazin-1-yl)prop-2-en-1-one hydrochloride mp: 224.7-224.8° C.

Example 428

(E)-3-[3-Chloro-4-({5-[3-fluoro-4-methylbenzyl)oxy]pyridin-2-yl}oxy)-5-methylphenyl]-1-(4-{4-[2-(4-methoxyphenoxy)ethyl]benzyl}piperazin-1-yl)prop-2-en-1-one hydrochloride mp: 219.8-220.2° C.

Example 429

(E)-3-[3-Chloro-4-({5-[(4-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride mp: 224.4-228.8° C.
$^1$H-NMR (DMSO-$d_6$) δ: 2.10 (3H, s), 2.80-3.80 (8H, m), 4.19 (2H, t, J=6.6 Hz), 4.32 (2H, brs), 4.45-4.63 (2H, m), 5.11 (2H, s), 6.90-6.98 (2H, m), 7.05-7.15 (3H, m), 7.29 (1H, d, J=15.5 Hz), 7.39-7.57 (9H, m), 7.58-7.65 (2H, m), 7.80 (1H, d, J=3.3 Hz), 7.84 (1H, d, J=1.6 Hz), 11.08 (1H, brs).

Example 430

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)prop-2-en-1-one hydrochloride mp: 227.1-227.2° C.

Example 431

(E)-3-[3-Chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride mp: 201.9-202.6° C.

Example 432

(E)-3-[3-Chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one hydrochloride mp: 232.1-232.7° C.

Example 433

(E)-3-[3-Chloro-4-({5-[2-(4-chlorophenyl)ethoxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 180.1-181.1° C.

Example 434

(E)-3-{3-Chloro-5-methyl-4-[(5-{[4-(propan-2-yl)benzyl]oxy}pyridin-2-yl)oxy]phenyl}-1-(4-{4-[2-(4-fluorophenoxy)ethyl]benzyl}piperazin-1-yl)prop-2-en-1-one hydrochloride mp: 225.9-226.5° C.

Example 435

(E)-3-[3-Chloro-4-({5-[(4-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride mp: 214.3-216.2° C.

Example 436

(E)-3-{3-Chloro-5-methyl-4-[(5-{[4-(trifluoromethyl)benzyl]oxy}pyridin-2-yl)oxy]phenyl}-1-(4-{4-[2-(4-fluorophenoxy)ethyl]benzyl}piperazin-1-yl)prop-2-en-1-one hydrochloride mp: 231.5-231.8° C.

Example 437

(E)-3-[3-Chloro-5-methyl-4-({5-[2-(4-methylphenyl)ethoxy]pyridin-2-yl}oxy)phenyl]-1-(4-{4-[2-(4-fluorophenoxy)ethyl]benzyl}piperazin-1-yl)prop-2-en-1-one hydrochloride mp: 228.9-229.5° C.

Example 438

(E)-3-[3-Chloro-4-({5-[(4-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride $^1$H-NMR (DMSO-$d_6$) δ: 1.16 (6H, d, J=6.9 Hz), 2.11 (3H, s), 2.82 (1H, septet, J=6.9 Hz), 2.90-3.50 (7H, m), 3.55 (1H, brs), 4.18 (2H, t, J=6.6 Hz), 4.33 (2H, brs), 4.45-4.62 (2H, m), 5.09 (2H, s), 6.80-6.88 (2H, m), 7.06-7.16 (3H, m), 7.18-7.32 (3H, m), 7.40-7.55 (7H, m), 7.56-7.65 (2H, m), 7.80 (1H, d, J=3.0 Hz), 7.84 (1H, d, J=1.6 Hz), 10.83 (1H, brs).

Example 439

(E)-3-[3-Chloro-4-({5-[(6-chloropyridin-3-yl)methoxy]pyridin-2-yl}oxy)-5-methylphenyl]-1-(4-{4-[2-(4-fluorophenoxy)ethyl]benzyl}piperazin-1-yl)prop-2-en-1-one hydrochloride mp: 230.5-230.6° C.

Example 440

(E)-3-[3-Chloro-5-methyl-4-({5-[(4-methylbenzyl)oxy]pyridin-2-yl}oxy)phenyl]-1-(4-{4-[2-(4-methoxyphenoxy)ethyl]benzyl}piperazin-1-yl)prop-2-en-1-one hydrochloride mp: 225.1-226.6° C.

Example 441

(E)-3-(3-Chloro-5-methyl-4-{[5-(pyridin-2-yl-methoxy)pyridin-2-yl]oxy}phenyl)-1-(4-{4-[2-(4-fluorophenoxy)ethyl]benzyl}piperazin-1-yl)prop-2-en-1-one hydrochloride mp: 240.5-241.0° C.

Example 442

(E)-3-(3-Chloro-5-methyl-4-{[5-(pyridin-3-yl-methoxy)pyridin-2-yl]oxy}phenyl)-1-(4-{4-[2-(4-fluorophenoxy)ethyl]benzyl}piperazin-1-yl)prop-2-en-1-one hydrochloride mp: 227.7-229.3° C.

Example 443

(E)-3-[3-Chloro-4-({5-[(6-chloropyridin-3-yl)methoxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 214.8-215.3° C.

Example 444

(E)-3-(3-Chloro-5-methyl-4-{[5-(pyridin-2-yl-methoxy)pyridin-2-yl]oxy}phenyl)-1-[4-(4-{2-[4-(propan-2-yl)phenoxy]ethyl}benzyl)piperazin-1-yl]prop-2-en-1-one hydrochloride mp: 180.9-182.0° C.

Example 445

(E)-3-(3-Chloro-5-methyl-4-{[5-(pyridin-3-yl-methoxy)pyridin-2-yl]oxy}phenyl)-1-[4-(4-{2-[4-(propan-2-yl)phenoxy]ethyl}benzyl)piperazin-1-yl]prop-2-en-1-one hydrochloride mp: 166.4-167.7° C.

Example 446

(E)-3-[3-Chloro-5-methyl-4-({5-[(6-methylpyridin-2-yl)methoxy]pyridin-2-yl}oxy)phenyl]-1-[4-(4-{2-[4-(propan-2-yl)phenoxy]ethyl}benzyl)piperazin-1-yl]prop-2-en-1-one hydrochloride $^1$H-NMR (DMSO-$d_6$) δ: 1.15 (6H, d, J=6.9 Hz), 2.11 (3H, s), 2.76-2.87 (1H, m), 3.00-3.11 (4H, m), 3.35-3.38 (7H, m), 4.18 (2H, t, J=6.8 Hz), 4.32 (2H, brs), 4.52-4.57 (2H, br m), 5.16 (2H, s), 6.84 (2H, d, J=8.6 Hz), 7.07-7.18 (3H, m), 7.21-7.70 (11H, m), 7.71-7.89 (3H, m), 10.73 (1H, s).

Example 447

(E)-3-[3-Chloro-4-({5-[(2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride mp: 224.0-224.5° C.

Example 448

(E)-3-[3-Chloro-5-methyl-4-({5-[(2-methylbenzyl)oxy]pyridin-2-yl}oxy)phenyl]-1-(4-{4-[2-(4-fluorophenoxy)ethyl]benzyl}piperazin-1-yl)prop-2-en-1-one hydrochloride mp: 210.3-210.6° C.

Example 449

(E)-3-[3-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride mp: 211.9-214.0° C.

Example 450

(E)-3-[3-Chloro-5-methyl-4-({5-[(2-methylbenzyl)oxy]pyridin-2-yl}oxy)phenyl]-1-(4-{4-[2-(4-methylphenoxy)ethyl]benzyl}piperazin-1-yl)prop-2-en-1-one hydrochloride $^1$H-NMR (DMSO-$d_6$) δ: 2.11 (3H, s), 2.22 (3H, s), 2.32 (3H, s), 2.89-3.40 (8H, m), 4.17 (2H, t, J=6.8 Hz), 4.30-4.34 (2H, m), 4.51-4.56 (2H, m), 5.10 (2H, s), 6.77-6.85 (2H, m), 7.01-7.14 (4H, m), 7.19-7.33 (4H, m), 7.39-7.56 (6H, m), 7.62-7.66 (2H, m), 7.81-7.87 (2H, m), 11.25 (1H, s).

Example 451

(E)-3-[3-Chloro-4-({5-[(2-fluorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride $^1$H-NMR (DMSO-$d_6$) δ: 2.11 (3H, s), 2.22 (3H, s), 3.03-3.59 (8H, m), 4.17 (2H, t, J=6.8 Hz), 4.31-4.34 (2H, m), 4.51-4.56 (2H, m), 5.15 (2H, s), 6.80-6.84 (2H, m), 7.07-7.12 (3H, m), 7.21-7.33 (3H, m), 7.44-7.63 (9H, m), 7.83-7.85 (2H, m), 11.06-11.10 (1H, m).

Example 452

(E)-3-[3-Chloro-4-({5-[(2-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride $^1$H-NMR (DMSO-$d_6$) δ: 2.12 (3H, s), 2.22 (3H, s), 2.94-3.60 (8H, m), 4.17 (2H, t, J=6.6 Hz), 4.31-4.35 (2H, m), 4.52-4.57 (2H, m), 5.17 (2H, s), 6.79-6.84 (2H, m), 7.10 (3H, dd, J=14.0, 8.7 Hz), 7.30 (1H, d, J=15.2 Hz), 7.37-7.54 (8H, m), 7.59-7.69 (3H, m), 7.82-7.87 (2H, m), 10.93-10.97 (1H, m).

Example 453

(E)-3-[3-Chloro-4-({5-[(4-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 218.0-218.2° C.

Example 454

(E)-3-[3-Chloro-4-({5-[(2-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 188.0-189.5° C.

Example 455

(E)-3-[3-Chloro-5-methyl-4-({5-[(2-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride mp: 168.4-169.8° C.

Example 456

(E)-3-[3-Chloro-5-methyl-4-({5-[(4-methylbenzyl)oxy]pyridin-2-yl}oxy)phenyl]-1-(4-{4-[2-(2-methylphenoxy)ethyl]benzyl}piperazin-1-yl)prop-2-en-1-one hydrochloride mp: 200.7-201.9° C.

Example 457

(E)-1-(4-{4-[2-(4-Butylphenoxy)ethyl]benzyl}piperazin-1-yl)-3-[3-chloro-5-methyl-4-({5-[(4-methylbenzyl)oxy]pyridin-2-yl}oxy)phenyl]prop-2-en-1-one hydrochloride mp: 176.0-177.8° C.

Example 458

(E)-3-[3-Chloro-4-({5-[(2-chlorobenzyl)oxy]pyridin-2-yl}oxy)-5-methylphenyl]-1-(4-{4-[2-(4-methoxyphenoxy)ethyl]benzyl}piperazin-1-yl)prop-2-en-1-one hydrochloride $^1$H-NMR (DMSO-$d_6$) δ: 2.11 (3H, s), 3.05 (2H, t, J=6.4 Hz), 3.14-3.62 (6H, m), 3.68 (3H, s), 4.15 (2H, t, J=6.4 Hz), 4.31-4.34 (2H, m), 4.52-4.57 (2H, m), 5.17 (2H, s), 6.85 (4H, s), 7.12 (1H, d, J=8.9 Hz), 7.27-7.54 (9H, m), 7.60-7.68 (3H, m), 7.83-7.86 (2H, m), 10.84 (1H, s).

Example 459

(E)-1-(4-{4-[2-(1,3-Benzodioxol-5-yloxy)ethyl]benzyl}piperazin-1-yl)-3-[3-chloro-4-({5-[(2-chlorobenzyl)oxy]pyridin-2-yl}oxy)-5-methylphenyl]prop-2-en-1-one hydrochloride mp: 182.0-182.5° C.

$^1$H-NMR (DMSO-$d_6$) δ: 2.11 (3H, s), 3.01-3.63 (8H, m), 4.13 (2H, t, J=6.6 Hz), 4.32 (2H, brs), 4.51-4.57 (2H, m), 5.17 (2H, s), 5.94 (2H, s), 6.36 (1H, dd, J=8.6, 2.6 Hz), 6.63 (1H, d, J=2.6 Hz), 6.79 (1H, d, J=8.6 Hz), 7.12 (1H, d, J=8.9 Hz), 7.28-7.67 (12H, m), 7.84-7.85 (2H, m), 11.36 (1H, brs).

Example 460

(E)-1-(4-{4-[2-(1,3-Benzodioxol-5-yloxy)ethyl]benzyl}piperazin-1-yl)-3-[3-chloro-5-methyl-4-({5-[(4-methylbenzyl)oxy]pyridin-2-yl}oxy)phenyl]prop-2-en-1-one hydrochloride mp: 229.5-231.3° C. (dec.)

$^1$H-NMR (DMSO-$d_6$) δ: 2.10 (3H, s), 2.30 (3H, s), 3.01-3.58 (8H, m), 4.13 (2H, t, J=6.6 Hz), 4.32 (2H, brs), 4.51-4.57 (2H, m), 5.05 (2H, s), 5.94 (2H, s), 6.36 (1H, dd, J=8.6, 2.6 Hz), 6.62 (1H, d, J=2.6 Hz), 6.79 (1H, d, J=8.6 Hz), 7.09 (1H, d, J=8.9 Hz), 7.18-7.63 (12H, m), 7.78-7.84 (2H, m), 11.01 (1H, brs).

Example 461

(E)-3-[3-Chloro-4-({5-[(2-chlorobenzyl)oxy]pyridin-2-yl}oxy)-5-methylphenyl]-1-[4-(4-{2-[3-(propan-2-yl)phenoxy]ethyl}benzyl)piperazin-1-yl]prop-2-en-1-one hydrochloride mp: 210.3-210.9° C.

Example 462

(E)-3-[3-Chloro-4-({5-[(2-chlorobenzyl)oxy]pyridin-2-yl}oxy)-5-methylphenyl]-1-(4-{4-[2-(3,4-dimethylphenoxy)ethyl]benzyl}piperazin-1-yl)prop-2-en-1-one hydrochloride $^1$H-NMR (DMSO-$d_6$) δ: 2.12 (6H, s), 2.16 (3H, s), 3.04-3.05 (3H, m), 3.13-3.67 (5H, m), 4.15 (2H, t, J=6.6 Hz), 4.33 (2H, s), 4.54 (2H, d, J=11.9 Hz), 5.17 (2H, s), 6.64 (1H, d, J=8.2 Hz), 6.73 (1H, s), 7.01 (1H, d, J=8.2 Hz), 7.13 (1H, d, J=8.7 Hz), 7.31 (1H, d, J=15.6 Hz), 7.38-7.53 (8H, m), 7.61-7.67 (3H, m), 7.83-7.87 (2H, m), 11.26 (1H, s).

Example 463

(E)-3-[3-Chloro-4-({5-[(2-chlorobenzyl)oxy]pyridin-2-yl}oxy)-5-methylphenyl]-1-(4-{4-[2-(3-methoxyphenoxy)ethyl]benzyl}piperazin-1-yl)prop-2-en-1-one hydrochloride $^1$H-NMR (DMSO-$d_6$) δ: 2.12 (3H, s), 2.99-3.19 (4H, m), 3.46-3.57 (4H, m), 3.72 (3H, s), 4.20 (2H, t, J=6.6 Hz), 4.32-4.35 (2H, m), 4.53-4.56 (2H, m), 5.17 (2H, s), 6.45-6.54 (3H, m), 7.12-7.19 (2H, m), 7.31 (1H, d, J=15.1 Hz), 7.38-7.54 (8H, m), 7.60-7.68 (3H, m), 7.83-7.87 (2H, m), 10.94 (1H, s).

Example 464

(E)-3-[3-Chloro-4-({5-[(2-chlorobenzyl)oxy]pyridin-2-yl}oxy)-5-methylphenyl]-1-(4-{4-[2-(2-chlorophenoxy)ethyl]benzyl}piperazin-1-yl)prop-2-en-1-one hydrochloride $^1$H-NMR (DMSO-$d_6$) δ: 2.11 (3H, s), 2.97-3.19 (4H, m), 3.35-3.61 (4H, m), 4.26-4.37 (4H, m), 4.53-4.56 (2H, m), 5.17 (2H, s), 6.94 (1H, t, J=7.6 Hz), 7.11-7.17 (2H, m),

Example 465

(E)-3-[3-Chloro-4-({5-[(2-chlorobenzyl)oxy]pyridin-2-yl}oxy)-5-methylphenyl]-1-(4-{4-[2-(4-iodophenoxy)ethyl]benzyl}piperazin-1-yl)prop-2-en-1-one hydrochloride mp: 214.2-214.7° C.
$^1$H-NMR (DMSO-$d_6$) δ: 2.11 (3H, s), 3.05-4.53 (14H, m), 5.17 (2H, s), 6.79 (2H, d, J=8.8 Hz), 7.13 (1H, d, J=8.8 Hz), 7.31 (1H, d, J=15.6 Hz), 7.40-7.43 (4H, m), 7.48-7.53 (4H, m), 7.58 (2H, d, J=8.3 Hz), 7.61-7.67 (3H, m), 7.84-7.85 (2H, m), 10.92 (1H, brs).

Example 466

(E)-3-[3-Chloro-4-({5-[(2-chlorobenzyl)oxy]pyridin-2-yl}oxy)-5-methylphenyl]-1-(4-{4-[2-(4-chlorophenoxy)ethyl]benzyl}piperazin-1-yl)prop-2-en-1-one hydrochloride $^1$H-NMR (DMSO-$d_6$) δ: 2.11 (3H, s), 3.00-3.16 (4H, m), 3.33-3.60 (4H, m), 4.21 (2H, t, J=6.6 Hz), 4.32 (2H, s), 4.53 (2H, s), 5.17 (2H, s), 6.96 (2H, d, J=8.8 Hz), 7.13 (1H, d, J=8.8 Hz), 7.28-7.34 (3H, m), 7.37-7.55 (8H, m), 7.60-7.68 (3H, m), 7.83-7.86 (2H, m), 10.99 (1H, s).

Example 467

(E)-3-[3-Chloro-4-({5-[(2-chlorobenzyl)oxy]pyridin-2-yl}oxy)-5-methylphenyl]-1-(4-{4-[2-(quinolin-6-yloxy)ethyl]benzyl}piperazin-1-yl)prop-2-en-1-one hydrochloride $^1$H-NMR (DMSO-$d_6$) δ: 2.11 (3H, s), 2.96-3.22 (4H, m), 3.32-3.76 (4H, m), 4.32-4.35 (2H, m), 4.42 (2H, t, J=6.6 Hz), 4.53-4.56 (2H, m), 5.17 (2H, s), 7.13 (1H, d, J=8.8 Hz), 7.31 (1H, d, J=15.1 Hz), 7.38-7.43 (2H, m), 7.48-7.53 (4H, m), 7.57-7.71 (7H, m), 7.83-7.89 (3H, m), 8.19 (1H, d, J=9.3 Hz), 8.77 (1H, d, J=8.3 Hz), 9.01 (1H, d, J=4.4 Hz), 11.39 (1H, s).

Example 468

(E)-3-[3-Chloro-4-({5-[(2-chlorobenzyl)oxy]pyridin-2-yl}oxy)-5-methylphenyl]-1-(4-{4-[2-(3-chlorophenoxy)ethyl]benzyl}piperazin-1-yl)prop-2-en-1-one hydrochloride $^1$H-NMR (DMSO-$d_6$) δ: 2.11 (3H, s), 3.07-3.08 (2H, m), 3.17-3.68 (6H, m), 4.25 (2H, t, J=6.6 Hz), 4.32-4.34 (2H, m), 4.53-4.55 (2H, m), 5.17 (2H, s), 6.91 (1H, d, J=6.3 Hz), 6.96-7.03 (2H, m), 7.13 (1H, d, J=8.8 Hz), 7.28-7.32 (2H, m), 7.38-7.54 (8H, m), 7.61-7.67 (3H, m), 7.82-7.86 (2H, m), 10.47 (1H, s).

Example 469

(E)-3-[3-Chloro-4-({5-[(2-chlorobenzyl)oxy]pyridin-2-yl}oxy)-5-methylphenyl]-1-(4-{4-[2-(3-methylphenoxy)ethyl]benzyl}piperazin-1-yl)prop-2-en-1-one hydrochloride $^1$H-NMR (DMSO-$d_6$) δ: 2.12 (3H, s), 2.26 (3H, s), 2.99-3.11 (4H, m), 3.18-3.65 (4H, m), 4.19 (2H, t, J=6.6 Hz), 4.31-4.34 (2H, m), 4.53-4.56 (2H, m), 5.17 (2H, s), 6.70-6.77 (3H, m), 7.11-7.16 (2H, m), 7.31 (1H, d, J=15.4 Hz), 7.38-7.44 (4H, m), 7.47-7.58 (4H, m), 7.60-7.67 (3H, m), 7.84-7.87 (2H, m), 11.32 (1H, s).

Example 470

(E)-3-[3-Chloro-4-({5-[(2-chlorobenzyl)oxy]pyridin-2-yl}oxy)-5-methylphenyl]-1-(4-{4-[2-(3,5-dimethylphenoxy)ethyl]benzyl}piperazin-1-yl)prop-2-en-1-one hydrochloride $^1$H-NMR (DMSO-$d_6$) δ: 2.12 (3H, s), 2.21 (6H, s), 3.00-3.07 (4H, m), 3.25-3.63 (4H, m), 4.16 (2H, t, J=6.6 Hz), 4.30-4.33 (2H, m), 4.53-4.56 (2H, m), 5.17 (2H, s), 6.53-6.56 (3H, m), 7.12 (1H, d, J=8.8 Hz), 7.31 (1H, d, J=15.4 Hz), 7.38-7.44 (4H, m), 7.47-7.57 (4H, m), 7.60-7.67 (3H, m), 7.84-7.86 (2H, m), 11.38 (1H, s).

Example 471

(E)-3-[3-Chloro-4-({5-[(2-chlorobenzyl)oxy]pyridin-2-yl}oxy)-5-methylphenyl]-1-(4-{4-[2-(2,3-dimethylphenoxy)ethyl]benzyl}piperazin-1-yl)prop-2-en-1-one hydrochloride $^1$H-NMR (DMSO-$d_6$) δ: 2.00 (3H, s), 2.12 (3H, s), 2.18 (3H, s), 2.97-3.67 (8H, m), 4.16 (2H, t, J=6.3 Hz), 4.31-4.34 (2H, m), 4.53-4.56 (2H, m), 5.17 (2H, s), 6.73 (1H, d, J=7.3 Hz), 6.78 (1H, d, J=8.1 Hz), 7.00 (1H, t, J=7.8 Hz), 7.13 (1H, d, J=9.0 Hz), 7.31 (1H, d, J=15.4 Hz), 7.38-7.48 (5H, m), 7.51-7.58 (3H, m), 7.60-7.68 (3H, m), 7.84-7.87 (2H, m), 11.30 (1H, s).

Example 472

(E)-3-[3-Chloro-4-({5-[(2-chlorobenzyl)oxy]pyridin-2-yl}oxy)phenyl]-1-(4-{4-[2-(3-methylphenoxy)ethyl]benzyl}piperazin-1-yl)prop-2-en-1-one hydrochloride mp: 201.2-202.5° C.

Example 473

(E)-3-[3-Chloro-4-({5-[(2-chlorobenzyl)oxy]pyridin-2-yl}oxy)phenyl]-1-(4-{4-[2-(4-fluorophenoxy)ethyl]benzyl}piperazin-1-yl)prop-2-en-1-one hydrochloride mp: 197.0-199.5° C.

Example 474

(E)-3-[3-Chloro-4-({5-[(2-chlorobenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride mp: 185.6-186.3° C.

Example 475

(E)-3-[3-Chloro-4-({5-[(2-chlorobenzyl)oxy]pyridin-2-yl}oxy)phenyl]-1-(4-{4-[2-(4-methylphenoxy)ethyl]benzyl}piperazin-1-yl)prop-2-en-1-one hydrochloride mp: 193.5-195.8° C.

Example 476

(E)-3-[4-({5-[(2-Chlorobenzyl)oxy]pyridin-2-yl}oxy)-2-methylphenyl]-1-(4-{4-[2-(4-fluorophenoxy)ethyl]benzyl}piperazin-1-yl)prop-2-en-1-one hydrochloride $^1$H-NMR (DMSO-d$_6$) δ: 2.36 (3H, s), 3.04-3.57 (8H, m), 4.19 (2H, t, J=6.6 Hz), 4.32 (2H, brs), 4.48-4.57 (2H, m), 5.20 (2H, s), 6.91-6.97 (4H, m), 7.05-7.12 (4H, m), 7.38-7.44 (4H, m), 7.51-7.55 (3H, m), 7.61-7.65 (2H, m), 7.74 (1H, d, J=15.1 Hz), 7.81 (1H, d, J=9.0 Hz), 7.99 (1H, d, J=3.2 Hz), 10.98 (1H, brs).

Example 477

(E)-3-[4-({5-[(2-Chlorobenzyl)oxy]pyridin-2-yl}oxy)-2-methylphenyl]-1-(4-{4-[2-(4-methylphenoxy)ethyl]benzyl}piperazin-1-yl)prop-2-en-1-one hydrochloride $^1$H-NMR (DMSO-d$_6$) δ: 2.21 (3H, s), 2.35 (3H, s), 3.03-3.54 (8H, m), 4.16 (2H, t, J=6.6 Hz), 4.32 (2H, brs), 4.48-4.56 (2H, m), 5.20 (2H, s), 6.81 (2H, m), 6.93-6.96 (2H, m), 7.05-7.12 (4H, m), 7.38-7.44 (4H, m), 7.49-7.54 (3H, m), 7.61-7.65 (2H, m), 7.74 (1H, d, J=15.1 Hz), 7.81 (1H, d, J=9.0 Hz), 7.99 (1H, d, J=3.2 Hz), 10.79 (1H, brs).

Example 478

(E)-3-[4-({5-[(2-Chlorobenzyl)oxy]pyridin-2-yl}oxy)-2-methylphenyl]-1-[4-(4-{2-[4-(propan-2-yl)phenoxy]ethyl}benzyl)piperazin-1-yl]prop-2-en-1-one hydrochloride mp: 209.6-212.0° C.
$^1$H-NMR (DMSO-d$_6$) δ: 1.15 (6H, d, J=6.9 Hz), 2.35 (3H, s), 2.81 (1H, septet, J=6.9 Hz), 3.03-3.56 (8H, m), 4.17 (2H, t, J=6.6 Hz), 4.32-4.53 (4H, m), 5.20 (2H, s), 6.81-6.87 (2H, m), 6.93-6.96 (2H, m), 7.04-7.14 (4H, m), 7.37-7.44 (4H, m), 7.50-7.55 (3H, m), 7.61-7.66 (2H, m), 7.74 (1H, d, J=15.5 Hz), 7.79-7.83 (1H, m), 7.99 (1H, d, J=3.0 Hz), 10.91 (1H, brs).

Example 479

(E)-3-[4-({5-[(2-Chlorobenzyl)oxy]pyridin-2-yl}oxy)-3-methoxyphenyl]-1-(4-{4-[2-(4-fluorophenoxy)ethyl]benzyl}piperazin-1-yl)prop-2-en-1-one hydrochloride mp: 194.9-197.8° C.

Example 480

(E)-3-[4-({5-[(2-Chlorobenzyl)oxy]pyridin-2-yl}oxy)-3-methoxyphenyl]-1-(4-{4-[2-(3-methylphenoxy)ethyl]benzyl}piperazin-1-yl)prop-2-en-1-one hydrochloride $^1$H-NMR (DMSO-d$_6$) δ: 2.26 (3H, s), 3.06 (2H, t, J=6.5 Hz), 3.14-3.67 (6H, m), 3.75 (3H, s), 4.19 (2H, t, J=6.5 Hz), 4.31-4.34 (2H, m), 4.52-4.55 (2H, m), 5.17 (2H, s), 6.70-6.76 (3H, m), 6.99 (1H, d, J=8.8 Hz), 7.09-7.17 (2H, m), 7.25 (1H, d, J=15.4 Hz), 7.31 (1H, d, J=8.1 Hz), 7.39-7.44 (4H, m), 7.49-7.62 (7H, m), 7.86 (1H, d, J=2.9 Hz), 11.07 (1H, s).

Example 481

(E)-3-[4-({5-[(2-Chlorobenzyl)oxy]pyridin-2-yl}oxy)-3-methoxyphenyl]-1-[4-(4-{2-[4-(propan-2-yl)phenoxy]ethyl}benzyl)piperazin-1-yl]prop-2-en-1-one hydrochloride mp: 196.7-198.7° C.

Example 482

(E)-3-[4-({5-[(2-Chlorobenzyl)oxy]pyridin-2-yl}oxy)-3-methoxyphenyl]-1-(4-{4-[2-(4-methylphenoxy)ethyl]benzyl}piperazin-1-yl)prop-2-en-1-one hydrochloride mp: 203.4-205.7° C.

Example 483

(E)-3-[3-Chloro-4-({5-[(2-chlorobenzyl)oxy]pyridin-2-yl}oxy)-5-methylphenyl]-1-(4-{4-[2-(3-ethoxyphenoxy)ethyl]benzyl}piperazin-1-yl)prop-2-en-1-one hydrochloride mp: 209.8-211.0° C.

Example 484

(E)-3-[3-Chloro-4-({5-[(3-chloro-2-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 181.4-182.0° C.

Example 485

(E)-3-[3-Chloro-4-({5-[(3-chloro-2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride mp: 228.9-229.4° C.

Example 486

(E)-3-[4-({5-[(2-Chlorobenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride $^1$H-NMR (DMSO-d$_6$) δ: 1.15 (6H, d, J=7.1 Hz), 2.78-2.85 (1H, m), 2.99-3.60 (6H, m), 3.06 (2H, t, J=6.6 Hz), 4.17 (2H, t, J=6.6 Hz), 4.32 (2H, brs), 4.53 (2H, brs), 5.21 (2H, s), 6.84 (2H, d, J=8.8 Hz), 7.07-7.14 (5H, m), 7.21 (1H, d, J=15.4 Hz), 7.40-7.43 (4H, m), 7.52-7.56 (4H, m), 7.62-7.67 (2H, m), 7.75 (2H, d, J=8.5 Hz), 8.00 (1H, d, J=3.2 Hz), 11.28 (1H, brs).

Example 487

(E)-3-[3-Chloro-4-({5-[(2,3-difluorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride $^1$H-NMR (DMSO-d$_6$) δ: 2.11 (3H, s), 2.22 (3H, s), 2.95-3.60 (8H, m), 4.17 (2H, t, J=6.6 Hz), 4.33 (2H, s), 4.53 (2H, s), 5.21 (2H, s), 6.82 (2H, d, J=−8.5 Hz), 7.07 (2H, d, J=8.5 Hz), 7.13 (1H, d, J=8.8 Hz), 7.23-7.32 (2H, m), 7.38-7.51 (7H, m), 7.64-7.68 (2H, m), 7.84-7.86 (2H, m), 10.71 (1H, s).

Example 488

(E)-3-[3-Chloro-4-({5-[(2,3-difluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 180.1-181.7° C.

Example 489

(E)-3-[3-Chloro-5-methyl-4-({5-[(4-methylbenzyl)oxy]pyridin-2-yl}oxy)phenyl]-1-(4-{4-[2-(4-nitrophenoxy)ethyl]benzyl}piperazin-1-yl)prop-2-en-1-one hydrochloride mp: 200.9-202.3° C.
$^1$H-NMR (DMSO-d$_6$) δ: 2.10 (3H, s), 2.30 (3H, s), 3.11-4.53 (14H, m), 5.05 (2H, s), 7.09 (1H, d, J=9.0 Hz), 7.16 (2H, d, J=8.6 Hz), 7.20 (2H, d, J=7.8 Hz), 7.30 (1H, d, J=15.4 Hz), 7.33 (2H, d, J=7.8 Hz), 7.44 (2H, d, J=7.8 Hz), 7.49 (1H, d, J=15.4 Hz), 7.54 (2H, d, J=7.3 Hz), 7.58-7.61 (1H, m), 7.63 (1H, brs), 7.79 (1H, d, J=2.9 Hz), 7.84 (1H, brs), 8.20 (2H, d, J=8.3 Hz), 11.09 (1H, brs).

Example 490

(E)-3-[3-Chloro-4-({5-[(2-chlorobenzyl)oxy]pyridin-2-yl}oxy)-5-methylphenyl]-1-(4-{4-[2-(4-nitrophenoxy)ethyl]benzyl}piperazin-1-yl)prop-2-en-1-one hydrochloride mp: 194.8-195.2° C.
$^1$H-NMR (DMSO-d$_6$) δ: 2.11 (3H, s), 3.11-4.53 (14H, m), 5.17 (2H, s), 7.12 (1H, d, J=9.0 Hz), 7.16 (2H, d, J=9.0 Hz), 7.30 (1H, d, J=15.4 Hz), 7.39-7.47 (5H, m), 7.51-7.55 (3H, m), 7.61-7.67 (3H, m), 7.84-7.85 (2H, m), 8.20 (2H, d, J=9.0 Hz), 10.98 (1H, brs).

Example 491

(E)-3-[3-Chloro-4-({5-[(2-chlorobenzyl)oxy]pyridin-2-yl}oxy)-5-methylphenyl]-1-(4-{4-[2-(cyclopropylmethoxy)ethyl]benzyl}piperazin-1-yl)prop-2-en-1-one hydrochloride mp: 200.2-202.1° C.

Example 492

(E)-3-[3-Chloro-4-({5-[(2-chlorobenzyl)oxy]pyridin-2-yl}oxy)-5-methylphenyl]-1-(4-{4-[2-(3,4-dichlorophenoxy)ethyl]benzyl}piperazin-1-yl)prop-2-en-1-one hydrochloride mp: 199.2-200.2° C.

Example 493

(E)-3-[4-({5-[(2-Chlorobenzyl)oxy]pyridin-2-yl}oxy)-3-methoxyphenyl]-1-(4-{4-[2-(4-chlorophenoxy)ethyl]benzyl}piperazin-1-yl)prop-2-en-1-one hydrochloride mp: 218.8-219.2° C.

Example 494

(E)-3-[3-Methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride $^1$H-NMR (DMSO-d$_6$) δ: 1.15 (6H, d, J=7.1 Hz), 2.13 (3H, s), 2.30 (3H, s), 2.81 (1H, septet, J=6.8 Hz), 2.90-3.70 (8H, m), 4.18 (2H, t, J=6.6 Hz), 4.32 (2H, s), 4.52 (2H, s), 5.08 (2H, s), 6.82-6.86 (2H, m), 6.98 (1H, d, J=8.3 Hz), 7.01 (1H, d, J=9.0 Hz), 7.11-7.15 (2H, m), 7.17-7.21 (3H, m), 7.33 (2H, d, J=8.1 Hz), 7.43 (2H, d, J=8.1 Hz), 7.49-7.59 (5H, m), 7.68 (1H, d, J=1.7 Hz), 7.87 (1H, d, J=3.2 Hz), 10.67 (1H, brs).

Example 495

(E)-3-[3-Methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one hydrochloride mp: 227.6-228.7° C.

Example 496

(E)-1-(4-{4-[2-(4-Methoxyphenoxy)ethyl]benzyl}piperazin-1-yl)-3-[3-methyl-4-({5-[(4-methylbenzyl)oxy]pyridin-2-yl}oxy)phenyl]prop-2-en-1-one hydrochloride mp: 216.2-216.9° C.

Example 497

(E)-3-[3-Chloro-4-({5-[(2-methoxybenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 171.1-172.6° C.

Example 498

(E)-3-[3-Chloro-4-({5-[(2-chloro-4-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 194.6-197.5° C.

Example 499

(E)-3-[3-Chloro-4-({5-[(3-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride mp: 186.5-186.8° C.

Example 500

(E)-3-[3-Chloro-5-methyl-4-({5-[(3-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride mp: 179.1-179.9° C.

Example 501

(E)-3-[3-Chloro-4-({5-[(3-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride $^1$H-NMR (DMSO-$d_6$) δ: 1.15 (6H, d, J=6.8 Hz), 2.11 (3H, s), 2.79-2.84 (1H, m), 2.99-3.64 (8H, m), 4.18 (2H, t, J=6.6 Hz), 4.31-4.34 (2H, m), 4.52-4.55 (2H, m), 5.13 (2H, s), 6.84 (2H, d, J=8.5 Hz), 7.10-7.15 (3H, m), 7.30 (1H, d, J=15.4 Hz), 7.40-7.48 (6H, m), 7.50-7.56 (3H, m), 7.61-7.65 (2H, m), 7.81 (1H, d, J=2.7 Hz), 7.85 (1H, s), 11.13 (1H, s).

Example 502

2-({[6-(2-Chloro-6-methyl-4-{(E)-3-oxo-3-[4-(4-{2-[4-(propan-2-yl)phenoxy]ethyl}benzyl)-piperazin-1-yl]prop-1-en-1-yl}phenoxy)pyridin-3-yl]oxy}methyl)benzonitrile hydrochloride mp: 180.7-181.2° C.

Example 503

(E)-3-[4-({5-[(2,3-Dichlorobenzyl)oxy]pyridin-2-yl}oxy)-3-methylphenyl]-1-(4-{4-[2-(4-methylphenoxy)ethyl]benzyl}piperazin-1-yl)prop-2-en-1-one hydrochloride $^1$H-NMR (DMSO-$d_6$) δ: 2.14 (3H, s), 2.22 (3H, s), 2.90-3.60 (8H, m), 4.17 (2H, t, J=6.7 Hz), 4.33 (2H, s), 4.54 (2H, s), 5.23 (2H, s), 6.80-6.83 (2H, m), 6.99-7.08 (4H, m), 7.20 (1H, d, J=15.1 Hz), 7.41-7.56 (7H, m), 7.60 (1H, dd, J=7.6, 1.5 Hz), 7.64 (1H, dd, J=9.0, 3.2 Hz), 7.67 (2H, dd, J=8.1, 1.5 Hz), 7.93 (1H, d, J=3.2 Hz), 10.56 (1H, brs).

Example 504

(E)-3-[4-({5-[(2,3-Dichlorobenzyl)oxy]pyridin-2-yl}oxy)-3-methylphenyl]-1-[4-(4-{2-[4-(propan-2-yl)phenoxy]ethyl}benzyl)piperazin-1-yl]prop-2-en-1-one hydrochloride mp: 171.3-172.3° C.

Example 505

(E)-3-[4-({5-[(2-Chlorobenzyl)oxy]pyridin-2-yl}oxy)-3-methylphenyl]-1-(4-{4-[2-(4-methylphenoxy)ethyl]benzyl}piperazin-1-yl)prop-2-en-1-one hydrochloride $^1$H-NMR (DMSO-$d_6$) δ: 2.14 (3H, s), 2.22 (3H, s), 2.90-3.70 (8H, m), 4.17 (2H, t, J=6.6 Hz), 4.32 (2H, s), 4.53 (2H, s), 5.19 (2H, s), 6.80-6.83 (2H, m), 7.00 (1H, d, J=8.3 Hz), 7.06 (3H, t, J=8.8 Hz), 7.21 (1H, d, J=15.1 Hz), 7.38-7.43 (4H, m), 7.49-7.56 (5H, m), 7.60-7.65 (2H, m), 7.69 (1H, d, J=2.0 Hz), 7.92 (1H, d, J=3.4 Hz), 10.91 (1H, brs).

Example 506

(E)-3-[4-({5-[(2-Chlorobenzyl)oxy]pyridin-2-yl}oxy)-3-methylphenyl]-1-(4-{4-[2-(4-fluorophenoxy)ethyl]benzyl}piperazin-1-yl)prop-2-en-1-one hydrochloride mp: 192.9-194.6° C.

Example 507

(E)-3-[4-({5-[(2-Chlorobenzyl)oxy]pyridin-2-yl}oxy)-3-methylphenyl]-1-[4-(4-{2-[4-(propan-2-yl)phenoxy]ethyl}benzyl)piperazin-1-yl]prop-2-en-1-one hydrochloride mp: 178.2-178.9° C.

Example 508

(E)-3-[4-({5-[(2-Chlorobenzyl)oxy]pyridin-2-yl}oxy)-3-methylphenyl]-1-(4-{4-[2-(3-methylphenoxy)ethyl]benzyl}piperazin-1-yl)prop-2-en-1-one hydrochloride mp: 174.5-174.9° C.

Example 509

(E)-3-[4-({5-[(2-Chlorobenzyl)oxy]pyridin-2-yl}oxy)-3-fluorophenyl]-1-(4-{4-[2-(4-methylphenoxy)ethyl]benzyl}piperazin-1-yl)prop-2-en-1-one hydrochloride mp: 203.1-203.8° C.

Example 510

(E)-3-[4-({5-[(2-Chlorobenzyl)oxy]pyridin-2-yl}oxy)-3-fluorophenyl]-1-(4-{4-[2-(4-fluorophenoxy)ethyl]benzyl}piperazin-1-yl)prop-2-en-1-one hydrochloride mp: 205.4-206.0° C.

Example 511

(E)-3-[4-({5-[(2-Chlorobenzyl)oxy]pyridin-2-yl}oxy)-3-fluorophenyl]-1-[4-(4-{2-[4-(propan-2-yl)phenoxy]ethyl}benzyl)piperazin-1-yl]prop-2-en-1-one hydrochloride mp: 196.6-197.3° C.

Example 512

(E)-3-[4-({5-[2-Chlorobenzyl)oxy]pyridin-2-yl}oxy)-3-fluorophenyl]-1-(4-{4-[2-(3-methylphenoxy)ethyl]benzyl}piperazin-1-yl)prop-2-en-1-one hydrochloride mp: 184.2-186.2° C.

Example 513

(E)-3-[3-Chloro-4-({5-[(4-fluorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride $^1$H-NMR (DMSO-d$_6$) δ: 2.11 (3H, s), 2.22 (3H, s), 2.80-3.80 (8H, m), 4.17 (2H, t, J=6.8 Hz), 4.32 (2H, brs), 4.51-4.56 (2H, m), 5.09 (2H, s), 6.82 (2H, d, J=8.6 Hz), 7.09 (3H, t, J=8.9 Hz), 7.19-7.26 (2H, m), 7.30 (1H, d, J=15.5 Hz), 7.41-7.55 (8H, m), 7.60-7.63 (2H, m), 7.81 (1H, d, J=3.0 Hz), 7.85 (1H, d, J=1.6 Hz), 11.15 (1H, brs).

Example 514

(E)-3-[3-Chloro-4-({5-[(3-fluoro-2-methylbenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride mp: 176.8-177.7° C.

Example 515

(E)-3-[2-Methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one hydrochloride mp: 212.6-212.9° C. (dec.)

$^1$H-NMR (DMSO-d$_6$) δ: 2.21 (3H, s), 2.31 (3H, s), 2.35 (3H, s), 3.03-3.45 (8H, m), 4.16 (2H, t, J=6.6 Hz), 4.32 (2H, brs), 4.52 (2H, brs), 5.09 (2H, s), 6.80-6.83 (2H, m), 6.91-6.93 (2H, m), 7.01-7.12 (4H, m), 7.20 (2H, d, J=7.8 Hz), 7.34 (2H, d, J=7.8 Hz), 7.41-7.43 (2H, m), 7.49-7.51 (2H, m), 7.57-7.60 (1H, m), 7.74 (1H, d, J=15.1 Hz), 7.79 (1H, d, J=9.5 Hz), 7.93-7.94 (1H, m), 10.76 (1H, brs).

Example 516

(E)-3-{3-Chloro-5-methyl-4-[(5-{[4-(trifluoromethyl)benzyl]oxy}pyridin-2-yl)oxy]phenyl}-1-(4-{4-[2-(4-iodophenoxy)ethyl]benzyl}piperazin-1-yl)prop-2-en-1-one hydrochloride $^1$H-NMR (DMSO-d$_6$) δ: 2.11 (3H, s), 3.05-3.15 (5H, m), 3.39-3.57 (3H, m), 4.20 (2H, t, J=6.6 Hz), 4.32-4.35 (2H, m), 4.52-4.56 (2H, m), 5.24 (2H, s), 6.77-6.81 (2H, m), 7.12 (1H, d, J=8.8 Hz), 7.30 (1H, d, J=15.4 Hz), 7.41-7.53 (5H, m), 7.56-7.59 (2H, m), 7.62-7.69 (4H, m), 7.78 (2H, d, J=8.3 Hz), 7.83 (1H, d, J=3.2 Hz), 7.85 (1H, d, J=1.5 Hz), 10.97 (1H, brs).

Example 517

(E)-3-{3-Chloro-5-methyl-4-[(5-{[4-(trifluoromethyl)benzyl]oxy}pyridin-2-yl)oxy]phenyl}-1-(4-{4-[2-(4-methylphenoxy)ethyl]benzyl}piperazin-1-yl)prop-2-en-1-one hydrochloride $^1$H-NMR (DMSO-d$_6$) δ: 2.10 (3H, s), 2.22 (3H, s), 3.04-3.15 (5H, m), 3.35-3.56 (3H, m), 4.17 (2H, t, J=6.6 Hz), 4.33 (2H, brs), 4.52-4.56 (2H, m), 5.24 (2H, s), 6.82 (2H, d, J=8.8 Hz), 7.07 (2H, d, J=8.8 Hz), 7.12 (1H, d, J=9.0 Hz), 7.30 (1H, d, J=15.4 Hz), 7.42-7.53 (5H, m), 7.62-7.69 (4H, m), 7.78 (2H, d, J=8.3 Hz), 7.83 (1H, d, J=3.2 Hz), 7.85 (1H, d, J=1.7 Hz), 10.89 (1H, brs).

Example 518

(E)-3-{3-Chloro-5-methyl-4-[(5-{[4-(trifluoromethyl)benzyl]oxy}pyridin-2-yl)oxy]phenyl}-1-(4-{4-[2-(4-chlorophenoxy)ethyl]benzyl}piperazin-1-yl)prop-2-en-1-one hydrochloride $^1$H-NMR (DMSO-d$_6$) δ: 2.11 (3H, s), 3.01-3.19 (3H, m), 3.34-3.62 (5H, m), 4.22 (2H, t, J=6.6 Hz), 4.31-4.33 (2H, m), 4.52-4.56 (2H, m), 5.24 (2H, s), 6.95-6.98 (2H, m), 7.12 (1H, d, J=9.0 Hz), 7.29-7.33 (3H, m), 7.41-7.56 (5H, m), 7.62-7.69 (4H, m), 7.78 (2H, d, J=8.1 Hz), 7.83 (1H, d, J=2.9 Hz), 7.85 (1H, s), 11.30 (1H, brs).

Example 519

(E)-3-{3-Chloro-5-methyl-4-[(5-{[4-(trifluoromethyl)benzyl]oxy}pyridin-2-yl)oxy]phenyl}-1-[4-(4-{2-[4-(propan-2-yl)phenoxy]ethyl}benzyl)piperazin-1-yl]prop-2-en-1-one hydrochloride $^1$H-NMR (DMSO-d$_6$) δ: 1.15 (6H, d, J=6.8 Hz), 2.10 (3H, s), 2.78-2.85 (1H, m), 3.04-3.08 (5H, m), 3.35-3.55 (3H, m), 4.18 (2H, t, J=6.7 Hz), 4.34 (2H, brs), 4.52-4.56 (2H, m), 5.24 (2H, s), 6.84 (2H, d, J=8.5 Hz), 7.11-7.14 (3H, m), 7.30 (1H, d, J=15.1 Hz), 7.42-7.52 (5H, m), 7.62-7.67 (4H, m), 7.78 (2H, d, J=8.1 Hz), 7.82 (1H, d, J=2.9 Hz), 7.85 (1H, s), 10.80 (1H, s).

Example 520

(E)-3-{3-Chloro-5-methyl-4-[(5-{[4-(trifluoromethyl)benzyl]oxy}pyridin-2-yl)oxy]phenyl}-1-(4-{4-[2-(5,6,7,8-tetrahydronaphthalen-2-yloxy)ethyl]benzyl}piperazin-1-yl)prop-2-en-1-one hydrochloride $^1$H-NMR (DMSO-d$_6$) δ: 1.68-1.70 (4H, m), 2.10 (3H, s), 2.61-2.66 (4H, m), 3.03-3.15 (5H, m), 3.35-3.54 (3H, m), 4.15 (2H, t, J=6.6 Hz), 4.33 (2H, brs), 4.51-4.54 (2H, m), 5.24 (2H, s), 6.60-6.66 (2H, m), 6.93 (1H, d, J=8.3 Hz), 7.12 (1H, d, J=8.8 Hz), 7.30 (1H, d, J=15.4 Hz), 7.41-7.51 (5H, m), 7.62-7.68 (4H, m), 7.77 (2H, d, J=8.3 Hz), 7.82 (1H, d, J=2.9 Hz), 7.85 (1H, s), 10.73 (1H, brs).

Example 521

(E)-3-{3-Chloro-5-methyl-4-[(5-{[4-(trifluoromethyl)benzyl]oxy}pyridin-2-yl)oxy]phenyl}-1-(4-{4-[2-(naphthalen-2-yloxy)ethyl]benzyl}piperazin-1-yl)prop-2-en-1-one hydrochloride $^1$H-NMR (DMSO-d$_6$) δ: 2.10 (3H, s), 3.11-3.18 (5H, m), 3.42-3.53 (3H, m), 4.33-4.36 (4H, m), 4.53-4.56 (2H, m), 5.24 (2H, s), 7.11-7.16 (2H, m), 7.29-7.35 (3H, m), 7.45-7.53 (6H, m), 7.62-7.69 (4H, m), 7.77-7.85 (7H, m), 10.64 (1H, brs).

Example 522

(E)-1-[4-(4-{2-[(6-Bromopyridin-3-yl)oxy]ethyl}benzyl)piperazin-1-yl]-3-{3-chloro-5-methyl-4-[(5-{[4-(trifluoromethyl)benzyl]oxy}pyridin-2-yl)oxy]phenyl}prop-2-en-1-one hydrochloride $^1$H-NMR (DMSO-d$_6$) δ: 2.11 (3H, s), 3.07-3.11 (5H, m), 3.36-3.54 (3H, m), 4.30-4.33 (4H, m), 4.52-4.54 (2H, m), 5.24 (2H, s), 7.12 (1H, d, J=8.8 Hz), 7.30 (1H, d, J=15.6 Hz), 7.39-7.55 (7H, m), 7.62-7.69 (4H, m), 7.77 (2H, d, J=8.3 Hz), 7.82 (1H, d, J=3.2 Hz), 7.85 (1H, s), 8.11 (1H, d, J=2.9 Hz), 10.70 (1H, brs).

Example 523

(E)-3-{3-Chloro-5-methyl-4-[(5-{[4-(trifluoromethyl)benzyl]oxy}pyridin-2-yl)oxy]phenyl}-1-(4-{4-[2-(4-ethoxyphenoxy)ethyl]benzyl}piperazin-1-yl)prop-2-en-1-one hydrochloride $^1$H-NMR (DMSO-d$_6$) δ: 1.28 (3H, t, J=7.1 Hz), 2.11 (3H, s), 3.01-3.15 (5H, m), 3.35-3.56 (3H, m), 3.93 (2H, q, J=7.1 Hz), 4.14 (2H, t, J=6.6 Hz), 4.33 (2H, brs), 4.52-4.56 (2H, m), 5.24 (2H, s), 6.81-6.86 (4H, m), 7.12 (1H, d, J=9.0 Hz), 7.30 (1H, d, J=15.4 Hz), 7.41-7.53 (5H, m), 7.63-7.69 (4H, m), 7.77 (2H, d, J=8.1 Hz), 7.83 (1H, d, J=3.2 Hz), 7.85 (1H, d, J=1.7 Hz), 10.93 (1H, brs).

Example 524

(E)-1-(4-{4-[2-(4-Acetylphenoxy)ethyl]benzyl}piperazin-1-yl)-3-[3-chloro-5-methyl-4-({5-[(4-methylbenzyl)oxy]pyridin-2-yl}oxy)phenyl]prop-2-en-1-one hydrochloride $^1$H-NMR (DMSO-d$_6$) δ: 2.10 (3H, s), 2.30 (3H, s), 2.50 (3H, s), 3.00-3.61 (8H, m), 4.30-4.34 (4H, m), 4.52-4.55 (2H, m), 5.05 (2H, s), 7.04 (2H, d, J=9.0 Hz), 7.09 (1H, d, J=9.0 Hz), 7.19 (2H, d, J=8.1 Hz), 7.28-7.34 (3H, m), 7.43-7.63 (7H, m), 7.79 (1H, d, J=2.9 Hz), 7.84-7.85 (1H, m), 7.91 (2H, d, J=8.8 Hz), 11.25 (1H, brs).

Example 525

4-{2-[4-({4-[(E)-3-{3-Chloro-5-methyl-4-[(5-{[4-(trifluoromethyl)benzyl]oxy}pyridin-2-yl)oxy]phenyl}prop-2-enoyl]piperazin-1-yl}methyl)phenyl]ethoxy}benzonitrile hydrochloride $^1$H-NMR (DMSO-d$_6$) δ: 2.11 (3H, s), 3.00-3.18 (5H, m), 3.42-3.60 (3H, m), 4.31-4.34 (4H, m), 4.52-4.56 (2H, m), 5.24 (2H, s), 7.11-7.14 (3H, m), 7.31 (1H, d, J=15.4 Hz), 7.43-7.55 (5H, m), 7.62-7.69 (4H, m), 7.75-7.79 (4H, m), 7.83 (1H, d, J=3.2 Hz), 7.85 (1H, s), 11.19 (1H, brs).

Example 526

(E)-3-{3-Chloro-5-methyl-4-[(5-{[4-(trifluoromethyl)benzyl]oxy}pyridin-2-yl)oxy]phenyl}-1-(4-{4-[2-(4-fluoro-3-methylphenoxy)ethyl]benzyl}piperazin-1-yl)prop-2-en-1-one hydrochloride $^1$H-NMR (DMSO-d$_6$) δ: 2.11 (3H, s), 2.19 (3H, d, J=1.7 Hz), 3.02-3.08 (5H, m), 3.39-3.56 (3H, m), 4.17 (2H, t, J=6.6 Hz), 4.34 (2H, brs), 4.52-4.55 (2H, m), 5.24 (2H, s), 6.72-6.76 (1H, m), 6.83-6.86 (1H, m), 7.02 (1H, t, J=9.2 Hz), 7.12 (1H, d, J=8.8 Hz), 7.30 (1H, d, J=15.4 Hz), 7.42-7.52 (5H, m), 7.64-7.68 (4H, m), 7.77 (2H, d, J=8.1 Hz), 7.82 (1H, d, J=2.9 Hz), 7.84 (1H, s), 10.83 (1H, brs).

Example 527

(E)-3-[3-Chloro-5-methyl-4-({5-[(4-nitrobenzyl)oxy]pyridin-2-yl}oxy)phenyl]-1-(4-{4-[2-(4-methylphenoxy)ethyl]benzyl}piperazin-1-yl)prop-2-en-1-one hydrochloride mp: 193.6-194.8° C.

$^1$H-NMR (DMSO-d$_6$) δ: 2.11 (3H, s), 2.22 (3H, s), 3.04-4.55 (14H, m), 5.29 (2H, s), 6.82 (2H, d, J=8.5 Hz), 7.07 (2H, d, J=8.3 Hz), 7.12 (1H, d, J=9.0 Hz), 7.29 (1H, d, J=15.4 Hz), 7.42 (2H, d, J=7.3 Hz), 7.47-7.51 (3H, m), 7.63-7.66 (2H, m), 7.73 (2H, d, J=8.5 Hz), 7.83-7.84 (2H, m), 8.27 (2H, d, J=8.5 Hz), 11.08 (1H, s).

Example 528

(E)-3-[3-Chloro-5-methyl-4-({5-[(4-nitrobenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride mp: 221.7-222.9° C.

$^1$H-NMR (DMSO-d$_6$) δ: 1.15 (6H, d, J=7.1 Hz), 2.10 (3H, s), 2.81 (1H, septet, J=6.8 Hz), 3.05-4.53 (14H, m), 5.29 (2H, s), 6.84 (2H, d, J=8.5 Hz), 7.12 (2H, d, J=9.3 Hz), 7.13 (1H, d, J=8.5 Hz), 7.29 (1H, d, J=15.4 Hz), 7.44-7.49 (5H, m), 7.63-7.66 (2H, m), 7.73 (2H, d, J=8.5 Hz), 7.83-7.84 (2H, m), 8.27 (2H, d, J=8.5 Hz), 10.61 (1H, brs).

Example 529

(E)-3-[3-Chloro-5-methyl-4-({5-[(2-nitrobenzyl)oxy]pyridin-2-yl}oxy)phenyl]-1-(4-{4-[2-(4-methylphenoxy)ethyl]benzyl}piperazin-1-yl)prop-2-en-1-one hydrochloride mp: 175.7-176.6° C.

$^1$H-NMR (DMSO-d$_6$) δ: 2.11 (3H, s), 2.22 (3H, s), 3.04-4.53 (14H, m), 5.47 (2H, s), 6.81 (2H, d, J=8.5 Hz), 7.07 (2H, d, J=8.3 Hz), 7.11 (1H, d, J=8.8 Hz), 7.29 (1H, d, J=15.4 Hz), 7.42-7.51 (5H, m), 7.62-7.66 (3H, m), 7.80-7.84 (4H, m), 8.13 (1H, d, J=8.1 Hz), 10.57 (1H, brs).

Example 530

(E)-3-[3-Chloro-5-methyl-4-({5-[(2-nitrobenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride mp: 182.3-184.5° C.

$^1$H-NMR (DMSO-d$_6$) δ: 1.15 (6H, d, J=6.8 Hz), 2.11 (3H, s), 2.81 (1H, qq, J=6.8, 6.8 Hz), 3.05-4.53 (14H, m), 5.47 (2H, s), 6.84 (2H, d, J=8.5 Hz), 7.11 (1H, d, J=8.5 Hz), 7.13 (2H, d, J=8.3 Hz), 7.29 (1H, d, J=15.4 Hz), 7.42-7.51 (5H, m), 7.63-7.66 (3H, m), 7.80-7.84 (4H, m), 8.13 (1H, d, J=8.1 Hz), 10.45 (1H, brs).

Example 531

(E)-3-[3-Chloro-5-methyl-4-({5-[(2-nitrobenzyl)oxy]pyridin-2-yl}oxy)phenyl]-1-(4-{4-[2-(4-methoxyphenoxy)ethyl]benzyl}piperazin-1-yl)prop-2-en-1-one hydrochloride mp: 156.6-159.1° C.
$^{1}$H-NMR (DMSO-d$_{6}$) δ: 2.11 (3H, s), 3.03-4.55 (17H, m), 5.47 (2H, s), 6.84 (2H, d, J=9.3 Hz), 6.87 (2H, d, J=9.5 Hz), 7.11 (1H, d, J=9.0 Hz), 7.30 (1H, d, J=15.4 Hz), 7.42 (2H, d, J=7.8 Hz), 7.49 (1H, d, J=15.6 Hz), 7.53 (2H, d, J=7.6 Hz), 7.62-7.66 (3H, m), 7.78-7.84 (4H, m), 8.13 (1H, d, J=8.3 Hz), 11.09 (1H, s).

Example 532

(E)-3-{3-Chloro-5-methyl-4-[(5-{[4-(trifluoromethyl)benzyl]oxy}pyridin-2-yl)oxy]phenyl}-1-[4-(4-{2-[(5-chloropyridin-2-yl)oxy]ethyl}benzyl)piperazin-1-yl]prop-2-en-1-one hydrochloride $^{1}$H-NMR (DMSO-d$_{6}$) δ: 2.11 (3H, s), 3.03-3.15 (5H, m), 3.34-3.57 (3H, m), 4.32 (2H, brs), 4.46-4.55 (4H, m), 5.24 (2H, s), 6.85 (1H, d, J=9.0 Hz), 7.12 (1H, d, J=8.8 Hz), 7.30 (1H, d, J=15.4 Hz), 7.41 (2H, d, J=7.6 Hz), 7.47-7.53 (3H, m), 7.62-7.69 (4H, m), 7.76-7.85 (5H, m), 8.21 (1H, d, J=2.7 Hz), 10.97 (1H, brs).

Example 533

(E)-3-[3-Chloro-4-({5-[(2-chlorobenzyl)oxy]pyridin-2-yl}oxy)-5-methylphenyl]-1-(4-{4-[1-(4-methylphenoxy)propan-2-yl]benzyl}piperazin-1-yl)prop-2-en-1-one hydrochloride $^{1}$H-NMR (DMSO-d$_{6}$) δ: 1.32 (3H, d, J=7.1 Hz), 2.11 (3H, s), 2.21 (3H, s), 3.06-3.59 (7H, m), 4.02 (1H, dd, J=9.5, 6.8 Hz), 4.07 (1H, dd, J=9.5, 6.8 Hz), 4.32 (2H, brs), 4.52-4.55 (2H, m), 5.17 (2H, s), 6.79 (2H, dt, J=9.2, 2.4 Hz), 7.06 (2H, d, J=8.1 Hz), 7.12 (1H, d, J=9.0 Hz), 7.30 (1H, d, J=15.4 Hz), 7.39-7.66 (11H, m), 7.84-7.85 (2H, m), 11.02 (1H, brs).

Example 534

(E)-3-[3-Chloro-5-methyl-4-({5-[(4-methylbenzyl)oxy]pyridin-2-yl}oxy)phenyl]-1-(4-{4-[2-(4-methylphenoxy)propyl]benzyl}piperazin-1-yl)prop-2-en-1-one hydrochloride $^{1}$H-NMR (DMSO-d$_{6}$) δ: 1.20 (3H, d, J=6.1 Hz), 2.10 (3H, s), 2.21 (3H, s), 2.30 (3H, s), 2.85-3.59 (6H, m), 2.87 (1H, dd, J=13.7, 5.6 Hz), 2.98 (1H, dd, J=13.7, 6.6 Hz), 4.31 (2H, brs), 4.51-4.54 (2H, m), 4.61-4.68 (1H, m), 5.05 (2H, s), 6.80 (2H, dt, J=9.0, 2.4 Hz), 7.05 (2H, d, J=8.1 Hz), 7.08 (1H, d, J=8.9 Hz), 7.20 (2H, d, J=7.8 Hz), 7.27-7.52 (8H, m), 7.59 (1H, dd, J=8.9, 3.1 Hz), 7.62 (1H, d, J=1.7 Hz), 7.79 (1H, d, J=3.1 Hz), 7.83 (1H, d, J=1.7 Hz), 11.14 (1H, brs).

Example 535

(E)-3-[3-Chloro-5-methyl-4-({5-[(4-methylbenzyl)oxy]pyridin-2-yl}oxy)phenyl]-1-(4-{4-[1-(4-methylphenoxy)propan-2-yl]benzyl}piperazin-1-yl)prop-2-en-1-one hydrochloride $^{1}$H-NMR (DMSO-d$_{6}$) δ: 1.32 (3H, d, J=7.1 Hz), 2.10 (3H, s), 2.21 (3H, s), 2.30 (3H, s), 3.06-3.56 (7H, m), 4.02 (1H, dd, J=9.6, 6.8 Hz), 4.07 (1H, dd, J=9.6, 7.0 Hz), 4.33 (2H, brs), 4.52-4.55 (2H, m), 5.05 (2H, s), 6.79 (2H, dt, J=9.3, 2.5 Hz), 7.05-7.10 (3H, m), 7.20 (2H, d, J=7.8 Hz), 7.29 (1H, d, J=15.6 Hz), 7.33 (2H, d, J=8.1 Hz), 7.43-7.53 (5H, m), 7.59 (1H, dd, J=8.9, 3.2 Hz), 7.62 (1H, d, J=1.7 Hz), 7.78 (1H, d, J=3.2 Hz), 7.84 (1H, d, J=1.7 Hz), 10.82 (1H, brs).

Example 536

(E)-3-{3-Chloro-5-methyl-4-[(5-{[4-(trifluoromethyl)benzyl]oxy}pyridin-2-yl)oxy]phenyl}-1-(4-{4-[2-(pyridin-2-yloxy)ethyl]benzyl}piperazin-1-yl)prop-2-en-1-one hydrochloride $^{1}$H-NMR (DMSO-d$_{6}$) δ: 2.11 (3H, s), 3.00-3.39 (7H, m), 3.63 (1H, brs), 4.32 (2H, brs), 4.48-4.55 (4H, m), 5.24 (2H, s), 6.81 (1H, d, J=8.3 Hz), 6.97-6.99 (1H, m), 7.12 (1H, d, J=9.0 Hz), 7.30 (1H, d, J=15.4 Hz), 7.39-7.56 (5H, m), 7.62-7.73 (5H, m), 7.77 (2H, d, J=8.3 Hz), 7.82-7.85 (2H, m), 8.16 (1H, dd, J=5.0, 1.3 Hz), 11.41 (1H, brs).

Example 537

(E)-3-{3-Chloro-5-methyl-4-[(5-{[4-(trifluoromethyl)benzyl]oxy}pyridin-2-yl)oxy]phenyl}-1-(4-{4-[2-(4-cyclopropylphenoxy)ethyl]benzyl}piperazin-1-yl)prop-2-en-1-one hydrochloride $^{1}$H-NMR (DMSO-d$_{6}$) δ: 0.53-0.57 (2H, m), 0.84-0.88 (2H, m), 1.80-1.87 (1H, m), 2.11 (3H, s), 3.00-3.07 (5H, m), 3.38-3.63 (3H, m), 4.17 (2H, t, J=6.6 Hz), 4.33 (2H, brs), 4.51-4.53 (2H, m), 5.24 (2H, s), 6.80-6.83 (2H, m), 6.97-6.99 (2H, m), 7.12 (1H, d, J=9.3 Hz), 7.30 (1H, d, J=15.4 Hz), 7.43-7.51 (5H, m), 7.62-7.68 (4H, m), 7.77 (2H, d, J=8.1 Hz), 7.83 (1H, d, J=2.7 Hz), 7.84 (1H, d, J=2.0 Hz), 10.87 (1H, brs).

Example 538

4-({[6-(2-Chloro-6-methyl-4-{(E)-3-oxo-3-[4-(4-{2-[4-(propan-2-yl)phenoxy]ethyl}benzyl)-piperazin-1-yl]prop-1-en-1-yl}phenoxy)pyridin-3-yl]oxy}methyl)benzonitrile hydrochloride mp: 219.4-221.0° C.

Example 539

4-{[(6-{2-Chloro-6-methyl-4-[(E)-3-(4-{4-[2-(4-methylphenoxy)ethyl]benzyl}piperazin-1-yl)-3-oxoprop-1-en-1-yl]phenoxy}pyridin-3-yl)oxy]methyl}benzonitrile hydrochloride $^{1}$H-NMR (DMSO-d$_{6}$) δ: 2.10 (3H, s), 2.22 (3H, s), 2.98-3.13 (5H, m), 3.35-3.41 (2H, m), 3.52-3.54 (1H, m), 4.17 (2H, t, J=6.6 Hz), 4.32-4.34 (2H, m), 4.53-4.55 (2H, m), 5.23 (2H, s), 6.81 (2H, d, J=8.3 Hz), 7.09 (3H, dd, J=18.9, 8.7 Hz), 7.29

(1H, d, J=15.1 Hz), 7.42-7.51 (5H, m), 7.62-7.66 (4H, m), 7.81-7.84 (2H, m), 7.88 (2H, d, J=8.3 Hz), 10.64 (1H, s).

Example 540

(E)-1-(4-{4-[2-(4-Bromophenoxy)ethyl]benzyl}piperazin-1-yl)-3-{3-chloro-5-methyl-4-[(5-({[4-(trifluoromethyl)benzyl]oxy}pyridin-2-yl)oxy]phenyl}prop-2-en-1-one hydrochloride $^1$H-NMR (DMSO-d$_6$) δ: 2.11 (3H, s), 3.01-3.08 (4H, m), 3.32-3.47 (3H, m), 3.58 (1H, brs), 4.21 (2H, t, J=6.6 Hz), 4.33 (2H, brs), 4.51-4.53 (2H, m), 5.24 (2H, s), 6.89-6.93 (2H, m), 7.12 (1H, d, J=9.0 Hz), 7.30 (1H, d, J=15.4 Hz), 7.42-7.53 (7H, m), 7.62-7.69 (4H, m), 7.77 (2H, d, J=8.1 Hz), 7.83 (1H, d, J=2.9 Hz), 7.84 (1H, d, J=2.0 Hz), 10.97 (1H, brs).

Example 541

[6-({5-[(2-Chlorobenzyl)oxy]pyridin-2-yl}oxy)naphthalen-2-yl][4-(4-{2-[4-(propan-2-yl)phenoxy]ethyl}benzyl)piperazin-1-yl]methanone hydrochloride mp: 198.1-199.8° C.

Example 542

[6-({5-[(2,3-Difluorobenzyl)oxy]pyridin-2-yl}oxy)naphthalen-2-yl][4-(4-{2-[4-(propan-2-yl)phenoxy]ethyl}benzyl)piperazin-1-yl]methanone hydrochloride $^1$H-NMR (DMSO-d$_6$) δ: 1.15 (6H, d, J=7.1 Hz), 2.81 (1H, septet, J=7.1 Hz), 3.05 (2H, t, J=6.7 Hz), 3.14-3.16 (2H, m), 3.24-3.70 (4H, m), 3.71-4.88 (2H, m), 4.17 (2H, t, J=6.6 Hz), 4.29-4.35 (2H, m), 5.26 (2H, s), 6.81-6.85 (2H, m), 7.10-7.15 (3H, m), 7.24-7.30 (1H, m), 7.36-7.55 (8H, m), 7.60 (1H, d, J=2.4 Hz), 7.68 (1H, dd, J=9.0, 3.2 Hz), 7.94 (1H, d, J=8.5 Hz), 8.00 (1H, dd, J=3.2, 0.5 Hz), 8.04 (2H, d, J=9.0 Hz), 10.83 (1H, brs).

Example 543

(E)-3-[4-({5-[(4-Methoxybenzyl)oxy]pyridin-2-yl}oxy)-3,5-dimethylphenyl]-1-(4-{4-[1-(4-methylphenoxy)propan-2-yl]benzyl}piperazin-1-yl)prop-2-en-1-one hydrochloride $^1$H-NMR (DMSO-d$_6$) δ: 1.32 (3H, d, J=7.1 Hz), 2.03 (6H, s), 2.21 (3H, s), 3.04-3.60 (7H, m), 3.75 (3H, s), 4.02 (1H, dd, J=9.5, 6.8 Hz), 4.07 (1H, dd, J=9.5, 6.8 Hz), 4.32 (2H, brs), 4.53 (2H, brs), 5.01 (2H, s), 6.79 (2H, dt, J=9.2, 2.4 Hz), 6.94 (2H, dt, J=9.2, 2.4 Hz), 6.99 (1H, d, J=9.1 Hz), 7.06 (2H, d, J=8.3 Hz), 7.19 (1H, d, J=15.4 Hz), 7.37 (2H, dt, J=9.1, 2.9 Hz), 7.42-7.50 (5H, m), 7.54-7.57 (3H, m), 7.78 (1H, d, J=2.9 Hz), 11.19 (1H, brs).

Example 544

(E)-3-[4-({5-[(4-Fluorobenzyl)oxy]pyridin-2-yl}oxy)-3,5-dimethylphenyl]-1-(4-{4-[1-(4-methylphenoxy)propan-2-yl]benzyl}piperazin-1-yl)prop-2-en-1-one hydrochloride $^1$H-NMR (DMSO-d$_6$) δ: 1.32 (3H, d, J=7.1 Hz), 2.03 (6H, s), 2.21 (3H, s), 3.03-3.60 (7H, m), 4.02 (1H, dd, J=9.4, 6.7 Hz), 4.07 (1H, dd, J=9.4, 6.7 Hz), 4.32 (2H, brs), 4.53 (2H, brs), 5.08 (2H, s), 6.79 (2H, dt, J=9.3, 2.5 Hz), 7.00 (1H, d, J=9.0 Hz), 7.06 (2H, d, J=8.1 Hz), 7.17-7.25 (3H, m), 7.42-7.60 (10H, m), 7.80 (1H, d, J=2.7 Hz), 11.15 (1H, brs).

Example 545

(E)-3-[3-Chloro-5-methyl-4-({5[(4-methylbenzyl)oxy]pyridin-2-yl}oxy)phenyl]-1-[4-(4-{2-[(5-methylpyridin-2-yl)oxy]ethyl}benzyl)piperazin-1-yl]prop-2-en-1-one hydrochloride $^1$H-NMR (DMSO-d$_6$) δ: 2.10 (3H, s), 2.20 (3H, s), 2.30 (3H, s), 3.01-3.08 (4H, m), 3.33-3.58 (4H, m), 4.32 (2H, brs), 4.44 (2H, t, J=6.8 Hz), 4.51-4.53 (2H, m), 5.06 (2H, s), 6.69 (1H, d, J=8.3 Hz), 7.09 (1H, d, J=9.0 Hz), 7.20 (2H, d, J=7.8 Hz), 7.27-7.34 (3H, m), 7.40 (2H, d, J=7.6 Hz), 7.47-7.53 (4H, m), 7.58-7.63 (2H, m), 7.79 (1H, d, J=3.2 Hz), 7.84 (1H, s), 7.96 (1H, s), 10.80 (1H, brs).

Example 546

(E)-3-[4-({5-[(2-Chlorobenzyl)oxy]pyridin-2-yl}oxy)-3,5-dimethylphenyl]-1-(4-{4-[2-(4-fluorophenoxy)ethyl]benzyl}piperazin-1-yl)prop-2-en-1-one hydrochloride mp: 196.3-196.9° C.

$^1$H-NMR (DMSO-d$_6$) δ: 2.04 (6H, s), 3.05-4.53 (14H, m), 5.16 (2H, s), 6.95 (2H, dd, J=7.3, 4.4 Hz), 7.02 (1H, d, J=9.0 Hz), 7.10 (2H, t, J=8.3 Hz), 7.19 (1H, d, J=15.4 Hz), 7.39-7.43 (4H, m), 7.46-7.53 (6H, m), 7.61-7.63 (2H, m), 7.84 (1H, brs), 11.24 (1H, brs).

Example 547

(E)-3-[3,5-Dimethyl-4-({5-[(4-methylbenzyl)oxy]pyridin-2-yl}oxy)phenyl]-1-(4-{4-[2-(4-methoxyphenoxy)ethyl]benzyl}piperazin-1-yl)prop-2-en-1-one hydrochloride mp: 212.1-212.5° C.

$^1$H-NMR (DMSO-d$_6$) δ: 2.03 (6H, s), 2.30 (3H, s), 3.03-4.53 (17H, m), 5.04 (2H, s), 6.82-6.88 (4H, m), 6.99 (1H, d, J=8.8 Hz), 7.17-7.20 (3H, m), 7.32 (2H, d, J=7.8 Hz), 7.42 (2H, d, J=7.6 Hz), 7.47 (2H, d, J=7.6 Hz), 7.49 (2H, d, J=7.6 Hz), 7.52 (1H, d, J=7.6 Hz), 7.55-7.58 (1H, m), 7.79 (1H, d, J=2.4 Hz), 10.90 (1H, s).

Example 548

(E)-3-[3,5-Dimethyl-4-({5-[(4-methylbenzyl)oxy]pyridin-2-yl}oxy)phenyl]-1-(4-{4-[2-(4-fluorophenoxy)ethyl]benzyl}piperazin-1-yl)prop-2-en-1-one hydrochloride mp: 221.1-221.5° C.

$^1$H-NMR (DMSO-d$_6$) δ: 2.03 (6H, s), 2.30 (3H, s), 3.05-4.53 (14H, m), 5.04 (2H, s), 6.94 (2H, dd, J=9.0, 4.4 Hz), 6.99 (1H, d, J=9.0 Hz), 7.10 (2H, t, J=8.8 Hz), 7.17-7.20 (3H, m), 7.32 (2H, d, J=7.8 Hz), 7.43 (2H, d, J=7.6 Hz), 7.47 (2H, d,

J=7.6 Hz), 7.49 (2H, d, J=7.6 Hz), 7.51-7.58 (3H, m), 7.79 (1H, d, J=2.9 Hz), 10.95 (1H, s).

Example 549

(E)-3-[4-({5-[(2-Chlorobenzyl)oxy]pyridin-2-yl}oxy)-3,5-dimethylphenyl]-1-(4-{4-[2-(4-methoxyphenoxy)ethyl]benzyl}piperazin-1-yl)prop-2-en-1-one hydrochloride mp: 172.6-173.8° C.
¹H-NMR (DMSO-d₆) δ: 2.04 (6H, s), 3.03-4.53 (17H, m), 5.16 (2H, s), 6.84 (2H, d, J=9.8 Hz), 6.87 (2H, d, J=9.8 Hz), 7.02 (1H, d, J=9.0 Hz), 7.19 (1H, d, J=15.4 Hz), 7.39-7.43 (4H, m), 7.46-7.55 (6H, m), 7.61-7.62 (2H, m), 7.84 (1H, d, J=2.2 Hz), 11.23 (1H, s).

Example 550

(E)-3-[3-Chloro-5-methyl-4-({5-[(4-methylbenzyl)oxy]pyridin-2-yl}oxy)phenyl]-1-[4-(4-{2-[(6-chloropyridin-3-yl)oxy]ethyl}benzyl)piperazin-1-yl]prop-2-en-1-one hydrochloride ¹H-NMR (DMSO-d₆) δ: 2.10 (3H, s), 2.30 (3H, s), 3.03-3.15 (5H, m), 3.30-3.48 (2H, m), 3.58 (1H, brs), 4.30-4.34 (4H, m), 4.52-4.55 (2H, m), 5.05 (2H, s), 7.09 (1H, d, J=9.0 Hz), 7.20 (2H, d, J=7.8 Hz), 7.27-7.34 (3H, m), 7.41-7.54 (7H, m), 7.59 (1H, dd, J=8.9, 3.1 Hz), 7.63 (1H, s), 7.79 (1H, d, J=3.2 Hz), 7.84 (1H, d, J=1.5 Hz), 8.11 (1H, d, J=3.2 Hz), 11.01 (1H, brs).

Example 551

(E)-3-[3-Chloro-4-({5-[(4-fluorobenzyl)oxy]pyridin-2-yl}oxy)phenyl]-1-(4-{4-[2-(4-fluorophenoxy)ethyl]benzyl}piperazin-1-yl)prop-2-en-1-one hydrochloride mp: 218.2-219.3° C.

Example 552

(E)-3-[3-Chloro-4-({5-[(4-fluorobenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrochloride mp: 179.6-180.7° C.

Example 553

(E)-3-[3-Chloro-4-({5-[(4-fluorobenzyl)oxy]pyridin-2-yl}oxy)phenyl]-1-(4-{4-[2-(4-methylphenoxy)ethyl]benzyl}piperazin-1-yl)prop-2-en-1-one hydrochloride mp: 211.1-212.3° C.

Example 554

(E)-3-[3-Chloro-5-methyl-4-({5-[(4-methylbenzyl)oxy]pyridin-2-yl}oxy)phenyl]-1-[4-(4-{2-[4-(propan-2-yloxy)phenoxy]ethyl}benzyl)piperazin-1-yl]prop-2-en-1-one hydrochloride mp: 187.3-189.2° C.
¹H-NMR (DMSO-d₆) δ: 1.21 (6H, d, J=5.9 Hz), 2.10 (3H, s), 2.30 (3H, s), 3.04-4.52 (14H, m), 5.05 (2H, s), 6.83 (4H, brs), 7.09 (1H, d, J=9.0 Hz), 7.20 (2H, d, J=7.8 Hz), 7.27-7.34 (3H, m), 7.42 (2H, d, J=7.8 Hz), 7.47-7.51 (3H, m), 7.59 (1H, dd, J=9.0, 2.9 Hz), 7.63 (1H, brs), 7.79 (1H, d, J=2.9 Hz), 7.84 (1H, brs), 10.83 (1H, brs).

Example 555

(E)-3-[3,5-Dimethyl-4-({5-[(4-methylbenzyl)oxy]pyridin-2-yl}oxy)phenyl]-1-[4-(4-{2-[4-(propan-2-yloxy)phenoxy]ethyl}benzyl)piperazin-1-yl]prop-2-en-1-one hydrochloride mp: 168.5-169.2° C.
¹H-NMR (DMSO-d₆) δ: 1.21 (6H, d, J=5.9 Hz), 2.03 (6H, s), 2.30 (3H, s), 3.04-4.52 (15H, m), 5.04 (2H, s), 6.83 (4H, brs), 6.99 (1H, d, J=8.8 Hz), 7.16-7.20 (3H, m), 7.32 (2H, d, J=7.6 Hz), 7.42 (2H, d, J=7.6 Hz), 7.46-7.57 (6H, m), 7.78 (1H, brs), 11.00 (1H, brs).

Example 556

(E)-3-[4-({5-[2-Chlorobenzyl)oxy]pyridin-2-yl}oxy)-3,5-dimethylphenyl]-1-[4-(4-{2-[4-(propan-2-yloxy)phenoxy]ethyl}benzyl)piperazin-1-yl]prop-2-en-1-one hydrochloride mp: 184.2-187.5° C.
¹H-NMR (DMSO-d₆) δ: 1.21 (6H, d, J=6.1 Hz), 2.04 (6H, s), 3.03-4.52 (15H, m), 5.16 (2H, s), 6.83 (4H, brs), 7.02 (1H, d, J=8.8 Hz), 7.19 (1H, d, J=15.4 Hz), 7.39-7.43 (4H, m), 7.46-7.51 (4H, m), 7.54 (2H, d, J=8.5 Hz), 7.60-7.63 (2H, m), 7.84 (1H, d, J=2.9 Hz), 11.23 (1H, brs).

Example 557

(E)-3-[3-Chloro-4-({5-[(2-chlorobenzyl)oxy]pyridin-2-yl}oxy)-5-methylphenyl]-1-[4-(4-{2-[4-(propan-2-yloxy)phenoxy]ethyl}benzyl)piperazin-1-yl]prop-2-en-1-one hydrochloride mp: 163.2-163.9° C.
¹H-NMR (DMSO-d₆) δ: 1.21 (6H, d, J=5.9 Hz), 2.11 (3H, s), 3.03-4.52 (15H, m), 5.17 (2H, s), 6.83 (4H, brs), 7.12 (1H, d, J=8.8 Hz), 7.30 (1H, d, J=15.4 Hz), 7.39-7.43 (4H, m), 7.47-7.53 (4H, m), 7.60-7.67 (3H, m), 7.84 (2H, brs), 11.02 (1H, brs).

Example 558

4-{[(6-{4-[(E)-3-(4-{4-[2-(4-Chlorophenoxy)ethyl]benzyl}piperazin-1-yl)-3-oxoprop-1-en-1-yl]-2,6-dimethylphenoxy}pyridin-3-yl)oxy]methyl}benzonitrile hydrochloride mp: 219.7-220.7° C.

Example 559

4-{[(6-{2-Chloro-4-[(E)-3-(4-{4-[2-(3-ethoxyphenoxy)ethyl]benzyl}piperazin-1-yl)-3-oxoprop-1-en-1-yl]phenoxy}pyridin-3-yl)oxy]methyl}benzonitrile hydrochloride mp: 217.3-219.0° C.

Example 560

4-{[(6-{2-Chloro-4-[(E)-3-(4-{4-[2-(3-methoxyphenoxy)ethyl]benzyl}piperazin-1-yl)-3-oxoprop-1-en-1-yl]phenoxy}pyridin-3-yl)oxy]methyl}benzonitrile hydrochloride mp: 186.1-187.6° C.

Example 561

(E)-3-[3-Chloro-4-({5-[(4-fluorobenzyl)oxy]pyridin-2-yl}oxy)phenyl]-1-(4-{4-[2-(3-ethoxyphenoxy)ethyl]benzyl}piperazin-1-yl)prop-2-en-1-one hydrochloride mp: 213.2-214.6° C.

Example 562

(E)-3-[3-Chloro-5-methyl-4-({5-[(4-methylbenzyl)oxy]pyridin-2-yl}oxy)phenyl]-1-[4-(4-{2-[(6-methylpyridin-3-yl)oxy]ethyl}benzyl)piperazin-1-yl]prop-2-en-1-one hydrochloride $^1$H-NMR (DMSO-$d_6$) δ: 2.10 (3H, s), 2.30 (3H, s), 2.59 (3H, s), 3.04-3.56 (8H, m), 4.32-4.43 (4H, m), 4.51-4.54 (2H, m), 5.06 (2H, s), 7.09 (1H, d, J=9.0 Hz), 7.20 (2H, d, J=7.6 Hz), 7.28-7.34 (3H, m), 7.43-7.49 (3H, m), 7.55-7.68 (5H, m), 7.79 (1H, d, J=2.9 Hz), 7.84 (1H, d, J=1.5 Hz), 7.95 (1H, brs), 8.45 (1H, s), 11.33 (1H, brs).

Example 563

(E)-1-[4-(4-{2-[(5-Bromopyridin-2-yl)oxy]ethyl}benzyl)piperazin-1-yl]-3-[3-chloro-5-methyl-4-({5-[(4-methylbenzyl)oxy]pyridin-2-yl}oxy)phenyl]prop-2-en-1-one hydrochloride $^1$H-NMR (DMSO-$d_6$) δ: 2.10 (3H, s), 2.30 (3H, s), 3.00-3.09 (4H, m), 3.38-3.47 (3H, m), 3.58 (1H, brs), 4.32 (2H, brs), 4.45-4.52 (4H, m), 5.06 (2H, s), 6.80 (1H, dd, J=8.8, 0.5 Hz), 7.09 (1H, d, J=8.8 Hz), 7.20 (2H, d, J=7.8 Hz), 7.28-7.34 (3H, m), 7.40 (2H, d, J=8.1 Hz), 7.47-7.53 (3H, m), 7.59 (1H, dd, J=8.9, 3.1 Hz), 7.63 (1H, s), 7.79 (1H, d, J=2.9 Hz), 7.84 (1H, d, J=2.0 Hz), 7.89 (1H, dd, J=8.8, 2.4 Hz), 8.28 (1H, dd, J=2.6, 0.6 Hz), 11.00 (1H, brs).

Example 564

(E)-3-[4-({5-[(3-Fluorobenzyl)oxy]pyridin-2-yl}oxy)-2-methylphenyl]-1-(4-{4-[2-(4-fluorophenoxy)ethyl]benzyl}piperazin-1-yl)prop-2-en-1-one hydrochloride mp: 209.6-210.0° C.

Example 565

(E)-1-(4-{4-[2-(4-Fluorophenoxy)ethyl]benzyl}piperazin-1-yl)-3-[2-methyl-4-({5-[(3-methylbenzyl)oxy]pyridin-2-yl}oxy)phenyl]prop-2-en-1-one hydrochloride mp: 194.2-195.2° C.

Example 566

(E)-1-(4-{4-[2-(4-Fluorophenoxy)ethyl]benzyl}piperazin-1-yl)-3-[4-({5-[(2-methoxybenzyl)oxy]pyridin-2-yl}oxy)-2-methylphenyl]prop-2-en-1-one hydrochloride mp: 182.8-182.9° C.

Example 567

4-{[(6-{4-[(E)-3-(4-{4-[2-(3,5-Dimethylphenoxy)ethyl]benzyl}piperazin-1-yl)-3-oxoprop-1-en-1-yl]-2,6-dimethylphenoxy}pyridin-3-yl)oxy]methyl}benzonitrile hydrochloride $^1$H-NMR (DMSO-$d_6$) δ: 2.03 (6H, s), 2.21 (6H, s), 3.04-3.06 (4H, m), 3.19-3.21 (1H, m), 3.33-3.36 (2H, m), 3.61-3.63 (1H, m), 4.16 (2H, t, J=6.6 Hz), 4.31-4.33 (2H, m), 4.51-4.54 (2H, m), 5.22 (2H, s), 6.54-6.55 (3H, m), 7.01 (1H, d, J=9.0 Hz), 7.19 (1H, d, J=15.4 Hz), 7.41-7.43 (2H, m), 7.47-7.49 (3H, m), 7.54-7.56 (2H, m), 7.60 (1H, dd, J=9.0, 3.2 Hz), 7.64 (2H, d, J=8.3 Hz), 7.82 (1H, d, J=2.9 Hz), 7.87 (2H, d, J=8.3 Hz), 11.37 (1H, brs).

Example 568

4-{[(6-{2,6-Dimethyl-4-[(E)-3-oxo-3-(4-{4-[2-(quinolin-6-yloxy)ethyl]benzyl}piperazin-1-yl)prop-1-en-1-yl]phenoxy}pyridin-3-yl)oxy]methyl)}benzonitrile hydrochloride $^1$H-NMR (DMSO-$d_6$) δ: 2.03 (6H, s), 3.02-3.04 (2H, m), 3.18-3.20 (3H, m), 3.32-3.35 (2H, m), 3.63-3.65 (1H, m), 4.31-4.34 (2H, m), 4.41 (21, t, J=6.6 Hz), 4.51-4.54 (2H, m), 5.22 (2H, s), 7.01 (1H, d, J=9.0 Hz), 7.19 (1H, d, J=15.4 Hz), 7.47-7.49 (5H, m), 7.56-7.65 (7H, m), 7.77 (1H, s), 7.82 (1H, d, J=2.9 Hz), 7.87 (2H, d, J=8.3 Hz), 8.12 (1H, d, J=8.3 Hz), 8.64 (1H, s), 8.94 (1H, s), 11.30 (1H, s).

Example 569

4-({[6-(2,6-Dimethoxy-4-{(E)-3-oxo-3-[4-(4-{2-[3-(propan-2-yl)phenoxy]ethyl}benzyl)-piperazin-1-yl]prop-1-en-1-yl}phenoxy)pyridin-3-yl]oxy}methyl)benzonitrile hydrochloride mp: 136.8-140.2° C.
$^1$H-NMR (DMSO-$d_6$) δ: 1.17 (6H, d, J=6.8 Hz), 2.80-2.87 (1H, m), 3.05-4.57 (20H, m), 5.22 (2H, s), 6.73-6.75 (1H, m), 6.77 (1H, s), 6.80 (1H, d, J=7.8 Hz), 6.93 (1H, d, J=9.0 Hz), 7.13 (2H, s), 7.18 (1H, t, J=7.8 Hz), 7.25 (1H, d, J=15.4 Hz), 7.43 (2H, d, J=7.8 Hz), 7.51-7.57 (4H, m), 7.64 (2H, d, J=8.1 Hz), 7.77 (1H, d, J=2.9 Hz), 7.87 (2H, d, J=8.3 Hz), 11.23 (1H, s).

Example 570

2-({[6-(2,6-Dimethoxy-4-{(E)-3-oxo-3-[4-(4-{2-[3-(propan-2-yl)phenoxy]ethyl}benzyl)-piperazin-1-yl]prop-1-en-1-yl}phenoxy)pyridin-3-yl]oxy}methyl)benzonitrile hydrochloride mp: 154.9-157.7° C.
$^1$H-NMR (DMSO-$d_6$) δ: 1.17 (6H, d, J=7.1 Hz), 2.80-2.87 (1H, m), 3.05-4.57 (20H, m), 5.24 (2H, s), 6.74 (1H, d, J=8.1 Hz), 6.77 (1H, s), 6.80 (1H, d, J=7.8 Hz), 6.95 (1H, d, J=9.0

Hz), 7.14 (2H, s), 7.18 (1H, t, J=7.8 Hz), 7.26 (1H, d, J=15.4 Hz), 7.43 (2H, d, J=7.8 Hz), 7.54-7.60 (5H, m), 7.72-7.78 (2H, m), 7.81 (1H, d, J=2.9 Hz), 7.92 (1H, d, J=7.8 Hz), 11.30 (1H, s).

Example 571

2-{[(6-{4-[(E)-3-(4-{4-[2-(4-Fluorophenoxy)ethyl]benzyl}piperazin-1-yl)-3-oxoprop-1-en-1-yl]-2,6-dimethoxyphenoxy}pyridin-3-yl)oxy]methyl}benzonitrile hydrochloride mp: 136.8-137.1° C.
$^{1}$H-NMR (DMSO-d$_{6}$) δ: 3.05-4.57 (20H, m), 5.24 (2H, s), 6.93-6.96 (3H, m), 7.10 (2H, t, J=8.8 Hz), 7.14 (2H, s), 7.26 (1H, d, J=15.4 Hz), 7.42 (2H, d, J=7.8 Hz), 7.54-7.61 (5H, m), 7.72-7.78 (2H, m), 7.81 (1H, d, J=2.9 Hz), 7.92 (1H, d, J=7.6 Hz), 11.29 (1H, s).

Example 572

4-{[(6-{4-[(E)-3-(4-{4-[2-(4-Fluorophenoxy)ethyl]benzyl}piperazin-1-yl)-3-oxoprop-1-en-1-yl]-2,6-dimethoxyphenoxy}pyridin-3-yl)oxy]methyl}benzonitrile hydrochloride mp: 142.0-143.6° C.
$^{1}$H-NMR (DMSO-d$_{6}$) δ: 3.05-4.57 (20H, m), 5.22 (2H, s), 6.92-6.96 (3H, m), 7.08-7.13 (4H, m), 7.25 (1H, d, J=15.4 Hz), 7.42 (2H, d, J=7.8 Hz), 7.51-7.57 (4H, m), 7.64 (2H, d, J=8.1 Hz), 7.77 (1H, d, J=2.9 Hz), 7.87 (2H, d, J=8.1 Hz), 11.31 (1H, s).

Example 573

(E)-3-[4-({5-[(2-Chloro-4-fluorobenzyl)oxy]pyridin-2-yl}oxy)-3,5-dimethylphenyl]-1-(4-{4-[2-(4-chlorophenoxy)ethyl]benzyl}piperazin-1-yl)prop-2-en-1-one hydrochloride mp: 178.3-180.6° C.

Example 574

(E)-1-(4-{4-[2-(3,4-Dimethylphenoxy)ethyl]benzyl}piperazin-1-yl)-3-(3,5-dimethyl-4-{[5-(pyridin-4-ylmethoxy)pyridin-2-yl]oxy}phenyl)prop-2-en-1-one hydrochloride mp: 186.7-189.5° C.

Example 575

(E)-3-[4-({5-[(3-Chlorobenzyl)oxy]pyridin-2-yl}oxy)-3,5-dimethylphenyl]-1-(4-{4-[2-(4-chlorophenoxy)ethyl]benzyl}piperazin-1-yl)prop-2-en-1-one hydrochloride mp: 186.9-189.4° C.

Example 576

(E)-3-[3-Chloro-5-methyl-4-({5-[(4-methylbenzyl)oxy]pyridin-2-yl}oxy)phenyl]-1-(4-{3-methyl-4-[2-(4-methylphenoxy)ethyl]benzyl}piperazin-1-yl)prop-2-en-1-one hydrochloride $^{1}$H-NMR (DMSO-d$_{6}$) δ: 2.10 (3H, s), 2.22 (3H, s), 2.30 (3H, s), 2.35 (3H, s), 3.00-3.58 (6H, m), 3.05 (2H, t, J=6.8 Hz), 4.15 (2H, t, J=6.8 Hz), 4.28 (2H, brs), 4.52-4.55 (2H, m), 5.06 (2H, s), 6.82 (2H, dt, J=9.2, 2.6 Hz), 7.06-7.10 (3H, m), 7.20 (2H, d, J=7.6 Hz), 7.28-7.39 (6H, m), 7.49 (1H, d, J=15.4 Hz), 7.59 (1H, dd, J=8.9, 3.2 Hz), 7.63 (1H, d, J=2.0 Hz), 7.79 (1H, dd, J=3.2, 0.5 Hz), 7.84 (1H, d, J=2.0 Hz), 10.99 (1H, brs).

Example 577

(E)-3-[4-({5-[(4-Fluorobenzyl)oxy]pyridin-2-yl}oxy)-3,5-dimethylphenyl]-1-(4-{3-methyl-4-[2-(4-methylphenoxy)ethyl]benzyl}piperazin-1-yl)prop-2-en-1-one hydrochloride $^{1}$H-NMR (DMSO-d$_{6}$) δ: 2.03 (6H, s), 2.22 (3H, s), 2.35 (3H, s), 3.00-3.57 (6H, m), 3.05 (2H, t, J=6.8 Hz), 4.15 (2H, t, J=6.8 Hz), 4.28 (2H, brs), 4.53 (2H, brs), 5.08 (2H, s), 6.82 (2H, dt, J=9.3, 2.6 Hz), 7.00 (1H, dd, J=9.0, 0.5 Hz), 7.06-7.08 (2H, m), 7.17-7.25 (3H, m), 7.33-7.39 (3H, m), 7.46-7.52 (5H, m), 7.58 (1H, dd, J=9.0, 3.2 Hz), 7.80 (1H, dd, J=3.2, 0.5 Hz), 10.96 (1H, brs).

Example 578

(E)-3-(3,5-Dimethyl-4-{[5-(pyridin-4-ylmethoxy)pyridin-2-yl]oxy}phenyl)-1-[4-(4-{2-[4-methylbenzyl)oxy]ethyl}benzyl)piperazin-1-yl]prop-2-en-1-one hydrochloride $^{1}$H-NMR (DMSO-d$_{6}$) δ: 2.04 (6H, s), 2.28 (3H, s), 2.88 (2H, t, J=6.6 Hz), 3.01-3.03 (2H, m), 3.30-3.32 (3H, m), 3.63-3.65 (3H, m), 4.29-4.32 (2H, m), 4.44 (2H, s), 4.50-4.52 (2H, m), 5.44 (2H, s), 7.06 (1H, d, J=9.0 Hz), 7.14-7.20 (5H, m), 7.33 (2H, d, J=7.8 Hz), 7.46-7.50 (3H, m), 7.54 (2H, d, J=8.1 Hz), 7.66 (1H, dd, J=9.0, 3.2 Hz), 7.87 (1H, d, J=2.9 Hz), 7.98 (2H, d, J=6.1 Hz), 8.88 (2H, d, J=6.1 Hz), 11.67 (1H, s).

Example 579

(E)-1-(4-{4-[2-(3-Chlorophenoxy)ethyl]benzyl}piperazin-1-yl)-3-(3,5-dimethyl-4-{[5-(pyridin-4-ylmethoxy)pyridin-2-yl]oxy}phenyl)prop-2-en-1-one hydrochloride $^{1}$H-NMR (DMSO-d$_{6}$) δ: 2.04 (6H, s), 3.06-3.08 (4H, m), 3.31-3.33 (3H, m), 3.64-3.66 (1H, m), 4.25 (2H, t, J=6.6 Hz), 4.30-4.33 (2H, m), 4.51-4.53 (2H, m), 5.44 (2H, s), 6.92 (1H, dd, J=8.3, 1.7 Hz), 6.98-7.08 (3H, m), 7.20 (1H, d, J=15.4 Hz), 7.29 (1H, t, J=8.1 Hz), 7.43-7.48 (5H, m), 7.57 (2H, d, J=8.1 Hz), 7.65 (1H, dd, J=8.9, 3.1 Hz), 7.87 (1H, d, J=2.9 Hz), 7.96 (2H, d, J=6.1 Hz), 8.87 (2H, d, J=6.3 Hz), 11.63 (1H, s).

Example 580

(E)-3-(3,5-Dimethyl-4-{[5-(pyridin-4-ylmethoxy)pyridin-2-yl]oxy}phenyl)-1-[4-(4-{2-[(4-fluorobenzyl)oxy]ethyl}benzyl)piperazin-1-yl]prop-2-en-1-one hydrochloride $^{1}$H-NMR (DMSO-d$_{6}$) δ: 2.04 (6H, s), 2.90 (2H, t, J=6.6 Hz), 2.94-3.01 (2H, m), 3.16-3.19 (1H, m), 3.31-3.34 (2H, m), 3.61-3.68 (3H, m), 4.30-4.32 (2H, m), 4.47 (2H, s), 4.50-4.53 (2H, m), 5.40 (2H, s), 7.05 (1H, d, J=9.0 Hz), 7.15-7.20

(3H, m), 7.30-7.35 (4H, m), 7.48-7.51 (5H, m), 7.64 (1H, dd, J=9.0, 2.9 Hz), 7.86-7.89 (3H, m), 8.82-8.85 (2H, m), 11.23 (1H, s).

Example 581

(E)-1-[4-(4-{2-[(4-Chlorobenzyl)oxy]ethyl}benzyl)piperazin-1-yl]-3-(3,5-dimethyl-4-{[5-(pyridin-4-ylmethoxy)pyridin-2-yl]oxy}phenyl)prop-2-en-1-one hydrochloride $^1$H-NMR (DMSO-d$_6$) δ: 2.04 (6H, s), 2.90 (2H, t, J=6.5 Hz), 3.01-3.03 (2H, m), 3.17-3.19 (1H, m), 3.31-3.34 (2H, m), 3.61-3.69 (3H, m), 4.30-4.32 (2H, m), 4.47-4.55 (4H, m), 5.40 (2H, s), 7.05 (1H, d, J=8.8 Hz), 7.19 (1H, d, J=15.4 Hz), 7.28-7.52 (11H, m), 7.64 (1H, dd, J=9.0, 2.9 Hz), 7.86-7.89 (3H, m), 8.83 (2H, d, J=5.9 Hz), 11.20 (1H, s).

Example 582

(E)-1-(4-{4-[2-(2-Chlorophenoxy)ethyl]benzyl}piperazin-1-yl)-3-[3,5-dimethyl-4-({5-[(6-methylpyridin-2-yl)methoxy]pyridin-2-yl}oxy)phenyl]prop-2-en-1-one hydrochloride $^1$H-NMR (DMSO-d$_6$) δ: 2.04 (6H, s), 2.63 (3H, s), 3.01-3.04 (2H, m), 3.11 (2H, t, J=6.5 Hz), 3.19-3.21 (1H, m), 3.33-3.35 (2H, m), 3.60-3.62 (1H, m), 4.28-4.31 (4H, m), 4.51-4.53 (2H, m), 5.30 (2H, s), 6.94 (1H, t, J=7.1 Hz), 7.04 (1H, d, J=9.0 Hz), 7.17-7.20 (2H, m), 7.26-7.30 (1H, m), 7.40 (1H, dd, J=7.9, 1.3 Hz), 7.46-7.48 (5H, m), 7.55-7.57 (3H, m), 7.65 (2H, dd, J=8.9, 3.1 Hz), 7.85 (1H, d, J=2.9 Hz), 8.10 (1H, s), 11.39 (1H, s).

Example 583

(E)-3-[3-Chloro-5-methyl-4-({5-[(4-methylbenzyl)oxy]pyridin-2-yl}oxy)phenyl]-1-[4-(4-{2-[(6-methoxypyridin-3-yl)oxy]ethyl}benzyl)piperazin-1-yl]prop-2-en-1-one hydrochloride $^1$H-NMR (DMSO-d$_6$) δ: 2.10 (3H, s), 2.30 (3H, s), 3.00-3.17 (5H, m), 3.34-3.47 (2H, m), 3.57 (1H, brs), 3.78 (3H, s), 4.23 (2H, t, J=6.6 Hz), 4.33 (2H, brs), 4.51-4.53 (2H, m), 5.06 (2H, s), 6.75 (1H, d, J=8.8 Hz), 7.09 (1H, d, J=9.0 Hz), 7.20 (2H, d, J=7.8 Hz), 7.27-7.32 (3H, m), 7.38 (1H, dd, J=9.0, 3.2 Hz), 7.42-7.53 (5H, m), 7.59 (1H, dd, J=8.9, 3.1 Hz), 7.63 (1H, s), 7.79 (1H, d, J=3.2 Hz), 7.84-7.85 (2H, m), 10.92 (1H, brs).

Example 584

(E)-3-(4-{[5-(1,3-Benzothiazol-6-ylmethoxy)pyridin-2-yl]oxy}-3,5-dimethoxyphenyl)-1-(4-{4-[2-(4-fluorophenoxy)ethyl]benzyl}piperazin-1-yl)prop-2-en-1-one hydrochloride mp: 133.1-134.4° C.
$^1$H-NMR (DMSO-d$_6$) δ: 3.05-4.57 (20H, m), 5.26 (2H, s), 6.92-6.96 (3H, m), 7.10 (2H, t, J=8.8 Hz), 7.12 (2H, s), 7.25 (1H, d, J=15.4 Hz), 7.43 (2H, d, J=7.6 Hz), 7.53-7.57 (4H, m), 7.61 (1H, d, J=8.3 Hz), 7.80 (1H, d, J=2.9 Hz), 8.10 (1H, d, J=8.3 Hz), 8.26 (1H, s), 9.41 (1H, s), 11.12 (1H, s).

Example 585

(E)-3-(4-{[5-(1,3-Benzothiazol-6-ylmethoxy)pyridin-2-yl]oxy}-3,5-dimethoxyphenyl)-1-[4-(4-{2-[4-(propan-2-yloxy)phenoxy]ethyl}benzyl)piperazin-1-yl]prop-2-en-1-one hydrochloride mp: 133.4-135.1° C.
$^1$H-NMR (DMSO-d$_6$) δ: 1.21 (6H, d, J=5.9 Hz), 3.03-4.57 (2H, m), 5.26 (2H, s), 6.82 (2H, d, J=9.8 Hz), 6.84 (2H, d, J=9.8 Hz), 6.92 (1H, d, J=9.0 Hz), 7.13 (2H, s), 7.25 (1H, d, J=15.4 Hz), 7.42 (2H, d, J=7.8 Hz), 7.53-7.57 (4H, m), 7.62 (1H, d, J=7.3 Hz), 7.80 (1H, d, J=2.9 Hz), 8.10 (1H, d, J=8.3 Hz), 8.26 (1H, s), 9.41 (1H, s), 11.23 (1H, s).

Example 586

(E)-3-[4-({5-[(4-Fluorobenzyl)oxy]pyridin-2-yl}oxy)-3,5-dimethylphenyl]-1-(4-{4-[2-(4-fluorophenoxy)ethyl]-3-methylbenzyl}piperazin-1-yl)prop-2-en-1-one hydrochloride $^1$H-NMR (DMSO-d$_6$) δ: 2.03 (6H, s), 2.36 (3H, s), 3.04-3.57 (6H, m), 3.06 (2H, t, J=6.8 Hz), 4.17 (2H, t, J=6.8 Hz), 4.28 (2H, brs), 4.53 (2H, brs), 5.08 (2H, s), 6.92-6.97 (2H, m), 7.00 (1H, d, J=8.9 Hz), 7.07-7.14 (2H, m), 7.17-7.25 (3H, m), 7.36-7.38 (3H, m), 7.46-7.52 (5H, m), 7.58 (1H, dd, J=8.9, 3.1 Hz), 7.80 (1H, d, J=3.1 Hz), 10.91 (1H, brs).

Example 587

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]-3-methylbenzyl}piperazin-1-yl)prop-2-en-1-one hydrochloride $^1$H-NMR (DMSO-d$_6$) δ: 2.10 (3H, s), 2.30 (3H, s), 2.36 (3H, s), 3.06 (2H, t, J=6.8 Hz), 3.06-3.55 (6H, m), 4.17 (2H, t, J=6.8 Hz), 4.29 (2H, brs), 4.52-4.56 (2H, m), 5.05 (2H, s), 6.92-6.97 (2H, m), 7.08-7.14 (3H, m), 7.20 (2H, d, J=7.8 Hz), 7.28-7.37 (6H, m), 7.49 (1H, d, J=15.4 Hz), 7.59 (1H, dd, J=8.9, 3.1 Hz), 7.63 (1H, d, J=1.7 Hz), 7.79 (1H, d, J=3.1 Hz), 7.84 (1H, d, J=1.7 Hz), 10.81 (1H, brs).

Example 588

(E)-1-[4-(4-{2-[(6-Chloro-1,3-benzoxazol-2-yl)oxy]ethyl}benzyl)piperazin-1-yl]-3-[3-chloro-5-methyl-4-({5-[(4-methylbenzyl)oxy]pyridin-2-yl}oxy)phenyl]prop-2-en-1-one hydrochloride $^1$H-NMR (DMSO-d$_6$) δ: 2.10 (3H, s), 2.30 (3H, s), 3.03-3.37 (6H, m), 3.41-3.56 (2H, m), 4.09 (2H, t, J=6.8 Hz), 4.30 (2H, brs), 4.50-4.53 (2H, m), 5.05 (2H, s), 7.09 (1H, d, J=9.3 Hz), 7.17-7.22 (4H, m), 7.29-7.33 (5H, m), 7.45-7.51 (4H, m), 7.59 (1H, dd, J=9.0, 3.2 Hz), 7.63 (1H, d, J=2.0 Hz), 7.79 (1H, d, J=2.7 Hz), 7.84 (1H, d, J=2.0 Hz), 10.87 (1H, brs).

Example 589

(E)-1-(4-{4-[2-(4-tert-Butylphenoxy)ethyl]benzyl}piperazin-1-yl)-3-[4-({5-[(3,4-difluorobenzyl)oxy]pyridin-2-yl}oxy)-3-fluorophenyl]prop-2-en-1-one hydrochloride $^1$H-NMR (DMSO-d$_6$) δ: 1.24 (9H, d, J=3.9 Hz), 2.90-3.45 (7H, m), 3.52 (1H, s), 4.18 (2H, t, J=6.6 Hz), 4.33 (2H, brs), 4.53 (2H, brs), 5.12 (2H, s), 6.82-6.86 (2H, m), 7.13 (1H, d, J=9.3 Hz), 7.26-7.33 (5H, m), 7.43-7.57 (8H, m), 7.63 (1H, dd, J=8.9, 3.1 Hz), 7.83 (1H, dd, J=12.0, 2.0 Hz), 7.87 (1H, d, J=2.4 Hz), 10.58 (1H, brs).

Example 590

4-({[6-(2,6-Dimethyl-4-{(E)-3-[4-(4-{2-[(6-methylpyridin-2-yl)oxy]ethyl}benzyl)piperazin-1-yl]-3-oxoprop-1-en-1-yl}phenoxy)pyridin-3-yl]oxy}methyl)benzonitrile hydrochloride $^1$H-NMR (DMSO-$d_6$) δ: 2.03 (6H, s), 2.37 (3H, s), 3.05-3.07 (4H, m), 3.15-3.18 (1H, m), 3.34-3.36 (2H, m), 3.58-3.60 (1H, m), 4.31-4.34 (2H, m), 4.45 (2H, t, J=6.7 Hz), 4.51-4.54 (2H, m), 5.22 (2H, s), 6.57 (1H, d, J=8.1 Hz), 6.82 (1H, d, J=7.1 Hz), 7.01 (1H, d, J=9.0 Hz), 7.19 (1H, d, J=15.4 Hz), 7.41 (2H, d, J=7.6 Hz), 7.51-7.61 (9H, m), 7.82 (1H, d, J=2.9 Hz), 7.87 (2H, d, J=8.1 Hz), 11.14 (1H, s).

Example 591

(E)-3-[3-Chloro-4-({5-[(2-chlorobenzyl)oxy]pyridin-2-yl}oxy)-5-methylphenyl]-1-(4-{4-[(4-methylphenoxy)acetyl]benzyl}piperazin-1-yl)prop-2-en-1-one hydrochloride $^1$H-NMR (DMSO-$d_6$) δ: 2.12 (3H, s), 2.23 (3H, s), 2.90-3.70 (7H, m), 4.47-4.54 (3H, m), 5.17 (2H, s), 5.53 (2H, s), 6.84-6.88 (2H, m), 7.07-7.13 (3H, m), 7.31 (1H, d, J=15.4 Hz), 7.37-7.44 (2H, m), 7.48-7.54 (2H, m), 7.60-7.67 (3H, m), 7.77 (2H, d, J=5.9 Hz), 7.84-7.86 (2H, m), 8.11 (2H, d, J=8.1 Hz), 11.07 (1H, brs).

Example 592

(E)-1-(4-{4-[2-(4-Fluorophenoxy)ethyl]-3-methylbenzyl}piperazin-1-yl)-3-[4-({5-[(4-methoxybenzyl)oxy]pyridin-2-yl}oxy)-3,5-dimethylphenyl]prop-2-en-1-one hydrochloride $^1$H-NMR (DMSO-$d_6$) δ: 2.03 (6H, s), 2.36 (3H, s), 3.06 (2H, t, J=6.8 Hz), 3.06-3.51 (6H, m), 3.75 (3H, s), 4.17 (2H, t, J=6.8 Hz), 4.28 (2H, brs), 4.53 (2H, brs), 5.01 (2H, s), 6.92-7.00 (5H, m), 7.07-7.14 (2H, m), 7.19 (1H, d, J=15.4 Hz), 7.35-7.38 (5H, m), 7.46-7.50 (3H, m), 7.56 (1H, dd, J=9.0, 3.2 Hz), 7.78 (1H, d, J=3.2 Hz), 10.82 (1H, brs).

Example 593

4-({[6-(2-Fluoro-4-{(E)-3-oxo-3-[4-(4-{2-[4-(propan-2-yl)phenoxy]ethyl}benzyl)piperazin-1-yl]prop-1-en-1-yl}phenoxy)pyridin-3-yl]oxy}methyl)benzonitrile hydrochloride $^1$H-NMR (DMSO-$d_6$) δ: 1.15 (6H, d, J=6.8 Hz), 2.81 (1H, septet, J=7.1 Hz), 2.90-3.65 (8H, m), 4.18 (2H, t, J=6.7 Hz), 4.33 (2H, brs), 4.53 (2H, brs), 5.26 (2H, s), 6.82-6.86 (2H, m), 7.11-7.15 (3H, m), 7.27-7.32 (2H, m), 7.42-7.58 (6H, m), 7.62-7.66 (3H, m), 7.83 (1H, dd, J=12.2, 2.0 Hz), 7.87-7.89 (3H, m), 10.71 (1H, brs).

Example 594

(E)-3-(3,5-Dimethyl-4-{[5-(1,3-thiazol-5-yl-methoxy)pyridin-2-yl]oxy}phenyl)-1-(4-{4-[2-(3-ethoxyphenoxy)ethyl]benzyl}piperazin-1-yl)prop-2-en-1-one hydrochloride mp: 190.4-191.8° C.

Example 595

(E)-3-(3,5-Dimethyl-4-{[5-(1,3-thiazol-5-yl-methoxy)pyridin-2-yl]oxy}phenyl)-1-[4-(4-{2-[4-(propan-2-yl)phenoxy]ethyl}benzyl)piperazin-1-yl]prop-2-en-1-one hydrochloride mp: 199.2-200.9° C.

Example 596

(E)-3-(3,5-Dimethyl-4-{[5-(1,3-thiazol-5-yl-methoxy)pyridin-2-yl]oxy}phenyl)-1-(4-{4-[2-(4-methylphenoxy)ethyl]benzyl}piperazin-1-yl)prop-2-en-1-one hydrochloride mp: 207.0-207.2° C.

Example 597

(E)-3-(3,5-Dimethyl-4-{[5-(1,3-thiazol-5-yl-methoxy)pyridin-2-yl]oxy}phenyl)-1-(4-{4-[2-(4-fluorophenoxy)ethyl]benzyl}piperazin-1-yl)prop-2-en-1-one hydrochloride mp: 216.7-216.9° C.

Example 598

(E)-3-(3,5-Dimethyl-4-{[5-(1,3-thiazol-5-yl-methoxy)pyridin-2-yl]oxy}phenyl)-1-[4-(4-{2-[4-(propan-2-yloxy)phenoxy]ethyl}benzyl)piperazin-1-yl]prop-2-en-1-one hydrochloride mp: 177.7-178.6° C.

Example 599

(E)-3-(3,5-Dimethyl-4-{[5-(1,3-thiazol-4-yl-methoxy)pyridin-2-yl]oxy}phenyl)-1-(4-{4-[2-(4-fluorophenoxy)ethyl]benzyl}piperazin-1-yl)prop-2-en-1-one hydrochloride $^1$H-NMR (DMSO-$d_6$) δ: 2.03 (6H, s), 3.04-3.58 (8H, m), 4.19 (2H, t, J=6.8 Hz), 4.32 (2H, brs), 4.52 (2H, brs), 5.22 (2H, s), 6.91-6.97 (2H, m), 7.00 (1H, d, J=9.0 Hz), 7.07-7.14 (2H, m), 7.19 (1H, d, J=15.4 Hz), 7.41-7.56 (7H, m), 7.62 (1H, dd, J=9.0, 3.2 Hz), 7.81 (1H, d, J=2.0 Hz), 7.83 (1H, d, J=3.2 Hz), 8.13 (1H, d, J=2.0 Hz), 10.97 (1H, brs).

Example 600

(E)-3-(3,5-Dimethyl-4-{[5-(1,3-thiazol-4-yl-methoxy)pyridin-2-yl]oxy}phenyl)-1-[4-(4-{2-[4-(propan-2-yl)phenoxy]ethyl}benzyl)piperazin-1-yl]prop-2-en-1-one hydrochloride $^1$H-NMR (DMSO-$d_6$) δ: 1.15 (6H, d, J=6.8 Hz), 2.03 (6H, s), 2.81 (1H, septet, J=6.8 Hz), 3.04-3.60 (8H, m), 4.17 (2H, t, J=6.8 Hz), 4.32 (2H, brs), 4.52 (2H, brs), 5.22 (2H, s), 6.82-6.87 (2H, m), 7.00 (1H, d, J=9.0 Hz), 7.11-7.15 (2H, m), 7.19 (1H, d, J=15.4 Hz), 7.41-7.55 (7H, m), 7.62 (1H, dd, J=8.8, 3.2 Hz), 7.81 (1H, d, J=2.0 Hz), 7.84 (1H, d, J=3.2 Hz), 9.13 (1H, d, J=2.0 Hz), 11.16 (1H, brs).

Example 601

(E)-3-(3,5-Dimethyl-4-{[5-(1,3-thiazol-4-yl-methoxy)pyridin-2-yl]oxy}phenyl)-1-(4-{2-[2-(4-methylphenoxy)ethyl]benzyl}piperazin-1-yl)prop-2-en-1-one hydrochloride $^1$H-NMR (DSMO-d$_6$) δ: 2.03 (6H, s), 2.21 (3H, s), 3.03-3.61 (8H, m), 4.16 (2H, t, J=6.8 Hz), 4.32 (2H, brs), 4.52 (2H, brs), 5.22 (2H, s), 6.79-6.84 (2H, m), 7.00 (1H, d, J=8.8 Hz), 7.06 (2H, d, J=8.3 Hz), 7.14 (1H, d, J=15.6 Hz), 7.40-7.56 (7H, m), 7.62 (1H, dd, J=8.8, 2.9 Hz), 7.81 (1H, d, J=2.0 Hz), 7.84 (1H, d, J=2.9 Hz), 9.13 (1H, d, J=2.0 Hz), 11.25 (1H, brs).

Example 602

(E)-1-(4-{4-[2-(1,3-Benzothiazol-2-yloxy)ethyl]benzyl}piperazin-1-yl)-3-[3-chloro-5-methyl-4-({5-[(4-methylbenzyl)oxy]pyridin-2-yl}oxy)phenyl]prop-2-en-1-one hydrochloride $^1$H-NMR (DMSO-d$_6$) δ: 2.11 (3H, s), 2.30 (3H, s), 2.95-3.03 (4H, m), 3.17-3.58 (4H, m), 4.20 (2H, t, J=7.1 Hz), 4.29 (2H, brs), 4.52 (2H, brs), 5.05 (2H, s), 7.09 (1H, d, J=9.0 Hz), 7.15-7.21 (3H, m), 7.28-7.34 (7H, m), 7.44-7.46 (2H, m), 7.50 (1H, d, J=15.4 Hz), 7.58-7.64 (3H, m), 7.79 (1H, d, J=3.2 Hz), 7.85 (1H, d, J=2.0 Hz), 10.97 (1H, brs).

Example 603

(E)-3-[3-Chloro-5-methyl-4-({5-[(4-methylbenzyl)oxy]pyridin-2-yl}oxy)phenyl]-1-[4-(4-{2-[(2-methyl-1,3-benzothiazol-5-yl)oxy]ethyl}benzyl)piperazin-1-yl]prop-2-en-1-one hydrochloride $^1$H-NMR (DMSO-d$_6$) δ: 2.10 (3H, s), 2.30 (3H, s), 2.76 (3H, s), 3.11-3.13 (5H, m), 3.36-3.57 (3H, m), 4.29-4.33 (4H, m), 4.52-4.55 (2H, m), 5.05 (2H, s), 7.02 (1H, dd, J=8.7, 2.6 Hz), 7.09 (1H, d, J=9.0 Hz), 7.20 (2H, d, J=7.8 Hz), 7.28-7.34 (3H, m), 7.45-7.55 (6H, m), 7.59 (1H, dd, J=8.9, 3.1 Hz), 7.63 (1H, s), 7.79 (1H, d, J=3.2 Hz), 7.84 (1H, d, J=1.7 Hz), 7.87 (1H, d, J=8.8 Hz), 10.98 (1H, brs).

Example 604

(E)-3-[3-Chloro-5-methyl-4-({5-[(4-methylbenzyl)oxy]pyridin-2-yl}oxy)phenyl]-1-{(3S)-3-[methyl(4-{2-[4-(propan-2-yl)phenoxy]ethyl}benzyl)amino]pyrrolidin-1-yl}prop-2-en-1-one hydrochloride $^1$H-NMR (DMSO-d$_6$) δ: 1.15 (6H, d, J=7.1 Hz), 2.11 (3H, s), 2.30 (3H, s), 2.33-2.47 (2H, m), 2.61 (3H, s), 2.78-2.85 (1H, m), 3.07 (2H, t, J=6.7 Hz), 3.35-3.44 (1H, m), 3.72-3.99 (4H, m), 4.16-4.20 (3H, m), 4.42-4.49 (1H, m), 5.05 (2H, s), 6.84-6.85 (2H, m), 7.05-7.12 (4H, m), 7.20 (2H, d, J=7.8 Hz), 7.33 (2H, d, J=7.3 Hz), 7.48-7.65 (7H, m), 7.79 (1H, d, J=3.2 Hz), 7.81-7.83 (1H, m), 10.75 (0.511, brs), 10.96 (0.5H, brs).

Example 605

4-{[(6-{4-[(E)-3-(4-{2-[2-(4-Fluorophenoxy)ethyl]-3-methylbenzyl}piperazin-1-yl)-3-oxoprop-1-en-1-yl]-2,6-dimethylphenoxy}pyridin-3-yl)oxy]methyl}benzonitrile hydrochloride $^1$H-NMR (DMSO-d$_6$) δ: 2.03 (6H, s), 2.36 (3H, s), 3.00-3.56 (6H, m), 3.06 (2H, t, J=6.8 Hz), 4.17 (2H, t, J=6.8 Hz), 4.28 (2H, brs), 4.53 (2H, brs), 5.22 (2H, s), 6.92-6.97 (2H, m), 7.02 (1H, d, J=9.3 Hz), 7.07-7.14 (2H, m), 7.19 (1H, d, J=15.4 Hz), 7.36-7.38 (3H, m), 7.46-7.50 (3H, m), 7.60 (1H, dd, J=9.3, 3.2 Hz), 7.64 (2H, d, J=8.3 Hz), 7.82 (1H, dd, J=3.2, 0.5 Hz), 7.88 (2H, dt, J=8.3, 1.8 Hz), 10.90 (1H, brs).

Example 606

(E)-3-[4-({5-[(4-Methoxybenzyl)oxy]pyridin-2-yl}oxy)-3,5-dimethylphenyl]-1-(4-{3-methyl-4-[2-(4-methylphenoxy)ethyl]benzyl}piperazin-1-yl)prop-2-en-1-one hydrochloride $^1$H-NMR (DMSO-d$_6$) δ: 2.03 (6H, s), 2.22 (3H, s), 2.35 (3H, s), 3.01-3.57 (6H, m), 3.05 (2H, t, J=6.8 Hz), 3.75 (3H, s), 4.15 (2H, t, J=6.8 Hz), 4.28 (2H, brs), 4.53 (2H, brs), 5.01 (2H, s), 6.82 (2H, dt, J=9.3, 2.5 Hz), 6.94 (2H, dt, J=9.3, 2.5 Hz), 6.99 (1H, d, J=9.0 Hz), 7.07 (2H, d, J=8.1 Hz), 7.19 (1H, d, J=15.4 Hz), 7.35-7.38 (5H, m), 7.46-7.50 (3H, m), 7.56 (1H, dd, J=9.0, 3.2 Hz), 7.78 (1H, d, J=3.2 Hz), 10.92 (1H, brs).

Example 607

(E)-3-{3-Chloro-4-[(5-{[4-(difluoromethoxy)benzyl]oxy}pyridin-2-yl)oxy]-5-methylphenyl}-1-(4-{4-[2-(4-methylphenoxy)ethyl]benzyl}piperazin-1-yl)prop-2-en-1-one hydrochloride mp: 206.1-206.4° C.

$^1$H-NMR (DMSO-d$_6$) δ: 2.10 (3H, s), 2.22 (3H, s), 3.04-4.55 (14H, m), 5.10 (2H, s), 6.80-7.41 (1H, m), 6.82 (2H, d, J=8.2 Hz), 7.07 (2H, d, J=8.2 Hz), 7.10 (1H, d, J=9.0 Hz), 7.20 (2H, d, J=8.5 Hz), 7.30 (1H, d, J=15.4 Hz), 7.43-7.52 (7H, m), 7.61 (1H, dd, J=9.0, 2.9 Hz), 7.63 (1H, brs), 7.80 (1H, d, J=2.9 Hz), 7.84 (1H, brs), 11.04 (1H, brs).

Example 608

(E)-3-[3-Chloro-4-({5-[(2-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride $^1$H-NMR (DMSO-d$_6$) δ: 1.15 (6H, d, J=6.9 Hz), 2.12 (3H, s), 2.81 (1H, septet, J=6.9 Hz), 2.90-3.18 (4H, m), 3.20-3.47 (3H, m), 3.60-3.80 (1H, m), 4.18 (2H, t, J=6.9 Hz), 4.34 (2H, brs), 4.56 (2H, d, J=13.7 Hz), 5.18 (2H, s), 6.82-6.88 (2H, m), 7.09-7.16 (3H, m), 7.33 (1H, d, J=15.6 Hz), 7.36-7.45 (4H, m), 7.47-7.55 (2H, m), 7.57-7.68 (5H, m), 7.86 (2H, d, J=2.7 Hz), 11.89 (1H, brs).

Example 609

(E)-3-[3-Chloro-5-methyl-4-({5-[(4-methylbenzyl)oxy]pyridin-2-yl}oxy)phenyl]-1-(4-{4-[2-(4-cyclopropylphenoxy)ethyl]benzyl}piperazin-1-yl)prop-2-en-1-one hydrochloride $^1$H-NMR (DMSO-$d_6$) δ: 0.53-0.57 (2H, m), 0.84-0.88 (2H, m), 1.80-1.87 (1H, m), 2.10 (3H, s), 2.30 (3H, s), 3.00-3.16 (5H, m), 3.31-3.75 (3H, m), 4.17 (2H, t, J=6.6 Hz), 4.32 (2H, brs), 4.52-4.54 (2H, m), 5.05 (2H, s), 6.80-6.83 (2H, m), 6.96-6.99 (2H, m), 7.09 (1H, dd, J=8.8, 0.5 Hz), 7.20 (2H, d, J=7.8 Hz), 7.29-7.32 (3H, m), 7.41-7.43 (2H, m), 7.47-7.52 (3H, m), 7.59 (1H, dd, J=9.0, 2.9 Hz), 7.63 (1H, d, J=2.0 Hz), 7.78 (1H, d, J=3.4 Hz), 7.84 (1H, d, J=2.0 Hz), 10.81 (1H, brs).

Example 610

(E)-3-[4-({5-[(4-Fluorobenzyl)oxy]pyridin-2-yl}oxy)-3,5-dimethylphenyl]-1-(4-{2-methyl-4-[2-(4-methylphenoxy)ethyl]benzyl}piperazin-1-yl)prop-2-en-1-one hydrochloride $^1$H-NMR (DMSO-$d_6$) δ: 2.04 (6H, s), 2.22 (3H, s), 2.42 (3H, s), 3.01 (2H, t, J=6.8 Hz), 3.19-3.63 (6H, m), 4.16 (2H, t, J=6.8 Hz), 4.34 (2H, brs), 4.54 (2H, brs), 5.08 (2H, s), 6.82 (2H, dt, J=9.3, 2.6 Hz), 7.00 (1H, d, J=9.3 Hz), 7.07 (2H, d, J=8.1 Hz), 7.18-7.26 (5H, m), 7.47-7.53 (5H, m), 7.55 (1H, d, J=7.8 Hz), 7.58 (1H, dd, J=9.3, 3.2 Hz), 7.80 (1H, d, J=3.2 Hz), 10.52 (1H, brs).

Example 611

(E)-3-[4-({5-[(4-Methoxybenzyl)oxy]pyridin-2-yl}oxy)-3,5-dimethylphenyl]-1-(4-{2-methyl-4-[2-(4-methylphenoxy)ethyl]benzyl}piperazin-1-yl)prop-2-en-1-one hydrochloride $^1$H-NMR (DMSO-$d_6$) δ: 2.04 (6H, s), 2.22 (3H, s), 2.42 (3H, s), 3.01 (2H, t, J=6.8 Hz), 3.18-3.62 (6H, m), 3.75 (3H, s), 4.16 (2H, t, J=6.8 Hz), 4.34 (2H, brs), 4.54 (2H, brs), 5.01 (2H, s), 6.82 (2H, dt, J=9.3, 2.5 Hz), 6.94 (2H, dt, J=9.3, 2.5 Hz), 6.99 (1H, d, J=9.0 Hz), 7.07 (2H, d, J=8.1 Hz), 7.18-7.26 (3H, m), 7.37 (2H, dt, J=9.0, 2.3 Hz), 7.47-7.58 (5H, m), 7.78 (1H, d, J=2.9 Hz), 10.59 (1H, brs).

Example 612

4-({[6-(2-Chloro-4-{(E)-3-[4-(4-{2-[4-(2-hydroxyethyl)phenoxy]ethyl}benzyl)piperazin-1-yl]-3-oxoprop-1-en-1-yl}-6-methylphenoxy)pyridin-3-yl]oxy}methyl)benzonitrile hydrochloride mp: 198.5-198.8° C.

Example 613

4-{[(6-{2-Chloro-6-methyl-4-[(E)-3-oxo-3-{4-[4-(2-{[5-(trifluoromethyl)pyridin-2-yl]oxy}-ethyl)benzyl]piperazin-1-yl}prop-1-en-1-yl]phenoxy}pyridin-3-yl)oxy]methyl}benzonitrile hydrochloride mp: 193.7-194.2° C.

Example 614

4-{[(6-{4-[(E)-3-(4-{4-[2-(4-Chlorophenoxy)ethyl]-3-fluorobenzyl}piperazin-1-yl)-3-oxoprop-1-en-1-yl]-2,6-dimethylphenoxy}pyridin-3-yl)oxy]methyl}benzonitrile hydrochloride mp: 240.5-243.5° C.

Example 615

(E)-3-[3-Chloro-4-({5-[(2-chlorobenzyl)oxy]pyridin-2-yl}oxy)-5-methylphenyl]-1-(4-{4-[2-(4-ethoxyphenoxy)ethyl]benzyl}piperazin-1-yl)prop-2-en-1-one hydrochloride mp: 161.0-163.1° C.

$^1$H-NMR (DMSO-$d_6$) δ: 1.28 (3H, t, J=6.8 Hz), 2.11 (3H, s), 3.03-4.56 (16H, m), 5.17 (2H, s), 6.82 (2H, d, J=9.5 Hz), 6.85 (2H, d, J=9.5 Hz), 7.12 (1H, d, J=9.0 Hz), 7.30 (1H, d, J=15.4 Hz), 7.39-7.43 (4H, m), 7.47-7.51 (4H, m), 7.60-7.67 (3H, m), 7.84-7.85 (2H, m), 10.87 (1H, brs).

Example 616

4-({[6-(4-{(E)-3-[4-(2-Fluoro-4-{2-[4-(trifluoromethyl)phenoxy]ethyl}benzyl)piperazin-1-yl]-3-oxoprop-1-en-1-yl}-2,6-dimethylphenoxy)pyridin-3-yl]oxy}methyl)benzonitrile hydrochloride $^1$H-NMR (DMSO-$d_6$) δ: 2.04 (6H, s), 3.05-3.20 (4H, m), 3.40-3.43 (3H, m), 3.61-3.63 (1H, m), 4.33-4.37 (4H, m), 4.53-4.56 (2H, m), 5.22 (2H, s), 7.01 (1H, d, J=8.8 Hz), 7.14-7.20 (3H, m), 7.31-7.35 (2H, m), 7.46-7.49 (3H, m), 7.60-7.64 (5H, m), 7.70-7.73 (1H, m), 7.82 (1H, d, J=2.9 Hz), 7.88 (2H, d, J=8.1 Hz), 11.34 (1H, s).

Example 617

4-{[(6-{2-Chloro-6-methyl-4-[(E)-3-oxo-3-{4-[4-(3-phenoxypropyl)benzyl]piperazin-1-yl}prop-1-en-1-yl]phenoxy}pyridin-3-yl)oxy]methyl}benzonitrile hydrochloride $^1$H-NMR (CDCl$_3$) δ: 2.11 (2H, tt, J=6.9, 6.9 Hz), 2.19 (3H, s), 2.72 (2H, brs), 2.85 (2H, t, J=6.9 Hz), 3.46 (2H, brs), 3.67 (1H, brs), 3.97 (2H, t, J=6.9 Hz), 4.15-4.23 (4H, m), 4.78 (1H, brs), 5.09 (2H, s), 6.70 (1H, d, J=15.3 Hz), 6.89 (2H, d, J=8.1 Hz), 6.93-6.98 (2H, m), 7.26-7.32 (5H, m), 7.38 (1H, dd, J=8.9, 3.1 Hz), 7.45 (1H, s), 7.52 (4H, d, J=7.8 Hz), 7.60 (1H, d, J=15.3 Hz), 7.68 (2H, d, J=7.8 Hz), 7.75 (1H, d, J=2.9 Hz), 13.52 (1H, brs).

Example 618

4-{[(6-{2-Chloro-4-[(E)-3-(4-{4-[3-(4-fluorophenoxy)propyl]benzyl}piperazin-1-yl)-3-oxoprop-1-en-1-yl]-6-methylphenoxy}pyridin-3-yl)oxy]methyl}benzonitrile hydrochloride mp: 166.2-166.7° C.

Example 619

4-({[6-(2-Chloro-4-{(E)-3-[4-(4-{3-[(6-chloropyridin-3-yl)oxy]propyl}benzyl)piperazin-1-yl]-3-oxoprop-1-en-1-yl}-6-methylphenoxy)pyridin-3-yl]oxy}methyl)benzonitrile hydrochloride mp: 168.5-170.0° C.

Example 620

4-({[6-(2-Chloro-6-methyl-4-{(E)-3-[4-(4-{3-[(6-methylpyridin-3-yl)oxy]propyl}benzyl)-piperazin-1-yl]-3-oxoprop-1-en-1-yl}phenoxy)pyridin-3-yl]oxy}methyl)benzonitrile hydrochloride $^1$H-NMR (DMSO-d$_6$) δ: 2.04-2.10 (5H, m), 2.59 (3H, s), 2.79 (2H, t, J=7.6 Hz), 3.38 (6H, brs), 4.16 (2H, t, J=6.2 Hz), 4.31 (2H, brs), 4.53 (2H, brs), 5.23 (2H, s), 7.12 (1H, d, J=9.0 Hz), 7.30 (1H, d, J=15.4 Hz), 7.35 (2H, d, J=8.1 Hz), 7.47-7.53 (3H, m), 7.62-7.69 (5H, m), 7.82 (1H, d, J=2.9 Hz), 7.84 (1H, d, J=2.0 Hz), 7.88 (2H, dt, J=8.3, 1.8 Hz), 7.93 (1H, d, J=8.5 Hz), 8.43 (1H, d, J=2.9 Hz), 11.24 (1H, brs).

Example 621

4-{[(6-{2-Chloro-6-methyl-4-[(E)-3-(4-{4-[3-(4-methylphenoxy)propyl]benzyl}piperazin-1-yl)-3-oxoprop-1-en-1-yl]phenoxy}pyridin-3-yl)oxy]methyl}benzonitrile hydrochloride mp: 193.0-194.8° C.

Example 622

4-({[6-(2-Chloro-6-methyl-4-{(E)-3-oxo-3-[4-(4-{3-[4-(propan-2-yl)phenoxy]propyl}benzyl)-piperazin-1-yl]prop-1-en-1-yl}phenoxy)pyridin-3-yl]oxy}methyl)benzonitrile hydrochloride mp: 197.8-198.7° C.

Example 623

(E)-3-[3-Chloro-4-({5-[(2-chlorobenzyl)oxy]pyridin-2-yl}oxy)-5-methylphenyl]-1-[4-(4-{[4-(propan-2-yloxy)phenoxy]methyl}benzyl)piperazin-1-yl]prop-2-en-1-one hydrochloride mp: 204.9-206.2° C.

Example 624

(E)-3-[3-Chloro-4-({5-[(2-chlorobenzyl)oxy]pyridin-2-yl}oxy)-5-methylphenyl]-1-(4-{4-[(4-methoxyphenoxy)methyl]benzyl}piperazin-1-yl)prop-2-en-1-one hydrochloride $^1$H-NMR (DMSO-d$_6$) δ: 2.12 (3H, s), 2.80-3.80 (6H, m), 3.69 (3H, s), 4.25-4.45 (2H, m), 4.46-4.62 (2H, m), 5.08 (2H, s), 5.17 (2H, s), 6.83-6.90 (2H, m), 6.92-6.99 (2H, m), 7.12 (1H, d, J=9.0 Hz), 7.27-7.57 (7H, m), 7.59-7.69 (5H, m), 7.82-7.89 (2H, m), 11.28 (1H, brs).

Example 625

(E)-3-[3-Chloro-4-({5-[(2-chlorobenzyl)oxy]pyridin-2-yl}oxy)-5-methylphenyl]-1-(4-{4-[(4-ethoxyphenoxy)methyl]benzyl}piperazin-1-yl)prop-2-en-1-one hydrochloride mp: 194.7-197.0° C.

Example 626

(E)-3-[3-Chloro-5-methyl-4-({5-[(4-methylbenzyl)oxy]pyridin-2-yl}oxy)phenyl]-1-[4-(4-{[4-(propan-2-yl)phenoxy]methyl}benzyl)piperazin-1-yl]prop-2-en-1-one hydrochloride mp: 203.8-204.4° C.

$^1$H-NMR (DMSO-d$_6$) δ: 1.16 (6H, d, J=6.9 Hz), 2.10 (3H, s), 2.30 (3H, s), 2.82 (1H, septet, J=6.9 Hz), 3.11-3.57 (6H, m), 4.36-4.57 (4H, m), 5.05 (2H, s), 5.11 (2H, s), 6.91-6.96 (2H, m), 7.07-7.34 (8H, m), 7.46-7.63 (7H, m), 7.78 (1H, d, J=3.0 Hz), 7.84 (1H, d, J=1.6 Hz), 10.98 (1H, brs).

Example 627

(E)-3-[3-Chloro-4-({5-[(2-chlorobenzyl)oxy]pyridin-2-yl}oxy)-5-methylphenyl]-1-[4-(4-{[4-(propan-2-yl)phenoxy]methyl}benzyl)piperazin-1-yl]prop-2-en-1-one hydrochloride mp: 209.6-212.0° C.

$^1$H-NMR (DMSO-d$_6$) δ: 1.16 (6H, d, J=6.8 Hz), 2.11 (3H, s), 2.82 (1H, septet, J=6.8 Hz), 3.02-3.59 (6H, m), 4.35-4.38 (2H, m), 4.53-4.57 (2H, m), 5.11 (2H, s), 5.17 (2H, s), 6.93 (2H, d, J=7.8 Hz), 7.11-7.17 (3H, m), 7.29-7.67 (12H, m), 7.84-7.85 (2H, m), 11.06 (1H, brs).

Example 628

(E)-3-[4-({5-[(2-Chlorobenzyl)oxy]pyridin-2-yl}oxy)-3-fluorophenyl]-1-[4-(4-{[4-(propan-2-yloxy)phenoxy]methyl}benzyl)piperazin-1-yl]prop-2-en-1-one hydrochloride $^1$H-NMR (DMSO-d$_6$) δ: 1.22 (6H, d, J=5.9 Hz), 2.90-3.60 (6H, m), 4.37 (2H, s), 4.44-4.50 (1H, m), 4.54 (2H, s), 5.07 (2H, s), 5.19 (2H, s), 6.83-6.87 (2H, m), 6.91-6.95 (2H, m), 7.15 (1H, d, J=8.8 Hz), 7.28-7.34 (2H, m), 7.38-7.44 (2H, m), 7.52-7.63 (8H, m), 7.66 (1H, dd, J=8.9, 3.1 Hz), 7.85 (1H, dd, J=12.1, 1.8 Hz), 7.91 (1H, d, J=2.9 Hz), 10.76 (1H, s).

Example 629

(E)-3-[3-Chloro-4-({5-[(2-chlorobenzyl)oxy]pyridin-2-yl}oxy)phenyl]-1-[4-(4-{[4-(propan-2-yloxy)phenoxy]methyl}benzyl)piperazin-1-yl]prop-2-en-1-one hydrochloride mp: 207.7-208.0° C.

Example 630

(E)-3-[3-Chloro-4-({5-[(2-chlorobenzyl)oxy]pyridin-2-yl}oxy)-5-methylphenyl]-1-[4-(4-{[4-(1H-pyrrol-1-yl)phenoxy]methyl}benzyl)piperazin-1-yl]prop-2-en-1-one hydrochloride mp: 199.9-201.6° C.

Example 631

(E)-3-[4-({5-[(2-Chlorobenzyl)oxy]pyridin-2-yl}oxy)-3-methoxyphenyl]-1-[4-(4-{[4-(propan-2-yloxy)phenoxy]methyl}benzyl)piperazin-1-yl]prop-2-en-1-one hydrochloride mp: 196.2-196.4° C.

Example 632

(E)-3-[4-({5-[(2-Chlorobenzyl)oxy]pyridin-2-yl}oxy)-2-methylphenyl]-1-[4-(4-{[4-(propan-2-yloxy)phenoxy]methyl}benzyl)piperazin-1-yl]prop-2-en-1-one hydrochloride mp: 182.5-183.2° C.
$^1$H-NMR (DMSO-$d_6$) δ: 1.22 (6H, d, J=6.2 Hz), 2.36 (3H, s), 3.04-3.59 (6H, m), 4.35-4.51 (5H, m), 5.07 (2H, s), 5.20 (2H, s), 6.82-6.96 (6H, m), 7.04-7.14 (2H, m), 7.37-7.66 (9H, m), 7.72-7.83 (2H, m), 7.99 (1H, d, J=3.0 Hz), 11.11 (1H, brs).

Example 633

(E)-3-[4-({5-[(2-Chlorobenzyl)oxy]pyridin-2-yl}oxy)phenyl]-1-[4-(4-{[4-(propan-2-yl)phenoxy]methyl}benzyl)piperazin-1-yl]prop-2-en-1-one hydrochloride $^1$H-NMR (DMSO-$d_6$) δ: 1.16 (6H, d, J=6.8 Hz), 2.79-2.86 (1H, m), 3.03-3.56 (6H, m), 4.36 (2H, brs), 4.53 (2H, brs), 5.11 (2H, s), 5.21 (2H, s), 6.93 (2H, dt, J=9.4, 2.5 Hz), 7.07-7.12 (3H, m), 7.16 (2H, dt, J=9.4, 2.5 Hz), 7.21 (1H, d, J=15.4 Hz), 7.38-7.45 (2H, m), 7.51-7.67 (8H, m), 7.75 (2H, d, J=8.5 Hz), 8.00 (1H, d, J=3.2 Hz), 10.91 (1H, brs).

Example 634

(E)-3-[2-Methyl-4-({5-[(4-methylbenzyl)oxy]pyridin-2-yl}oxy)phenyl]-1-[4-(4-{[4-(propan-2-yl)phenoxy]methyl}benzyl)piperazin-1-yl]prop-2-en-1-one hydrochloride mp: 189.6-190.9° C. (dec.)
$^1$H-NMR (DMSO-$d_6$) δ: 1.16 (6H, d, J=6.8 Hz), 2.31 (3H, s), 2.35 (3H, s), 2.82 (1H, septet, J=6.8 Hz), 3.09-3.52 (6H, m), 4.36 (2H, brs), 4.53 (2H, brs), 5.09 (2H, s), 5.11 (2H, s), 6.92-6.94 (4H, m), 7.03 (1H, d, J=8.8 Hz), 7.10 (1H, d, J=15.1 Hz), 7.15 (2H, d, J=8.5 Hz), 7.20 (2H, d, J=8.3 Hz), 7.34 (1H, d, J=8.3 Hz), 7.53-7.60 (5H, m), 7.74 (1H, d, J=15.1 Hz), 7.79-7.81 (1H, m), 7.94 (1H, d, J=3.2 Hz), 10.73 (1H, brs).

Example 635

(E)-3-[3-Chloro-5-methyl-4-({5-[(4-methylbenzyl)oxy]pyridin-2-yl}oxy)phenyl]-2-methyl-1-[4-(4-{[4-(propan-2-yl)phenoxy]methyl}benzyl)piperazin-1-yl]but-2-en-1-one hydrochloride mp: 181.4-182.3° C.

Example 636

(E)-3-[3-Chloro-5-methyl-4-({5-[(4-methylbenzyl)oxy]pyridin-2-yl}oxy)phenyl]-1-[4-(4-{[(4-fluorobenzyl)oxy]methyl}benzyl)piperazin-1-yl]prop-2-en-1-one hydrochloride $^1$H-NMR (DMSO-$d_6$) δ: 2.10 (3H, s), 2.30 (3H, s), 2.97-3.62 (6H, m), 4.34-4.36 (2H, m), 4.52-5.57 (6H, m), 5.05 (2H, s), 7.09 (1H, d, J=9.0 Hz), 7.17-7.22 (4H, m), 7.28-7.34 (3H, m), 7.38-7.51 (5H, m), 7.57-7.63 (4H, m), 7.78 (1H, d, J=2.9 Hz), 7.84 (1H, d, J=1.7 Hz), 11.08 (1H, brs).

Example 637

(E)-3-[3-Chloro-4-({5-[(2-chlorobenzyl)oxy]pyridin-2-yl}oxy)-5-methylphenyl]-1-[4-(4-{[(4-fluorobenzyl)oxy]methyl}benzyl)piperazin-1-yl]prop-2-en-1-one hydrochloride $^1$H-NMR (DMSO-$d_6$) δ: 2.11 (3H, s), 2.97-3.65 (6H, m), 4.34-4.36 (2H, m), 4.52-4.57 (6H, m), 5.17 (2H, s), 7.12 (1H, d, J=8.8 Hz), 7.16-7.22 (2H, m), 7.31 (1H, d, J=15.4 Hz), 7.37-7.54 (8H, m), 7.58-7.67 (5H, m), 7.84-7.86 (2H, m), 11.28 (1H, brs).

Example 638

4-{[(6-{2-Chloro-4-[(E)-3-(4-{2-fluoro-4-[(4-fluorophenoxy)methyl]benzyl}piperazin-1-yl)-3-oxoprop-1-en-1-yl]-6-methylphenoxy}pyridin-3-yl)oxy]methyl}benzonitrile hydrochloride $^1$H-NMR (DMSO-$d_6$) δ: 2.11 (3H, s), 3.09-3.22 (3H, m), 3.41-3.46 (2H, m), 3.60-3.62 (1H, m), 4.40-4.42 (2H, m), 4.54-4.56 (2H, m), 5.15 (2H, s), 5.23 (2H, s), 7.03-7.06 (2H, m), 7.10-7.17 (3H, m), 7.31 (1H, d, J=15.4 Hz), 7.38-7.43 (2H, m), 7.49 (1H, d, J=15.4 Hz), 7.62-7.67 (4H, m), 7.76-7.90 (5H, m), 11.29 (1H, s).

Example 639

(E)-3-[3-Chloro-5-methyl-4-({5[(4-methylbenzyl)oxy]pyridin-2-yl}oxy)phenyl]-1-(4-{2-fluoro-4-[(4-fluorophenoxy)methyl]benzyl}piperazin-1-yl)prop-2-en-1-one hydrochloride $^1$H-NMR (DMSO-$d_6$) δ: 2.10 (3H, s), 2.30 (3H, s), 3.12-3.14 (2H, m), 3.43-3.46 (2H, m), 3.54-3.56 (2H, m), 4.41-4.43 (2H, m), 4.55-4.57 (2H, m), 5.05 (2H, s), 5.15 (2H, s), 7.02-7.21 (7H, m), 7.28-7.32 (2H, m), 7.34 (1H, s), 7.39-7.44 (2H, m), 7.49 (1H, d, J=15.4 Hz), 7.59 (1H, dd, J=8.9, 3.1 Hz), 7.63 (1H, s), 7.71 (1H, s), 7.79 (1H, d, J=2.9 Hz), 7.84 (1H, s), 10.78 (1H, s).

Example 640

4-({[6-(2-Chloro-4-{(E)-3-[4-(3-fluoro-4-{[4-(propan-2-yloxy)phenoxy]methyl}benzyl)-piperazin-1-yl]-3-oxoprop-1-en-1-yl}-6-methylphenoxy)pyridin-3-yl]oxy}methyl)benzonitrile hydrochloride mp: 141.8-141.9° C.

Example 641

4-{[(6-{2-Chloro-4-[(E)-3-(4-{3-fluoro-4-[(4-fluorophenoxy)methyl]benzyl}piperazin-1-yl)-3-oxoprop-1-en-1-yl]-6-methylphenoxy}pyridin-3-yl)oxy]methyl}benzonitrile hydrochloride mp: 218.0-220.5° C.

Example 642

(E)-3-[3-Chloro-4-({5-[(2-chlorobenzyl)oxy]pyridin-2-yl}oxy)-5-methylphenyl]-1-[4-(3-fluoro-4-{[4-(propan-2-yloxy)phenoxy]methyl}benzyl)piperazin-1-yl]prop-2-en-1-one hydrochloride mp: 176.7-176.9° C.

Example 643

4-{[(6-{2-Chloro-4-[(E)-3-(4-{3-fluoro-4-[(4-propylphenoxy)methyl]benzyl}piperazin-1-yl)-3-oxoprop-1-en-1-yl]-6-methylphenoxy}pyridin-3-yl)oxy]methyl}benzonitrile hydrochloride $^1$H-NMR (DMSO-$d_6$) δ: 0.87 (3H, t, J=7.2 Hz), 1.53-1.56 (2H, m), 2.10 (3H, s), 3.09-3.12 (3H, m), 3.35-3.57 (5H, m), 4.39-4.41 (2H, m), 4.53-4.55 (2H, m), 5.13 (2H, s), 5.23 (2H, s), 6.94 (2H, d, J=8.5 Hz), 7.12 (3H, d, J=8.5 Hz), 7.30 (1H, d, J=15.4 Hz), 7.39-7.54 (3H, m), 7.62-7.67 (5H, m), 7.82 (1H, d, J=2.9 Hz), 7.84 (1H, s), 7.88 (2H, d, J=8.1 Hz), 10.71 (1H, s).

Example 644

(E)-3-[3-Chloro-4-({5-[(2-chlorobenzyl)oxy]pyridin-2-yl}oxy)-5-methylphenyl]-1-(4-{3-fluoro-4-[(4-fluorophenoxy)methyl]benzyl}piperazin-1-yl)prop-2-en-1-one hydrochloride $^1$H-NMR (DMSO-$d_6$) δ: 2.12 (3H, s), 3.00-3.18 (3H, m), 3.35-3.60 (3H, m), 4.38-4.40 (2H, m), 4.53-4.57 (2H, m), 5.15 (2H, s), 5.17 (2H, s), 7.04-7.08 (2H, m), 7.10-7.17 (3H, m), 7.30 (1H, d, J=15.4 Hz), 7.38-7.53 (6H, m), 7.60-7.67 (4H, m), 7.83-7.86 (2H, m), 11.01 (1H, s).

Example 645

(E)-3-[3-Chloro-5-methyl-4-({5-[(4-methylbenzyl)oxy]pyridin-2-yl}oxy)phenyl]-1-(4-{3-fluoro-4-[(4-propylphenoxy)methyl]benzyl}piperazin-1-yl)prop-2-en-1-one hydrochloride $^1$H-NMR (DMSO-$d_6$) δ: 0.87 (3H, t, J=7.3 Hz), 1.50-1.60 (2H, m), 2.10 (3H, s), 2.30 (3H, s), 3.03-3.09 (2H, m), 3.20-3.23 (1H, m), 3.37-3.47 (3H, m), 3.62-3.65 (2H, m), 4.37-4.40 (2H, m), 4.53-4.56 (2H, m), 5.06 (2H, s), 5.13 (2H, s), 6.94 (2H, d, J=8.3 Hz), 7.07-7.15 (3H, m), 7.20 (2H, d, J=7.8 Hz), 7.28-7.35 (3H, m), 7.45-7.52 (2H, m), 7.58-7.63 (4H, m), 7.79 (1H, d, J=2.9 Hz), 7.84 (1H, s), 11.52 (1H, s).

Example 646

4-{[(6-{4-[(E)-3-(4-{[(4-Chlorophenoxy)methyl]benzyl}piperazin-1-yl)-3-oxoprop-1-en-1-yl]-2,6-dimethylphenoxy}pyridin-3-yl)oxy]methyl}benzonitrile hydrochloride mp: 213.9-214.8° C.

Example 647

4-({[6-(2,6-Dimethyl-4-{(E)-3-oxo-3-[4-(4-{[4-(propan-2-yloxy)phenoxy]methyl}benzyl)-piperazin-1-yl]prop-1-en-1-yl}phenoxy)pyridin-3-yl]oxy}methyl)benzonitrile hydrochloride mp: 216.2-219.2° C.

Example 648

(E)-3-(3,5-Dimethyl-4-{[5-(1,3-thiazol-4-yl-methoxy)pyridin-2-yl]oxy}phenyl)-1-[4-(4-{[4-(propan-2-yl)phenoxy]methyl}benzyl)piperazin-1-yl]prop-2-en-1-one hydrochloride $^1$H-NMR (DMSO-$d_6$) δ: 1.16 (6H, d, J=6.8 Hz), 2.04 (6H, s), 2.82 (1H, septet, J=6.8 Hz), 3.04-3.60 (6H, m), 4.36 (2H, brs), 4.53 (2H, brs), 5.11 (2H, s), 5.22 (2H, s), 6.91-6.95 (2H, m), 7.00 (1H, d, J=8.8 Hz), 7.14-7.22 (3H, m), 7.46-7.55 (5H, m), 7.60-7.64 (3H, m), 7.81 (1H, d, J=2.0 Hz), 7.84 (1H, d, J=2.9 Hz), 9.13 (1H, d, J=2.0 Hz), 11.23 (1H, brs).

Example 649

(2E)-3-[4-({5-[(4-Fluorobenzyl)oxy]pyridin-2-yl}oxy)-3,5-dimethylphenyl]-1-(4-{4-[(1E)-3-phenoxyprop-1-en-1-yl]benzyl}piperazin-1-yl)prop-2-en-1-one hydrochloride mp: 207.4-207.6° C.

Example 650

4-{[(6-{2,6-Dimethyl-4-[(1E)-3-oxo-3-(4-{4-[(1E)-3-phenoxyprop-1-en-1-yl]benzyl}piperazin-1-yl)prop-1-en-1-yl]phenoxy}pyridin-3-yl)oxy]methyl}benzonitrile hydrochloride $^1$H-NMR (CDCl$_3$) δ: 2.12 (6H, s), 2.72 (2H, brs), 3.45-3.66 (3H, m), 4.15 (4H, brs), 4.72-4.78 (3H, m), 5.09 (2H, s), 6.48 (1H, dt, J=16.1, 5.5 Hz), 6.68 (1H, d, J=15.1 Hz), 6.75 (1H, d, J=16.1 Hz), 6.86 (1H, d, J=9.0 Hz), 6.95-7.00 (3H, m), 7.25-7.36 (5H, m), 7.47-7.70 (9H, m), 7.78 (1H, d, J=2.7 Hz), 13.58 (1H, brs).

Example 651

(2E)-3-[4-({5-[(4-Fluorobenzyl)oxy]pyridin-2-yl}oxy)-3,5-dimethylphenyl]-1-(4-{3-methyl-4-[(1E)-3-(4-methylphenoxy)prop-1-en-1-yl]benzyl}piperazin-1-yl)prop-2-en-1-one hydrochloride $^1$H-NMR (DMSO-$d_6$) δ: 2.03 (6H, s), 2.23 (3H, s), 2.33 (3H, s), 3.07-3.52 (6H, m), 4.30 (2H, brs), 4.53 (2H, brs), 4.73

(2H, dd, J=5.7, 1.1 Hz), 5.08 (2H, s), 6.43 (1H, dt, J=15.9, 5.7 Hz), 6.89 (2H, dt, J=9.3, 2.5 Hz), 6.98 (1H, d, J=15.9 Hz), 7.00 (1H, d, J=9.0 Hz), 7.10 (2H, dd, J=8.7, 0.6 Hz), 7.17-7.25 (3H, m), 7.37 (2H, brs), 7.46-7.52 (5H, m), 7.58 (1H, dd, J=9.0, 3.2 Hz), 7.63 (1H, d, J=8.3 Hz), 7.80 (1H, dd, J=3.2, 0.5 Hz), 10.59 (1H, brs).

Example 652

4-{[(6-{2-Chloro-4-[(1E)-3-(4-{4-[(1E)-3-(4-methoxyphenoxy)prop-1-en-1-yl]benzyl}piperazin-1-yl)-3-oxoprop-1-en-1-yl]-6-methylphenoxy}pyridin-3-yl)oxy]methyl}benzonitrile hydrochloride mp: 188.2-189.1° C.

Example 653

4-{[(2E)-3-{4-[(4-{(2E)-3-[3-Chloro-4-({5-[(4-cyanobenzyl)oxy]pyridin-2-yl}oxy)-5-methylphenyl]prop-2-enoyl}piperazin-1-yl)methyl]phenyl}prop-2-en-1-yl]oxy}benzonitrile hydrochloride mp: 210.4-212.2° C.

Example 654

(2E)-3-[4-({5-[(4-Methoxybenzyl)oxy]pyridin-2-yl}oxy)-3,5-dimethylphenyl]-1-(4-{2-methyl-4-[(1E)-3-(4-methylphenoxy)prop-1-en-1-yl]benzyl}piperazin-1-yl)prop-2-en-1-one hydrochloride ¹H-NMR (DMSO-d₆) δ: 2.04 (6H, s), 2.23 (3H, s), 2.43 (3H, s), 3.15-3.57 (6H, m), 3.75 (3H, s), 4.36 (2H, brs), 4.55 (2H, brs), 4.70 (2H, d, J=5.4 Hz), 5.01 (2H, s), 6.57 (1H, dt, J=15.6, 5.4 Hz), 6.73 (1H, d, J=15.6 Hz), 6.88 (2H, dt, J=9.2, 2.4 Hz), 6.94 (2H, dt, J=9.2, 2.4 Hz), 6.99 (1H, d, J=9.0 Hz), 7.09 (2H, d, J=8.1 Hz), 7.20 (1H, d, J=15.6 Hz), 7.35-7.38 (2H, m), 7.48-7.51 (5H, m), 7.56 (2H, dd, J=9.0, 3.1 Hz), 7.78 (1H, d, J=3.1 Hz), 10.34 (1H, brs).

Example 655

4-({[6-(2-Chloro-4-{(1E)-3-[4-(4-{(1E)-3-[(6-chloropyridin-3-yl)oxy]prop-1-en-1-yl}benzyl)-piperazin-1-yl]-3-oxoprop-1-en-1-yl}-6-methylphenoxy)pyridin-3-yl]oxy}methyl)benzonitrile hydrochloride mp: 204.7-206.2° C.

Example 656

4-({[6-(2-Chloro-6-methyl-4-{(1E)-3-[4-(4-{(1E)-3-[(6-methylpyridin-3-yl)oxy]prop-1-en-1-yl}benzyl)piperazin-1-yl]-3-oxoprop-1-en-1-yl}phenoxy)pyridin-3-yl]oxy}methyl)benzonitrile hydrochloride mp: 162.7-163.3° C.

Example 657

4-({[6-(4-{(1E)-3-[4-(4-{(1E)-3-[(5-Bromopyridin-2-yl)oxy]prop-1-en-1-yl}benzyl)piperazin-1-yl]-3-oxoprop-1-en-1-yl}-2-chloro-6-methylphenoxy)pyridin-3-yl]oxy}methyl)benzonitrile hydrochloride mp: 145.0-145.8° C.

Example 658

4-({[6-(2-Chloro-6-methyl-4-{(1E)-3-[4-(4-{(1E)-3-[(5-methylpyridin-2-yl)oxy]prop-1-en-1-yl}benzyl)piperazin-1-yl]-3-oxoprop-1-en-1-yl}phenoxy)pyridin-3-yl]oxy}methyl)benzonitrile hydrochloride mp: 169.5-170.0° C.

Example 659

(2E)-3-[4-({5-[(4-Fluorobenzyl)oxy]pyridin-2-yl}oxy)-3,5-dimethylphenyl]-1-(4-{4-[(2E)-4-(4-methylphenoxy)but-2-en-2-yl]benzyl}piperazin-1-yl)prop-2-en-1-one hydrochloride ¹H-NMR (DMSO-d₆) δ: 2.04 (6H, s), 2.12 (3H, s), 2.23 (3H, s), 3.04-3.60 (6H, m), 4.35 (2H, brs), 4.53 (2H, brs), 4.75 (2H, d, J=6.3 Hz), 5.08 (2H, s), 6.10 (1H, t, J=6.3 Hz), 6.88 (2H, dt, J=9.2, 2.4 Hz), 7.00 (1H, d, J=9.0 Hz), 7.09 (2H, d, J=8.3 Hz), 7.17-7.25 (3H, m), 7.46-7.52 (5H, m), 7.55-7.60 (5H, m), 7.80 (1H, d, J=3.2 Hz), 11.21 (1H, s).

Example 660

(2E)-3-[4-({5-[4-Fluorobenzyl)oxy]pyridin-2-yl}oxy)-3,5-dimethylphenyl]-1-(4-{4-[(1E)-2-methyl-3-(4-methylphenoxy)prop-1-en-1-yl]benzyl}piperazin-1-yl)prop-2-en-1-one hydrochloride ¹H-NMR (DMSO-d₆) δ: 1.93 (3H, s), 2.03 (6H, s), 2.23 (3H, s), 3.06-3.57 (6H, m), 4.35 (2H, brs), 4.53 (2H, brs), 4.58 (2H, s), 5.08 (2H, s), 6.64 (1H, brs), 6.90 (2H, dt, J=9.2, 2.4 Hz), 7.00 (1H, d, J=8.8 Hz), 7.09 (2H, d, J=8.3 Hz), 7.17-7.24 (3H, m), 7.40 (2H, d, J=8.1 Hz), 7.46-7.52 (5H, m), 7.56-7.60 (3H, m), 7.80 (1H, d, J=2.9 Hz), 10.95 (1H, brs).

Example 661

(E)-3-[3-Chloro-5-methyl-4-({5-[(4-methylbenzyl)oxy]pyridin-2-yl}oxy)phenyl]-1-{4-[4-(2-{[4-(propan-2-yl)phenyl]amino}ethyl)benzyl]piperazin-1-yl}prop-2-en-1-one dihydrochloride ¹H-NMR (DMSO-d₆) δ: 1.19 (6H, d, J=6.8 Hz), 2.10 (3H, s), 2.30 (3H, s), 2.70-4.00 (13H, m), 4.20-4.40 (2H, m), 4.45-4.62 (2H, m), 5.56 (2H, s), 7.08 (1H, dd, J=8.8, 0.5 Hz), 7.19 (2H, d, J=7.8 Hz), 7.25-7.35 (7H, m), 7.37 (2H, d, J=8.1 Hz), 7.48 (1H, d, J=15.4 Hz), 7.54-7.62 (3H, m), 7.63 (1H, d, J=2.0 Hz), 7.78 (1H, dd, J=3.1, 0.5 Hz), 7.84 (1H, d, J=2.0 Hz), 11.59 (1H, brs).

Example 662

(E)-3-[3-Chloro-4-({5-[(2-chlorobenzyl)oxy]pyridin-2-yl}oxy)-5-methylphenyl]-1-{4-[4-(2-{[4-(propan-2-yl)phenyl]amino}ethyl)benzyl]piperazin-1-yl}prop-2-en-1-one dihydrochloride ¹H-NMR (DMSO-d₆) δ: 1.19 (6H, d, J=6.8 Hz), 2.11 (3H, s), 2.70-4.00 (13H, m), 4.24-4.40 (2H, m), 4.45-4.61 (2H, m), 5.17 (2H, s), 7.11 (1H, d, J=9.5 Hz), 7.25-7.69 (16H, m), 7.82-7.88 (2H, m), 11.57 (1H, brs).

Example 663

(E)-3-[3-Chloro-5-methyl-4-({5-[(4-methylbenzyl)oxy]pyridin-2-yl}oxy)phenyl]-1-{4-[4-(2-{methyl[4-(propan-2-yl)phenyl]amino}ethyl)benzyl]piperazin-1-yl}prop-2-en-1-one hydrochloride mp: 184.2-186.2° C.

Example 664

(E)-3-[3-Chloro-4-({5-[(2-chlorobenzyl)oxy]pyridin-2-yl}oxy)-5-methylphenyl]-1-[4-(4-{2-[(4-fluorophenyl)(methyl)amino]ethyl}benzyl)piperazin-1-yl]prop-2-en-1-one dihydrochloride mp: 204.6-208.5° C.

Example 665

(E)-3-[3-Chloro-4-({5-[(2-chlorobenzyl)oxy]pyridin-2-yl}oxy)-5-methylphenyl]-1-[4-(4-{2-[(4-fluorophenyl)amino]ethyl}benzyl)piperazin-1-yl]prop-2-en-1-one dihydrochloride mp: 206.3-207.8° C.

Example 666

(E)-3-[3-Chloro-5-methyl-4-({5-[(4-methylbenzyl)oxy]pyridin-2-yl}oxy)phenyl]-1-[4-(4-{2-[(4-fluorophenyl)(methyl)amino]ethyl}benzyl)piperazin-1-yl]prop-2-en-1-one dihydrochloride mp: 200.3-202.4° C.

Example 667

(E)-3-[3-Chloro-5-methyl-4-({5-[(4-methylbenzyl)oxy]pyridin-2-yl}oxy)phenyl]-1-[4-(4-{2-[(4-fluorophenyl)amino]ethyl}benzyl)piperazin-1-yl]prop-2-en-1-one dihydrochloride mp: 193.7-194.9° C.

Example 668

4-({[6-(2-Chloro-4-{(E)-3-[4-(4-{2-[(4-fluorophenyl)amino]ethyl}benzyl)piperazin-1-yl]-3-oxoprop-1-en-1-yl}phenoxy)pyridin-3-yl]oxy}methyl)benzonitrile dihydrochloride mp: 211.2-211.9° C.

Example 669

4-({[6-(2-Chloro-4-{(E)-3-[4-(4-{2-[(4-methoxyphenyl)amino]ethyl}benzyl)piperazin-1-yl]-3-oxoprop-1-en-1-yl}phenoxy)pyridin-3-yl]oxy}methyl)benzonitrile dihydrochloride mp: 219.5-222.3° C.

Example 670

(E)-3-[3-Chloro-4-({5-[4-fluorobenzyl)oxy]pyridin-2-yl}oxy)phenyl]-1-[4-(4-{2-[(4-methoxyphenyl)amino]ethyl}benzyl)piperazin-1-yl]prop-2-en-1-one dihydrochloride mp: 219.5-221.3° C.

Example 671

(E)-3-[3-Chloro-5-methyl-4-({5-[(4-methylbenzyl)oxy]pyridin-2-yl}oxy)phenyl]-1-[4-(4-{2-[(4-methoxyphenyl)amino]ethyl}benzyl)piperazin-1-yl]prop-2-en-1-one dihydrochloride mp: 217.5-218.4° C.

Example 672

(E)-3-[3-Chloro-5-methyl-4-({5-[(4-methylbenzyl)oxy]pyridin-2-yl}oxy)phenyl]-1-[4-({4-[2-(4-methylphenoxy)ethyl]phenyl}amino)piperidin-1-yl]prop-2-en-1-one hydrochloride mp: 191.3-192.5° C.

Example 673

(E)-3-[3-Chloro-5-methyl-4-({5-[(4-methylbenzyl)oxy]pyridin-2-yl}oxy)phenyl]-1-(4-{[4-(2-{[4-(propan-2-yl)phenyl]amino}ethyl)phenyl]amino}piperidin-1-yl)prop-2-en-1-one dihydrochloride $^1$H-NMR (DMSO-d$_6$) δ: 1.19 (6H, d, J=6.8 Hz), 1.45-1.71 (2H, m), 1.90-2.06 (2H, m), 2.10 (3H, s), 2.30 (3H, s), 2.72 (1H, t, J=12.0 Hz), 2.91 (1H, septet, J=6.8 Hz), 2.98-3.07 (2H, m), 3.13 (1H, t, J=12.2 Hz), 3.30-4.00 (7H, m), 4.32-4.58 (2H, m), 5.06 (2H, s), 7.08 (1H, dd, J=9.0, 0.5 Hz), 7.19 (2H, d, J=7.8 Hz), 7.28-7.47 (12H, m), 7.59 (1H, dd, J=9.0, 3.2 Hz), 7.63 (1H, d, J=2.0 Hz), 7.79 (1H, dd, J=3.2, 0.5 Hz), 7.83 (1H, d, J=2.0 Hz).

Example 674

(E)-3-[3-Chloro-5-methyl-4-({5-[(4-methylbenzyl)oxy]pyridin-2-yl}oxy)phenyl]-1-[4-({4-[2-(4-fluorophenoxy)ethyl]phenyl}amino)piperidin-1-yl]prop-2-en-1-one hydrochloride mp: 171.7-174.5° C.

Example 675

(E)-3-[3-Chloro-4-({5-[(2-chlorobenzyl)oxy]pyridin-2-yl}oxy)-5-methylphenyl]-1-(4-{[2-(4-methoxyphenoxy)quinolin-6-yl]methyl}piperazin-1-yl)prop-2-en-1-one hydrochloride mp: 228.0-228.9° C.

Example 676

(E)-3-[3-Chloro-4-({5-[(2-chlorobenzyl)oxy]pyridin-2-yl}oxy)-5-methylphenyl]-1-[4-({2-[4-(propan-2-yl)phenoxy]quinolin-6-yl}methyl)piperazin-1-yl]prop-2-en-1-one hydrochloride ¹H-NMR (DMSO-d$_6$) δ: 1.25 (6H, d, J=6.8 Hz), 2.11 (3H, s), 2.96 (1H, septet, J=6.8 Hz), 3.00-3.80 (6H, m), 4.42-4.64 (4H, m), 5.17 (2H, s), 7.12 (1H, d, J=8.8 Hz), 7.15-7.20 (2H, m), 7.25-7.55 (8H, m), 7.59-7.69 (3H, m), 7.72 (1H, d, J=8.8 Hz), 7.82-7.90 (3H, m), 8.12 (1H, brs), 8.43 (1H, d, J=8.8 Hz), 11.22 (1H, brs).

Example 677

(E)-3-{3-Chloro-5-methyl-4-[(5-{[4-(trifluoromethyl)benzyl]oxy}pyridin-2-yl)oxy]phenyl}-1-(4-{4-[2-(4-methylphenoxy)ethoxy]benzyl}piperazin-1-yl)prop-2-en-1-one hydrochloride ¹H-NMR (DMSO-d$_6$) δ: 2.11 (3H, s), 2.23 (3H, s), 2.99-3.13 (3H, m), 3.40-3.54 (3H, m), 4.28-4.33 (6H, m), 4.53-4.56 (2H, m), 5.24 (2H, s), 6.87 (2H, d, J=8.5 Hz), 7.07-7.14 (5H, m), 7.31 (1H, d, J=15.4 Hz), 7.49-7.52 (3H, m), 7.64-7.67 (4H, m), 7.78 (2H, d, J=8.1 Hz), 7.83 (1H, d, J=3.2 Hz), 7.85 (1H, s), 10.99 (1H, brs).

Example 678

(E)-3-[3-Chloro-4-({5-[(2-chlorobenzyl)oxy]pyridin-2-yl}oxy)-5-methylphenyl]-1-(4-{4-[2-(4-fluorophenyl)-2-oxoethoxy]benzyl}piperazin-1-yl)prop-2-en-1-one hydrochloride mp: 190.3-191.9° C.

Example 679

(E)-3-{3-Chloro-5-methyl-4-[(5-{[4-(trifluoromethyl)benzyl]oxy}pyridin-2-yl)oxy]phenyl}-1-(4-{4-[2-(4-chlorophenoxy)ethoxy]benzyl}piperazin-1-yl)prop-2-en-1-one hydrochloride ¹H-NMR (DMSO-d$_6$) δ: 2.11 (3H, s), 3.02-3.14 (3H, m), 3.34-3.55 (3H, m), 4.30-4.34 (6H, m), 4.52-4.56 (2H, m), 5.24 (2H, s), 7.00-7.04 (2H, m), 7.07-7.12 (3H, m), 7.28-7.37 (3H, m), 7.47-7.51 (3H, m), 7.62-7.68 (4H, m), 7.77 (2H, d, J=8.3 Hz), 7.82 (1H, d, J=2.9 Hz), 7.84 (1H, d, J=1.5 Hz), 10.80 (1H, brs).

Example 680

4-{[(6-{2-Chloro-4-[(E)-3-(4-{[2-(4-methoxyphenoxy)quinolin-6-yl]methyl}piperazin-1-yl)-3-oxoprop-1-en-1-yl]phenoxy}pyridin-3-yl)oxy]methyl}benzonitrile hydrochloride mp: 232.0-234.1° C.

Example 681

(E)-3-[4-({5-[(2,3-Dichlorobenzyl)oxy]pyridin-2-yl}oxy)-3-methylphenyl]-1-(4-{4-[2-(4-methylphenyl)-2-oxoethoxy]benzyl}piperazin-1-yl)prop-2-en-1-one hydrochloride mp: 178.9-181.1° C.

Example 682

(E)-3-[3-Chloro-5-methyl-4-({5-[(4-methylbenzyl)oxy]pyridin-2-yl}oxy)phenyl]-1-(4-{4-[4-(propan-2-yl)phenoxy]benzyl}piperazin-1-yl)prop-2-en-1-one hydrochloride mp: 227.6-228.9° C.

Example 683

(E)-3-[3-Chloro-4-({5-[(2-chlorobenzyl)oxy]pyridin-2-yl}oxy)-5-methylphenyl]-1-{4-[4-(4-chlorophenoxy)benzyl]piperazin-1-yl}prop-2-en-1-one hydrochloride mp: 227.1-228.0° C.

Example 684

(E)-3-[3-Chloro-5-methyl-4-({5-[(4-methylbenzyl)oxy]pyridin-2-yl}oxy)phenyl]-1-{4-[4-(4-chlorophenoxy)benzyl]piperazin-1-yl}prop-2-en-1-one hydrochloride mp: 221.4-221.6° C.

Example 685

(E)-1-[4-(Biphenyl-4-ylmethyl)piperazin-1-yl]-3-[3-chloro-4-({5-[(2-chlorobenzyl)oxy]pyridin-2-yl}oxy)-5-methylphenyl]prop-2-en-1-one hydrochloride mp: 228.3-230.2° C.

Example 686

(E)-1-[4-(Biphenyl-4-ylmethyl)piperazin-1-yl]-3-[3-chloro-5-methyl-4-({5-[(4-methylbenzyl)-oxy]pyridin-2-yl}oxy)phenyl]prop-2-en-1-one hydrochloride mp: 225.0-227.1° C.

Example 687

(E)-3-{3-Chloro-5-methyl-4-[(5-{[4-(trifluoromethyl)benzyl]oxy}pyridin-2-yl)oxy]phenyl}-1-(4-{4-[2-(4-methylphenyl)ethoxy]benzyl}piperazin-1-yl)prop-2-en-1-one hydrochloride ¹H-NMR (DMSO-d$_6$) δ: 2.11 (3H, s), 2.27 (3H, s), 3.00-3.14 (5H, m), 3.39-3.55 (3H, m), 4.19 (2H, t, J=6.8 Hz), 4.27 (2H, brs), 4.52-4.55 (2H, m), 5.24 (2H, s), 7.02 (2H, d, J=8.5 Hz), 7.12 (3H, d, J=8.8 Hz), 7.21 (2H, d, J=7.8 Hz), 7.29 (1H, d, J=15.6 Hz), 7.47-7.51 (3H, m), 7.62-7.68 (4H, m), 7.77 (2H, d, J=8.3 Hz), 7.82 (1H, d, J=2.9 Hz), 7.84 (1H, d, J=1.7 Hz), 10.80 (1H, brs).

Example 688

(E)-3-{3-Chloro-5-methyl-4-[(5-{[4-(trifluoromethyl)benzyl]oxy}pyridin-2-yl)oxy]phenyl}-1-(4-{4-[2-(4-methoxyphenyl)ethoxy]benzyl}piperazin-1-yl)prop-2-en-1-one hydrochloride ¹H-NMR (DMSO-d$_6$) δ: 2.11 (3H, s), 2.97-3.12 (5H, m), 3.33-3.54 (3H, m), 3.72 (3H, s), 4.17 (2H, t, J=6.8 Hz), 4.28

(2H, brs), 4.52-4.55 (2H, m), 5.24 (2H, s), 6.86-6.89 (2H, m), 7.02 (2H, d, J=8.5 Hz), 7.12 (1H, d, J=8.8 Hz), 7.23-7.27 (2H, m), 7.29 (1H, d, J=15.4 Hz), 7.45-7.51 (3H, m), 7.62-7.68 (4H, m), 7.77 (2H, d, J=8.3 Hz), 7.82 (1H, d, J=2.9 Hz), 7.84 (1H, d, J=2.0 Hz), 10.71 (1H, brs).

Example 689

4-{[(6-{2-Chloro-6-methyl-4-[(E)-3-oxo-3-(4-{4-[4-(propan-2-yl)phenoxy]benzyl}piperazin-1-yl)prop-1-en-1-yl]phenoxy}pyridin-3-yl)oxy]methyl}benzonitrile hydrochloride $^1$H-NMR (DMSO-d$_6$) δ: 1.21 (6H, d, J=6.8 Hz), 2.11 (3H, s), 2.87-2.94 (1H, m), 3.01-3.17 (2H, m), 3.36-3.39 (2H, m), 3.55-3.58 (2H, m), 4.31-4.34 (2H, m), 4.53-4.56 (2H, m), 5.23 (2H, s), 6.99 (2H, d, J=8.5 Hz), 7.05 (2H, d, J=8.3 Hz), 7.12 (1H, d, J=9.0 Hz), 7.28-7.33 (3H, m), 7.49 (1H, d, J=15.4 Hz), 7.56 (2H, d, J=8.3 Hz), 7.62-7.66 (4H, m), 7.81-7.89 (4H, m), 10.90 (1H, s).

Example 690

(E)-3-[4-({5-[(2,3-Difluorobenzyl)oxy]pyridin-2-yl}oxy)-3-fluorophenyl]-1-[4-(4-{2-[4-(propan-2-yl)phenyl]ethoxy}benzyl)piperazin-1-yl]prop-2-en-1-one hydrochloride mp: 196.5-197.4° C.

Example 691

(E)-3-[4-({5-[(2,4-Difluorobenzyl)oxy]pyridin-2-yl}oxy)-3-fluorophenyl]-1-[4-(4-{2-[4-(propan-2-yl)phenyl]ethoxy}benzyl)piperazin-1-yl]prop-2-en-1-one hydrochloride mp: 195.2-198.7° C.
$^1$H-NMR (DMSO-d$_6$) δ: 1.16 (6H, d, J=6.8 Hz), 2.82 (1H, septet, J=6.8 Hz), 2.90-3.65 (8H, m), 4.18 (2H, t, J=6.7 Hz), 4.32 (2H, brs), 4.52 (2H, brs), 5.14 (2H, s), 6.84 (2H, d, J=8.8 Hz), 7.12-7.17 (4H, m), 7.27-7.34 (3H, m), 7.43 (2H, d, J=7.8 Hz), 7.50-7.56 (4H, m), 7.60-7.66 (2H, m), 7.83 (1H, dd, J=12.1, 1.8 Hz), 7.89 (1H, d, J=3.2 Hz), 10.76 (1H, brs).

Example 692

4-{[(6-{4-[(E)-3-{4-[4-(4-Chlorophenoxy)benzyl]piperazin-1-yl}-3-oxoprop-1-en-1-yl]-2,6-dimethylphenoxy}pyridin-3-yl)oxy]methyl}benzonitrile hydrochloride mp: 231.9-233.7° C.

Example 693

4-({[6-(4-{(E)-3-[4-(Biphenyl-4-ylmethyl)piperazin-1-yl]-3-oxoprop-1-en-1-yl}-2,6-dimethylphenoxy)pyridin-3-yl]oxy}methyl)benzonitrile hydrochloride mp: 231.3-231.5° C.

Example 694

(E)-3-[3-Chloro-4-({5-[(2-chlorobenzyl)oxy]pyridin-2-yl}oxy)-5-methylphenyl]-1-(4-{4-[2-(4-methoxyphenyl)ethoxy]benzyl}piperazin-1-yl)prop-2-en-1-one hydrochloride mp: 200.2-200.3° C.

$^1$H-NMR (DMSO-d$_6$) δ: 2.11 (3H, s), 2.96-4.55 (17H, m), 5.17 (2H, s), 6.87 (2H, d, J=8.5 Hz), 7.02 (2H, d, J=8.1 Hz), 7.12 (1H, d, J=8.8 Hz), 7.24 (2H, d, J=8.5 Hz), 7.30 (1H, d, J=15.4 Hz), 7.39-7.42 (2H, m), 7.46-7.53 (4H, m), 7.60-7.67 (3H, m), 7.84-7.84 (2H, m), 10.83 (1H, brs).

Example 695

(E)-1-[4-(4-Methylbenzyl)piperazin-1-yl]-3-[2-methyl-4-({5-[(4-methylbenzyl)oxy]pyridin-2-yl}oxy)phenyl]prop-2-en-1-one hydrochloride mp: 224.8-225.5° C. (dec.)

Example 696

(E)-1-[4-(4-Chlorobenzyl)piperazin-1-yl]-3-[2-methyl-4-({5-[(4-methylbenzyl)oxy]pyridin-2-yl}oxy)phenyl]prop-2-en-1-one hydrochloride mp: 222.2-224.2° C. (dec.)

Example 697

(E)-1-[4-(4-Chlorobenzyl)piperazin-1-yl]-3-[3-chloro-4-({5-[2-(3,4-dichlorophenyl)ethoxy]-pyridin-2-yl}oxy)-5-methylphenyl]prop-2-en-1-one hydrochloride mp: 218.3-218.5° C.

Example 698

4-({[6-(2-Chloro-6-methyl-4-{(E)-3-[4-(4-methylbenzyl)piperazin-1-yl]-3-oxoprop-1-en-1-yl}phenoxy)pyridin-3-yl]oxy}methyl)benzonitrile hydrochloride mp: 152.0-152.1° C.

Example 699

4-({[6-(2-Chloro-4-{(E)-3-[4-(4-chlorobenzyl)piperazin-1-yl]-3-oxoprop-1-en-1-yl}-6-methylphenoxy)pyridin-3-yl]oxy}methyl)benzonitrile hydrochloride mp: 223.7-223.8° C.

Example 700

(2E)-3-[3-Chloro-5-methyl-4-({5-[(4-methylbenzyl)oxy]pyridin-2-yl}oxy)phenyl]-1-(4-{4-[(1E)-3-methoxyprop-1-en-1-yl]benzyl}piperazin-1-yl)prop-2-en-1-one hydrochloride $^1$H-NMR (DMSO-d$_6$) δ: 2.10 (3H, s), 2.30 (3H, s), 3.06-3.57 (6H, m), 3.29 (3H, s), 4.06 (2H, dd, J=5.5, 1.3 Hz), 4.34 (2H, brs), 4.52-4.55 (2H, m), 5.05 (2H, s), 6.45 (1H, dt, J=16.1, 5.5 Hz), 6.64 (1H, d, J=16.1 Hz), 7.09 (1H, d, J=9.3 Hz), 7.20 (2H, d, J=7.8 Hz), 7.28-7.34 (3H, m), 7.49 (1H, d, J=15.4 Hz), 7.52-7.57 (4H, m), 7.59 (1H, dd, J=9.3, 3.2 Hz), 7.63 (1H, d, J=2.0 Hz), 7.79 (1H, d, J=3.2 Hz), 7.84 (1H, d, J=2.0 Hz), 10.93 (1H, brs).

Example 701

4-({[6-(2,6-Dimethyl-4-{(E)-3-[4-(4-methylbenzyl)piperazin-1-yl]-3-oxoprop-1-en-1-yl}phenoxy)pyridin-3-yl]oxy}methyl)benzonitrile hydrochloride mp: 224.7-226.0° C.

Example 702

(E)-3-{3-Chloro-4-[(5-{[4-(difluoromethoxy)benzyl]oxy}pyridin-2-yl)oxy]-5-methylphenyl}-1-[4-(4-methylbenzyl)piperazin-1-yl]prop-2-en-1-one hydrochloride mp: 216.1-216.5° C.
$^1$H-NMR (DMSO-$d_6$) δ: 2.11 (3H, s), 2.34 (3H, s), 3.05-4.56 (10H, m), 5.11 (2H, s), 7.10 (1H, d, J=8.8 Hz), 7.21 (2H, d, J=7.8 Hz), 7.26 (1H, t, J=74.0 Hz), 7.26-7.33 (3H, m), 7.48-7.53 (5H, m), 7.60-7.64 (2H, m), 7.81 (1H, brs), 7.85 (1H, brs), 11.62 (1H, brs).

Example 703

4-{[(6-{2-Chloro-4-[(E)-3-{4-[4-(3-hydroxypropyl)benzyl]piperazin-1-yl]-3-oxoprop-1-en-1-yl]-6-methylphenoxy}pyridin-3-yl)oxy]methyl}benzonitrile hydrochloride mp: 191.6-193.1° C.

Example 704

4-{[(6-{2-Chloro-4-[(1E)-3-(4-{4-[(1E)-3-hydroxyprop-1-en-1-yl]benzyl}piperazin-1-yl)-3-oxoprop-1-en-1-yl]-6-methylphenoxy}pyridin-3-yl)oxy]methyl}benzonitrile hydrochloride $^1$H-NMR (DMSO-$d_6$) δ: 2.11 (3H, s), 3.04-3.61 (6H, m), 4.15 (2H, dd, J=4.6, 1.5 Hz), 4.32 (2H, brs), 4.54 (2H, brs), 5.23 (2H, s), 6.48 (1H, dt, J=16.0, 4.8 Hz), 6.60 (1H, dt, J=16.0, 1.5 Hz), 7.12 (1H, dd, J=9.0, 0.5 Hz), 7.30 (1H, d, J=15.4 Hz), 7.47-7.56 (5H, m), 7.62-7.66 (4H, m), 7.82 (1H, dd, J=3.2, 0.5 Hz), 7.84 (1H, d, J=2.0 Hz), 7.88 (2H, dt, J=8.3, 1.7 Hz), 11.12 (1H, brs).

Example 705

4-{[(6-{2-Chloro-4-[(E)-3-(4-{3-fluoro-4-[(1-hydroxy-2-methylpropan-2-yl)oxy]benzyl}-piperazin-1-yl)-3-oxoprop-1-en-1-yl]-6-methylphenoxy}pyridin-3-yl)oxy]methyl}benzonitrile hydrochloride mp: 170.2-170.5° C.

Example 706

(E)-3-[3-Chloro-5-methyl-4-({5-[(4-methylbenzyl)oxy]pyridin-2-yl}oxy)phenyl]-2-methyl-1-(4-{2-(4-methylphenoxy)ethyl]benzyl}piperazin-1-yl)but-2-en-1-one hydrobromide mp: 205.5-206.5° C.

Example 707

(E)-3-[3-Chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]but-2-en-1-one hydrobromide mp: 147.6-149.7° C.

Example 708

(E)-3-[3-Chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)but-2-en-1-one hydrobromide mp: 156.5-158.2° C.

Example 709

(E)-3-[3-Chloro-5-methyl-4-({5-[(4-methylbenzyl)oxy]pyridin-2-yl}oxy)phenyl]-2-methyl-1-[4-(4-{2-[4-(propan-2-yl)phenoxy]ethyl}benzyl)piperazin-1-yl]but-2-en-1-one hydrobromide mp: 197.8-198.4° C.

Example 710

(E)-3-[3-Chloro-4-({5-[(2-chlorobenzyl)oxy]pyridin-2-yl}oxy)-5-methylphenyl]-2-methyl-1-(4-{4-[2-(4-methylphenoxy)ethyl]benzyl}piperazin-1-yl)but-2-en-1-one hydrobromide mp: 196.4-197.6° C.

Example 711

(E)-3-[3-Chloro-4-({5-[(2-chlorobenzyl)oxy]pyridin-2-yl}oxy)-5-methylphenyl]-1-(4-{4-[2-(4-methylphenoxy)ethyl]benzyl}piperazin-1-yl)but-2-en-1-one hydrobromide mp: 155.5-157.0° C.

Example 712

(E)-3-[3-Chloro-4-({5-[(2-chlorobenzyl)oxy]pyridin-2-yl}oxy)-5-methylphenyl]-1-(4-{4-[2-(4-chlorophenoxy)ethyl]benzyl}piperazin-1-yl)but-2-en-1-one hydrobromide mp: 142.2-144.1° C.

Example 713

(E)-3-[3-Chloro-4-({5-[(2-chlorobenzyl)oxy]pyridin-2-yl}oxy)-5-methylphenyl]-1-(4-{4-[2-(4-methoxyphenoxy)ethyl]benzyl}piperazin-1-yl)but-2-en-1-one hydrobromide mp: 144.3-145.8° C.

Example 714

(E)-1-(4-{4-[2-(4-Acetylphenoxy)ethyl]benzyl}piperazin-1-yl)-3-[3-chloro-4-({5-[(2-chlorobenzyl)oxy]pyridin-2-yl}oxy)-5-methylphenyl]prop-2-en-1-one hydrobromide ¹H-NMR (DMSO-d₆) δ: 2.11 (3H, s), 2.51 (3H, s), 3.05-3.44 (8H, m), 4.31-4.57 (6H, m), 5.17 (2H, s), 7.03 (2H, d, J=8.8 Hz), 7.12 (1H, d, J=9.0 Hz), 7.29-7.53 (9H, m), 7.60-7.67 (3H, m), 7.83-7.85 (2H, m), 7.92 (2H, d, J=8.8 Hz), 9.87 (1H, brs).

Example 715

(E)-3-[3-Chloro-4-({5-[(2-chlorobenzyl)oxy]pyridin-2-yl}oxy)-5-methylphenyl]-1-(4-{4-[2-(4-methylphenoxy)propyl]benzyl}piperazin-1-yl)prop-2-en-1-one hydrobromide ¹H-NMR (DMSO-d₆) δ: 1.21 (3H, d, J=6.1 Hz), 2.12 (3H, s), 2.21 (3H, s), 2.89 (1H, dd, J=13.9, 5.4 Hz), 2.98 (1H, dd, J=13.9, 6.6 Hz), 3.05-3.46 (6H, m), 4.35 (2H, brs), 4.54-4.56 (2H, m), 4.61-4.69 (1H, m), 5.17 (2H, s), 6.79 (2H, dt, J=9.2, 2.4 Hz), 7.05 (2H, d, J=8.1 Hz), 7.12 (1H, d, J=9.5 Hz), 7.30 (1H, d, J=15.4 Hz), 7.37-7.53 (8H, m), 7.60-7.67 (3H, m), 7.84 (1H, d, J=3.2 Hz), 7.85 (1H, d, J=2.0 Hz), 9.85 (1H, brs).

Example 716

(E)-3-[4-({5-[(4-Methoxybenzyl)oxy]pyridin-2-yl}oxy)-3,5-dimethylphenyl]-1-(4-{4-[2-(4-methylphenoxy)propyl]benzyl}piperazin-1-yl)prop-2-en-1-one hydrobromide ¹H-NMR (DMSO-d₆) δ: 1.21 (3H, d, J=6.1 Hz), 2.03 (6H, s), 2.21 (3H, s), 2.89 (1H, dd, J=13.8, 5.7 Hz), 2.99 (1H, dd, J=13.8, 6.6 Hz), 3.05-3.39 (6H, m), 3.76 (3H, s), 4.35 (2H, brs), 4.55 (2H, brs), 4.62-4.67 (1H, m), 5.01 (2H, s), 6.79 (2H, dt, J=9.3, 2.6 Hz), 6.94 (2H, dt, J=9.3, 2.6 Hz), 6.99 (1H, d, J=9.0 Hz), 7.05 (2H, d, J=8.3 Hz), 7.19 (1H, d, J=15.4 Hz), 7.35-7.50 (9H, m), 7.56 (1H, dd, J=9.0, 3.2 Hz), 7.78 (1H, d, J=3.2 Hz), 9.87 (1H, brs).

Example 717

(E)-3-[4-({5-[(4-Fluorobenzyl)oxy]pyridin-2-yl}oxy)-3,5-dimethylphenyl]-1-(4-{4-[2-(4-methylphenoxy)propyl]benzyl}piperazin-1-yl)prop-2-en-1-one hydrobromide ¹H-NMR (DMSO-d₆) δ: 1.21 (3H, d, J=6.1 Hz), 2.04 (6H, s), 2.21 (3H, s), 2.89 (1H, dd, J=13.8, 5.7 Hz), 2.99 (1H, dd, J=13.8, 6.7 Hz), 3.06-3.47 (6H, m), 4.35 (2H, brs), 4.53-4.56 (2H, m), 4.61-4.69 (1H, m), 5.08 (2H, s), 6.79 (2H, dt, J=9.0, 2.4 Hz), 7.00 (1H, d, J=9.3 Hz), 7.05 (2H, d, J=8.1 Hz), 7.17-7.25 (3H, m), 7.39 (2H, d, J=8.3 Hz), 7.44-7.52 (7H, m), 7.58 (1H, dd, J=9.3, 3.2 Hz), 7.80 (1H, d, J=3.2 Hz), 9.90 (1H, brs).

Example 718

(E)-3-[5-Chloro-4-({5-[(2-chlorobenzyl)oxy]pyridin-2-yl}oxy)-2-methylphenyl]-1-(4-{4-[2-(4-fluorophenoxy)ethyl]benzyl}piperazin-1-yl)prop-2-en-1-one hydrobromide ¹H-NMR (DMSO-d₆) δ: 2.34 (3H, s), 3.05-3.41 (8H, m), 4.20 (2H, t, J=6.4 Hz), 4.37 (2H, brs), 4.55-4.58 (2H, m), 5.19 (2H, s), 6.92-6.95 (2H, m), 7.08-7.14 (4H, m), 7.24 (1H, d, J=15.1 Hz), 7.38-7.53 (7H, m), 7.61-7.70 (3H, m), 7.91-7.92 (1H, m), 8.02 (1H, s), 9.92 (1H, brs).

Example 719

(E)-3-[5-Chloro-2-methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrobromide ¹H-NMR (DMSO-d₆) δ: 1.15 (6H, d, J=6.8 Hz), 2.30 (3H, s), 2.33 (3H, s), 2.81 (1H, septet, J=6.8 Hz), 3.05-3.63 (8H, m), 4.18 (2H, t, J=6.6 Hz), 4.37 (2H, brs), 4.55-4.58 (2H, m), 5.08 (2H, s), 6.82-6.85 (2H, m), 7.07-7.14 (4H, m), 7.19-7.25 (3H, m), 7.33 (2H, d, J=8.1 Hz), 7.43-7.48 (4H, m), 7.59 (1H, dd, J=9.0, 3.2 Hz), 7.68 (1H, d, J=15.1 Hz), 7.86 (1H, d, J=3.2 Hz), 8.01 (1H, s), 9.93 (1H, brs).

Example 720

(E)-3-[5-Chloro-2-methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one hydrobromide ¹H-NMR (DMSO-d₆) δ: 2.21 (3H, s), 2.30 (3H, s), 2.33 (3H, s), 3.04-3.60 (8H, m), 4.17 (2H, t, J=6.6 Hz), 4.36 (2H, brs), 4.55-4.58 (2H, m), 5.08 (2H, s), 6.79-6.83 (2H, m), 7.06-7.12 (4H, m), 7.19-7.25 (3H, m), 7.33 (2H, d, J=7.8 Hz), 7.43-7.48 (4H, m), 7.59 (1H, dd, J=9.0, 3.2 Hz), 7.67 (1H, d, J=15.4 Hz), 7.86 (1H, d, J=3.2 Hz), 8.01 (1H, s), 9.93 (1H, brs).

Example 721

(E)-3-[2-Chloro-4-({5-[(2-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrobromide ¹H-NMR (DMSO-d₆) δ: 2.15 (3H, s), 2.21 (3H, s), 3.04-3.42 (8H, m), 4.17 (2H, t, J=6.6 Hz), 4.35 (2H, brs), 4.55 (2H, brs), 5.20 (2H, s), 6.80-6.82 (2H, m), 7.08 (2H, d, J=8.1 Hz), 7.11 (1H, d, J=9.3 Hz), 7.16 (1H, s), 7.29 (1H, d, J=15.1 Hz), 7.36-7.44 (6H, m), 7.51-7.53 (1H, m), 7.61-7.67 (2H, m), 7.80 (1H, d, J=15.1 Hz), 7.95-7.96 (2H, m), 9.83 (1H, brs).

Example 722

(E)-3-[2-Chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)piperazin-1-yl]prop-2-en-1-one hydrobromide ¹H-NMR (DMSO-d₆) δ: 1.15 (6H, d, J=7.1 Hz), 2.14 (3H, s), 2.30 (3H, s), 2.81 (1H, septet, J=7.1 Hz), 3.05-3.56 (8H, m), 4.18 (2H, t, J=6.6 Hz), 4.36-4.55 (4H, m), 5.09 (2H, s), 6.82-6.85 (2H, m), 7.08 (1H, d, J=8.8 Hz), 7.11-7.14 (3H, m), 7.20 (2H, d, J=7.8 Hz), 7.29 (1H, d, J=15.1 Hz), 7.33 (2H, d, J=7.8 Hz), 7.45 (4H, brs), 7.60 (1H, dd, J=8.8, 2.9 Hz), 7.80 (1H, d, J=15.1 Hz), 7.90-7.91 (1H, m), 7.96 (1H, s), 9.86 (1H, brs).

Example 723

(E)-3-[2-Chloro-4-({5-[(2-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrobromide $^1$H-NMR (DMSO-$d_6$) δ: 1.15 (6H, d, J=6.8 Hz), 2.15 (3H, s), 2.81 (1H, septet, J=6.8 Hz), 3.05-3.38 (8H, m), 4.18 (2H, t, J=6.4 Hz), 4.36-4.55 (4H, m), 5.20 (2H, s), 6.82-6.84 (2H, m), 7.10-7.16 (4H, m), 7.29 (1H, d, J=15.4 Hz), 7.38-7.54 (7H, m), 7.61-7.67 (2H, m), 7.80 (1H, d, J=15.4 Hz), 7.95-7.96 (2H, m), 9.84 (1H, brs).

Example 724

(E)-3-[2-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrobromide $^1$H-NMR (DMSO-$d_6$) δ: 2.15 (3H, s), 3.05-3.48 (8H, m), 4.20 (2H, t, J=6.6 Hz), 4.36-4.55 (4H, m), 5.20 (2H, s), 6.92-6.96 (2H, m), 7.07-7.16 (4H, m), 7.29 (1H, d, J=15.1 Hz), 7.37-7.54 (7H, m), 7.61-7.68 (2H, m), 7.80 (1H, d, J=15.1 Hz), 7.95-7.96 (2H, m), 9.87 (1H, brs).

Example 725

(E)-1-(4-{4-[2-(4-Fluorophenoxy)propyl]benzyl}piperazin-1-yl)-3-[4-({5-[(4-methoxybenzyl)-oxy]pyridin-2-yl}oxy)-3,5-dimethylphenyl]prop-2-en-1-one hydrobromide $^1$H-NMR (DMSO-$d_6$) δ: 1.22 (3H, d, J=5.9 Hz), 2.03 (6H, s), 2.90 (1H, dd, J=13.9, 5.4 Hz), 2.99 (1H, dd, J=13.9, 6.6 Hz), 3.05-3.38 (6H, m), 3.76 (3H, s), 4.35 (2H, brs), 4.56 (2H, brs), 4.62-4.71 (1H, m), 5.01 (2H, s), 6.90-6.96 (4H, m), 6.99 (1H, d, J=9.3 Hz), 7.05-7.12 (2H, m), 7.19 (1H, d, J=15.4 Hz), 7.35-7.50 (9H, m), 7.57 (1H, dd, J=9.3, 3.2 Hz), 7.78 (1H, d, J=3.2 Hz), 9.88 (1H, brs).

Example 726

(E)-3-[4-({5-[(4-Fluorobenzyl)oxy]pyridin-2-yl}oxy)-3,5-dimethylphenyl]-1-(4-{4-[2-(4-fluorophenoxy)propyl]benzyl}piperazin-1-yl)prop-2-en-1-one hydrobromide $^1$H-NMR (DMSO-$d_6$) δ: 1.22 (3H, d, J=6.1 Hz), 2.03 (6H, s), 2.90 (1H, dd, J=13.9, 5.6 Hz), 2.99 (1H, dd, J=13.9, 6.7 Hz), 3.04-3.39 (6H, m), 4.35 (2H, brs), 4.55 (2H, brs), 4.62-4.70 (1H, m), 5.08 (2H, s), 6.89-6.94 (2H, m), 7.01 (1H, d, J=9.0 Hz), 7.05-7.11 (2H, m), 7.17-7.26 (3H, m), 7.39-7.52 (9H, m), 7.59 (1H, dd, J=9.0, 3.2 Hz), 7.80 (1H, d, J=3.2 Hz), 9.85 (1H, brs).

Example 727

(E)-3-[3-Chloro-5-methyl-4-({5-[(4-methylbenzyl)oxy]pyridin-2-yl}oxy)phenyl]-2-methyl-1-[4-(4-{[4-(propan-2-yl)phenoxy]methyl}benzyl)piperazin-1-yl]prop-2-en-1-one hydrobromide mp: 197.0-199.1° C.

Example 728

(E)-3-[3-Chloro-5-methyl-4-({5-[(4-methylbenzyl)oxy]pyridin-2-yl}oxy)phenyl]-1-[4-(4-{[4-(propan-2-yl)phenoxy]methyl}benzyl)piperazin-1-yl]but-2-en-1-one hydrobromide mp: 166.7-168.8° C.

Example 729

(E)-3-[3-Chloro-4-({5-[(2-chlorobenzyl)oxy]pyridin-2-yl}oxy)-5-methylphenyl]-2-methyl-1-[4-(4-{[4-(propan-2-yl)phenoxy]methyl}benzyl)piperazin-1-yl]prop-2-en-1-one hydrobromide mp: 211.3-211.9° C.

Example 730

(E)-3-[3-Chloro-4-({5-[(2-chlorobenzyl)oxy]pyridin-2-yl}oxy)-5-methylphenyl]-1-[4-(4-{3-[4-(propan-2-yl)phenoxy]propyl}benzyl)piperazin-1-yl]prop-2-en-1-one hydrobromide $^1$H-NMR (DMSO-$d_6$) δ: 1.16 (6H, d, J=6.8 Hz), 1.99-2.05 (2H, m), 2.11 (3H, s), 2.76-3.48 (9H, m), 3.94 (2H, t, J=6.4 Hz), 4.36 (2H, brs), 4.54-4.57 (2H, m), 5.17 (2H, s), 6.82-6.85 (2H, m), 7.11-7.14 (3H, m), 7.29-7.53 (9H, m), 7.59-7.67 (3H, m), 7.83-7.86 (2H, m), 9.88-9.96 (1H, m).

Example 731

(E)-3-[3-Chloro-4-({5-[(2-chlorobenzyl)oxy]pyridin-2-yl}oxy)-5-methylphenyl]-2-methyl-1-[4-(4-{[4-(propan-2-yl)phenoxy]methyl}benzyl)piperazin-1-yl]but-2-en-1-one hydrobromide mp: 200.5-202.1° C.

Example 732

(E)-3-[3-Chloro-4-({5-[(2-chlorobenzyl)oxy]pyridin-2-yl}oxy)-5-methylphenyl]-1-[4-(4-{[4-(propan-2-yl)phenoxy]methyl}benzyl)piperazin-1-yl]but-2-en-1-one hydrobromide mp: 167.3-168.9° C.

Example 733

(E)-3-[3-Chloro-5-methyl-4-({5-[(4-methylbenzyl)oxy]pyridin-2-yl}oxy)phenyl]-1-{4-[4-({[4-(propan-2-yl)benzyl]oxy}methyl)benzyl]piperazin-1-yl}prop-2-en-1-one hydrobromide $^1$H-NMR (DMSO-$d_6$) δ: 1.19 (6H, d, J=6.8 Hz), 2.10 (3H, s), 2.30 (3H, s), 2.85-3.48 (7H, m), 4.38 (2H, brs), 4.52-4.56 (6H, m), 5.05 (2H, s), 7.08 (1H, d, J=9.0 Hz), 7.18-7.24 (4H, m), 7.27-7.33 (5H, m), 7.46-7.51 (5H, m), 7.58-7.62 (2H, m), 7.78 (1H, d, J=2.9 Hz), 7.84 (1H, d, J=1.7 Hz), 9.89 (1H, brs).

Example 734

(E)-3-[3-Chloro-4-({5-[(2-chlorobenzyl)oxy]pyridin-2-yl}oxy)-5-methylphenyl]-1-{4-[4-({[4-(propan-2-yl)benzyl]oxy}methyl)benzyl]piperazin-1-yl}prop-2-en-1-one hydrobromide $^1$H-NMR (DMSO-d$_6$) δ: 1.19 (6H, d, J=6.8 Hz), 2.11 (3H, s), 2.85-3.54 (7H, m), 4.39 (2H, brs), 4.52-4.56 (6H, m), 5.17 (2H, s), 7.12 (1H, d, J=9.0 Hz), 7.22-7.32 (5H, m), 7.37-7.32 (8H, m), 7.60-7.66 (3H, m), 7.83-7.85 (2H, m), 9.93 (1H, brs).

Example 735

(E)-3-[5-Chloro-4-({5-[(2-chlorobenzyl)oxy]pyridin-2-yl}oxy)-2-methylphenyl]-1-[4-(4-{[4-(propan-2-yl)phenoxy]methyl}benzyl)piperazin-1-yl]prop-2-en-1-one hydrobromide $^1$H-NMR (DMSO-d$_6$) δ: 1.16 (6H, d, J=6.8 Hz), 2.34 (3H, s), 2.83 (1H, septet, J=6.8 Hz), 3.06-3.60 (6H, m), 4.40 (2H, brs), 4.55-4.58 (2H, m), 5.12 (2H, s), 5.19 (2H, s), 6.91-6.95 (2H, m), 7.11-7.17 (4H, m), 7.24 (1H, d, J=15.1 Hz), 7.37-7.44 (2H, m), 7.50-7.70 (8H, m), 7.91-7.92 (1H, m), 8.02 (1H, s), 9.92 (1H, brs).

Example 736

(E)-3-[3-Chloro-4-({5-[(4-fluorobenzyl)oxy]pyridin-2-yl}oxy)phenyl]-1-[4-(4-{2-[(4-fluorophenyl)amino]ethyl}benzyl)piperazin-1-yl]prop-2-en-1-one dihydrobromide mp: 194.9-196.6° C.

Example 737

(E)-3-[5-Chloro-2-methyl-4-({5-[(4-methylbenzyl)oxy]pyridin-2-yl}oxy)phenyl]-1-[4-(4-{[4-(propan-2-yl)phenoxy]methyl}benzyl)piperazin-1-yl]prop-2-en-1-one hydrobromide $^1$H-NMR (DMSO-d$_6$) δ: 1.16 (6H, d, J=6.8 Hz), 2.30 (3H, s), 2.33 (3H, s), 2.83 (1H, septet, J=6.8 Hz), 3.07-3.40 (6H, m), 4.40-4.58 (4H, m), 5.08 (2H, s), 5.12 (2H, s), 6.91-6.95 (2H, m), 7.07-7.25 (7H, m), 7.33 (2H, d, J=8.1 Hz), 7.53-7.61 (5H, m), 7.68 (1H, d, J=15.1 Hz), 7.86-7.87 (1H, m), 8.01 (1H, s), 9.91 (1H, brs).

Example 738

(E)-3-[2-Chloro-4-({5-[(2-chlorobenzyl)oxy]pyridin-2-yl}oxy)-5-methylphenyl]-1-[4-(4-{[4-(propan-2-yl)phenoxy]methyl}benzyl)piperazin-1-yl]prop-2-en-1-one hydrobromide $^1$H-NMR (DMSO-d$_6$) δ: 1.16 (6H, d, J=6.8 Hz), 2.15 (3H, s), 2.83 (1H, septet, J=6.8 Hz), 3.09-3.58 (6H, m), 4.41-4.57 (4H, m), 5.12 (2H, s), 5.20 (2H, s), 6.93 (2H, d, J=8.6 Hz), 7.10-7.17 (4H, m), 7.31 (1H, d, J=15.4 Hz), 7.38-7.44 (2H, m), 7.50-7.68 (7H, m), 7.81 (1H, d, J=15.4 Hz), 7.95 (1H, d, J=3.2 Hz), 7.98 (1H, s), 9.97 (1H, brs).

Example 739

4-({[6-(2-Chloro-5-methyl-4-{(E)-3-oxo-3-[4-(4-{[4-(propan-2-yl)phenoxy]methyl}benzyl)-piperazin-1-yl]prop-1-en-1-yl}phenoxy)pyridin-3-yl]oxy}methyl)benzonitrile hydrobromide $^1$H-NMR (DMSO-d$_6$) δ: 1.16 (6H, d, J=6.8 Hz), 2.34 (3H, s), 2.83 (1H, septet, J=6.8 Hz), 3.06-3.63 (6H, m), 4.41-4.58 (4H, m), 5.12 (2H, s), 5.26 (2H, s), 6.91-6.95 (2H, m), 7.10-7.18 (4H, m), 7.24 (1H, d, J=15.1 Hz), 7.56 (4H, s), 7.61-7.70 (4H, m), 7.87-7.90 (3H, m), 8.02 (1H, s), 10.00 (1H, brs).

Example 740

(2E)-3-[4-({5-[(4-Fluorobenzyl)oxy]pyridin-2-yl}oxy)-3,5-dimethylphenyl]-1-(4-{4-[(1E)-3-methoxyprop-1-en-1-yl]benzyl}piperazin-1-yl)prop-2-en-1-one hydrobromide $^1$H-NMR (DMSO-d$_6$) δ: 2.03 (6H, s), 3.05-3.52 (6H, m), 3.30 (3H, s), 4.06 (2H, dd, J=5.5, 1.3 Hz), 4.37 (2H, brs), 4.55 (2H, brs), 5.08 (2H, s), 6.46 (1H, dt, J=16.4, 5.5 Hz), 6.65 (1H, d, J=16.4 Hz), 7.01 (1H, d, J=8.8 Hz), 7.18-7.25 (3H, m), 7.46-7.52 (7H, m), 7.57-7.60 (3H, m), 7.80 (1H, d, J=3.2 Hz), 9.87 (1H, brs).

Example 741

4-{[(6-{4-[(E)-3-{4-[4-(2-Hydroxyethyl)benzyl]piperazin-1-yl}-3-oxoprop-1-en-1-yl]-2,6-dimethylphenoxy}pyridin-3-yl)oxy]methyl}benzonitrile hydrobromide $^1$H-NMR (DMSO-d$_6$) δ: 2.03 (6H, s), 2.77 (2H, t, J=7.0 Hz), 3.05-3.07 (3H, m), 3.39-3.41 (3H, m), 3.63 (2H, t, J=7.0 Hz), 4.34-4.37 (2H, m), 4.55-4.57 (2H, m), 5.22 (2H, s), 7.02 (1H, d, J=8.8 Hz), 7.20 (1H, d, J=15.4 Hz), 7.34 (2H, d, J=7.8 Hz), 7.43-7.50 (5H, m), 7.60-7.64 (3H, m), 7.82-7.88 (3H, m), 9.90 (1H, s).

Example 742

(E)-3-(3,5-Dimethyl-4-{[5-(pyridin-4-ylmethoxy)pyridin-2-yl]oxy}phenyl)-1-{4-[4-(2-hydroxyethyl)benzyl]piperazin-1-yl}prop-2-en-1-one hydrobromide $^1$H-NMR (DMSO-d$_6$) δ: 2.04 (6H, s), 2.77 (2H, t, J=6.8 Hz), 3.08-3.10 (3H, m), 3.38-3.41 (3H, m), 3.63 (2H, t, J=6.8 Hz), 4.36-4.38 (2H, m), 4.54-4.56 (2H, m), 5.45 (2H, s), 7.06 (1H, d, J=9.0 Hz), 7.21 (1H, d, J=15.4 Hz), 7.34 (2H, d, J=8.1 Hz), 7.46-7.49 (5H, m), 7.66 (1H, dd, J=8.9, 2.9 Hz), 7.87 (1H, d, J=2.9 Hz), 7.98 (2H, d, J=6.3 Hz), 8.89 (2H, d, J=6.3 Hz), 10.03 (1H, s).

Example 743

(2E)-3-[4-({5-[(4-Methoxybenzypoxy]pyridin-2-yl}oxy)-3,5-dimethylphenyl]-1-(4-{4-[(1E)-3-methoxyprop-1-en-1-yl]benzyl}piperazin-1-yl)prop-2-en-1-one hydrobromide $^1$H-NMR (DMSO-d$_6$) δ: 2.03 (6H, s), 3.06-3.42 (6H, m), 3.30 (3H, s), 3.75 (3H, s), 4.06 (2H, dd, J=5.6, 1.2 Hz), 4.37

(2H, brs), 4.56 (2H, brs), 5.01 (2H, s), 6.46 (1H, dt, J=15.9, 5.6 Hz), 6.65 (1H, d, J=15.9 Hz), 6.94 (2H, dt, J=9.4, 2.6 Hz), 6.99 (1H, d, J=9.0 Hz), 7.20 (1H, d, J=15.4 Hz), 7.37 (2H, dt, J=9.4, 2.6 Hz), 7.47-7.50 (5H, m), 7.55-7.59 (3H, m), 7.78 (1H, d, J=3.2 Hz), 9.91 (1H, brs).

Example 744

(E)-3-[4-({5-[(2-Chlorobenzyl)oxy]pyridin-2-yl}oxy)-3-methoxyphenyl]-1-{4-[4-(2-hydroxyethyl)benzyl]piperazin-1-yl}prop-2-en-1-one hydrobromide mp: 206.8-207.6° C.

Example 745

(E)-3-{3-Chloro-4-[(5-{[4-(difluoromethoxy)benzyl]oxy}pyridin-2-yl)oxy]-5-methylphenyl}-1-{4-[4-(propan-2-yloxy)benzyl]piperazin-1-yl}prop-2-en-1-one hydrobromide mp: 176.7-178.2° C.
$^1$H-NMR (DMSO-$d_6$) δ: 1.28 (6H, d, J=6.1 Hz), 2.11 (3H, s), 3.03-4.57 (10H, m), 4.66 (1H, septet, J=6.1 Hz), 5.10 (2H, s), 7.01 (2H, d, J=8.5 Hz), 7.11 (1H, d, J=8.8 Hz), 7.20 (2H, d, J=8.3 Hz), 7.24 (1H, t, J=74.0 Hz), 7.30 (1H, d, J=15.1 Hz), 7.41-7.52 (5H, m), 7.60-7.63 (2H, m), 7.80 (1H, d, J=2.9 Hz), 7.84 (1H, brs), 9.75 (1H, brs).

Example 746

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)but-2-en-1-one ethanedioate mp: 211.3-211.7° C.

Example 747

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)-2-methyl-prop-2-en-1-one ethanedioate mp: 196.8-197.0° C.

Example 748

(E)-3-[3-Chloro-4-({5-[(2-chlorobenzyl)oxy]pyridin-2-yl}oxy)-5-methylphenyl]-2-methyl-1-[4-(4-{2-[4-(propan-2-yl)phenoxy]ethyl}benzyl)piperazin-1-yl]prop-2-en-1-one ethanedioate mp: 198.6-198.8° C.

Example 749

(E)-3-[3-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)-2-methylprop-2-en-1-one ethanedioate mp: 201.4-201.6° C.

Example 750

(E)-3-[3-Chloro-4-({5-[(2-chlorobenzyl)oxy]pyridin-2-yl}oxy)-5-methylphenyl]-2-methyl-1-(4-{4-[2-(4-methylphenoxy)ethyl]benzyl}piperazin-1-yl)prop-2-en-1-one ethanedioate mp: 199.2-199.6° C.

Example 751

(E)-3-[3-Chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)-2-methyl-but-2-en-1-one ethanedioate mp: 236.1-236.6° C.

Example 752

(E)-3-[3-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)-2-methylbut-2-en-1-one ethanedioate mp: 234.4-235.2° C.

Example 753

(E)-3-[3-Chloro-4-({5-[(2-chlorobenzyl)oxy]pyridin-2-yl}oxy)-5-methylphenyl]-2-methyl-1-[4-(4-{2-[4-(propan-2-yl)phenoxy]ethyl}benzyl)piperazin-1-yl]but-2-en-1-one ethanedioate mp: 233.5-233.9° C.

Example 754

(E)-3-[3-Chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)but-2-en-1-one ethanedioate mp: 174.1-175.0° C.

Example 755

(E)-3-[3-Chloro-4-({5-[(2-chlorobenzyl)oxy]pyridin-2-yl}oxy)-5-methylphenyl]-1-[4-(4-{2-[4-(propan-2-yl)phenoxy]ethyl}benzyl)piperazin-1-yl]but-2-en-1-one ethanedioate mp: 167.3-169.4° C.

Example 756

(E)-3-[3-Chloro-4-({5-[(2-chlorobenzyl)oxy]pyridin-2-yl}oxy)-5-methylphenyl]-1-[4-(4-ethenylbenzyl)piperazin-1-yl]prop-2-en-1-one (2Z)-but-2-enedioate $^1$H-NMR (DMSO-$d_6$) δ: 2.11 (3H, s), 2.93-4.05 (10H, m), 5.17 (2H, s), 5.31 (1H, d, J=11.0 Hz), 5.88 (1H, d, J=17.6 Hz), 6.11 (2H, s), 6.76 (1H, dd, J=17.6, 11.0 Hz), 7.11 (1H, d, J=9.0 Hz), 7.29 (1H, d, J=15.4 Hz), 7.37-7.55 (8H, m), 7.60-7.66 (3H, m), 7.83-7.85 (2H, m).

Example 757

To a solution of (E)-3-[3-chloro-4-({5-[(4-fluorobenzyl)oxy]pyridin-2-yl}oxy)phenyl]prop-2-enoic acid (212 mg) in DMF (7.0 mL) were added 1-{4-[2-(3-methoxyphenoxy)ethyl]benzyl}piperazine (190 mg), HOBT (89 mg) and WSC (112 mg) at room temperature, then the reaction mixture was stirred over night. The reaction mixture was basified with saturated aqueous NaHCO$_3$, extracted with AcOEt. The organic layer was washed with water and saturated aqueous NaCl, dried over anhydrous Na$_2$SO$_4$, and concentrated under reduced pressure. The residue was purified by silica gel column chromatography (n-hexane/AcOEt=1/4 to 0/1 and then MeOH/AcOEt=1/9) to afford (E)-3-[3-chloro-4-({5-[(4-fluorobenzyl)oxy]pyridin-2-yl}oxy)phenyl]-1-(4-{2-(3-methoxyphenoxy)ethyl]benzyl}-piperazin-1-yl)prop-2-en-1-one (387 mg) as a colorless amorphous. To a solution of that amorphous (387 mg) in AcOEt (7.0 mL) was added 6 M aqueous HCl (0.088 mL) at room temperature, and then the reaction mixture was stirred for 30 minutes. The reaction mixture was filtered off, and the crude crystal was recrystallized from EtOH—H$_2$O to afford (E)-3-[3-chloro-4-({5-[(4-fluorobenzyl)oxy]pyridin-2-yl}oxy)phenyl]-1-(4-{4-[2-(3-methoxyphenoxy)ethyl]benzyl}piperazin-1-yl)prop-2-en-1-one hydrochloride as a colorless powder (333 mg).

mp: 201.5-202.0° C.

The following compounds were produced in the same manner as in Example 757 using appropriate starting materials.

Example 758

(E)-3-[3-Chloro-5-methyl-4-({5-[(4-methylbenzyl)oxy]pyridin-2-yl}oxy)phenyl]-2-methyl-1-[4-(4-{2-[4-(propan-2-yl)phenoxy]ethyl}benzyl)piperazin-1-yl]prop-2-en-1-one ethanedioate mp: 193.3-193.5° C.

Example 759

(E)-1-[4-(4-Chlorobenzyl)piperazin-1-yl]-3-[3-chloro-5-methyl-4-({5-[(4-methylbenzyl)oxy]-pyridin-2-yl}oxy)phenyl]-2-methylprop-2-en-1-one hydrobromide mp: 212.4-213.0° C.

Example 760

(E)-3-[3-Chloro-5-methyl-4-({5-[(4-methylbenzyl)oxy]pyridin-2-yl}oxy)phenyl]-1-[4-(4-methylbenzyl)piperazin-1-yl]but-2-en-1-one hydrobromide mp: 188.2-188.5° C.

Example 761

(E)-1-[4-(4-Chlorobenzyl)piperazin-1-yl]-3-[3-chloro-5-methyl-4-({5-[(4-methylbenzyl)oxy]-pyridin-2-yl}oxy)phenyl]but-2-en-1-one hydrobromide mp: 194.5-195.2° C.

Example 762

(E)-3-[3-Chloro-4-({5-[2-(4-chlorophenyl)ethoxy]pyridin-2-yl}oxy)-5-methylphenyl]-1-[4-(4-methylbenzyl)piperazin-1-yl]prop-2-en-1-one hydrochloride mp: 217.7-218.4° C.

Example 763

(E)-3-[3-Chloro-4-({5-[2-(4-chlorophenyl)ethoxy]pyridin-2-yl}oxy)-5-methylphenyl]-1-[4-(4-methoxybenzyl)piperazin-1-yl]prop-2-en-1-one hydrochloride mp: 192.9-193.4° C.

Example 764

(E)-3-[3-Chloro-4-({5-[2-(4-chlorophenyl)ethoxy]pyridin-2-yl}oxy)-5-methylphenyl]-1-{4-[4-(trifluoromethoxy)benzyl]piperazin-1-yl}prop-2-en-1-one hydrochloride mp: 202.4-203.2° C.

Example 765

(E)-1-[4-(4-Chlorobenzyl)piperazin-1-yl]-3-[3-chloro-4-({5-[2-(4-chlorophenyl)ethoxy]pyridin-2-yl}oxy)-5-methylphenyl]prop-2-en-1-one hydrochloride mp: 220.0-220.9° C.

Example 766

(E)-3-[3-Chloro-5-methyl-4-({5-[2-(4-methylphenyl)ethoxy]pyridin-2-yl}oxy)phenyl]-1-[4-(4-methylbenzyl)piperazin-1-yl]prop-2-en-1-one hydrochloride mp: 219.7-220.0° C.

Example 767

(E)-3-[3-Chloro-4-({5-[2-(3,4-dichlorophenyl)ethoxy]pyridin-2-yl}oxy)-5-methylphenyl]-1-[4-(4-methylbenzyl)piperazin-1-yl]prop-2-en-1-one hydrochloride mp: 208.3-209.7° C.

Example 768

(E)-3-[3-Chloro-5-methyl-4-({5-[(4-methylbenzyl)oxy]pyridin-2-yl}oxy)phenyl]-2-methyl-1-[4-(4-methylbenzyl)piperazin-1-yl]prop-2-en-1-one hydrochloride mp: 194.2-195.0° C.

Example 769

(E)-3-[3-Chloro-4-({5-[(2-chlorobenzyl)oxy]pyridin-2-yl}oxy)-5-methylphenyl]-2-methyl-1-[4-(4-methylbenzyl)piperazin-1-yl]prop-2-en-1-one hydrobromide mp: 205.8-205.9° C.

Example 770

(E)-1-[4-(4-Chlorobenzyl)piperazin-1-yl]-3-[3-chloro-4-({5-[(2-chlorobenzyl)oxy]pyridin-2-yl}oxy)-5-methylphenyl]-2-methylprop-2-en-1-one hydrobromide mp: 209.3-209.6° C.

Example 771

(E)-3-[3-Chloro-5-methyl-4-({5-[(4-methylbenzyl)oxy]pyridin-2-yl}oxy)phenyl]-2-methyl-1-[4-(4-methylbenzyl)piperazin-1-yl]but-2-en-1-one hydrobromide mp: 228.2-228.5° C.

Example 772

(E)-1-[4-(4-Chlorobenzyl)piperazin-1-yl]-3-[3-chloro-5-methyl-4-({5-[(4-methylbenzyl)oxy]-pyridin-2-yl}oxy)phenyl]-2-methylbut-2-en-1-one hydrobromide mp: 227.5-228.3° C.

Example 773

(E)-1-[4-(4-Chlorobenzyl)piperazin-1-yl]-3-[3-chloro-4-({5-[(2-chlorobenzyl)oxy]pyridin-2-yl}oxy)-5-methylphenyl]-2-methylbut-2-en-1-one hydrobromide mp: 242.4-243.1° C.

Example 774

(E)-3-[3-Chloro-4-({5-[(2-chlorobenzyl)oxy]pyridin-2-yl}oxy)-5-methylphenyl]-2-methyl-1-[4-(4-methylbenzyl)piperazin-1-yl]but-2-en-1-one hydrobromide mp: 240.4-240.9° C.

Example 775

(E)-1-[4-(4-Chlorobenzyl)piperazin-1-yl]-3-[3-chloro-4-({5-[(2-chlorobenzyl)oxy]pyridin-2-yl}oxy)-5-methylphenyl]but-2-en-1-one hydrobromide mp: 205.8-206.5° C.

Example 776

(E)-3-[3-Chloro-4-({5-[(2-chlorobenzyl)oxy]pyridin-2-yl}oxy)-5-methylphenyl]-1-[4-(4-methylbenzyl)piperazin-1-yl]but-2-en-1-one hydrobromide mp: 156.4-158.6° C.

Example 777

To a solution of (E)-3-{3-chloro-4-[(5-hydroxypyridin-2-yl)oxy]-5-methylphenyl}-1-(4-{4-[2-(4-methylphenoxy)ethyl]benzyl}piperazin-1-yl)prop-2-en-1-one (479 mg) and p-chlorobenzyl chloride (129 mg) in DMF (5.0 mL) was added NaH (41.6 mg, 60% in mineral oil) at 0° C. Then the reaction mixture was stirred over night at room temperature. The reaction mixture was quenched by addition of saturated aqueous NH$_4$Cl, and extracted with AcOEt. The organic layer was washed with water and saturated aqueous NaCl, dried over anhydrous Na$_2$SO$_4$, and concentrated under reduced pressure. The residue was purified by silica gel column chromatography (n-hexane/AcOEt=1/0 to 9/1) to afford (E)-3-[3-chloro-4-({5-[(4-chlorobenzyl)oxy]pyridin-2-yl}oxy)-5-methylphenyl]-1-(4-{4-[2-(4-methylphenoxy)-ethyl]benzyl}piperazin-1-yl)prop-2-en-1-one (507 mg) as a colorless amorphous. To a solution of that amorphous (507 mg) in EtOH (10 mL) was added 6 M aqueous HCl (0.129 mL) at room temperature, then the reaction mixture was stirred for 3 hours. The reaction mixture was filtered off, and the precipitate was dried at 50° C. under reduced pressure to afford (E)-3-[3-chloro-4-({5-[(4-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride (486 mg) as a colorless crystal.

mp: 220.1-220.3° C.

The following compounds were produced in the same manner as in Example 777 using appropriate starting materials.

Example 778

(E)-3-{3-Chloro-5-methyl-4-[(5-{[4-(trifluoromethyl)benzyl]oxy}pyridin-2-yl)oxy]phenyl}-1-[4-(4-methylbenzyl)piperazin-1-yl]prop-2-en-1-one hydrochloride mp: 227.1-228.2° C.

Example 779

(E)-3-[3-Chloro-4-({5-[(4-fluorobenzyl)oxy]pyridin-2-yl}oxy)-5-methylphenyl]-1-[4-(4-methylbenzyl)piperazin-1-yl]prop-2-en-1-one hydrochloride mp: 223.9-224.5° C.

Example 780

(E)-3-[3-Chloro-4-({5-[(3,4-dichlorobenzyl)oxy]pyridin-2-yl}oxy)-5-methylphenyl]-1-[4-(4-methylbenzyl)piperazin-1-yl]prop-2-en-1-one hydrochloride mp: 218.7-220.1° C.

Example 781

(E)-3-[3-Chloro-4-({5-[(4-chlorobenzyl)oxy]pyridin-2-yl}oxy)-5-methylphenyl]-1-[4-(4-methylbenzyl)piperazin-1-yl]prop-2-en-1-one hydrochloride mp: 223.1-224.0° C.

Pharmacological Test

Antiproliferative Effect on Cancer Cell (in vitro)

The growth inhibition on a bicalutamide resistant human prostate cancer cell line established from LNCaP.FGC (LNCaP-Bic) (Hobisch A, et al. Prostate. 2006; 66(4):413-20.) was determined by a WST-8 assay according to the method of Singh A K, et al. (Cancer Lett. 1996 Oct. 1; 107(1): 109-15.). In this method, LNCaP-Bic cells were seeded in RPMI 1640 medium containing 10% fetal bovine serum in a 96-well microplate and incubated at 37° C. for 24 hours in the presence of 5% carbon dioxide. Then, the test compound was added and the cells were incubated for another 5 days. After incubation, a 15-μL volume of WST-8 (2-(2-methoxy-4-nitrophenyl)-3-(4-nitrophenyl)-5-(2,4-disulfenyl)-2H-tetrazolium, monosodium salt) was added. After the incubation for the time, the color reaction was stopped by adding 15 μL of 1% SDS (sodium dodecyl sulfate) solution and the optical density was determined at the measurement wavelength of 450 nm and the reference wavelength of 630 nm, and the difference was calculated. The cell growth activity in each well was defined as the value determined by subtracting the OD in the control well not containing cells (the difference in absorbance between 450 nm and 630 nm) from that in the test well.

The 50% inhibitory concentration ($IC_{50}$ (nM)) of the test compound was determined by comparing the cell growth activity in the well containing the test compound with that of the control not containing the test compound.

The growth inhibition on a human prostate (carcinoma) cell line (LNCaP.FGC) (van Bokhoven A, et al. Prostate. 2003; 57(3):205-25.) was also determined by the above method.

The growth inhibition on a human prostate (adenocarcinoma) cell line (VcaP) (Korenchuk S, et al. In Vivo. 2001; 15(2):163-8.) was also determined by the above method.

The growth inhibition on a human prostate (carcinoma) cell line (DU 145) (van Bokhoven A, et al. Prostate. 2003; 57(3):205-25.) was also determined by the above method.

The growth inhibition on a human prostate (adenocarcinoma) cell line (PC-3) (van Bokhoven A, et al. Prostate. 2003; 57(3):205-25.) was also determined by the above method.

The results are shown in Table 2.

Growth inhibition of a human breast cancer cell line (MDA-MB-468) was determined by the sulforhodamine B method based on the method of Skehan P. et al. (J Natl Cancer Inst. 1990 Jul. 4; 82(13): 1107-12). In the study, MDA-MB-468 cells were seeded on DMEM medium containing 10% fetal bovine serum in a 96-well microplate. After 24-h incubation at 37° C. in the presence of 5% carbon dioxide, the test compound was added and the cells were incubated for another 5 days. After incubation, a trichloroacetic acid solution was added to yield the final concentration of 10% and the cells were left to stand at 4° C. for 1 hour to fix. Then, the cells were washed with water to remove the medium and trichloroacetic acid and dried in the air. The dried cells were stored at 4° C. until they were stained with sulforhodamine B. To each well, 1% acetic acid solution containing 0.4% sulforhodamine B was added and left to stand for 20 to 30 minutes at room temperature. After discarding the supernatant, each well was washed with 1% acetic acid solution, and 10 mM Tris(trishydroxyaminomethane) solution was added while stirring to elute the dye taken into the cells. Then, the optical density was determined at the measurement wavelength of 492 nm and the reference wavelength of 690 nm, and the difference was calculated. The cell growth activity in each well was defined as the value determined by subtracting the OD in the control well not containing cells (the difference in absorbance between 492 nm and 690 nm) from that in the test well.

The 50% inhibitory concentration ($IC_{50}$ (nM)) of the test compound was determined by comparing the cell growth activity in the well containing the test compound with that of the control not containing the test compound.

The results are shown in Table 3.

The growth inhibition on a human hepatic cancer cell line (HuH-7) was also determined by the above method.

The results are shown in Table 4.

Antitumor Effect on Prostate Cancer Cells, LNCaP-Bic (in vivo)

Human prostate cancer cells (LNCaP-Bic) were transplanted in nude mice (6 males/group) and the inhibitory effect of the invention on their growth was examined. In the study, the tumor cell suspension with matrigel was inoculated at 0.12 mL/body ($2.4 \times 10^6$ cells/body) into the subcutaneous space of the right axillary region to prepare tumor bearing mice. When the tumor diameter became 5 mm or more, the animals were allocated to groups based on the tumor volume. The test compound was administered orally as a suspension in 5% gum arabic, once daily, for 14 consecutive days. The control group received 5% gum arabic. Tumor volumes were measured on the following day of the last administration. Tumors were removed and the wet weight of the tumor was measured using an electronic balance. The ratio of the tumor weight in the treated group to that in the control group (T/C %) was calculated as the index for the effect.

$T/C$ %=(Mean tumor weight in the treatment group/ Mean tumor weight in the control group)×100.

The results are shown in Table 5.

The heparinized blood was collected from the postcava under diethylether anesthesia. The plasma levels of PSA were measured using ELISA. The ratio of the plasma levels of PSA in the treated group to that in the control group (T/C %) was calculated as the index for the effect.

$T/C$ %=(Mean plasma levels of *PSA* in the treatment group/Mean plasma levels of PSA in the control group)×100.

The results are shown in Table 6.

TABLE 2

| | $IC_{50}$(nM) | | | | |
|---|---|---|---|---|---|
| Test compound | LNCaP-Bic | LNCaP•FGC | VcaP | DU 145 | PC-3 |
| Compound of Example 1 | <10 | <10 | <10 | <10 | <10 |
| Compound of Example 392 | <10 | <10 | <10 | <10 | <10 |
| Compound of Example 408 | <10 | <10 | <10 | <10 | <10 |
| Compound of Example 427 | <10 | <10 | <10 | <10 | <10 |
| Compound of Example 429 | <10 | <10 | <10 | <10 | <10 |
| Compound of Example 430 | <10 | <10 | <10 | <10 | <10 |
| Compound of Example 432 | <10 | <10 | <10 | <10 | <10 |
| Compound of Example 435 | <10 | <10 | <10 | <10 | <10 |
| Compound of Example 438 | <10 | <10 | <10 | <10 | <10 |
| Compound of Example 440 | <10 | <10 | <10 | <10 | <10 |
| Compound of Example 447 | <10 | <10 | <10 | <10 | <10 |
| Compound of Example 448 | <10 | <10 | <10 | <10 | <10 |
| Compound of Example 451 | <10 | <10 | <10 | <10 | <10 |
| Compound of Example 452 | <10 | <10 | <10 | <10 | <10 |
| Compound of Example 454 | <10 | <10 | <10 | <10 | <10 |
| Compound of Example 466 | <10 | <10 | <10 | <10 | <10 |
| Compound of Example 507 | <10 | <10 | <10 | <10 | <10 |
| Compound of Example 558 | <10 | <10 | <10 | <10 | <10 |
| Compound of Example 593 | <10 | <10 | <10 | <10 | <10 |
| Compound of Example 594 | <10 | <10 | <10 | <10 | <10 |
| Compound of Example 595 | <10 | <10 | <10 | <10 | <10 |
| Compound of Example 600 | <10 | <10 | <10 | <10 | <10 |
| Compound of Example 601 | <10 | <10 | <10 | <10 | <10 |
| Compound of Example 608 | <10 | <10 | <10 | <10 | <10 |
| Compound of Example 611 | <10 | <10 | <10 | <10 | <10 |
| Compound of Example 613 | <10 | <10 | <10 | <10 | <10 |
| Compound of Example 621 | <10 | <10 | <10 | <10 | <10 |
| Compound of Example 657 | <10 | <10 | <10 | <10 | <10 |
| Compound of Example 669 | <10 | <10 | <10 | <10 | <10 |
| Compound of Example 777 | <10 | <10 | <10 | <10 | <10 |

TABLE 3

| Test compound | IC$_{50}$(nM) |
|---|---|
| Compound of Example 123 | <10 |
| Compound of Example 289 | <10 |
| Compound of Example 321 | <10 |
| Compound of Example 359 | <10 |
| Compound of Example 408 | <10 |
| Compound of Example 411 | <10 |
| Compound of Example 430 | <10 |
| Compound of Example 432 | <10 |
| Compound of Example 435 | <10 |
| Compound of Example 438 | <10 |
| Compound of Example 448 | <10 |
| Compound of Example 454 | <10 |
| Compound of Example 485 | <10 |
| Compound of Example 487 | <10 |
| Compound of Example 534 | <10 |
| Compound of Example 608 | <10 |
| Compound of Example 614 | <10 |
| Compound of Example 616 | <10 |
| Compound of Example 618 | <10 |
| Compound of Example 640 | <10 |
| Compound of Example 641 | <10 |
| Compound of Example 648 | <10 |
| Compound of Example 706 | <10 |
| Compound of Example 708 | <10 |
| Compound of Example 725 | <10 |
| Compound of Example 746 | <10 |
| Compound of Example 765 | <10 |
| Compound of Example 777 | <10 |
| Compound of Example 779 | <10 |
| Compound of Example 781 | <10 |

TABLE 4

| Test compound | IC50(nM) |
|---|---|
| Compound of Example 315 | <10 |
| Compound of Example 358 | <10 |
| Compound of Example 384 | <10 |
| Compound of Example 391 | <10 |
| Compound of Example 402 | <10 |
| Compound of Example 407 | <10 |
| Compound of Example 408 | <10 |
| Compound of Example 428 | <10 |
| Compound of Example 430 | <10 |
| Compound of Example 432 | <10 |
| Compound of Example 435 | <10 |
| Compound of Example 438 | <10 |
| Compound of Example 443 | <10 |
| Compound of Example 445 | <10 |
| Compound of Example 448 | <10 |
| Compound of Example 449 | <10 |
| Compound of Example 454 | <10 |
| Compound of Example 482 | <10 |
| Compound of Example 542 | <10 |
| Compound of Example 558 | <10 |
| Compound of Example 596 | <10 |
| Compound of Example 600 | <10 |
| Compound of Example 608 | <10 |
| Compound of Example 647 | <10 |
| Compound of Example 675 | <10 |
| Compound of Example 688 | <10 |
| Compound of Example 692 | <10 |
| Compound of Example 751 | <10 |
| Compound of Example 757 | <10 |
| Compound of Example 777 | <10 |

TABLE 5

| Test compound | T/C(%) (10 mg/kg/day) |
|---|---|
| Compound of Example 408 | <50 |
| Compound of Example 429 | <50 |
| Compound of Example 430 | <50 |

TABLE 5-continued

| Test compound | T/C(%) (10 mg/kg/day) |
|---|---|
| Compound of Example 432 | <50 |
| Compound of Example 435 | <50 |
| Compound of Example 438 | <50 |
| Compound of Example 440 | <50 |
| Compound of Example 777 | <50 |

TABLE 6

| Test compound | T/C(%) (10 mg/kg/day) |
|---|---|
| Compound of Example 408 | <50 |
| Compound of Example 429 | <50 |
| Compound of Example 430 | <50 |
| Compound of Example 432 | <50 |
| Compound of Example 435 | <50 |
| Compound of Example 438 | <50 |
| Compound of Example 440 | <50 |
| Compound of Example 777 | <50 |

The invention claimed is:

1. A compound represented by the following general formula (1) or a salt thereof;

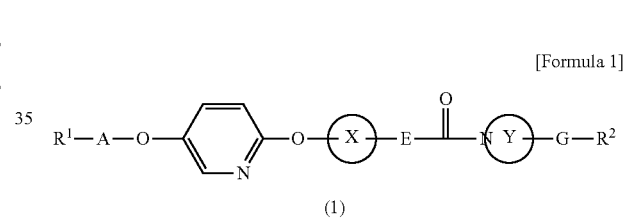

(1)

wherein

R$^1$ is the following formula:

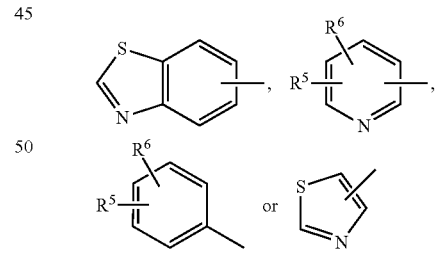

wherein R$^5$ and R$^6$ are the same or different, and are each independently hydrogen, halogen, cyano, nitro, lower alkoxy which may be substituted with one or more halogen, or lower alkyl which may be substituted with one or more halogen, the partial structural formula:

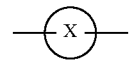

is the following formula:

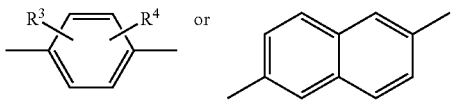

wherein R³ and R⁴ are the same or different, and are each independently hydrogen, halogen, lower alkyl or lower alkoxy, the partial structural formula:

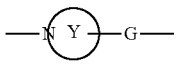

is the following formula:

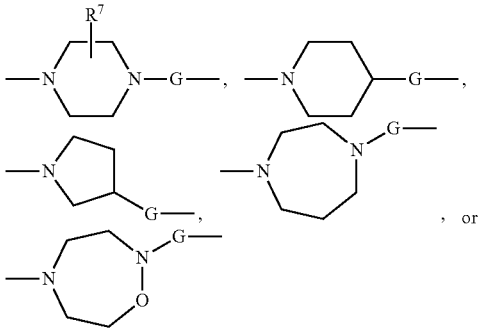

wherein $R^7$ is hydrogen or lower alkyl,
$R^2$ is:
(i) phenyl which may be substituted with one or more substituents selected from the group consisting of halogen, cyano, nitro, methylenedioxy, trimethylene, tetramethylene, pyrrolyl, lower alkyl carbonyl, lower alkyl sulfonyl, lower alkyl which may be substituted with one or more halogen, lower alkoxy which may be substituted with one or more halogen, cyclo lower alkyl, lower alkoxy lower alkyl, lower alkenyl, hydroxy lower alkenyl, lower alkoxy lower alkenyl, hydroxy lower alkyl, amino which may be substituted with one or more lower alkyl, and hydroxy lower alkoxy,
(ii) naphthyl,
(iii) pyridyl which may be substituted with one or more substituents selected from the group consisting of halogen, lower alkyl which may be substituted with one or more halogen, and lower alkoxy,
(iv) benzoxazolyl which may be substituted with one or more halogen,
(v) benzothiazolyl which may be substituted with one or more lower alkyl, or
(vi) quinolyl,
A is lower alkylene,
E is bond or lower alkenylene,
G is —NH-$G_2$-, —N(lower alkyl)-$G_2$-, —NH—CH$_2$-$G_2$-, —N(lower alkyl)-CH$_2$-$G_2$- or —CH$_2$-$G_2$-,
wherein $G_2$ of said G binds to $R^2$,
$G_2$-$R^2$ is bond-$R^2$, phenylene-$G_3$-$R^2$, phenylene-$G_4$-O—$R^2$, phenylene-$G_5$-NH—$R^2$, phenylene-$G_6$-N(lower alkyl)-$R^2$ or quinolinediyl-O—$R^2$, wherein the phenylene of said phenylene-$G_3$-$R^2$, phenylene-$G_4$-O—$R^2$, phenylene-$G_5$-NH—$R^2$ and phenylene-$G_6$-N(lower alkyl)-$R^2$ is optionally substituted with one or more substituents selected from the group consisting of halogen and lower alkyl,
$G_3$-$R^2$ is bond-$R^2$, —O-lower alkylene-$R^2$, lower alkylene-O- lower alkylene-$R^2$ or —O-lower alkylene-CO—$R^2$,
$G_4$-O— is bond-O—, lower alkylene-O—, lower alkenylene-O—, —O-lower alkylene-O— or —CO-lower alkylene-O—, and
$G_5$ and $G_6$ are each lower alkylene.

2. The compound according to claim 1 or a salt thereof; wherein
G is —NH-$G_2$-, —N(lower alkyl)-CH$_2$-$G_2$- or —CH$_2$-$G_2$, wherein $G_2$ of said G binds to $R^2$,
$G_2$-$R^2$ is phenylene-$G_3$-$R^2$, phenylene-$G_4$-O—$R^2$, phenylene-$G_5$-NH—$R^2$, phenylene-$G_6$-N(lower alkyl)-$R^2$ or quinolinediyl-O—$R^2$, wherein the phenylene of said phenylene-$G_3$-$R^2$, phenylene-$G_4$-O—$R^2$, phenylene-$G_5$-NH—$R^2$ and phnylene-$G_6$-N(lower alkyl)-$R^2$ is optionally substituted with one or more substituents selected from the group consisting of halogen and lower alkyl.

3. The compound according to claim 1 or a salt thereof, wherein G of the general formula (1) is methylene.

4. The compound according to claim 1 or a salt thereof, which is selected from the group consisting of:
(2E)-3-[4-({5-[(4-methoxybenzyl)oxy]pyridin-2-yl}oxy)-3,5-dimethylphenyl]-1-(4-{4-[(1E)-3-(4-methylphenoxy)prop-1-en-1-yl]benzyl}piperazin-1-yl)prop-2-en-1-one,
(E)-3-[3-chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)-1,4-diazepan-1-yl]prop-2-en-1-one,
4-{2-[4-({4-[(E)-3-{3-chloro-5-methyl-4-[(5-{[4-(trifluoromethyl)benzyl]oxy}pyridin-2-yl)oxy]phenyl}prop-2-enoyl]piperazin-1-yl}methyl)phenyl]ethoxy}benzonitrile,
(E)-3-[3-chloro-5-methyl-4-({5-[(4-methylbenzyl)oxy]pyridin-2-yl}oxy)phenyl]-1-(4-{4-[2-(4-ethoxyphenoxy)ethoxy]benzyl}piperazin-1-yl)prop-2-en-1-one,
(E)-3-[3-chloro-5-methyl-4-({5-[(4-methylbenzyl)oxy]-pyridin-2-yl}oxy)phenyl]-1-[4-(4-{2-[4-(dimethylamino)phenoxy]ethyl}benzyl)piperazin-1-yl]prop-2-en-1-one,
(E)-3-{3-chloro-5-methyl-4-[(5-{[4-(propan-2-yl)benzyl]oxy}pyridin-2-yl)oxy]phenyl}-1-[4-(4-methylbenzyl)piperazin-1-yl]prop-2-en-1-one,
(E)-3-[3-chloro-5-methyl-4-({5-[(4-methylbenzyl)oxy]pyridin-2-yl}oxy)phenyl]-1-[4-(4-methylbenzyl)piperazin-1-yl]prop-2-en-1-one,
(E)-1-[4-(4-{2-[(4-chlorobenzyl)oxy]ethyl}benzyl)piperazin-1-yl]-3-(3,5-dimethyl-4-{[5-(pyridin-4-ylmethoxy)pyridin-2-yl]oxy}phenyl)prop-2-en-1-one,
(E)-3-[3-chloro-4-({5-[(2-chlorobenzyl)oxy]pyridin-2-yl}oxy)-5-methylphenyl]-1-[4-(4-ethenylbenzyl)piperazin-1-yl]prop-2-en-1-one,
(E)-3-[3-chloro-5-methyl-4-({5-[(4-methylbenzyl)oxy]pyridin-2-yl}oxy)phenyl]-1-[(3S)-4-{4-[2-(4-fluorophenoxy)ethyl]-benzyl}-3-methylpiperazin-1-yl]prop-2-en-1-one,
4-{[(6-{4-[(E)-3-(2-{4-[2-(4-methoxyphenoxy)ethyl]benzyl}-1,2,5-oxadiazepan-5-yl)-3-oxoprop-1-en-1-yl]-2,6-dimethylphenoxy}pyridin-3-yl)oxy]methyl}benzonitrile, (2E)-3-[4-({5-[(4-fluorobenzyl)oxy]pyridin-2-yl}oxy)-3,
  5-dimethylphenyl]-1-(4-{3-methyl-4-[(1E)-3-(4-methylphenoxy)prop-1-en-1-yl]benzyl}piperazin-1-yl)
  prop-2-en-1-one,
(E)-3-[3-chloro-5-methyl-4-({5-[(4-methylbenzyl)oxy]
  pyridin-2-yl}oxy)phenyl]-1-(4-{4-[2-(4-chlorophenoxy)ethyl]benzyl}piperazin-1-yl)prop-2-en-1-one,
(E)-3-[3-chloro-5-methyl-4-({5-[(4-methylbenzyl)oxy]
  pyridin-2-yl}oxy)phenyl]-2-methyl-1-(4-{4-[2-(4-methylphenoxy)ethyl]benzyl}piperazin-1-yl)prop-2-en-1-
  one,
(E)-3-[3-chloro-4-({5-[(3-fluoro-4-methylbenzyl)oxy]
  pyridin-2-yl}oxy)-5-methylphenyl]-1-(4-{4-[2-(4-chlorophenoxy)ethyl]benzyl}piperazin-1-yl)prop-2-
  en-1-one,
(E)-3-[3-chloro-4-({5-[(3-fluoro-4-methylbenzyl)oxy]
  pyridin-2-yl}oxy)-5-methylphenyl]-1-(4-{4-[2-(4-methoxyphenoxy)ethyl]benzyl}piperazin-1-yl)prop-2-
  en-1-one,
(E)-3-[3-chloro-4-({5-[(4-chlorobenzyl)oxy]pyridin-2-
  yl}oxy)-5-methylphenyl]-1-(4-{4-[2-(4-fluorophenoxy)ethyl]benzyl}piperazin-1-yl)prop-2-en-1-one,
(E)-3-[3-chloro-5-methyl-4-({5-[(4-methylbenzyl)oxy]
  pyridin-2-yl}oxy)phenyl]-1-(4-{4-[2-(4-fluorophenoxy)ethyl]benzyl}piperazin-1-yl)prop-2-en-1-one,
(E)-3-[3-chloro-5-methyl-4-({5-[(4-methylbenzyl)oxy]
  pyridin-2-yl}oxy)phenyl]-1-(4-{4-[2-(4-methylphenoxy)ethyl]benzyl}piperazin-1-yl)prop-2-en-1-one,
(E)-3-[3-chloro-4-({5-[(4-fluorobenzyl)oxy]pyridin-2-
  yl}oxy)-5-methylphenyl]-1-(4-{4-[2-(4-fluorophenoxy)ethyl]benzyl}piperazin-1-yl)prop-2-en-1-one,
(E)-3-[3-chloro-4-({5-[(4-fluorobenzyl)oxy]pyridin-2-
  yl}oxy)-5-methylphenyl]-1-[4-(4-{2-[4-(propan-2-yl)
  phenoxy]ethyl}benzyl)piperazin-1-yl]prop-2-en-1-
  one,
(E)-3-[3-chloro-5-methyl-4-({5-[(4-methylbenzyl)oxy]
  pyridin-2-yl}oxy)phenyl]-1-(4-{4-[2-(4-methoxyphenoxy)ethyl]benzyl}piperazin-1-yl)prop-2-en-1-one,
(E)-3-[3-chloro-4-({5-[(6-chloropyridin-3-yl)methoxy]
  pyridin-2-yl}oxy)-5-methylphenyl]-1-[4-(4-{2-[4-
  (propan-2-yl)phenoxy]ethyl}benzyl)piperazin-1-yl]
  prop-2-en-1-one,
(E)-3-(3-chloro-5-methyl-4-{[5-(pyridin-3-ylmethoxy)
  pyridin-2-yl]oxy}phenyl)-1-[4-(4-{2-[4-(propan-2-yl)
  phenoxy]ethyl}benzyl)piperazin-1-yl]prop-2-en-1-
  one,
(E)-3-[3-chloro-4-({5-[(2-fluorobenzyl)oxy]pyridin-2-
  yl}oxy)-5-methylphenyl]-1-(4-{4-[2-(4-fluorophenoxy)ethyl]benzyl}piperazin-1-yl)prop-2-en-1-one,
(E)-3-[3-chloro-5-methyl-4-({5-[(2-methylbenzyl)oxy]
  pyridin-2-yl}oxy)phenyl]-1-(4-{4-[2-(4-fluorophenoxy)ethyl]benzyl}piperazin-1-yl)prop-2-en-1-one,
(E)-3-[3-chloro-4-({5-[(2-chlorobenzyl)oxy]pyridin-2-
  yl}oxy)-5-methylphenyl]-1-(4-{4-[2-(4-fluorophenoxy)ethyl]benzyl}piperazin-1-yl)prop-2-en-1-one,
(E)-3-[3-chloro-4-({5-[(2-fluorobenzyl)oxy]pyridin-2-
  yl}oxy)-5-methylphenyl]-1-(4-{4-[2-(4-methylphenoxy)ethyl]benzyl}piperazin-1-yl)prop-2-en-1-one,
(E)-3-[3-chloro-4-({5-[(2-chlorobenzyl)oxy]pyridin-2-
  yl}oxy)-5-methylphenyl]-1-(4-{4-[2-(4-methylphenoxy)ethyl]benzyl}piperazin-1-yl)prop-2-en-1-one,
(E)-3-[3-chloro-4-({5-[(2-fluorobenzyl)oxy]pyridin-2-
  yl}oxy)-5-methylphenyl]-1-[4-(4-{2-[4-(propan-2-yl)
  phenoxy]ethyl}benzyl)piperazin-1-yl]prop-2-en-1-
  one,
(E)-3-[3-chloro-4-({5-[(2-chlorobenzyl)oxy]pyridin-2-
  yl}oxy)-5-methylphenyl]-1-(4-{4-[2-(4-chlorophenoxy)ethyl]benzyl}piperazin-1-yl)prop-2-en-1-one,
(E)-3-[4-({5-[(2-chlorobenzyl)oxy]pyridin-2-yl}oxy)-3-
  methoxyphenyl]-1-(4-{4-[2-(4-methylphenoxy)ethyl]
  benzyl}piperazin-1-yl)prop-2-en-1-one,
(E)-3-[3-chloro-4-({5-[(3-chloro-2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-
  one,
(E)-3-[3-chloro-4-({5-[(2,3-difluorobenzyl)oxy]pyridin-
  2-yl}oxy)-5-methylphenyl]-1-(4-{4-[2-(4-methylphenoxy)ethyl]benzyl}piperazin-1-yl)prop-2-en-1-one,
(E)-3-[4-({5-[(2-chlorobenzyl)oxy]pyridin-2-yl}oxy)-3-
  methylphenyl]-1-[4-(4-{2-[4-(propan-2-yl)phenoxy]
  ethyl}benzyl)piperazin-1-yl]prop-2-en-1-one,
(E)-3-[3-chloro-5-methyl-4-({5-[(4-methylbenzyl)oxy]
  pyridin-2-yl}oxy)phenyl]-1-(4-{4-[2-(4-methylphenoxy)propyl]benzyl}piperazin-1-yl)prop-2-en-1-one,
[6-({5-[(2,3-difluorobenzyl)oxy]pyridin-2-yl}oxy)naphthalen-2-yl][4-(4-{2-[4-(propan-2-yl)phenoxy]
  ethyl}benzyl)piperazin-1-yl]methanone,
4-{[(6-{4-[(E)-3-(4-{4-[2-(4-chlorophenoxy)ethyl]
  benzyl}piperazin-1-yl)-3-oxoprop-1-en-1-yl]-2,6-
  dimethylphenoxy}pyridin-3-yl)oxy]
  methyl}benzonitrile,
4-({[6-(2-fluoro-4-{(E)-3-oxo-3-[4-(4-{2-[4-(propan-2-
  yl)phenoxy]ethyl}benzyl)piperazin-1-yl]prop-1-en-1-
  yl}phenoxy)pyridin-3-yl]oxy}methyl)benzonitrile,
(E)-3-(3,5-dimethyl-4-{[5-(1,3-thiazol-5-ylmethoxy)pyridin-2-yl]oxy}phenyl)-1-(4-{4-[2-(3-ethoxyphenoxy)
  ethyl]benzyl}piperazin-1-yl)prop-2-en-1-one,
(E)-3-(3,5-dimethyl-4-{[5-(1,3-thiazol-5-ylmethoxy)pyridin-2-yl]oxy}phenyl)-1-[4-(4-{2-[4-(propan-2-yl)
  phenoxy]ethyl}benzyl)piperazin-1-yl]prop-2-en-1-
  one,
(E)-3-(3,5-dimethyl-4-{[5-(1,3-thiazol-5-ylmethoxy)pyridin-2-yl]oxy}phenyl)-1-(4-{4-[2-(4-methylphenoxy)
  ethyl]benzyl}piperazin-1-yl)prop-2-en-1-one,
(E)-3-(3,5-dimethyl-4-{[5-(1,3-thiazol-4-ylmethoxy)pyridin-2-yl]oxy}phenyl)-1-[4-(4-{2-[4-(propan-2-yl)
  phenoxy]ethyl}benzyl)piperazin-1-yl]prop-2-en-1-
  one,
(E)-3-(3,5-dimethyl-4-{[5-(1,3-thiazol-4-ylmethoxy)pyridin-2-yl]oxy}phenyl)-1-(4-{4-[2-(4-methylphenoxy)
  ethyl]benzyl}piperazin-1-yl)prop-2-en-1-one,
(E)-3-[3-chloro-4-({5-[(2-chlorobenzyl)oxy]pyridin-2-
  yl}oxy)-5-methylphenyl]-1-[4-(4-{2-[4-(propan-2-yl)
  phenoxy]ethyl}benzyl)piperazin-1-yl]prop-2-en-1-
  one,
(E)-3-[4-({5-[(4-methoxybenzyl)oxy]pyridin-2-yl}oxy)-
  3,5-dimethylphenyl]-1-(4-{2-methyl-4-[2-(4-methylphenoxy)ethyl]benzyl}piperazin-1-yl)prop-2-en-1-
  one,
4-{[(6-{2-chloro-6-methyl-4-[(E)-3-oxo-3-{4-[4-(2-{[5-
  (trifluoromethyl)pyridin-2-yl]oxy}ethyl)benzyl]piperazin-1-yl}prop-1-en-1-yl]phenoxy}pyridin-3-yl)oxy]
  methyl}benzonitrile,
4-{[(6-{4-[(E)-3-(4-{4-[2-(4-chlorophenoxy)ethyl]-3-
  fluorobenzyl}piperazin-1-yl)-3-oxoprop-1-en-1-yl]-2,
  6-dimethylphenoxy}pyridin-3-yl)oxy]
  methyl}benzonitrile,
4-({[6-(4-{(E)-3-[4-(2-fluoro-4-{2-[4-(trifluoromethyl)
  phenoxy]ethyl}benzyl)piperazin-1-yl]-3-oxoprop-1-
  en-1-yl}-2,6-dimethylphenoxy)pyridin-3-yl]
  oxy}methyl)benzonitrile, 4-{[(6-{2-chloro-4-[(E)-3-(4-{4-[3-(4-fluorophenoxy)propyl]benzyl}piperazin-1-yl)-3-oxoprop-1-en-1-yl]-6-methylphenoxy}pyridin-3-yl)oxy]methyl}benzonitrile, 4-{[(6-{2-chloro-6-methyl-4-[(E)-3-(4-{4-[3-(4-methylphenoxy)propyl]benzyl}piperazin-1-yl)-3-oxoprop-1-en-1-yl]phenoxy}pyridin-3-yl)oxy]methyl}benzonitrile, 4-({[6-(2-chloro-4-{(E)-3-[4-(3-fluoro-4-{[4-(propan-2-yloxy)phenoxy]methyl}benzyl)piperazin-1-yl]-3-oxoprop-1-en-1-yl}-6-methylphenoxy)pyridin-3-yl]oxy}methyl)benzonitrile, 4-{[(6-{2-chloro-4-[(E)-3-(4-{3-fluoro-4-[(4-fluorophenoxy)methyl]benzyl}piperazin-1-yl)-3-oxoprop-1-en-1-yl]-6-methylphenoxy}pyridin-3-yl)oxy]methyl}benzonitrile 4-({[6-(2,6-dimethyl-4-{(E)-3-oxo-3-[4-(4-{[4-(propan-2-yloxy)phenoxy]methyl}benzyl)piperazin-1-yl]prop-1-en-1-yl}phenoxy)pyridin-3-yl]oxy}methyl)benzonitrile, (E)-3-(3,5-dimethyl-4-{[5-(1,3-thiazol-4-ylmethoxy)pyridin-2-yl]oxy}phenyl)-1-[4-(4-{[4-(propan-2-yl)phenoxy]methyl}benzyl)piperazin-1-yl]prop-2-en-1-one, 4-({[6-(4-{(1E)-3-[4-(4-{(1E)-3-[(5-bromopyridin-2-yl)oxy]prop-1-en-1-yl}benzyl)piperazin-1-yl]-3-oxoprop-1-en-1-yl}-2-chloro-6-methylphenoxy)pyridin-3-yl]oxy}methyl)benzonitrile, 4-({[6-(2-chloro-4-{(E)-3-[4-(4-{2-[(4-methoxyphenyl)amino]ethyl}benzyl)piperazin-1-yl]-3-oxoprop-1-en-1-yl}phenoxy)pyridin-3-yl]oxy}methyl)benzonitrile, (E)-3-[3-chloro-4-({5-[(2-chlorobenzyl)oxy]pyridin-2-yl}oxy)-5-methylphenyl]-1-(4-{[2-(4-methoxyphenoxy)quinolin-6-yl]methyl}piperazin-1-yl)prop-2-en-1-one, (E)-3-{3-chloro-5-methyl-4-[(5-{[4-(trifluoromethyl)benzyl]oxy}pyridin-2-yl)oxy]phenyl}-1-(4-{4-[2-(4-methoxyphenyl)ethoxy]benzyl}piperazin-1-yl)prop-2-en-1-one, 4-{[(6-{4-[(E)-3-{4-[4-(4-chlorophenoxy)benzyl]piperazin-1-yl}-3-oxoprop-1-en-1-yl]-2,6-dimethylphenoxy}pyridin-3-yl)oxy]methyl}benzonitrile, (E)-3-[3-chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)but-2-en-1-one, (E)-3-[3-chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)but-2-en-1-one, (E)-1-(4-{4-[2-(4-fluorophenoxy)propyl]benzyl}piperazin-1-yl)-3-[4-({5-[(4-methoxybenzyl)oxy]pyridin-2-yl}oxy)-3,5-dimethylphenyl]prop-2-en-1-one, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)but-2-en-1-one, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)-2-methylbut-2-en-1-one, (E)-3-[3-chloro-4-({5-[(4-fluorobenzyl)oxy]pyridin-2-yl}oxy)phenyl]-1-(4-{4-[2-(3-methoxyphenoxy)ethyl]benzyl}piperazin-1-yl)prop-2-en-1-one, (E)-1-[4-(4-chlorobenzyl)piperazin-1-yl]-3-[3-chloro-4-({5-[2-(4-chlorophenyl)ethoxy]pyridin-2-yl}oxy)-5-methylphenyl]prop-2-en-1-one, (E)-3-[3-chloro-4-({5-[(4-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one, (E)-3-[3-chloro-4-({5-[(4-fluorobenzyl)oxy]pyridin-2-yl}oxy)-5-methylphenyl]-1-[4-(4-methylbenzyl)piperazin-1-yl]prop-2-en-1-one, and (E)-3-[3-chloro-4-({5-[(4-chlorobenzyl)oxy]pyridin-2-yl}oxy)-5-methylphenyl]-1-[4-(4-methylbenzyl)piperazin-1-yl]prop-2-en-1-one.

5. The compound according to claim 1, which is selected from the group consisting of:

(2E)-3-[4-({5-[(4-methoxybenzyl)oxy]pyridin-2-yl}oxy)-3,5-dimethylphenyl]-1-(4-{4-[(1E)-3-(4-methylphenoxy)prop-1-en-1-yl]benzyl}piperazin-1-yl)prop-2-en-1-one, (E)-3-[3-chloro-5-methyl-4-({5-[(4-methylbenzyl)oxy]pyridin-2-yl}oxy)phenyl]-1-[4-(4-{2-[4-(propan-2-yl)phenoxy]ethyl}benzyl)-1,4-diazepan-1-yl]prop-2-en-1-one, 4-{2-[4-({4-[(E)-3-{3-chloro-5-methyl-4-[(5-{[4-(trifluoromethyl)benzyl]oxy}pyridin-2-yl)oxy]phenyl}prop-2-enoyl]piperazin-1-yl}methyl)phenyl]ethoxy}benzonitrile, (E)-3-[3-chloro-5-methyl-4-({5-[(4-methylbenzyl)oxy]pyridin-2-yl}oxy)phenyl]-1-(4-{4-[2-(4-ethoxyphenoxy)ethoxy]benzyl}piperazin-1-yl)prop-2-en-1-one, (E)-3-[3-chloro-5-methyl-4-({5-[(4-methylbenzyl)oxy]-pyridin-2-yl}oxy)phenyl]-1-[4-(4-{2-[4-(dimethylamino)phenoxy]ethyl}benzyl)piperazin-1-yl]prop-2-en-1-one, (E)-3-{3-chloro-5-methyl-4-[(5-{[4-(propan-2-yl)benzyl]oxy}pyridin-2-yl)oxy]phenyl}-1-[4-(4-methylbenzyl)piperazin-1-yl]prop-2-en-1-one, (E)-3-[3-chloro-5-methyl-4-({5-[(4-methylbenzyl)oxy]pyridin-2-yl}oxy)phenyl]-1-[4-(4-methylbenzyl)piperazin-1-yl]prop-2-en-1-one, (E)-1-[4-(4-{2-[(4-chlorobenzyl)oxy]ethyl}benzyl)piperazin-1-yl]-3-(3,5-dimethyl-4-{[5-(pyridin-4-ylmethoxy)pyridin-2-yl]oxy}phenyl)prop-2-en-1-one, (E)-3-[3-chloro-4-({5-[(2-chlorobenzyl)oxy]pyridin-2-yl}oxy)-5-methylphenyl]-1-[4-(4-ethenylbenzyl)piperazin-1-yl]prop-2-en-1-one, (E)-3-[3-chloro-5-methyl-4-({5-[(4-methylbenzyl)oxy]pyridin-2-yl}oxy)phenyl]-1-[(3S)-4-{4-[2-(4-fluorophenoxy)ethyl]-benzyl}-3-methylpiperazin-1-yl]prop-2-en-1-one, 4-[(6-(4-[(E)-3-(2-{4-[2-(4-methoxyphenoxy)ethyl]benzyl}-1,2,5-oxadiazepan-5-yl)-3-oxoprop-1-en-1-yl]-2,6-dimethylphenoxy pyridin-3-yl)oxy]methyl)benzonitrile, (2E)-3-[4-({5-[(4-fluorobenzyl)oxy]pyridin-2-yl}oxy)-3,5-dimethylphenyl]-1-(4-{3-methyl-4-[(1E)-3-(4-methylphenoxy)prop-1-en-1-yl]benzyl}piperazin-1-yl)prop-2-en-1-one, (E)-3-[3-chloro-5-methyl-4-({5-[(4-methylbenzyl)oxy]pyridin-2-yl}oxy)phenyl]-1-(4-{4-[2-(4-chlorophenoxy)ethyl]benzyl}piperazin-1-yl)prop-2-en-1-one hydrochloride, (E)-3-[3-chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)prop-2-en-1-one hydrochloride, (E)-3-[3-chloro-4-({5-[(3-fluoro-4-methylbenzyl)oxy]pyridin-2-yl}oxy)-5-methylphenyl]-1-(4-{4-[2-(4-chlorophenoxy)ethyl]benzyl}piperazin-1-yl)prop-2-en-1-one hydrochloride, (E)-3-[3-chloro-4-({5-[(3-fluoro-4-methylbenzyl)oxy]pyridin-2-yl}oxy)-5-methylphenyl]-1-(4-{4-[2-(4-methoxyphenoxy)ethyl]benzyl}piperazin-1-yl)prop-2-en-1-one hydrochloride, (E)-3-[3-chloro-4-({5-[(4-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)prop-2-en-1-one hydrochloride, (E)-3-[3-chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)prop-2-en-1-one hydrochloride, (E)-3-[3-chloro-4-({5-[(4-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-4-({5-[(4-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride, (E)-3-[3-chloro-5-methyl-4-({5-[(4-methylbenzyl)oxy]pyridin-2-yl}oxy)phenyl]-1-(4-{4-[2-(4-methoxyphenoxy)ethyl]benzyl}piperazin-1-yl)prop-2-en-1-one hydrochloride, (E)-3-[3-chloro-4-({5-[(6-chloropyridin-3-yl)methoxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride, (E)-3-(3-chloro-5-methyl-4-{[5-(pyridin-3-ylmethoxy)pyridin-2-yl]oxy}phenyl)-1-[4-(4-{2-[4-(propan-2-yl)phenoxy]ethyl}benzyl)piperazin-1-yl]prop-2-en-1-one hydrochloride, (E)-3-[3-chloro-4-({5-[(2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-5-methyl-4-({5-[(2-methylbenzyl)oxy]pyridin-2-yl}oxy)phenyl]-1-(4-{4-[2-(4-fluorophenoxy)ethyl]benzyl}piperazin-1-yl)prop-2-en-1-one hydrochloride, (E)-3-[3-chloro-4-({5-[(2-chlorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-4-({5-[(2-fluorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride, (E)-3-[3-chloro-4-({5-[(2-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride, (E)-3-[3-chloro-4-({5-[(2-fluorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride, (E)-3-[3-chloro-4-({5-[(2-chlorobenzyl)oxy]pyridin-2-yl}oxy)-5-methylphenyl]-1-(4-{4-[2-(4-chlorophenoxy)ethyl]benzyl}piperazin-1-yl)prop-2-en-1-one hydrochloride, (E)-3-[4-({5-[(2-chlorobenzyl)oxy]pyridin-2-yl}oxy)-3-methoxyphenyl]-1-(4-{4-[2-(4-methylphenoxy)ethyl]benzyl}piperazin-1-yl)prop-2-en-1-one hydrochloride, (E)-3-[3-chloro-4-({5-[(3-chloro-2-fluorobenzyl)oxy]pyridin-2-yl}oxy)-5-methylphenyl]-1-(4-{4-[2-(4-fluorophenoxy)ethyl]benzyl}piperazin-1-yl)prop-2-en-1-one hydrochloride, (E)-3-[3-chloro-4-({5-[(2,3-difluorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride, (E)-3-[4-({5-[(2-chlorobenzyl)oxy]pyridin-2-yl}oxy)-3-methylphenyl]-1-[4-(4-{2-[4-(propan-2-yl)phenoxy]ethyl}benzyl)piperazin-1-yl]prop-2-en-1-one hydrochloride, (E)-3-[3-chloro-5-methyl-4-({5-[(4-methylbenzyl)oxy]pyridin-2-yl}oxy)phenyl]-1-(4-{4-[2-(4-methylphenoxy)propyl]benzyl}piperazin-1-yl)prop-2-en-1-one hydrochloride,

[6-({5-[(2,3-difluorobenzyl)oxy]pyridin-2-yl}oxy)naphthalen-2-yl][4-(4-{2-[4-(propan-2-yl)phenoxy]ethyl}benzyl)piperazin-1-yl]methanone hydrochloride, 4-[(6-{4-[(E)-3-(4-{4-[2-(4-chlorophenoxy)ethyl]benzyl}piperazin-1-yl)-3-oxoprop-1-en-1-yl]-2,6-dimethylphenoxy}pyridin-3-yl)oxy]methyl benzonitrile hydrochloride, 4-({[6-(2-fluoro-4-{(E)-3-oxo-3-[4-(4-{2-[4-(propan-2-yl)phenoxy]ethyl}benzyl)piperazin-1-yl]prop-1-en-1-yl}phenoxy)pyridin-3-yl]oxy}methyl)benzonitrile hydrochloride, (E)-3-(3,5-dimethyl-4-{[5-(1,3-thiazol-5-ylmethoxy)pyridin-2-yl]oxy}phenyl)-1-(4-{4-[2-(3-ethoxyphenoxy)ethyl]benzyl}piperazin-1-yl)prop-2-en-1-one hydrochloride, (E)-3-(3,5-dimethyl-4-{[5-(1,3-thiazol-5-ylmethoxy)pyridin-2-yl]oxy}phenyl)-1-[4-(4-{2-[4-(propan-2-yl)phenoxy]ethyl}benzyl)piperazin-1-yl]prop-2-en-1-one hydrochloride, (E)-3-(3,5-dimethyl-4-{[5-(1,3-thiazol-5-ylmethoxy)pyridin-2-yl]oxy}phenyl)-1-(4-{4-[2-(4-methylphenoxy)ethyl]benzyl}piperazin-1-yl)prop-2-en-1-one hydrochloride, (E)-3-(3,5-dimethyl-4-{[5-(1,3-thiazol-4-ylmethoxy)pyridin-2-yl]oxy}phenyl)-1-[4-(4-{2-[4-(propan-2-yl)phenoxy]ethyl}benzyl)piperazin-1-yl]prop-2-en-1-one hydrochloride, (E)-3-(3,5-dimethyl-4-{[5-(1,3-thiazol-4-ylmethoxy)pyridin-2-yl]oxy}phenyl)-1-(4-{4-[2-(4-methylphenoxy)ethyl]benzyl}piperazin-1-yl)prop-2-en-1-one hydrochloride, (E)-3-[3-chloro-4-({5-[(2-chlorobenzyl)oxy]pyridin-2-yl}oxy)-5-methylphenyl]-1-[4-(4-{2-[4-(propan-2-yl)phenoxy]ethyl}benzyl)piperazin-1-yl]prop-2-en-1-one hydrochloride, (E)-3-[4-({5-[(4-methoxybenzyl)oxy]pyridin-2-yl}oxy)-3,5-dimethylphenyl]-1-(4-{2-methyl-4-[2-(4-methylphenoxy)ethyl]benzyl}piperazin-1-yl)prop-2-en-1-one hydrochloride, 4-{[(6-{2-chloro-6-methyl-4-[(E)-3-oxo-3-{4-[4-(2-{[5-(trifluoromethyl)pyridin-2-yl]oxy}ethyl)benzyl]piperazin-1-yl}prop-1-en-1-yl]phenoxy}pyridin-3-yl)oxy]methyl}benzonitrile hydrochloride, 4-{[(6-{4-[(E)-3-(4-{4-[2-(4-chlorophenoxy)ethyl]-3-fluorobenzyl}piperazin-1-yl)-3-oxoprop-1-en-1-yl]-2,6-dimethylphenoxy}pyridin-3-yl)oxy]methyl}benzonitrile hydrochloride, 4-({[6-(4-{(E)-3-[4-(2-fluoro-4-{2-[4-(trifluoromethyl)phenoxy]ethyl}benzyl)piperazin-1-yl]-3-oxoprop-1-en-1-yl}-2,6-dimethylphenoxy)pyridin-3-yl]oxy}methyl)benzonitrile hydrochloride, 4-{[(6-{2-chloro-4-[(E)-3-(4-{4-[3-(4-fluorophenoxy)propyl]benzyl}piperazin-1-yl)-3-oxoprop-1-en-1-yl]-6-methylphenoxy}pyridin-3-yl)oxy]methyl}benzonitrile hydrochloride, 4-{[(6-{2-chloro-6-methyl-4-[(E)-3-(4-{4-[3-(4-methylphenoxy)propyl]benzyl}piperazin-1-yl)-3-oxoprop-1-en-1-yl]phenoxy}pyridin-3-yl)oxy]methyl}benzonitrile hydrochloride, 4-({[6-(2-chloro-4-{(E)-3-[4-(3-fluoro-4-{[4-(propan-2-yloxy)phenoxy]methyl}benzyl)piperazin-1-yl]-3-oxoprop-1-en-1-yl}-6-methylphenoxy)pyridin-3-yl]oxy}methyl)benzonitrile hydrochloride, 4-{[(6-{2-chloro-4-[(E)-3-(4-{3-fluoro-4-[(4-fluorophenoxy)methyl]benzyl}piperazin-1-yl)-3-oxoprop-1-en-1-yl]-6-methylphenoxy}pyridin-3-yl)oxy]methyl}benzonitrile hydrochloride, 4-({[6-(2,6-dimethyl-4-{(E)-3-oxo-3-[4-(4-{[4-(propan-2-yloxy)phenoxy]methyl}benzyl)piperazin-1-yl]prop-1-en-1-yl}phenoxy)pyridin-3-yl]oxy}methyl)benzonitrile hydrochloride, (E)-3-(3,5-dimethyl-4-{[5-(1,3-thiazol-4-ylmethoxy)pyridin-2-yl]oxy}phenyl)-1-[4-(4-{[4-(propan-2-yl)phenoxy]methyl}benzyl)piperazin-1-yl]prop-2-en-1-one hydrochloride, 4-({[6-(4-{(1E)-3-[4-(4-{(1E)-3-[(5-bromopyridin-2-yl)oxy]prop-1-en-1-yl}benzyl)piperazin-1-yl]-3-oxoprop-1-en-1-yl}-2-chloro-6-methylphenoxy)pyridin-3-yl]oxy}methyl)benzonitrile hydrochloride, 4-({[6-(2-chloro-4-{(E)-3-[4-(4-{2-[(4-methoxyphenyl)amino]ethyl}benzyl)piperazin-1-yl]-3-oxoprop-1-en-1-yl}phenoxy)pyridin-3-yl]oxy}methyl)benzonitrile dihydrochloride, (E)-3-[3-chloro-4-({5-[(2-chlorobenzyl)oxy]pyridin-2-yl}oxy)-5-methylphenyl]-1-(4-{[2-(4-methoxyphenoxy)quinolin-6-yl]methyl}piperazin-1-yl)prop-2-en-1-one hydrochloride, (E)-3-{3-chloro-5-methyl-4-[(5-{[4-(trifluoromethyl)benzyl]oxy}pyridin-2-yl)oxy]phenyl}-1-(4-{4-[2-(4-methoxyphenyl)ethoxy]benzyl}piperazin-1-yl)prop-2-en-1-one hydrochloride, 4-{[(6-{4-[(E)-3-{4-[4-(4-chlorophenoxy)benzyl]piperazin-1-yl}-3-oxoprop-1-en-1-yl]-2,6-dimethylphenoxy}pyridin-3-yl)oxy]methyl}benzonitrile hydrochloride, (E)-3-[3-chloro-5-methyl-4-({5-[(4-methylbenzyl)oxy]pyridin-2-yl}oxy)phenyl]-2-methyl-1-(4-{4-[2-(4-methylphenoxy)ethyl]benzyl}piperazin-1-yl)but-2-en-1-one hydrobromide, (E)-3-[3-chloro-5-methyl-4-({5-[(4-methylbenzyl)oxy]pyridin-2-yl}oxy)phenyl]-1-(4-{4-[2-(4-methylphenoxy)ethyl]benzyl}piperazin-1-yl)but-2-en-1-one hydrobromide, (E)-1-(4-{4-[2-(4-fluorophenoxy)propyl]benzyl}piperazin-1-yl)-3-[4-({5-[(4-methoxybenzyl)oxy]pyridin-2-yl}oxy)-3,5-dimethylphenyl]prop-2-en-1-one hydrobromide, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)but-2-en-1-one ethanedioate, (E)-3-[3-chloro-5-methyl-4-({5-[(4-methylbenzyl)oxy]pyridin-2-yl}oxy)phenyl]-1-(4-{4-[2-(4-fluorophenoxy)ethyl]benzyl}piperazin-1-yl)-2-methylbut-2-en-1-one ethanedioate, (E)-3-[3-chloro-4-({5-[(4-fluorobenzyl)oxy]pyridin-2-yl}oxy)phenyl]-1-(4-{4-[2-(3-methoxyphenoxy)ethyl]benzyl}piperazin-1-yl)prop-2-en-1-one hydrochloride, (E)-1-[4-(4-chlorobenzyl)piperazin-1-yl]-[3-chloro-4-({5-[2-(4-chlorophenyl)ethoxy]pyridin-2-yl}oxy)-5-methylphenyl]prop-2-en-1-one hydrochloride, (E)-3-[3-chloro-4-({5-[(4-chlorobenzyl)oxy]pyridin-2-yl}oxy)-5-methylphenyl]-1-(4-{4-[2-(4-methylphenoxy)ethyl]benzyl}piperazin-1-yl)prop-2-en-1-one hydrochloride, (E)-3-[3-chloro-4-({5-[(4-fluorobenzyl)oxy]pyridin-2-yl}oxy)-5-methylphenyl]-1-[4-(4-methylbenzyl)piperazin-1-yl]prop-2-en-1-one hydrochloride, and (E)-3-[3-chloro-4-({5-[(4-chlorobenzyl)oxy]pyridin-2-yl}oxy)-5-methylphenyl]-1-[4-(4-methylbenzyl)piperazin-1-yl]prop-2-en-1-one hydrochloride.

6. A pharmaceutical composition comprising a compound represented by the general formula (1) or a salt thereof according to claim 1, and a pharmacologically acceptable carrier.

7. A pharmaceutical composition comprising a compound or a salt thereof according to claim 2, and a pharmacologically acceptable carrier.

8. A pharmaceutical composition comprising a compound or a salt thereof according to claim 3, and a pharmacologically acceptable carrier.

9. A pharmaceutical composition comprising a compound or a salt thereof according to claim 4, and a pharmacologically acceptable carrier.

10. A pharmaceutical composition comprising a compound or a salt thereof according to claim 5, and a pharmacologically acceptable carrier.

* * * * *

UNITED STATES PATENT AND TRADEMARK OFFICE
CERTIFICATE OF CORRECTION

PATENT NO. : 8,722,663 B2
APPLICATION NO. : 13/318053
DATED : May 13, 2014
INVENTOR(S) : Hideki Takasu et al.

It is certified that error appears in the above-identified patent and that said Letters Patent is hereby corrected as shown below:

In the Claims

Claim 1, col. 275, lines 2-6, should read

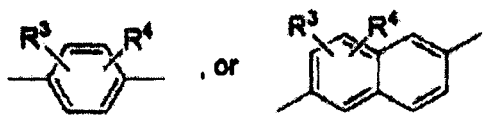

Signed and Sealed this
Eighteenth Day of August, 2015

Michelle K. Lee
*Director of the United States Patent and Trademark Office*